US012692249B2

(12) United States Patent
Lee et al.

(10) Patent No.: US 12,692,249 B2
(45) Date of Patent: Jul. 28, 2026

(54) WDR5 INHIBITORS AND MODULATORS

(71) Applicant: Vanderbilt University, Nashville, TN (US)

(72) Inventors: Taekyu Lee, Brentwood, TN (US); Kevin B. Teuscher, Nashville, TN (US); Jianhua Tian, Montgomery Village, MD (US); Kenneth M. Meyers, Nashville, TN (US); Somenath Chowdhury, Nashville, TN (US); Stephen W. Fesik, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 981 days.

(21) Appl. No.: 17/775,174

(22) PCT Filed: Nov. 8, 2020

(86) PCT No.: PCT/US2020/059585
§ 371 (c)(1),
(2) Date: May 6, 2022

(87) PCT Pub. No.: WO2021/092525
PCT Pub. Date: May 14, 2021

(65) Prior Publication Data

US 2023/0026466 A1 Jan. 26, 2023

Related U.S. Application Data

(60) Provisional application No. 62/933,065, filed on Nov. 8, 2019.

(51) Int. Cl.

| | |
|---|---|
| ***C07D 401/14*** | (2006.01) |
| ***C07D 405/14*** | (2006.01) |
| ***C07D 413/14*** | (2006.01) |
| ***C07D 471/04*** | (2006.01) |
| ***C07D 487/04*** | (2006.01) |
| ***C07D 491/048*** | (2006.01) |
| ***C07D 498/04*** | (2006.01) |

(52) U.S. Cl.
CPC ......... *C07D 401/14* (2013.01); *C07D 405/14* (2013.01); *C07D 413/14* (2013.01); *C07D 471/04* (2013.01); *C07D 487/04* (2013.01); *C07D 491/048* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 10,246,433 B2 | 4/2019 | Edwards et al. | |
| 10,807,959 B2 | 10/2020 | Gogliotti et al. | |
| 10,844,044 B2 | 11/2020 | Alvarado et al. | |
| 11,999,716 B2 * | 6/2024 | Lee | C07D 409/14 |
| 2003/0195211 A1 | 10/2003 | Sadhu et al. | |
| 2005/0124614 A1 | 6/2005 | Gangloff et al. | |
| 2008/0085890 A1 | 4/2008 | Tsou et al. | |
| 2011/0046114 A1 | 2/2011 | Molino et al. | |
| 2015/0361067 A1 | 12/2015 | Collins et al. | |
| 2016/0347744 A1 | 12/2016 | Corkey et al. | |
| 2018/0086767 A1 | 3/2018 | Fesik et al. | |
| 2018/0265517 A1 | 9/2018 | Marx et al. | |
| 2018/0362516 A1 | 12/2018 | Sugimoto et al. | |
| 2020/0055824 A1 | 2/2020 | Gogliotti et al. | |
| 2020/0102288 A1 | 4/2020 | Alvarado et al. | |
| 2023/0012362 A1 | 1/2023 | Lee et al. | |

FOREIGN PATENT DOCUMENTS

| | | |
|---|---|---|
| WO | 2001081346 A2 | 11/2001 |
| WO | 2002081446 A1 | 10/2002 |
| WO | 2007122482 A1 | 11/2007 |
| WO | 2017040449 A1 | 3/2017 |
| WO | 2018068017 A1 | 4/2018 |
| WO | 2018169777 A1 | 9/2018 |
| WO | 2020086857 A1 | 4/2020 |
| WO | 2021026672 A1 | 2/2021 |
| WO | 2021028806 A1 | 2/2021 |

OTHER PUBLICATIONS

Aho et al., "Displacement of WDR5 from Chromatin by a WIN Site Inhibitor with Picomolar Affinity", Cell Reports, vol. 26, No. 11, 2019, pp. 2916-2928.

Balgobind et al., "The heterogeneity of pediatric MLL-rearranged acute myeloid leukemia", Leukemia, 2011, vol. 8, pp. 1239-1248.

Cao et al., "Targeting MLL1 H3K4 Methyltransferase Activity in Mixed-Lineage Leukemia", Molecular Cell, 2014, vol. 53, pp. 247-261.

Carugo et al., "In Vivo Funcitonal Platform Targeting Patient-Derived Xenografts Identifies WDR5-Myc Association as a Critical Determinant of Pancreatic Cancer", Cell Reports, 2016, vol. 16, pp. 133-147.

Caslini et al., "Interaction of MLL Amino Terminal Sequences with Menin Is Required for Transformation", Cancer Res., 2007, vol. 67, pp. 7275-7283.

Chen et al., "Upregulated WDR5 promotes proliferation, self-renewal and chemoresistance in bladder cancer via mediating H3K4 trimethylation", Scientific Reports, 2015, vol. 5, pp. 8293.

Dai et al., "WDR5 Expression Is Prognostic of Breast Cancer Outcome", PLoSOne, 2015, vol. 10, PMC4565643.

Dess et al., "Readily available 12-I-5 oxidant for the conversion of primary and secondary alcohols to aldehydes and ketones", J. Org. Chem., 1983, vol. 48, p. 4155.

(Continued)

*Primary Examiner* — Clinton A Brooks
*Assistant Examiner* — Nicola Maria Bauer
(74) *Attorney, Agent, or Firm* — MICHAEL BEST & FRIEDRICH LLP

(57) ABSTRACT

Isoquinolmone compounds and derivatives inhibit WDR5 and associated protein-protein interactions, and the compounds and their pharmaceutical compositions are useful for treating disorders and conditions in a subject, such as cancer cell proliferation.

29 Claims, No Drawings

(56) References Cited

OTHER PUBLICATIONS

Dias et al., "Structural analysis of the KANSL1/WDR5/KANSL2 complex reveals that WDR5 is required for efficient assembly and chromatin targeting of the NSL complex", Genes and Development, 2014, vol. 28, pp. 929-942.
Dimartino et al., "Review: MLL Rearrangements in Haematological Malignancies: Lessons from Clinical and Biological Studies", British Journal of Haematol., 1999, vol. 106, pp. 614-626.
Ee et al., "An Embryonic Stem Cell-Specific NuRD Complex Functions through Interaction with WDR5", Stem Cell Reports, 2017, vol. 8, pp. 1488-1496.
International Preliminary Report on Patentability for Application No. PCT/US19/57877 dated Apr. 27, 2021 (5 pages).
International Preliminary Report on Patentability for Application No. PCT/US2020/059585 dated May 10, 2022 (7 pages).
International Search Report and Written Opinion for Application No. PCT/US19/57877 dated Jan. 6, 2020 (12 pages).
International Search Report and Written Opinion for Application No. PCT/US2020/059585 dated Mar. 1, 2021 (15 pages).
Karatas et al., "Discovery of a Highly Potent, Cell-Permeable Macrocyclic Peptidomimetic (MM-589) Targeting the WD Repeat Doman 5 Protein (WDR5)-Mixed Lineage Leukemia (MLL) Protein-Protein Interaction", J. Med. Chem., 2017, vol. 60, pp. 4818-4839.
Li et al., "MOF and H4 K16 Acetylation Play Important Roles in DNA Damage Repar by Modulating Recruitment of DNA Damanage Repair Protein Mdc1", Molecular and Cellular Biology, 2010, vol. 30, pp. 5335-5347.
Littke, Fu, "Palladium-Catalyzed Coupling Reactions of Aryl Chlorides", Angew. Chem., Int. Ed., 2002, vol. 41, pp. 4176-4211.
Marschalek, "Mechamisms of leukemogenesis by MLL fusion proteins", British Journal of Haematol., 2011, vol. 152, pp. 141-54.
Milne et al., "Leukemogenic MLL Fusion Proteins Bind across a Broad Region of the Hox a9 Locus, Promoting Transcription and Multiple Histone Modifications", Cancer Res., 2005, vol. 65, pp. 11367-74.
Milne et al., "MLL Targets SET Domain Methyltransferase Activity to Hox Gene Promoters", Mol. Cell, 2002, vol. 10, pp. 1107-17.
Miyaura et al., "Palladium Catalyzed Cross-Coupling Reactions of Organoboron Compounds", Chem. Rev., 1995, p. 2457.
Nakamura et al., "ALL-1 Is a Histone Methyltransferase that Assemblesl a Supercomplex of Proteins Involved in Transcriptional Regulation", Mol. Cell., 2002, vol. 10, pp. 1119-1128.
Patel et al., "On the Mechanism of Multiple Lysine Methylation by the Human Mixed Lineage Luekemia Protein-1 (MLL1) Core Complex", Biol. Chem., 2009, vol. 284, pp. 24242-56.
Pigazzi et al., "MLL Partner genes drive distinct gene expression profiles and genomic alterations in pediatric acute myeloid leukemia: an AIEOP study", Leukemia, 2011, vol. 25, pp. 560-563.
Pui et al., "Clinical heterogeneity in childhood acute lymphoblastic leukemia with 11q23 rearrangements", Leukemia, 2003, vol. 4, pp. 700-706.
Senisterra et al., "Small-molecule inhibition of MLL activity by disruption of its interaction with WDR5", Biochem J., 2013, vol. 449, pp. 151-159.
Slany, "The molecular biology of mixed lineage leukemia", Haematologica, 2009, vol. 94, pp. 984-993.
Song et al., "WDR5 Interacts with Mixed Lineage Leukemia (MLL) Protein via the Histone H3-binding Pocket", J. Biol. Chem., 2008, vol. 283, pp. 35258-64.
Sun et al., "WDR5 Supports an N-Myc Transcriptional Complex That Drives a Protumorigenic Gene Expression Signature in Neuroblastoma", Cancer Research, 2015, vol. 75, pp. 5143-5154.
Tamai et al., "11q23/MLL Acute Leukemia: Update of Clinical Aspects", J. Clin. Exp. Hematop., 2010, vol. 50, pp. 91-98.
Tan et al., "PI3K/AKT-mediated upregulation of WDR5 promotes colorectal cancer metastasis by directly targeting ZNF407", Cell Death & Disease, 2017, vol. 8, e2686, 12 pages.
Thachuk et al., "Involvement of a Homolog of *Drosophila trithorax* by 11q23 Chromosomal Translocations in Acute Leukemias", Cell, 1992, vol. 71, pp. 691-700.
Thomas et al., "Interaction with WDR5 Promotes Target Gene Recognition and Tumorigenesis by MYC", Molecular Cell, 2015, vol. 58, pp. 440-452.
Tian et al.,, "Discovery and Structure Based Optimization of Potent and Selective WD Repeat Domain 5 (WDR5) Inhibitors Containing a Dihydroisoquinolinone Bicyclic Core", J. Med. Chem., 2020, vol. 63, pp. 656-675.
Tomizawa et al., "Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group", Leukemia, 2007, vol. 21, pp. 2258-2263.
Wang et al., "Discovery of Potent 2-Aryl-6,7-dihydro-5 H-pyrrolo[1,2-a] imidazoles as WDR5-WIN-Site Inhibitors Using Fragment-Based Methods and Structure-Based Design", Journal of Medicinal Chemistry, vol. 61, No. 13, 2018, pp. 5623-5642.
Wolff, "The Schmidt Reaction", Organic Reactions, 2011, pp. 307-336.
Yokoyama et al., "Leukemia Proto-Oncoprotein MLL Forms a SET1-Like Histone Methyltransferase Complex with Menin to Regulate Hox Gene Expression", Mol. Cell Biol., 2004, vol. 24, pp. 5639-5649.
Yokoyama et al., "The Menin Tumor Suppressor Protein Is an Essential Oncogenic Cofactor for MLL-Associated Leukemogenesis", Cell, 2005, vol. 123, pp. 207-218.
Yu et al., "MLL, a mammalian trithorax-group gene, functions as a transcriptional maintenance factor in morphogenesis", Proc. Natl. Acad. Sci., 1998, vol. 95, pp. 10632-10636.

* cited by examiner

WDR5 INHIBITORS AND MODULATORS

RELATED APPLICATIONS

This patent application is the U.S. national stage entry, under 35 U.S.C. § 371. of International Application Number PCT/US2020/059585, filed Nov. 8, 2020, which claims priority to U.S. Provisional Application No. 62/933,065, filed Nov. 8, 2019, the entire contents of each of which are hereby incorporated by reference.

STATEMENT OF GOVERNMENT INTEREST

This invention was made with government support under Contract No. HHSN261200800001E, awarded by the National Institutes of Health. The government has certain rights in the invention.

TECHNICAL FIELD

The present invention relates generally to compounds that inhibit the binding of transcription factors, regulatory regulators, and chromatin to WDR5 and methods of use thereof. In particular embodiments, the present invention provides compositions comprising imino-azacycle-benzamide compounds and methods of use thereof to inhibit or modulate the interaction of WDR5 with chromatin, cognate transcription and other regulatory factors, including for example the histone methyltransferase MLL1, for the treatment of leukemia, solid cancers and other diseases dependent on activity of WDR5.

BACKGROUND

Mixed lineage leukemia (MLL) presents a heterogeneous group of acute myeloid leukemia and acute lymphoblastic leukemia bearing features of more than one hematopoietic cell lineage. MLL accounts for about 80% of infant acute leukemia cases (Tomizava, D.; et. al. *Leukemia,* 2007, 11, 2258-63) and 10% of all acute leukemia cases (Marschalek, R. *Br. J. Haematol.* 2011, 152, 141-54). MLL leukemia patients have a poor prognosis with overall 5-year survival ratio around 35% (Dimartino, J. F.; Cleary, M. L., *Br. J. Haematol.* 1999, 106, 614-626; Pui, C., et al. *Leukemia,* 2003, 4, 700-706; Tomizawa, D.; et. al. *Leukemia,* 2007, 21, 2258-63).

MLL is composed of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila trithorax* (Trx) (Thachuk, D. C.; et al. *Cell,* 1992, 71, 691-700). Wild type MLL binds to regulatory regions of homeox (HOX) genes (Milne, T. A.; et al. *Cancer Res.,* 2005, 65, 11367-74) through the amino terminal fragment while the catalytic C-terminal domain catalyzes the Histone 3 lysine 4 (H3K4) methylation via interaction with WDR5 and up regulates target gene transcription (Nakamura, T.; et al *Mol. Cell,* 2002, 10, 1119-28; Yokoyama, A. et al. *Mol. Cell Biol.,* 2004, 24, 5639-49; Milne, T. A.; et al. *Mol. Cell,* 2002, 10, 1107-17). Wild type MLL in conjunction with WDR5 is required for maintenance HOX genes expression and is widely expressed not only during embryo development but also in adult tissues including myeloid and lymphoid cells (Yu, B. D.; et al. *Proc. Natl. Acad. Sci.,* 1998, 95, 10632-10636). Reciprocal translocations of MLL gene result in-frame fusion of the 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, C., et al. *Leukemia,* 2003, 4, 700-706; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, C.; et al. *Cancer Res.,* 2007, 67, 7275-83; Yokoyama, A.; et al. *Cell,* 2005, 123, 207-18). The numerous chromosomal translocations of MLL gene and partner genes add to the complexity of MLL leukemia treatment. Although HOX9 and MEIS1 overexpression are commonly observed among MLL leukemia patients, each rearrangement leads to distinct dysregulated target gene expression patterns and downstream events (Slany, R. K., *Haematologica,* 2009, 94, 984-993). Clinical studies reveal that MLL of different chromosomal translocations are associated with different prognosis and are treated differently under current protocols (Tamai, H., et al. *J. Clin. Exp. Hematop.,* 2010, 50, 91-98; Balgobind, B. V., et al. *Leukemia,* 2011, 8, 1239-1248; Pigazzi, M.; et al. Leukemia, 2011, 25, 560-563).

Intrinsic histone methyltransferase (HMT) activity of MLL1 is extremely low and requires a complex assembly of WDR5, RbBP5, ASH2L, and DPY30 protein partners for effective H3K4 trimethylation, the so-called WRAD complex (Patel, A.; et al. *J. Biol. Chem.,* 2009, 284, 24242-56). The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidonimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, F.; et al. *Molecular Cell,* 2014, 53, 247-61, Karatas, H.; et al. *J. Med. Chem.,* 2017, 60, 4818-4839). In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. In addition to the highly characterized WDR5-MLL1 interaction, disruption of WDR5 with other transcription factors/epigenetic writers or displacement from chromatin itself could have a desirable benefit as a cancer treatment strategy. For example, WDR5 acts as a scaffold protein with the following chromatin complexes/structures, including histone H3 (via R2 residues, e.g. see Song, J.-J., et al. *J. Biol. Chem.* 2008, 283, 35258-64), NSL/MOF (Li, X, et al. Molecular and Cellular Biology, 2010, 30, 5335-47, Dias, J., et al. *Genes & Development,* 2014, 28, 929-942), C/EBP□ p30 (Senisterra, G., et al. *Biochem. J.,* 2013, 449, 151-159), c-MYC (Thomas, L. R.; et al. *Molecular Cell,* 2015, 58, 440-52, herein incorporated by reference in its entirety), and the NuRD complex (Ee, L.-S., et al. Stem Cell Reports, 2017, 8, 1488-96). In addition, WDR5 expression levels have been reported to be correlative and connected to patient prognosis in several other cancer types, including neuroblastoma (Sun, Y. et al. *Cancer Research,* 2015, 75, 5143-

54), breast cancer (Dai, X. et al. *PLoSOne,* 2015, 10, PMC4565643), bladder cancer (Chen, X. et al. *Scientific Reports,* 2015, 5, 8293), and colorectal cancer (Tan, X. et al. *Cell Death & Disease,* 2017, 8, PMC5386518). In addition, in an unbiased shRNA screen in human xenografts, WDR5 was identified as an important target in pancreatic cancer (Carugo, A. et al. *Cell Reports,* 2016, 16, 133-147). Based on the growing number of complexes identified, which utilize WDR5 to maintain tumor fitness and growth, the emerging importance of WDR5 in several cancer types is not unexpected. In the case of the c-MYC-WDR5 interaction, the MYC oncoprotein utilizes a molecularly defined interaction with WDR5 to bind to its target genes on chromatin. MYC is overexpressed in a majority of malignancies and contributes to an estimated 70,000-100,000 cancer deaths per year in the United States. Thus, disruption of WDR5 from chromatin as a strategy to displace MYC from its target genes may provide a beneficial strategy to treat MYC-driven tumors.

SUMMARY

The molecules described herein can inhibit or modulate the interaction of WDR5 with chromatin, cognate transcription and other regulatory factors, including for example the histone methyltransferase MLL1, and can provide a therapeutic approach to treat cancers associated with such interactions (e.g., the MLL1-WDR5 interaction).

In one aspect, the invention provides compounds of formula (I),

[I]

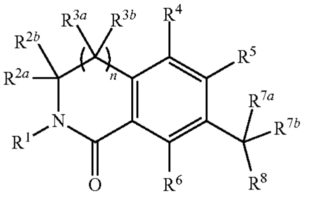

or a pharmaceutically acceptable salt thereof, wherein:

n is 0, 1, or 2;

$R^1$ is $G^1$;

$G^1$ is a 9- to 12-membered bicyclic aryl, an 8- to 12-membered bicyclic heteroaryl, an 8- to 12-membered fused bicyclic heterocyclyl, or a $C_{3-10}$carbocyclyl fused to a 6-membered arene or to a 5- to 6-membered heteroarene, wherein $G^1$ is optionally substituted with 1-5 substituents independently selected from the group consisting of halogen, $C_{1-6}$alkyl, $C_{1-6}$haloalkyl, oxo, $-L^1-X^1$, and $-L^1-G^{1a}$.

$X^1$, at each occurrence, is independently $—OR^{1a}$, $—N(R^{1a})_2$, $—SR^{1a}$, cyano, $—C(O)OR^{1a}$, $—C(O)N(R^{1a})_2$, $—C(O)N(R^{1a})SO_2R^{1b}$, $—C(NH)NHOH$, $—C(O)H$, $—C(O)R^{1b}$, $—SOR^{1b}$, $—SO_2R^{1b}$, $SO_2N(R^{1a})_2$, $—NR^{1a}(O)H$, $—NR^{1a}C(O)R^{1b}$, $—NR^{1a}C(O)OR^{1a}$, $—NR^{1a}C(O)N(R^{1a})_2$, $—NR^{1a}S(O)_2R^{1b}$, or $—NR^{1a}S(O)_2N(R^{1a})_2$;

$R^{1a}$, at each occurrence, is independently hydrogen, $C_{1-6}$-alkyl, $C_{1-6}$haloalkyl, $—C_{2-4}$alkylene-$OR^{1c}$—, $—C_{2-4}$alkylene-$N(R^{1e})_2$, $—C_{2-4}$alkylene-$N(R^{1c})C(O)R^{1e}$, $G^{1a}$, or $—C_{1-6}$alkylene-$G^{1a}$;

$R^{1b}$, at each occurrence, is independently $C_{1-6}$alkyl, $C_{1-6}$haloalkyl, $—C_{1-4}$alkylene-$OR^{1e}$, $—C_{1-4}$alkylene-$N(R^{1e})_2$, $—C_{1-4}$alkylene-$N(R^{1c})C(O)R^{1e}$, $G^{1a}$, or $—C_{1-6}$alkylene-$G^{1a}$;

$L^1$, at each occurrence, is independently a bond or $C_{1-3}$alkylene;

$G^{1a}$ at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, $-L^2-X^2$, and $-L^2-G^{1b}$;

$X^2$, at each occurrence, is independently $—OR^{1c}$, $—N(R^{1c})_2$, $—SR^{1c}$, cyano, $—C(O)OR^{1c}$, $—C(O)N(R^{1c})_2$, $—C(O)R^{1c}$, $—SOR^{1d}$, $—SO_2R^{1d}$, $—SO_2N(R^{1c})_2$, $—NR^{1c}C(O)R^{1c}$, $—NR^{1c}C(O)OR^{1c}$, $—NR^{1c}C(O)N(R^{1c})_2$, $—NR^{1c}S(O)_2R^{1d}$, or $—NR^{1c}S(O)_2N(R^{1c})_2$;

$R^{1c}$, at each occurrence, is independently hydrogen, $C_{1-6}$alkyl, $C_{1-6}$haloalkyl, $G^{1b}$, or $—C_{1-3}$alkylene-$G^{1b}$, wherein alternatively two $R^{1c}$, together with a common nitrogen atom to which the $R^{1c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and $—OC_{1-4}$alkyl;

$R^{1d}$, at each occurrence, is independently $C_{1-6}$alkyl, $C_{1-6}$haloalkyl, $G^{1b}$, or $—C_{1-3}$alkylene-$G^{1b}$;

$R^{1e}$, at each occurrence, is independently hydrogen, $C_{1-4}$alkyl, $C_{1-4}$haloalkyl, $G^{1b}$, or $—C_{1-3}$alkylene-$G^{1b}$, wherein alternatively two $R^{1e}$, together with a common nitrogen atom to which the $R^{1e}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and $—OC_{1-4}$alkyl;

$L^2$, at each occurrence, is independently a bond or $C_{1-3}$alkylene;

$G^{1b}$ is a $C_{3-6}$cycloalkyl, a 4- to 6-membered monocyclic heterocyclyl containing 1-2 heteroatoms independently selected from O, N, and S, a 5- to 6-membered heteroaryl containing 1-4 heteroatoms independently selected from O, N, and S, or a phenyl, wherein $G^{1b}$ is optionally substituted with 1-4 substituents independently selected from the group consisting of halogen, cyano, $C_{1-4}$alkyl, $C_{1-4}$haloalkyl, oxo, —OH, and $—OC_{1-4}$alkyl; $R^{2a}$, $R^{2b}$, $R^{3a}$, and $R^{3b}$ are independently hydrogen, halogen, $C_{1-4}$alkyl, $C_{1-4}$haloalkyl, or $—OC_{1-4}$alkyl; or alternatively any two of $R^{2a}$, $R^{2b}$, $R^{3a}$, and $R^{3b}$ are taken together with the atom or atoms to which they attach to form a 3-8 membered saturated or partially unsaturated carbocyclic or heterocyclic ring that is optionally substituted with 1-4 substituents independently selected from the group consisting of halogen, $C_{1-4}$alkyl, $C_{1-4}$haloalkyl, and $—OC_{1-4}$alkyl;

or alternatively one $R^{3a}$ and one $R^{3b}$ are taken together to form an oxo group;

$R^4$ is hydrogen, halogen. $C_{1-6}$alkyl, $C_{1-6}$-haloalkyl, $C_{1-6}$haloalkenyl, $—OR^{4a}$, $—SR^{4a}$, $—N(R^{4a})_2$, $—S(O)R^{4b}$, $—S(O)_2R^{4b}$, $—S(O)N(R^{4a})_2$, $—C(O)N(R^{4a})_2$, $—C(O)^{4a}$, $—NR^{4a}C(O)R^{4a}$, $—NR^{4a}C(O)OR^{4a}$, $—NR^{4a}C(O)N(R^{4a})_2$, $—NR^{4a}S(O)_2R^{4b}$, $—NR^{4a}S(O)_2N(R^{4a})_2$, or $G^2$;

$R^{4a}$ at each occurrence, is independently hydrogen, $C_{1-6}$alkyl, $C_{1-6}$haloalkyl, $G^2$, or $—C_{1-3}$alkylene-$G^2$;

$R^{4b}$ is $C_{1-6}$alkyl, $C_{1-6}$haloalkyl, $G^2$, or $—C_{1-3}$alkylene-$G^2$;

$G^2$, at each occurrence, is independently a $C_{3-10}$carbocyclyl, a 6- to 12-membered aryl, a 5- to 12-membered heteroaryl, or a 4- to 12-membered heterocyclyl, wherein $G^2$ is optionally substituted with 1-5 substituents independently selected from the group consisting of halogen, $C_{1-6}$alkyl, $C_{1-6}$haloalkyl, oxo, —$OR^{4c}$, —$N(R^{4c})_2$, —$SR^{4c}$, cyano, —$C(O)OR^{4c}$, —$C(O)N(R^{4c})_2$, —$C(O)R^{4c}$, —$SOR^{4d}$, —$SO_2R^{4d}$, —$SO_2N(R^{4c})_2$, —$NR^{4c}C(O)R^{4c}$, —$NR^{4c}(O)OR^{4c}$, —$NR^{4c}C(O)N(R^{4c})_2$, —$NR^{4c}S(O)_2R^{4d}$—$NR^{4c}S(O)_2N(R^{4c})_2$, $C_{3-8}$cycloalkyl, and —$C_{1-3}$alkylene-$C_{3-8}$-cycloalkyl, wherein each $C_{3-8}$cycloalkyl is optionally substituted with 1-4 substituents independently selected from the group consisting, of $C_{1-4}$alkyl and halogen;

$R^{4c}$, at each occurrence, is independently hydrogen, $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein alternatively two $R^{4c}$, together with a common nitrogen atom to which the $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{4d}$, at each occurrence, is independently $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^5$ and $R^6$ are each independently hydrogen, halogen, $C_{1-4}$alkyl, $C_{1-4}$haloalkyl, or —$OC_{1-4}$alkyl;

$R^{7a}$ and $R^{7b}$ are independently selected from the group consisting of hydrogen, halogen, hydroxy, $C_{1-4}$alkyl, and $C_{1-4}$haloalkyl, or $R^{7a}$ and $R^{7b}$ are taken together to form an oxo group; and $R^8$ is a 5- to 6-membered heterocyclic ring containing 1-3 heteroatoms and 1-3 double bonds, wherein one of the 1-3 heteroatoms is a nitrogen and the remaining heteroatoms are independently selected from nitrogen and oxygen, wherein R is optionally substituted with 1-3 substituents independently selected from the group consisting of halogen, $C_{1-4}$alkyl, $C_{1-4}$haloalkyl, imino, oxo, $NO_2$, $NH_2$, —$NH(C_{1-4}alkyl)$, —$N(C_{1-4}alkyl)_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

In another aspect, the invention provides a pharmaceutical composition comprising a compound of formula (I), or a pharmaceutically acceptable salt thereof, and a pharmaceutically acceptable carrier.

In another aspect, the invention provides a method for the treatment of cancer, comprising administering to a subject in need thereof a therapeutically effective amount of a compound of formula (I), or a pharmaceutically acceptable salt or composition thereof.

In another aspect, the invention provides a method for inhibiting the binding of MLL1 to WDR5, comprising administering to a subject in need thereof a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of cancer.

In another aspect, the invention provides a compound of formula (I), or a pharmaceutically acceptable salt or composition thereof, for use in the inhibition of binding of MLL1 to WDR5.

In another aspect, the invention provides the use of a compound of formula (I), or a pharmaceutically acceptable salt or composition thereof, in the manufacture of a medicament for the treatment of cancer.

In another aspect, the invention provides the use of a compound of formula (I), or a pharmaceutically acceptable salt or composition thereof, in the manufacture of a medicament for the inhibition of binding of MLL1 to WDR5.

In another aspect, the invention provides a kit comprising a compound of formula (I), or a pharmaceutically acceptable salt or composition thereof, and instructions for use.

DETAILED DESCRIPTION

Disclosed herein are inhibitors of WDR5, which bind at the WDR5 interaction or WIN-site. The inhibitors can be compounds of formula (I). Compounds of formula (I) can be used to treat cancers associated with the MLL1-WDR5 interaction. In one aspect, disclosed are compounds of formula (I) as WDR5-WIN-site inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, isobutyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched chain hydrocarbon, for example, of 2 to 5 carbon atoms. Representative examples of alkylene include, but are not limited to, $—CH—_2CH_2—$, $—CH_2CH_2CH_2—$, $—CH_2CH_2CH_2CH_2—$, and $—CH_2CH_2CH_2CH_2CH_2—$.

The term "aryl," as used herein, refers to a phenyl or a phenyl appended to the parent molecular moiety and fused to a cycloalkane group (e.g., the aryl may be indan-4-yl), fused to a 6-membered arene group (i.e., the aryl is naphthyl), or fused to a non-aromatic heterocycle (e.g., the aryl may be benzo[d][1,3]dioxol-5-yl). The term "phenyl" is used when referring to a substituent and the term 6-membered arene is used when referring to a fused ring. The 6-membered arene is monocyclic (e.g., benzene or benzo). The aryl may be monocyclic (phenyl) or bicyclic (e.g., a 9- to 12-membered fused bicyclic system).

The term "cycloalkyl" or "cycloalkane," as used herein, refers to a saturated ring system containing all carbon atoms as ring members and zero double bonds. The term "cycloalkyl" is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl" or "cycloalkene," as used herein, means a non-aromatic monocyclic or multicyclic ring system containing all carbon atoms as ring members and at least one carbon-carbon double bond and preferably having from 5-10 carbon atoms per ring. The term "cycloalkenyl" is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptenyl). Exemplary monocyclic cycloalkenyl rings include cyclopentenyl, cyclohexenyl or cycloheptenyl.

The term "carbocyclyl" means a "cycloalkyl" or a "cycloalkenyl." The term "carbocycle" means a "cycloalkane" or a "cycloalkene." The term "carbocyclyl" refers to a "carbocycle" when present as a substituent.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaromatic ring (bicyclic heteroaryl). The term "heteroaryl" is used herein to refer to a heteroarene when present as a substituent. The monocyclic heteroaryl are five or six membered rings containing at least one heteroatom independently selected from the group consisting of N, O and S (e.g. 1, 2, 3, or 4 heteroatoms independently selected from 0, S, and N). The five membered aromatic monocyclic rings have two double bonds and the six membered aromatic monocyclic rings have three double bonds. The bicyclic heteroaryl is an 8-to 12-membered ring system and includes a fused bicyclic heteroaromatic ring system (i.e., 10π electron system) such as a monocyclic heteroaryl ring fused to a 6-membered arene (e.g., quinolin-4-yl, indol-1-yl), a monocyclic heteroaryl ring fused to a monocyclic heteroarene (e.g., naphthyridinyl), and a phenyl fused to a monocyclic heteroarene (e.g., quinolin-5-yl, indol-4-yl). A bicyclic heteroaryl/heteroarene group includes a 9-membered fused bicyclic heteroaromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. A bicyclic heteroaryl also includes a fused bicyclic ring system composed of one heteroaromatic ring and one non-aromatic ring such as a monocyclic heteroaryl ring fused to a monocyclic carbocyclic ring (e.g., 6,7-dihydro-5H-cyclopenta[b]pyridinyl), or a monocyclic heteroaryl ring fused to a monocyclic heterocycle (e.g., 2,3-dihydrofuro[3,2-b]pyridinyl). The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane, or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indol-1-yl, isoindolin-2-yl, octahydrocyclopenta[c]pyrrolyl, octahydropyrrolopyridinyl, and tetrahydroisoquinolinyl. Tricyclic heterocycles are exemplified by a bicyclic heterocycle fused to a 6-membered arene, or a bicyclic heterocycle fused to a monocyclic cycloalkane, or a bicyclic heterocycle fused to a monocyclic cycloalkene, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety at a non-aromatic ring atom.

The term "imino" refers to the group "=NH."

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups may include, for example, halogen, =O (oxo), =5 (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed are compounds of formula (I), wherein $R^1$, $R^{2a}$, $R^{2b}$, $R^{3a}$, $R^{3b}$, $R^4$, $R^5$, $R^6$, $R^{7a}$, $R^{7b}$, $R^8$, and n are as defined herein. Embodiments of formula (I) include the following descriptions of $R^1$, $R^{2a}$, $R^{2b}$, $R^{3a}$, $R^{3b}$, $R^4$, $R^5$, $R^6$, $R^{7a}$, $R^{7b}$, $R^8$, and n, and any combinations thereof.

$R^8$ is a 5- to 6-membered heterocyclic ring containing 1-3 heteroatoms and 1-3 double bonds, wherein one of the 1-3 heteroatoms is a nitrogen and the remaining heteroatoms are independently selected from nitrogen and oxygen, wherein $R^8$ is optionally substituted with 1-3 substituents independently selected from the group consisting of halogen, $C_{1-4}$alkyl, $C_{1-4}$haloalkyl, imino, oxo, $NO_2$, $NH_2$, —NH($C_{1-4}$alkyl), —N($C_{1-4}$alkyl)$_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —O$C_{1-4}$alkyl. $R^8$ may be unsubstituted or substituted with 1-3 substituents independently selected from the group consisting of halogen, $C_{1-4}$alkyl, $C_{1-4}$-haloalkyl, imino, oxo, $NH_2$, —NH($C_{1-4}$alkyl), —N($C_{1-4}$alkyl)$_2$, $C_{3-8}$cycloalkyl, and —$C_{1-4}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —O$C_{1-4}$alkyl. For example, $R^8$ may be an optionally substituted imidazolyl or pyridinyl. $R^8$ may be a 5-membered heterocyclic ring containing 2 heteroatoms, wherein one of the 2 heteroatoms is a nitrogen and the remaining heteroatom is nitrogen or oxygen and the 5-membered heterocyclic ring is substituted with an imino group (i.e., "=NH").

$R^8$ may be an optionally substituted imidazolyl, as defined herein. $R^8$ may be selected from the group consisting of

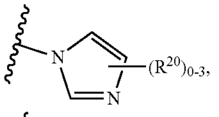,
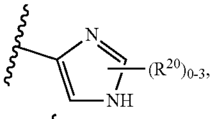,
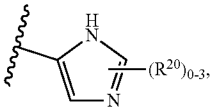, or
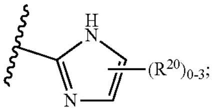;

wherein $R^{20}$, at each occurrence, is independently halogen, $C_{1-4}$alkyl, $C_{1-4}$haloalkyl, $NH_2$, —NH($C_{1-4}$alkyl), —N($C_{1-4}$alkyl)$_2$, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —O$C_{1-4}$alkyl. $R^8$ may be selected from the group consisting of

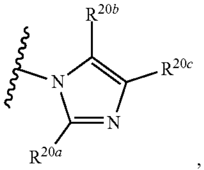,

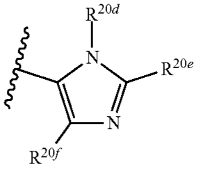,

-continued

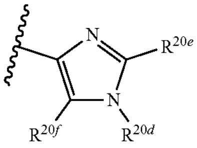, and

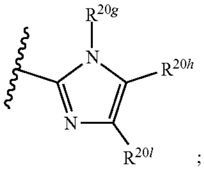;

wherein $R^{20a}$ is hydrogen, $C_{1-4}$alkyl (e.g., methyl, ethyl, isopropyl), $NH_2$, —NH($C_{1-4}$alkyl) (e.g., —$NHCH_3$), —N($C_{1-4}$alkyl)$_2$, or $C_{3-8}$cycloalkyl (e.g., cyclopropyl); and $R^{20b}$, $R^{20c}$, $R^{20d}$, $R^{20e}$, $R^{20f}$, $R^{20g}$, $R^{20h}$, and $R^{20}$, are each independently hydrogen, $C_{1-4}$alkyl (e.g., methyl, ethyl), or $C_{3-8}$cycloalkyl. The optionally substituted imidazolyl at $R^8$ may be selected from the group consisting of

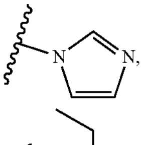
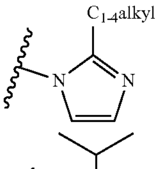 (e.g., 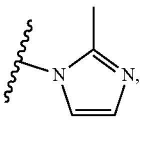
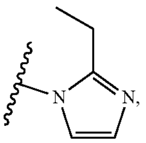
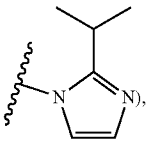),
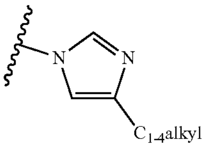

(e.g., 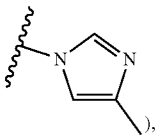),
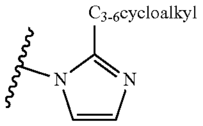

(e.g., 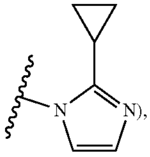),
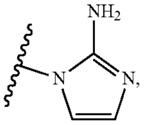

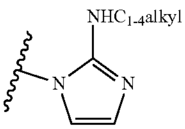 (e.g., 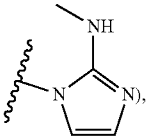),

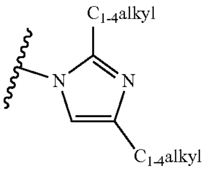 (e.g., 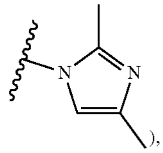),

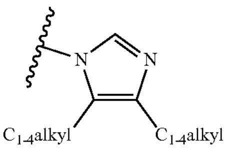 (e.g., 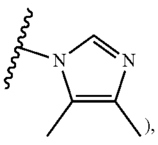),

-continued

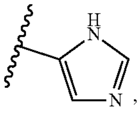, 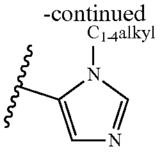 (e.g., 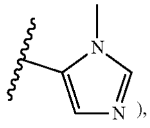),

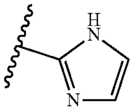, and 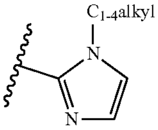

(e.g., 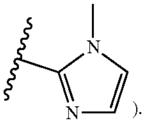).

$R^8$ may be

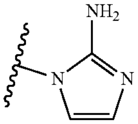 or 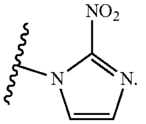

$R^8$ may be an optionally substituted pyridinyl, as defined herein. For example $R^8$ may be

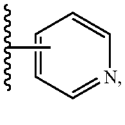

such as

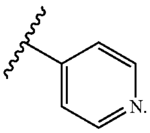 [SMILES: *c1ccncc1]

$R^1$ is $G^1$, and $G^1$ is a 9- to 12-membered bicyclic aryl, an 8- to 12-membered bicyclic heteroaryl, an 8- to 12-membered fused bicyclic heterocyclyl, or a $C_{3-10}$carbocyclyl fused to a 6-membered arene or to a 5- to 6-membered heteroarene, wherein $G^1$ is optionally substituted with 1-5 substituents independently selected from the group consisting of halogen, $C_{1-6}$alkyl, $C_{1-6}$haloalkyl, oxo, $-L^1-X^1$, and $-L^1-G^{1a}$; wherein $L^1$, $X^1$, and $G^{1a}$ are as defined herein.

$X^1$, at each occurrence, is independently $—OR^{1a}$, $—N(R^{1a})_2$, $—SR^{1a}$, cyano, $—C(O)OR^{1a}$, $—C(O)N(R^{1a})_2$, $—C(O)N(R^{1a})SO_2R^{1b}$, —C(NH)NHOH, —C(O)H, $—C(O)R^{1b}$, $—SOR^{1b}$, $—SO_2R^{1b}$, $—SO_2N(R^{1a})_2$, $—NR^{1a}C(O)H$, $—NR^{1a}C(O)R^{1b}$, $—NR^{1a}C(O)OR^{1a}$, $—NR^{1a}C(O)N(R^{1a})_2$, $—NR^{1a}S(O)_2R^{1b}$, or $—NR^{1a}S(O)_2N(R^{1a})_2$.

In some embodiments, $G^1$ is optionally substituted with 1-5 substituents independently selected from the group consisting of halogen, $C_{1-6}$alkyl, $C_{1-6}$haloalkyl, oxo, $—OR^{1a}$, $—N(R^{1a})_2$, $—SR^{1a}$ cyano, $—C(O)OR^{1a}$, $—C(O)N(R^{1a})_2$, —C(O)H, $—C(O)R^{1b}$, $—SOR^{1b}$, $—SO_2R^{1b}$, $—SO_2N(R^{1a})_2$, $—NR^{1a}C(O)H$, $—NR^{1a}C(O)R^{1b}$, $—NR^{1a}C(O)OR^{1a}$, $—NR^{1a}C(O)N(R^{1a})_2$, $—NR^{1a}S(O)_2R^{1b}$, $—NR^{1a}S(O)_2N(R^{1a})_2$, and $-L^1-G^{1a}$; wherein $R^{1a}$, $R^{1b}$, $L^1$, and $G^{1a}$ are as defined herein.

At $G^1$, The 8- to 12-membered fused bicyclic heterocyclyl and the $C_{3-10}$carbocyclyl fused to a 6-membered arene or to a 5- to 6-membered heteroarene may have (S) or (R) stereochemistry at the point of attachment to the parent molecular moiety.

$L^1$ is a bond or $C_{1-3}$alkylene. In some embodiments, $L^1$ is a bond. In other embodiments, $L^1$ is $C_{1-3}$alkylene (e.g., $CH_2$, $CH_2CH_2$).

At $G^1$, the 9- to 12-membered bicyclic aryl may be a naphthalenyl; the 8- to 12-membered bicyclic heteroaryl may be an 8- to 10-membered fused bicyclic heteroaromatic ring system; the 8- to 12-membered fused bicyclic heterocyclyl may be a 5- to 7-membered monocyclic heterocyclyl fused to a 6-membered arene or fused to a 5- to 6-membered heteroarene; and the $C_{3-10}$carbocyclyl fused to a 6-membered arene or to a 5- to 6-membered heteroarene may be a $C_{5-7}$carbocyclyl fused to a 6-membered arene or fused to a 5- to 6-membered heteroarene, wherein these $G^1$ options are optionally substituted with 1-5 substituents independently selected from the group consisting of halogen, $C_{1-6}$alkyl, $C_{1-6}$haloalkyl, oxo, $—OR^{1a}$, $—N(R^{1a})_2$, $—SR^{1a}$, cyano, $—C(O)OR^{1a}$, $—C(O)N(R^{1a})_2$, —C(O)H, $—C(O)R^{1b}$, $—SOR^{1b}$, $—SO_2R^{1b}$, $—SO_2N(R^{1a})_2$, $—NR^{1a}C(O)H$, $—NR^{1a}C(O)R^{1b}$, $—NR^{1a}C(O)OR^{1a}$, $—NR^{1a}C(O)N(R^{1a})_2$, $—NR^{1a}S(O)_2R^{1b}$, $—NR^{1a}S(O)_2N(R^{1a})_2$, and $-L^1-G^{1a}$.

In the compounds and embodiments described herein, $G^1$ may be optionally substituted with 1-3 substituents independently selected from the group consisting of halogen, $C_{1-6}$alkyl, $C_{1-6}$haloalkyl, $—OR^{1a}$, $—N(R^{1a})_2$, $—C(O)OR^{1a}$, $—C(O)N(R^{1a})_2$, $—C(O)R^{1b}$, and $G^{1a}$, wherein $G^{1a}$ is optionally substituted with 1-4 substituents independently selected from the group consisting of halogen, $C_{1-4}$alkyl, $C_{1-4}$haloalkyl, oxo, —OH (i.e., $—OR^{1c}$ where $R^{1c}$ is hydrogen), $—OC_{1-4}$alkyl (i.e., —OR where $R^{1c}$ is $C_{1-4}$alkyl), $—C(O)C_{1-4}$alkyl (i.e., $—C(O)R^{1c}$ where $R^{1c}$ is $C_{1-4}$alkyl), $—C(O)OC_{1-4}$alkyl (i.e., $—C(O)OR^{1c}$ where $R^{1c}$ is $C_{1-4}$alkyl), $C_{3-6}$cycloalkyl, and $—C_{1-3}$alkylene-$C_{3-6}$cycloalkyl. In the compounds and embodiments described herein, $G^1$ may be optionally substituted with 1-3 substituents independently selected from the group consisting of halogen, $C_{1-4}$alkyl, $C_{1-4}$haloalkyl, $—OC_{1-4}$alkyl (i.e., $—OR^{1a}$ where $R^{1a}$ is $C_{1-4}$alkyl), $—OC_{1-4}$haloalkyl (i.e., $—OR^{1a}$ where $R^{1a}$ is $C_{1-4}$haloalkyl), $—NH_2$ (i.e., $—N(R^{1a})_2$ where $R^{1a}$ is hydrogen), $—NHC_{1-4}$alkyl (i.e., $—N(R^{1a})_2$ where one $R^{1a}$ is hydrogen and one $R^{1a}$ is $C_{1-4}$alkyl), $—N(C_{1-4}alkyl)_2$ (i.e., $—N(R^{1a})_2$ where $R^{1a}$ is $C_{1-4}$alkyl), $—N(C_{1-4}$alkyl)-$C_{2-4}$alkylene-$N(C_{1-4}alkyl)_2$ (i.e., $—N(R^{1a})_2$ where one $R^{1a}$ is $C_{1-4}$alkyl and one $R^{1a}$ is $—C_{2-4}$alkylene-$N(C_{1-4}alkyl)_2$), —C(O)OH (i.e., $—C(O)OR^{1a}$ where $R^{1a}$ is hydrogen), $—C(O)OC_{1-4}$alkyl (i.e., $—C(O)OR^{1a}$ where $R^{1a}$ is $C_{1-4}$alkyl), $—C(O)NH_2$ (i.e., $—C(O)N(R^{1a})_2$ where $R^{1a}$ is hydrogen), $—C(O)NH(C_{1-4}$alkyl) (i.e., $—C(O)N(R^{1a})_2$ where one $R^{1a}$ is hydrogen and one $R^{1a}$ is $C_{1-4}$alkyl), —C(O)NH—$C_{2-4}$alkylene-$OC_{1-4}$alkyl (i.e., $—C(O)N(R^{1a})_2$ where one $R^{1a}$ is hydrogen and one $R^{1a}$ is $—C_{2-4}$alkylene-$OC_{1-4}$alkyl), $—C(O)N(C_{1-4}alkyl)_2$ (i.e., $—C(O)N(R^{1a})_2$ where $R^{1a}$ is $C_{1-4}$alkyl), $—C(O)G^{1a}$ (i.e., $—C(O)R^{1b}$ where $R^{1b}$ is $G^{1a}$), and $G^{1a}$, wherein $G^{1a}$ is optionally substituted with 1-4 substituents independently selected from the group consisting of halogen, $C_{1-4}$alkyl, $C_{1-4}$haloalkyl, oxo, —OH, $—OC_{1-4}$alkyl, $—C(O)C_{1-4}$alkyl, $—C(O)OC_{1-4}$alkyl, $C_{3-6}$cycloalkyl, and $—C_{1-3}$alkylene-$C_{3-6}$cycloalkyl.

$R^{1a}$, at each occurrence, is independently hydrogen, $C_{1-6}$alkyl, $C_{1-6}$haloalkyl, $—C_{2-4}$alkylene-$OR^{1e}$, $—C_{2-4}$alkylene-$N(R^{1e})_2$, $—C_{2-4}$alkylene-$N(R^{1e})C(O)R^{1e}$, $G^{1a}$, or $—C_{1-6}$alkylene-$G^{1a}$, wherein $R^{1e}$ and $G^{1a}$ are as defined herein. In some embodiments, $R^{1a}$, at each occurrence, is independently hydrogen, $C_{1-6}$alkyl, $C_{1-6}$haloalkyl, —$C_{2-4}$alkylene-$OR^{1e}$, —$C_{2-4}$alkylene-$N(R^{1e})_2$, $G^{1a}$, or —$C_{1-6}$alkylene-$G^{1a}$. In the compounds and embodiments described herein, $R^{1a}$ may be hydrogen, $C_{1-4}$alkyl, $C_{1-4}$haloalkyl, —$C_{2-4}$alkylene-$OR^{1e}$, —$C_{2-4}$alkylene-$N(R^{1e})_2$, or $G^{1a}$, wherein $R^{1e}$ is $C_{1-4}$alkyl; and $G^{1a}$ is optionally substituted with 1-4 substituents independently selected from the group consisting of halogen, $C_{1-4}$alkyl, $C_{1-4}$haloalkyl, oxo, —OH (i.e., —$OR^{1c}$ where $R^{1c}$ is hydrogen), —$OC_{1-4}$alkyl (i.e., —$OR^{1e}$ where $R^{1e}$ is $C_{1-4}$alkyl), —$C(O)C_{1-4}$alkyl (i.e., —$C(O)R^{1c}$ where $R^{1c}$ is $C_{1-4}$alkyl), —$C(O)OC_{1-4}$alkyl (i.e., —$C(O)OR^{1c}$ where $R^{1c}$ is $C_{1-4}$alkyl), $C_{3-6}$cycloalkyl, and —$C_{1-3}$alkylene-$C_{3-6}$cycloalkyl. In the compounds and embodiments described herein, $R^{1a}$ may be hydrogen, $C_{1-4}$alkyl, $C_{1-4}$haloalkyl, —$C_{2-4}$alkylene-$OR^{1e}$, or —$C_{2-4}$alkylene-$N(R^{1e})_2$, wherein $R^{1e}$ is $C_{1-4}$alkyl.

$R^{1b}$, at each occurrence, is independently $C_{1-6}$alkyl, $C_{1-6}$haloalkyl, —$C_{1-4}$alkylene-$OR^{1e}$, —$C_{1-4}$alkylene-$N(R_{1e})_2$, —$C_{1-4}$alkylene-$N(R^{1e})C(O)R^{1e}$, $G^{1a}$, or —$C_{1-6}$alkylene-$G^{1a}$, wherein $R^{1e}$ and $G^{1a}$ are as defined herein. In some embodiments, $R^{1b}$, at each occurrence, is independently $C_{1-6}$alkyl, $C_{1-6}$haloalkyl, —$C_{1-4}$alkylene-$OR^{1e}$, —$C_{1-4}$alkylene-$N(R^{1e})_2$, $G^{1a}$, or —$C_{1-6}$alkylene-$G^{1a}$. In the compounds and embodiments described herein, $R^{1b}$ may be $C_{1-4}$alkyl, $C_{1-4}$haloalkyl, —$C_{1-4}$alkylene-$OR^{1e}$, —$C_{1-4}$alkylene-$N(R^{1e})_2$, or $G^{1a}$, wherein $R^{1e}$ is $C_{1-4}$alkyl; and $G^{1a}$ is optionally substituted with 1-4 substituents independently selected from the group consisting of halogen, $C_{1-4}$alkyl, $C_{1-4}$haloalkyl, oxo, —OH (i.e., —$OR^{1c}$ where $R^{1c}$ is hydrogen), —$OC_{1-4}$alkyl (i.e., —$OR^{1c}$ where $R^{1c}$ is $C_{1-4}$alkyl), —$C(O)C_{1-4}$alkyl (i.e., —$C(O)R^{1c}$ where $R^{1c}$ is $C_{1-4}$alkyl), —$C(O)OC_{1-4}$alkyl (i.e., —$C(O)OR^{1c}$ where $R^{1c}$ is $C_{1-4}$alkyl), $C_{3-6}$cycloalkyl, and —$C_{1-3}$alkylene-$C_{3-6}$cycloalkyl. In the compounds and embodiments described herein, $R^{1b}$ may be $G^{1a}$, wherein $G^{1a}$ is optionally substituted with 1-4 substituents independently selected from the group consisting of halogen, $C_{1-4}$alkyl, $C_{1-4}$haloalkyl, oxo, —OH (i.e., —$OR^{1c}$ where $R^{1c}$ is hydrogen), —$OC_{1-4}$alkyl (i.e., —$OR^{1c}$ where $R^{1c}$ is $C_{1-4}$alkyl), —$C(O)C_{1-4}$alkyl (i.e., —$C(O)R^{1c}$ where $R^{1c}$ is $C_{1-4}$alkyl), —$C(O)OC_{1-4}$alkyl (i.e., —$C(O)OR^{1c}$ where $R^{1c}$ is $C_{1-4}$alkyl), $C_{3-6}$cycloalkyl, and —$C_{1-3}$alkylene-$C_{3-6}$cycloalkyl.

$R^{1c}$, at each occurrence, is independently hydrogen, $C_{1-6}$alkyl, $C_{1-6}$haloalkyl, $G^{1b}$, or —$C_{1-3}$alkylene-$G^{1b}$, wherein alternatively two $R^{1c}$, together with a common nitrogen atom to which the $R^{1c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl, wherein $G^{1b}$ is as defined herein. In some embodiments, $R^{1c}$, at each occurrence, is independently hydrogen, $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein alternatively two $R^{1c}$, together with a common nitrogen atom to which the $R^{1c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl. In the compounds and embodiments described herein, $R^{1c}$ may be hydrogen or $C_{1-4}$alkyl.

$R^{1d}$, at each occurrence, is independently $C_{1-6}$alkyl, $C_{1-6}$haloalkyl, $G^{1b}$, or —$C_{1-3}$alkylene-$G^{1b}$, wherein $G^{1b}$ is as defined herein. In some embodiments, $R^{1d}$, at each occurrence, is independently $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen. In the compounds and embodiments described herein $R^{1d}$ may be $C_{1-4}$alkyl.

$R^{1e}$, at each occurrence, is independently hydrogen, $C_{1-4}$alkyl, $C_{1-4}$haloalkyl, $G^{1b}$, or —$C_{1-3}$alkylene-$G^{1b}$, wherein alternatively two $R^{1e}$, together with a common nitrogen atom to which the $R^{1e}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl, wherein $G^{1b}$ is as defined herein. In some embodiments, $R^{1e}$, at each occurrence, is independently hydrogen, $C_{1-4}$alkyl, $C_{1-4}$haloalkyl, $C_{3-6}$cycloalkyl, or —$C_{1-3}$alkylene-$C_{3-6}$cycloalkyl, wherein alternatively two $R^{1e}$, together with a common nitrogen atom to which the $R^{1e}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl. In the compounds and embodiments described herein $R^{1e}$ may be $C_{1-4}$alkyl.

$G^{1a}$, at each occurrence, is independently $C_{3-8}$cycloalkyl, 6- to 10-membered aryl, 5-to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, -$L^2$-$X^2$, and -$L^2$-$G^{1b}$; wherein $L^2$, $X^2$, and $G^{1b}$ are as defined herein.

$L^2$, at each occurrence, is independently a bond or $C_{1-3}$alkylene. In some embodiments, $L^2$ is a bond. In other embodiments, $L^2$ is $C_{1-3}$alkylene (e.g., $CH_2$, $CH_2CH_2$).

$X^2$, at each occurrence, is independently —$OR^{1c}$, —$N(R^{1c})_2$, —$SR^{1c}$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NR^{1c}C(O)R^{1c}$, —$NR^{1c}(O)OR^{1c}$, —$NR^{1c}C(O)N(R^{1c})_2$, —$NR^{1c}S(O)_2R^{1d}$, or —$NR^{1c}S(O)_2N(R^{1c})_2$.

In some embodiments, $G^{1a}$ is optionally substituted with 1-4 substituents independently selected from the group consisting of halogen, $C_{1-4}$alkyl, $C_{1-4}$haloalkyl, oxo, —$OR^{1c}$, —$N(R^{1c})_2$, —$SR^{1c}$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NR^{1c}(O)R^{1c}$, —$NR^{1c}(O)OR^{1c}$, —$NR^{1c}(O)N(R^{1c})_2$, —$NR^{1c}S(O)_2R^{1d}$, —$NR^{1c}S(O)_2N(R^{1c})_2$, $C_{3-6}$cycloalkyl, and —$C_{1-3}$alkylene-$C_{3-6}$cycloalkyl. In the compounds and embodiments described herein, $G^{1a}$ may be the optionally substituted 4- to 10-membered heterocyclyl. The optionally substituted heterocyclyl may be a 4- to 8-membered monocyclic heterocyclyl.

In some embodiments, $G^{1a}$ is optionally substituted with 1-4 substituents independently selected from the group consisting of halogen, $C_{1-4}$alkyl, $C_{1-4}$haloalkyl, oxo, —$OR^{1c}$, —$N(R^{1c})_2$, —$SR^{1c}$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NRC(O)R^{1c}$, —$NR^{1c}C(O)OR^{1c}$, —$NR^{1c}C(O)N(R^{1c})_2$, —$NR^{1c}S(O)_2R^{1d}$, —$NR^{1c}S(O)_2N(R^{1c})_2$, $C_{3-6}$cycloalkyl, and —$C_{1-3}$alkylene-$C_{3-6}$cycloalkyl. In the compounds and embodiments described herein, $G^{1a}$ may be optionally substituted with 1-4 substituents independently selected from the group consisting of halogen, $C_{1-4}$alkyl, $C_{1-4}$haloalkyl, oxo, —OH (i.e., —$OR^{1c}$ where $R^{1c}$ is hydrogen), —$OC_{1-4}$alkyl (i.e., —$OR^{1c}$ where $R^{1c}$ is $C_{1-4}$alkyl), —$C(O)C_{1-4}$alkyl (i.e., —$C(O)R^{1c}$ where $R^{1c}$ is $C_{1-4}$alkyl), —$C(O)OC_{1-4}$alkyl (i.e., —$C(O)OR^{1c}$ where $R^{1c}$ is $C_{1-4}$alkyl), $C_{3-6}$cycloalkyl, and —$C_{1-3}$alkylene-$C_{3-6}$-cycloalkyl.

The optionally substituted heterocyclyl at $G^{1a}$ may have a first nitrogen ring atom and optionally a second ring heteroatom selected from nitrogen and oxygen, the heterocyclyl of $G^{1a}$ being attached at the first nitrogen ring atom and being optionally substituted with 1-4 substituents independently selected from the group consisting of halogen, $C_{1-4}$alkyl, $C_{1-4}$haloalkyl, oxo, —C(O)$C_{1-4}$alkyl, —C(O)O$C_{1-4}$alkyl, $C_{3-6}$cycloalkyl, and —$C_{1-3}$alkylene-$C_{3-6}$cycloalkyl. For example, the heterocyclyl of $G^{1a}$ may be a pyrrolidin-1-yl, morpholin-4-yl, or piperazin-1-yl, and optionally substituted with $C_{1-4}$alkyl, oxo, or —C(O)$C_{1-4}$alkyl.

In some embodiments, $G^1$ may be the optionally substituted naphthalenyl. In some embodiments, $G^1$ is naphthalen-1-yl.

In some embodiments, $G^1$ may be the optionally substituted 8- to 10-membered fused bicyclic heteroaromatic ring system. The 8- to 10-membered fused bicyclic heteroaromatic ring system may be quinolinyl, isoquinolinyl, indolyl, indazolyl, benzoxazolyl, quinazolinyl, or pyrrolo[2,3-b]pyridinyl. The 8- to 10-membered fused bicyclic heteroaromatic ring system may be quinolin-4-yl, quinolin-5-yl, isoquinolin-1-yl, isoquinolin-4-yl, quinazolin-4-yl, indol-3-yl, indol-4-yl, indazol-3-yl, benzo[d]oxazol-7-yl, pyrrolo[2,3-b]pyridin-3-yl, or pyrrolo[2,3-b]pyridin-4-yl. Accordingly, $G^1$ may be

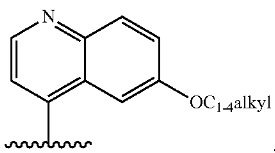

,

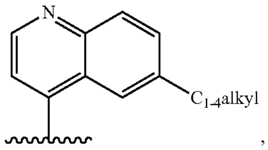

,

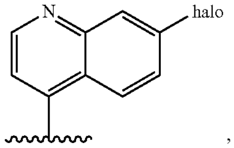

,

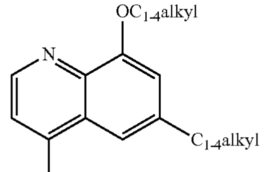

,

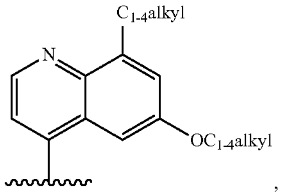

,

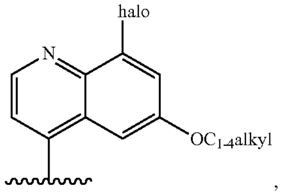

,

-continued

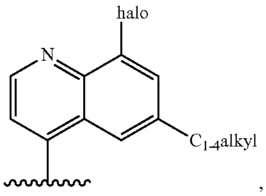

,

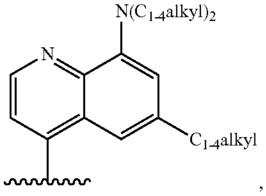

,

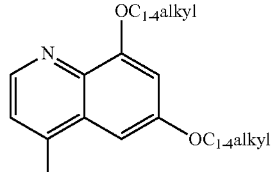

,

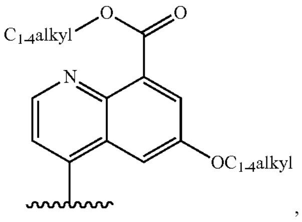

,

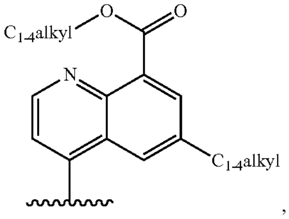

,

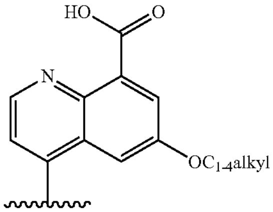

,

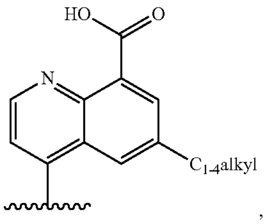

,

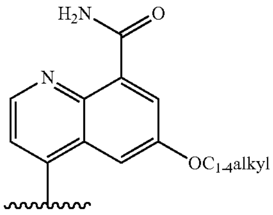

,

-continued
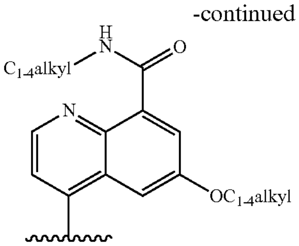
,
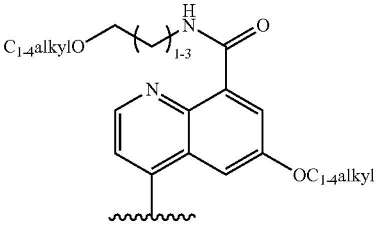
,
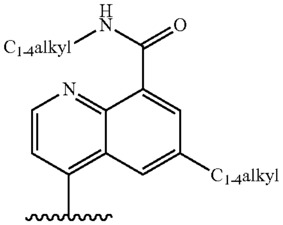
,
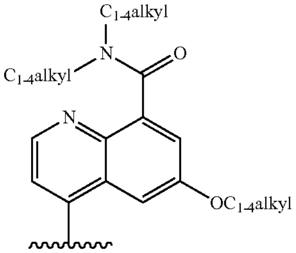
,
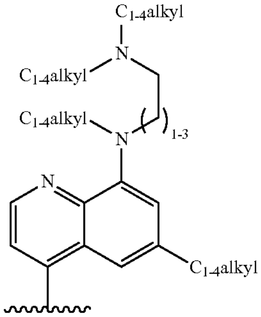
,
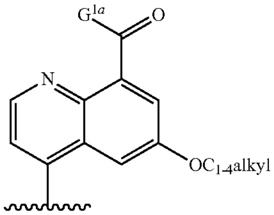
,
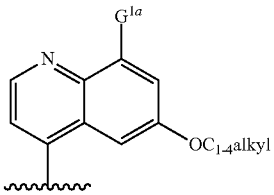
,
-continued
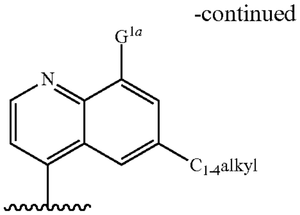
,
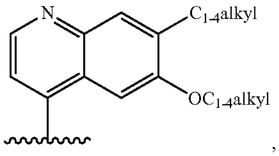
,
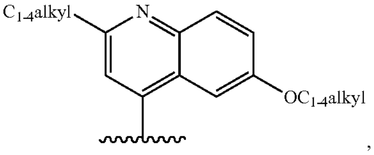
,
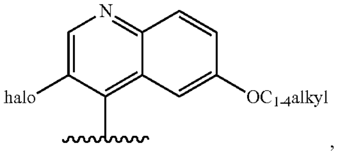
,
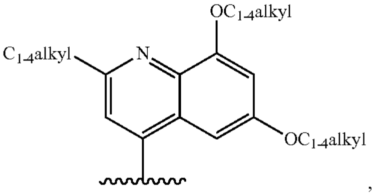
,
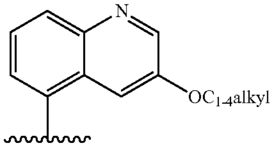
,
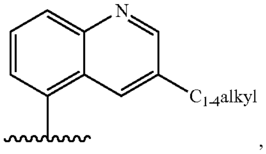
,
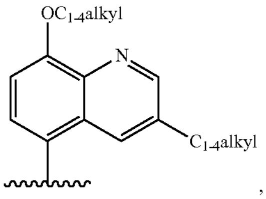
,
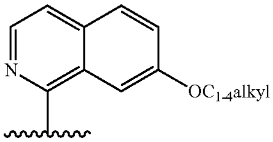
,
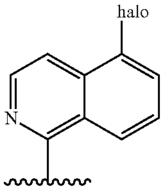
, -continued
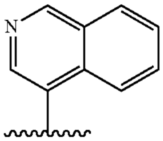
,
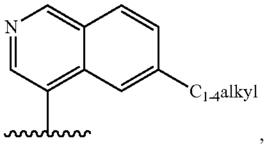
,
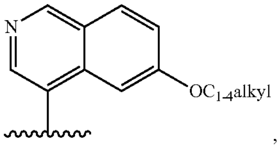
,
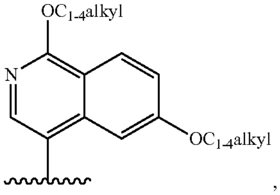
,
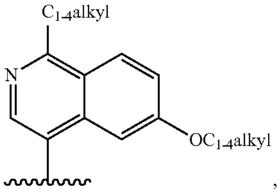
,
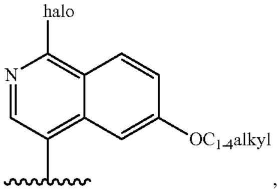
,
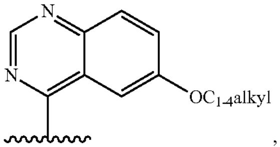
,
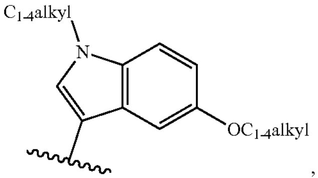
,
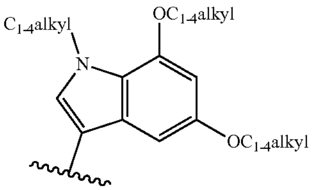
,
-continued
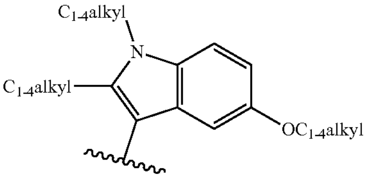
,
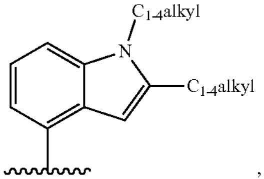
,
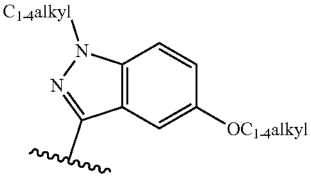
,
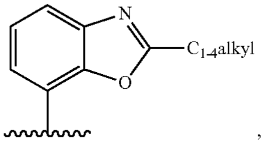
,
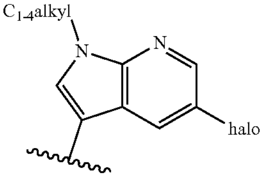
,
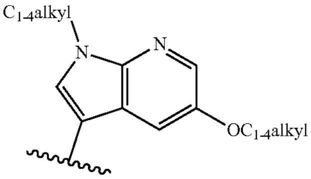
, or
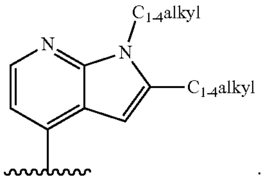
.
For example, $G^1$ may be
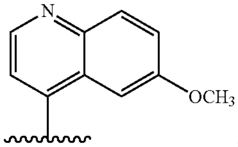
,
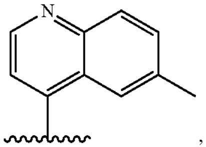
, -continued
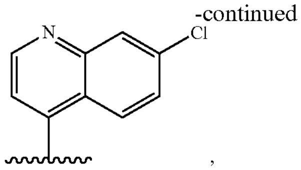
,
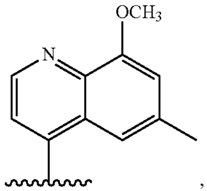
,
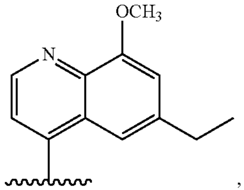
,
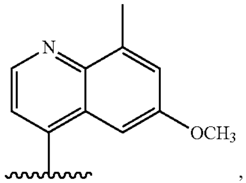
,
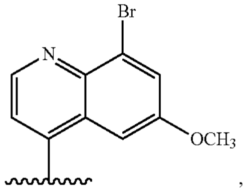
,
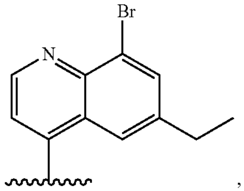
,
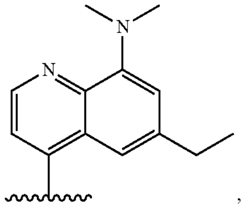
,
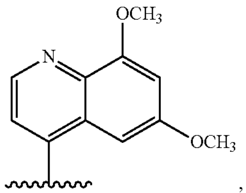
,
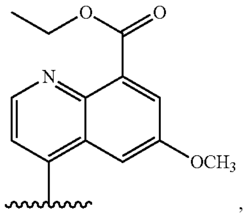
,
-continued
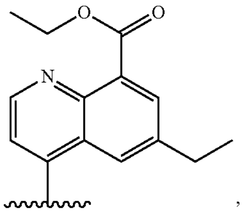
,
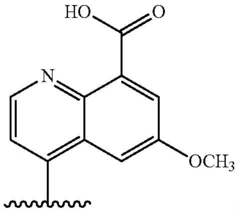
,
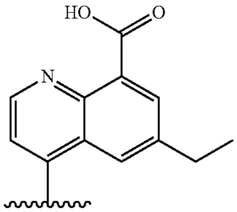
,
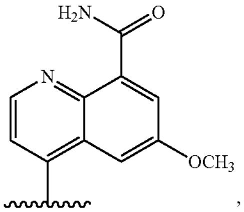
,
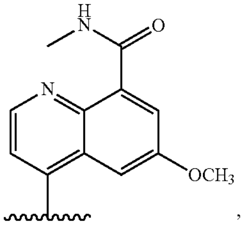
,
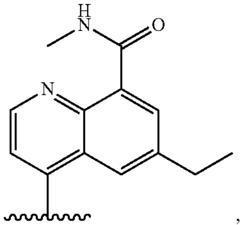
,
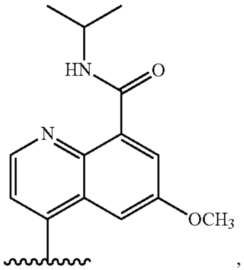
, -continued
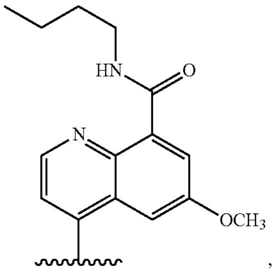
,
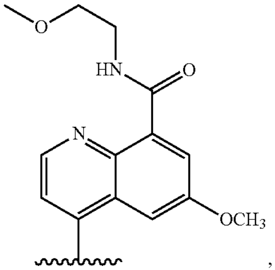
,
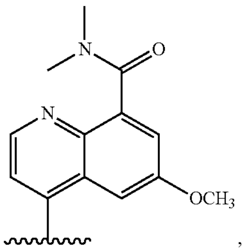
,
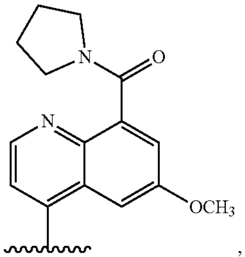
,
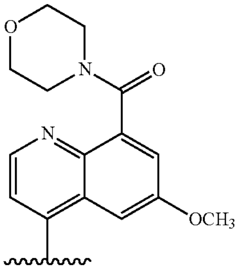
,
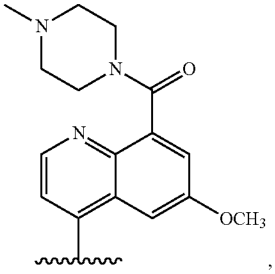
,
-continued
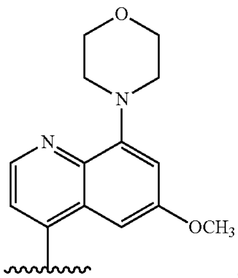
,
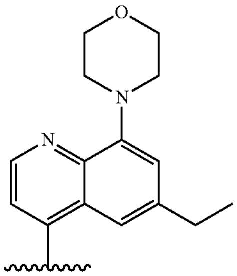
,
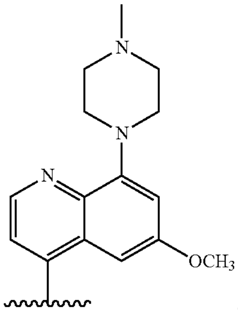
,
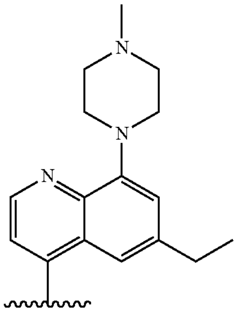
,
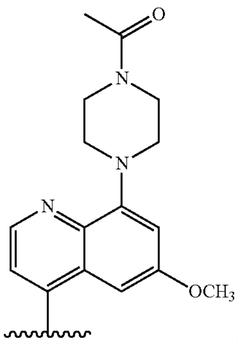
, -continued
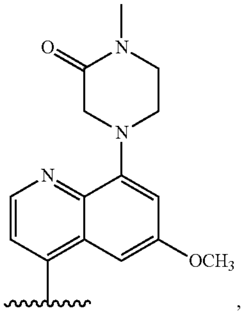
,
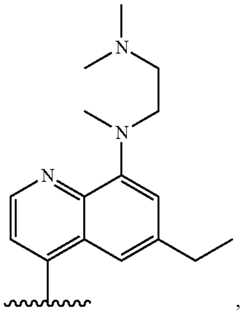
,
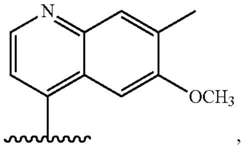
,
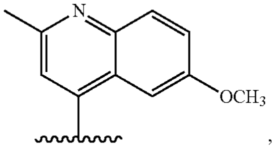
,
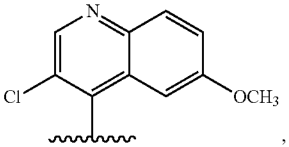
,
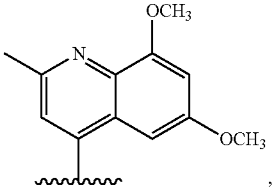
,
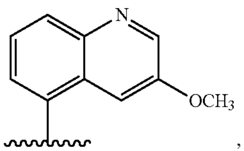
,
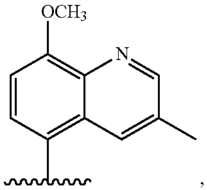
,
-continued
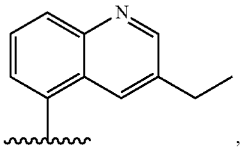
,
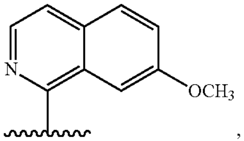
,
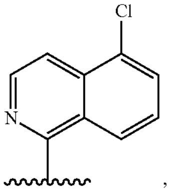
,
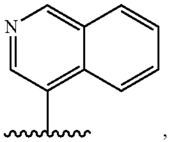
,
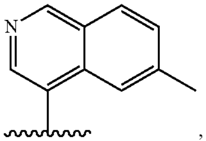
,
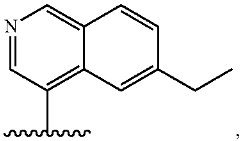
,
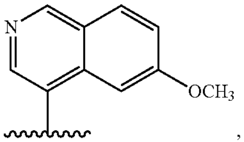
,
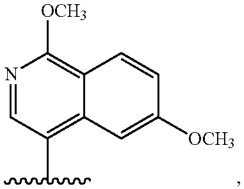
,
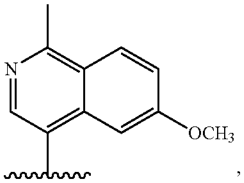
,
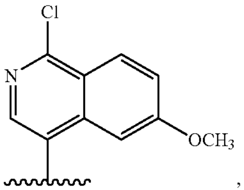
, -continued

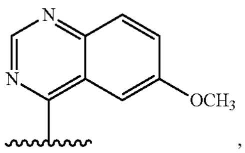

,

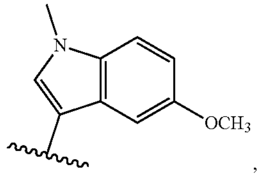

,

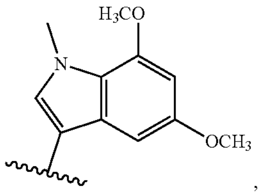

,

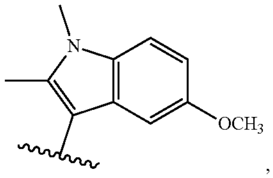

,

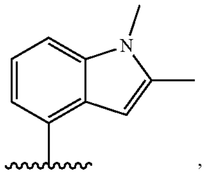

,

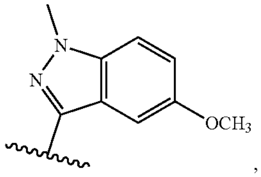

,

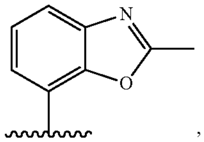

,

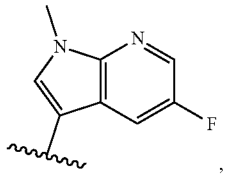

,

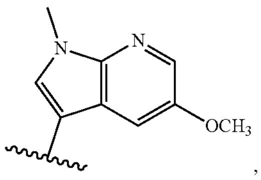

,

-continued

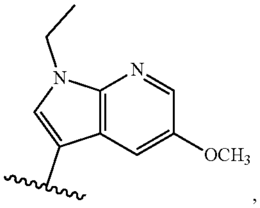

, or

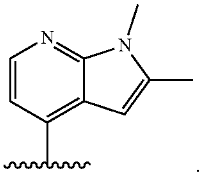

.

In some embodiments, $G^1$ may be the optionally substituted 5- to 7-membered monocyclic heterocyclyl fused to a 6-membered arene or fused to a 5- to 6-membered heteroarene. The 5- to 7-membered monocyclic heterocyclyl fused to a 6-membered arene or fused to a 5- to 6-membered heteroarene may have (S) or (R) stereochemistry at the point of attachment to the parent molecular moiety. The 5- to 7-membered monocyclic heterocyclyl fused to a 6-membered arene or fused to a 5- to 6-membered heteroarene may be a 5- to 7-membered monocyclic heterocyclyl having one oxygen ring atom or one nitrogen atom and fused to a 6-membered arene or fused to a 5- to 6-membered heteroarene. The 5- to 6-membered heteroarene may be a pyridine. A fused 6-membered arene or pyridine may be optionally substituted with 1-2 substituents independently selected from the group consisting of halo, $C_{1-4}$alkyl, $—OC_{1-4}$alkyl, and $C_{3-6}$cycloalkyl. Accordingly, $G^1$ may be

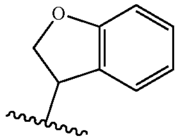

,

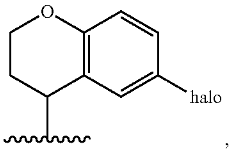

,

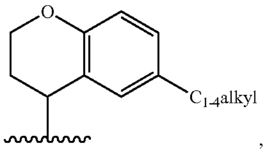

,

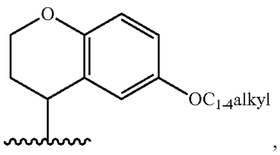

,

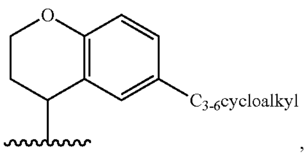

,

-continued
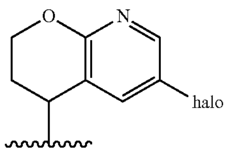
, or
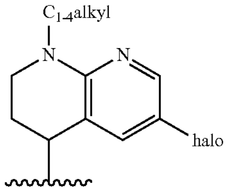
, such as
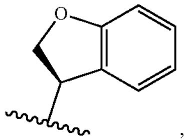
,
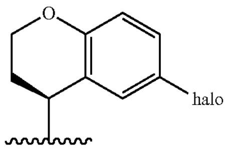
,
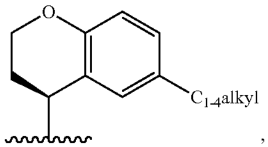
,
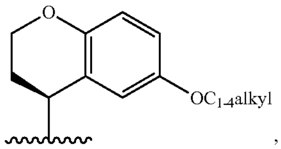
,
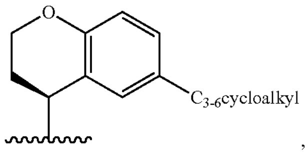
,
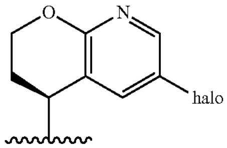
, or
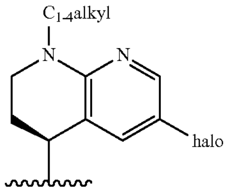
. For example, $G^1$ may be
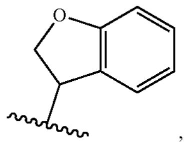
,
-continued
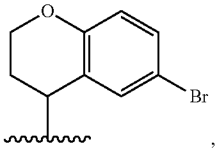
,
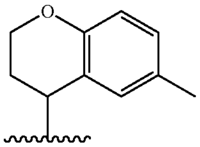
,
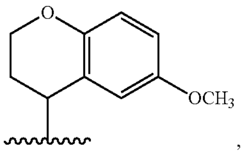
,
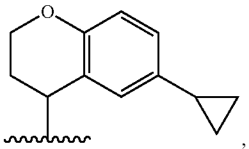
,
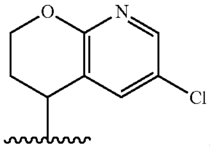
, or
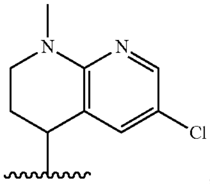
, such as
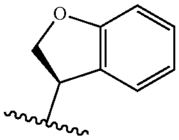
,
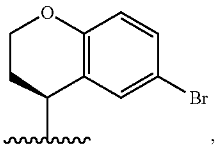
,
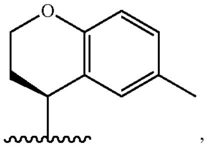
,
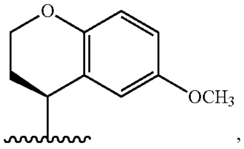
,
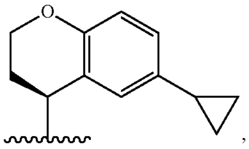
, -continued

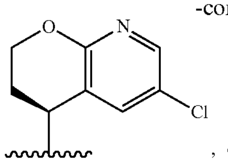

, or

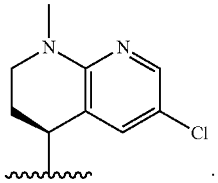

.

$G^1$ may be

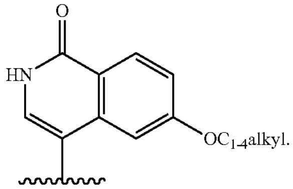

For example, $G^1$ may be

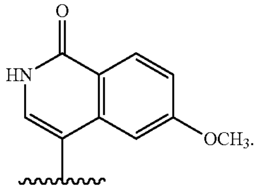 [SMILES: *c1c[nH]c(=O)c2ccc(OC)cc12]

In some embodiments, $G^1$ may be the optionally substituted $C_{5-7}$carbocyclyl fused to a 6-membered arene or fused to a 5- to 6-membered heteroarene. The $C_{5-7}$carbocyclyl fused to a 6-membered arene or fused to a 5- to 6-membered heteroarene may have (S) or (R) stereochemistry at the point of attachment to the parent molecular moiety. The $C_{5-7}$carbocyclyl fused to a 6-membered arene or fused to a 5- to 6-membered heteroarene may be a monocyclic $C_{5-7}$cycloalkyl fused to a 6-membered arene or fused to a 5- to 6-membered heteroarene. The 5- to 6-membered heteroarene may be a pyridine. A fused 6-membered arene or pyridine may be optionally substituted with halo, $C_{1-4}$alkyl, —$OC_{1-4}$alkyl, or $C_{3-6}$cycloalkyl. Accordingly, $G^1$ may be

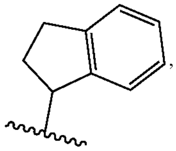
,
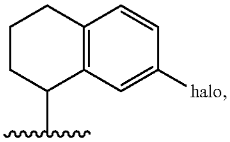

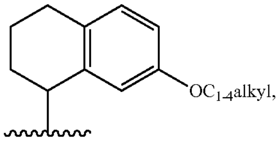

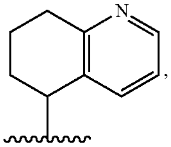
, or

-continued

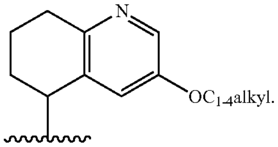

such as

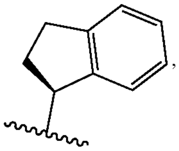
,
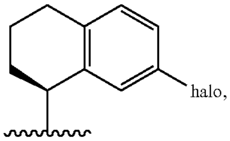

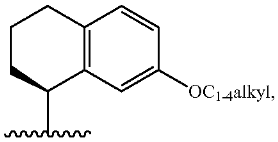

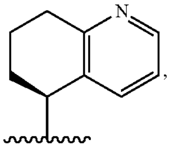
, or

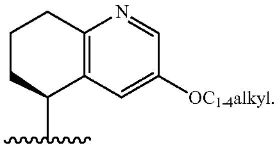

For example $G^1$ may be

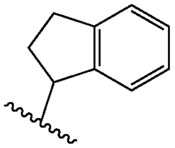
,
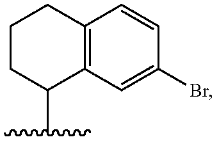

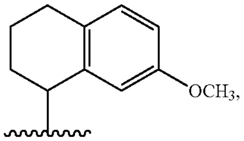

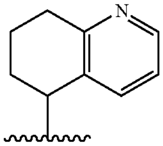
, or

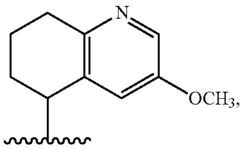

such as

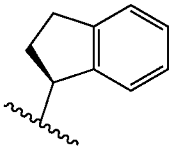,
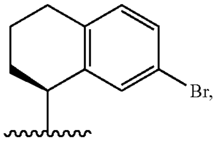
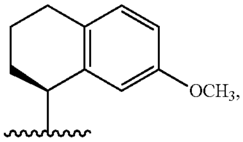
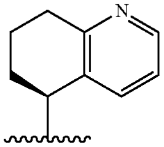, or
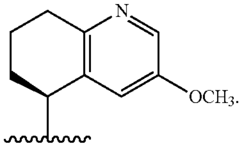

In the compounds and embodiments described herein, $G^1$ may attach at a ring atom in $G^1$ adjacent to a ring fusion in $G^1$, (e.g.,
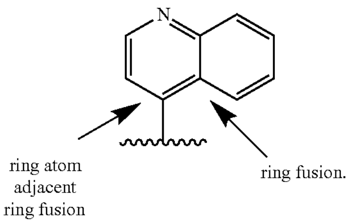

)

In the compounds and embodiments described herein, $G^1$ may be

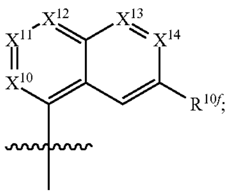

wherein $X^{10}$ is $CR^{10a}$ or N;

$X^{11}$ is $CR^{10b}$ or N;

$X^{12}$ is $CR^{10c}$ or N, $X^{13}$ is $CR^{10d}$ or N;

$X^{14}$ is $CR^{10e}$ or N;

provided that no more than two of $X^{10}$-$X^{14}$ are N;

$R^{10a}$ is hydrogen, halogen, $C_{1-4}$alkyl, or $C_{1-4}$fluoroalkyl;

$R^{10b}$ is hydrogen, halogen, $C_{1-4}$alkyl, or $C_{1-4}$fluoroalkyl;

$R^{10c}$ is hydrogen, halogen, $C_{1-4}$alkyl, $C_{1-4}$fluoroalkyl, or $OC_{1-4}$alkyl;

$R^{10d}$ is hydrogen, halogen, $C_{1-4}$alkyl, $C_{1-4}$fluoroalkyl, $-L^1-X^1$, or $-L^1-G^{1a}$;

$R^{10e}$ is hydrogen, halogen, $C_{1-4}$alkyl, or $C_{1-4}$fluoroalkyl; and $R^{10f}$ is hydrogen, halogen, $C_{1-4}$alkyl, $C_{1-4}$fluoroalkyl, OH, $OC_{1-4}$alkyl, $OC_{1-4}$fluoroalkyl, $NH_2$, $NHC_{1-4}$alkyl, $N(C_{1-4}alkyl)_2$, or a 4- to 8-membered monocyclic heterocyclyl containing 1-2 heteroatoms selected from N, O, and S, wherein the heterocyclyl is optionally substituted with 1-4 substituents independently selected from the group consisting of halogen, cyano, oxo, $C_{1-4}$alkyl, $C_{1-4}$fluoroalkyl, OH, $OC_{1-4}$alkyl, $OC_{1-4}$fluoroalkyl, $NH_2$, $NHC_{1-4}$alkyl, and $N(C_{1-4}alkyl)_2$.

In the compounds and embodiments described herein, $G^1$ may be an optionally substituted 10-membered fused bicyclic ring system of formula

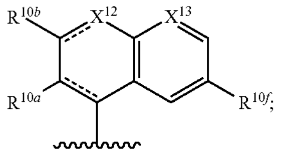

each "⎓" represents a double bond or a single bond;

$X^{12}$ is N, $CR^{10c}$ or $CHR^{10c}$;

$X^{13}$ is $CR^{10d}$ or N;

$X^{14}$ is $CR^{10e}$ or N;

$R^{10a}$ is hydrogen, halogen, $C_{1-4}$alkyl, or $C_{1-4}$fluoroalkyl;

$R^{10b}$ is hydrogen, halogen, $C_{1-4}$alkyl, or $C_{1-4}$fluoroalkyl;

$R^{10c}$ is hydrogen, halogen, $C_{1-4}$alkyl, $C_{1-4}$fluoroalkyl, or $—OC_{1-4}$alkyl;

$R^{10d}$ is $-L^1-X^1$, hydrogen, halogen, $C_{1-4}$alkyl, $C_{1-4}$fluoroalkyl, or $-L^1-G^{1a}$;

$R^{10e}$ is hydrogen, halogen, $C_{1-4}$alkyl, or $C_{1-4}$fluoroalkyl; and $R^{10f}$ is $C_{1-4}$alkyl, $—OC_{1-4}$alkyl, hydrogen, halogen, $C_{1-4}$fluoroalkyl, OH, $—OC_{1-4}$fluoroalkyl, $NH_2$, $NHC_{1-4}$alkyl, $N(C_{1-4}alkyl)_2$, or a 4- to 8-membered monocyclic heterocyclyl containing 1-2 heteroatoms selected from N, O, and S, wherein the heterocyclyl is optionally substituted with 1-4 substituents independently selected from the group consisting of halogen, cyano, oxo, $C_{1-4}$alkyl, $C_{1-4}$fluoroalkyl, OH, $—OC_{1-4}$alkyl, $—OC_{1-4}$fluoroalkyl, $NH_2$, $—NHC_{1-4}$alkyl, and $—N(C_{1-4}alkyl)_2$.

In some embodiments, each "⎓" represents a double bond; $X^{12}$ is N; and $X^{13}$ is $CR^{10d}$. In some embodiments, $R^{10a}$ is hydrogen; $R^{10b}$ is hydrogen or $C_{1-4}$alkyl; $R^{10d}$ is $—C(O)N(R^{1a})_2$ or $—OR^{1a}$; $R^{10e}$ is hydrogen; and $R^{10f}$ is $C_{1-4}$alkyl or $OC_{1-4}$alkyl.

In some embodiments, each "⎓" resent a double bond; $X^{12}$ is $CR^{10c}$; $X^{13}$ is N; and $X^{14}$ is $CR^{10e}$. In some embodiments, $R^{10a}$ is hydrogen; $R^{10b}$ is hydrogen or $C_{1-4}$alkyl; $R^{10c}$ is hydrogen, $C_{1-4}$alkyl, or $—OC_{1-4}$alkyl; $R^{10e}$ is hydrogen or $C_{1-4}$alkyl; and $R^{10f}$ is $C_{1-4}$alkyl or $—OC_{1-4}$alkyl. Accordingly, $G^1$ may be

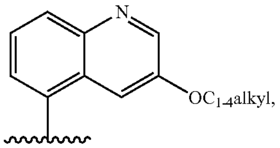
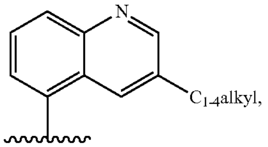

-continued
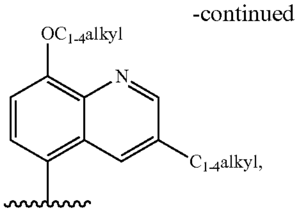
,
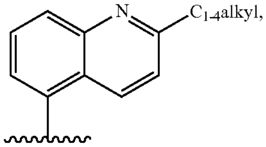
,
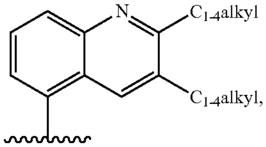
,
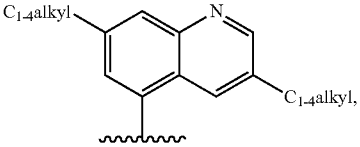
,
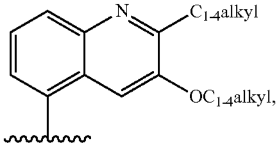
,
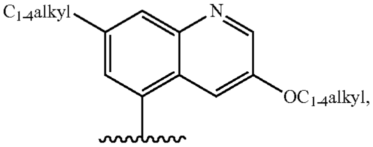
,
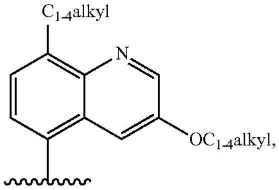
, or
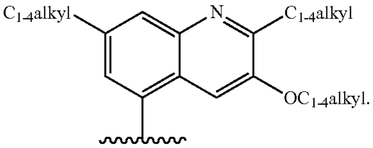
.
For example, $G^1$ may be
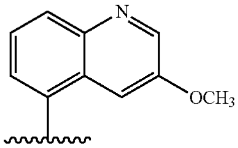
,
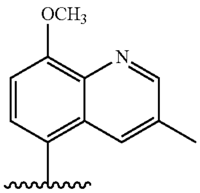
,
-continued
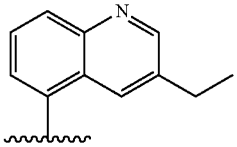
,
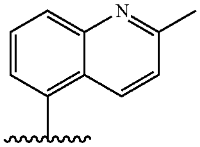
,
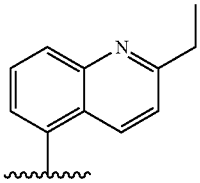
,
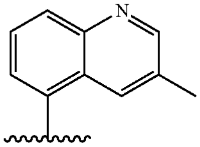
,
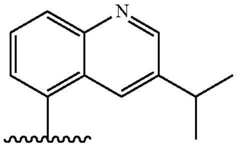
,
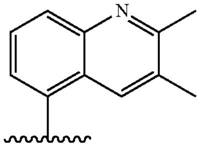
,
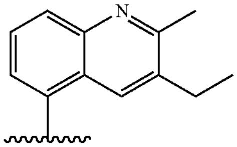
,
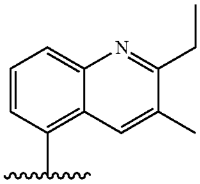
,
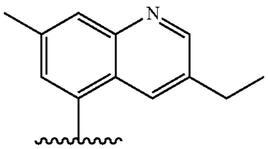
,
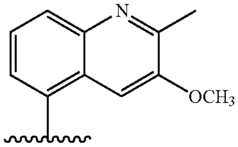
, -continued

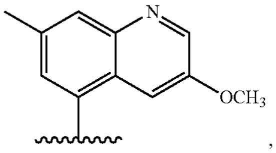

,

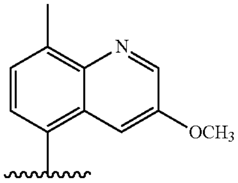

,

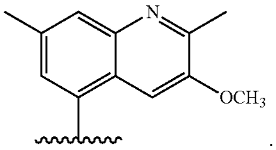

.

In some embodiments, each "$\overset{---}{\_\_\_}$" represents a single bond; $X^{12}$ is $CHR^{10c}$; $X^{13}$ is N; and $X^{14}$ is $CR^{10e}$, In some embodiments, $R^{10a}$ is hydrogen; $R^{10b}$ is hydrogen or $C_{1-4}$alkyl; $R^{10c}$ is hydrogen or $C_{1-4}$alkyl; $R^{10e}$ is hydrogen or $C_{1-4}$alkyl; and $R^{10f}$ is $C_{1-4}$alkyl or —$OC_{1-4}$alkyl. Accordingly, $G^1$ may be

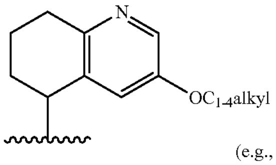

(e.g.,

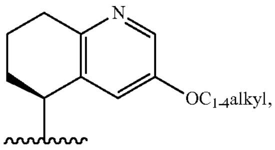

such as

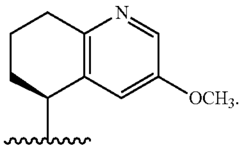

)

$R^{10a}$ may be hydrogen or chloro.

$R^{10b}$ may be hydrogen or methyl.

$R^{10c}$ may be hydrogen, methyl, chloro, or $OCH_3$.

$R^{10d}$ may be hydrogen, halogen, $C_{1-4}$alkyl, cyano, $OC_{1-4}$alkyl, $OC_{1-4}$fluoroalkyl, $NH_2$, $NHC_{1-4}$alkyl, $N(C_{1-4}alkyl)_2$, $NHC(O)C_{1-4}$alkyl, $N(C_{1-4}alkyl)C(O)C_{1-4}$alkyl,

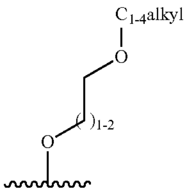

,

-continued

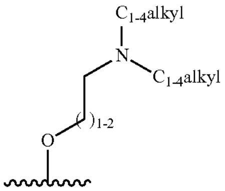

,

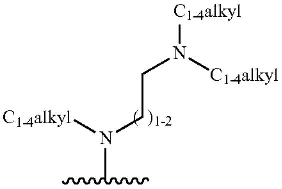

,

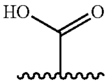

,

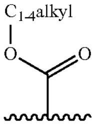

,

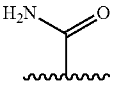

,

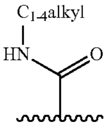

,

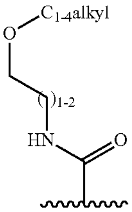

,

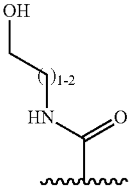

,

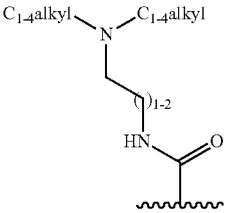

,

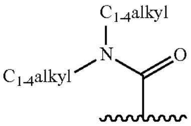

,

-continued
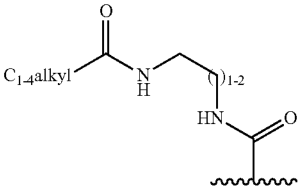
,
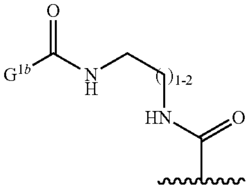
,
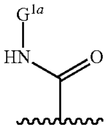
,
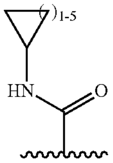
,
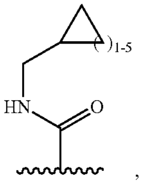
,
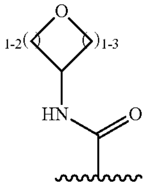
,
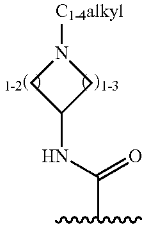
,
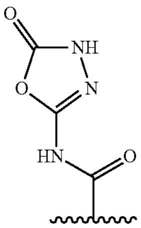
,
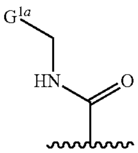
,
-continued
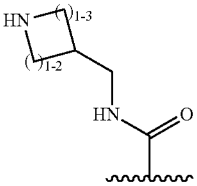
,
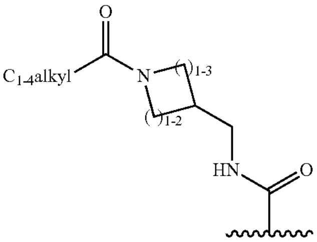
,
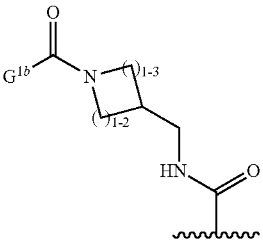
,
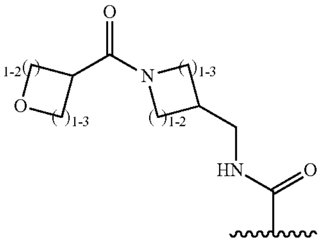
,
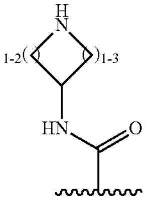
,
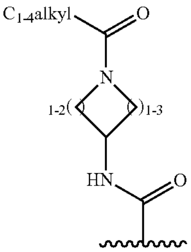
,
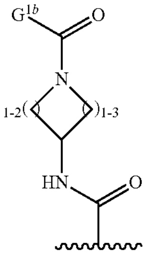
, -continued
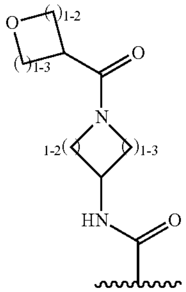
,
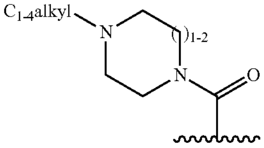
,
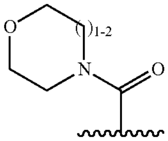
,
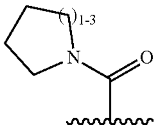
,
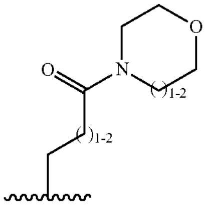
,
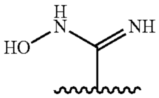
,
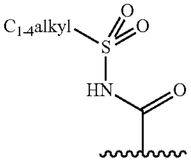
,
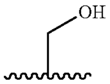
,
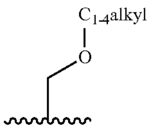
,
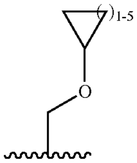
,
-continued
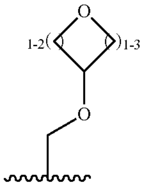
,
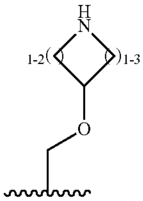
,
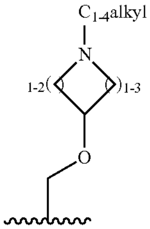
,
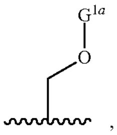
,
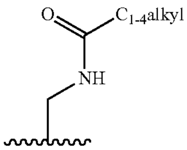
,
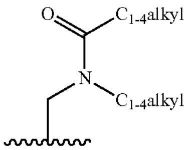
,
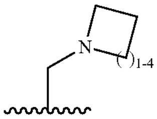
,
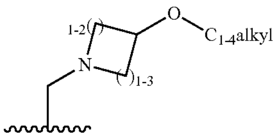
,
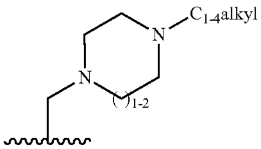
,
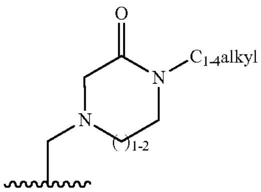
, -continued
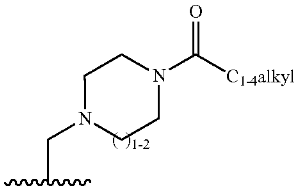
,
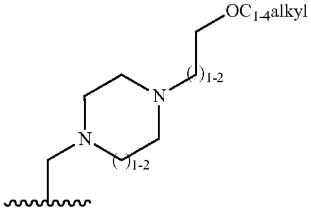
,
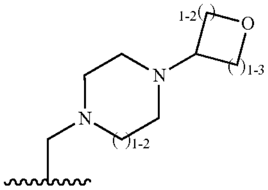
,
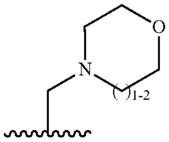
,
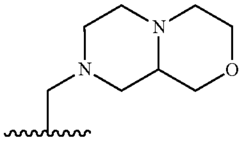
,
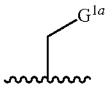
,
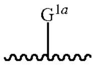
,
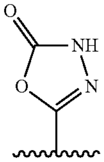
,
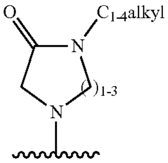
,
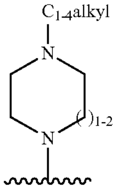
,
-continued
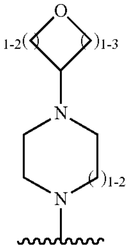
,
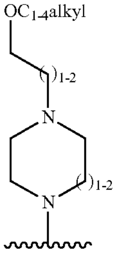
,
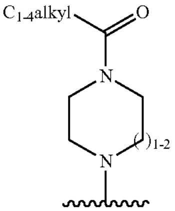
,
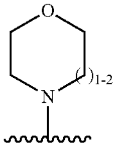
,
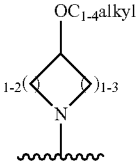
,
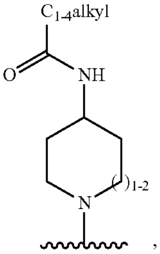
,
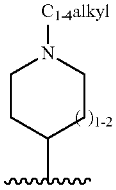
,
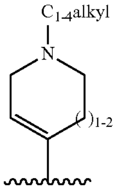
, -continued

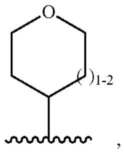

,

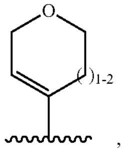

,

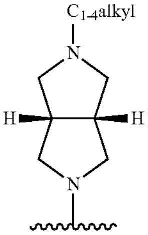

,

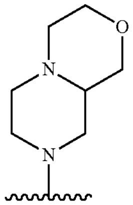

, or

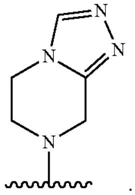

.

In $R^{10d}$, $G^{1a}$ may be a 5- to 6-membered heteroaryl containing 1-4 heteroatoms independently selected from O, N, and S, and optionally substituted with 1-3 substituents independently selected from the group consisting of halogen, cyano, $C_{1-4}$alkyl, $C_{1-4}$fluoroalkyl, $OC_{1-4}$alkyl, $OC_{1-4}$fluoroalkyl, $C_{3-4}$cycloalkyl, and $CH_2C_{3-4}$cycloalkyl. In $R^{10d}$, $G^{1b}$ may be a 5- to 6-membered heteroaryl containing 1-4 heteroatoms independently selected from O, N, and S, and optionally substituted with 1-3 substituents independently selected from the group consisting of halogen, cyano, $C_{1-4}$alkyl, $C_{1-4}$fluoroalkyl, $OC_{1-4}$alkyl, $OC_{1-4}$fluoroalkyl, $C_{3-4}$cycloalkyl, and $CH_2C_{3-4}$cycloalkyl. For example, $R^{10d}$ may be hydrogen, fluoro, chloro, bromo, methyl, ethyl, cyano, $OCH_3$, $OCF_3$, $NH_2$, $N(CH_3)_2$, $NHC(O)CH_3$,

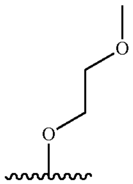

,

-continued

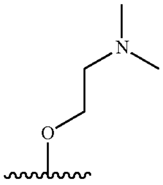

,

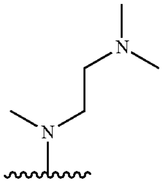

,

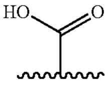

,

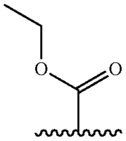

,

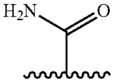

,

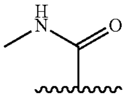

,

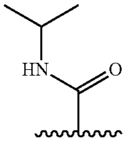

,

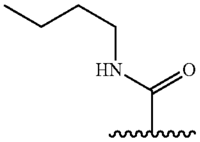

,

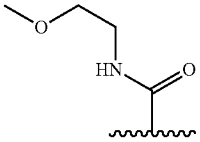

,

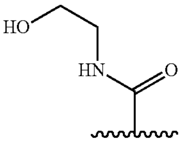

,

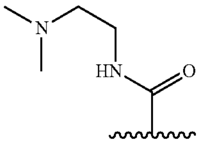

,

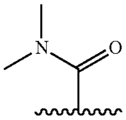

,

-continued
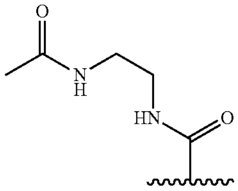
,
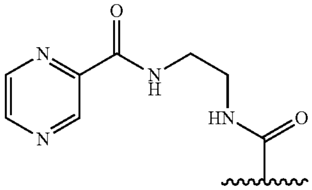
,
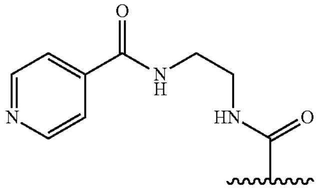
,
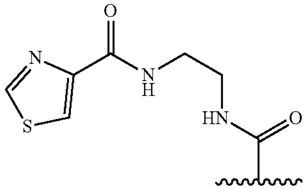
,
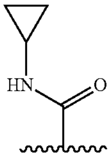
,
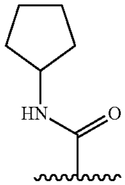
,
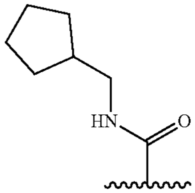
,
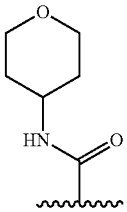
,
-continued
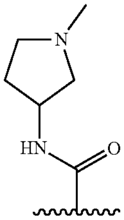
,
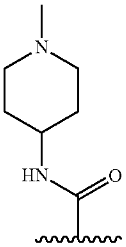
,
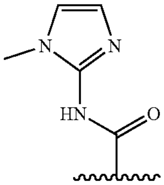
,
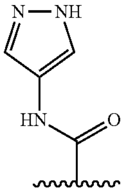
,
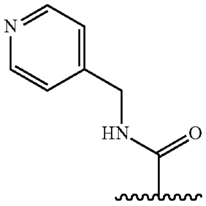
,
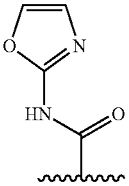
,
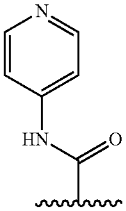
,
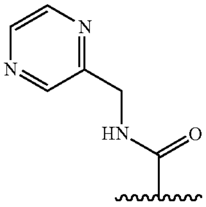
, -continued
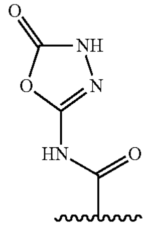
,
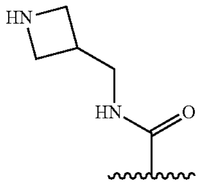
,
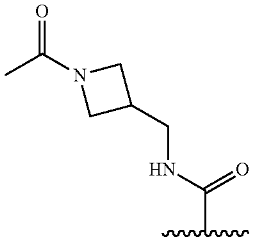
,
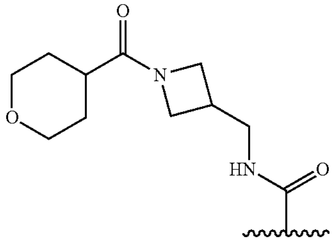
,
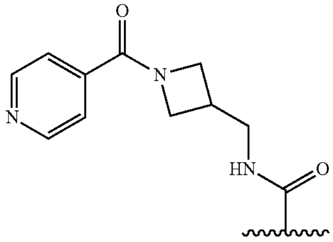
,
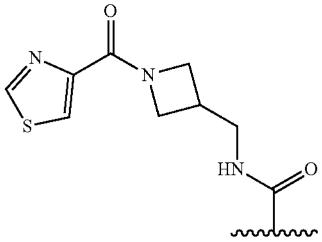
,
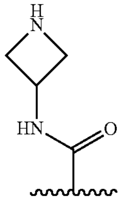
,
-continued
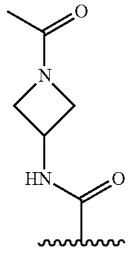
,
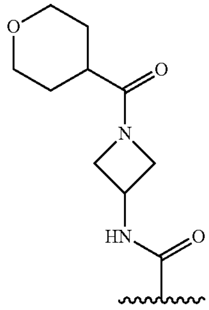
,
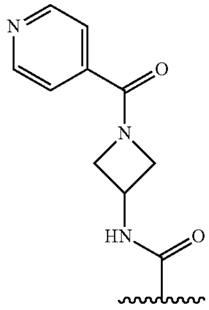
,
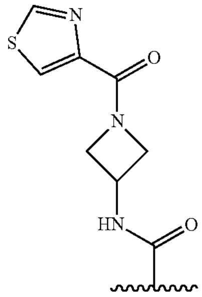
,
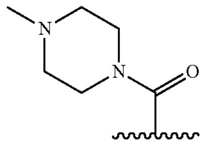
,
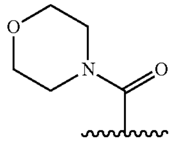
,
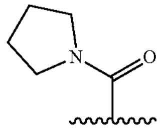
, -continued
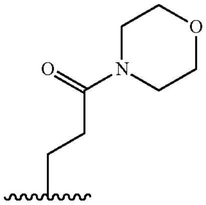
,
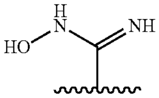
,
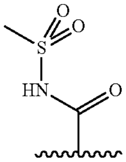
,
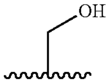
,
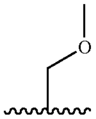
,
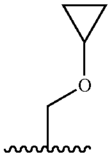
,
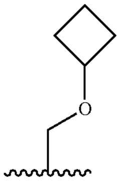
,
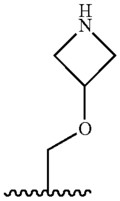
,
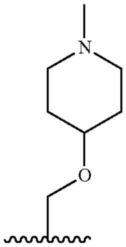
,
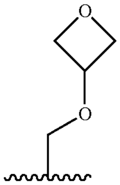
,
-continued
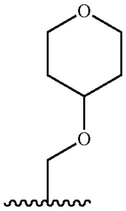
,
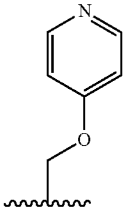
,
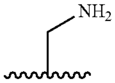
,
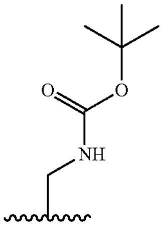
,
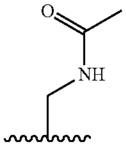
,
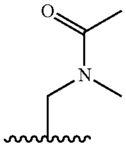
,
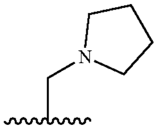
,
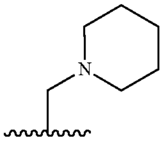
,
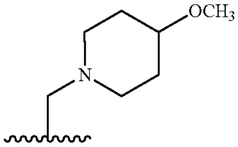
,
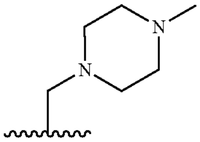
, -continued
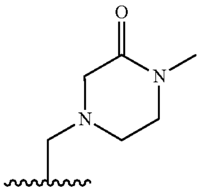
,
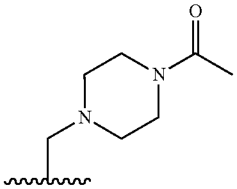
,
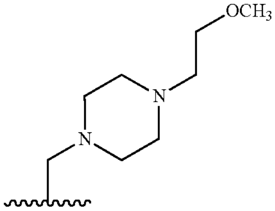
,
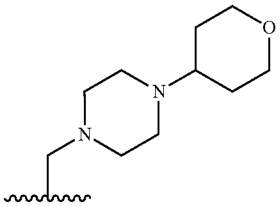
,
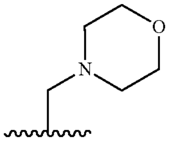
,
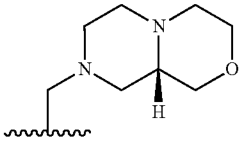
,
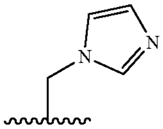
,
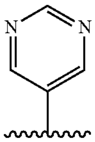
,
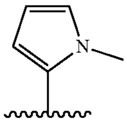
,
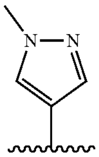
,
-continued
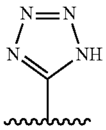
,
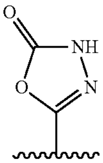
,
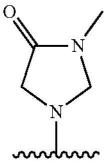
,
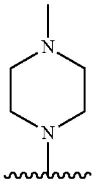
,
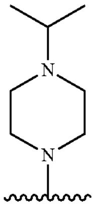
,
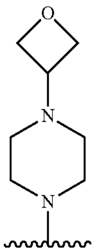
,
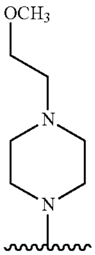
,
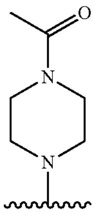
, -continued

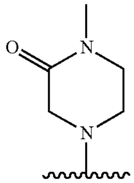,

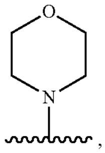,

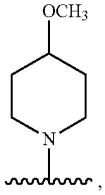,

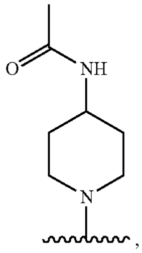,

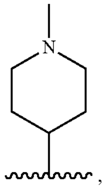,

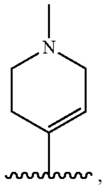,

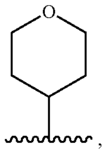,

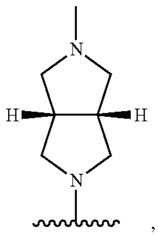,

-continued

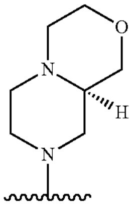,

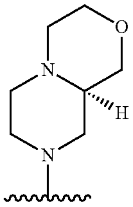, or

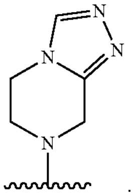.

$R^{10e}$ may be hydrogen, methyl, ethyl, or chloro.

$R^{10f}$ may be hydrogen, methyl, ethyl, isopropyl, $OCH_3$, $NH_2$, $NHCH_3$ or 4-fluoroazeidin-1-yl. $R^{10f}$ may be hydrogen, methyl, ethyl, isopropyl, or $OCH_3$. $R^{10f}$ may be ethyl or $OCH_3$.

The compounds and embodiments described herein include compounds and embodiments wherein $X^{10}$ is N; $X^{11}$ is $CR^{10b}$; $X^{12}$ is $CR^{10c}$; $X^{13}$ is $CR^{10d}$; and $X^{14}$ is $CR^{10c}$.

The compounds and embodiments described herein include compounds and embodiments wherein $X^{10}$ is $CR^{10a}$; $X^{11}$ is N; $X^{12}$ is $CR^{10c}$; $X^{13}$ is $CR^{10d}$; and $X^{14}$ is $CR^{10e}$.

The compounds and embodiments described herein include compounds and embodiments wherein $X^{10}$ is $CR^{10a}$; $X^{11}$ is $CR^{10b}$; $X^{12}$ is N; $X^{13}$ is $CR^{10d}$; and $X^{14}$ is $CR^{10e}$.

The compounds and embodiments described herein include compounds and embodiments wherein $X^{10}$ is $CR^{10a}$; $X^{11}$ is $CR^{10b}$; $X^{12}$ is $CR^{10c}$; $X^{13}$ is N; and $X^{14}$ is $CR^{10e}$.

The compounds and embodiments described herein include compounds and embodiments wherein $X^{10}$ is N; $X^{11}$ is $CR^{10b}$; $X^{12}$ is N; $X^{13}$ is $CR^{10d}$; and $X^{14}$ is $CR^{10e}$.

The compounds and embodiments described herein include compounds and embodiments wherein $X^{10}$ is $CR^{10a}$; $X^{11}$ is $CR^{10b}$; $X^{12}$ is N; $X^{13}$ is $CR^{10d}$; and $X^{14}$ is N.

The compounds and embodiments described herein include compounds and embodiments wherein $X^{10}$ is $CR^{10a}$; $X^{11}$ is N; $X^{12}$ is $CR^{10c}$; $X^{13}$ is N; and $X^{14}$ is $CR^{10e}$.

The compounds and embodiments described herein include compounds and embodiments wherein $X^{10}$ is $CR^{10a}$; $X^{11}$ is N; $X^{12}$ is N; $X^{13}$ is $CR^{10d}$; and $X^{14}$ is $CR^{10e}$.

In the compounds and embodiments described herein, $G^1$ may be

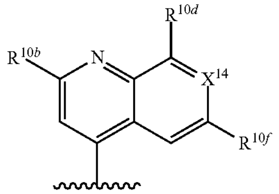

wherein $X^{14}$ is $CR^{10e}$ or N; $R^{10b}$ is hydrogen, halogen, $C_{1-4}$alkyl, or $C_{1-4}$fluoroalkyl; $R^{10d}$ is hydrogen, halogen, $C_{1-4}$alkyl, $C_{1-4}$fluoroalkyl, $-L^1-X^1$, or $-L^1-G^{1a}$; $R^{10e}$ is hydrogen, halogen, $C_{1-4}$alkyl, or $C_{1-4}$fluoroalkyl; and $R^{10f}$ is hydrogen, halogen, $C_{1-4}$alkyl, $C_{1-4}$fluoroalkyl, OH, $OC_{1-4}$alkyl, $OC_{1-4}$fluoroalkyl, $NH_2$, $NHC_{1-4}$alkyl, or $N(C_{1-4}alkyl)_2$. Included are compounds and embodiments, wherein $X^{14}$ is $CR^{10c}$ Included are compounds and embodiments, wherein $X^{14}$ is N. Included are compounds and embodiments, wherein $R^{10d}$ is $-L^1-X^1$. In $-L^1-X^1$, $X^1$ may be $—OR^{1a}$, $—N(R^{1a})_2$, cyano, $—C(O)OR^{1a}$, $—C(O)N(R^{1a})_2$, $—C(O)N(R^{1a})SO_2R^{1b}$, —C(NH)NHOH, $—C(O)R^{1b}$, $—NR^{1a}C(O)H$, or $—NR^{1a}C(O)R^{1b}$, wherein $R^{1a}$ and $R^{1b}$ are as defined herein. In $R^{1a}$ and $R^{1b}$ in $-L^1-X^1$, $G^{1a}$ ray be $C_{3-8}$cycloalkyl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, $L^2-X^2$, and $-L^2-G^{1b}$; wherein $X^2$, at each occurrence, is independently $—OR^{1c}$, $—N(R^{1c})_2$, $—C(O)N(R^{1c})_2$, $—C(O)R^{1c}$, $—NR^{1c}C(O)R^{1c}$, and $L^2$, $G^{1b}$, and $R^{1c}$ are as defined herein. In $-L^1-X^1$, $R^{1b}$, at each occurrence, may be independently $C_{1-6}$alkyl or $G^{1a}$. In $R^{1a}$ and $R^{1b}$ in $-L^1-X^1$, $R^{1c}$, at each occurrence, may be independently hydrogen, $C_{1-4}$alkyl, or ($G^{1b}$. In $-L^1-X^1$, $X^2$, at each occurrence, may be independently $—C(O)R^{1c}$. In $-L^1-X^1$, $G^{1a}$ may be a $C_{3-8}$cycloalkyl, a 5- to 6-membered heteroaryl containing 1-2 heteroatoms independently selected from O, N, and S, or a 4- to 8-membered monocyclic heterocyclyl containing 1-3 heteroatoms independently selected from O, N, and S, the heterocyclyl being attached at a ring carbon atom, wherein $G^{1a}$ is optionally substituted with 1-4 substituents independently selected from the group consisting of halogen, $C_{1-4}$alkyl, $C_{1-4}$haloalkyl, oxo, $-L^2-X^2$, and $-L^2-G^{1b}$. In $-L^1-X^1$, $G^{1b}$ may be a 4- to 6-membered monocyclic heterocyclyl containing 1-2 heteroatoms independently selected from O, N, and S, or a 5- to 6-membered heteroaryl containing 1-2 heteroatoms independently selected from O, N, and S. In $-L^1-X^1$, $R^{1c}$, at each occurrence, may be independently hydrogen, $C_{1-6}$alkyl or $G^{1b}$.

In the compounds and embodiments described herein, $G^1$ may be

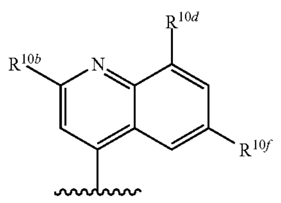

wherein $R^{10b}$ is hydrogen or $C_{1-4}$alkyl; $R^{10d}$ is $—C(O)OR^{1a}$, $—C(O)N(R^{1a})_2$, —C(NH)NHOH, or $—C(O)N(H)SO_2R^{1b}$; and $R^{10f}$ is $C_{1-4}$alkyl or $OC_{1-4}$alkyl.

In the compounds and embodiments described herein, $R^{10d}$ may be $—C(O)NHR^{1a}$.

In the $R^{1a}$ of $R^{10d}$, are compounds and embodiments wherein at least one occurrence of $R^{1a}$ is $G^{1a}$ or $—C_{1-6}alkylene-G^{1a}$. The $G^{1a}$ may be $C_{3-6}$cycloalkyl, 4- to 6-membered heterocyclyl containing 1-3 heteroatoms independently selected from O, N, and S and attached at a ring carbon atom, or a 5- to 6-membered heteroaryl containing 1-2 heteroatoms independently selected from O, N, and S, wherein $G^{1a}$ is optionally substituted with $C_{1-4}$alkyl, oxo, or $—C(O)R^{1c}$. The 4- to 6-membered heterocyclyl at $G^{1a}$ may be tetrahydropyranyl, azetidinyl, pyrrolidinyl, piperidinyl, or 2,3-dihydro-1,3,4-oxadiazolyl; and the 5- to 6-membered heteroaryl at $G^{1a}$ may be imidazolyl, pyrazolyl, oxazolyl, pyridinyl, or pyrazinyl. In embodiments wherein $R^{10d}$ is $—C(O)NHR^{1a}$, $R^{1a}$ is $G^{1a}$ or $—C_{1-6}alkylene-G^{1a}$, $G^{1a}$ is cyclopropyl, cyclopentyl, tetrahydropyranyl, pyrrolidinyl, piperidinyl, 2,3-dihydro-1,3,4-oxadiazolyl, imidazolyl, pyrazolyl, oxazolyl, pyridinyl, or pyrazinyl, and $G^{1a}$ is optionally substituted with $C_{1-4}$alkyl or oxo, $R^{10d}$ may be

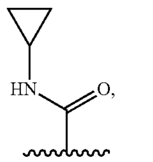 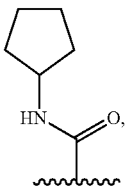 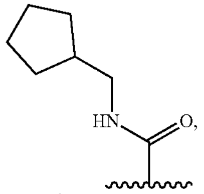

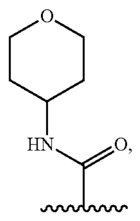 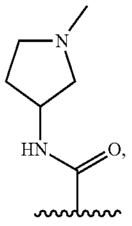 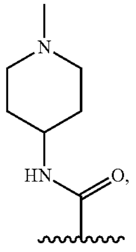

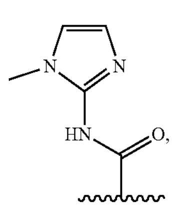 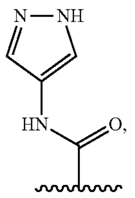 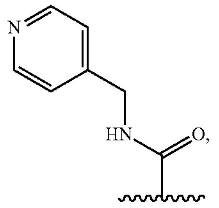

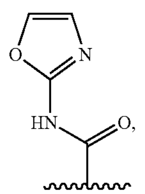 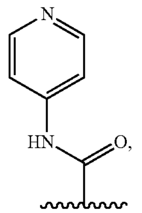

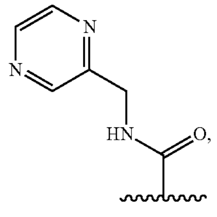 or 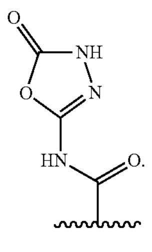

In embodiments wherein $R^{10d}$ is $—C(O)NHR^{1a}$, $R^{1a}$ is $G^{1a}$ or $—C_{1-6}alkylene-G^{1a}$, $G^{1a}$ is azetidinyl, $G^{1a}$ is optionally substituted with $—C(O)R^{1c}$, $R^{1c}$ is $C_{1-6}$alkyl or ($G^{1b}$ and $G^{1b}$ is tetrahydropyranyl, pyridinyl, or thiazolyl, $R^{10d}$ may be

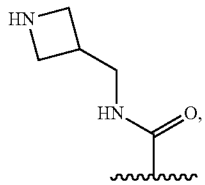,
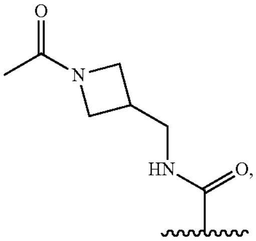,
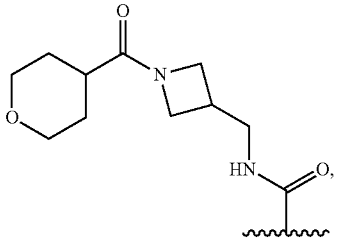,
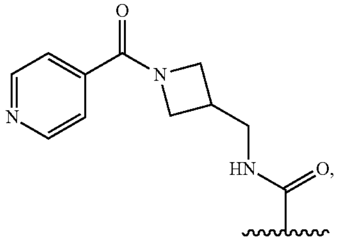,
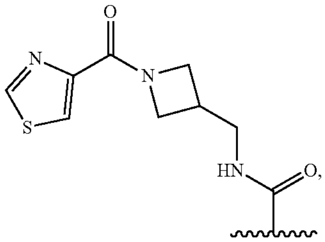,
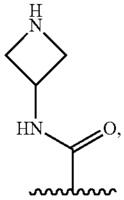,
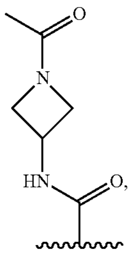,
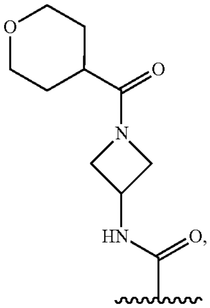,
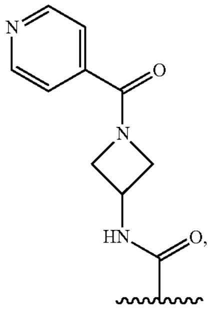, or
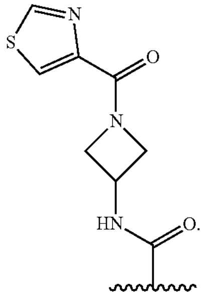.

$G^1$ may be

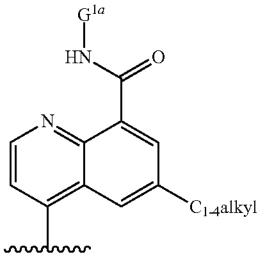 or

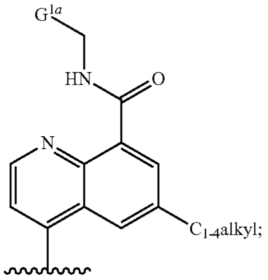;

and $G^{1a}$ is as defined above.

In the $R^{1a}$ of $R^{10d}$, are compounds and embodiments wherein $R^{1a}$, at each occurrence, is independently hydrogen, $C_{1-6}$alkyl, $C_{1-6}$haloalkyl, —$C_{2-4}$alkylene-OH, —$C_{2-4}$alkylene-O$C_{1-4}$alkyl, —$C_{2-4}$alkylene-N($C_{1-4}$alkyl)$_2$, —$C_{2-4}$alkylene-N(H)C(O)$C_{1-4}$alkyl, or —$C_{2-4}$alkylene-N(H)C(O)$G^{1b}$ and $G^{1b}$ is as defined herein. In embodiments wherein $R^{10d}$ is —C(O)NHR$^{1a}$, and $R^{1a}$, at each occurrence, is independently hydrogen, $C_{1-6}$alkyl, $C_{1-6}$haloalkyl, —$C_{2-4}$alkylene-OH, —$C_{2-4}$alkylene-O$C_{1-4}$alkyl, —$C_{2-4}$alkylene-N($C_{1-4}$alkyl)$_2$, or —$C_{2-4}$alkylene-N(H)C(O)$C_{1-4}$alkyl, $R^{10d}$ may be

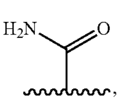,
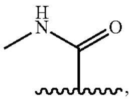,
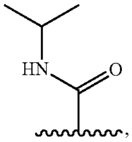,
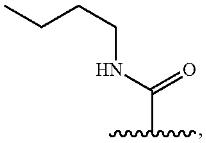,
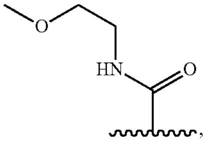,
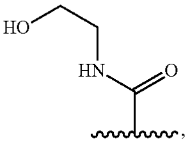,
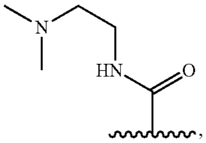,
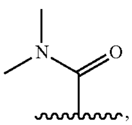, or
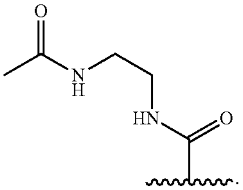.

In embodiments wherein $R^{10d}$ is —C(O)NHR$^{1a}$, $R^{1a}$, at each occurrence, is independently hydrogen or —$C_{2-4}$alkylene-N(H)C(O)$G^{1b}$, and $G^{1b}$ is pyrazinyl, pyridinyl or thiazolyl, $R^{10d}$ may be

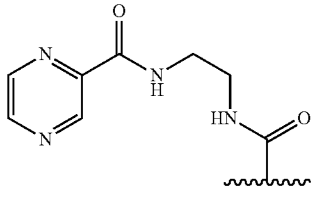

,

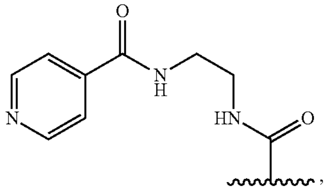

, or

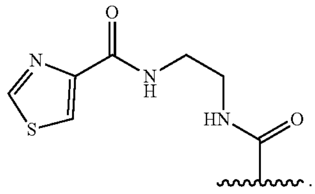

.

In the compounds and embodiments described herein, $G^1$ may be

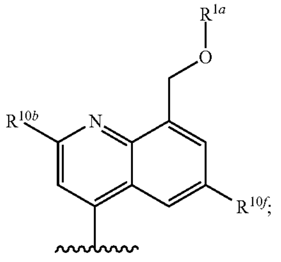

$R^{1a}$ is $C_{1-4}$alkyl or $G^{1a}$; $G^{1a}$ is $C_{3-8}$cycloalkyl, a 5- to 6-membered heteroaryl containing 1-2 heteroatoms independently selected from O, N, and S, or a 4- to 8-membered monocyclic heterocyclyl containing one heteroatom selected from O, N, and S, the heterocyclyl being attached at a ring carbon atom, wherein $G^{1a}$ is optionally substituted with $C_{1-4}$alkyl; $R^{10b}$ is hydrogen or $C_{1-4}$alkyl; and $R^{10f}$ is $C_{1-4}$alkyl or $OC_{1-4}$alkyl. $G^{1a}$ may be cyclopropyl, cyclobutyl, azetidinyl, piperidinyl, oxetanyl, tetrahydropyranyl, or pyridinyl, wherein the azetidinyl, piperidinyl, oxetanyl, and tetrahydropyranyl are attached at a ring carbon atom and $G^{1a}$ is optionally substituted with $C_{1-2}$alkyl. $G^{1a}$ may be cyclopropyl, cyclobutyl, azetidin-3-yl, piperidin-4-yl, oxetan-3-yl, tetrahydropyran-4-yl, or pyridin-4-yl, wherein $G^{1a}$ is optionally substituted with $C_{1-2}$alkyl. $G^1$ may be

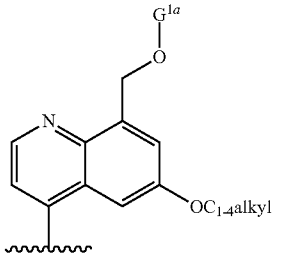

or

-continued

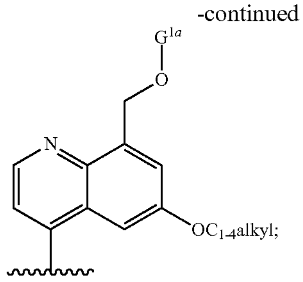

wherein $G^{1a}$ is as defined above.

Included

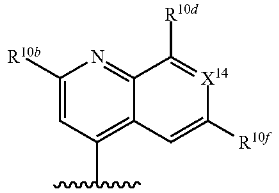

and

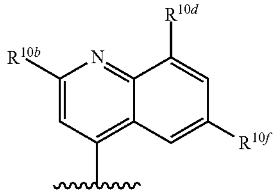

are compounds and embodiments, wherein $R^{10d}$ is $-L^1-G^{1a}$. In $-L^1-G^{1a}$, $G^{1a}$ may be independently a 5- to 10-membered heteroaryl or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, $-L^2-X^2$, and $-L^2-G^{1b}$ wherein $G^{1b}$ is a $C_{3-6}$cycloalkyl or a 4- to 6-membered monocyclic heterocyclyl containing 1-2 heteroatoms independently selected from O, N, and S, wherein $G^{1b}$ is optionally substituted with 1-4 substituents independently selected from the group consisting of halogen, cyano, $C_{1-4}$alkyl, $C_{1-4}$haloalkyl, oxo, —OH, and —$OC_{1-4}$alkyl; $X^2$, at each occurrence, is independently —$OR^{1c}$, —$N(R^{1c})_2$, —$C(O)N(R^{1c})_2$, —$C(O)R^{1c}$, or —$NR^{1c}C(O)R^{1c}$; and $R^{1c}$, at each occurrence, is independently hydrogen, $C_{1-6}$alkyl, $C_{1-6}$haloalkyl, $G^{1b}$, or —$C_{1-3}$alkylene-$G^{1b}$, wherein alternatively two $R^{1c}$, together with a common nitrogen atom to which the $R^{1c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl. $G^{1b}$ may be a 4- to 6-membered monocyclic heterocyclyl containing 1-2 heteroatoms independently selected from O, N, and S. $X^2$, at each occurrence, may be independently —$OR^{1c}$, —$C(O)R^{1c}$, or —$NR^{1c}C(O)R^{1c}$. $R^{1c}$, at each occurrence, may be independently $C_{1-6}$alkyl.

In the compounds and embodiments described herein, $G^1$ may be

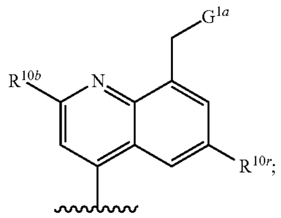

wherein $G^{1a}$ is a 5-membered heteroaryl containing 1-3 heteroatoms independently selected from O, N, and S, a 4- to 8-membered monocyclic heterocyclyl containing 1-2 heteroatoms independently selected from O, N, and S, or an 8- to 10-membered fused bicyclic heterocyclyl containing 1-3 heteroatoms independently selected from O, N, and S, the heterocyclyl and heteroaryl being attached at a ring nitrogen atom, wherein the 4- to 8-membered monocyclic heterocyclyl is optionally substituted with 1-2 substituents independently selected from oxo, $C_{1-4}$alkyl, $OC_{1-4}$alkyl, $C(O)C_{1-4}$alkyl, —$C_{2-3}$alkylene-$OC_{1-4}$alkyl, $G^{1b}$, and —$C_{1-3}$alkylene-$G^{1b}$; $G^{1b}$ is $C_{3-6}$cycloalkyl or a 4- to 6-membered monocyclic heterocyclyl containing 1-2 heteroatoms independently selected from O, N, and S; $R^{10b}$ is hydrogen or $C_{1-4}$alkyl; and $R^{10f}$ is $C_{1-4}$alkyl or $OC_{1-4}$alkyl. $G^{1a}$ may be a piperazin-1-yl, piperidin-1-yl, pyrrolidin-1-yl, morpholin-4-yl, imidazol-1-yl or hexahydropyrazino[2,1-c][1,4]oxazin-8(1H)-yl, wherein the piperazin-1-yl and piperidin-1-yl are optionally substituted with 1-2 substituents independently selected from oxo, $C_{1-4}$alkyl, $OC_{1-4}$alkyl, $C(O)C_{1-4}$alkyl, —$C_{2-3}$alkylene-$OC_{1-4}$alkyl, and $G^{1b}$. $G^{1a}$ may be

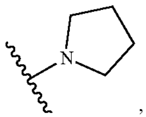 , 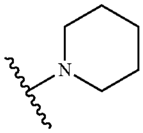 ,

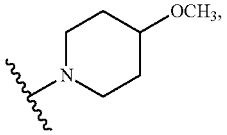 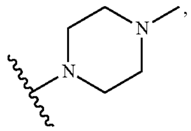

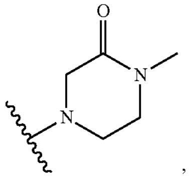 , 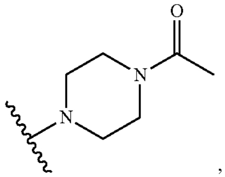 ,

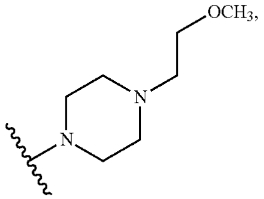 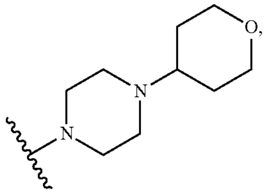

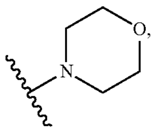 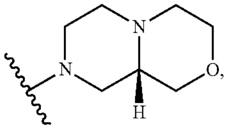 or

-continued

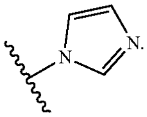

$G^{1a}$ may be

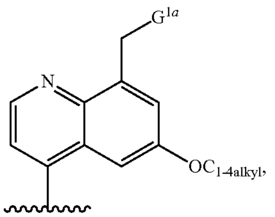

wherein $G^{1a}$ is as described above.

In the compounds and embodiments described herein, $G^{1}$ may be

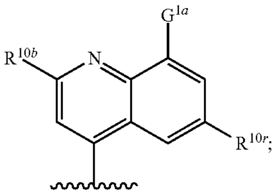

wherein $G^{1a}$ is a 5- to 6-membered heteroaryl containing 1-4 heteroatoms independently selected from O, N, and S, a 4- to 8-membered monocyclic heterocyclyl containing 1-2 heteroatoms independently selected from O, N, and S, or an 8- to 10-membered fused bicyclic heterocyclyl containing 1-3 heteroatoms independently selected from O, N, and S, wherein $G^{1a}$ is optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, $G^{1b}$, and —$C_{1-3}$alkylene-$G^{1b}$; $G^{1b}$ is $C_{3-6}$cycloalkyl or a 4- to 6-membered monocyclic heterocyclyl containing 1-2 heteroatoms independently selected from O, N, and S; $R^{10b}$ is hydrogen or $C_{1-4}$alkyl; and $R^{10f}$ is $C_{1-4}$alkyl or $OC_{1-4}$alkyl. $G^{1a}$ may be a piperazinyl, piperidinyl, tetrahydropyridinyl, morpholinyl, imidazolidinyl, tetrahydropyranyl, dihydropyranyl, 1,3,4-oxadiazol-2(3H)-yl, pyrimidinyl, pyrrolyl, pyrazolyl, tetrazolyl, hexahydropyrazino[2,1-c][1,4]oxazin-8(1H)-yl, hexahydropyrrolo[3,4-c]pyrrol-2(1H)-yl, or 5,6-dihydro-[1,2,4]triazolo[4,3-a]pyrazin-7(8H)-yl, wherein $G^{1a}$ is optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl. $G^{1b}$, and —$C_{1-3}$alkylene-$G^{1b}$. $G^{1a}$ may be a piperazin-1-yl, piperidin-1-yl, piperidin-4-yl, tetrahydropyridin-4-yl, morpholin-4-yl, imidazolidin-1-yl, tetrahydropyran-4-yl, dihydropyran-4-yl, 1,3,4-oxadiazol-2(3H)-yl, pyrimidin-5-yl, pyrrol-2-yl, pyrazol-4-yl, tetrazol-5-yl, hexahydropyrazino[2,1-c][1,4]oxazin-8(1H)-yl, hexahydropyrrolo[3,4-c]pyrrol-2(1H)-yl, or 5,6-dihydro-[1,2,4]triazolo[4,3-a]pyrazin-7(8H)-yl, wherein the piperazin-1-yl, piperidin-1-yl, piperidin-4-yl, tetrahydropyridin-4-yl, morpholin-4-yl, imidazolidin-1-yl, tetrahydropyran-4-yl, dihydropyran-4-yl, 1,3,4-oxadiazol-2(3H)-yl, pyrimidin-5-yl, pyrrol-2-yl, pyrazol-4-yl, and hexahydropyrrolo[3,4-c]pyrrol-2(1H)-yl are optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, $G^{1b}$, and —$C_{1-4}$-alkylene-$G^{1b}$. $G^{1a}$ optionally substituted with oxo, $C_{1-3}$alkyl, $OC_{1-4}$alkyl, $C(O)C_{1-4}$alkyl, —$NHC(O)C_{1-4}$alkyl, or —$C_{2-3}$alkylene-$OC_{1-4}$alkyl include

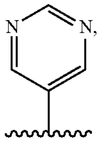 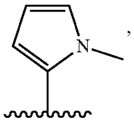 , 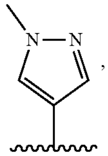 , 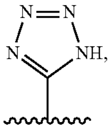

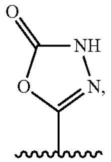 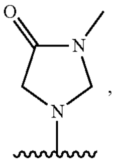 , 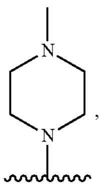 , 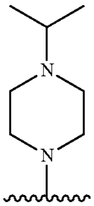 ,

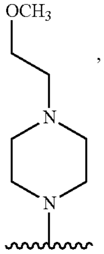 , 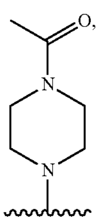 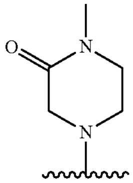 , 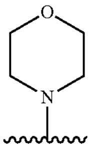 ,

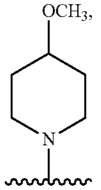 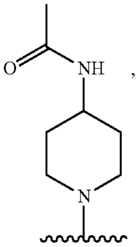 , 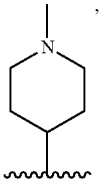 , 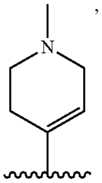 ,

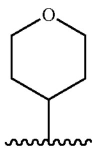 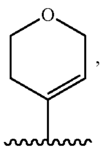 , 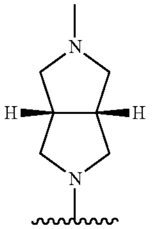 , 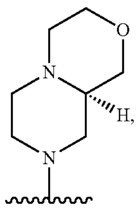

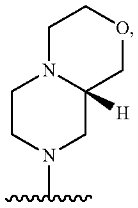 or 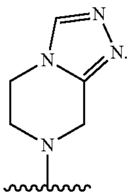

$G^{1a}$ optionally substituted with $G^{1b}$, wherein $G^{1b}$ is oxetanyl, include

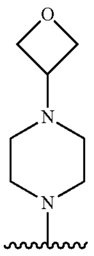 .

$G^1$ may be

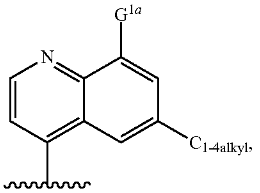

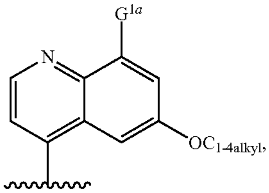

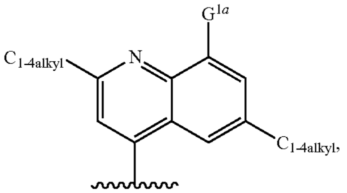 or

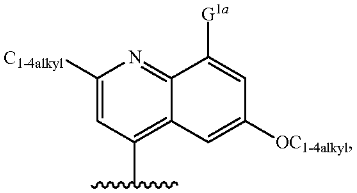

wherein $G^{1a}$ is as described above.

$G^1$ may be

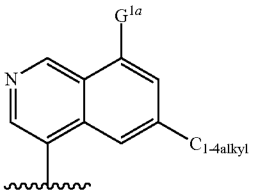 or

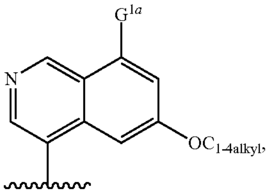

wherein $G^{1a}$ is as defined herein. $G^{1a}$ may be a 5- to 6-membered heteroaryl containing 1-4 heteroatoms independently selected from O, N, and S, a 4- to 8-membered monocyclic heterocyclyl containing 1-2 heteroatoms independently selected from O, N, and S, or an 8- to 10-membered fused bicyclic heterocyclyl containing 1-3 heteroatoms independently selected from O, N, and S, wherein $G^{1a}$ is optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, $G^{1b}$, and —$C_{1-3}$alkylene-$G^{1b}$; $G^{1b}$ is $C_{3-6}$cycloalkyl or a 4- to 6-membered monocyclic heterocyclyl containing 1-2 heteroatoms independently selected from O, N, and S. $G^{1a}$ may be a piperazinyl, piperidinyl, tetrahydropyridinyl, morpholinyl, imidazolidinyl, tetrahydropyranyl, dihydropyranyl, 1,3,4-oxadiazol-2(3H)-yl, pyrimidinyl, pyrrolyl, pyrazolyl, tetrazolyl, hexahydropyrazino[2,1-c][1,4]oxazin-8(1H)-yl, hexahydropyrrolo[3,4-c]pyrrol-2(1H)-yl, or 5,6-dihydro-[1,2,4]triazolo[4,3-a]pyrazin-7(8H)-yl, wherein $G^{1b}$ is optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, $G^{1b}$, and —$C_{1-3}$alkylene-$G^{1b}$. $G^{1a}$ may be a piperazin-1-yl, piperidin-1-yl, piperidin-4-yl, tetrahydropyridin-4-yl, morpholin-4-yl, imidazolidin-1-yl tetrahydropyran-4-yl, dihydropyran-4-yl, 1,3,4-oxadiazol-2(3H)-yl, pyrimidin-5-yl, pyrrol-2-yl, pyrazol-4-yl, tetrazol-5-yl, hexahydropyrazino[2,1-c][1,4]oxazin-8(1H)-yl, hexahydropyrrolo[3,4-c]pyrrol-2(1H)-yl, or 5,6-dihydro-[1,2,4]triazolo[4,3-a]pyrazin-7(8H)-yl, wherein the piperazin-1-yl, piperidin-1-yl, piperidin-4-yl, tetrahydropyridin-4-yl, morpholin-4-yl, imidazolidin-1-yl, tetrahydropyran-4-yl, dihydropyran-4-yl, 1,3,4-oxadiazol-2(3H)-yl, pyrimidin-5-yl, pyrrol-2-yl, pyrazol-4-yl, and hexahydropyrrolo[3,4-c]pyrrol-2(1H)-yl are optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, $G^{1b}$, and —$C_{1-3}$alkylene-$G^{1b}$. $G^{1a}$ optionally substituted with oxo, $C_{1-4}$alkyl, $OC_{1-4}$alkyl, $C(O)C_{1-4}$alkyl, —$NHC(O)C_{1-4}$alkyl, or —$C_{2-3}$alkylene-$OC_{1-4}$alkyl include

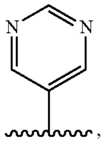, 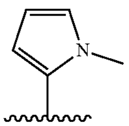, 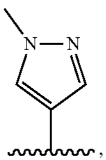,

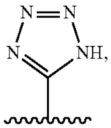 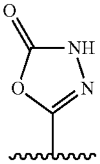 , 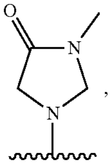 ,

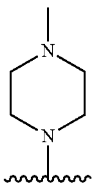, 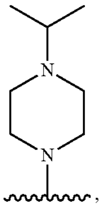, 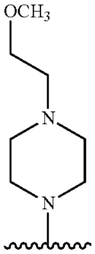, 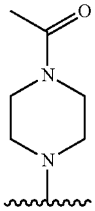,

-continued

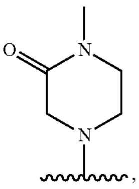, 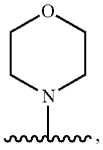, 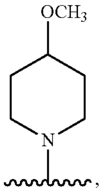,

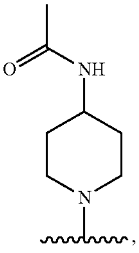, 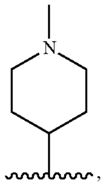, 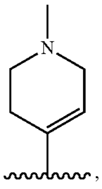, 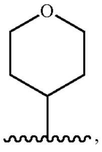,

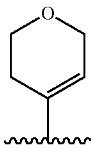, 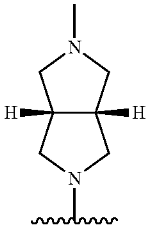 , 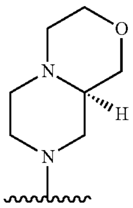 ,

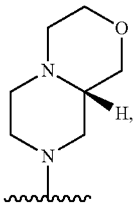 or 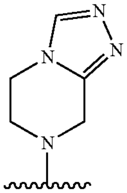 .

$G^1$ may be

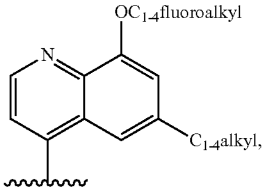

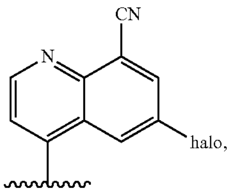

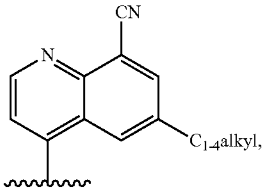

-continued
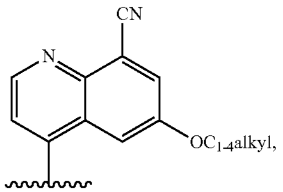
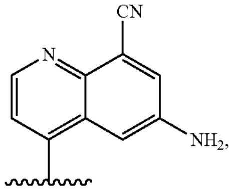
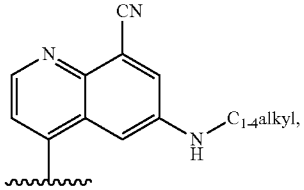
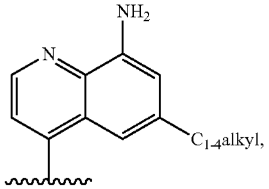
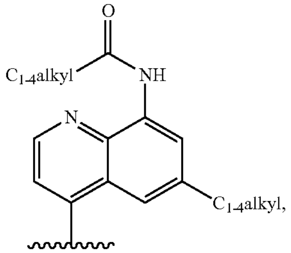
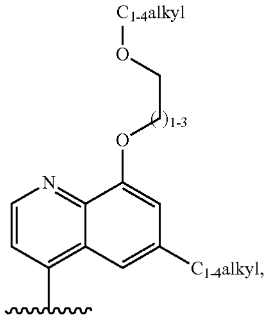
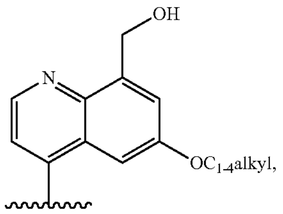
-continued
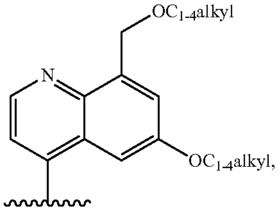
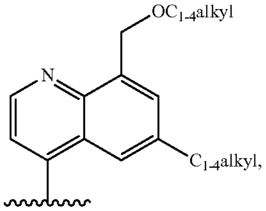
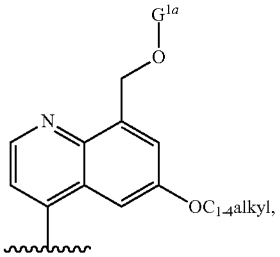
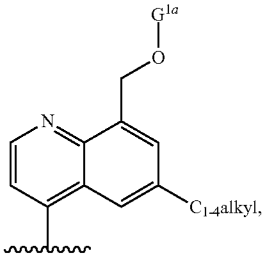
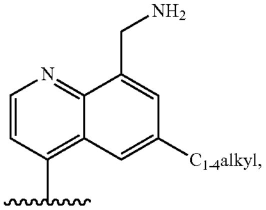
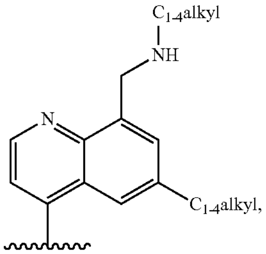
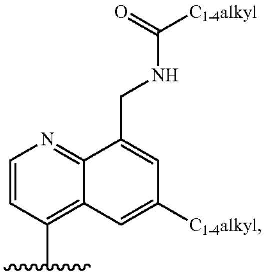

-continued
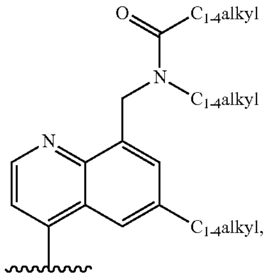
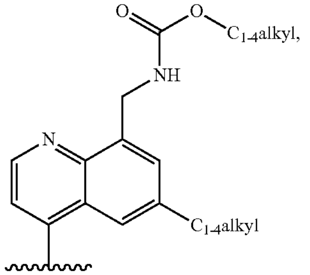
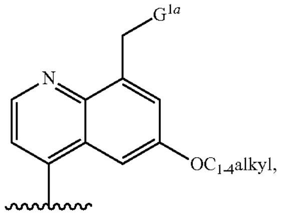
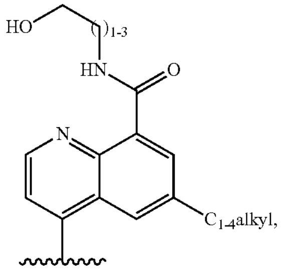
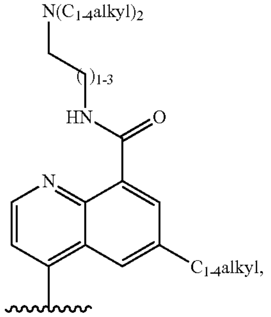
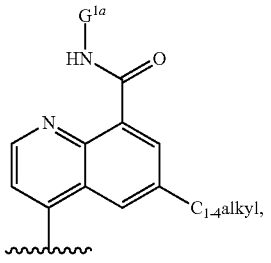
-continued
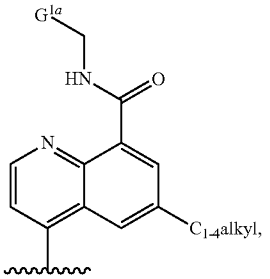
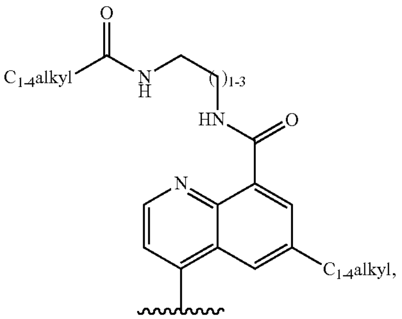
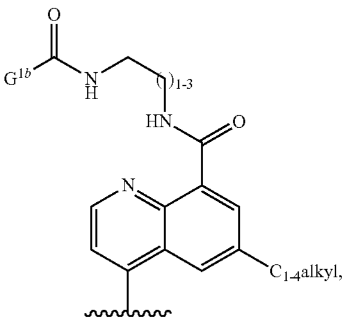
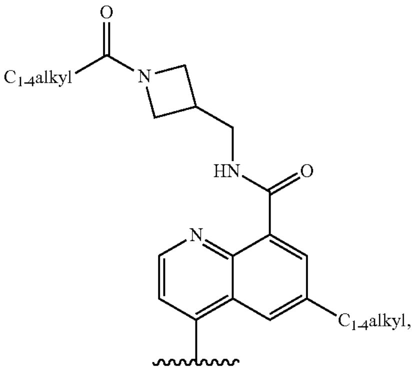
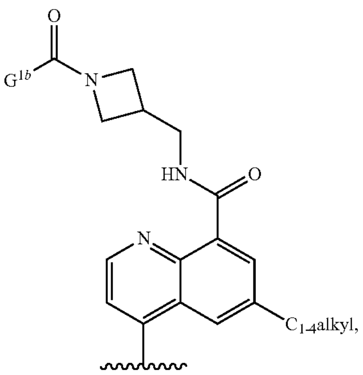

-continued
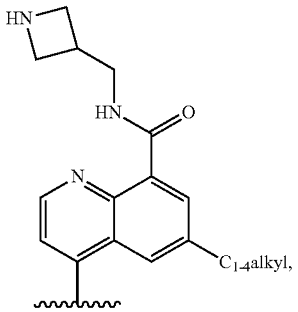
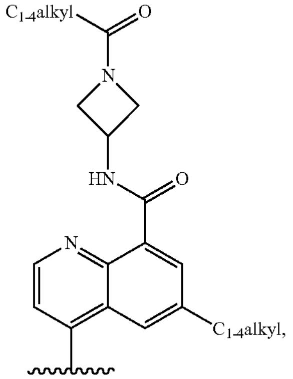
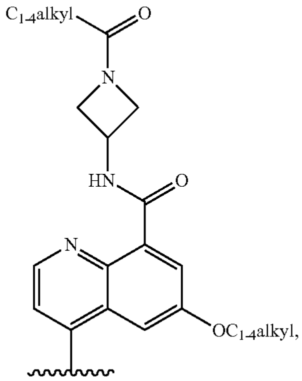
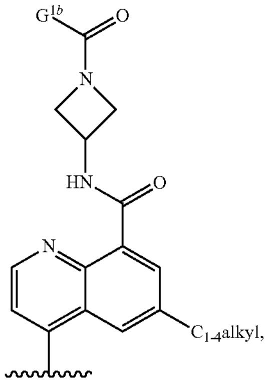
-continued
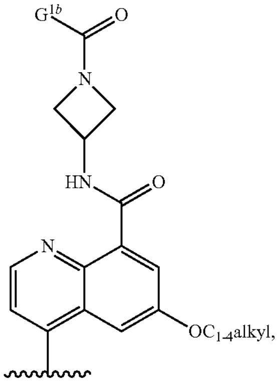
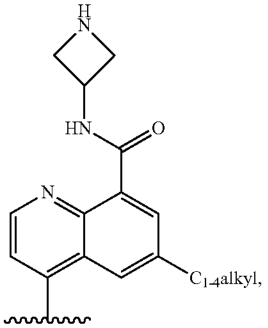
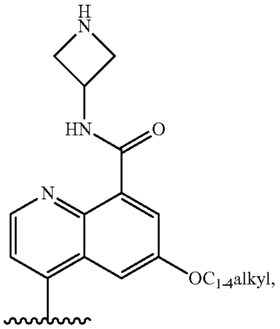
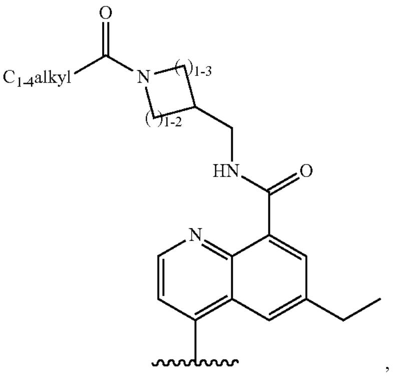

-continued
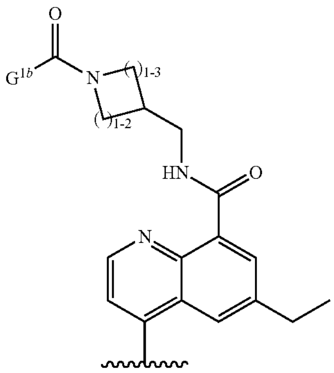
,
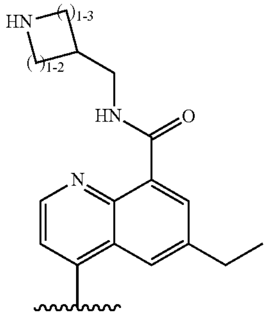
,
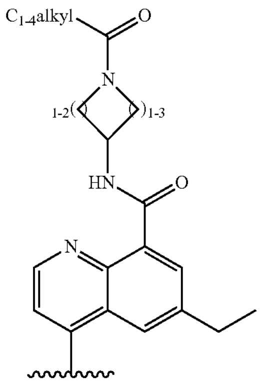
,
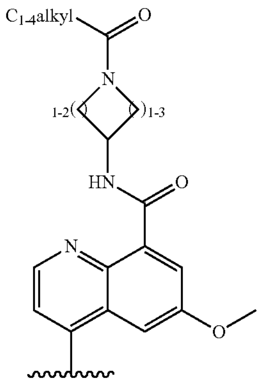
,
-continued
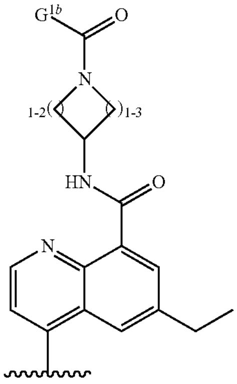
,
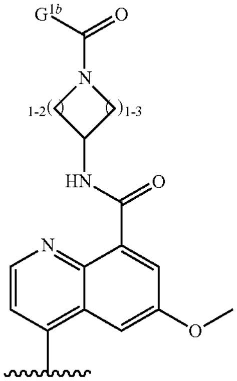
,
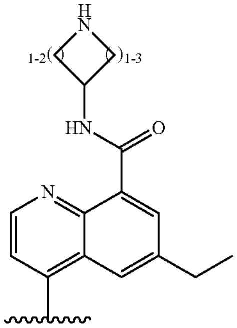
,
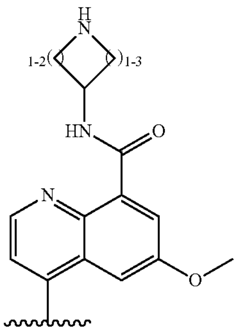
,
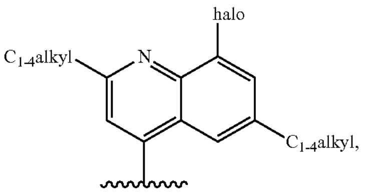

-continued
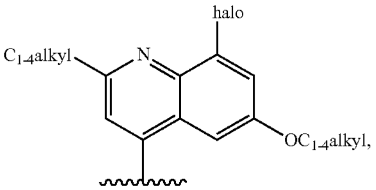
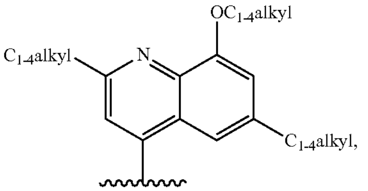
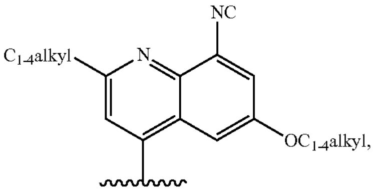
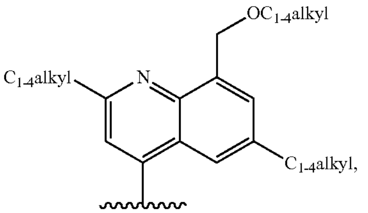
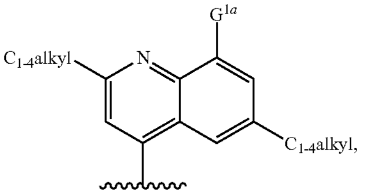
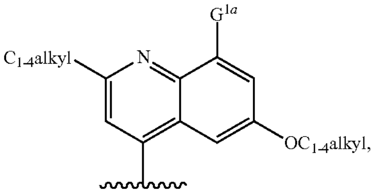
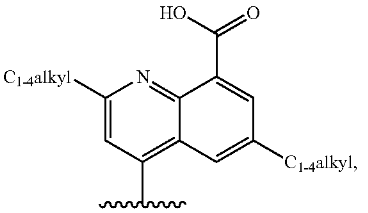
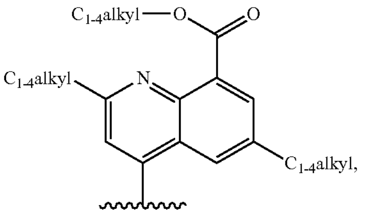
-continued
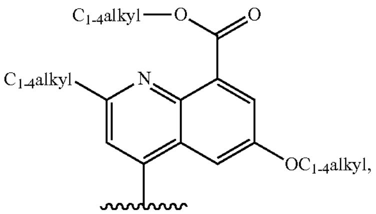
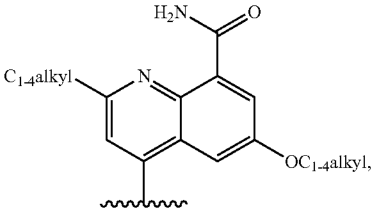
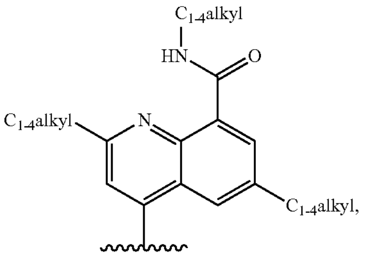
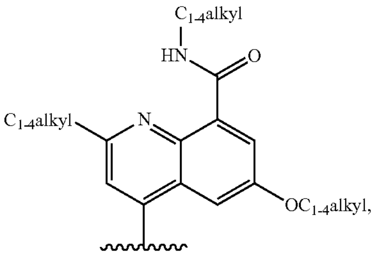
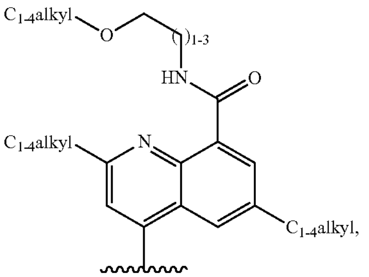
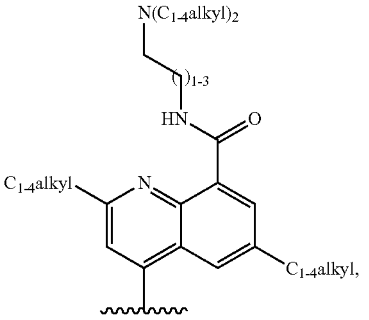

-continued
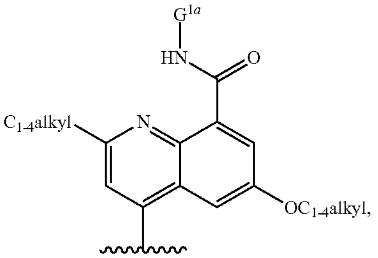
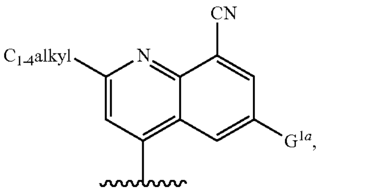
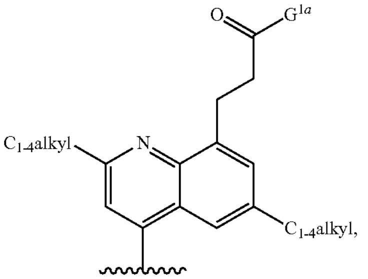
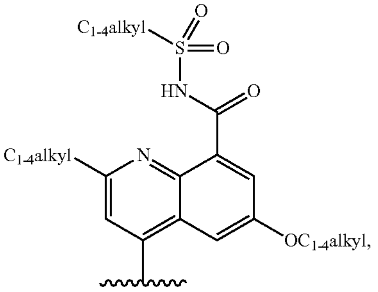
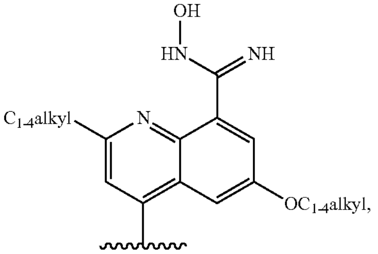
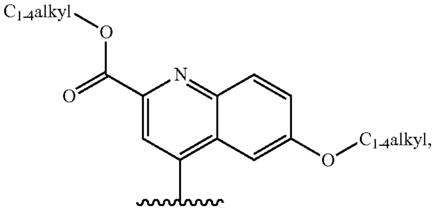
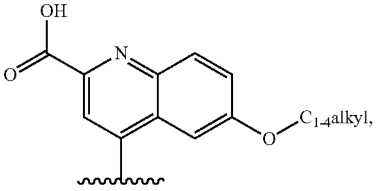
-continued
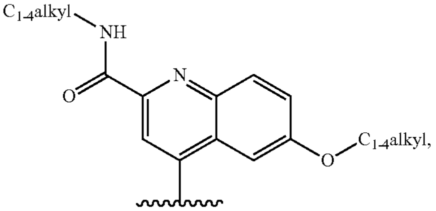
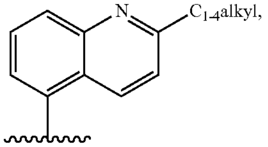
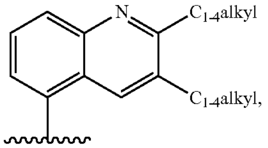
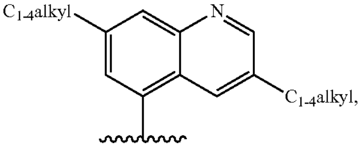
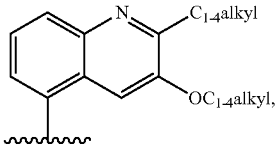
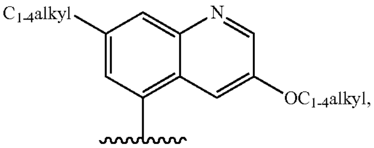
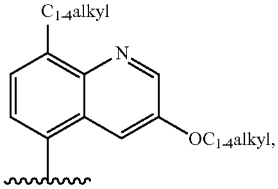
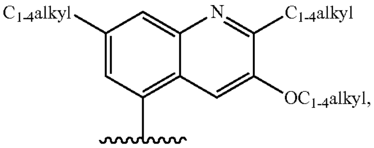
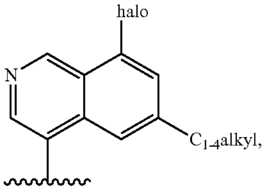
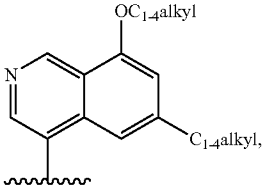

-continued
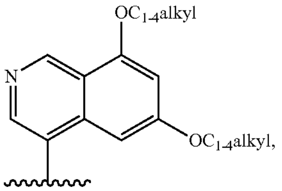
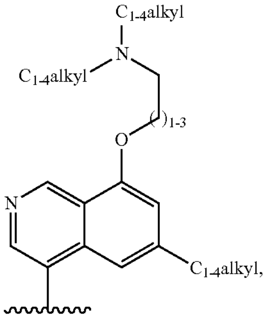
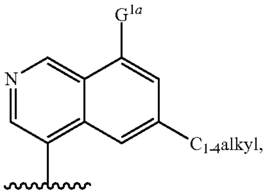
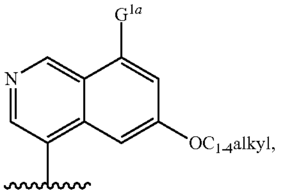
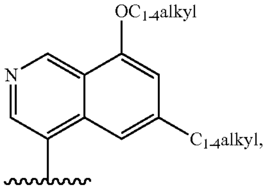
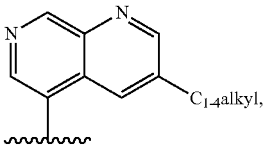
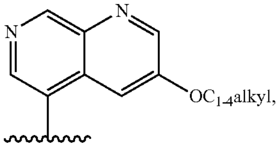
or
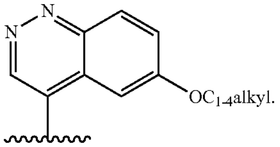
$G^1$ may be
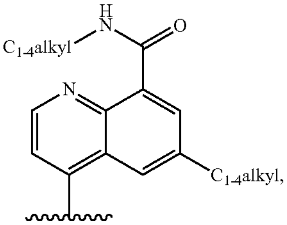
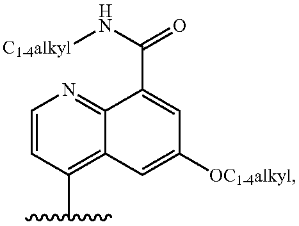
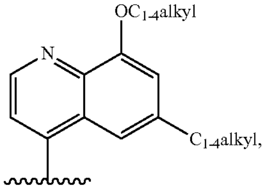
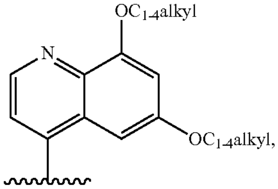
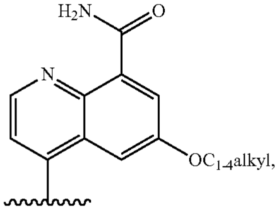
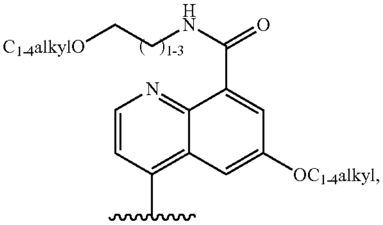
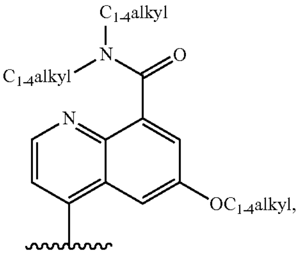
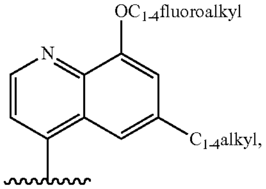

-continued
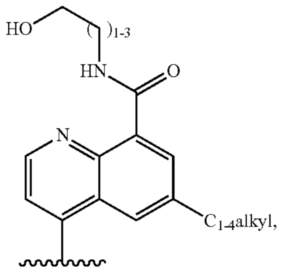
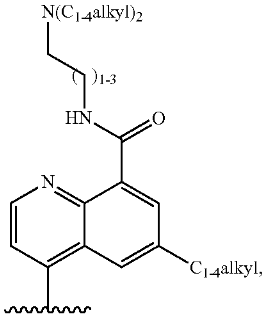
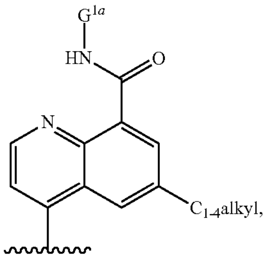
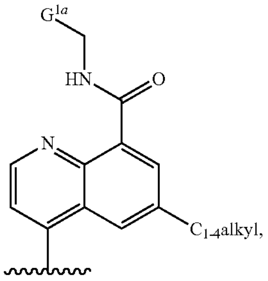
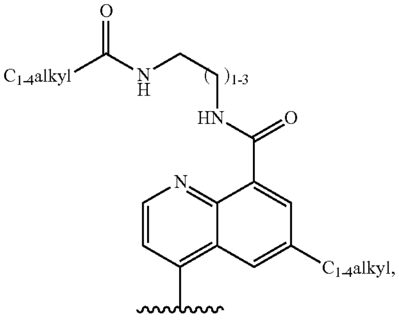
-continued
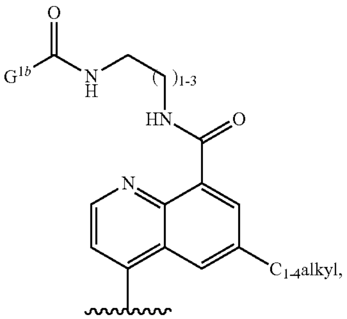
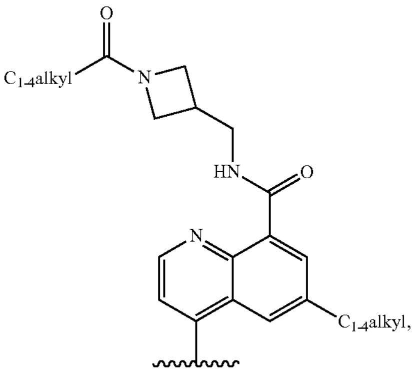
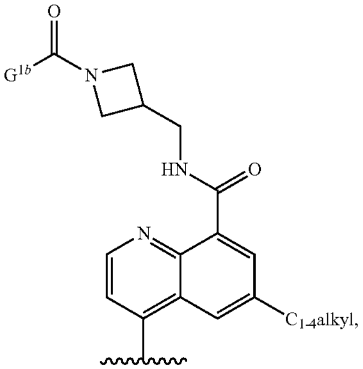
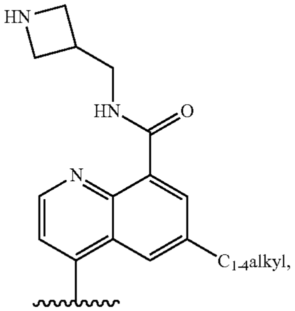

-continued
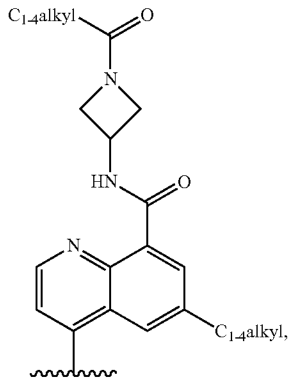
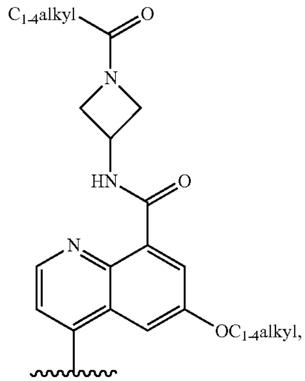
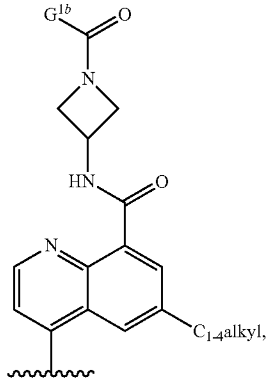
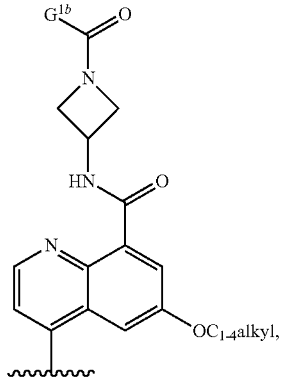
-continued
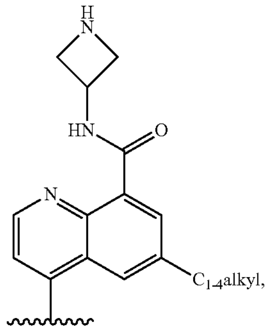
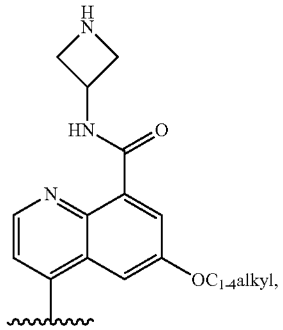
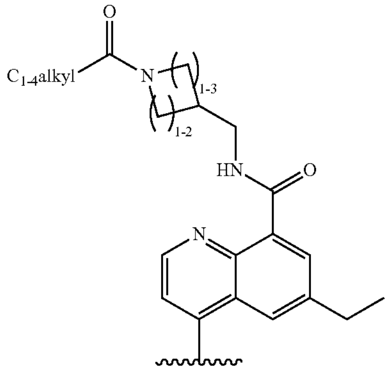
,
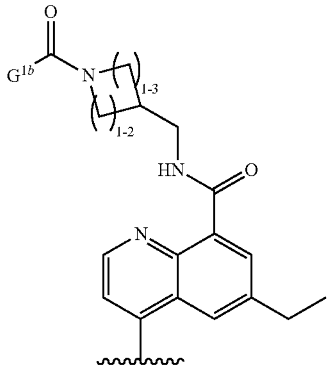
,
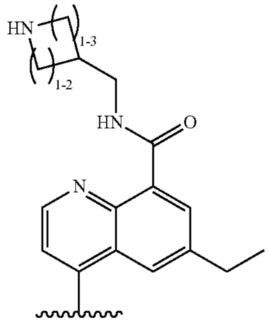
, -continued
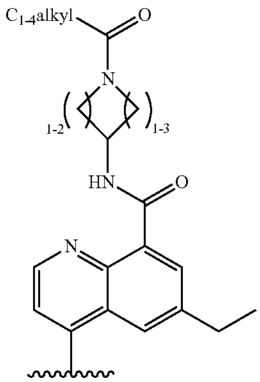
,
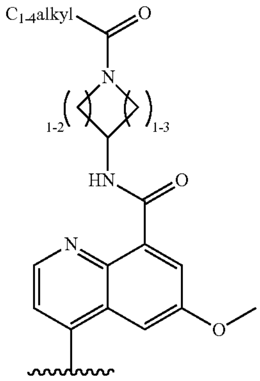
,
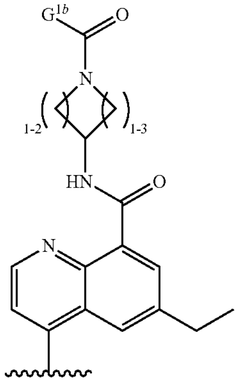
,
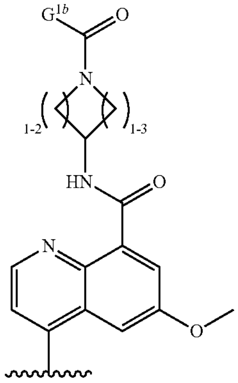
,
-continued
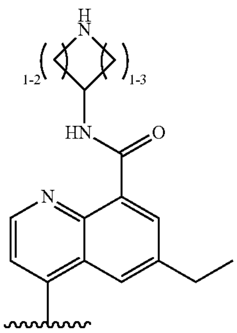
,
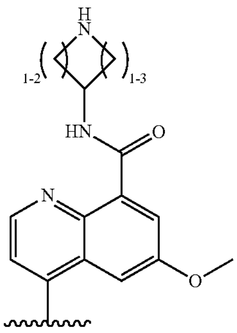
,
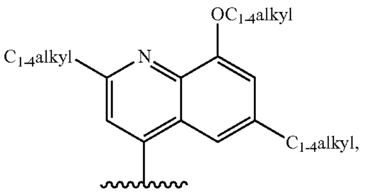
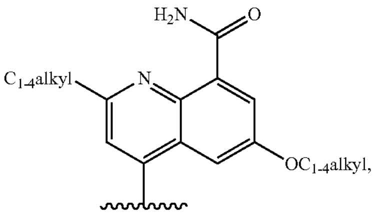
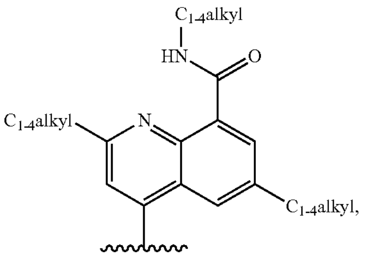
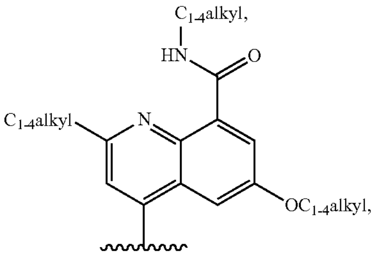

-continued
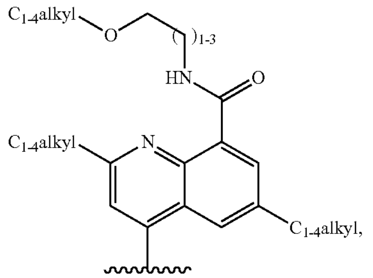
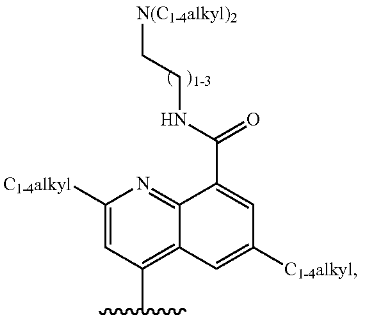
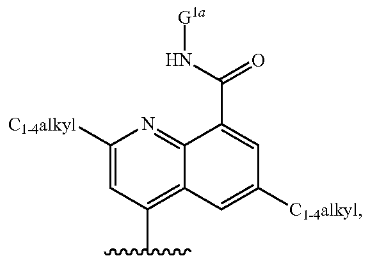
or
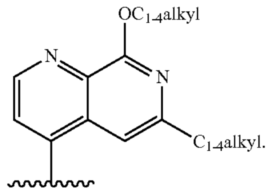
In the compounds and embodiments, wherein $G^1$ is
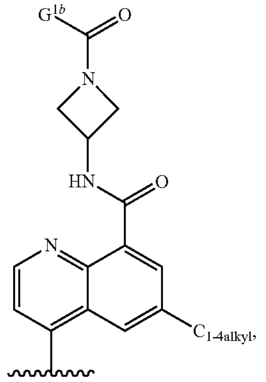
-continued
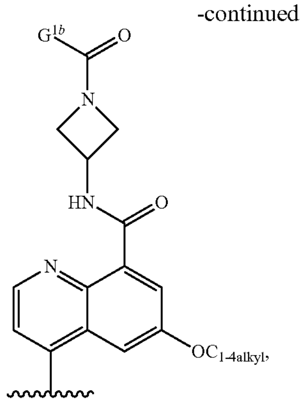
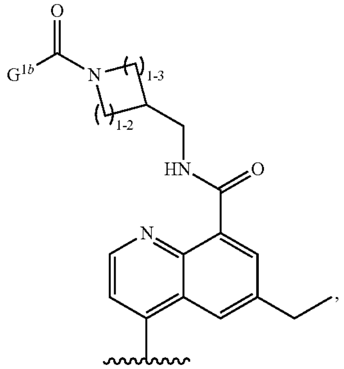
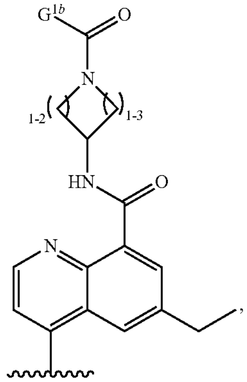
or
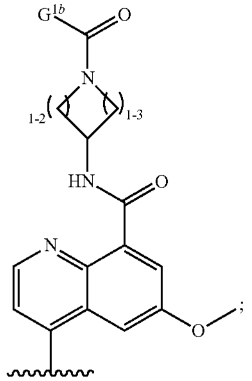
$G^{1b}$ may be a 4- to 6-membered monocyclic heterocyclyl containing 1-2 heteroatoms independently selected from O, N, and S, or a 5- to 6-membered heteroaryl containing 1-2 heteroatoms independently selected from O, N, and S.

$G^1$ may be
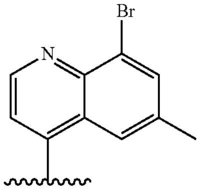,
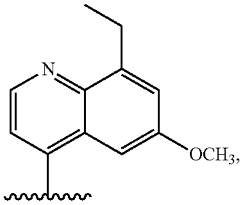
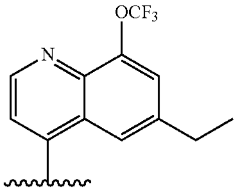,
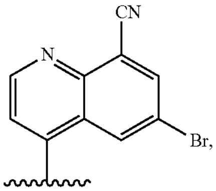
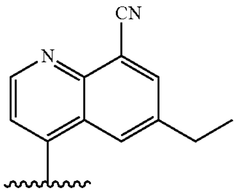,
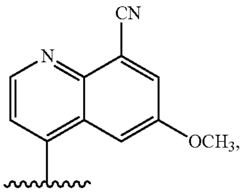
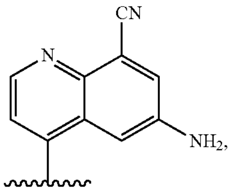
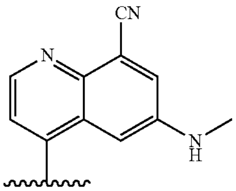,
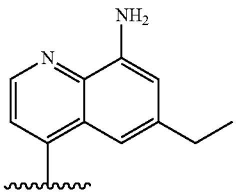,
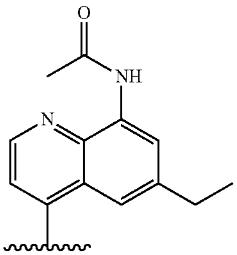,
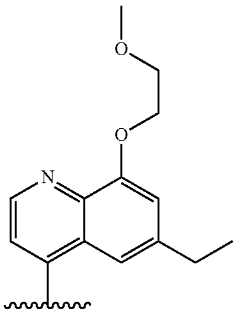,
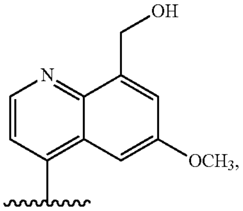
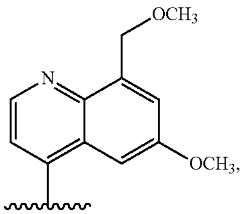
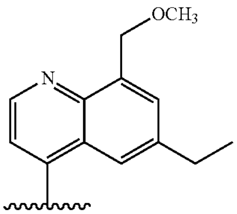,
-continued
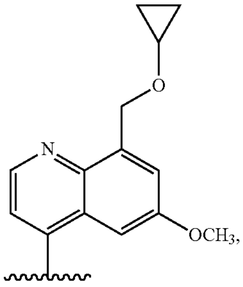
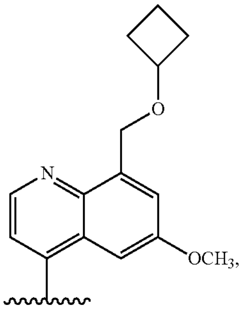
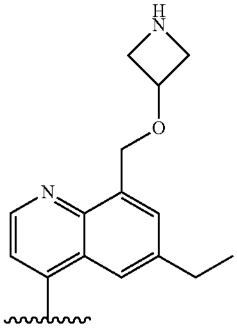,
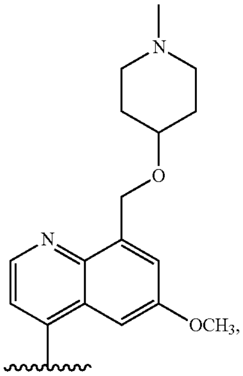
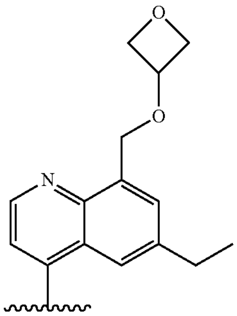,
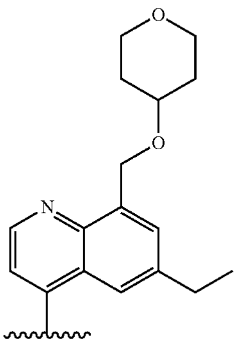,
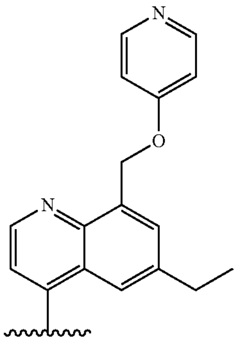,
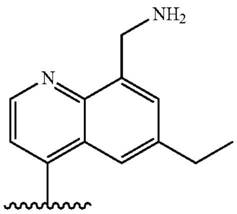,
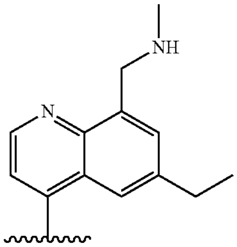,
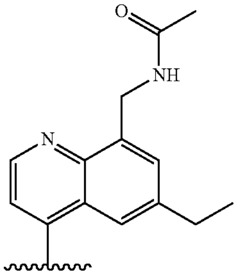, -continued
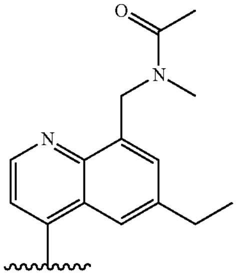
,
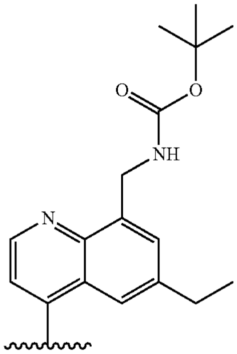
,
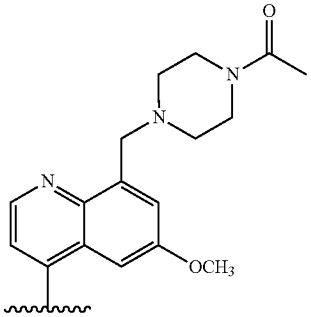
,
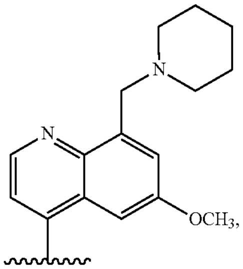
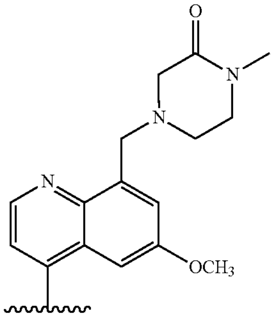
,
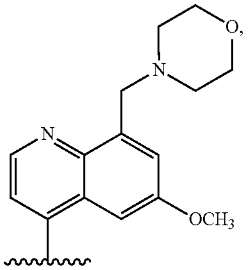
-continued
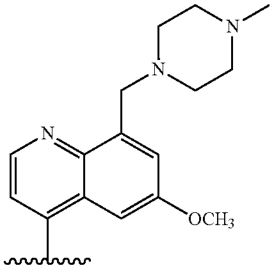
,
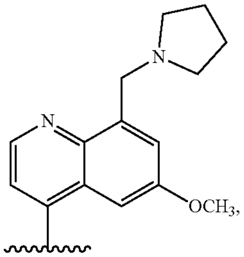
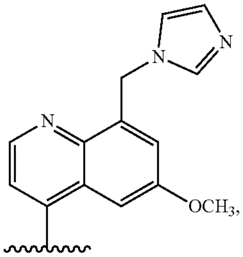
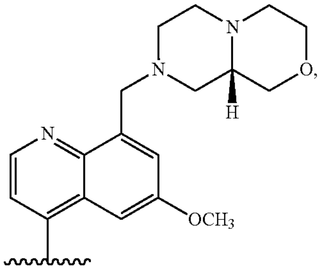
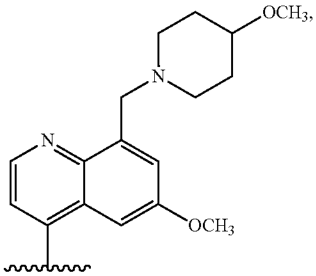
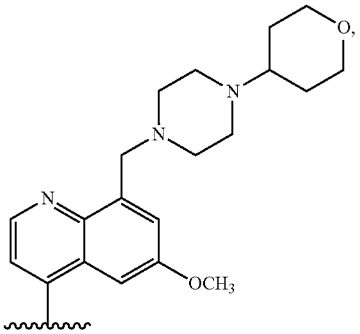

-continued
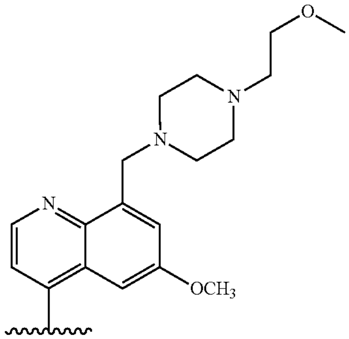
,
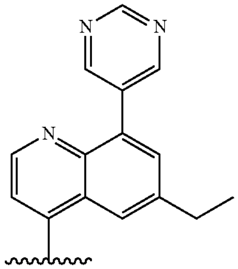
,
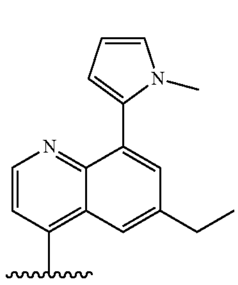
,
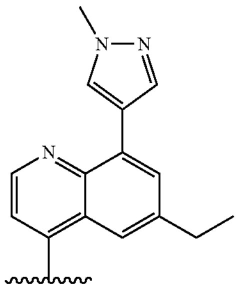
,
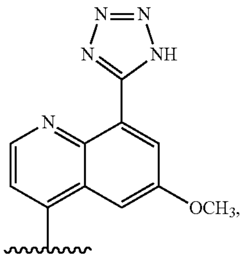
,
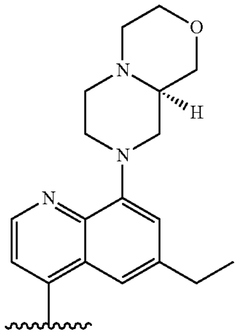
,
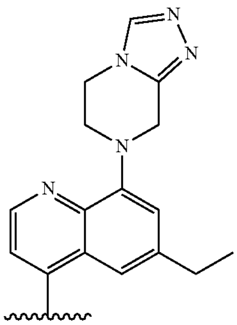
,
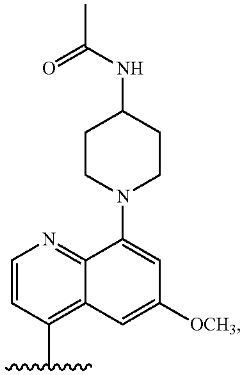
,
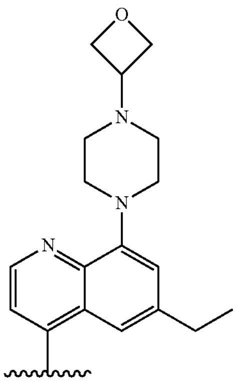
,
-continued
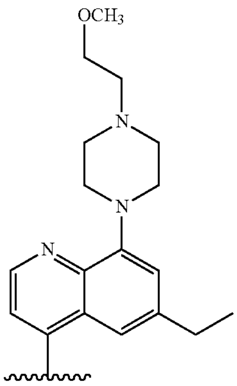
,
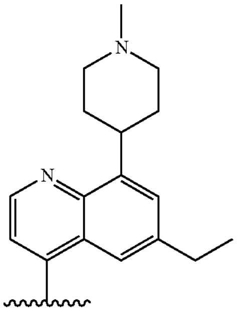
,
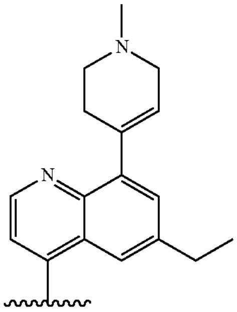
,
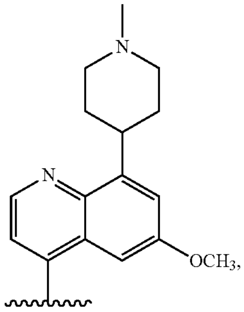
,
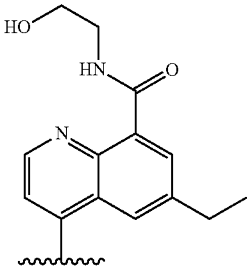
,
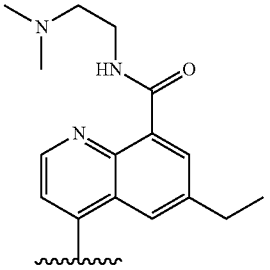
,
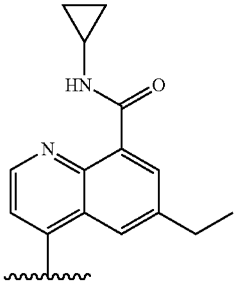
,
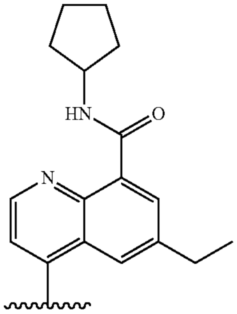
, -continued
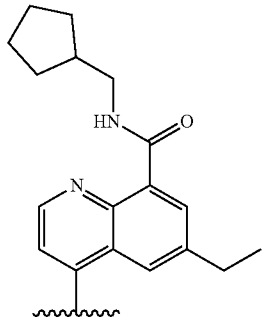
,
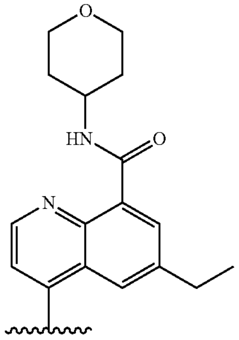
,
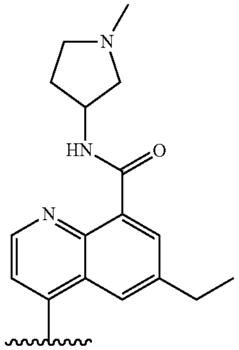
,
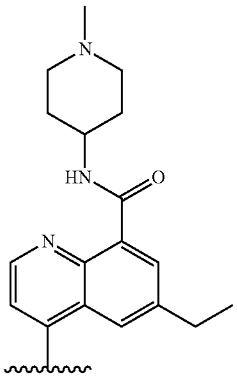
,
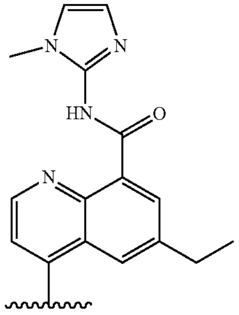
,
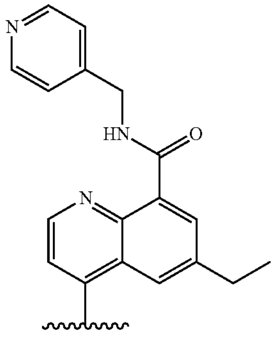
,
-continued
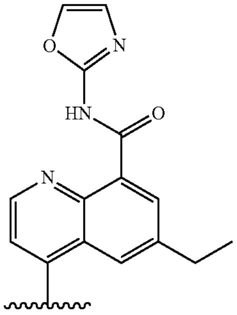
,
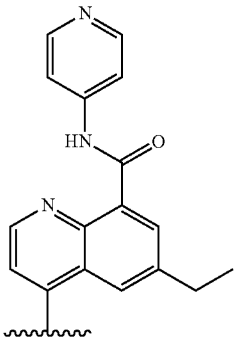
,
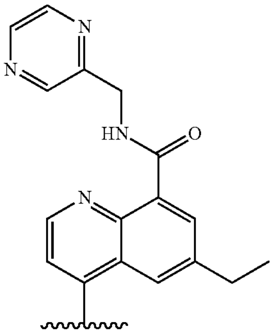
,
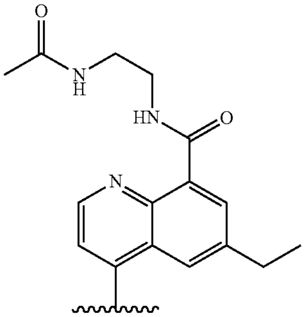
,
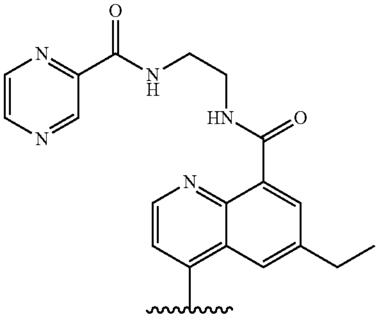
,
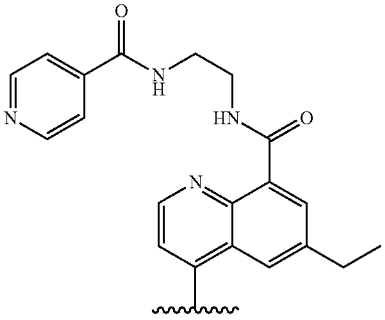
, -continued
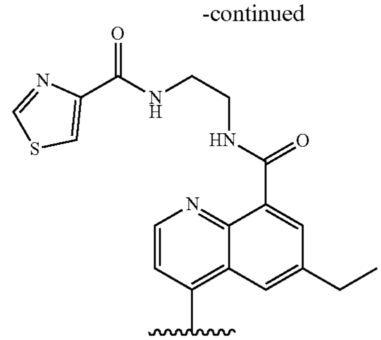,
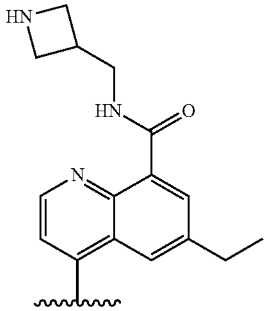,
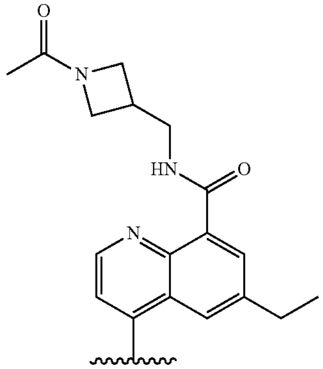,
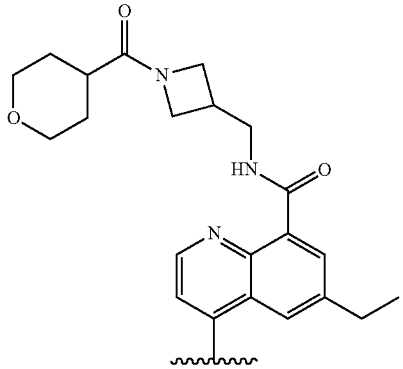,
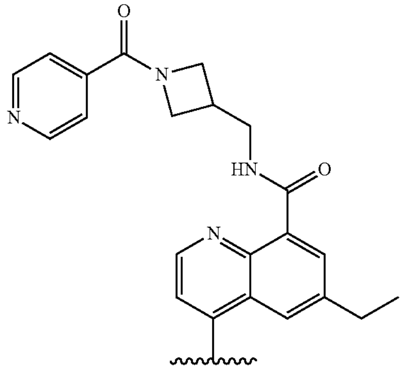,
-continued
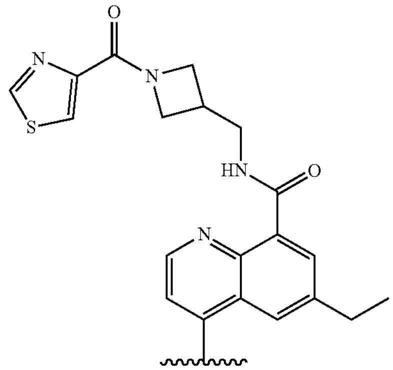,
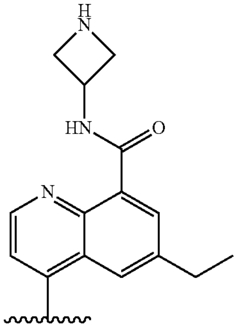, 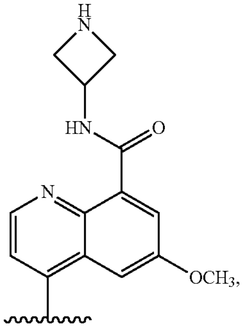
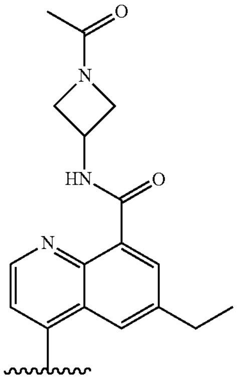, 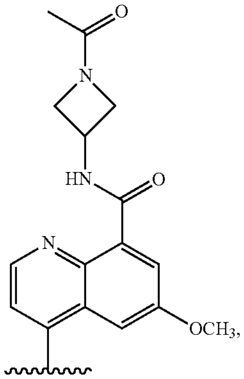
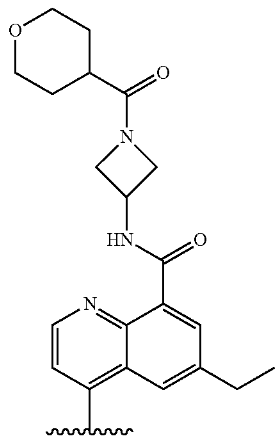, -continued
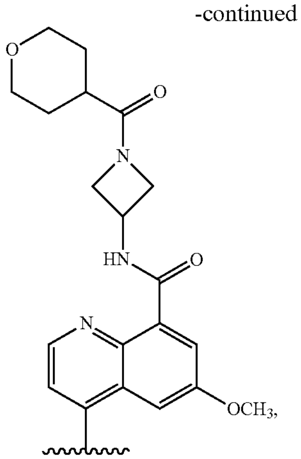
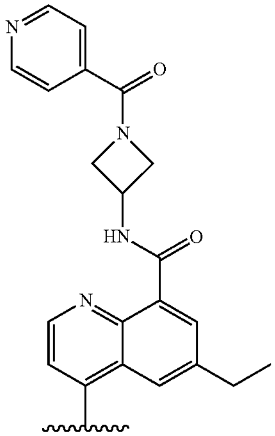
,
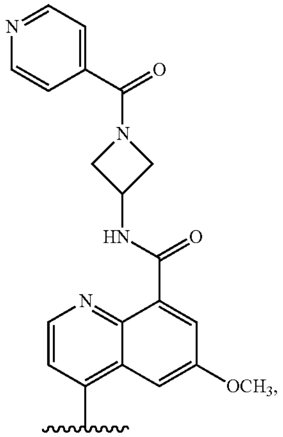
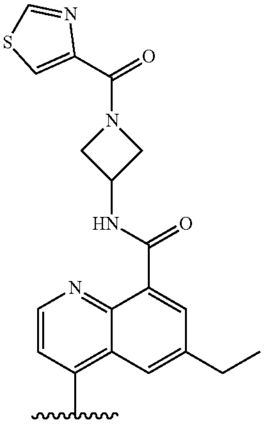
,
-continued
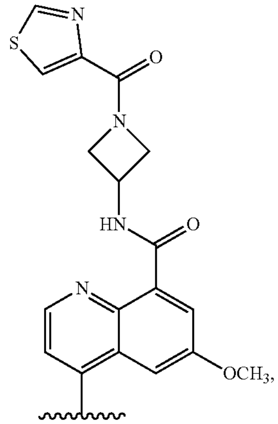
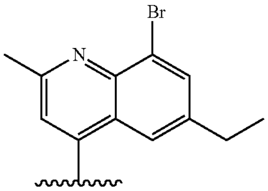
,
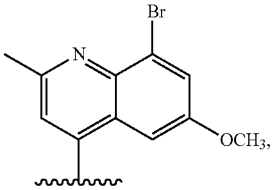
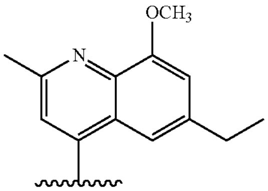
,
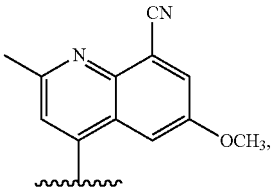
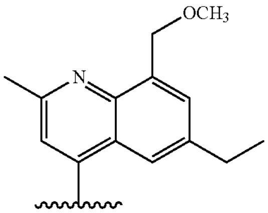
,
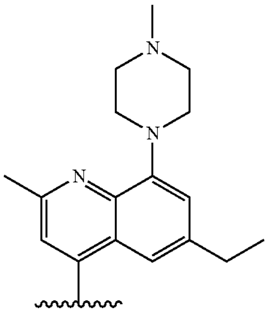
, -continued
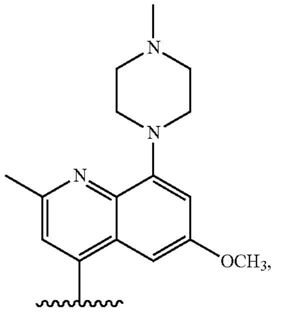
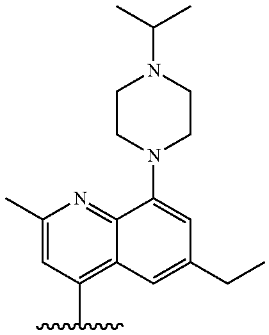
,
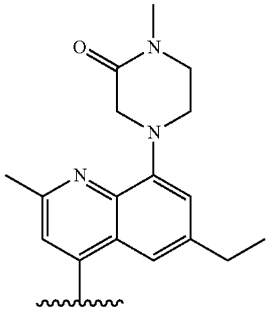
,
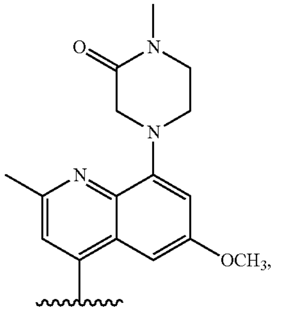
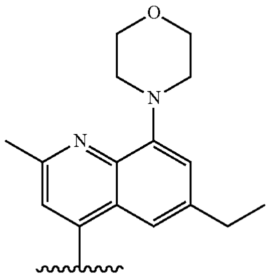
,
-continued
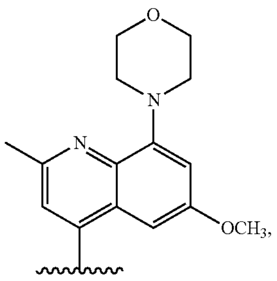
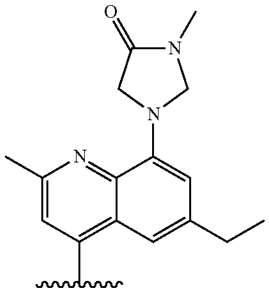
,
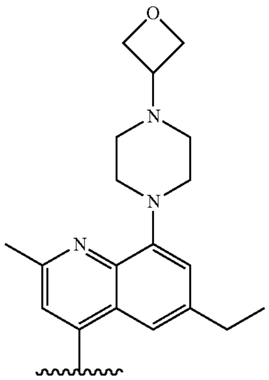
,
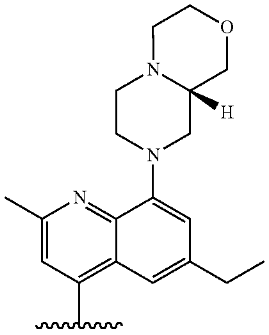
,
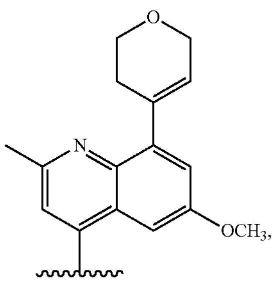

-continued
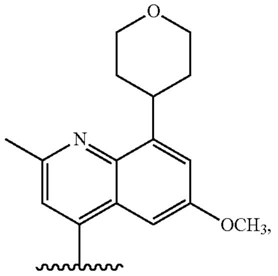
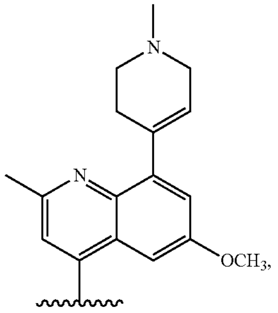
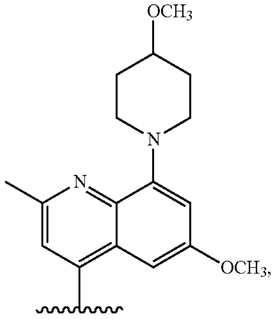
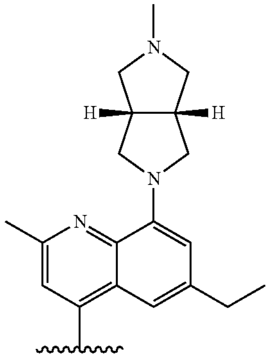
,
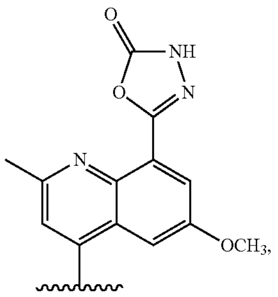
-continued
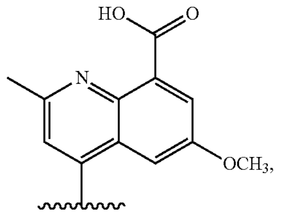
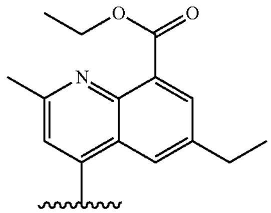
,
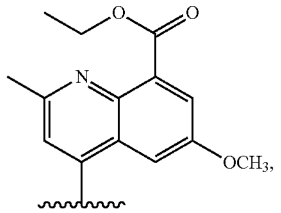
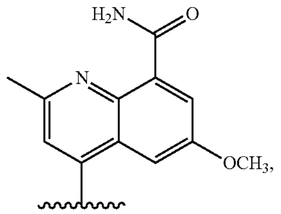
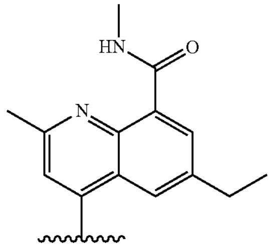
,
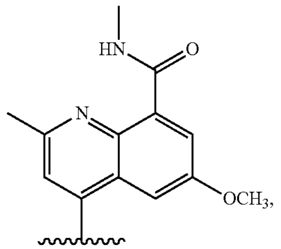
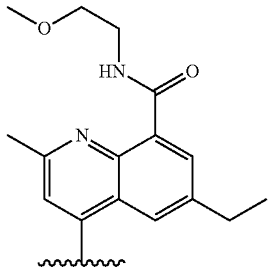
, -continued
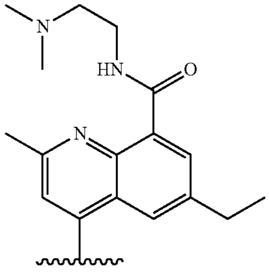
,
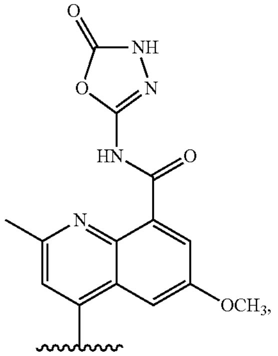
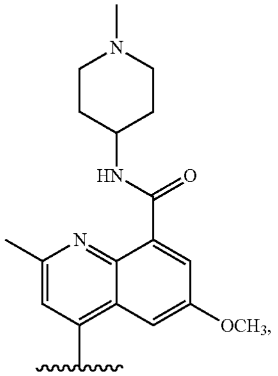
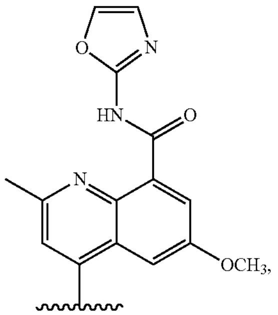
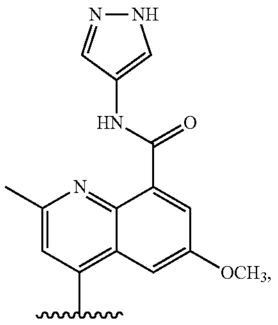
-continued
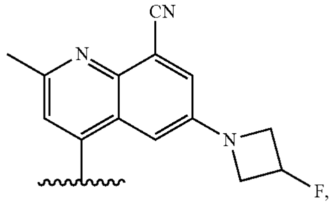
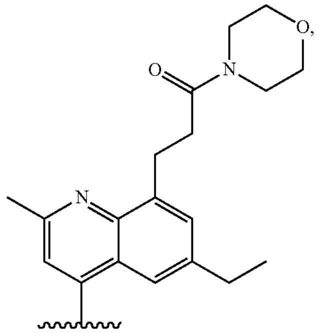
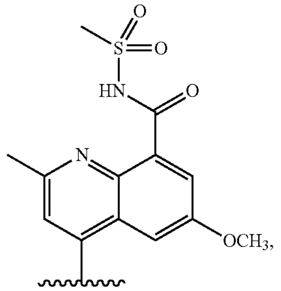
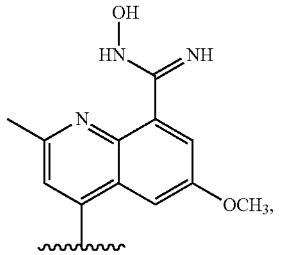
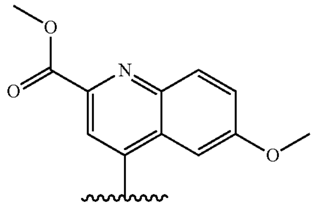
,
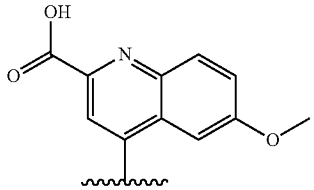
,
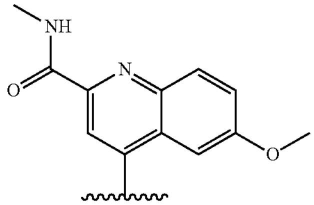
, -continued

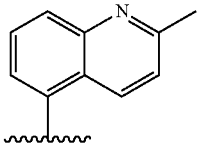,
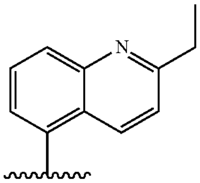,
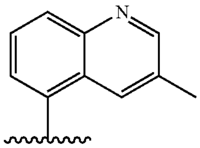,
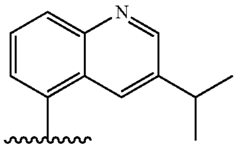,
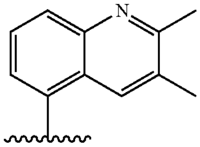,
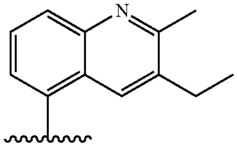,
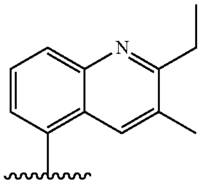,
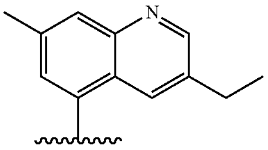,
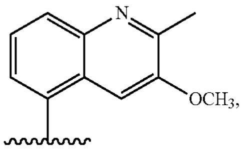
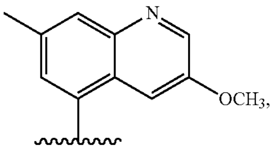
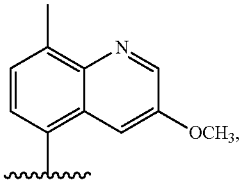
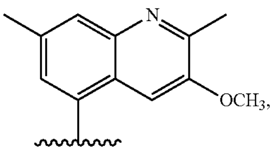
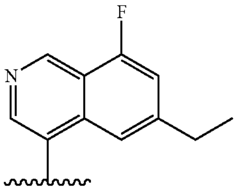,
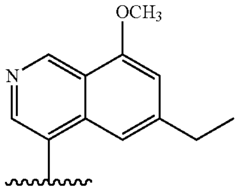,
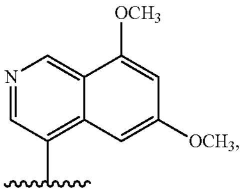
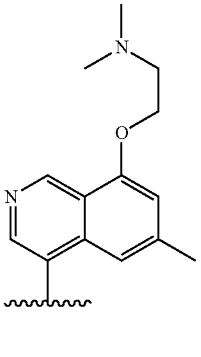, -continued

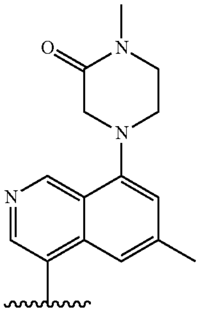,
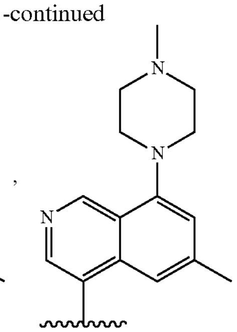,
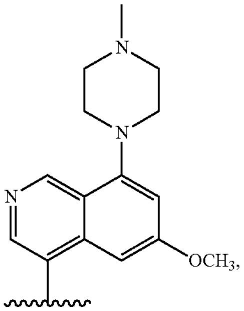
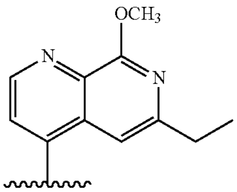,
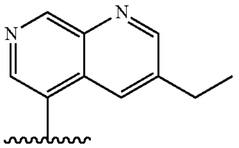,
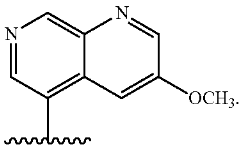 or
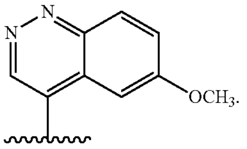

In the compounds and embodiments described herein, $R^4$ is hydrogen, halogen, $C_{1-6}$alkyl, $C_{1-6}$haloalkyl, $C_{1-6}$haloalkenyl, $—OR^{4a}$, $—SR^{4a}$, $—N(R^{4a})_2$, $—S(O)R^{4b}$, $—S(O)_2R^{4b}$, $—S(O)_2N(R^{4a})_2$, $—C(O)N(R^{4a})_2$, $—C(O)R^{4a}$, $—NR^{4a}C(O)R^{4a}$, $—NR^{4a}C(O)OR^{4a}$, $—NR^{4a}C(O)N(R^{4a})_2$, $—NR^{4a}S(O)_2R^{4b}$, $—NR^{4a}S(O)_2N(R^{4a})_2$, or $G^2$, wherein $R^{4a}$, $R^{4b}$, and $G^2$ are as described herein.

In some embodiments, $R^4$ is $G^2$, wherein $G^2$ is as defined herein. Compounds wherein $R^4$ is $G^2$, include formula (I-b), wherein $G^1$, $G^2$, $R^5$, $R^6$, and $R^8$ are as defined herein.

(I-b)

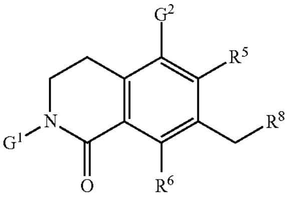

In some embodiments, $R^4$ is $G^2$; and $G^2$ is a $C_{3-10}$carbocyclyl, a 6- to 12-membered aryl, or a 5- to 12-membered heteroaryl, and optionally substituted as defined herein, $R^4$ may be $G^2$, wherein $G^2$ may be a $C_{3-8}$cycloalkyl, a phenyl, or a 5- to 6-membered heteroaryl, and optionally substituted as defined herein. The 5- to 6-membered heteroaryl of $G^2$ may contain 1-3 heteroatoms independently selected from the group consisting of oxygen and nitrogen. $R^4$ may be $G^2$, wherein $G^2$ may be phenyl, pyridinyl, pyrimidinyl, pyrazolyl, imidazolyl, or isoxazolyl, and $G^2$ is optionally substituted as defined herein. For example, $G^2$ may be substituted with 1-4 substituents independently selected from the group consisting of halogen, $C_{1-6}$alkyl, and $C_{1-6}$haloalkyl. In further embodiments, $R^4$ may be phenyl,

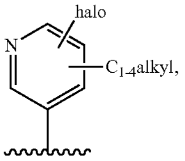
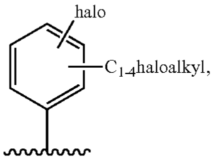
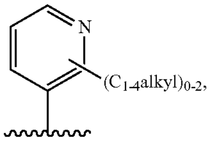
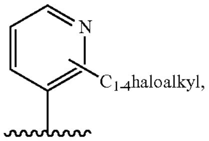
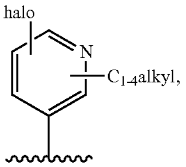
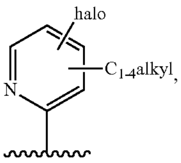
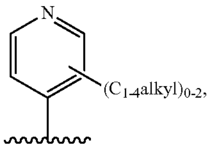
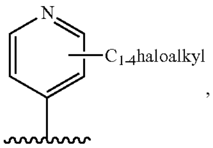
,
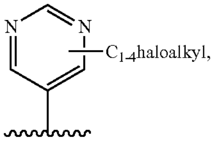
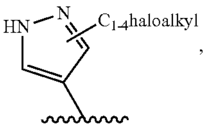
,
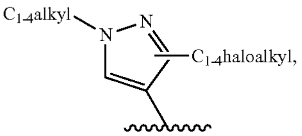
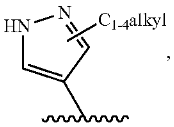
,
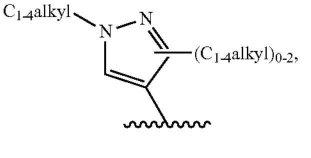
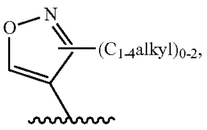
or
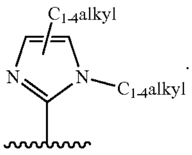
.

In still further embodiments, $R^4$ may be phenyl,

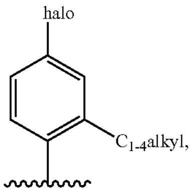
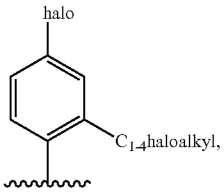
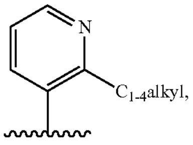
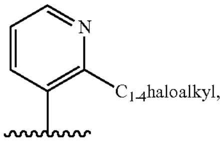
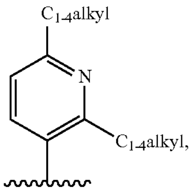
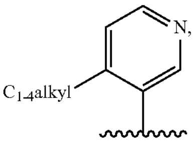
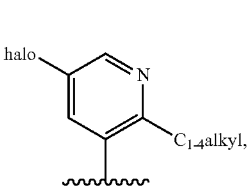
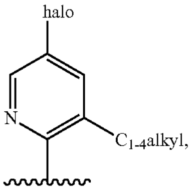
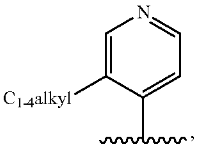
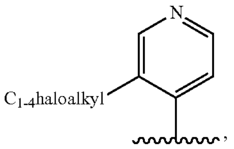
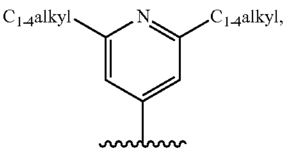
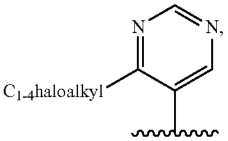
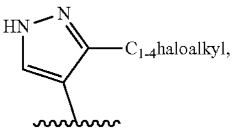
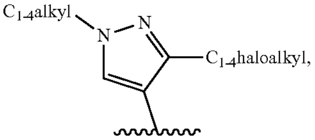
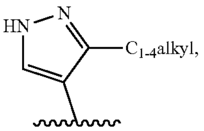
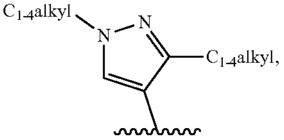
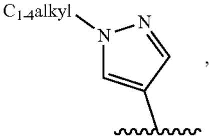
,
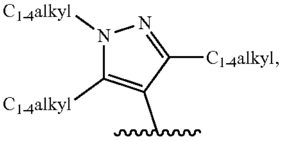

-continued

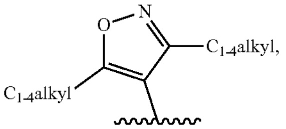

or

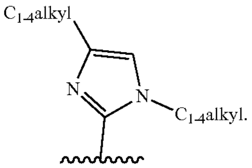

In yet further embodiments, $R^4$ may be phenyl

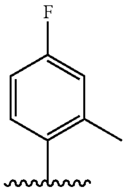

,

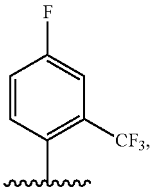

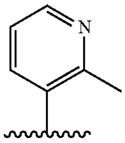

,

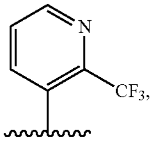

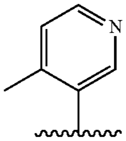

,

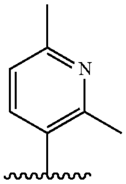

,

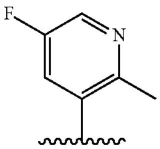

,

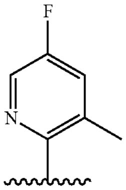

,

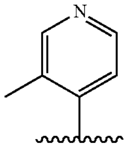

,

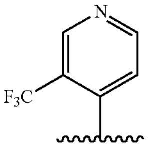

,

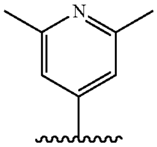

,

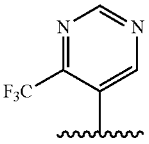

,

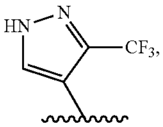

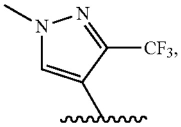

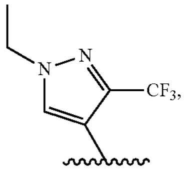

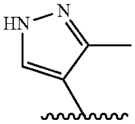

,

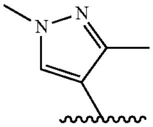

,

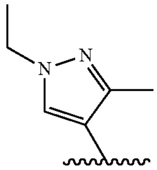

,

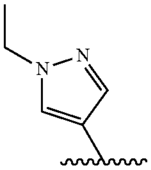

,

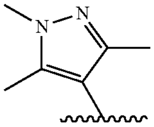

,

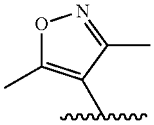

, or

-continued

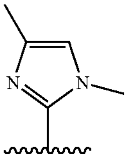

.

In yet further embodiments, $R^4$ may be

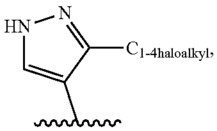

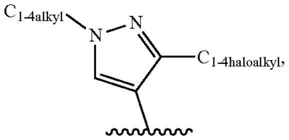

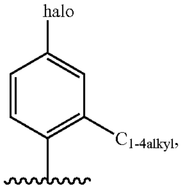

or

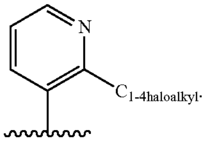

In yet further embodiments, $R^4$ may be

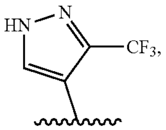

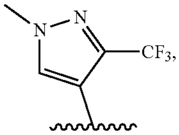

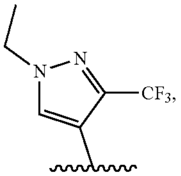

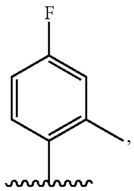

, or

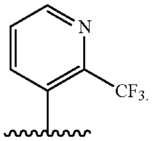

In the embodiments and compounds described herein, $R^{4c}$, at each occurrence, may independently be hydrogen, $C_{1-6}$alkyl, or $C_{1-6}$haloalkyl.

In the embodiments and compounds described herein, $R^{4d}$, at each occurrence, may independently be $C_{1-6}$alkyl or $C_{1-6}$haloalkyl.

Included in the embodiments herein $R^{2a}$, $R^{1b}$, $R^{3a}$, and $R^{3b}$ may each be hydrogen.

In the embodiments herein n may be 0. In the embodiments herein n may be 1. In the embodiments herein n may be 2.

In the embodiments herein, $R^5$ may be hydrogen or halogen.

In the embodiments herein, $R^6$ may be hydrogen.

In the embodiments herein, $R^{7a}$ and $R^{7b}$ may each be hydrogen. In the embodiments and compounds described herein $R^{7a}$ may be hydroxy and $R^{7b}$ may be hydrogen.

In the compounds of formula (I) are compounds of formula (I-a), wherein $R^1$, $R^4$, and $R^8$ are as defined herein.

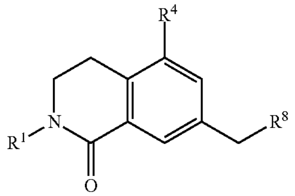

(I-a)

In certain embodiments, the compound of formula (I) is selected from the group consisting of the compounds in Table 1, or a pharmaceutically acceptable salt thereof.

TABLE 1

Exemplary compounds.

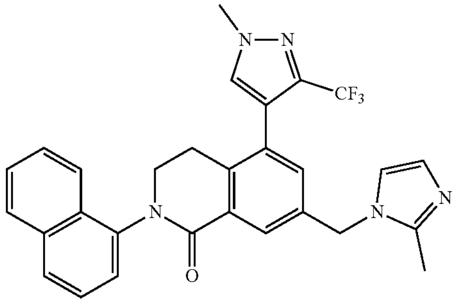 [SMILES: Cc1nccn1Cc1cc2c(c(-c3cn(C)nc3C(F)(F)F)c1)CCN(c1cccc3ccccc13)C2=O]

I-1

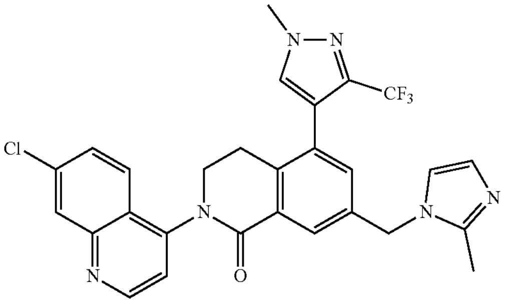 [SMILES: Cc1nccn1Cc1cc2c(c(-c3cn(C)nc3C(F)(F)F)c1)CCN(c1ccnc3cc(Cl)ccc13)C2=O]

I-2

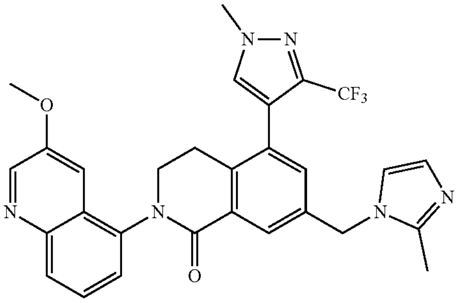 [SMILES: COc1cnc2cccc(N3CCc4c(cc(Cn5ccnc5C)cc4-c4cn(C)nc4C(F)(F)F)C3=O)c2c1]

I-3

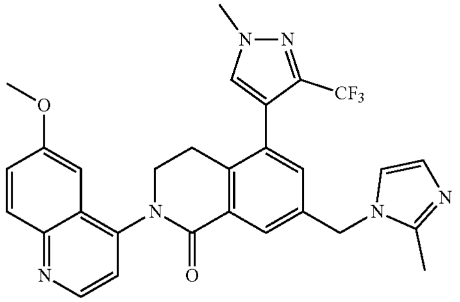 [SMILES: COc1ccc2nccc(N3CCc4c(cc(Cn5ccnc5C)cc4-c4cn(C)nc4C(F)(F)F)C3=O)c2c1]

I-4

TABLE 1-continued
| Exemplary compounds. |
| --- |
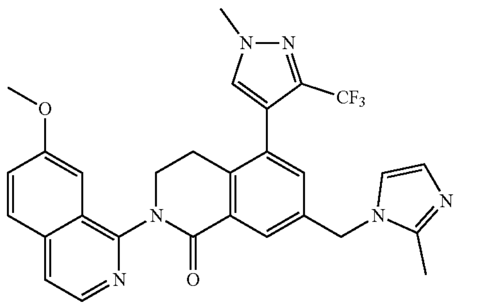 [SMILES: COc1ccc2ccnc(N3CCc4c(cc(Cn5ccnc5C)cc4-c4cn(C)nc4C(F)(F)F)C3=O)c2c1]
I-5
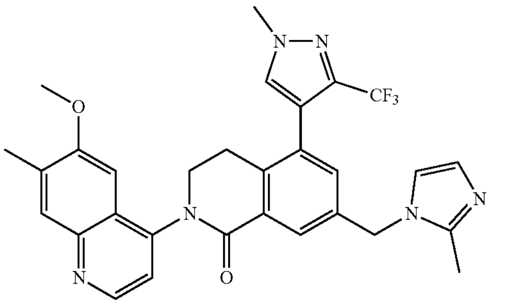 [SMILES: COc1cc2c(N3CCc4c(cc(Cn5ccnc5C)cc4-c4cn(C)nc4C(F)(F)F)C3=O)ccnc2cc1C]
I-6
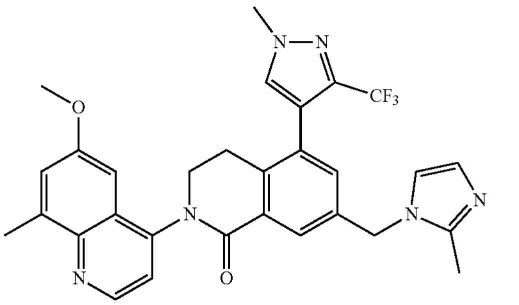 [SMILES: COc1cc(C)c2nccc(N3CCc4c(cc(Cn5ccnc5C)cc4-c4cn(C)nc4C(F)(F)F)C3=O)c2c1]
I-7
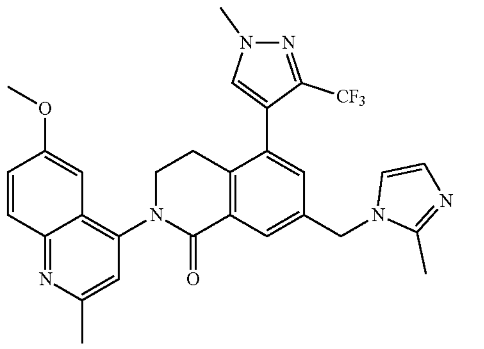 [SMILES: COc1ccc2nc(C)cc(N3CCc4c(cc(Cn5ccnc5C)cc4-c4cn(C)nc4C(F)(F)F)C3=O)c2c1]
I-8
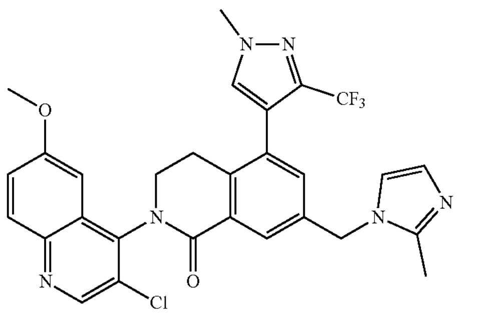 [SMILES: COc1ccc2ncc(Cl)c(N3CCc4c(cc(Cn5ccnc5C)cc4-c4cn(C)nc4C(F)(F)F)C3=O)c2c1]
I-9

TABLE 1-continued
Exemplary compounds.
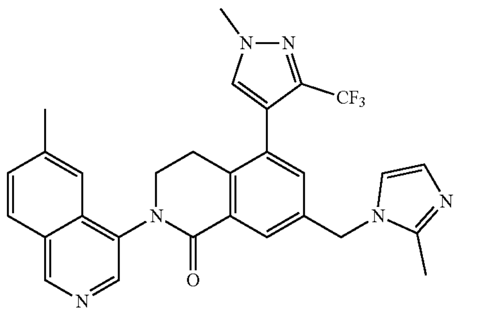 [SMILES: Cc1ccc2cncc(N3CCc4c(cc(Cn5ccnc5C)cc4-c4cn(C)nc4C(F)(F)F)C3=O)c2c1]
I-10
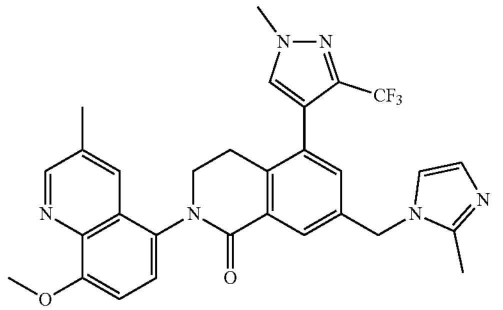 [SMILES: COc1ccc(N2CCc3c(cc(Cn4ccnc4C)cc3-c3cn(C)nc3C(F)(F)F)C2=O)c2cc(C)cnc12]
I-11
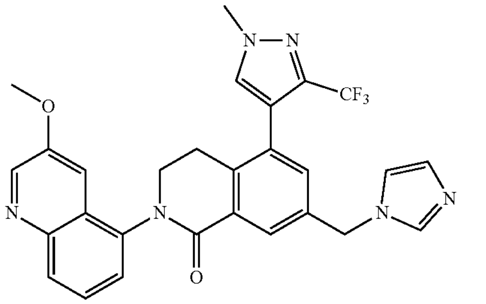 [SMILES: COc1cnc2cccc(N3CCc4c(cc(Cn5ccnc5)cc4-c4cn(C)nc4C(F)(F)F)C3=O)c2c1]
I-12
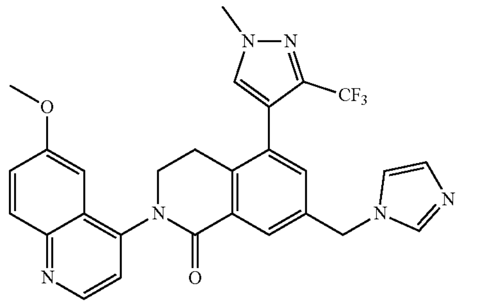 [SMILES: COc1ccc2nccc(N3CCc4c(cc(Cn5ccnc5)cc4-c4cn(C)nc4C(F)(F)F)C3=O)c2c1]
I-13
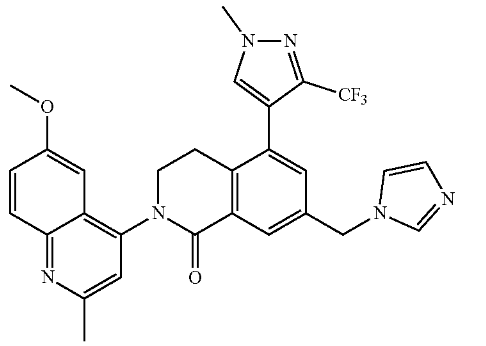 [SMILES: COc1ccc2nc(C)cc(N3CCc4c(cc(Cn5ccnc5)cc4-c4cn(C)nc4C(F)(F)F)C3=O)c2c1]
I-14

TABLE 1-continued
| Exemplary compounds. |
| --- |
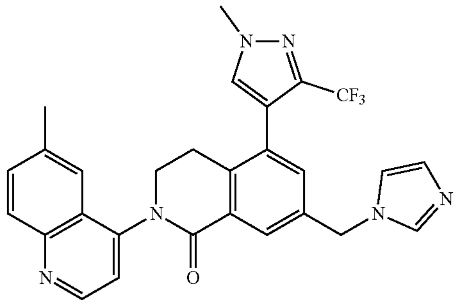 [SMILES: Cc1ccc2nccc(N3CCc4c(cc(Cn5ccnc5)cc4-c4cn(C)nc4C(F)(F)F)C3=O)c2c1]
I-15
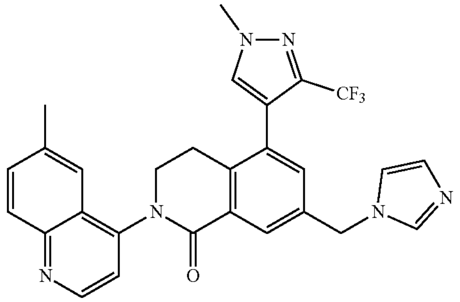 [SMILES: Cc1ccc2nccc(N3CCc4c(cc(Cn5ccnc5)cc4-c4cn(C)nc4C(F)(F)F)C3=O)c2c1]
I-16
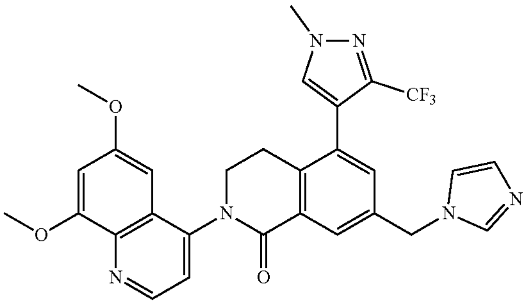 [SMILES: COc1cc(OC)c2nccc(N3CCc4c(cc(Cn5ccnc5)cc4-c4cn(C)nc4C(F)(F)F)C3=O)c2c1]
I-17
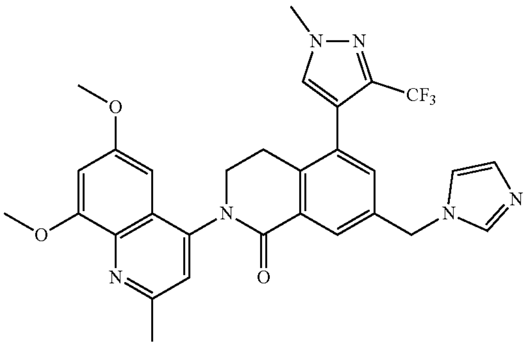
I-18
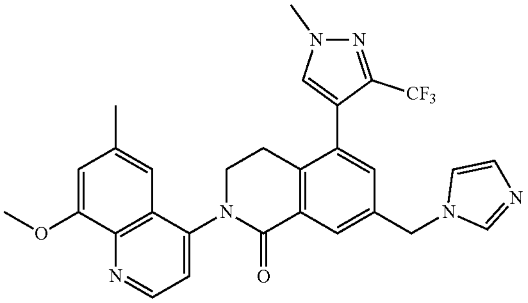 [SMILES: COc1cc(C)cc2c(N3CCc4c(cc(Cn5ccnc5)cc4-c4cn(C)nc4C(F)(F)F)C3=O)ccnc12]
I-19

TABLE 1-continued
Exemplary compounds.
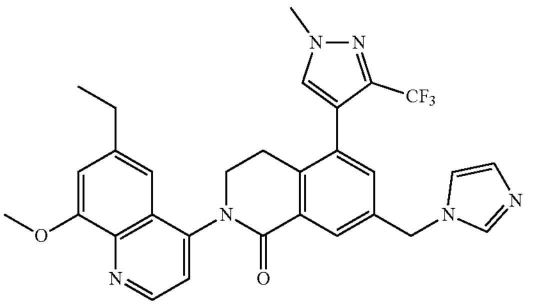 [SMILES: CCc1cc(OC)c2nccc(N3CCc4c(cc(Cn5ccnc5)cc4-c4cn(C)nc4C(F)(F)F)C3=O)c2c1]
I-20
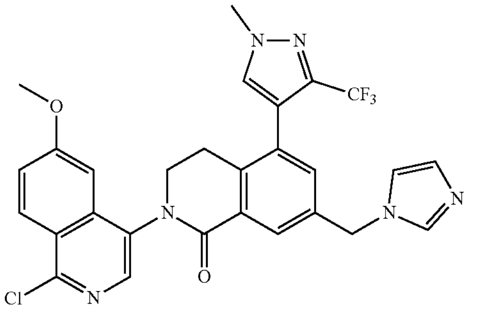 [SMILES: COc1ccc2c(Cl)ncc(N3CCc4c(cc(Cn5ccnc5)cc4-c4cn(C)nc4C(F)(F)F)C3=O)c2c1]
I-21
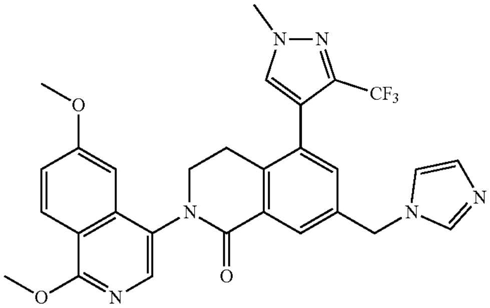 [SMILES: COc1ccc2c(OC)ncc(N3CCc4c(cc(Cn5ccnc5)cc4-c4cn(C)nc4C(F)(F)F)C3=O)c2c1]
I-22
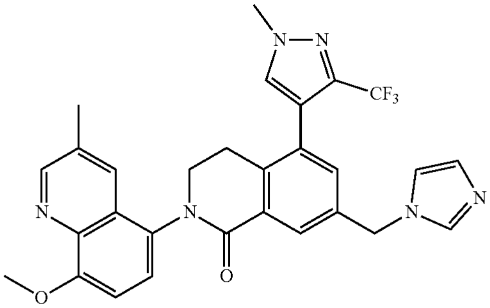 [SMILES: COc1ccc(N2CCc3c(cc(Cn4ccnc4)cc3-c3cn(C)nc3C(F)(F)F)C2=O)c2cc(C)cnc12]
I-23
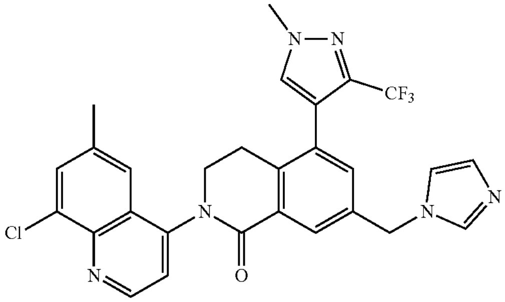 [SMILES: Cc1cc(Cl)c2nccc(N3CCc4c(cc(Cn5ccnc5)cc4-c4cn(C)nc4C(F)(F)F)C3=O)c2c1]
I-24

TABLE 1-continued
Exemplary compounds.
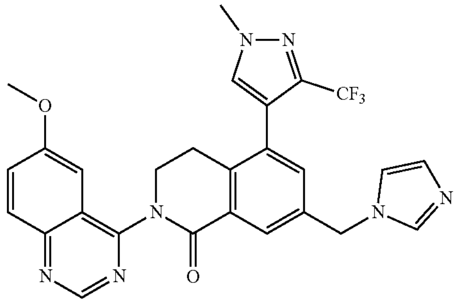 [SMILES: COc1ccc2ncnc(N3CCc4c(cc(Cn5ccnc5)cc4-c4cn(C)nc4C(F)(F)F)C3=O)c2c1]
I-25
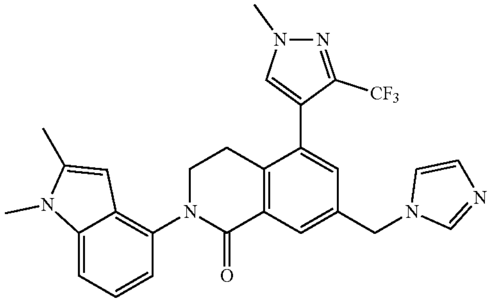 [SMILES: Cc1cc2c(N3CCc4c(cc(Cn5ccnc5)cc4-c4cn(C)nc4C(F)(F)F)C3=O)cccc2n1C]
I-26
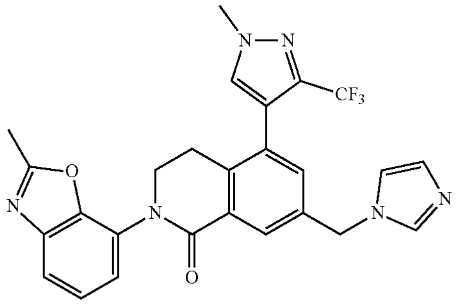 [SMILES: Cc1nc2cccc(N3CCc4c(cc(Cn5ccnc5)cc4-c4cn(C)nc4C(F)(F)F)C3=O)c2o1]
I-27
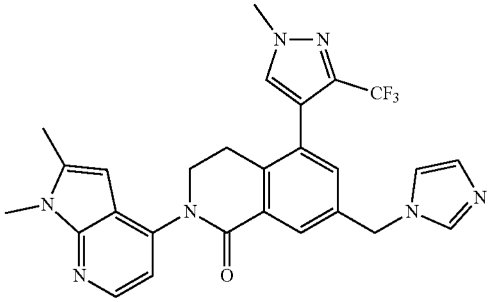
I-28
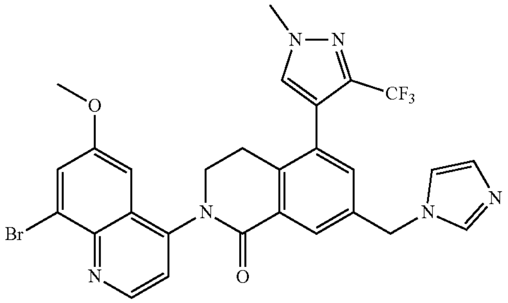 [SMILES: COc1cc(Br)c2nccc(N3CCc4c(cc(Cn5ccnc5)cc4-c4cn(C)nc4C(F)(F)F)C3=O)c2c1]
I-29

TABLE 1-continued
| Exemplary compounds. |
| --- |
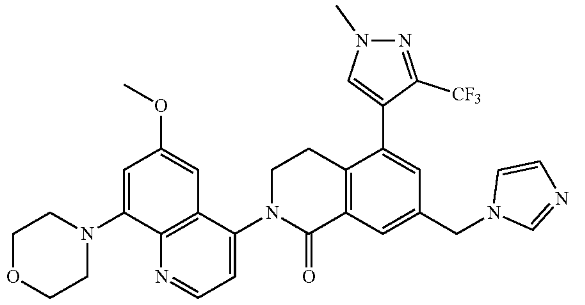 [SMILES: COc1cc(N2CCOCC2)c2nccc(N3CCc4c(cc(Cn5ccnc5)cc4-c4cn(C)nc4C(F)(F)F)C3=O)c2c1]
I-30
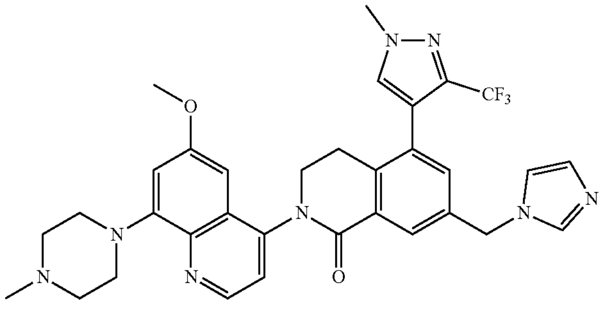 [SMILES: COc1cc(N2CCN(C)CC2)c2nccc(N3CCc4c(cc(Cn5ccnc5)cc4-c4cn(C)nc4C(F)(F)F)C3=O)c2c1]
I-31
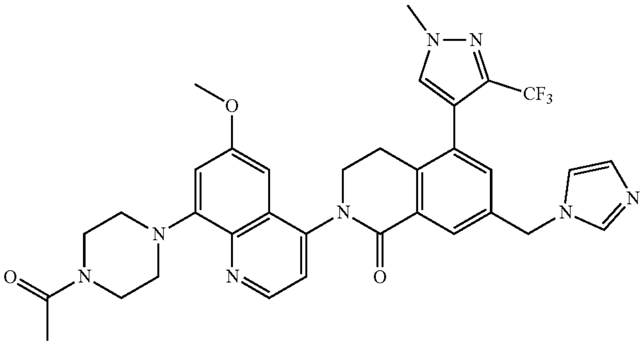 [SMILES: COc1cc(N2CCN(C(C)=O)CC2)c2nccc(N3CCc4c(cc(Cn5ccnc5)cc4-c4cn(C)nc4C(F)(F)F)C3=O)c2c1]
I-32
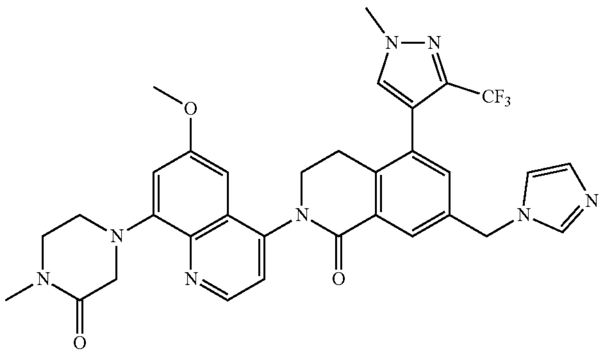 [SMILES: COc1cc(N2CCN(C)C(=O)C2)c2nccc(N3CCc4c(cc(Cn5ccnc5)cc4-c4cn(C)nc4C(F)(F)F)C3=O)c2c1]
I-33

TABLE 1-continued
Exemplary compounds.
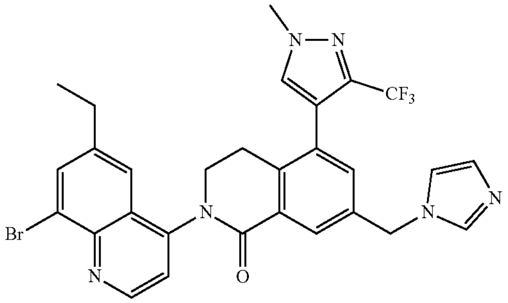 [SMILES: CCc1cc(Br)c2nccc(N3CCc4c(cc(Cn5ccnc5)cc4-c4cn(C)nc4C(F)(F)F)C3=O)c2c1]
I-34
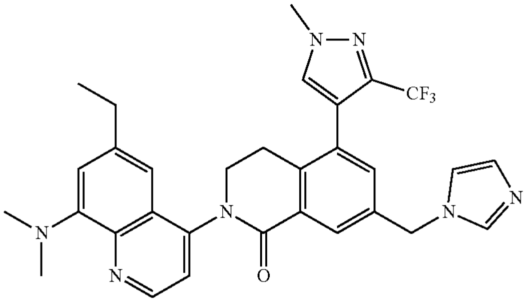 [SMILES: CCc1cc(N(C)C)c2nccc(N3CCc4c(cc(Cn5ccnc5)cc4-c4cn(C)nc4C(F)(F)F)C3=O)c2c1]
I-35
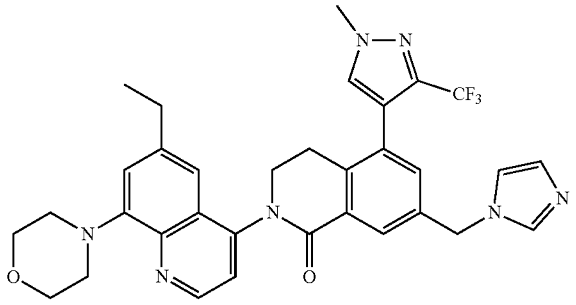 [SMILES: CCc1cc(N2CCOCC2)c2nccc(N3CCc4c(cc(Cn5ccnc5)cc4-c4cn(C)nc4C(F)(F)F)C3=O)c2c1]
I-36
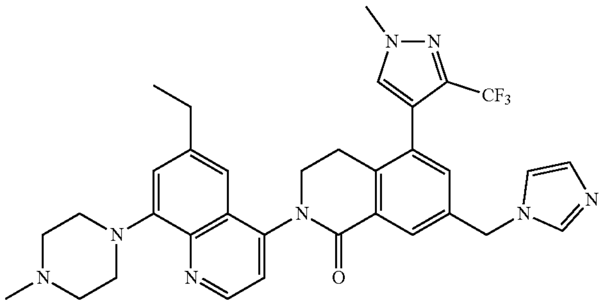 [SMILES: CCc1cc(N2CCN(C)CC2)c2nccc(N3CCc4c(cc(Cn5ccnc5)cc4-c4cn(C)nc4C(F)(F)F)C3=O)c2c1]
I-37
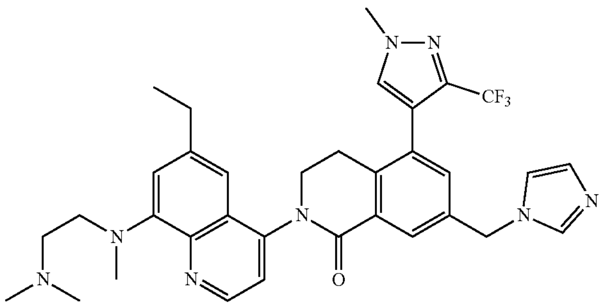 [SMILES: CCc1cc(N(C)CCN(C)C)c2nccc(N3CCc4c(cc(Cn5ccnc5)cc4-c4cn(C)nc4C(F)(F)F)C3=O)c2c1]
I-38

TABLE 1-continued
Exemplary compounds.
I-39
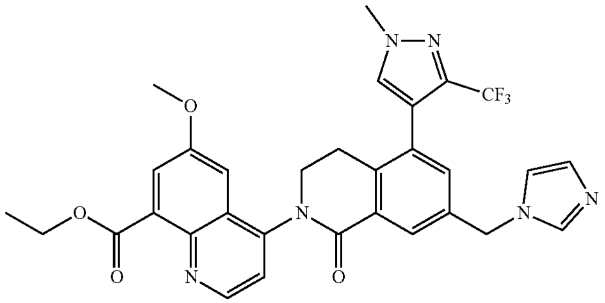 [SMILES: CCOC(=O)c1cc(OC)cc2c(N3CCc4c(cc(Cn5ccnc5)cc4-c4cn(C)nc4C(F)(F)F)C3=O)ccnc12]
I-40
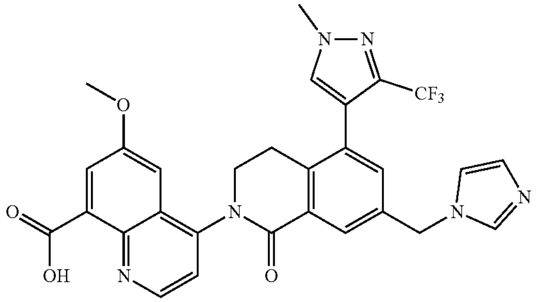
I-41
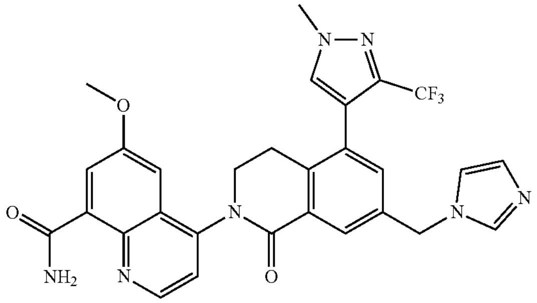
I-42
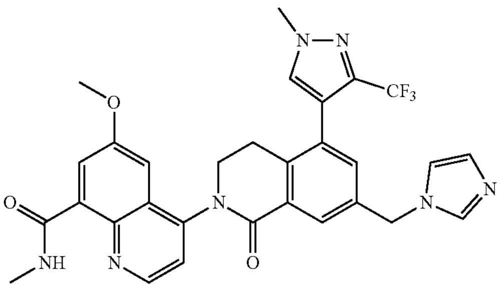 [SMILES: CNC(=O)c1cc(OC)cc2c(N3CCc4c(cc(Cn5ccnc5)cc4-c4cn(C)nc4C(F)(F)F)C3=O)ccnc12]

TABLE 1-continued
| Exemplary compounds. |
| --- |
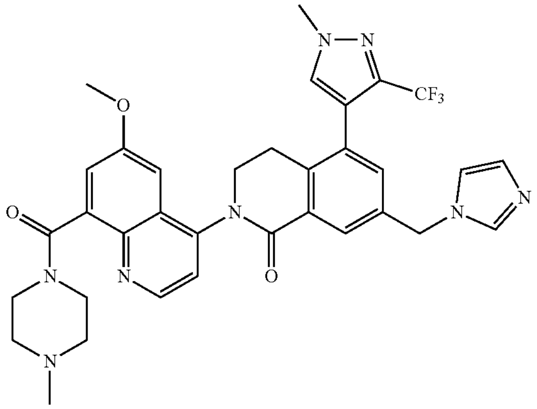 [SMILES: COc1cc(C(=O)N2CCN(C)CC2)c2nccc(N3CCc4c(cc(Cn5ccnc5)cc4-c4cn(C)nc4C(F)(F)F)C3=O)c2c1]
I-43
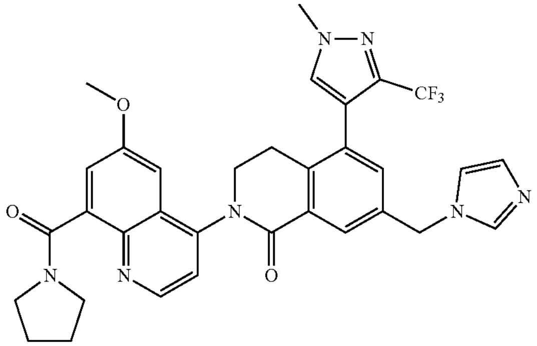 [SMILES: COc1cc(C(=O)N2CCCC2)c2nccc(N3CCc4c(cc(Cn5ccnc5)cc4-c4cn(C)nc4C(F)(F)F)C3=O)c2c1]
I-44
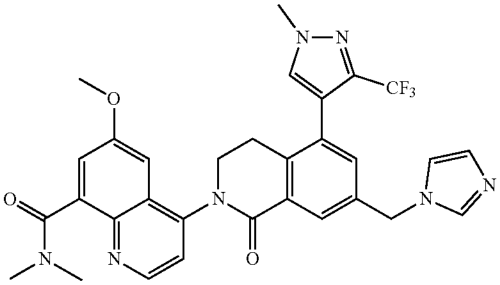 [SMILES: COc1cc(C(=O)N(C)C)c2nccc(N3CCc4c(cc(Cn5ccnc5)cc4-c4cn(C)nc4C(F)(F)F)C3=O)c2c1]
I-45
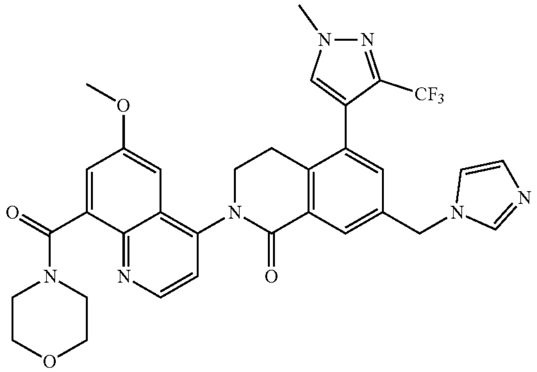 [SMILES: COc1cc(C(=O)N2CCOCC2)c2nccc(N3CCc4c(cc(Cn5ccnc5)cc4-c4cn(C)nc4C(F)(F)F)C3=O)c2c1]
I-46

TABLE 1-continued
Exemplary compounds.
I-47
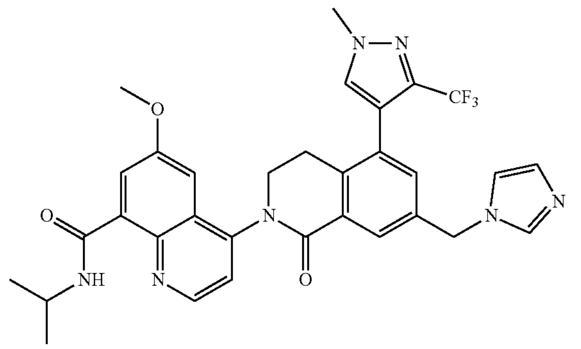 [SMILES: COc1cc(C(=O)NC(C)C)c2nccc(N3CCc4c(cc(Cn5ccnc5)cc4-c4cn(C)nc4C(F)(F)F)C3=O)c2c1]
I-48
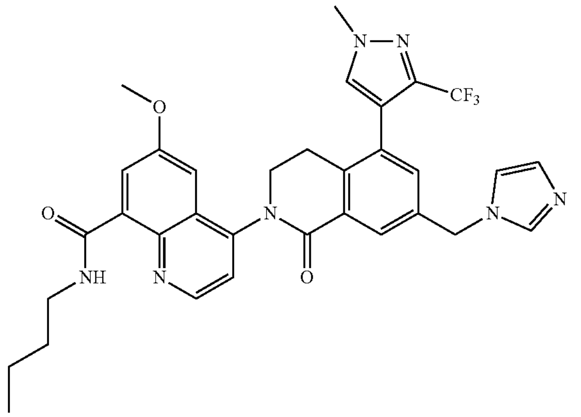 [SMILES: CCCCNC(=O)c1cc(OC)cc2c(N3CCc4c(cc(Cn5ccnc5)cc4-c4cn(C)nc4C(F)(F)F)C3=O)ccnc12]
I-49
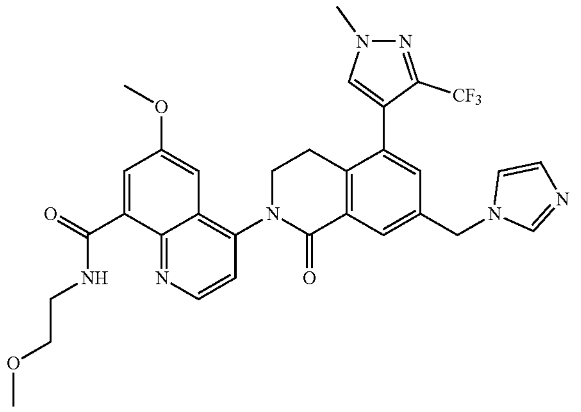 [SMILES: COCCNC(=O)c1cc(OC)cc2c(N3CCc4c(cc(Cn5ccnc5)cc4-c4cn(C)nc4C(F)(F)F)C3=O)ccnc12]
I-50
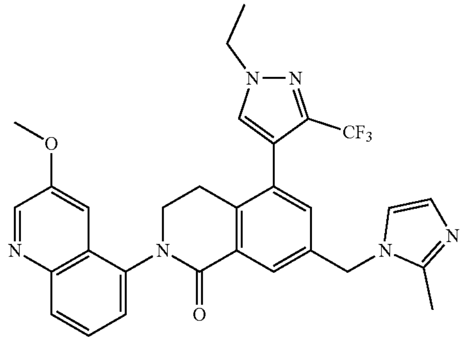 [SMILES: CCn1cc(-c2cc(Cn3ccnc3C)cc3c2CCN(c2cccc4ncc(OC)cc24)C3=O)c(C(F)(F)F)n1]

TABLE 1-continued
| Exemplary compounds. |
| --- |
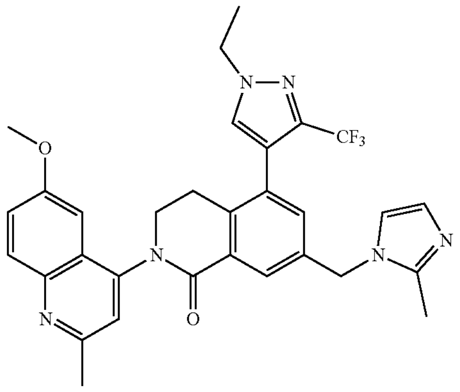 [SMILES: CCn1cc(-c2cc(Cn3ccnc3C)cc3c2CCN(c2cc(C)nc4ccc(OC)cc24)C3=O)c(C(F)(F)F)n1]
I-51
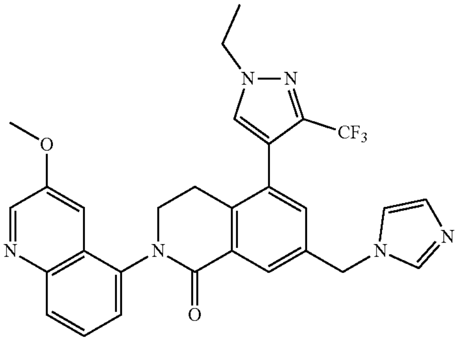 [SMILES: CCn1cc(-c2cc(Cn3ccnc3)cc3c2CCN(c2cccc4ncc(OC)cc24)C3=O)c(C(F)(F)F)n1]
I-52
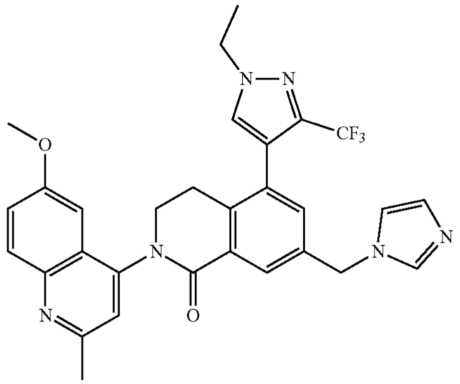 [SMILES: CCn1cc(-c2cc(Cn3ccnc3)cc3c2CCN(c2cc(C)nc4ccc(OC)cc24)C3=O)c(C(F)(F)F)n1]
I-53
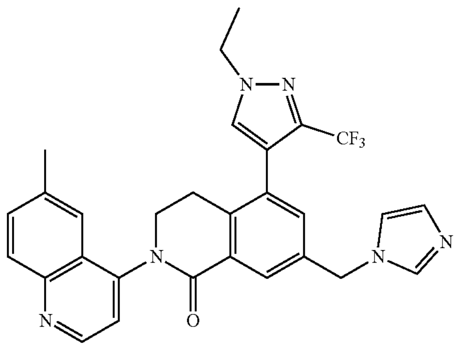 [SMILES: CCn1cc(-c2cc(Cn3ccnc3)cc3c2CCN(c2ccnc4ccc(C)cc24)C3=O)c(C(F)(F)F)n1]
I-54

TABLE 1-continued
Exemplary compounds.
I-55
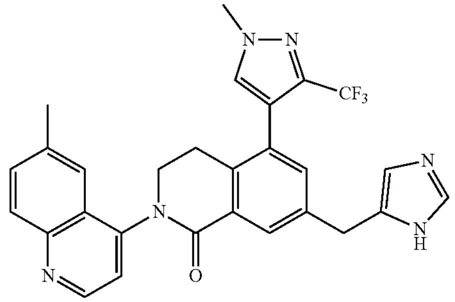 [SMILES: Cc1ccc2nccc(N3CCc4c(cc(Cc5cnc[nH]5)cc4-c4cn(C)nc4C(F)(F)F)C3=O)c2c1]
I-56
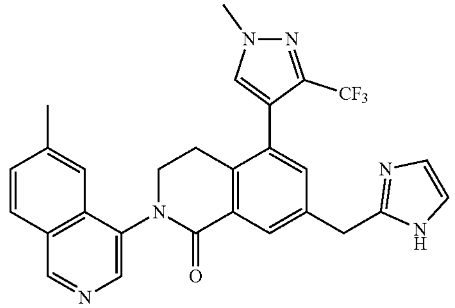 [SMILES: Cc1ccc2cncc(N3CCc4c(cc(Cc5ncc[nH]5)cc4-c4cn(C)nc4C(F)(F)F)C3=O)c2c1]
I-57
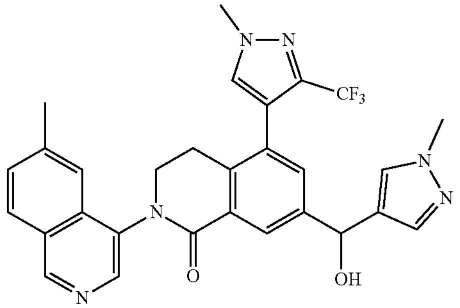 [SMILES: Cc1ccc2cncc(N3CCc4c(cc(C(O)c5cnn(C)c5)cc4-c4cn(C)nc4C(F)(F)F)C3=O)c2c1]
I-58
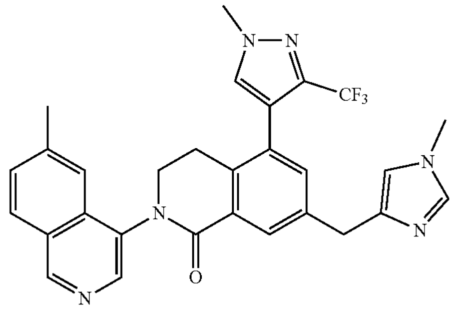 [SMILES: Cc1ccc2cncc(N3CCc4c(cc(Cc5cn(C)cn5)cc4-c4cn(C)nc4C(F)(F)F)C3=O)c2c1]
I-59
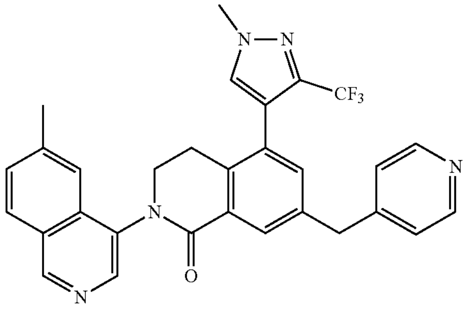 [SMILES: Cc1ccc2cncc(N3CCc4c(cc(Cc5ccncc5)cc4-c4cn(C)nc4C(F)(F)F)C3=O)c2c1]

TABLE 1-continued
Exemplary compounds.
I-60
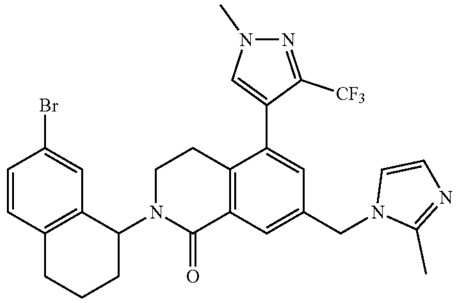 [SMILES: Cc1nccn1Cc1cc2c(c(-c3cn(C)nc3C(F)(F)F)c1)CCN(C1CCCc3ccc(Br)cc31)C2=O]
I-61
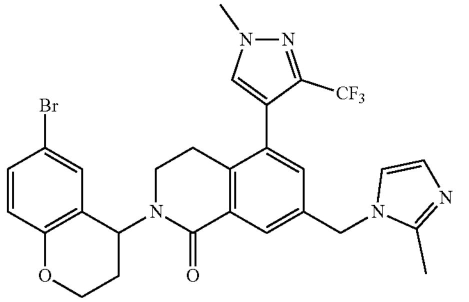
I-62
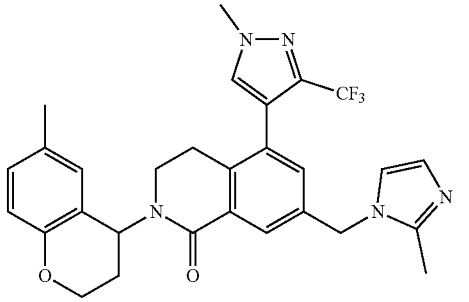 [SMILES: Cc1ccc2c(c1)C(N1CCc3c(cc(Cn4ccnc4C)cc3-c3cn(C)nc3C(F)(F)F)C1=O)CCO2]
I-63
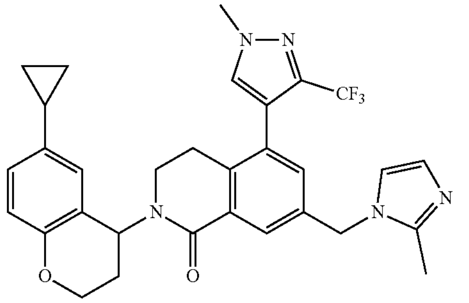 [SMILES: Cc1nccn1Cc1cc2c(c(-c3cn(C)nc3C(F)(F)F)c1)CCN(C1CCOc3ccc(C4CC4)cc31)C2=O]
I-64
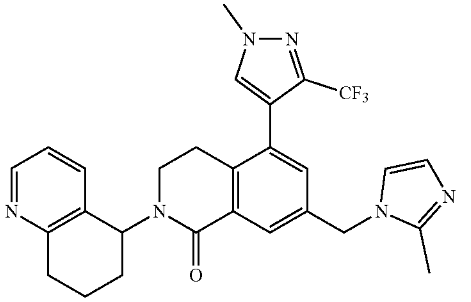 [SMILES: Cc1nccn1Cc1cc2c(c(-c3cn(C)nc3C(F)(F)F)c1)CCN(C1CCCc3ncccc31)C2=O]

TABLE 1-continued
| Exemplary compounds. |
| --- |
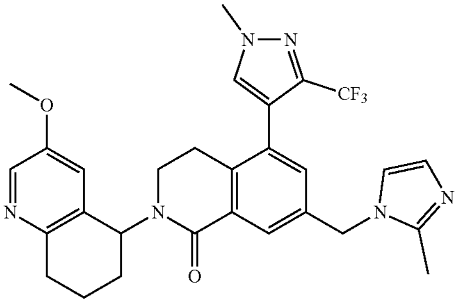 [SMILES: COc1cnc2c(c1)C(N1CCc3c(cc(Cn4ccnc4C)cc3-c3cn(C)nc3C(F)(F)F)C1=O)CCC2]
I-65
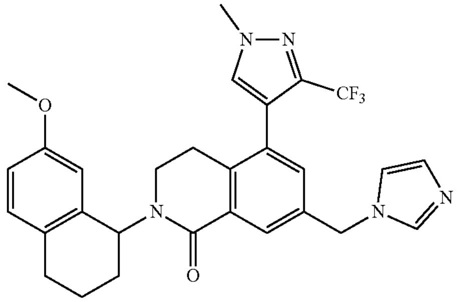 [SMILES: COc1ccc2c(c1)C(N1CCc3c(cc(Cn4ccnc4)cc3-c3cn(C)nc3C(F)(F)F)C1=O)CCC2]
I-66
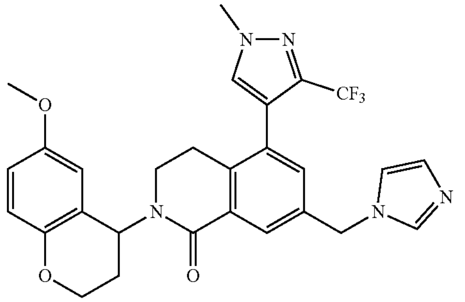 [SMILES: COc1ccc2c(c1)C(N1CCc3c(cc(Cn4ccnc4)cc3-c3cn(C)nc3C(F)(F)F)C1=O)CCO2]
I-67
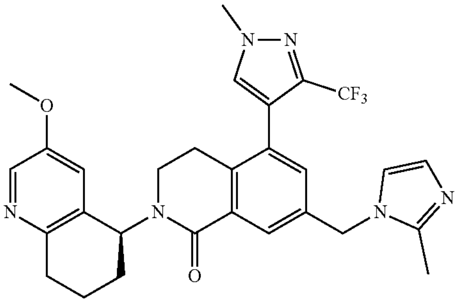 [SMILES: COc1cnc2c(c1)[C@@H](N1CCc3c(cc(Cn4ccnc4C)cc3-c3cn(C)nc3C(F)(F)F)C1=O)CCC2]
I-68
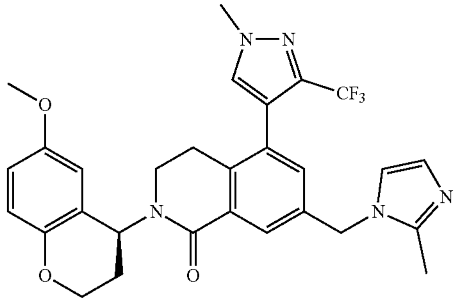 [SMILES: COc1ccc2c(c1)[C@@H](N1CCc3c(cc(Cn4ccnc4C)cc3-c3cn(C)nc3C(F)(F)F)C1=O)CCO2]
I-69

TABLE 1-continued
| Exemplary compounds. |
| --- |
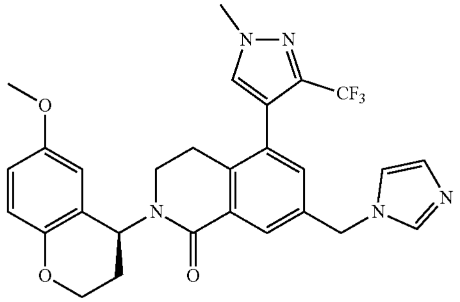 [SMILES: COc1ccc2c(c1)[C@@H](N1CCc3c(cc(Cn4ccnc4)cc3-c3cn(C)nc3C(F)(F)F)C1=O)CCO2]
I-70
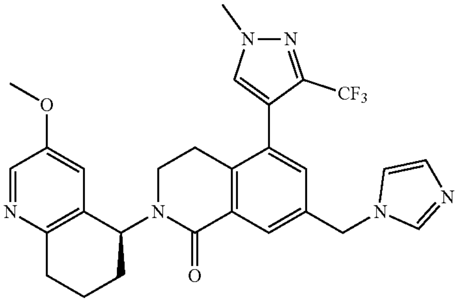 [SMILES: COc1cnc2c(c1)[C@@H](N1CCc3c(cc(Cn4ccnc4)cc3-c3cn(C)nc3C(F)(F)F)C1=O)CCC2]
I-71
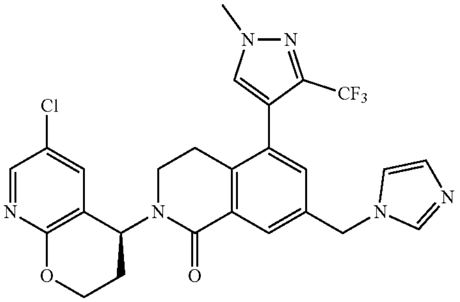 [SMILES: Cn1cc(-c2cc(Cn3ccnc3)cc3c2CCN([C@H]2CCOc4ncc(Cl)cc42)C3=O)c(C(F)(F)F)n1]
I-72
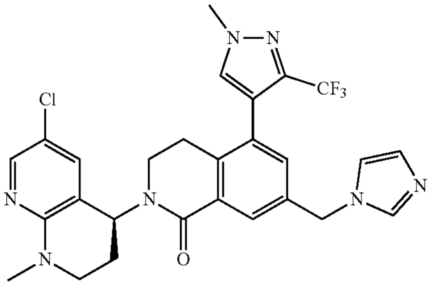 [SMILES: CN1CC[C@H](N2CCc3c(cc(Cn4ccnc4)cc3-c3cn(C)nc3C(F)(F)F)C2=O)c2cc(Cl)cnc21]
I-73
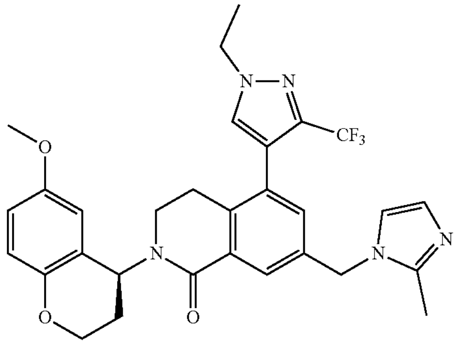 [SMILES: CCn1cc(-c2cc(Cn3ccnc3C)cc3c2CCN([C@H]2CCOc4ccc(OC)cc42)C3=O)c(C(F)(F)F)n1]
I-74

TABLE 1-continued
Exemplary compounds.
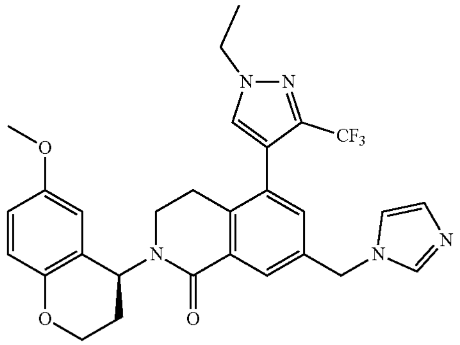 [SMILES: CCn1cc(-c2cc(Cn3ccnc3)cc3c2CCN([C@H]2CCOc4ccc(OC)cc42)C3=O)c(C(F)(F)F)n1]
I-75
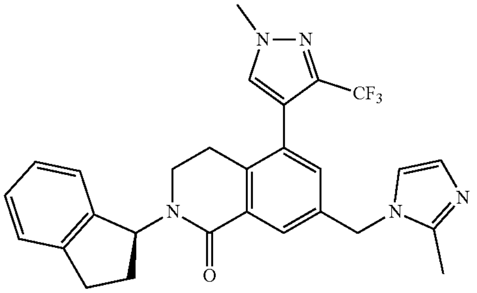 [SMILES: Cc1nccn1Cc1cc2c(c(-c3cn(C)nc3C(F)(F)F)c1)CCN([C@H]1CCc3ccccc31)C2=O]
I-76
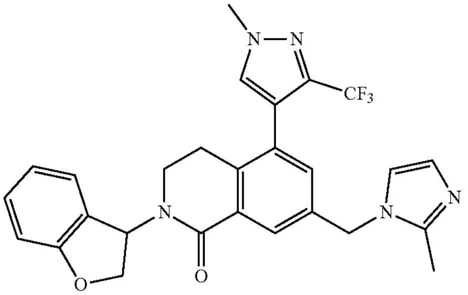 [SMILES: Cc1nccn1Cc1cc2c(c(-c3cn(C)nc3C(F)(F)F)c1)CCN(C1COc3ccccc31)C2=O]
I-77
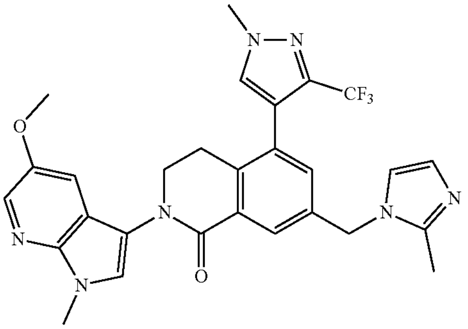 [SMILES: COc1cnc2c(c1)c(N1CCc3c(cc(Cn4ccnc4C)cc3-c3cn(C)nc3C(F)(F)F)C1=O)cn2C]
I-78
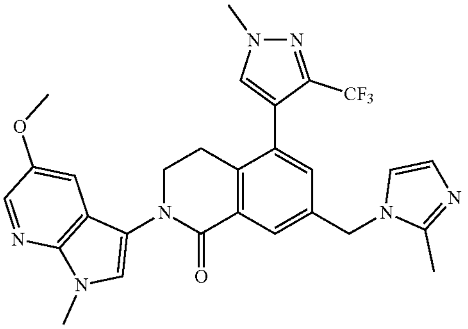 [SMILES: COc1cnc2c(c1)c(N1CCc3c(cc(Cn4ccnc4C)cc3-c3cn(C)nc3C(F)(F)F)C1=O)cn2C]
I-79

TABLE 1-continued
| Exemplary compounds. |
| --- |
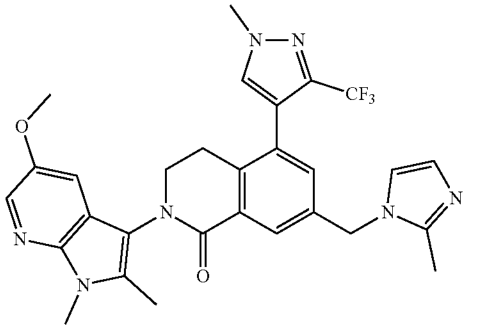 [SMILES: COc1cnc2c(c1)c(N1CCc3c(cc(Cn4ccnc4C)cc3-c3cn(C)nc3C(F)(F)F)C1=O)c(C)n2C]
I-80
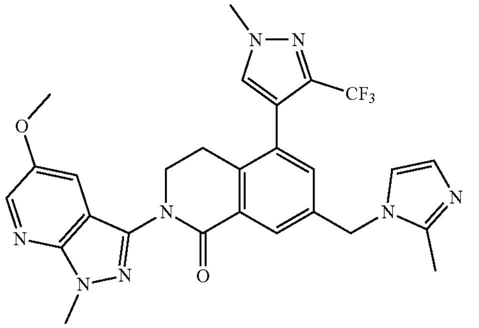 [SMILES: COc1cnc2c(c1)c(N1CCc3c(cc(Cn4ccnc4C)cc3-c3cn(C)nc3C(F)(F)F)C1=O)nn2C]
I-81
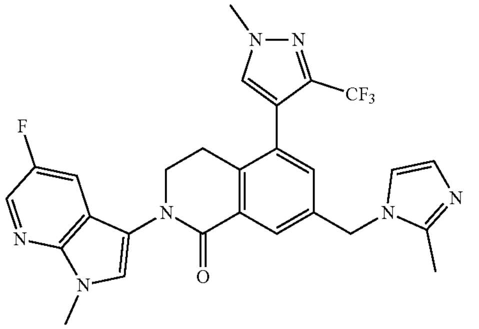 [SMILES: Cc1nccn1Cc1cc2c(c(-c3cn(C)nc3C(F)(F)F)c1)CCN(c1cn(C)c3ncc(F)cc13)C2=O]
I-82
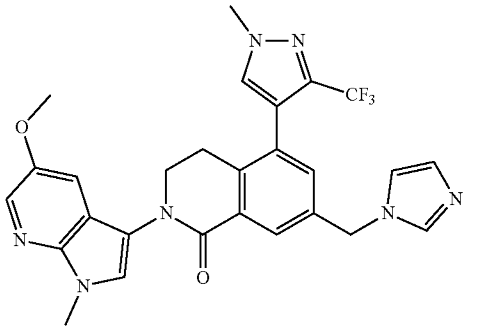 [SMILES: COc1cnc2c(c1)c(N1CCc3c(cc(Cn4ccnc4)cc3-c3cn(C)nc3C(F)(F)F)C1=O)cn2C]
I-83

TABLE 1-continued
| Exemplary compounds. |
|---|
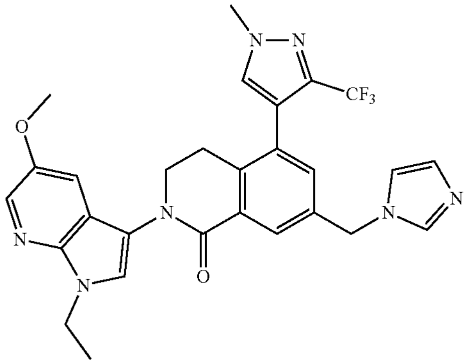 [SMILES: CCn1cc(N2CCc3c(cc(Cn4ccnc4)cc3-c3cn(C)nc3C(F)(F)F)C2=O)c2cc(OC)cnc21]
I-84
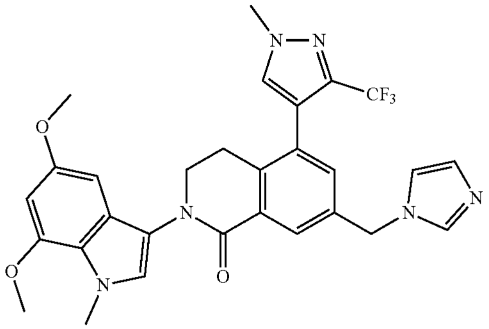 [SMILES: COc1cc(OC)c2c(c1)c(N1CCc3c(cc(Cn4ccnc4)cc3-c3cn(C)nc3C(F)(F)F)C1=O)cn2C]
I-85
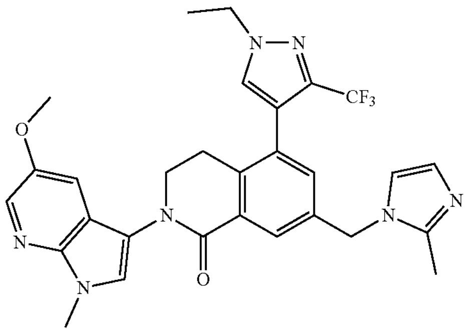 [SMILES: CCn1cc(-c2cc(Cn3ccnc3C)cc3c2CCN(c2cn(C)c4ncc(OC)cc24)C3=O)c(C(F)(F)F)n1]
I-86
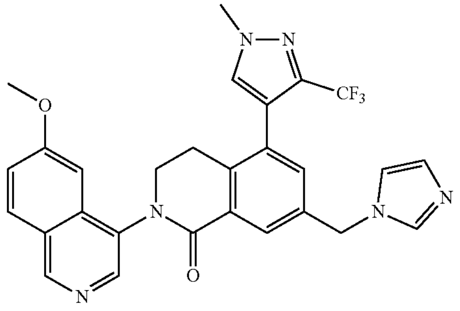 [SMILES: COc1ccc2cncc(N3CCc4c(cc(Cn5ccnc5)cc4-c4cn(C)nc4C(F)(F)F)C3=O)c2c1]
I-87

TABLE 1-continued
Exemplary compounds.
I-88
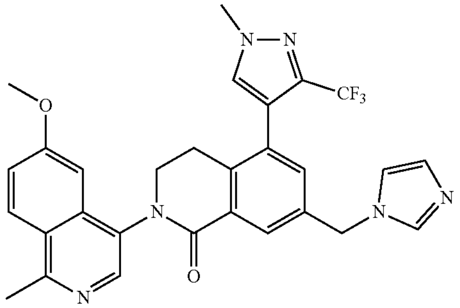 [SMILES: COc1ccc2c(C)ncc(N3CCc4c(cc(Cn5ccnc5)cc4-c4cn(C)nc4C(F)(F)F)C3=O)c2c1]
I-89
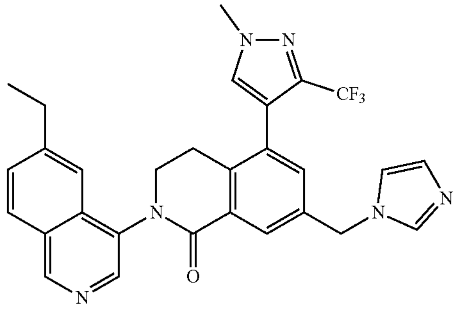 [SMILES: CCc1ccc2cncc(N3CCc4c(cc(Cn5ccnc5)cc4-c4cn(C)nc4C(F)(F)F)C3=O)c2c1]
I-90
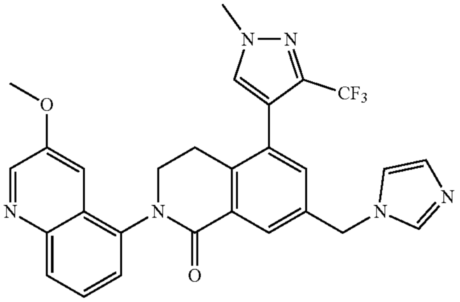 [SMILES: COc1cnc2cccc(N3CCc4c(cc(Cn5ccnc5)cc4-c4cn(C)nc4C(F)(F)F)C3=O)c2c1]
I-91
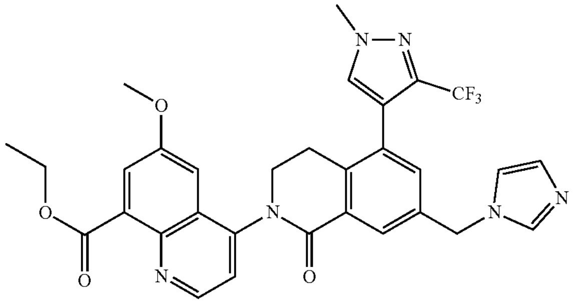 [SMILES: CCOC(=O)c1cc(OC)cc2c(N3CCc4c(cc(Cn5ccnc5)cc4-c4cn(C)nc4C(F)(F)F)C3=O)ccnc12]
I-92
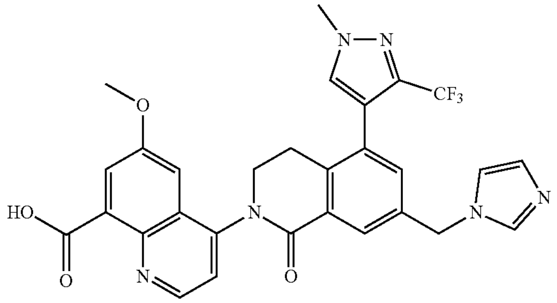 [SMILES: COc1cc(C(=O)O)c2nccc(N3CCc4c(cc(Cn5ccnc5)cc4-c4cn(C)nc4C(F)(F)F)C3=O)c2c1]

TABLE 1-continued
| Exemplary compounds. |
| --- |
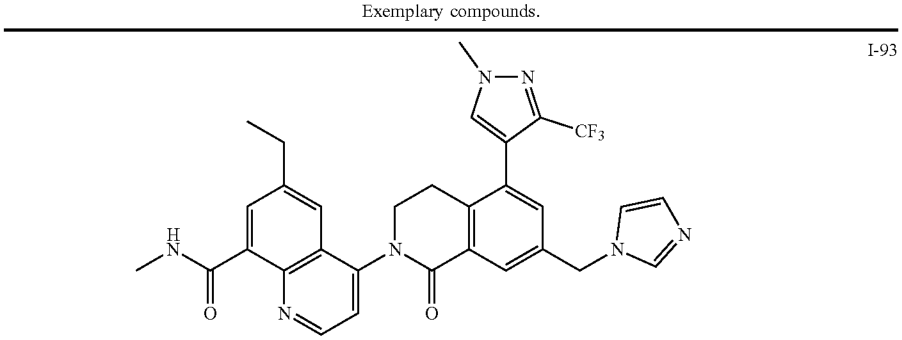
I-93
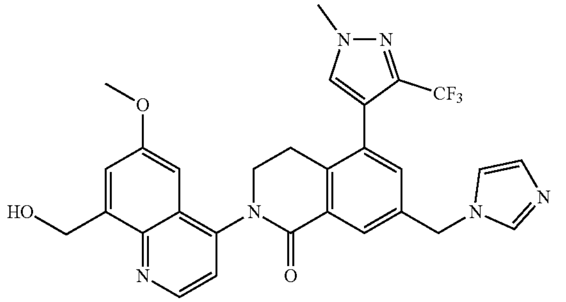
I-94
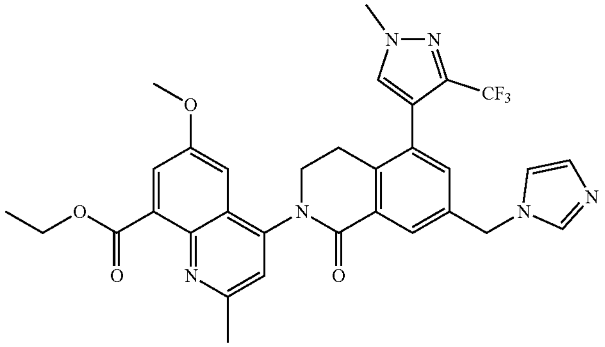 [SMILES: CCOC(=O)c1cc(OC)cc2c(N3CCc4c(cc(Cn5ccnc5)cc4-c4cn(C)nc4C(F)(F)F)C3=O)cc(C)nc12]
I-95
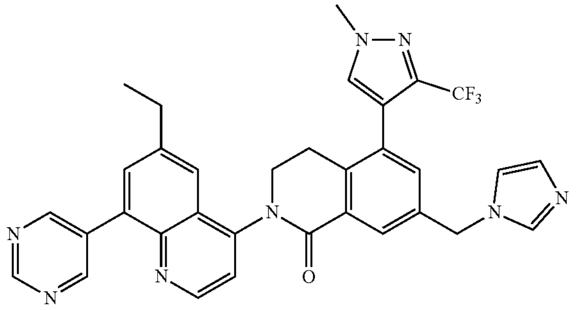 [SMILES: CCc1cc(-c2cncnc2)c2nccc(N3CCc4c(cc(Cn5ccnc5)cc4-c4cn(C)nc4C(F)(F)F)C3=O)c2c1]
I-96
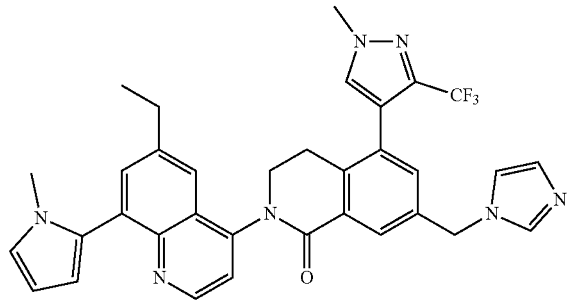 [SMILES: CCc1cc(-c2cccn2C)c2nccc(N3CCc4c(cc(Cn5ccnc5)cc4-c4cn(C)nc4C(F)(F)F)C3=O)c2c1]
I-97

TABLE 1-continued
Exemplary compounds.
I-98
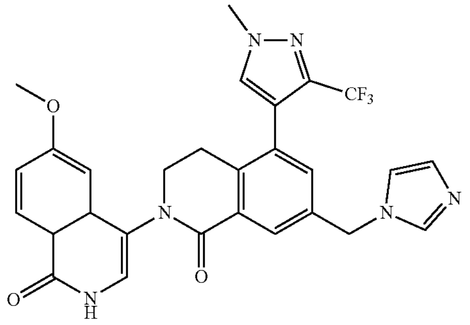 [SMILES: COC1=CC2C(N3CCc4c(cc(Cn5ccnc5)cc4-c4cn(C)nc4C(F)(F)F)C3=O)=CNC(=O)C2C=C1]
I-99
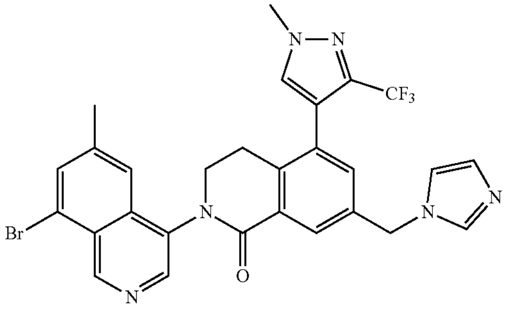 [SMILES: Cc1cc(Br)c2cncc(N3CCc4c(cc(Cn5ccnc5)cc4-c4cn(C)nc4C(F)(F)F)C3=O)c2c1]
I-100
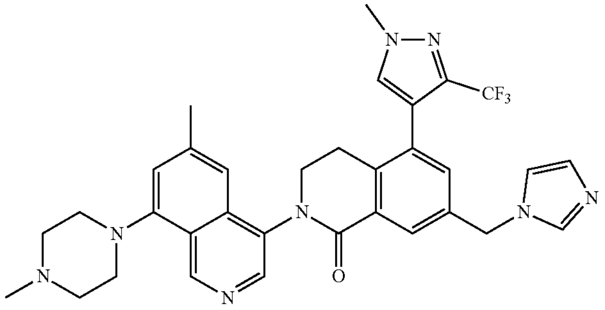 [SMILES: Cc1cc(N2CCN(C)CC2)c2cncc(N3CCc4c(cc(Cn5ccnc5)cc4-c4cn(C)nc4C(F)(F)F)C3=O)c2c1]
I-101
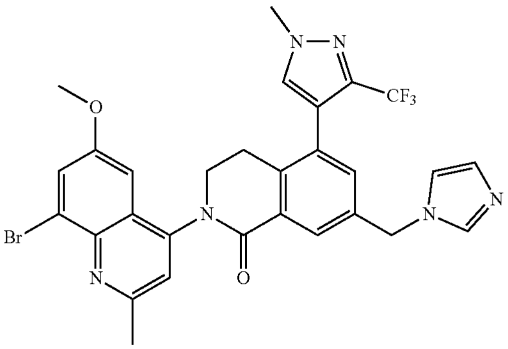 [SMILES: COc1cc(Br)c2nc(C)cc(N3CCc4c(cc(Cn5ccnc5)cc4-c4cn(C)nc4C(F)(F)F)C3=O)c2c1]

TABLE 1-continued
| Exemplary compounds. |
| --- |
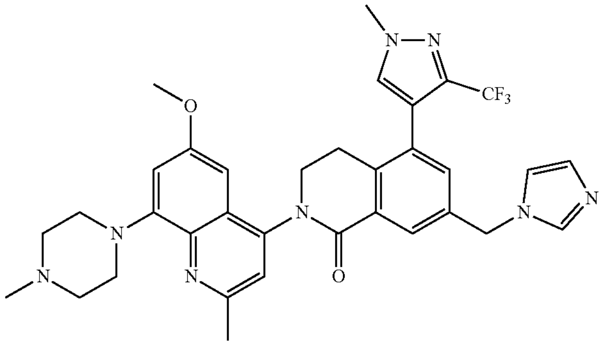 [SMILES: COc1cc(N2CCN(C)CC2)c2nc(C)cc(N3CCc4c(cc(Cn5ccnc5)cc4-c4cn(C)nc4C(F)(F)F)C3=O)c2c1]
I-102
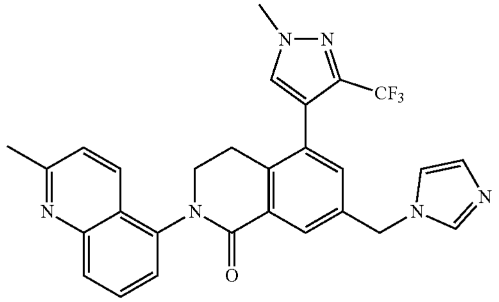 [SMILES: Cc1ccc2c(N3CCc4c(cc(Cn5ccnc5)cc4-c4cn(C)nc4C(F)(F)F)C3=O)cccc2n1]
I-103
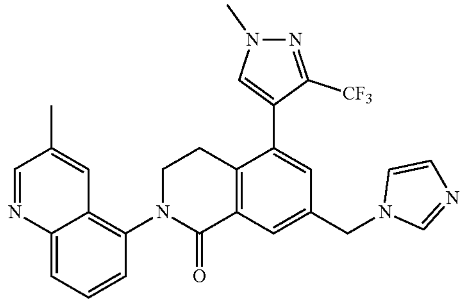 [SMILES: Cc1cnc2cccc(N3CCc4c(cc(Cn5ccnc5)cc4-c4cn(C)nc4C(F)(F)F)C3=O)c2c1]
I-104
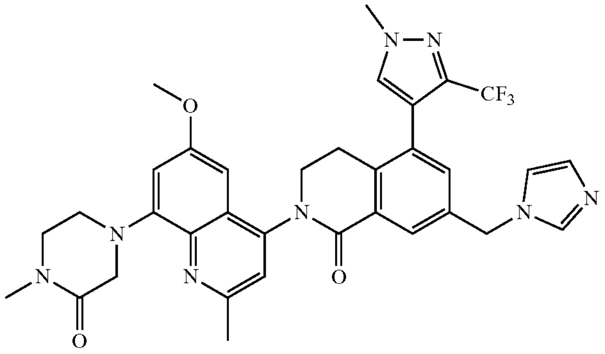 [SMILES: COc1cc(N2CCN(C)C(=O)C2)c2nc(C)cc(N3CCc4c(cc(Cn5ccnc5)cc4-c4cn(C)nc4C(F)(F)F)C3=O)c2c1]
I-105

TABLE 1-continued
Exemplary compounds.
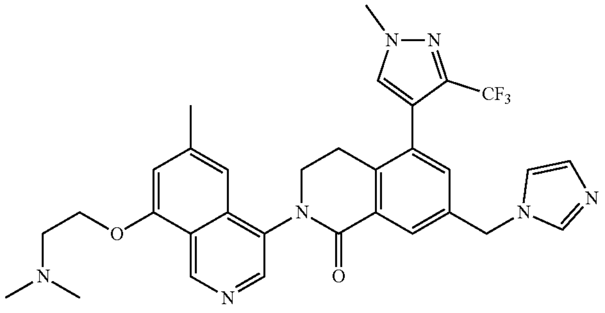 [SMILES: Cc1cc(OCCN(C)C)c2cncc(N3CCc4c(cc(Cn5ccnc5)cc4-c4cn(C)nc4C(F)(F)F)C3=O)c2c1]
I-106
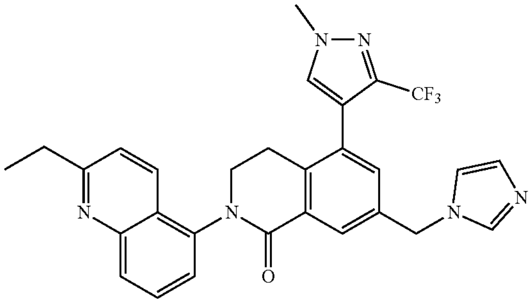 [SMILES: CCc1ccc2c(N3CCc4c(cc(Cn5ccnc5)cc4-c4cn(C)nc4C(F)(F)F)C3=O)cccc2n1]
I-107
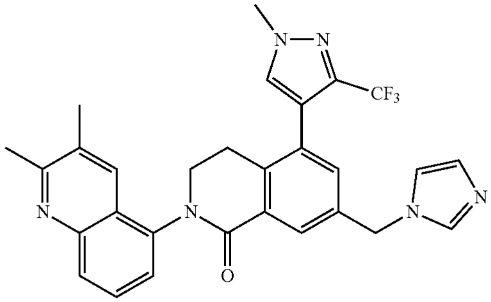 [SMILES: Cc1cc2c(N3CCc4c(cc(Cn5ccnc5)cc4-c4cn(C)nc4C(F)(F)F)C3=O)cccc2nc1C]
I-108
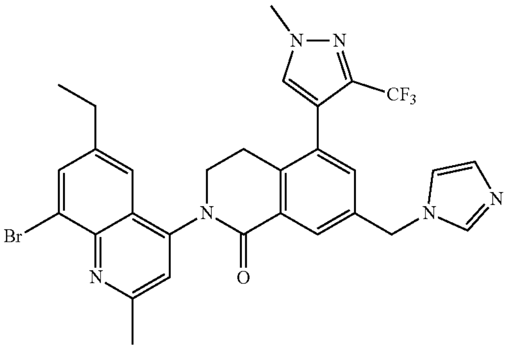 [SMILES: CCc1cc(Br)c2nc(C)cc(N3CCc4c(cc(Cn5ccnc5)cc4-c4cn(C)nc4C(F)(F)F)C3=O)c2c1]
I-109

TABLE 1-continued
| Exemplary compounds. |
|---|
| 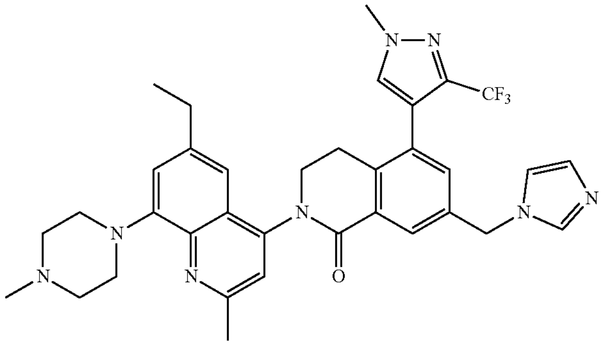 [SMILES: CCc1cc(N2CCN(C)CC2)c2nc(C)cc(N3CCc4c(cc(Cn5ccnc5)cc4-c4cn(C)nc4C(F)(F)F)C3=O)c2c1] I-110 |
| 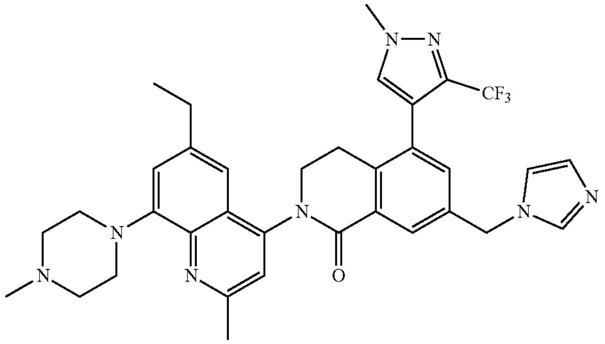 [SMILES: CCc1cc(N2CCN(C)CC2)c2nc(C)cc(N3CCc4c(cc(Cn5ccnc5)cc4-c4cn(C)nc4C(F)(F)F)C3=O)c2c1] I-111 |
| 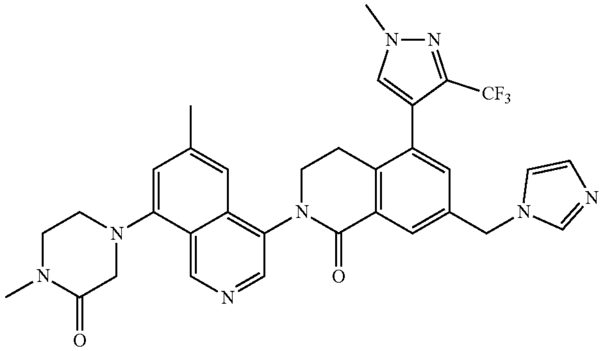 [SMILES: Cc1cc(N2CCN(C)C(=O)C2)c2cncc(N3CCc4c(cc(Cn5ccnc5)cc4-c4cn(C)nc4C(F)(F)F)C3=O)c2c1] I-112 |
| 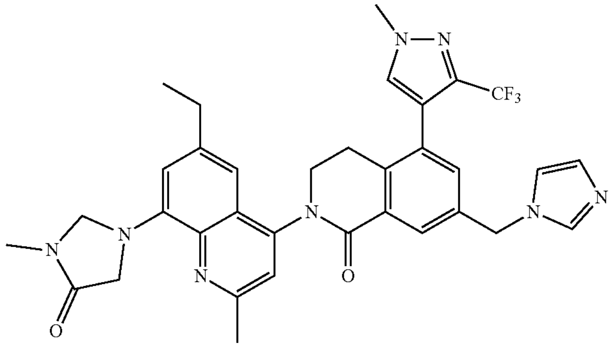 [SMILES: CCc1cc(N2CC(=O)N(C)C2)c2nc(C)cc(N3CCc4c(cc(Cn5ccnc5)cc4-c4cn(C)nc4C(F)(F)F)C3=O)c2c1] I-113 |

TABLE 1-continued
Exemplary compounds.
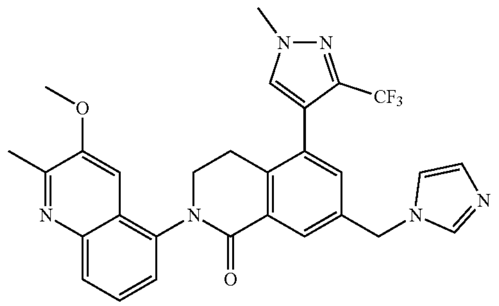 [SMILES: COc1cc2c(N3CCc4c(cc(Cn5ccnc5)cc4-c4cn(C)nc4C(F)(F)F)C3=O)cccc2nc1C]
I-114
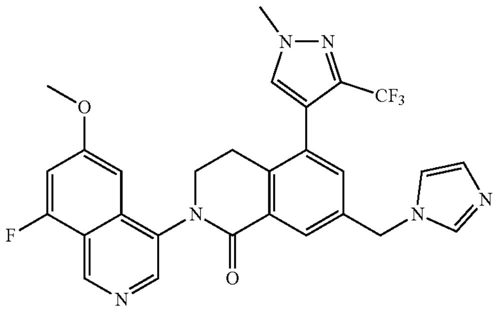
I-115
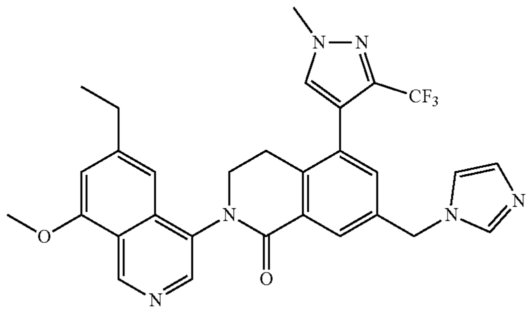 [SMILES: CCc1cc(OC)c2cncc(N3CCc4c(cc(Cn5ccnc5)cc4-c4cn(C)nc4C(F)(F)F)C3=O)c2c1]
I-116
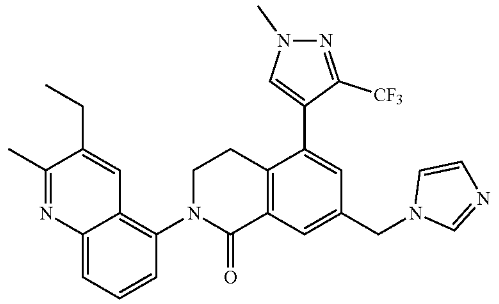 [SMILES: CCc1cc2c(N3CCc4c(cc(Cn5ccnc5)cc4-c4cn(C)nc4C(F)(F)F)C3=O)cccc2nc1C]
I-117
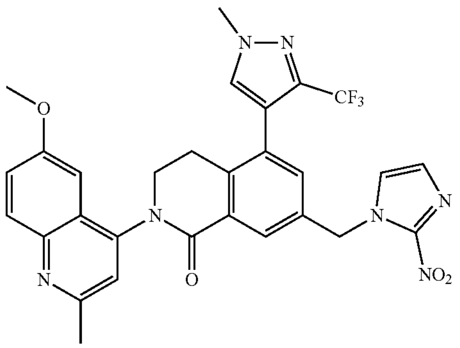 [SMILES: COc1ccc2nc(C)cc(N3CCc4c(cc(Cn5ccnc5[N+](=O)[O-])cc4-c4cn(C)nc4C(F)(F)F)C3=O)c2c1]
I-118

TABLE 1-continued
| Exemplary compounds. |
|---|
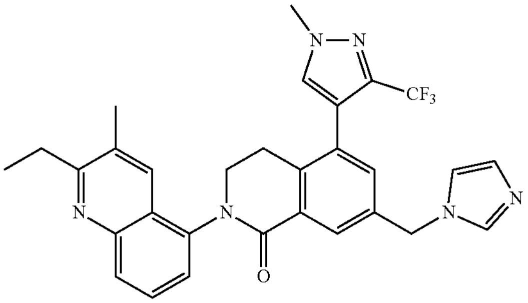 [SMILES: CCc1nc2cccc(N3CCc4c(cc(Cn5ccnc5)cc4-c4cn(C)nc4C(F)(F)F)C3=O)c2cc1C]
I-119
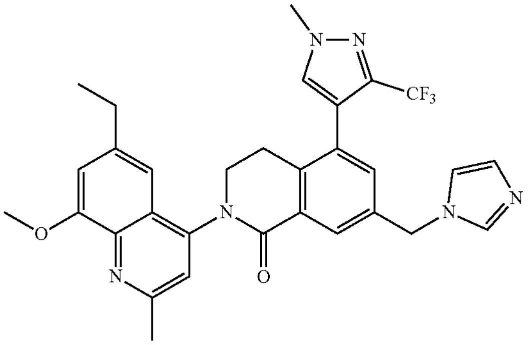 [SMILES: CCc1cc(OC)c2nc(C)cc(N3CCc4c(cc(Cn5ccnc5)cc4-c4cn(C)nc4C(F)(F)F)C3=O)c2c1]
I-120
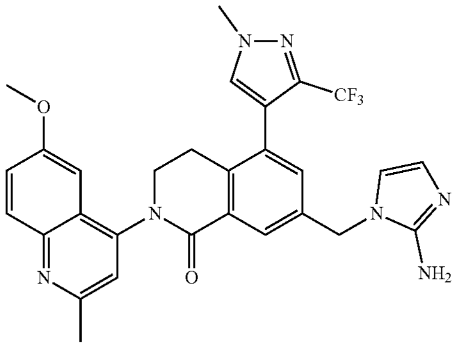
I-121
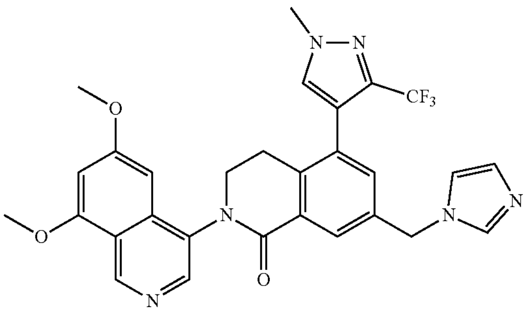
I-122

TABLE 1-continued
| Exemplary compounds. |
| --- |
| 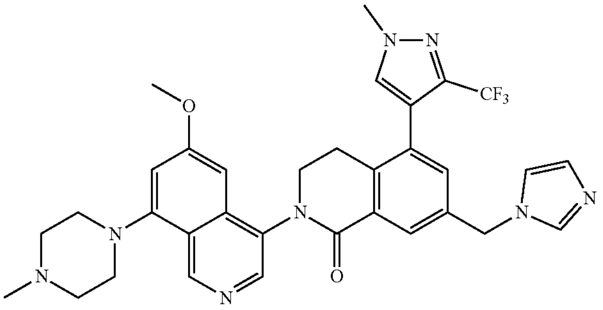 [SMILES: COc1cc(N2CCN(C)CC2)c2cncc(N3CCc4c(cc(Cn5ccnc5)cc4-c4cn(C)nc4C(F)(F)F)C3=O)c2c1] I-123 |
| 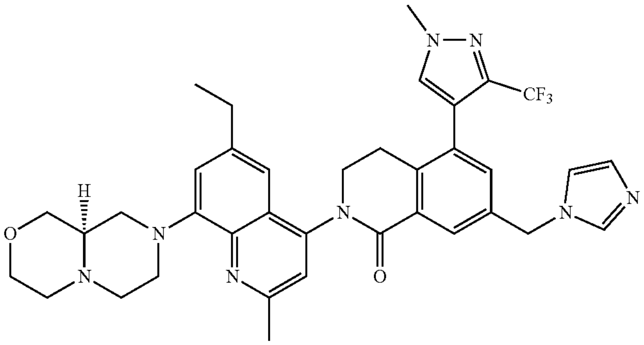 [SMILES: CCc1cc(N2CCN3CCOC[C@H]3C2)c2nc(C)cc(N3CCc4c(cc(Cn5ccnc5)cc4-c4cn(C)nc4C(F)(F)F)C3=O)c2c1] I-124 |
| 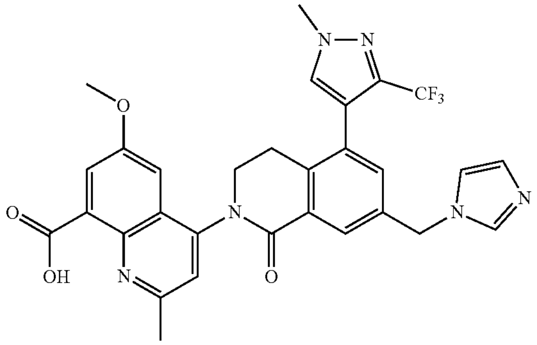 [SMILES: COc1cc(C(=O)O)c2nc(C)cc(N3CCc4c(cc(Cn5ccnc5)cc4-c4cn(C)nc4C(F)(F)F)C3=O)c2c1] I-125 |
| 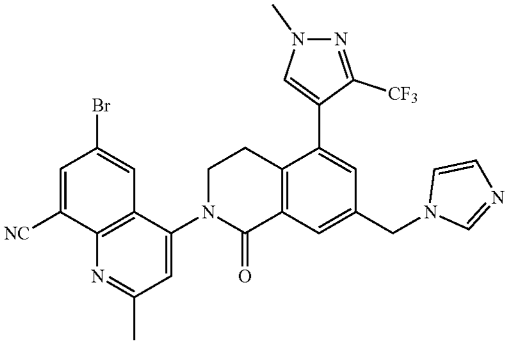 [SMILES: Cc1cc(N2CCc3c(cc(Cn4ccnc4)cc3-c3cn(C)nc3C(F)(F)F)C2=O)c2cc(Br)cc(C#N)c2n1] I-126 |

TABLE 1-continued
Exemplary compounds.
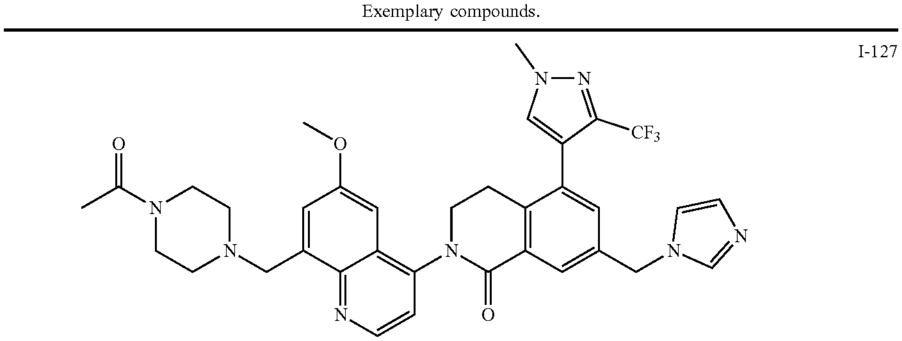
I-127
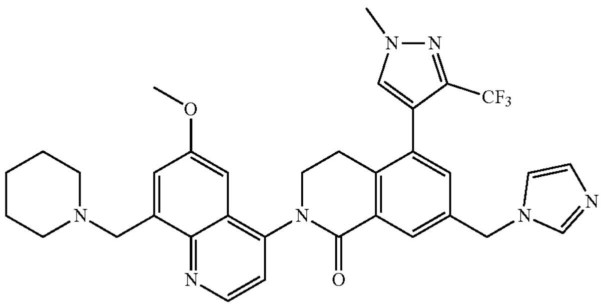 [SMILES: COc1cc(CN2CCCCC2)c2nccc(N3CCc4c(cc(Cn5ccnc5)cc4-c4cn(C)nc4C(F)(F)F)C3=O)c2c1]
I-128
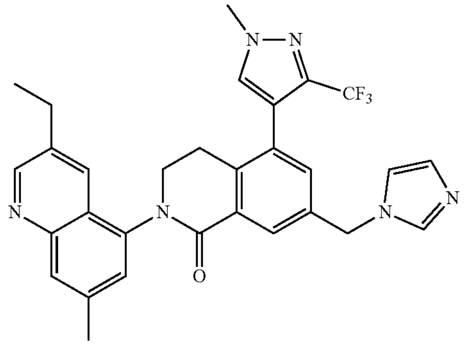 [SMILES: CCc1cnc2cc(C)cc(N3CCc4c(cc(Cn5ccnc5)cc4-c4cn(C)nc4C(F)(F)F)C3=O)c2c1]
I-129
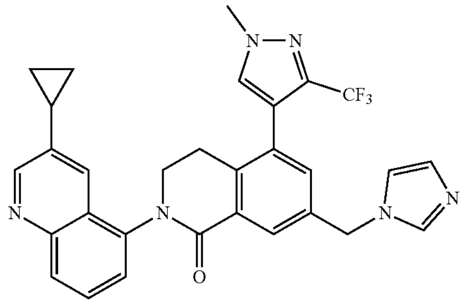 [SMILES: Cn1cc(-c2cc(Cn3ccnc3)cc3c2CCN(c2cccc4ncc(C5CC5)cc24)C3=O)c(C(F)(F)F)n1]
I-130
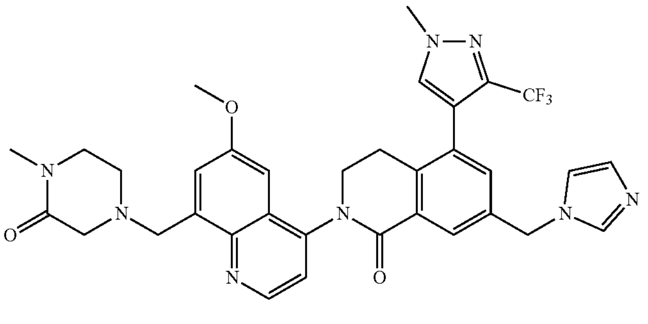 [SMILES: COc1cc(CN2CCN(C)C(=O)C2)c2nccc(N3CCc4c(cc(Cn5ccnc5)cc4-c4cn(C)nc4C(F)(F)F)C3=O)c2c1]
I-131

TABLE 1-continued
| Exemplary compounds. |
| --- |
| 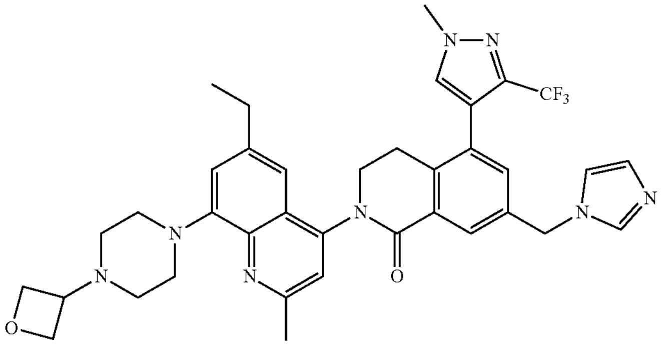 [SMILES: CCc1cc(N2CCN(C3COC3)CC2)c2nc(C)cc(N3CCc4c(cc(Cn5ccnc5)cc4-c4cn(C)nc4C(F)(F)F)C3=O)c2c1] I-132 |
| 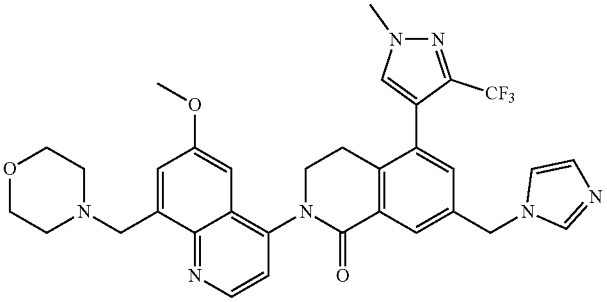 [SMILES: COc1cc(CN2CCOCC2)c2nccc(N3CCc4c(cc(Cn5ccnc5)cc4-c4cn(C)nc4C(F)(F)F)C3=O)c2c1] I-133 |
| 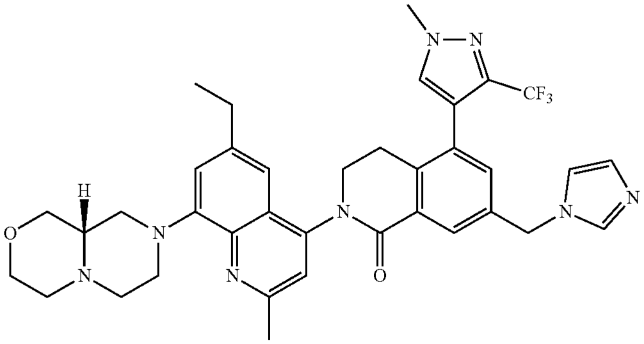 [SMILES: CCc1cc(N2CCN3CCOC[C@@H]3C2)c2nc(C)cc(N3CCc4c(cc(Cn5ccnc5)cc4-c4cn(C)nc4C(F)(F)F)C3=O)c2c1] I-134 |
| 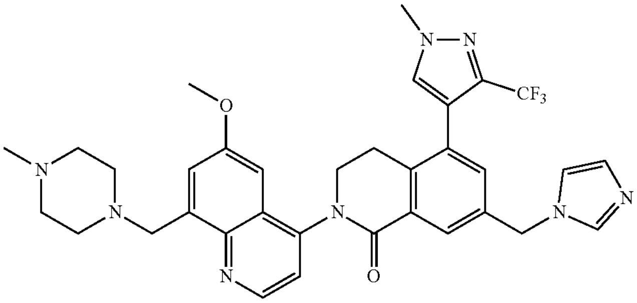 [SMILES: COc1cc(CN2CCN(C)CC2)c2nccc(N3CCc4c(cc(Cn5ccnc5)cc4-c4cn(C)nc4C(F)(F)F)C3=O)c2c1] I-135 |

TABLE 1-continued
Exemplary compounds.
I-136
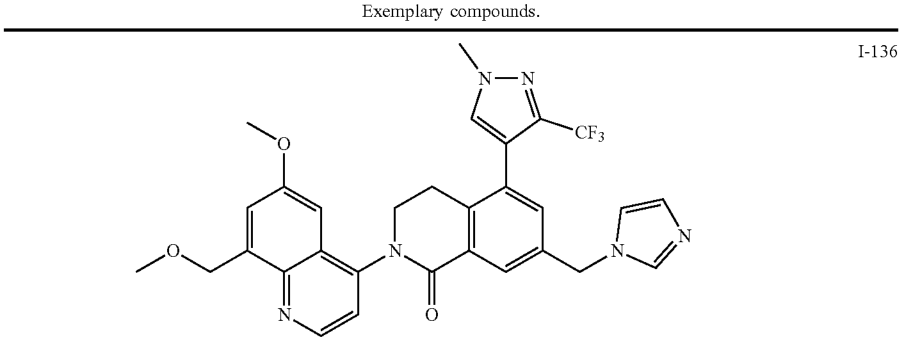
I-137
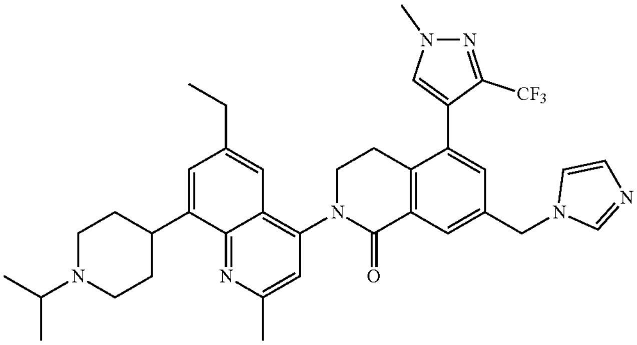 [SMILES: CCc1cc(C2CCN(C(C)C)CC2)c2nc(C)cc(N3CCc4c(cc(Cn5ccnc5)cc4-c4cn(C)nc4C(F)(F)F)C3=O)c2c1]
I-138
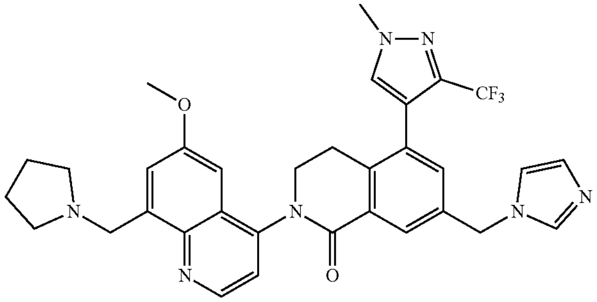 [SMILES: COc1cc(CN2CCCC2)c2nccc(N3CCc4c(cc(Cn5ccnc5)cc4-c4cn(C)nc4C(F)(F)F)C3=O)c2c1]
I-139
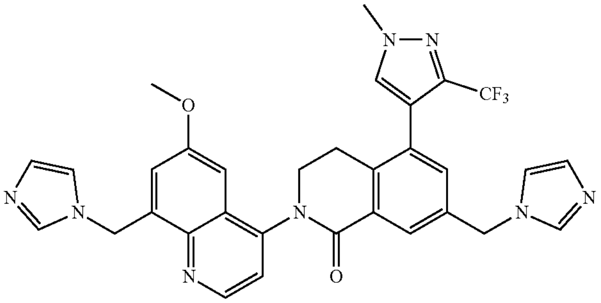 [SMILES: COc1cc(Cn2ccnc2)c2nccc(N3CCc4c(cc(Cn5ccnc5)cc4-c4cn(C)nc4C(F)(F)F)C3=O)c2c1]
I-140
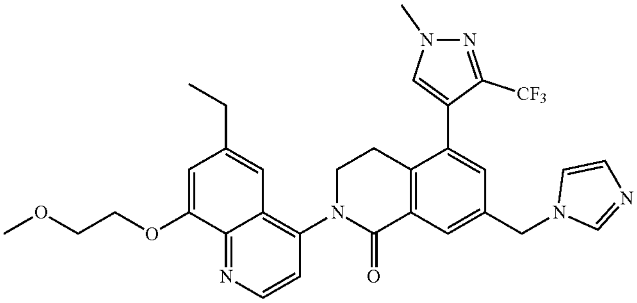 [SMILES: CCc1cc(OCCOC)c2nccc(N3CCc4c(cc(Cn5ccnc5)cc4-c4cn(C)nc4C(F)(F)F)C3=O)c2c1]

TABLE 1-continued
Exemplary compounds.
I-141
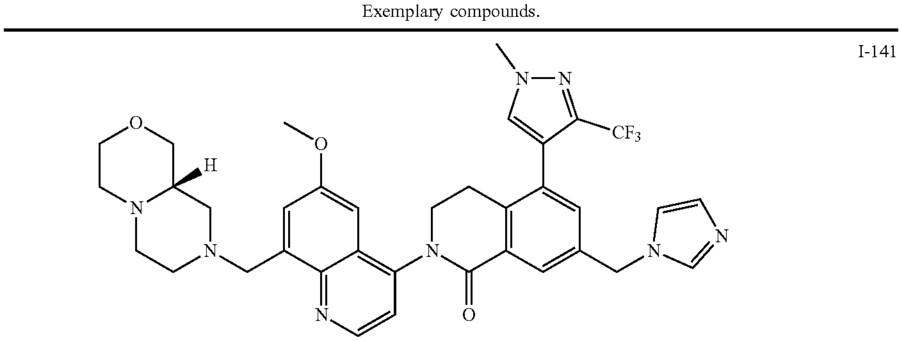
I-142
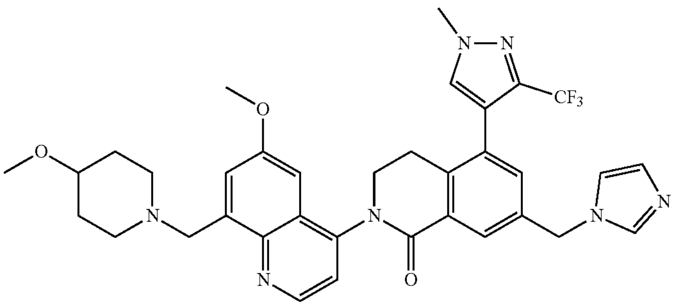 [SMILES: COc1cc(CN2CCC(OC)CC2)c2nccc(N3CCc4c(cc(Cn5ccnc5)cc4-c4cn(C)nc4C(F)(F)F)C3=O)c2c1]
I-143
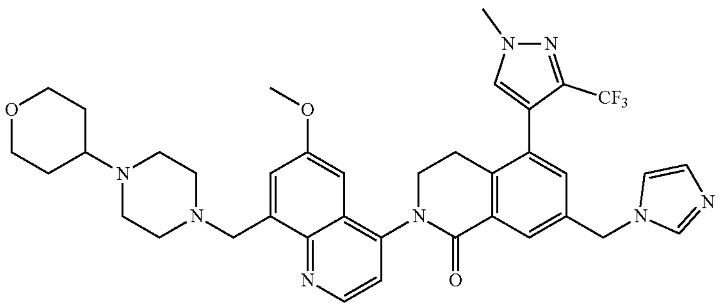 [SMILES: COc1cc(CN2CCN(C3CCOCC3)CC2)c2nccc(N3CCc4c(cc(Cn5ccnc5)cc4-c4cn(C)nc4C(F)(F)F)C3=O)c2c1]
I-144
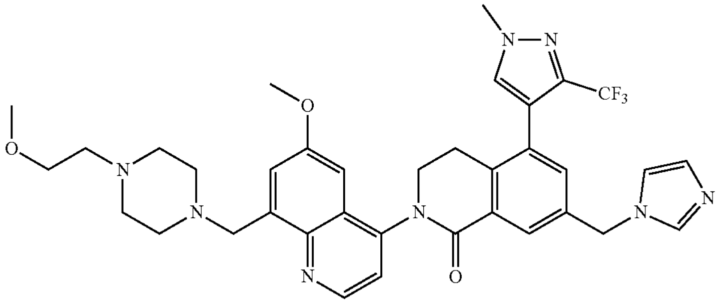 [SMILES: COCCN1CCN(Cc2cc(OC)cc3c(N4CCc5c(cc(Cn6ccnc6)cc5-c5cn(C)nc5C(F)(F)F)C4=O)ccnc23)CC1]
I-145
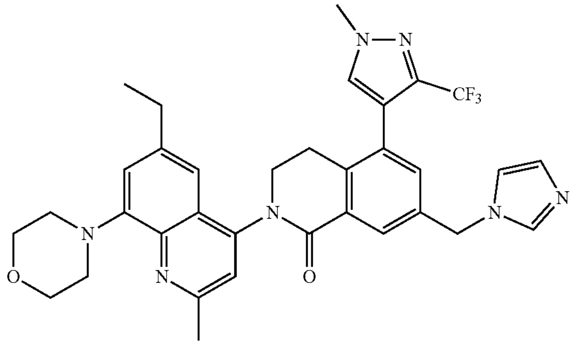 [SMILES: CCc1cc(N2CCOCC2)c2nc(C)cc(N3CCc4c(cc(Cn5ccnc5)cc4-c4cn(C)nc4C(F)(F)F)C3=O)c2c1]

TABLE 1-continued
| Exemplary compounds. |
| --- |
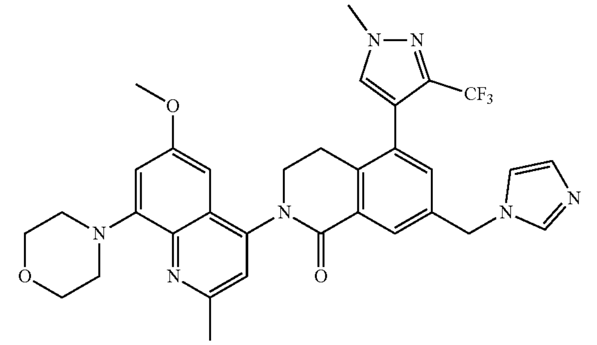 [SMILES: COc1cc(N2CCOCC2)c2nc(C)cc(N3CCc4c(cc(Cn5ccnc5)cc4-c4cn(C)nc4C(F)(F)F)C3=O)c2c1]
I-146
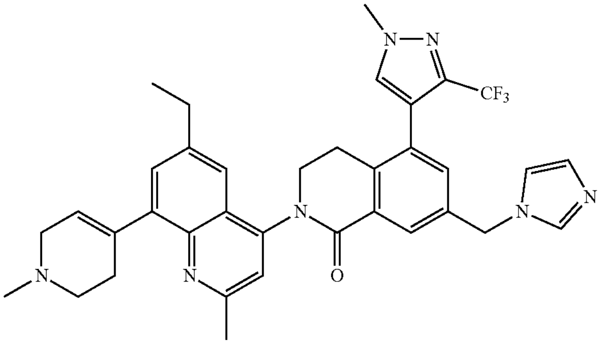 [SMILES: CCc1cc(C2=CCN(C)CC2)c2nc(C)cc(N3CCc4c(cc(Cn5ccnc5)cc4-c4cn(C)nc4C(F)(F)F)C3=O)c2c1]
I-147
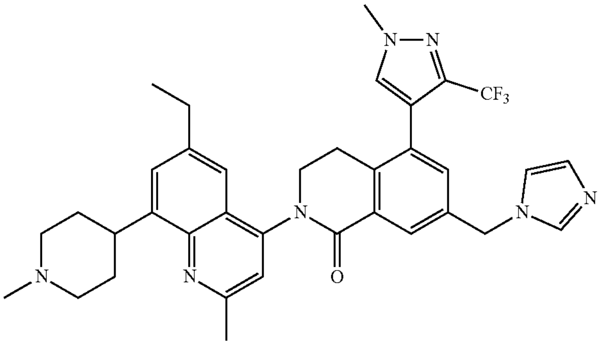 [SMILES: CCc1cc(C2CCN(C)CC2)c2nc(C)cc(N3CCc4c(cc(Cn5ccnc5)cc4-c4cn(C)nc4C(F)(F)F)C3=O)c2c1]
I-148
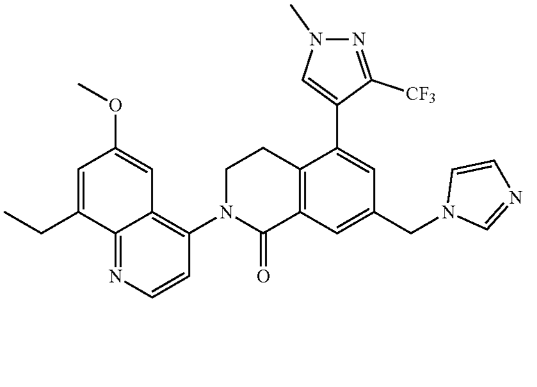 [SMILES: CCc1cc(OC)cc2c(N3CCc4c(cc(Cn5ccnc5)cc4-c4cn(C)nc4C(F)(F)F)C3=O)ccnc12]
I-149

TABLE 1-continued
| Exemplary compounds. |
| --- |
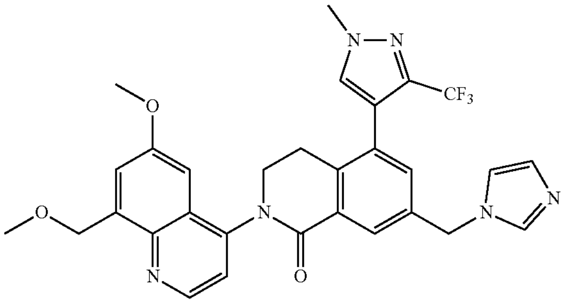 [SMILES: COCc1cc(OC)cc2c(N3CCc4c(cc(Cn5ccnc5)cc4-c4cn(C)nc4C(F)(F)F)C3=O)ccnc12]
I-150
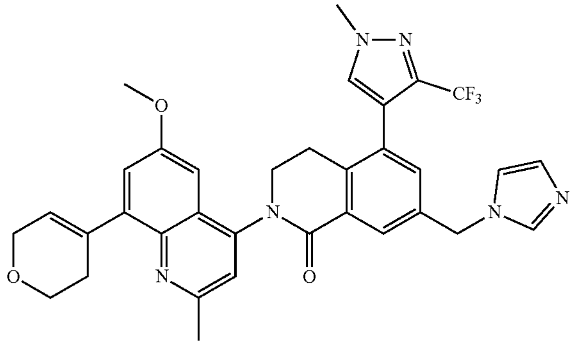 [SMILES: COc1cc(C2=CCOCC2)c2nc(C)cc(N3CCc4c(cc(Cn5ccnc5)cc4-c4cn(C)nc4C(F)(F)F)C3=O)c2c1]
I-151
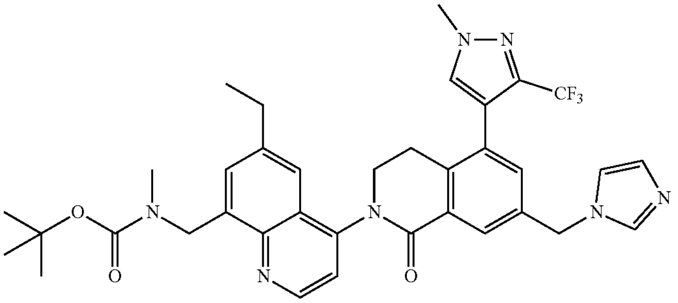 [SMILES: CCc1cc(CN(C)C(=O)OC(C)(C)C)c2nccc(N3CCc4c(cc(Cn5ccnc5)cc4-c4cn(C)nc4C(F)(F)F)C3=O)c2c1]
I-152
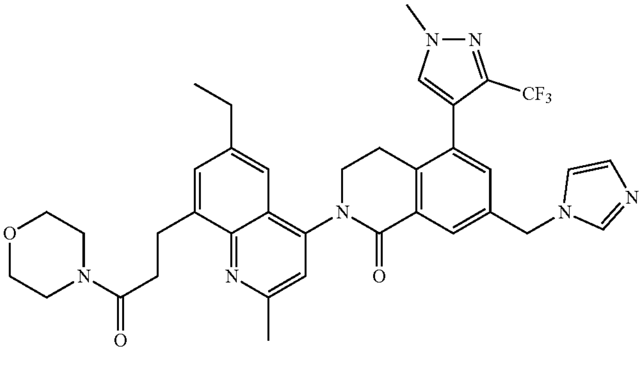 [SMILES: CCc1cc(CCC(=O)N2CCOCC2)c2nc(C)cc(N3CCc4c(cc(Cn5ccnc5)cc4-c4cn(C)nc4C(F)(F)F)C3=O)c2c1]
I-153

TABLE 1-continued
| Exemplary compounds. |
| --- |
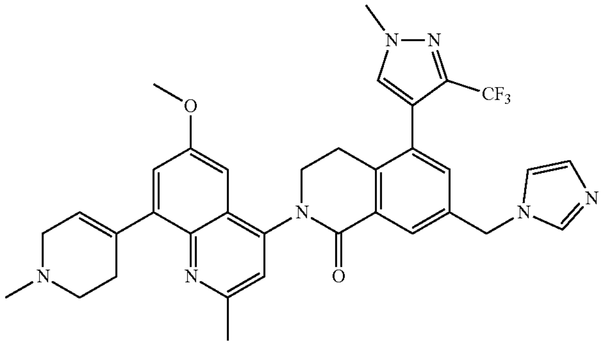 [SMILES: COc1cc(C2=CCN(C)CC2)c2nc(C)cc(N3CCc4c(cc(Cn5ccnc5)cc4-c4cn(C)nc4C(F)(F)F)C3=O)c2c1]
I-154
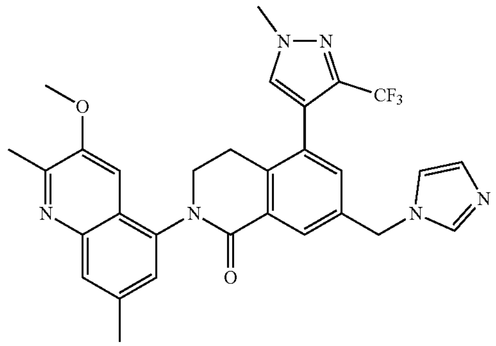 [SMILES: COc1cc2c(N3CCc4c(cc(Cn5ccnc5)cc4-c4cn(C)nc4C(F)(F)F)C3=O)cc(C)cc2nc1C]
I-155
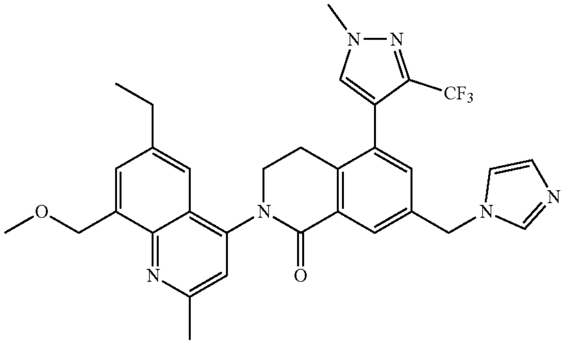 [SMILES: CCc1cc(COC)c2nc(C)cc(N3CCc4c(cc(Cn5ccnc5)cc4-c4cn(C)nc4C(F)(F)F)C3=O)c2c1]
I-156
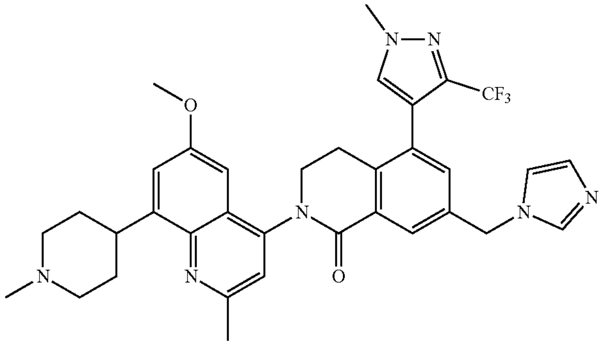 [SMILES: COc1cc(C2CCN(C)CC2)c2nc(C)cc(N3CCc4c(cc(Cn5ccnc5)cc4-c4cn(C)nc4C(F)(F)F)C3=O)c2c1]
I-157

TABLE 1-continued
Exemplary compounds.
I-158
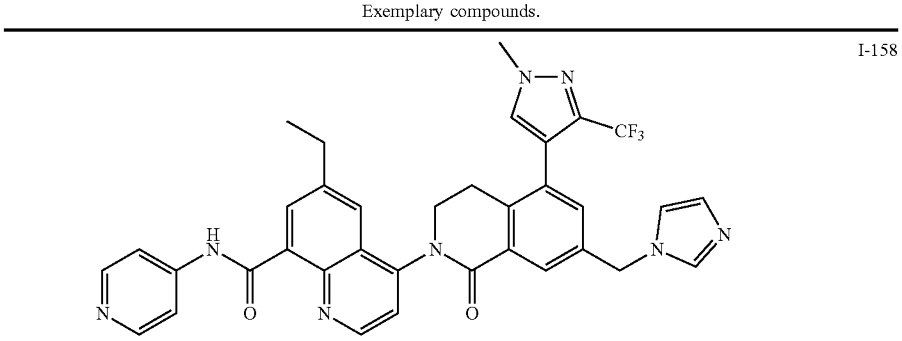
I-159
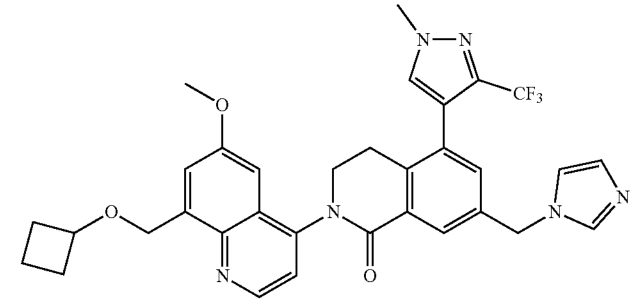 [SMILES: COc1cc(COC2CCC2)c2nccc(N3CCc4c(cc(Cn5ccnc5)cc4-c4cn(C)nc4C(F)(F)F)C3=O)c2c1]
I-160
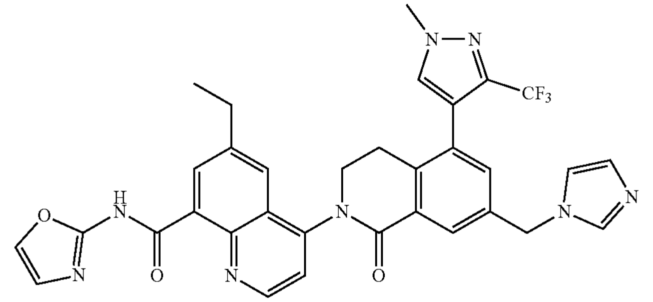 [SMILES: CCc1cc(C(=O)Nc2ncco2)c2nccc(N3CCc4c(cc(Cn5ccnc5)cc4-c4cn(C)nc4C(F)(F)F)C3=O)c2c1]
I-161
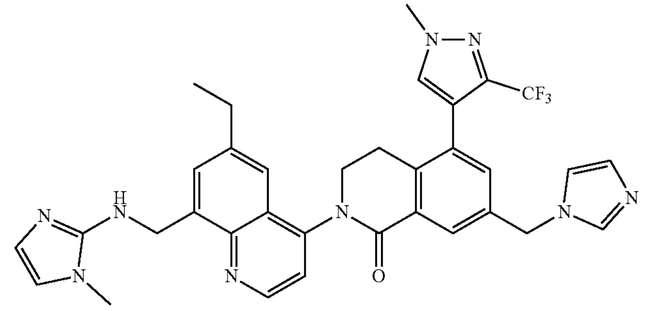 [SMILES: CCc1cc(CNc2nccn2C)c2nccc(N3CCc4c(cc(Cn5ccnc5)cc4-c4cn(C)nc4C(F)(F)F)C3=O)c2c1]
I-162
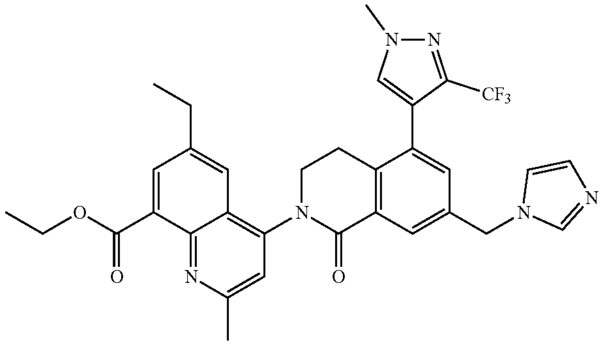 [SMILES: CCOC(=O)c1cc(CC)cc2c(N3CCc4c(cc(Cn5ccnc5)cc4-c4cn(C)nc4C(F)(F)F)C3=O)cc(C)nc12]

TABLE 1-continued
| Exemplary compounds. |
| --- |
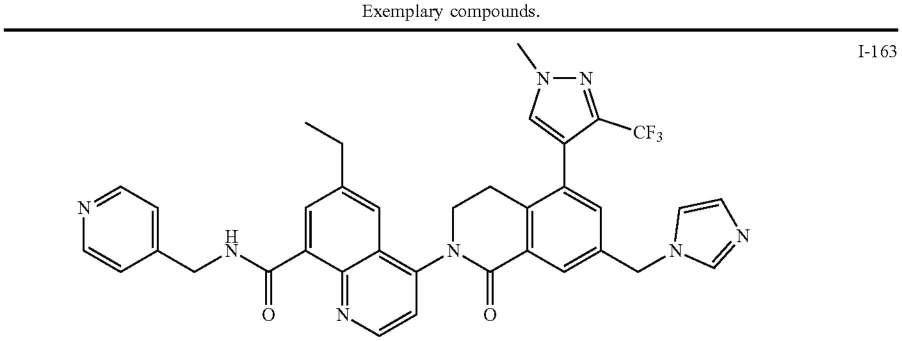
I-163
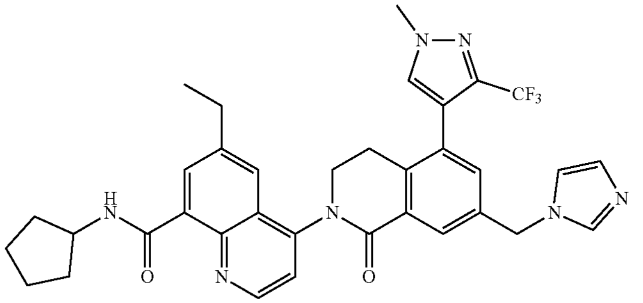 [SMILES: CCc1cc(C(=O)NC2CCCC2)c2nccc(N3CCc4c(cc(Cn5ccnc5)cc4-c4cn(C)nc4C(F)(F)F)C3=O)c2c1]
I-164
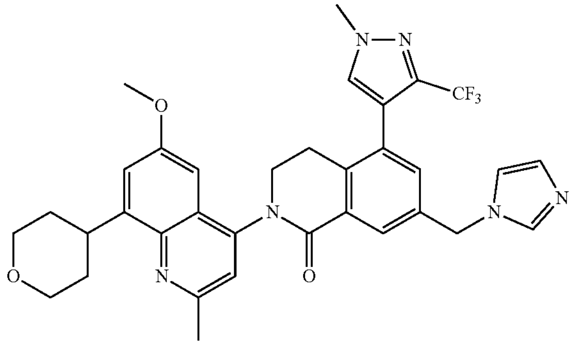 [SMILES: COc1cc(C2CCOCC2)c2nc(C)cc(N3CCc4c(cc(Cn5ccnc5)cc4-c4cn(C)nc4C(F)(F)F)C3=O)c2c1]
I-165
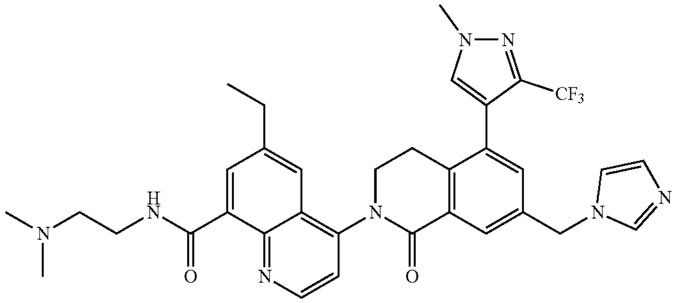 [SMILES: CCc1cc(C(=O)NCCN(C)C)c2nccc(N3CCc4c(cc(Cn5ccnc5)cc4-c4cn(C)nc4C(F)(F)F)C3=O)c2c1]
I-166
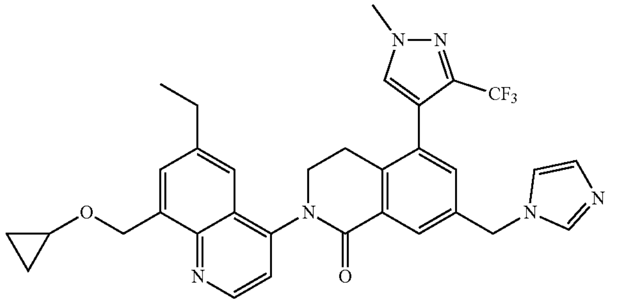
I-167

TABLE 1-continued
| Exemplary compounds. |
| --- |
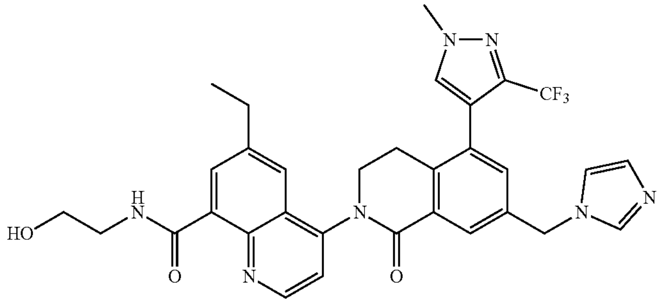 [SMILES: CCc1cc(C(=O)NCCO)c2nccc(N3CCc4c(cc(Cn5ccnc5)cc4-c4cn(C)nc4C(F)(F)F)C3=O)c2c1]
I-168
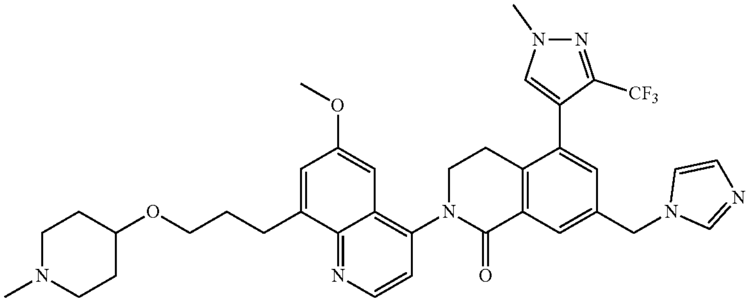 [SMILES: COc1cc(CCCOC2CCN(C)CC2)c2nccc(N3CCc4c(cc(Cn5ccnc5)cc4-c4cn(C)nc4C(F)(F)F)C3=O)c2c1]
I-169
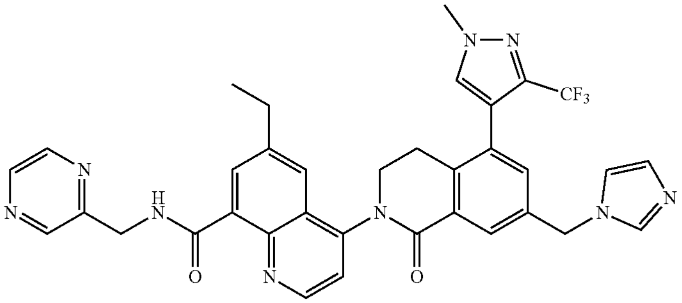 [SMILES: CCc1cc(C(=O)NCc2cnccn2)c2nccc(N3CCc4c(cc(Cn5ccnc5)cc4-c4cn(C)nc4C(F)(F)F)C3=O)c2c1]
I-170
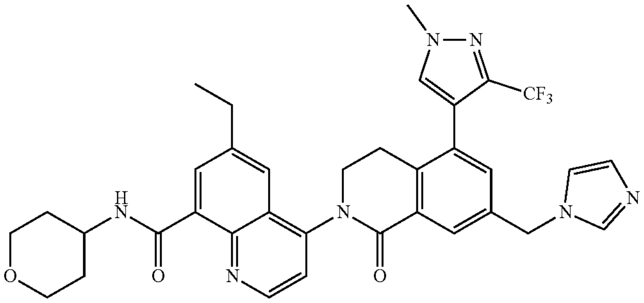 [SMILES: CCc1cc(C(=O)NC2CCOCC2)c2nccc(N3CCc4c(cc(Cn5ccnc5)cc4-c4cn(C)nc4C(F)(F)F)C3=O)c2c1]
I-171
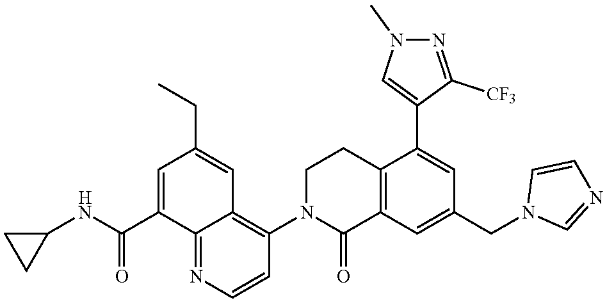 [SMILES: CCc1cc(C(=O)NC2CC2)c2nccc(N3CCc4c(cc(Cn5ccnc5)cc4-c4cn(C)nc4C(F)(F)F)C3=O)c2c1]
I-172

TABLE 1-continued
Exemplary compounds.
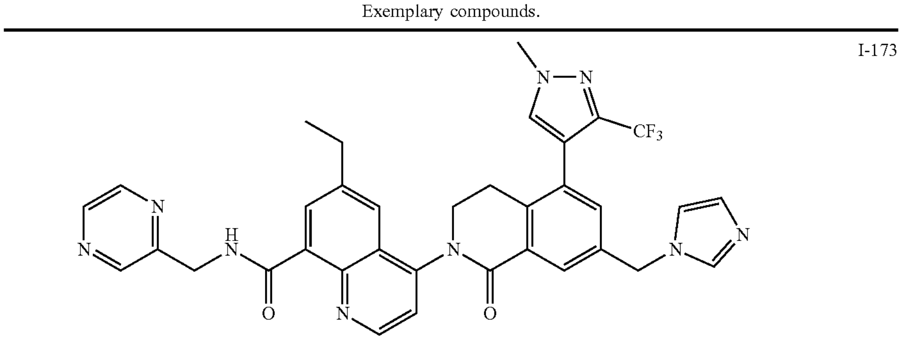
I-173
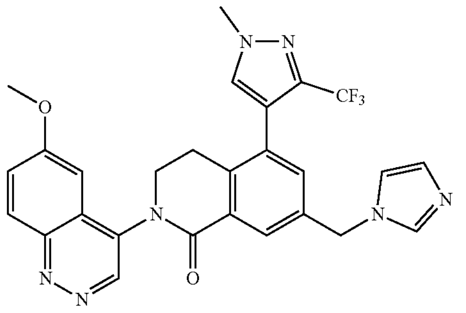 [SMILES: COc1ccc2nncc(N3CCc4c(cc(Cn5ccnc5)cc4-c4cn(C)nc4C(F)(F)F)C3=O)c2c1]
I-174
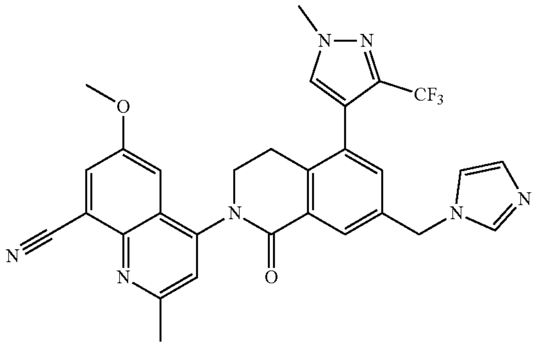 [SMILES: COc1cc(C#N)c2nc(C)cc(N3CCc4c(cc(Cn5ccnc5)cc4-c4cn(C)nc4C(F)(F)F)C3=O)c2c1]
I-175
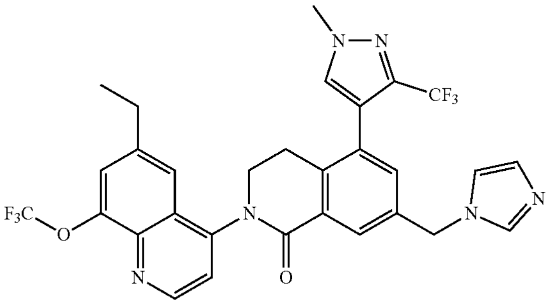 [SMILES: CCc1cc(OC(F)(F)F)c2nccc(N3CCc4c(cc(Cn5ccnc5)cc4-c4cn(C)nc4C(F)(F)F)C3=O)c2c1]
I-176
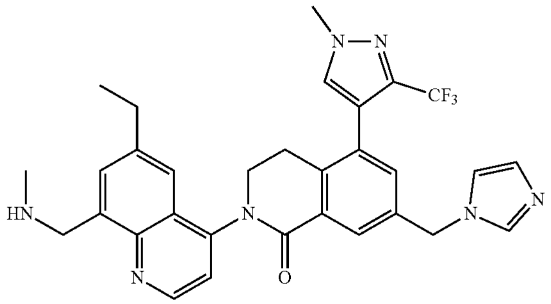 [SMILES: CCc1cc(CNC)c2nccc(N3CCc4c(cc(Cn5ccnc5)cc4-c4cn(C)nc4C(F)(F)F)C3=O)c2c1]
I-177

TABLE 1-continued
| Exemplary compounds. |
|---|
| 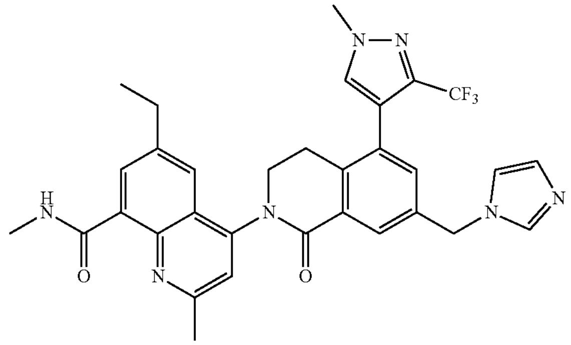 [SMILES: CCc1cc(C(=O)NC)c2nc(C)cc(N3CCc4c(cc(Cn5ccnc5)cc4-c4cn(C)nc4C(F)(F)F)C3=O)c2c1] I-178 |
| 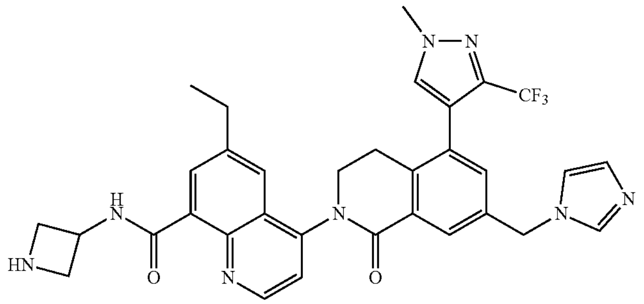 [SMILES: CCc1cc(C(=O)NC2CNC2)c2nccc(N3CCc4c(cc(Cn5ccnc5)cc4-c4cn(C)nc4C(F)(F)F)C3=O)c2c1] I-179 |
| 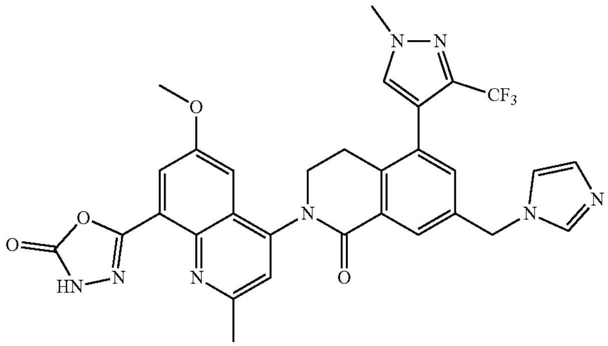 [SMILES: COc1cc(-c2n[nH]c(=O)o2)c2nc(C)cc(N3CCc4c(cc(Cn5ccnc5)cc4-c4cn(C)nc4C(F)(F)F)C3=O)c2c1] I-180 |
| 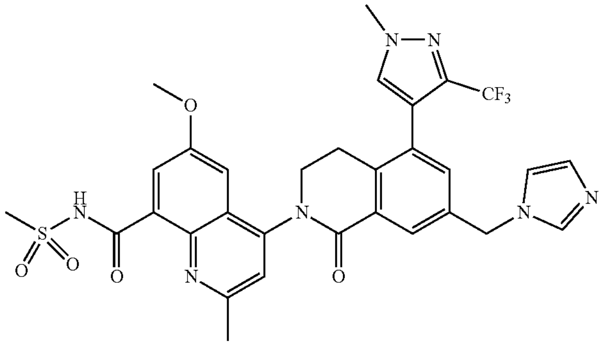 [SMILES: COc1cc(C(=O)NS(C)(=O)=O)c2nc(C)cc(N3CCc4c(cc(Cn5ccnc5)cc4-c4cn(C)nc4C(F)(F)F)C3=O)c2c1] I-181 |

TABLE 1-continued
| Exemplary compounds. |
| --- |
I-182
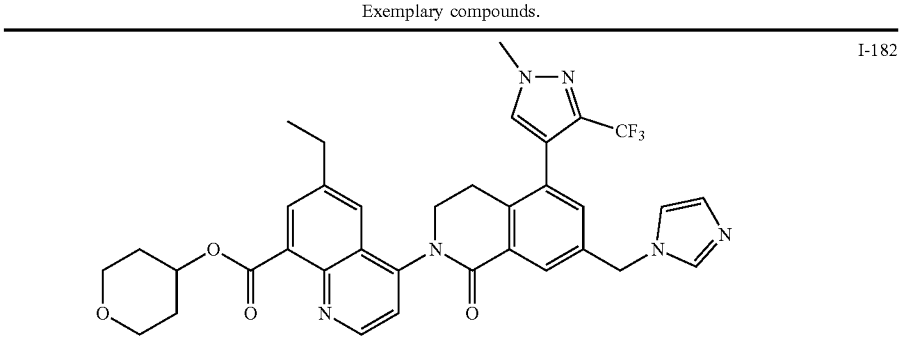
I-183
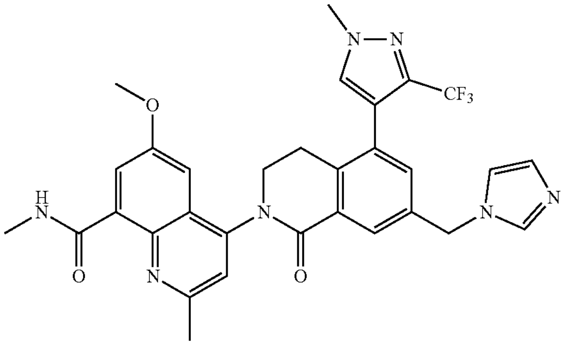 [SMILES: CNC(=O)c1cc(OC)cc2c(N3CCc4c(cc(Cn5ccnc5)cc4-c4cn(C)nc4C(F)(F)F)C3=O)cc(C)nc12]
I-184
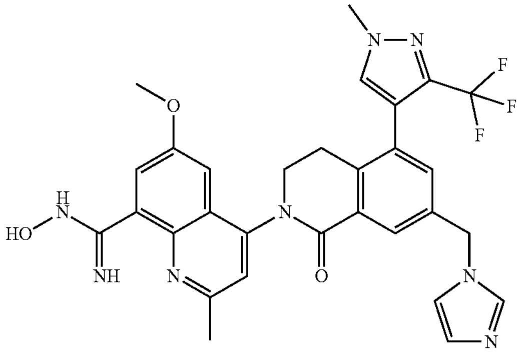 [SMILES: COc1cc(C(=N)NO)c2nc(C)cc(N3CCc4c(cc(Cn5ccnc5)cc4-c4cn(C)nc4C(F)(F)F)C3=O)c2c1]
I-185
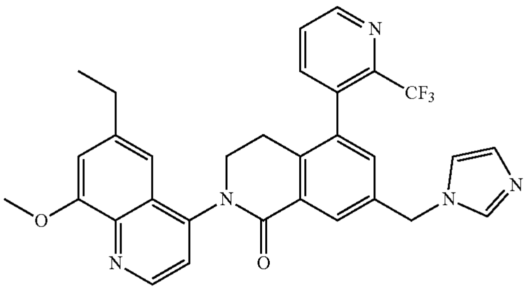 [SMILES: CCc1cc(OC)c2nccc(N3CCc4c(cc(Cn5ccnc5)cc4-c4cccnc4C(F)(F)F)C3=O)c2c1]
I-186
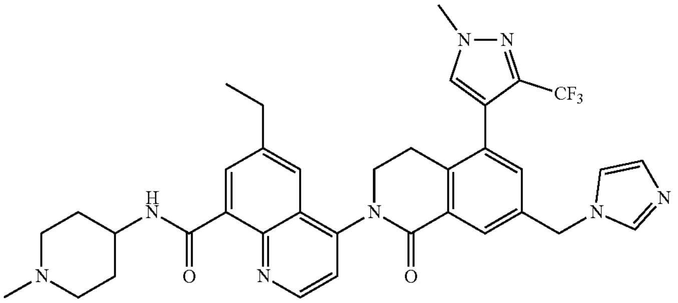 [SMILES: CCc1cc(C(=O)NC2CCN(C)CC2)c2nccc(N3CCc4c(cc(Cn5ccnc5)cc4-c4cn(C)nc4C(F)(F)F)C3=O)c2c1]

TABLE 1-continued
| Exemplary compounds. |
| --- |
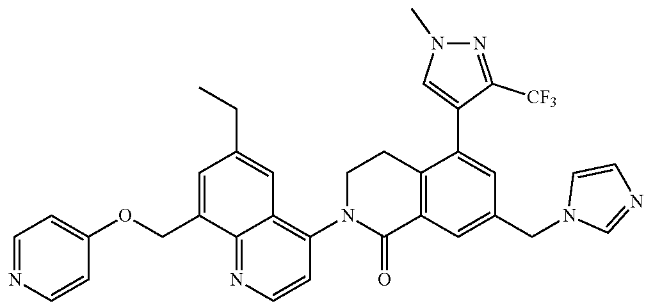 [SMILES: CCc1cc(COc2ccncc2)c2nccc(N3CCc4c(cc(Cn5ccnc5)cc4-c4cn(C)nc4C(F)(F)F)C3=O)c2c1]
I-187
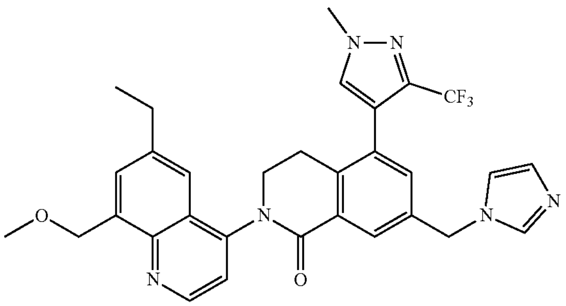 [SMILES: CCc1cc(COC)c2nccc(N3CCc4c(cc(Cn5ccnc5)cc4-c4cn(C)nc4C(F)(F)F)C3=O)c2c1]
I-188
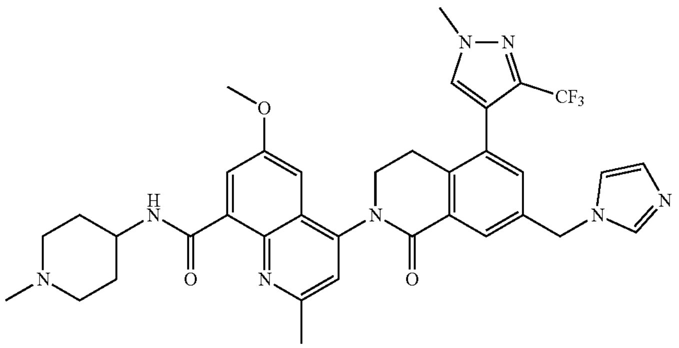 [SMILES: COc1cc(C(=O)NC2CCN(C)CC2)c2nc(C)cc(N3CCc4c(cc(Cn5ccnc5)cc4-c4cn(C)nc4C(F)(F)F)C3=O)c2c1]
I-189
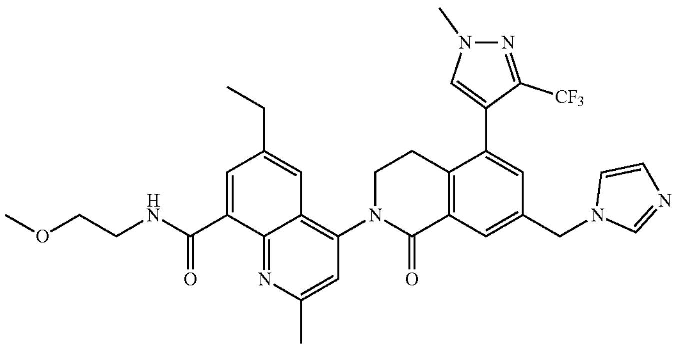 [SMILES: CCc1cc(C(=O)NCCOC)c2nc(C)cc(N3CCc4c(cc(Cn5ccnc5)cc4-c4cn(C)nc4C(F)(F)F)C3=O)c2c1]
I-190

TABLE 1-continued
| Exemplary compounds. |
| --- |
| 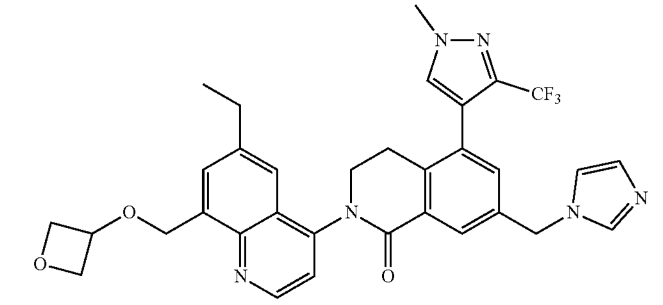 [SMILES: CCc1cc(COC2COC2)c2nccc(N3CCc4c(cc(Cn5ccnc5)cc4-c4cn(C)nc4C(F)(F)F)C3=O)c2c1] I-191 |
| 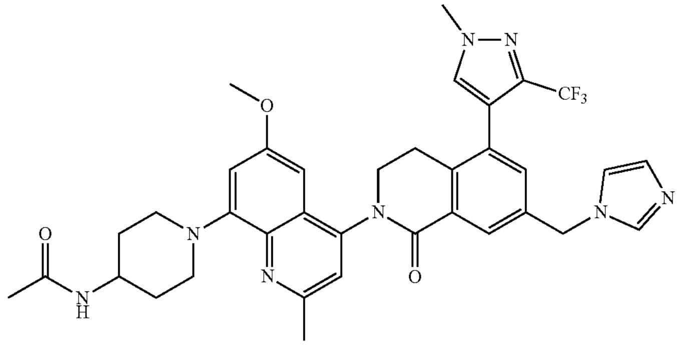 [SMILES: COc1cc(N2CCC(NC(C)=O)CC2)c2nc(C)cc(N3CCc4c(cc(Cn5ccnc5)cc4-c4cn(C)nc4C(F)(F)F)C3=O)c2c1] I-192 |
| 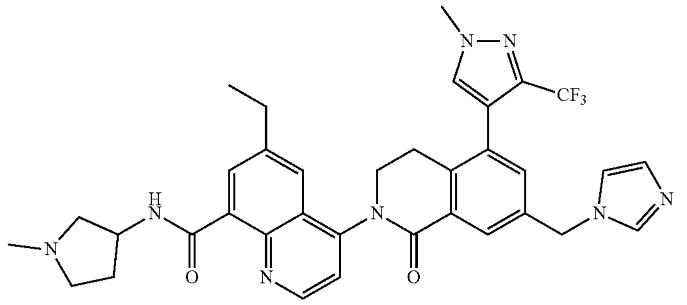 [SMILES: CCc1cc(C(=O)NC2CCN(C)C2)c2nccc(N3CCc4c(cc(Cn5ccnc5)cc4-c4cn(C)nc4C(F)(F)F)C3=O)c2c1] I-193 |
| 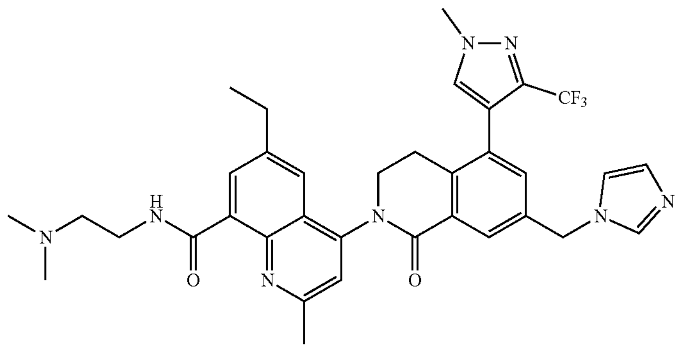 [SMILES: CCc1cc(C(=O)NCCN(C)C)c2nc(C)cc(N3CCc4c(cc(Cn5ccnc5)cc4-c4cn(C)nc4C(F)(F)F)C3=O)c2c1] I-194 |

TABLE 1-continued
| Exemplary compounds. |
| --- |
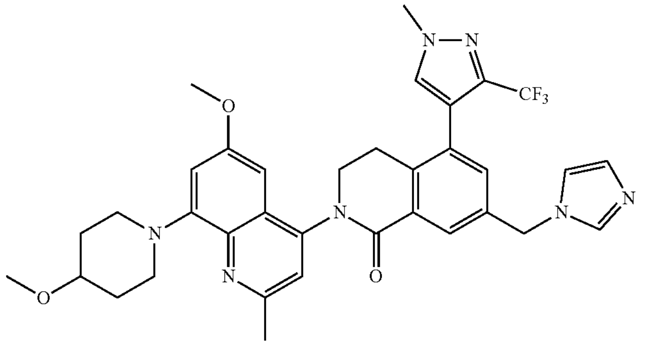 [SMILES: COc1cc(N2CCC(OC)CC2)c2nc(C)cc(N3CCc4c(cc(Cn5ccnc5)cc4-c4cn(C)nc4C(F)(F)F)C3=O)c2c1]
I-195
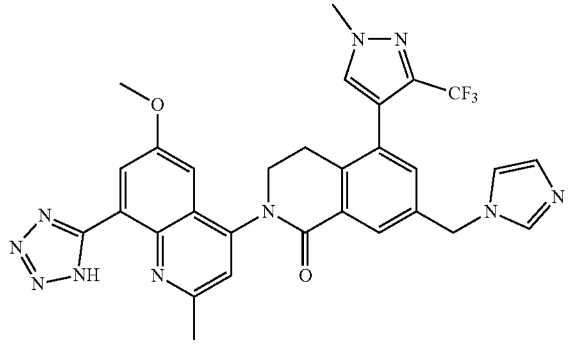 [SMILES: COc1cc(-c2nnn[nH]2)c2nc(C)cc(N3CCc4c(cc(Cn5ccnc5)cc4-c4cn(C)nc4C(F)(F)F)C3=O)c2c1]
I-196
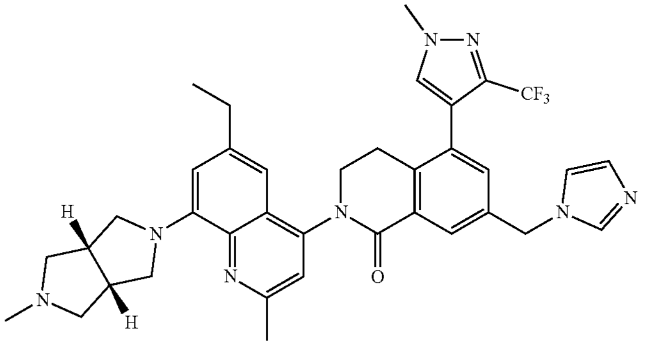 [SMILES: CCc1cc(N2C[C@H]3CN(C)C[C@H]3C2)c2nc(C)cc(N3CCc4c(cc(Cn5ccnc5)cc4-c4cn(C)nc4C(F)(F)F)C3=O)c2c1]
I-197
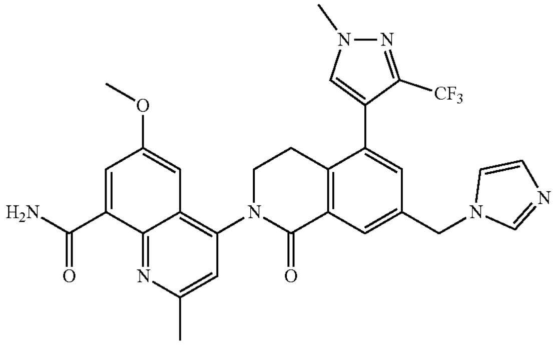 [SMILES: COc1cc(C(N)=O)c2nc(C)cc(N3CCc4c(cc(Cn5ccnc5)cc4-c4cn(C)nc4C(F)(F)F)C3=O)c2c1]
I-198

TABLE 1-continued
| Exemplary compounds. |
| --- |
I-199
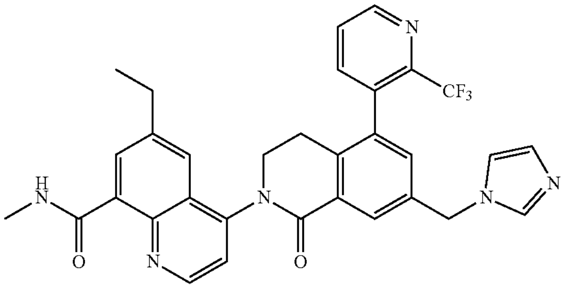 [SMILES: CCc1cc(C(=O)NC)c2nccc(N3CCc4c(cc(Cn5ccnc5)cc4-c4cccnc4C(F)(F)F)C3=O)c2c1]
I-200
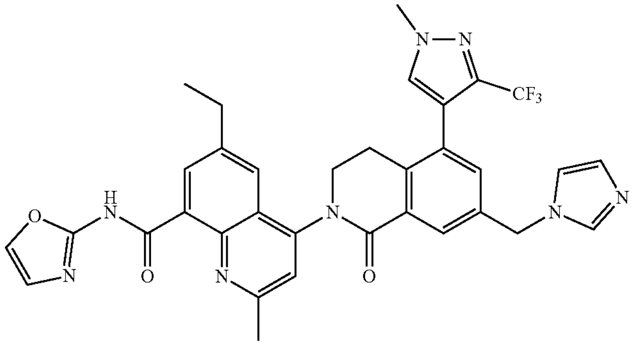 [SMILES: CCc1cc(C(=O)Nc2ncco2)c2nc(C)cc(N3CCc4c(cc(Cn5ccnc5)cc4-c4cn(C)nc4C(F)(F)F)C3=O)c2c1]
I-201
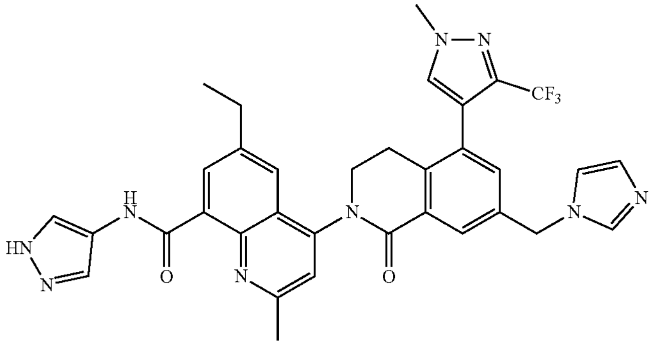 [SMILES: CCc1cc(C(=O)Nc2cn[nH]c2)c2nc(C)cc(N3CCc4c(cc(Cn5ccnc5)cc4-c4cn(C)nc4C(F)(F)F)C3=O)c2c1]
I-202
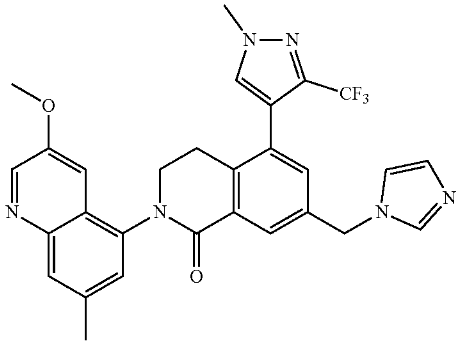

TABLE 1-continued
Exemplary compounds.
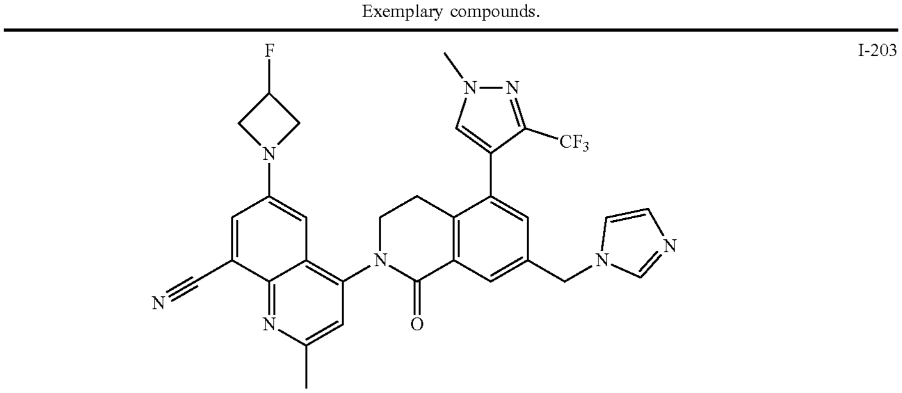
I-203
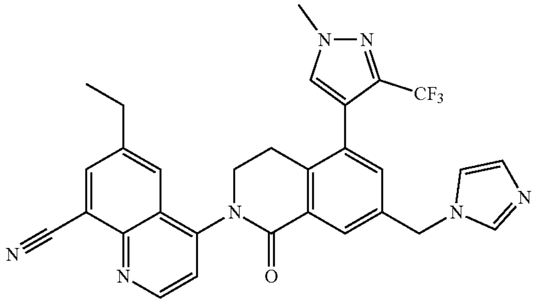 [SMILES: CCc1cc(C#N)c2nccc(N3CCc4c(cc(Cn5ccnc5)cc4-c4cn(C)nc4C(F)(F)F)C3=O)c2c1]
I-204
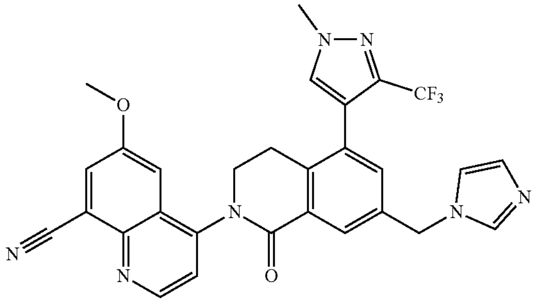
I-205
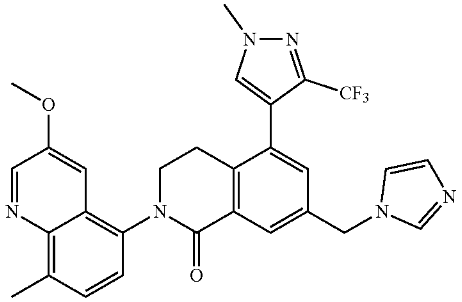 [SMILES: COc1cnc2c(C)ccc(N3CCc4c(cc(Cn5ccnc5)cc4-c4cn(C)nc4C(F)(F)F)C3=O)c2c1]
I-206
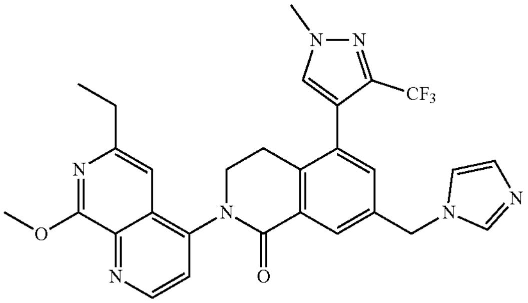 [SMILES: CCc1cc2c(N3CCc4c(cc(Cn5ccnc5)cc4-c4cn(C)nc4C(F)(F)F)C3=O)ccnc2c(OC)n1]
I-207

TABLE 1-continued
| Exemplary compounds. |
|---|
I-208
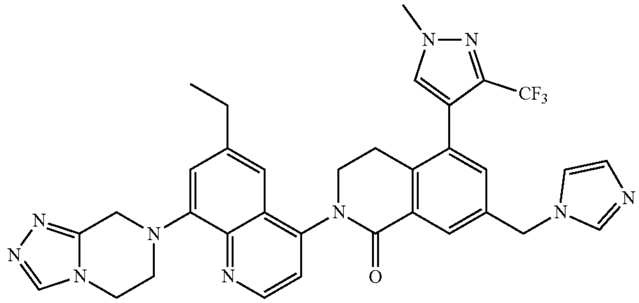 [SMILES: CCc1cc(N2CCn3cnnc3C2)c2nccc(N3CCc4c(cc(Cn5ccnc5)cc4-c4cn(C)nc4C(F)(F)F)C3=O)c2c1]
I-209
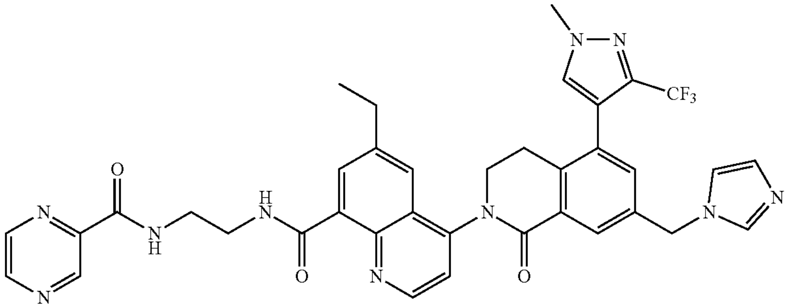 [SMILES: CCc1cc(C(=O)NCCNC(=O)c2cnccn2)c2nccc(N3CCc4c(cc(Cn5ccnc5)cc4-c4cn(C)nc4C(F)(F)F)C3=O)c2c1]
I-210
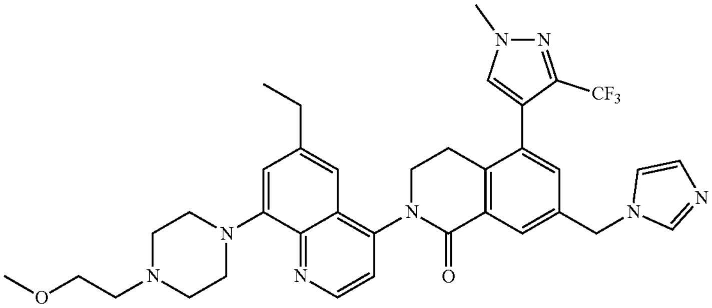 [SMILES: CCc1cc(N2CCN(CCOC)CC2)c2nccc(N3CCc4c(cc(Cn5ccnc5)cc4-c4cn(C)nc4C(F)(F)F)C3=O)c2c1]
I-211
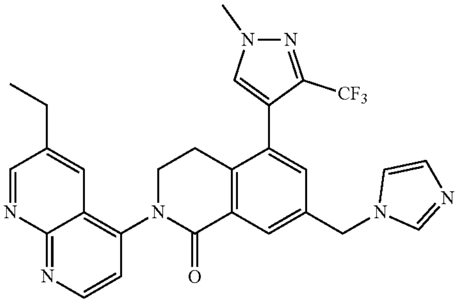
I-212
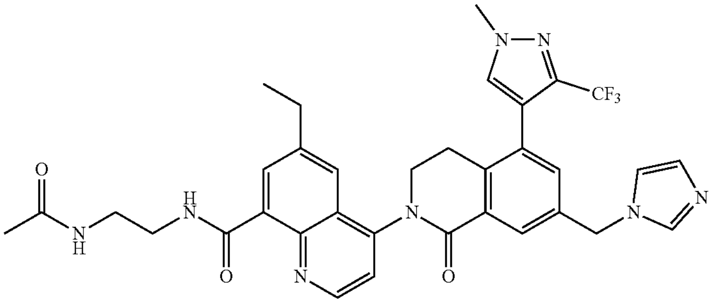 [SMILES: CCc1cc(C(=O)NCCNC(C)=O)c2nccc(N3CCc4c(cc(Cn5ccnc5)cc4-c4cn(C)nc4C(F)(F)F)C3=O)c2c1]

TABLE 1-continued
Exemplary compounds.
I-213
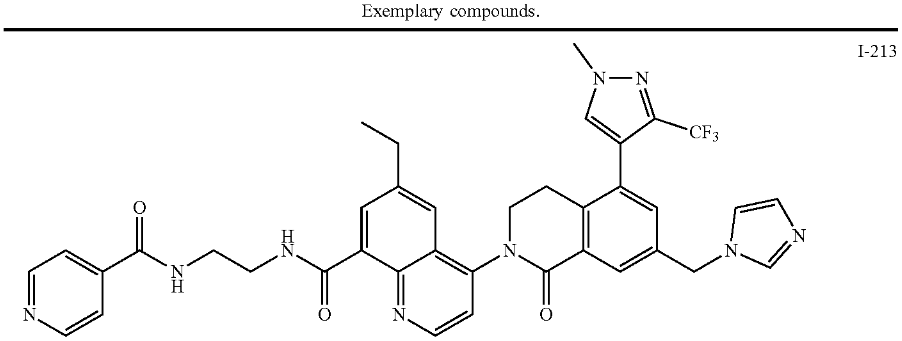
I-214
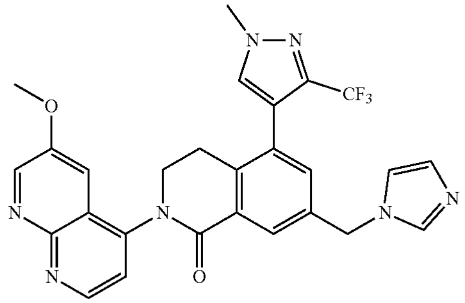
I-215
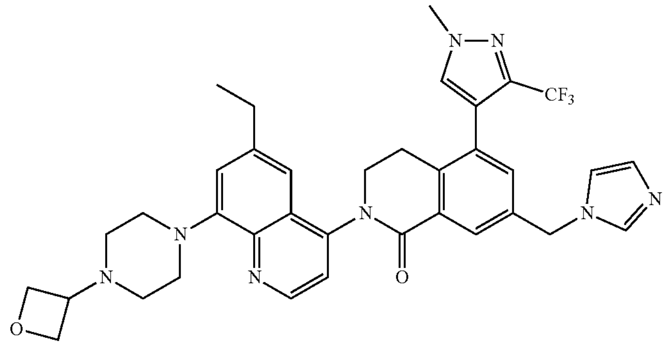 [SMILES: CCc1cc(N2CCN(C3COC3)CC2)c2nccc(N3CCc4c(cc(Cn5ccnc5)cc4-c4cn(C)nc4C(F)(F)F)C3=O)c2c1]
I-216
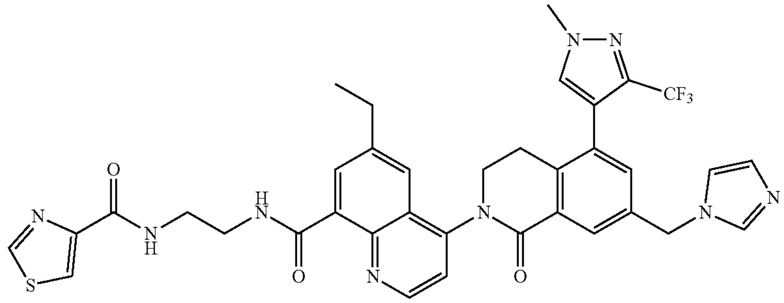 [SMILES: CCc1cc(C(=O)NCCNC(=O)c2cscn2)c2nccc(N3CCc4c(cc(Cn5ccnc5)cc4-c4cn(C)nc4C(F)(F)F)C3=O)c2c1]
I-217
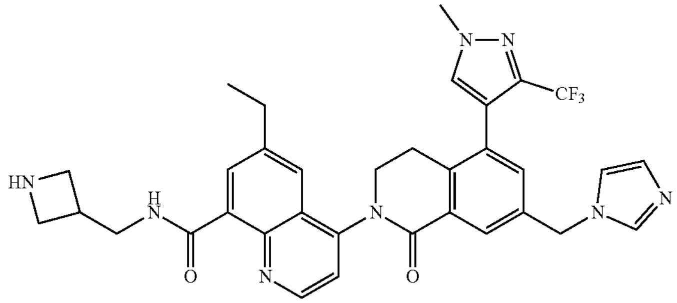 [SMILES: CCc1cc(C(=O)NCC2CNC2)c2nccc(N3CCc4c(cc(Cn5ccnc5)cc4-c4cn(C)nc4C(F)(F)F)C3=O)c2c1]

TABLE 1-continued
Exemplary compounds.
I-218
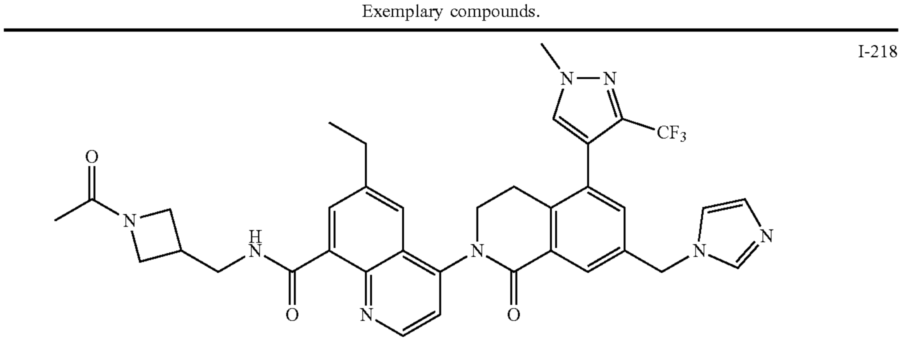
I-219
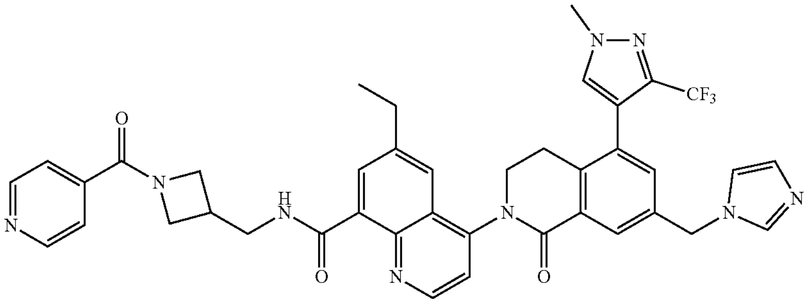 [SMILES: CCc1cc(C(=O)NCC2CN(C(=O)c3ccncc3)C2)c2nccc(N3CCc4c(cc(Cn5ccnc5)cc4-c4cn(C)nc4C(F)(F)F)C3=O)c2c1]
I-220
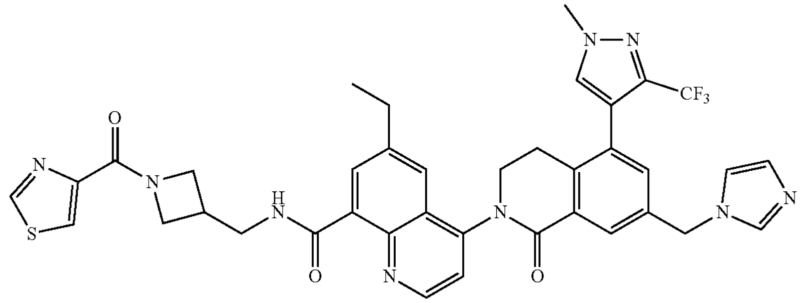 [SMILES: CCc1cc(C(=O)NCC2CN(C(=O)c3cscn3)C2)c2nccc(N3CCc4c(cc(Cn5ccnc5)cc4-c4cn(C)nc4C(F)(F)F)C3=O)c2c1]
I-221
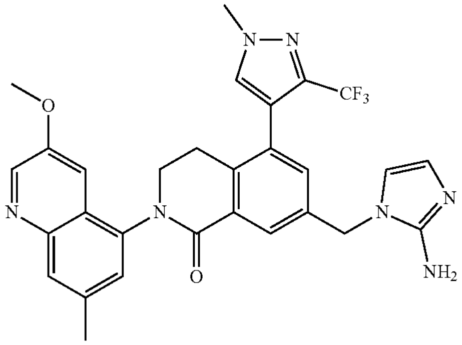 [SMILES: COc1cnc2cc(C)cc(N3CCc4c(cc(Cn5ccnc5N)cc4-c4cn(C)nc4C(F)(F)F)C3=O)c2c1]
I-222
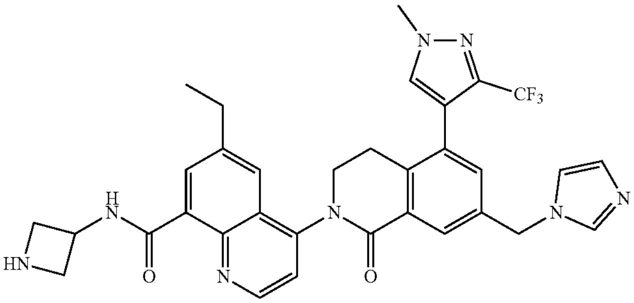 [SMILES: CCc1cc(C(=O)NC2CNC2)c2nccc(N3CCc4c(cc(Cn5ccnc5)cc4-c4cn(C)nc4C(F)(F)F)C3=O)c2c1]

TABLE 1-continued
Exemplary compounds.
I-223
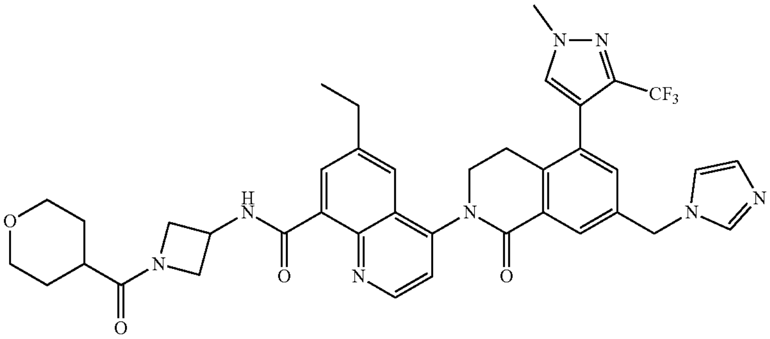 [SMILES: CCc1cc(C(=O)NC2CN(C(=O)C3CCOCC3)C2)c2nccc(N3CCc4c(cc(Cn5ccnc5)cc4-c4cn(C)nc4C(F)(F)F)C3=O)c2c1]
I-224
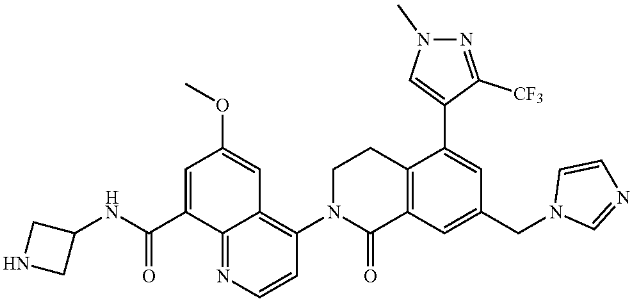 [SMILES: COc1cc(C(=O)NC2CNC2)c2nccc(N3CCc4c(cc(Cn5ccnc5)cc4-c4cn(C)nc4C(F)(F)F)C3=O)c2c1]
I-225
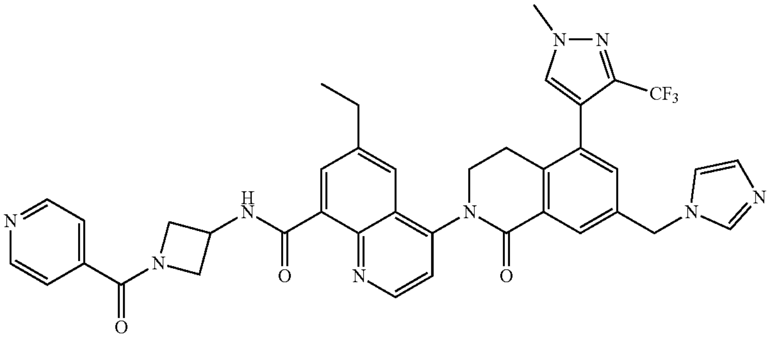 [SMILES: CCc1cc(C(=O)NC2CN(C(=O)c3ccncc3)C2)c2nccc(N3CCc4c(cc(Cn5ccnc5)cc4-c4cn(C)nc4C(F)(F)F)C3=O)c2c1]
I-226
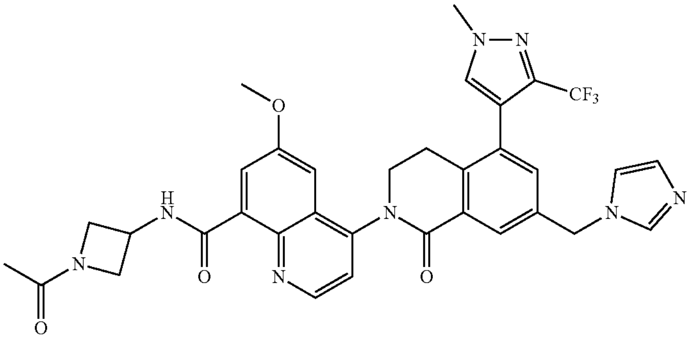 [SMILES: COc1cc(C(=O)NC2CN(C(C)=O)C2)c2nccc(N3CCc4c(cc(Cn5ccnc5)cc4-c4cn(C)nc4C(F)(F)F)C3=O)c2c1]

TABLE 1-continued
| Exemplary compounds. |
| --- |
I-227
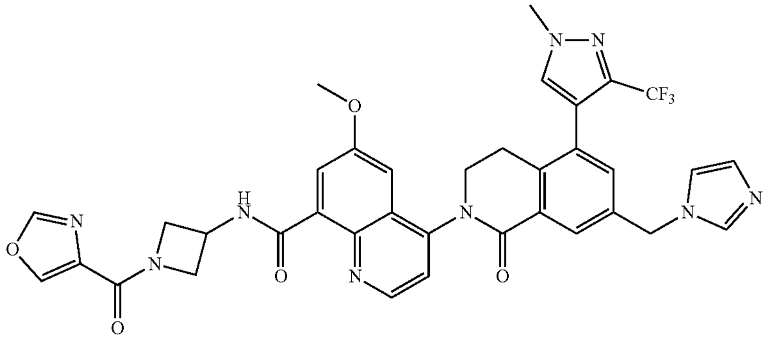 [SMILES: COc1cc(C(=O)NC2CN(C(=O)c3cocn3)C2)c2nccc(N3CCc4c(cc(Cn5ccnc5)cc4-c4cn(C)nc4C(F)(F)F)C3=O)c2c1]
I-228
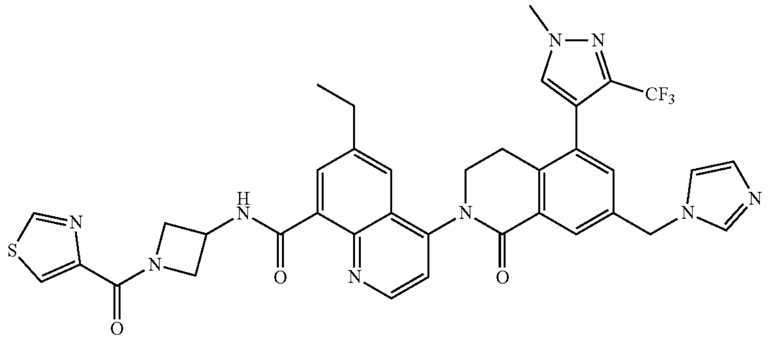 [SMILES: CCc1cc(C(=O)NC2CN(C(=O)c3cscn3)C2)c2nccc(N3CCc4c(cc(Cn5ccnc5)cc4-c4cn(C)nc4C(F)(F)F)C3=O)c2c1]
I-229
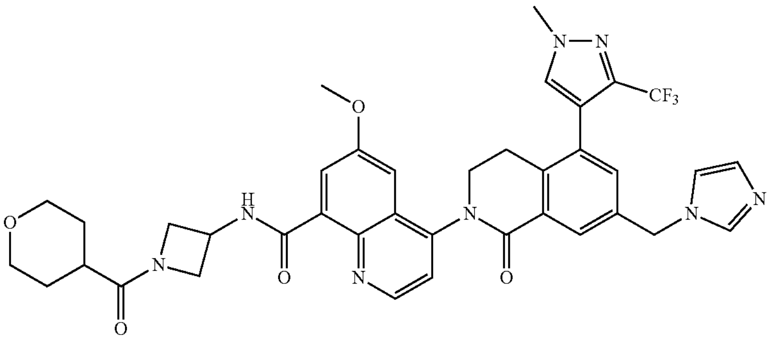 [SMILES: COc1cc(C(=O)NC2CN(C(=O)C3CCOCC3)C2)c2nccc(N3CCc4c(cc(Cn5ccnc5)cc4-c4cn(C)nc4C(F)(F)F)C3=O)c2c1]
I-230
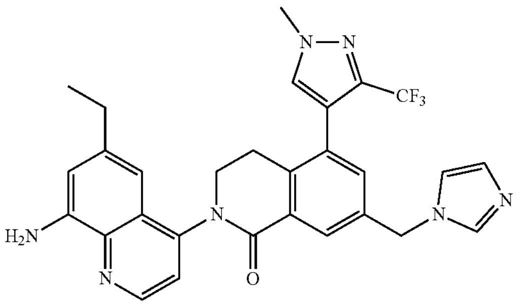 [SMILES: CCc1cc(N)c2nccc(N3CCc4c(cc(Cn5ccnc5)cc4-c4cn(C)nc4C(F)(F)F)C3=O)c2c1]

TABLE 1-continued
| Exemplary compounds. |
| --- |
I-231
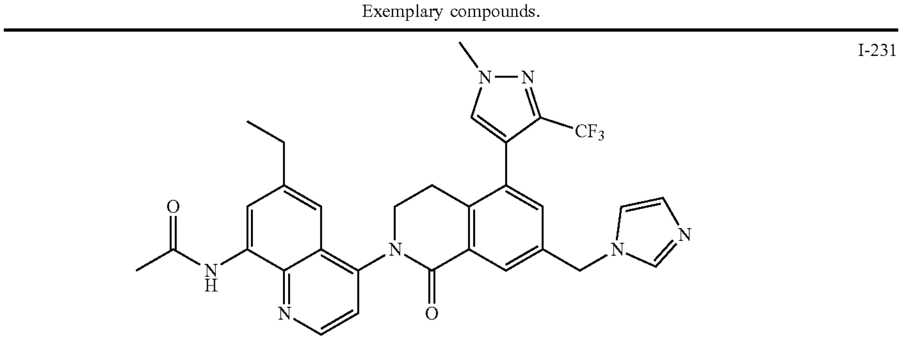
I-232
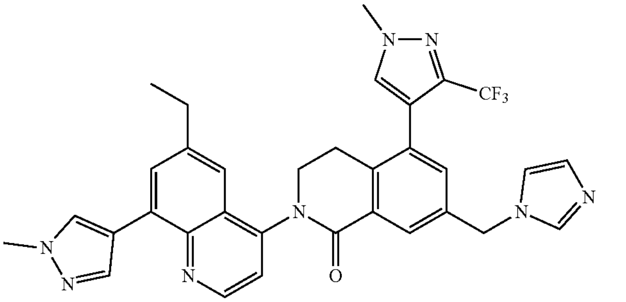 [SMILES: CCc1cc(-c2cnn(C)c2)c2nccc(N3CCc4c(cc(Cn5ccnc5)cc4-c4cn(C)nc4C(F)(F)F)C3=O)c2c1]
I-233
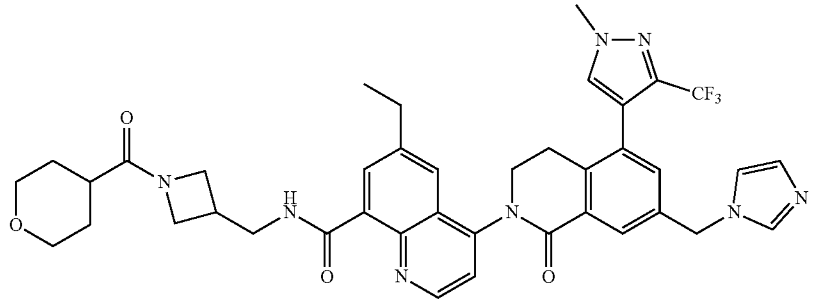 [SMILES: CCc1cc(C(=O)NCC2CN(C(=O)C3CCOCC3)C2)c2nccc(N3CCc4c(cc(Cn5ccnc5)cc4-c4cn(C)nc4C(F)(F)F)C3=O)c2c1]
I-234
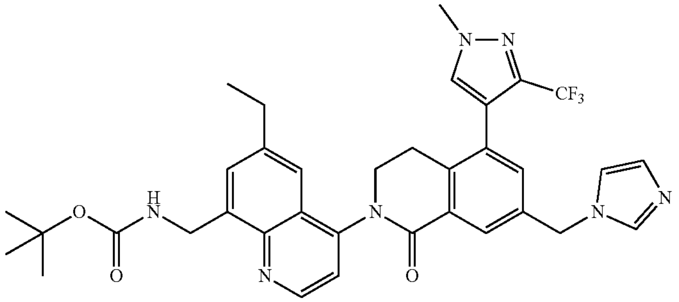 [SMILES: CCc1cc(CNC(=O)OC(C)(C)C)c2nccc(N3CCc4c(cc(Cn5ccnc5)cc4-c4cn(C)nc4C(F)(F)F)C3=O)c2c1]
I-235
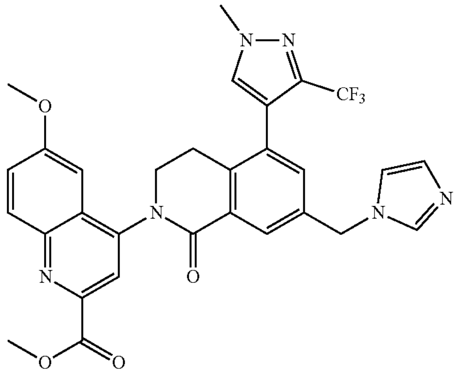 [SMILES: COC(=O)c1cc(N2CCc3c(cc(Cn4ccnc4)cc3-c3cn(C)nc3C(F)(F)F)C2=O)c2cc(OC)ccc2n1]

TABLE 1-continued
| Exemplary compounds. |
| --- |
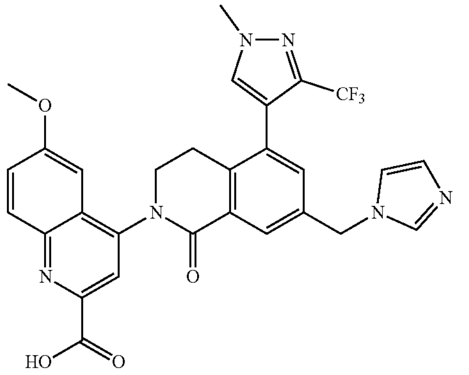 [SMILES: COc1ccc2nc(C(=O)O)cc(N3CCc4c(cc(Cn5ccnc5)cc4-c4cn(C)nc4C(F)(F)F)C3=O)c2c1]
I-236
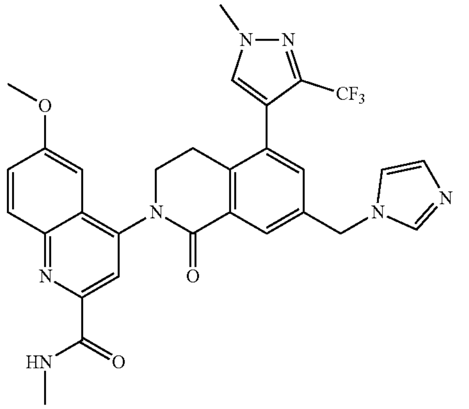 [SMILES: CNC(=O)c1cc(N2CCc3c(cc(Cn4ccnc4)cc3-c3cn(C)nc3C(F)(F)F)C2=O)c2cc(OC)ccc2n1]
I-237
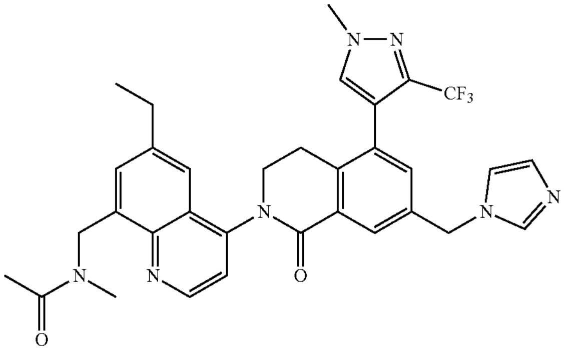 [SMILES: CCc1cc(CN(C)C(C)=O)c2nccc(N3CCc4c(cc(Cn5ccnc5)cc4-c4cn(C)nc4C(F)(F)F)C3=O)c2c1]
I-238
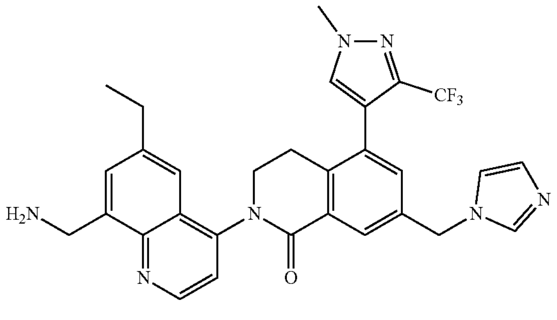 [SMILES: CCc1cc(CN)c2nccc(N3CCc4c(cc(Cn5ccnc5)cc4-c4cn(C)nc4C(F)(F)F)C3=O)c2c1]
I-239

TABLE 1-continued

Exemplary compounds.

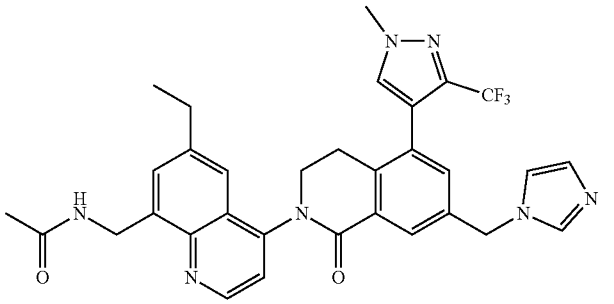 [SMILES: CCc1cc(CNC(C)=O)c2nccc(N3CCc4c(cc(Cn5ccnc5)cc4-c4cn(C)nc4C(F)(F)F)C3=O)c2c1]

I-240

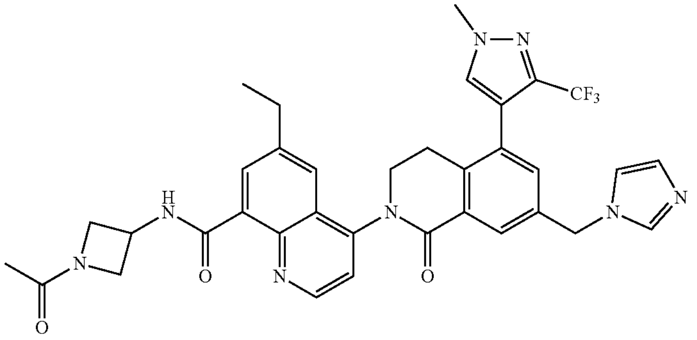 [SMILES: CCc1cc(C(=O)NC2CN(C(C)=O)C2)c2nccc(N3CCc4c(cc(Cn5ccnc5)cc4-c4cn(C)nc4C(F)(F)F)C3=O)c2c1]

I-241

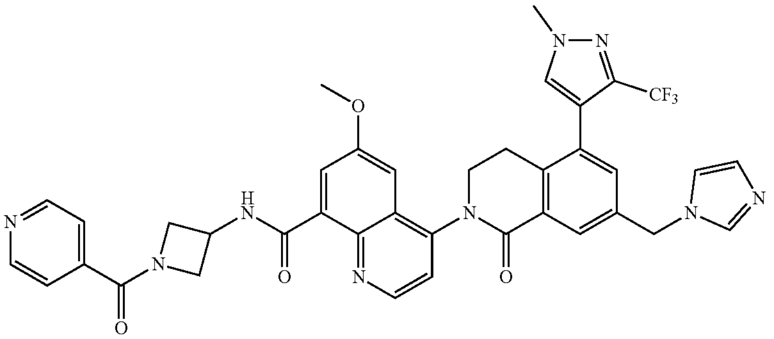 [SMILES: COc1cc(C(=O)NC2CN(C(=O)c3ccncc3)C2)c2nccc(N3CCc4c(cc(Cn5ccnc5)cc4-c4cn(C)nc4C(F)(F)F)C3=O)c2c1]

I-242

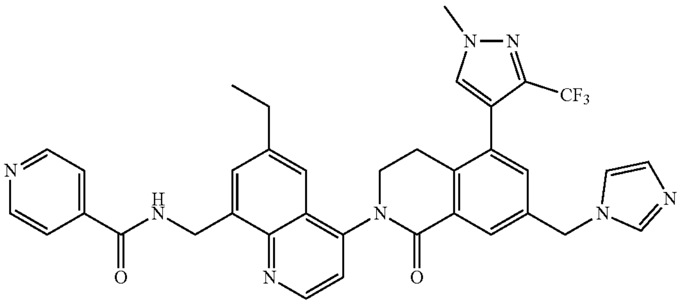 [SMILES: CCc1cc(CNC(=O)c2ccncc2)c2nccc(N3CCc4c(cc(Cn5ccnc5)cc4-c4cn(C)nc4C(F)(F)F)C3=O)c2c1]

I-243

Compound names are assigned by using Struct=Name naming algorithm as part of CHEMDRAW® ULTRA.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature, Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

In the compounds of formula (I), any "hydrogen" or "H," whether explicitly recited or implicit in the structure, encompasses hydrogen isotopes $^{1}H$ (protium) and $^{2}H$ (deuterium).

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A. Binding to WDR5

The disclosed compounds may bind to WDR5 and prevent the association of MLL1 or other transcription factors and proteins dependent on WDR5. The compounds may bind to WDR5 and prevent oncogenic processes associated with MLL1, c-MYC, or other oncogenic proteins dependent on WDR5.

Compounds of formula (I) can bind to WDR5 resulting in a $K_i$ ranging from about 0.01 nM to about 250 μM. The compounds may have a $K_i$ of about 250 μM, about 200 μM, about 150 μM, about 100 μM, about 90 μM, about 80 μM, about 70 μM, about 60 μM, about 50 μM, about 40 μM, about 30 μM, about 20 μM, about 10 μM, about 9 μM, about 8 μM, about 7 μM, about 6 μM, about 5 μM, about 4 μM, about 3 μM, about 2 μM, about 1 μM, about 950 nM, about 900 nM about 850 nM, about 800 nM, about 850 nM, about 800 nM, about 750 nM, about 700 nM, about 650 nM, about 600 nM, about 550 nM, about 500 nM/1, about 450 nM, about 400 nM, about 350 nM, about 300 nM, about 250 nM, about 200 nM, about 150 nM, about 100 nM, about 50 nM, about 10 nM, about 5 nM, about 1 nM, about 0.3 nM, about 0.1 nM, about 0.03 nM, or about 0.01 nM. Compounds of formula (I) can bind to WDR5 resulting in a $K_i$ of less than 250 μM, less than 200 μM, less than 150 μM, less than 100 μM, less than 90 μM, less than 80 μM, less than 70 μM, less than 60 μM, less than 50 μM, less than 40 μM, less than 30 μM, less than 20 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, less than 1 nM, less than 0.3 nM, less than 0.1 nM, or less than 0.03 nM.

B. General Synthesis

Compounds of formula (I) may be prepared by synthetic processes or by metabolic processes. Preparation of the compounds by metabolic processes includes those occurring in the human or animal body (in vivo) or processes occurring in vitro.

The compounds of the present disclosure can be prepared in a number of ways well known to one skilled in the art of organic synthesis. The compounds of the present disclosure can be synthesized using the methods described below, together with synthetic methods known in the art of synthetic organic chemistry, or variations thereon as appreciated by those skilled in the art Preferred methods include, but are not limited to, those described below. All references cited herein are hereby incorporated in their entirety by reference as to the subject matter referenced herein. Compounds of formula (I) may be also prepared by metabolic processes. Preparation of the compounds by metabolic processes includes those occurring in the human or animal body (in vivo) or processes occurring in vitro.

The compounds of the disclosure may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein, One skilled in the art of organic synthesis understands that the functionality present on various portions of the edict molecule must be compatible with the reagents and reactions proposed. Not all compounds of the disclosure falling into a given class may be compatible with some of the reaction conditions required in some of the methods described. Such restrictions to the substituents, which are compatible with the reaction conditions, will be readily apparent to one skilled in the art and alternate methods can be used.

Scheme 1.

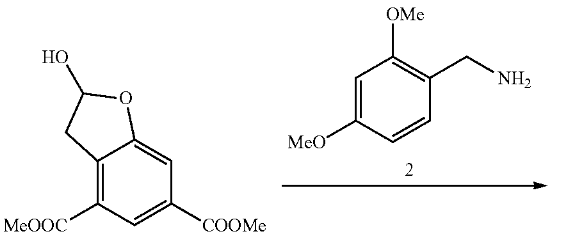

1

2

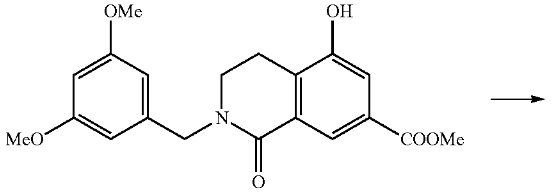

3

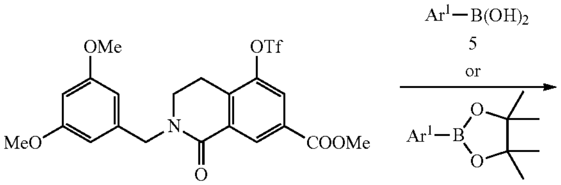

4

6

-continued

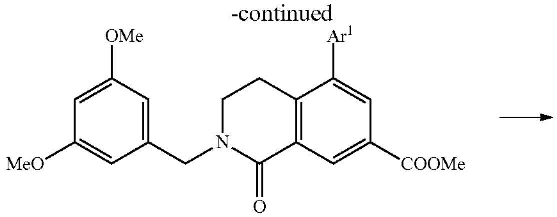

7

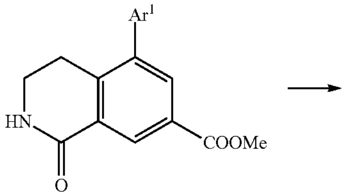

8

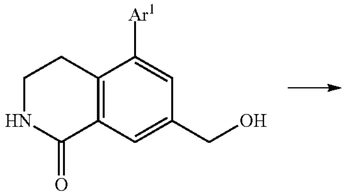

9

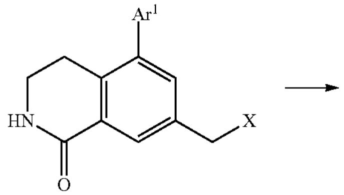

10

X = Cl, Br, I, OMs, OTs

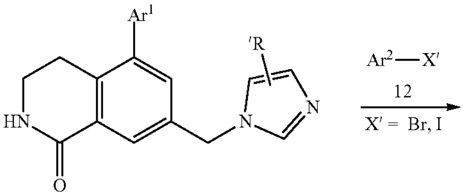

11

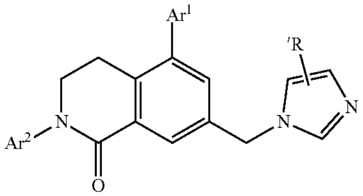

13

In some embodiments, compounds of Formula 13 may be synthesized by procedures illustrated in Scheme 1. Hemiacetal 1 can be coupled with (2,4-dimethoxyphenyl) ethanamine 2 under the reductive amination condition employing a reducing agent including, but not limited to, $NaBH(OAc)_3$ or $NaCNBH_3$ followed by spontaneous cyclization to yield intermediate 3. After activation of phenol moiety of 3 as a triflate, intermediate 4 may be coupled with a variety of boronic acids 5 or borates 6, which are commercially available or can be prepared, via e.g., Suzuki-Miyaura coupling protocol to afford biaryl adducts 7 (Miyaura, N., Suzuki, A., *Chem. Rev.* (1995), 2457) in the presence of a catalytic Pd species, such as $Pd(PPh_3)_4$, $PdCl_2(dppf)$, $Pd(PPh_3)_2Cl_2$, $Pd(OAc)_2$, $Pd_2(dba)_3$ and a suitable ligand such as $PPh_3$, $AsPh_3$, etc., or other such Pd catalyst, and a base such as $Na_2CO_3$, $Cs_2CO_3$, $K_2CO_3$, $Ba(OH)_2$ or $Et_3N$. The dimethoxybenzyl moiety of 7 can be removed using, but not limited to, TFA to prepare lactam 8. The methyl ester functional group of 8 may be converted to an alcohol under various reduction conditions that are routine for those skilled in the art of organic synthesis. The hydroxy group of formula 9 may be activated by converting to a bromide, chloride, mesylate or tosylate group by a number of conditions that are routine for those skilled in the art of organic synthesis. The resulting intermediate 10 may be reacted with variety of nucleophiles such as optionally substituted imidazole in the presence of appropriate bases, such as DIEA, TEA, $Cs_2CO_3$, $K_2CO_3$, LiOH or NaOH, to yield Intermediate 11. The lactam NH of 11 may undergo cross-coupling reactions with a variety of aryl or heteroaryl halides of formula 12, wherein X' is Br or I, in the presence of a catalytic Pd species, such as $Pd(OAc)_2$ or $Pd_2(dba)_3$ and a suitable ligand such as Xantphos or BrettPhos and a base such as $Na_2CO_3$, $Cs_2CO_3$, or $K_2CO_3$ to generate compounds of formula 13. Alternatively, compounds of formula 13 can be produced using the Ullman coupling conditions in the presence of CuI and a suitable ligand such as (trans)-1,2-N,N'-dimethylaminocyclohexane or L-Proline and a base such as $Cs_2CO_3$, $K_2CO_3$ or $K_2PO_4$ in a suitable solvent such as toluene or DMF.

Scheme 2.

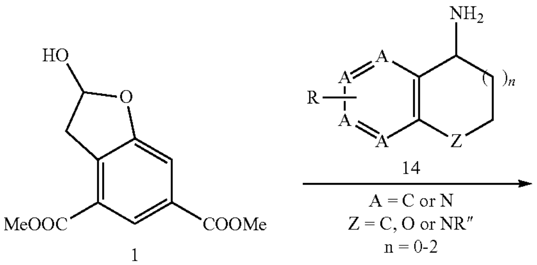

1

-continued

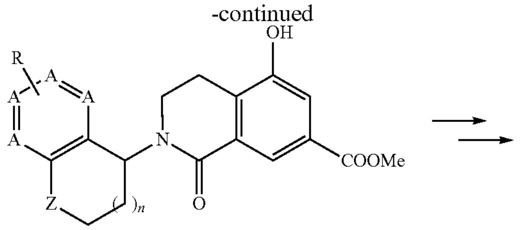

15

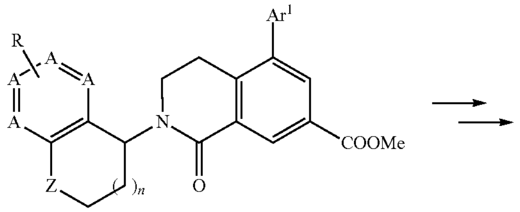

16

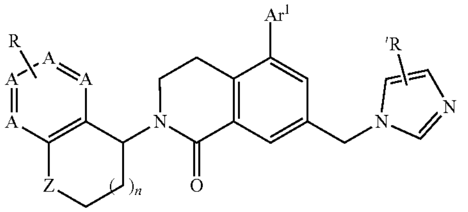

17

In some embodiments, provided compounds of this invention may be prepared as shown in Scheme 2. Optionally substituted partially unsaturated fused-bicyclic amine 14 may be coupled with hemiacetal 1 under the reductive amination conditions described above to give intermediate 15. Then, it can be subjected to the reaction sequence illustrated in Scheme 1 from intermediate 3 to 7 to afford intermediate 16 followed by the sequence from intermediate 8 to 11 to obtain compounds of formula 17.

Scheme 3.

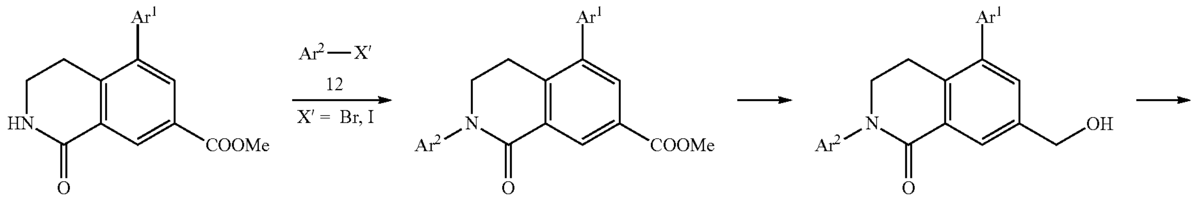

8 18 19

-continued

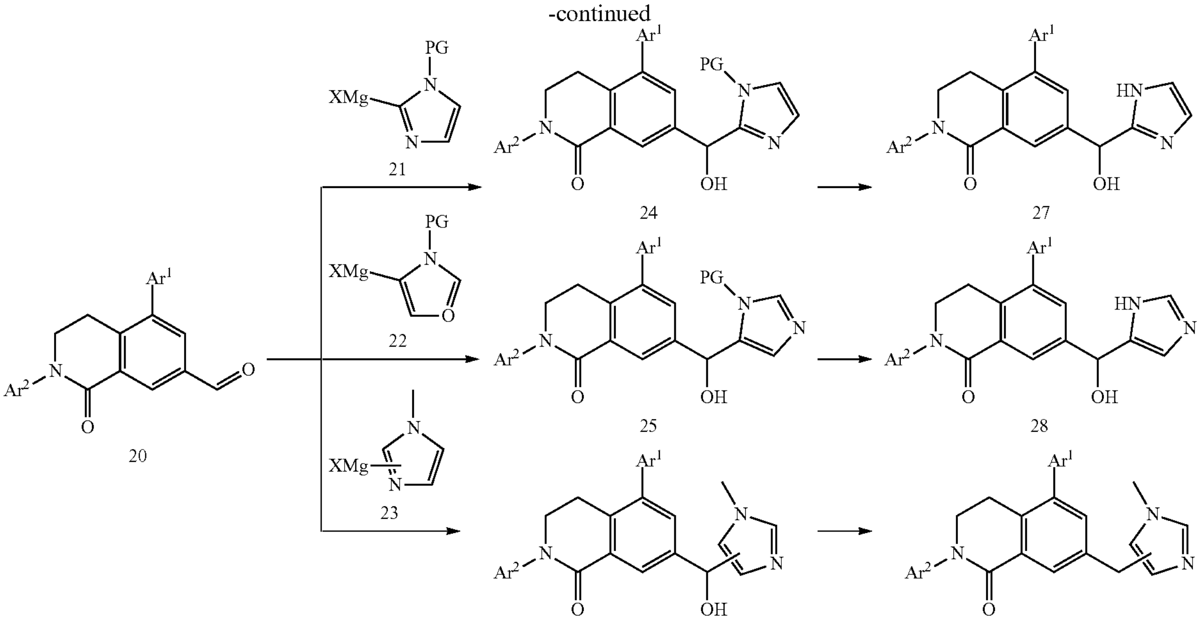

20, 21, 22, 23, 24, 25, 26, 27, 28, 29

Alternatively, intermediates of formula 8 may undergo cross-coupling reactions with a variety of aryl or heteroaryl halides of formula 12 under the condition described in Scheme 1 to give intermediate 18. The methyl ester functional group of 18 may be converted to an alcohol under various reduction conditions that are routine for those skilled in the art of organic synthesis. The primary alcohol of intermediate 19 may be oxidized by appropriate reagents at a number of conditions that are routine for those skilled in the art to give aldehyde 20. A variety of N-substituted imidazolyl Grignard reagents such (i.e. 21-23) as (1-trityl-1H-imidazol-5-yl)magnesium iodide, (1-trityl-1H-imidazol-2-yl)magnesium iodide or (1-methyl-1H-imidazol-2-yl) magnesium iodide, but not limited to, may react with aldehyde 20 to generate corresponding secondary alcohols 24-26. Compounds of formula 27-29 may be produced by reduction of corresponding alcohols 24-26 using, but not limited to, triethylsilane and TFA in a polar aprotic solvent such as 1,2-dichloroethane with heat.

Scheme 4.

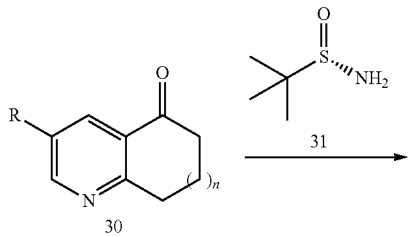

30, 31

-continued

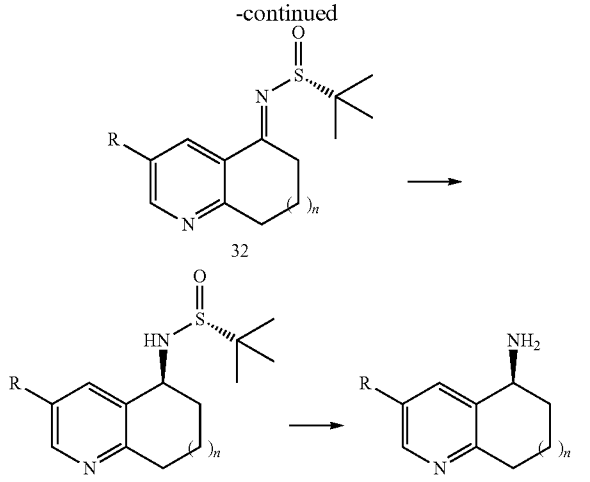

32, 33, 34

Optically pure amine intermediate of formula 34 may be prepared by procedures illustrated in Scheme 4. Suitably substituted bicyclic ketone 30 ray undergo condensation reaction with optically pure tert-butanesulfinamide using $Ti(OEt)_4$ as a Lewis acid and water scavenger. The resulting optically pure N-sulfinyl imine intermediate 32 may be then reduced using appropriate hydrides, such as $NaBH_4$ or L-Selectride, to afford the diastereomerically enriched sulfinamide 33. The tert-butanesulfinyl group may be then removed by appropriate acids to yield optically pure bicyclic amine of formular 34.

Scheme 5.

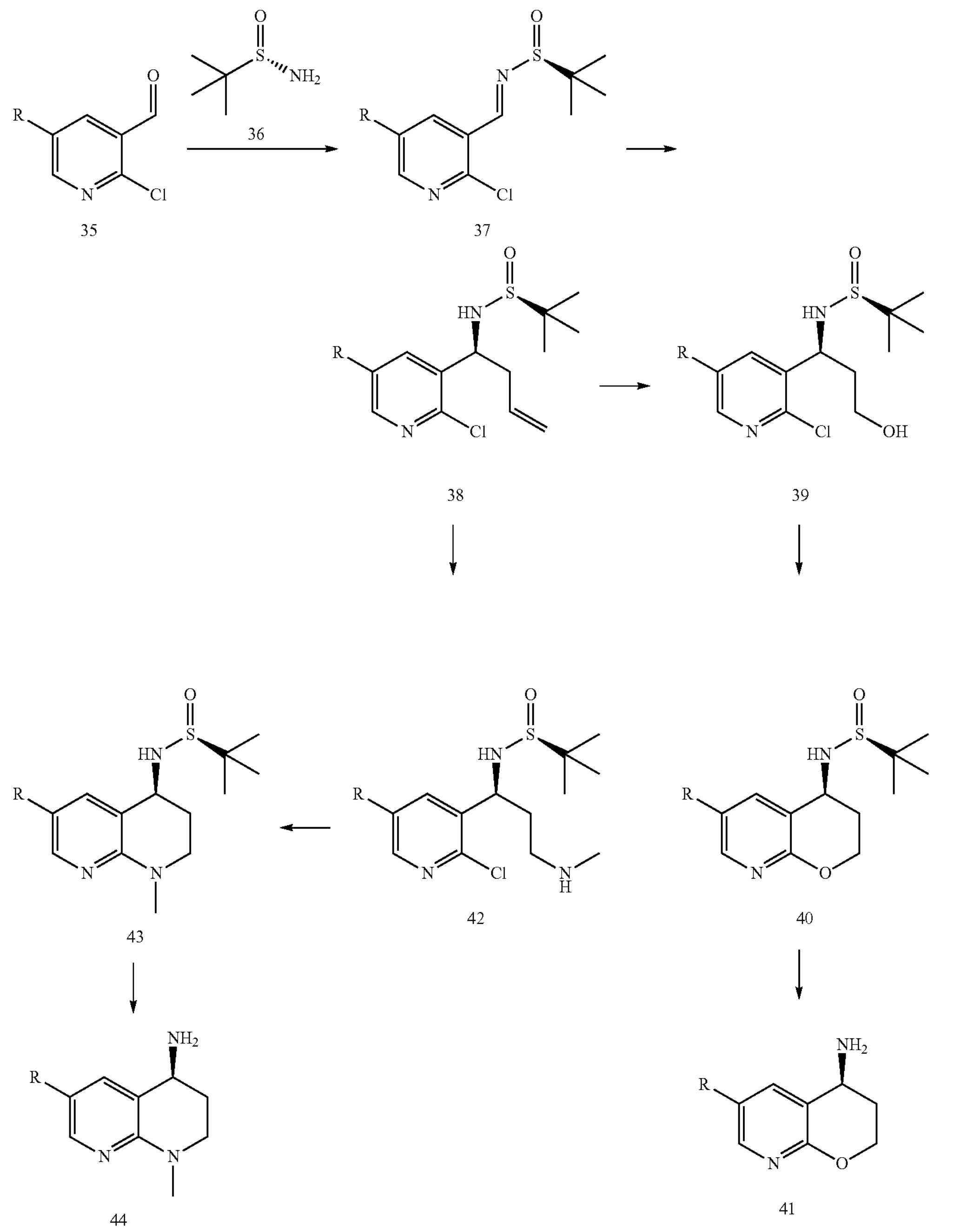

In some embodiments, optically pure bicyclic amines of formula 41 and 44 were used as reagents and may be synthesized by procedures illustrated in Scheme 5 using optionally substituted 2-chloronicotinaldehyde 35, which may be converted to optically pure N-sulfinyl imine intermediate 37 using the condensation protocol descried in Scheme 4 using CuSO4 as a Lewis acid. Allylmagnesium bromide may react with the imine functional group of Intermediate 37 in stereoselective manner to yield the diastereomerically enriched sulfinamide 38. Subsequent ozonalysis followed by reductive work-up in the presence of $NaBH_4$, but not limited to, using Intermediate 38 may be performed. The resulting alcohol 39 may be cyclized through $SN_{Ar}$ reaction using potassium tert-butoxide, but not limited to, as a base to yield dihydro-pyranopyridine intermediate 40. Alternatively, the secondary amine 42 may be produced from Intermediate 38 through ozonalysis followed by reductive amination work-up using methylamine and $NaBH_3CN$, which is routine for those skilled in the art of organic synthesis. Intermediate 42 may be then cyclized to tetrahydro-1,8-naphthyridine 43 under the $SN_{Ar}$ reaction condition using organic base, such as DIPEA, at high temperature. The tert-butanesulfinyl group of both Intermediate 40 and 43 may be removed under acidic condition to yield chiral amines 41 and 44.

Scheme 6.

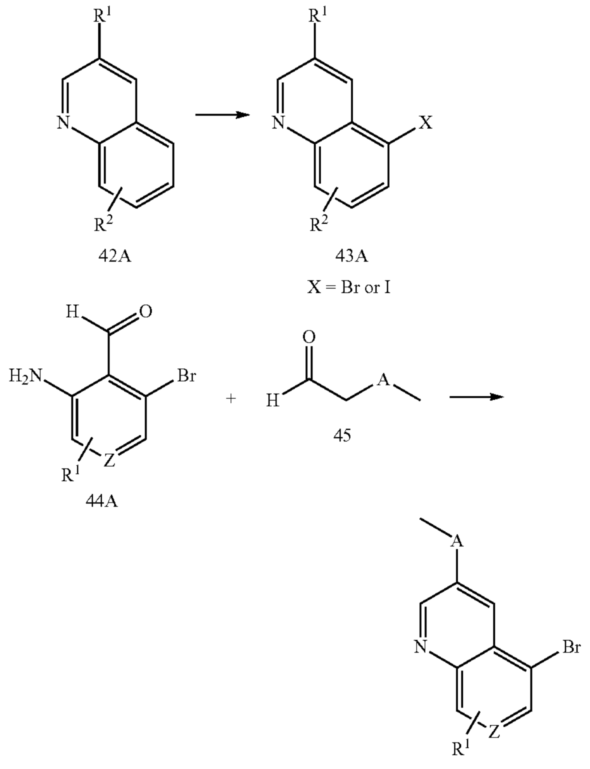

42A

43A

X = Br or I

44A

45

46

A = $CH_2$ or O
Z = C, N

Intermediates of formula 43A and 46 may be prepared by reactions shown in Scheme 6. Suitably substituted quinolone 42A may be halogenated in a regio-selective manner using, but not limited to, NBS or NBI to yield 5-halo-quinoline 43A. In addition, optionally substituted 2-amino-6-bromobenzaldehyde or 3-amino-5-bromoisonicotinaldehyde 44A may undergo a thermal condensation reaction with butyraldehyde or 2-methoxyacetaldehyde under microwave irradiation to give the corresponding 5-halo-quinoline or 5-bromo-1,7-naphthyridine 46. In some embodiments, intermediate of formula 43A and 46 were coupled to lactam 8 or 11 in Scheme 1 and 3.

Scheme 7.

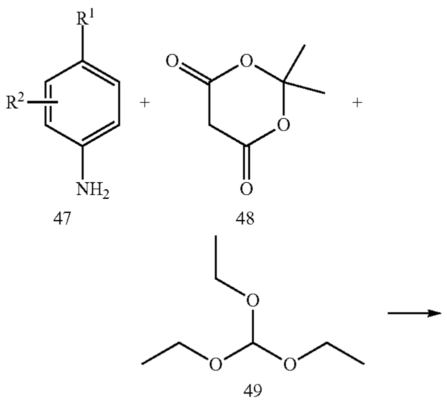

47

48

49

-continued

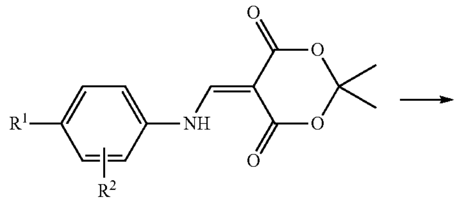

50

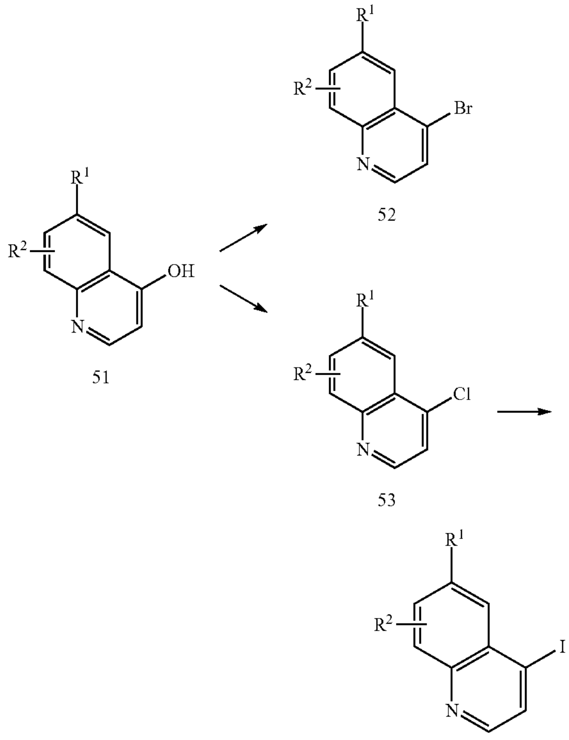

52

51

53

54

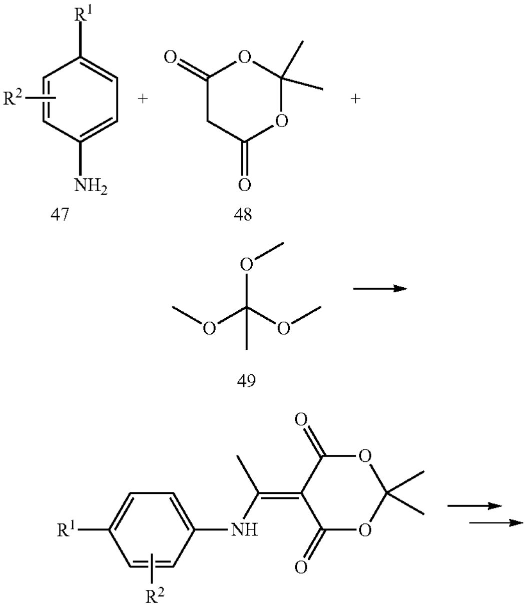

47

48

49

56

-continued

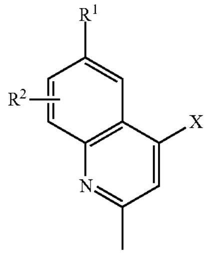

57

X = Cl, Br, I

In some embodiments, 4-halo-quinoline of formula 52 and 54 were used as reagents and may be prepared by procedures illustrated in Scheme 7. A mixture of suitably substituted aniline 47, Meldrum's acid 48 and triethyl orthoformate 49 may be heated to produce intermediate 50, which may undergo thermal cyclization to give quinolin-4-ol 51. 4-Bromo-quinoline 52 may be prepared directly from 51 using, but not limited to, $PBr_3$. Similarly, intermediate 51 may be converted to 4-chloro-quinoline 53 using a chlorination reagent such as $POCl_3$. 4-Iodoquinoline 54 may be generated from 53 using KI under acidic condition. Alternatively, intermediate of formula 57 may be prepared using the same sequences of reaction by substituting trimethyl orthoacetate 55 for triethyl orthoformate 49 in the first step.

Scheme 8.

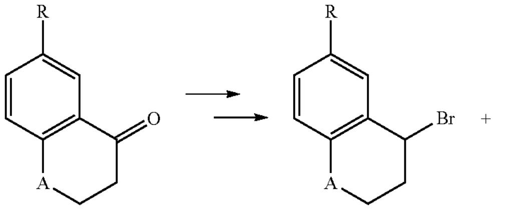

58 59

A = $CH_2$ or O

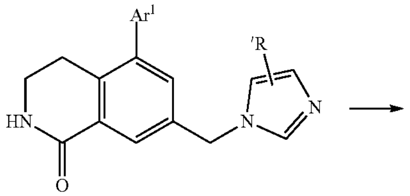

11

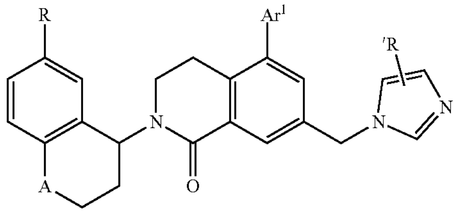

60

In some embodiments, compounds of formula 60 can be synthesized by procedures depicted in Scheme 8. Bicyclic ketone 58 may be converted to bromide 59 by reduction of the carbonyl group followed by bromination of the resulting alcohol intermediate using a number of conditions that are routine for those skilled in the art of organic synthesis. Lactam 11 may be deprotonated using, but not limited to, sodium hydride as a base then may react with bromide 59 under the $S_N2$ reaction condition to yield products of formula 60.

Scheme 9.

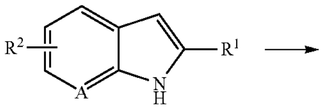

61

A = C or N

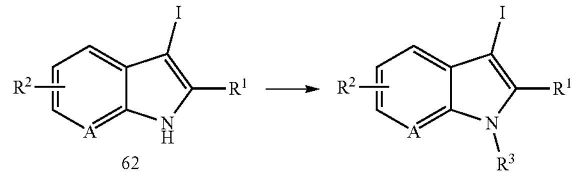

62 63

Preparation of intermediate of formula 63 is depicted in Scheme 9 Suitably substituted indole or azaindole 61 may be regio-selectively iodinated using KI and iodine in the presence of base such as aqueous NaOH to produce 3-iodo intermediate 62. A variety of alkyl groups may be introduced to the NH of 62 using a number of conditions that are routine for those skilled in the art of organic synthesis to give intermediate of formula 63, which may be reacted with lactam 11 in Scheme 1.

Scheme 10.

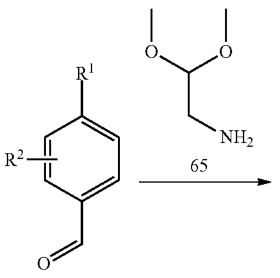

64

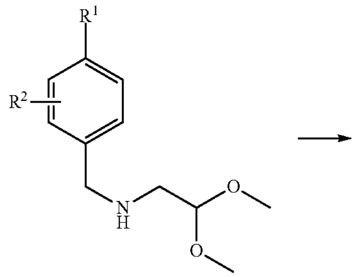

66

-continued

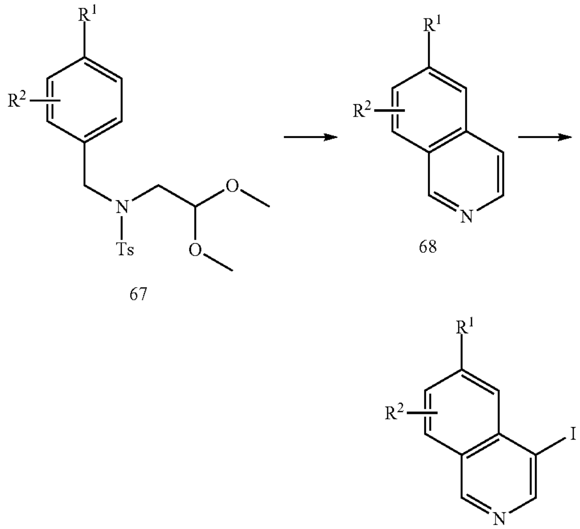

67

68

69

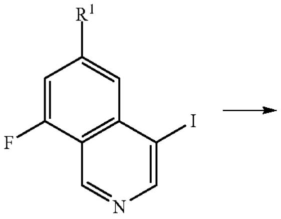

70

-continued

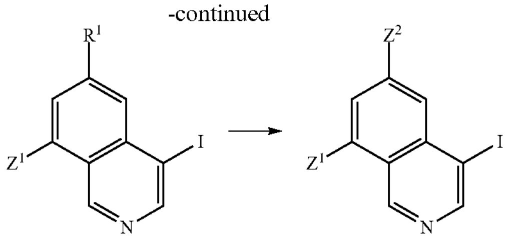

71

$Z^1$ = OR or $NR^1R^2$

72

$Z^2$ = OR or $NR^1R^2$

In some embodiments, isoquinoline of formula 69 were used as a substrate for lactam 11 in Buchwald-Hartwig coupling reaction and may be synthesized by procedures depicted in Scheme 10. Appropriately substituted benzaldehyde 64 may undergo a reductive amination reaction with acetal-amine 65 to produce benzyl amine 66. The secondary amino-group of 66 may be tosylated, and the resulting intermediate 67 may undergo Friedel-Craft reaction followed by aromatization using, but not limited to, $AlCl_3$ as a Lewis acid to yield isoquinoline 68. Then it may be regioselectively iodinated using, but not limited to, NBI to yield 4-iodo-isoquinoline 69. In addition, 6-Bromo-8-fluoro-4-iodoisoquinoline 70, which was prepared using the above reaction sequence, may undergo regioselective sequential $S_NAr$ reactions to introduce alkoxy or alkyl amino group to produce isoquinoline 72.

Scheme 11.

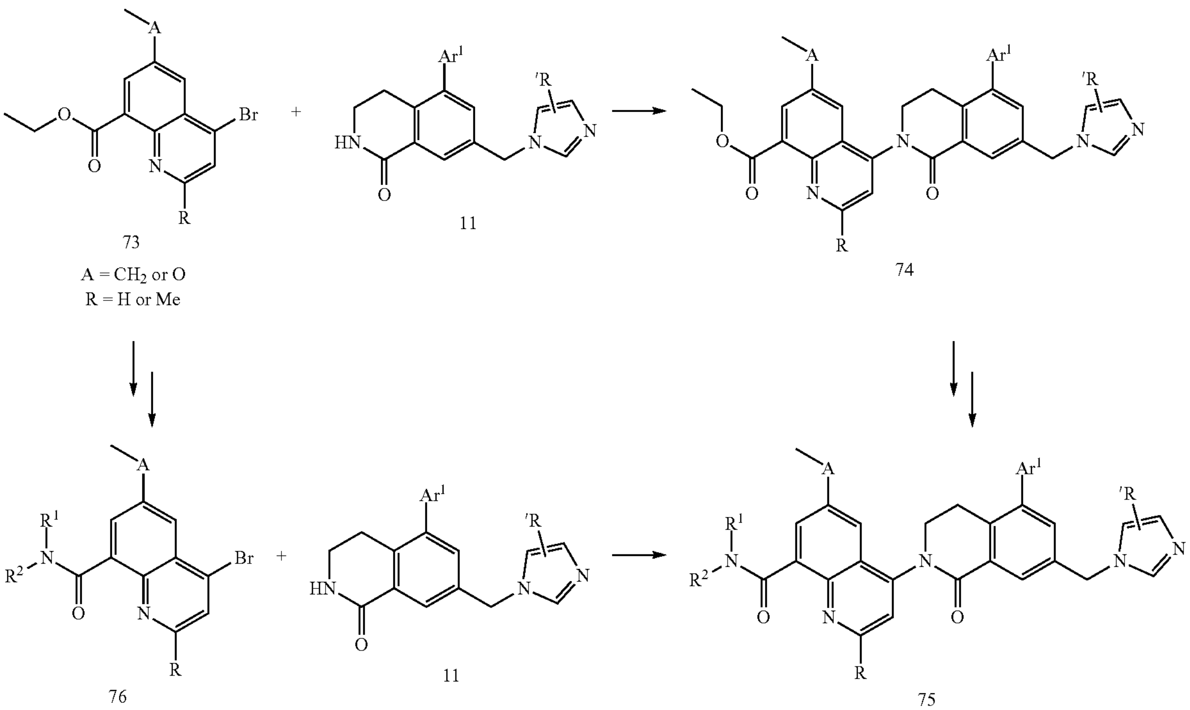

73

A = $CH_2$ or O

R = H or Me

11

74

76

11

75

In some embodiments, compounds of Formula 75 may be synthesized by procedures illustrated in Scheme 11. Optionally substituted ethyl 4-bromo-quinolineacetate 73, which was produced by the reaction sequence depicted in Scheme 7, may be coupled to lactam 11 to yield compounds of formula 74. The ester functional group of 74 may be converted to amide to give a product of formula 75 through saponification followed by amide coupling reaction sequence that are routine for those skilled in the art of organic synthesis. Alternatively, the same reaction sequence may be applied to ester 73 to generate intermediate 76, which may be coupled to lactam 11 to form product 75.

Scheme 12.

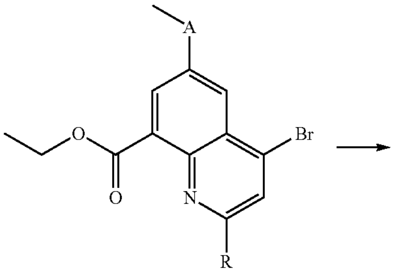

73

A = $CH_2$ or O

R = H or Me

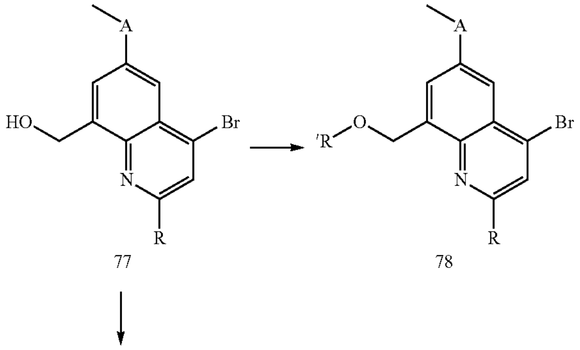

77

78

-continued

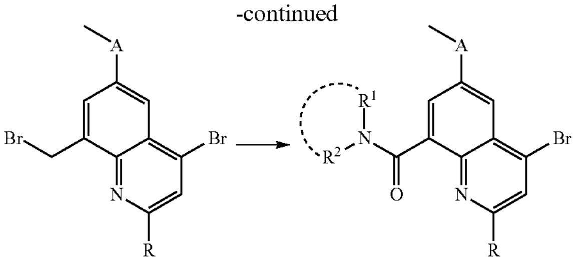

79

80

Additional utility of a versatile ethyl 4-bromo-quinolineacetate 73 is illustrated in Scheme 12. The ester functional group of 73 may be reduced to alcohol 77 using a number of conditions that are routine for those skilled in the art of organic synthesis. Ether 78 may be prepared by alkylating 77 using, but not limited to, an alkyl halide in the presence of base. Alternatively, alcohol 77 may be converted to bromide 79 using procedures that are routine for those skilled in the art of organic synthesis. Subsequent $S_N2$ reactions with nucleophilic amines or nitrogen containing heterocycles may produce intermediates of formula 80. Both 4-bromo-quinoline 78 and 80 may be coupled to lactam 11 to produce some embodiments using the protocol illustrated in Scheme 1

Scheme 13.

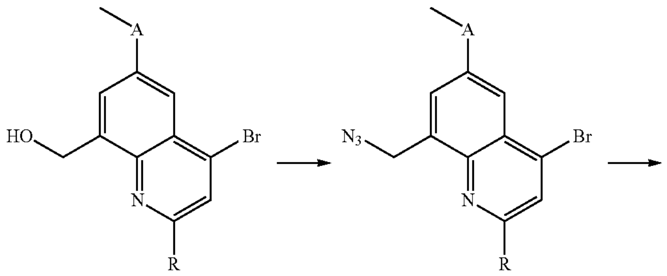

77

81

-continued

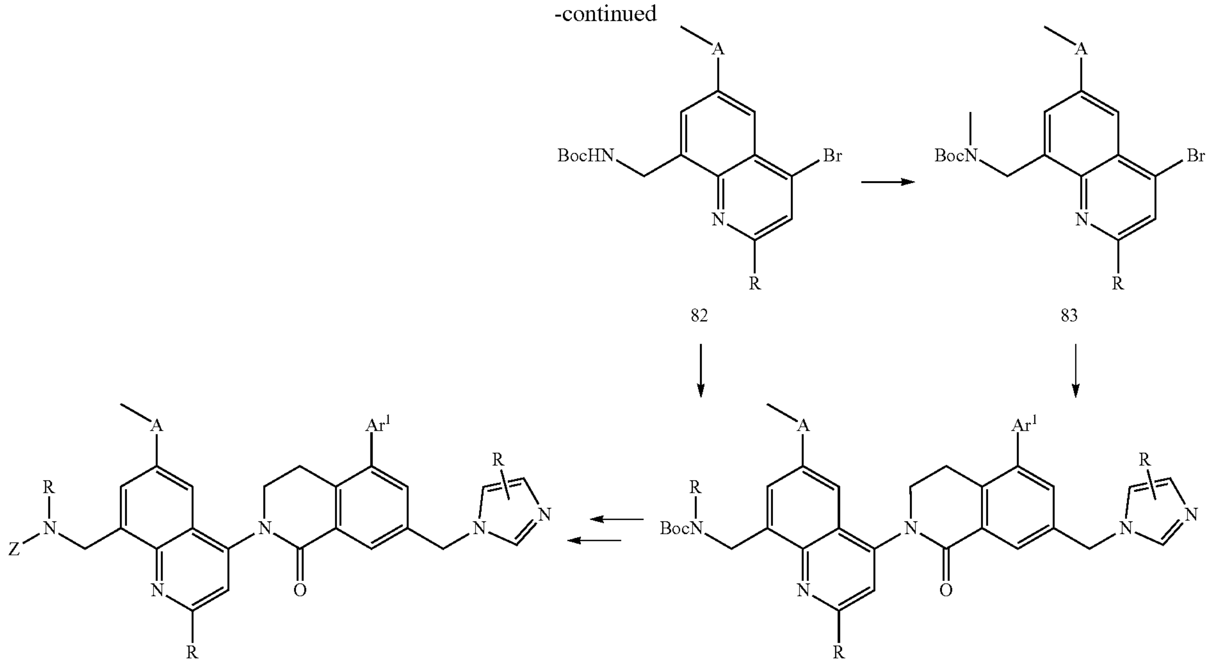

82

83

85
Z = alkyl,
CO—R′

84
A = $CH_2$ or O
R = H or Me

In some embodiments, compounds of formula 85 may be synthesized using the protocols shown in Scheme 13. Alcohol 77 may be converted to azide 81 using, but not limited to, diphenylphosphinyl azide in the presence of an organic base such as 2,3,4,6,7,8,9,10-octahydropyrimido[1,2-a]azepine. Subsequent reduction of an azide followed by in situ protection of the resulting primary amine using $(Boc)_2O$ may give intermediate 82, which may be methylated to yield intermediate 83. Both quinolone 82 and 83 may be coupled with lactam 11 using the protocol depicted in Scheme 1. The Boc protecting group in 84 may be removed, and the resulting free amine may be subjected to a number of reactions, including alkylation, reductive amination and amide coupling, that are routine for those skilled in the art of organic synthesis to produce compounds of formula 85.

Scheme 14.

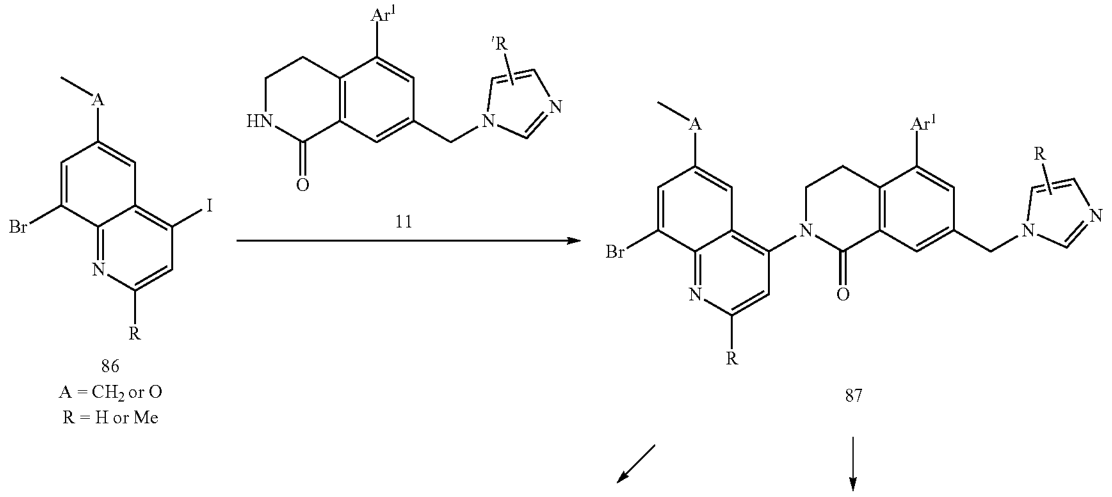

86
A = $CH_2$ or O
R = H or Me

87

-continued

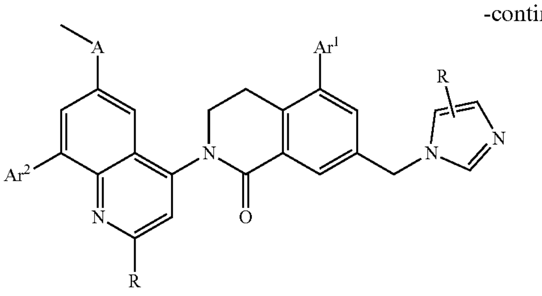

88

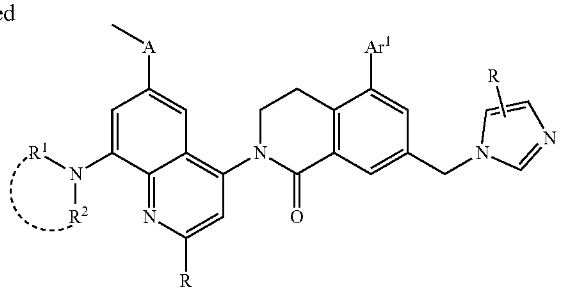

89

In some embodiments, compounds of Formula 88 and 89 may be prepared using procedures shown in Scheme 14. Optionally substituted 8-bromo-4-iodo-quinoline 86, which was produced by reaction sequence depicted in Scheme 7, may be coupled to lactam 11 to yield compounds of formula 87. Using the bromide group of 87, compounds of formula 88 and 89 may be produced through Suzuki-Miyaura coupling and Buchwald-Hartwig coupling protocols that were described in Scheme 1.

Precursor reagents and intermediates for core aryl or phenyl structure were either commercially available or prepared using known methods in the literature. Procedures towards key intermediates are detailed within specified examples or below.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in “Vogel's Textbook of Practical Organic Chemistry”, 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

C. EXAMPLES

Abbreviations

The following abbreviations are employed in the Examples and elsewhere herein:

AcOH=acetic acid
$Ad_2PBu$=di(1-adamantyl)-n-butylphosphine
AIBN=Azobisisobutyronitrile
aq.=aqueous
BINAP=2,2'-bis(diphenylphosphino)-1,1'-binaphthyl
$(Boc)_2O$=di-tert-butyl dicarbonate
BrettPhos=2-(Dicyclohexylphosphino)3,6-dimethoxy-2',4',6'-triisopropyl-1,1'-biphenyl $CH_2Cl_2$=methylene chloride
conc.=concentrated
$Cs_2CO_3$=cesium carbonate
DBU=1,8-diazabicyclo[5.4.0]undec-7-ene
DCE=dichloroethane
DCM=dichloromethane
DIPEA/DIEA=N,N-diisopropylethylamine
DMA=dimethylacetamide
DMF=dimethylformamide
DMSO=dimethylsulfoxide
Dowtherm A=eutectic mixture of 26.5% diphenyl+73.5% diphenyl oxide
EDC=1-Ethyl-3-(3-dimethylaminopropyl)carbodiimide
eq. or equiv=equivalent(s)
ether=diethyl ether
$Et_3N$=triethylamine
EtOAc=ethyl acetate
EtOH=ethanol
g=gram(s)
h or hr=hour(s)
HATU=1-[Bis(dimethylamino)methylene]-1H-1,2,3-triazolo[4,5-b]pyridinium 3-oxid hexafluorophosphate
HCl=hydrochloric acid
Hex=hexanes
HOBt=hydroxybenzotriazole
$K_2CO_3$=potassium carbonate
KOH=potassium hydroxide
LRMS=low resolution mass spectrometry
L-selectride=Lithium tri-sec-butylborohydride
$[M+H]^+$=the protonated mass of the free base of the compound
MeCN=acetonitrile
MeOH=methanol
MeONa=sodium methoxide
2-MeTHF=2-methyltetrahydrofuran
mg=milligram(s)
$MgSO_4$ magnesium sulfate
min=minute(s)
mL or ml milliliter
mmol=millimole(s)
$Na_2CO_3$=sodium carbonate
NaH=sodium hydride
$NaHCO_3$=sodium bicarbonate
$NaN_3$=sodium azide
NaOH=sodium hydroxide
NBS=N-bromo succinimide
NIS=N-iodo succinimide
NMP=N-methyl-2-pyrrolidone
NMR=nuclear magnetic resonance
$PdCl_2(dppf)/Pd(dppf)Cl_2$=[1,1'-Bis(diphenylphosphino)ferrocene]dichloropalladium(II)
$Pd_2(dba)_3$=Tris(dibenzylideneacetone)dipalladium(0)
$Pd(PPh_3)$=tetrakis(triphenylphosphine)palladium(0)
$Pd(PPh_3)_2Cl_2$=Bis(triphenylphosphine)palladium(II) dichloride
$Pd(OAc)_2$=Palladium(II) acetate
$Pd(t\text{-}Bu_3P)_2$=Bis(tri-tert-butylphosphine)palladium(0)
$PPh_3$=triphenylphosphine
RockPhos=2-Di(tert-butyl)phosphino-2',4',6'-triisopropyl-3-methoxy-6-methylbiphenyl
RT or r.t.=room temperature
$R_T$=retention time (in minutes)
sat.=saturated
SPhos=2-Dicyclohexylphosphino-2',6'-dimethoxybiphenyl
TBAF=tetra n-butyl ammonium fluoride
TEA=triethylamine
THF=tetrahydrofuran
TFA=trifluoroacetic acid
trityl=triphenylmethyl
wt.=weight
Xantphos=4,5-Bis(diphenylphosphino)-9,9-dimethylxanthene
min=minute(s)
h or hr=hour(s)
mL or ml=milliliter
g=gram(s)
mg=milligram(s)
mmol=millimole(s)
RT or r.t.=room temperature
LRMS=low resolution mass spectrometry
NMR=nuclear magnetic resonance
$[M+H]^+$=the protonated mass of the free base of the compound
$R_T$=retention time (in minutes)

Microwave assisted reactions are performed in a single-mode reactor: Emrys™ Optimizer microwave reactor (Personal Chemistry A.B., currently Biotage).

Hydrogenation reactions are performed using an atmospheric balloon or using a Parr hydrogenation shaker apparatus.

Normal phase flash silica gel-based column chromatography is performed using ready-to-connect cartridges from ISCO, on irregular silica gel, particle size 15-40 μm on a Combi-flash Companion chromatography system from ISCO.

Low resolution mass spectra are obtained on an Agilent 1200 series 6130 mass spectrometer. Analytical HPLC is performed on an HP1100 with UV detection at 214 and 254 nm along with ELSD detection, LI/MS (J-Sphere80-C18, 3.0×50 mm, 4.1 min gradient, 5%[0.05% TFA/$CH_3CN$]:95%[0.05% TFA/$H_2O$] to 100%[0.05% TFA/$CH_3CN$]. Preparative RP-HPLC purification is performed on a custom HP1100 automated purification system with collection triggered by mass detection or using a Gilson Inc. preparative UV-based system using a Phenomenex Luna C18 column (50×30 mm I.D., 5 μm) with an acetonitrile (unmodified)-water (0.1% TFA) custom gradient.

For LC-MS characterization of the compounds of the present invention, the following methods are used.

Method 1: The HPLC measurement is performed using an Agilent 1200 system comprising a binary pump with degasser, an autosampler, a column oven, a diode-array detector (DAD) and a column as specified in the respective methods below. Flow from the column is split to a SQ mass spectrometer and Polymer Labs ELSD. The MS detector is configured with an ES ionization source. Nitrogen is used as the nebulizer gas. The source temperature is maintained at 350° C. Data acquisition is performed with Agilent Chemstation software. Reversed phase HPLC is carried out on a Kinetex C18 column (2.6 μm, 2.1×30 μm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 μL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 2: Using method 1 instrument and column conditions. The gradient conditions used are: 95% A (water+0.1% TFA), 5% B (acetonitrile), to 95% B in 2.0 minutes, returning to initial conditions at 2.11 minutes. Injection volume 1 μL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 3: Using method 1 instrument and column conditions. The gradient conditions used are: 50% A (water+0.1% TFA), 50% B (acetonitrile), to 95% B in 2.0 minutes, returning to initial conditions at 2.11 minutes. Injection volume 1 μL Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

$^1$H NMR spectra are recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which is used as internal standard, Coupling constants (J-values) are reported in Hz.

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

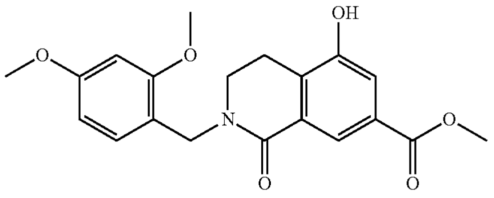

Intermediate 1

Methyl 2-(2,4-dimethoxybenzyl)-5-hydroxy-1-oxo-1,2,3,4-tetrahydroisoquinoline-7-carboxylate Standard Reductive Amination Procedure: Dimethyl 2-hydroxy-2,3-dihydro benzofuran-4,6-dicarboxylate (15.0 g, 59.5 mmol, equiv) and (2,4-dimethoxyphenyl)methanamine (13.4 mL, 89.2 mmol, 1.5 equiv) were dissolved in $CH_2Cl_2$ (200 mL) and stirred at 30° C. for 30 min. Then sodium triacetoxyborohydride (25.2 g, 118.9 mmol, 2 equiv) was added and the reaction was stirred at 30° C. for 3 h. The reaction mixture was concentrated and dissolved in 1,4-dioxane (100 mL) and heated at 110° C. overnight. Saturated aqueous $NaHCO_3$ was added and the mixture was extracted with $CH_2Cl_2$ (3×30 mL). The combined organic phases were dried over $MgSO_4$ and concentrated under reduced pressure to afford the title compound (22 g, 59.2 mmol, quant.), which was used without further purification. $^1$H NMR (400 MHz, Chloroform-d) δ 8.26 (d, J=1.6 Hz, 1H), 7.71 (d, J=1.6 Hz, 1H), 7.22 (d, J=8.0 Hz, 1H), 6.39 (d, J=7.8 Hz, 2H), 4.73 (s, 2H), 3.76 (s, 3H), 3.75 (s, 3H), 3.74 (s, 3H), 3.50 (t, J=6.7 Hz, 2H), 2.94 (t, J=6.7 Hz, 2H); LCMS (ESI): Method 2: $R_T$=1.965 min, m/z=372.1 $[M+H]^+$.

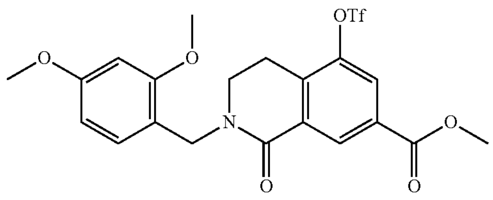

Intermediate 2

Methyl 2-(2,4-dimethoxybenzyl)-1-oxo-5-((trifluoromethyl)sulfonyl)oxy)-1,2,3,4-tetrahydroisoquinoline-7-carboxylate Standard Triflation Procedure: Phenyl triflimide (34.6 g, 96.9 mmol, 1.2 equiv) was added to a solution of methyl 2-(2,4-dimethoxybenzyl)-5-hydroxy-1-oxo-1,2,3,4-tetrahydroisoquinoline-7-carboxylate (Intermediate 1, 30.0 g, 80.8 mmol, 1 equiv) and N,N-diisopropylethylamine (35 mL, 201.9 mmol, 2.5 equiv) in THF:$CH_2Cl_2$ (5:1, 360 mL) at 23° C. and stirred for 14 h. Saturated aqueous $NaHCO_3$ was added and the mixture was extracted with $CH_2Cl_2$·(3×30 mL). The combined organic phases were dried over $MgSO_4$ and concentrated under reduced pressure. The residue was purified by flash chromatography (Combi-flash Rf, Hex/EtOAc=0-100% gradient) to afford the title compound (24.5 g, 48.7 mmol, 82% yield) as an oil. $^1$H NMR (400 MHz, Chloroform-d) δ 8.80 (d, J=1.6 Hz, 1H), 8.02 (d, J=1.6 Hz, 1H), 7.33-7.27 (m, 1H), 6.49-6.43 (m, 2H), 4.74 (s, 2H), 3.95 (s, 3H), 3.82 (s, 3H), 3.80 (s, 3H), 3.59 (t, J=6.6 Hz, 2H), 3.04 (t, J=6.6 Hz, 2H); LCMS (ESI): Method 3: $R_T$=2.546 min, m/z=504.0 $[M+H]^+$.

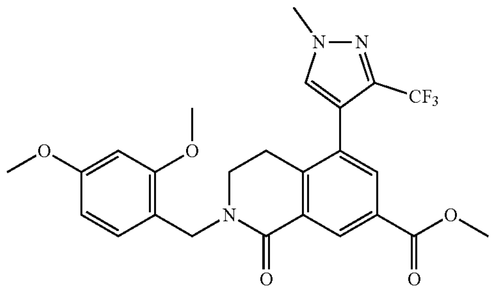

Intermediate 3

Methyl 2-(2,4-dimethoxybenzyl)-5-(1-methyl-3-(trifluoromethyl)-1H-pyrazol-4-yl)-1-oxo-1,2,3,4-tetrahydroisoquinoline-7-carboxylate Standard Suzuki Coupling Procedure: Methyl 2-(2,4-dimethoxybenzyl)-1-oxo-5-(((trifluoromethyl)sulfonyl)

oxy)-1,2,3,4-tetrahydroisoquinoline-7-carboxylate (Intermediate 2, 12.3 g, 24.3 mmol, 1 equiv), (1-methyl-3-(trifluoromethyl)-1H-pyrazol-4-yl)boronic acid (7.1 mg, 36.4 mmol, 1.5 equiv), potassium carbonate (8.4 mg, 60.8 mmol, 2.5 equiv), and $PdCl_2$(dppf) (890 mg, 1.2 mmol, 0.05 equiv) were dissolved in 1,4-dioxane:water (4:1, 5 mL) under an Ar atmosphere in a sealed tube. The reaction mixture was stirred for 14 h at 90° C. then cooled to 23° C. Brine was added to the mixture and extracted with EtOAc (3×20 mL). The combined organic layers were dried over $MgSO_4$ and concentrated under reduced pressure. The residue was purified by flash chromatography (Combi-flash Rf, Hex/EtOAc=0-100% gradient) to afford the title compound (11.0 g, 21.8 mmol, 90% yield). $^1$H NMR (400 MHz, Chloroform-d) δ 8.81 (d, J=1.9 Hz, 1H), 7.99 (d, J=1.8 Hz, 1H), 7.36 (d, J=1.1 Hz, 1H), 7.31-7.27 (m, 1H), 6.45 (dd, J=6.2, 2.5 Hz, 2H), 4.73 (s, 2H), 4.00 (s, 3H), 3.92 (s, 3H), 3.80 (s, 3H), 3.79 (s, 3H), 3.46 (t, J=6.6 Hz, 2H), 2.75 (t, J=6.5 Hz, 2H); LCMS (ESI): Method 2: $R_T$=1.072 min, m/z=504.4 [M+H]$^+$.

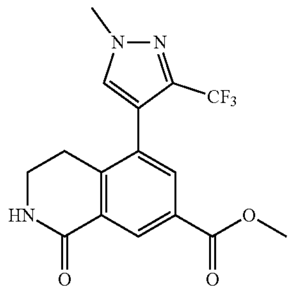 [SMILES: COC(=O)c1cc2c(c(-c3cn(C)nc3C(F)(F)F)c1)CCNC2=O]

Intermediate 4

Methyl 5-(1-methyl-3-(trifluoromethyl)-1H-pyrazol-4-yl)-1-oxo-1,2,3,4-tetrahydroisoquinoline-7-carboxylate Standard TFA Deprotection Procedure: Anisole (24 mL, 218 mmol, 5 equiv.) was added to a solution of methyl 2-(2,4-dimethoxybenzyl)-5-(1-methyl-3-(trifluoromethyl)-1H-pyrazol-4-yl)-1-oxo-1,2,3,4-tetrahydroisoquinoline-7-carboxylate (Intermediate 3, 22.0 g, 43.7 mmol, 1 equiv.) in $CH_2Cl_2$ (50 mL) and TFA (100 mL). The reaction was stirred at room temperature overnight then concentrated under reduced pressure. The residue was dissolved in EtOAc, and washed with sat. $NaHCO_3$. The organic layer was dried ($MgSO_4$) and concentrated. The residue was purified by flash chromatography (Combi-flash Rf, Hex/EtOAc=0-100% gradient followed by MeOH/$CH_2Cl_2$=0-10% gradient) to provide the title compound (13.5 g, 38.2 mmol, 87% yield). $^1$H NMR (400 MHz, Chloroform-d) δ 8.77 (d, J=1.6 Hz, 1H), 8.05 (d, J=1.6 Hz, 1H), 7.40 (s, 1H), 6.25 (s, 1H), 4.03 (s, 3H), 3.92 (s, 3H), 3.51 (td, J=6.5, 2.8 Hz, 2H), 2.84 (t, J=6.5 Hz, 1H); LCMS (ESI): Method 2: $R_T$=1.363 min, m/z=354.1 [M+H]$^+$.

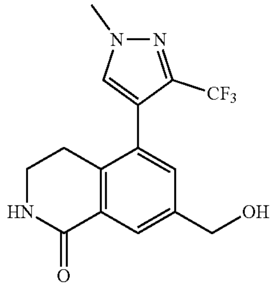 [SMILES: Cn1cc(-c2cc(CO)cc3c2CCNC3=O)c(C(F)(F)F)n1]

Intermediate 5

7-(Hydroxymethyl)-5-(1-methyl-3-(trifluoromethyl)-1H-pyrazol-4-yl)-3,4-dihydroisoquinolin-1(2H)-one Standard Methylester Reduction Procedure: Lithium triethylborohydride (4 mL, 3.9 mmol, 3 equiv) was added dropwise to a solution of methyl 5-(1-methyl-3-(trifluoromethyl)-1H-pyrazol-4-yl)-1-oxo-1,2,3,4-tetrahydroisoquinoline-7-carboxylate (Intermediate 4, 457 mg, 1.3 mmol, 1 equiv) in THF at 0° C. The reaction was stirred for 40 min, then quenched with sat. aq. $NaHCO_3$. The mixture was extracted with EtOAc. The combined organic layers were dried over $MgSO_4$, concentrated, and dried under reduced pressure to provide the title compound (420 mg, 1.3 mmol, quant.), which was used without further purification. LCMS (ESI): Method 2: $R_T$=1.145 min, m/z=326.1 [M+H]$^+$.

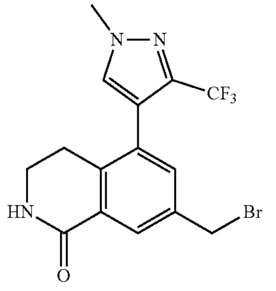 [SMILES: Cn1cc(-c2cc(CBr)cc3c2CCNC3=O)c(C(F)(F)F)n1]

Intermediate 6

7-(Bromomethyl)-5-(1-methyl-3-(trifluoromethyl)-1H-pyrazol-4-yl)-3,4-dihydroisoquinolin-1(2H)-one Standard Bromination Procedure: $PBr_3$ (0.2 mL, 2.6 mmol, 2 equiv) was added to a solution of 7-(hydroxymethyl)-5-(1-methyl-3-(trifluoromethyl)-1H-pyrazol-4-yl)-3,4-dihydroisoquinolin-1(2H)-one (Intermediate 5, 420 mg, 1.3 mmol, 1 equiv) in $CH_2Cl_2$ (10 mL) at 0° C. The reaction was warmed to room temperature and stirred overnight. Sat. aq. $NaHCO_3$ was added and the mixture was extracted with EtOAc. The combined organic layers were dried over $MgSO_4$, concentrated to provide the title compound (440 mg, 1.3 mmol, quant.), which was used in the next step without further purification. $^1$H NMR (400 MHz, Chloroform-d) δ 8.15 (d, J=2.0 Hz, 1H), 7.42 (d, J=2.0 Hz, 1H), 7.40 (d, J=1.1 Hz, 1H), 4.51 (s, 2H), 4.02 (s, 3H), 3.48 (td, J=6.5, 2.7 Hz, 2H), 2.79 (t, J=6.5 Hz, 2H); LCMS (ESI): m/z=387.9 [M+H]$^+$.

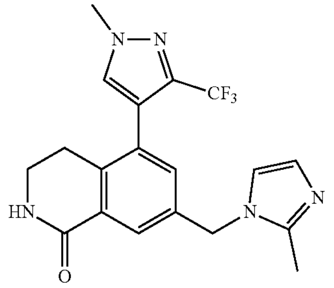 [SMILES: Cc1nccn1Cc1cc2c(c(-c3cn(C)nc3C(F)(F)F)c1)CCNC2=O]

Intermediate 7

7-((2-Methyl-1H-imidazol-1-yl)methyl)-5-(1-methyl-3-(trifluoromethyl)1H-pyrazol-4-yl)-3,4-dihydroisoquinolin-1(2H)-one Standard Bromide Displacement Procedure: 2-Methyl-1H-imidazole (846 mg, 10.3 mmol, 4 equiv) was added to a solution of 7-(bromomethyl)-5-(1-methyl-3-(trifluoromethyl)-1H-pyrazol-4-yl)-3,4-dihydroisoquinolin-(2H)-one (Intermediate 6, 1.0 g, 2.6 mmol, 1 equiv) in Acetonitrile (15 mL) at 23° C. The reaction mixture was stirred for 12 h at 50° C., then cooled to ambient temperature, filtered and concentrated. The residue was purified by flash chromatography (Combi-flash Rf, DCM/MeOH=0-10% gradient) to afford the title compound (700 mg, 1.8 mmol, 70% yield). $^1$H NMR (400 MHz, Chloroform-d) δ 8.01 (d, J=2.0 Hz, 1H), 7.32 (s, 1H), 6.95 (d, J=1.4 Hz, 1H), 6.94 (d, J=2.0 Hz, 1H), 6.85 (d, J=1.4 Hz, 1H), 5.99 (s, 1H), 5.09 (s, 2H), 4.00 (s, 3H), 3.48 (td, J=6.5, 2.8 Hz, 2H), 2.79 (t, J=6.5 Hz, 2H), 2.35 (s, 3H); LCMS (ESI): Method 2: $R_T$=0.973 min, m/z 390.0 $[M+H]^+$.

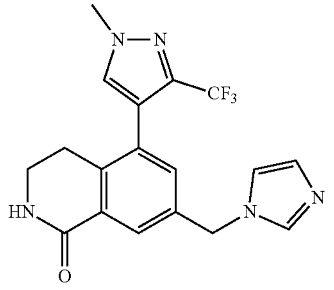 [SMILES: Cn1cc(-c2cc(Cn3ccnc3)cc3c2CCNC3=O)c(C(F)(F)F)n1]

Intermediate 8

7-((1H-Imidazol-1-yl)methyl)-5-(1-methyl-3-(trifluoromethyl)-1H-pyrazol-4-yl)-3,4-dihydroisoquinolin-1(2H)-one The title compound (750 mg, 2 mmol, 60% yield) was prepared following the bromide displacement procedure described for Intermediate 7, substituting 1H-Imidazole for 2-methyl-1H-imidazole (0.91 g, 13 mmol, 4 equiv). $^1$H NMR (400 MHz, DMSO-$d_6$) δ 8.03 (brs, 1H), 8.01 (d, J=1.1 Hz, 1H), 7.81 (d, J=2.0 Hz, 1H), 7.75 (d, J=1.2 Hz, 1H), 7.26 (d, J=2.0 Hz, 1H), 7.19-7.15 (m, 1H), 6.90 (t, J=1.1 Hz, 1H), 5.25 (s, 2H), 3.96 (s, 3H), 3.26 (td, J=6.6, 2.7 Hz, 2H), 2.64 (t, J=6.5 Hz, 2H); LCMS (ESI): Method 2: $R_T$=0.979 min, m/z=376.0 $[M+H]^+$.

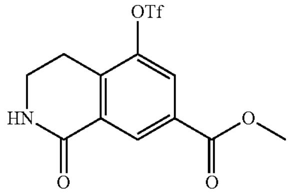 [SMILES: COC(=O)c1cc(OS(=O)(=O)C(F)(F)F)c2c(c1)C(=O)NCC2]

Intermediate 9

Methyl 1-oxo-5-(((trifluoromethyl)sulfonyl)oxy)-1,2,3,4-tetrahydroisoquinoline-7-carboxylate The title compound (1.0 g, 2.8 mmol, 78% yield) was prepared following the TFA deprotection procedure described for Intermediate 4 using methyl 2-(2,4-dimethoxybenzyl)-1-oxo-5-(((trifluoromethyl)sulfonyl)oxy)-1,2,3,4-tetrahydroisoquinoline-7-carboxylate (Intermediate 2). $^1$H NMR (400 MHz, $CDCl_3$) δ 8.77 (s, 1H), 8.09 (s, 1H), 6.74 (brs, 1H), 3.97 (s, 3H), 3.65 (m, 2H), 3.16 (t, J=6.4 Hz, 2H); LCMS (ESI): Method 2: $R_T$=1.517 min, m/z 354.2 $[M+H]^+$.

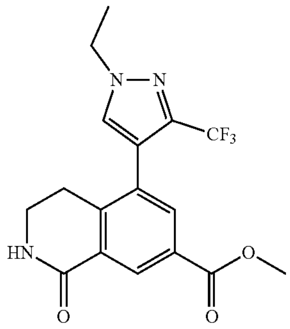 [SMILES: CCn1cc(-c2cc(C(=O)OC)cc3c2CCNC3=O)c(C(F)(F)F)n1]

Intermediate 10

Methyl 5-(1-ethyl-3-(trifluoromethyl)-1H-pyrazol-4-yl)-1-oxo-1,2,3,4-tetrahydroisoquinoline-7-carboxylate The title compound (2.6 g, 5.7 mmol, 98% yield) was prepared following the Suzuki coupling procedure described for Intermediate 3, substituting (1-ethyl-3-(trifluoromethyl)-1H-pyrazol-4-yl)boronic acid (1.3 g, 6.2 mmol, 1.1 equiv) for (1-methyl-3-(trifluoromethyl)-1H-pyrazol-4-yl)boronic acid and tetrakis(triphenylphosphine)palladium(0) for $PdCl_2$(dppf) (196 mg, 0.17 mmol, 0.03 equiv) at 80° C.; LCMS (ESI): m/z=368.0 $[M+H]^+$.

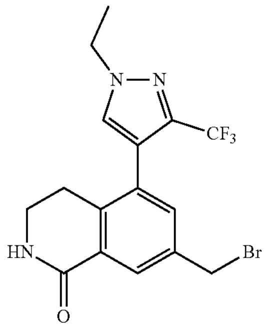 [SMILES: CCn1cc(-c2cc(CBr)cc3c2CCNC3=O)c(C(F)(F)F)n1]

Intermediate 11

7-(Bromomethyl)-5-(1-ethyl-3-(trifluoromethyl)-1H-pyrazol-4-yl)-3,4-dihydroisoquinolin-1(2H)-one The title compound (2.0 g, 5.7 mmol, 87% yield, 2 steps) was prepared following the methylester reduction procedure described for Intermediate 5 followed by the bromination procedure described for Intermediate 6 using methyl 5-(1-ethyl-3-(trifluoromethyl)-1H-pyrazol-4-yl)-1-oxo-1,2,3,4-tetrahydroisoquinoline-7-carboxylate (Intermediate 10, 2.6 g, 5.7 mmol). LCMS (ESI): m/z=402.9 $[M+H]^+$.

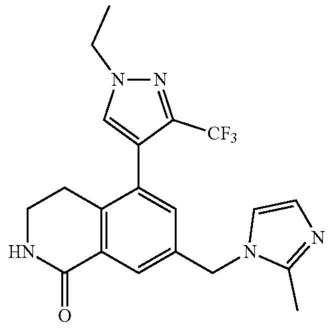 [SMILES: CCn1cc(-c2cc(Cn3ccnc3C)cc3c2CCNC3=O)c(C(F)(F)F)n1]

Intermediate 12

5-(1-Ethyl-3-(trifluoromethyl)-1H-pyrazol-4-yl)-7-((2-methyl-1H-imidazol-1-yl)methyl)-3,4-dihydroisoquinolin-1(2H)-one The title compound (522 mg, 1.3 mmol, 57% yield) was prepared following the bromide displacement procedure described for Intermediate 7 substituting 7-(bromomethyl)-5-(1-ethyl-3-(trifluoromethyl)-1H-pyrazol-4-yl)-3,4-dihydroisoquinolin-1(2H)-one for 7-(bromomethyl)-5-(1-methyl-3-(trifluoromethyl)-1H-pyrazol-4-yl)-3,4-dihydroisoquinolin-1(2H)-one. $^1$H NMR (400 MHz, Chloroform-d) δ 8.01 (d, J=2.1 Hz, 1H), 7.34 (d, J=1.1 Hz, 1H), 6.96 (d, J=2.0 Hz, 1H), 6.94 (d, J=1.4 Hz, 1H), 6.85 (d, J=1.4 Hz, 1H), 5.97 (s, 1H), 5.09 (s, 2H), 4.26 (q, J=7.3 Hz, 2H), 3.48 (td, J=6.5, 2.8 Hz, 2H), 2.78 (t, J=6.5 Hz, 2H), 2.34 (s, 3H), 1.58 (t, J=7.3 Hz, 3H); LCMS (ESI): m/z=404.0 $[M+H]^+$.

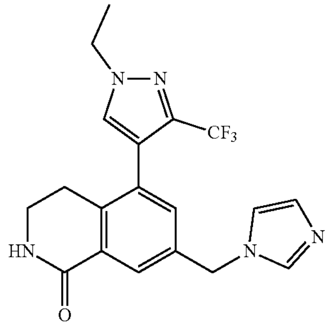 [SMILES: CCn1cc(-c2cc(Cn3ccnc3)cc3c2CCNC3=O)c(C(F)(F)F)n1]

Intermediate 13

7-((1H-imidazol-1-yl)methyl)-5-(1-ethyl-3-(trifluoromethyl)-1H-pyrazol-4-yl)-3,4-dihydroisoquinolin-1(2H)-one The title compound (548 mg, 1.4 mmol, 57% yield) was prepared following the bromide displacement procedure described for Intermediate 7, substituting 1H-Imidazole (506 mg, 0.4 mmol, 3 equiv) for 2-methyl-1H-imidazole. $^1$H NMR (400 MHz, Chloroform-d) δ 8.04 (d, J=2.0 Hz, 1H), 7.55 (d, J=1.2 Hz, 1H), 7.35 (d, J=1.1 Hz, 1H), 7.11 (d, J=2.0 Hz, 1H), 7.08 (t, J=1.1 Hz, 1H), 6.91 (t, J=1.3 Hz, 1H), 6.26 (s, 1H), 5.15 (s, 2H), 4.26 (q, 3=7.3 Hz, 2H), 3.48 (td, J=6.5, 2.8 Hz, 2H), 2.79 (t, J=6.5 Hz, 2H), 1.57 (t, J=7.4 Hz, 3H); LCMS (ESI): m/z=390.0 $[M+H]^+$.

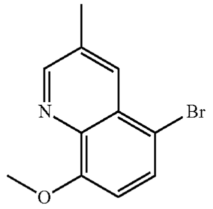

Intermediate 14

5-Bromo-8-methoxy-3-methylquinoline

To a solution of 8-methoxy-3-methylquinoline (100 mg, 0.58 mmol, 1 equiv) in MeCN (4 mL) was added NBS (103 mg, 0.58 mmol, 1 equiv) at 0° C. the reaction mixture was warmed to 23° C. and stirred overnight then concentrated tinder reduced pressure. The residue was purified by flash chromatography (Combi-flash Rf, Hex/EtOAc=0-100% gradient) to afford the title compound (150 mg, 0.60 mmol, quant.). $^1$H NMR (400 MHz, Chloroform-d) δ 8.79 (s, 1H), 8.28-8.20 (m, 1H), 7.69 (dd, J=8.3, 1.4 Hz, 1H), 6.87 (d, J=8.3 Hz, 1H), 4.07 (s, 3H), 2.58 (s, 3H); LCMS (ESI): Method 2: $R_T$=1.352 min, m/z=252.0 $[M+H]^+$.

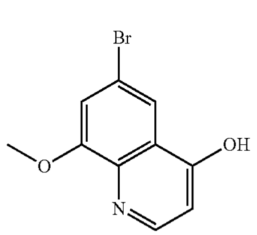

Intermediate 15

6-Bromo-8-methoxyquinolin-4-ol

Step A. Preparation of 5-(((4-bromo-2-methoxyphenyl)amino)methylene)-2,2-dimethyl-1,3-dioxane-4,6-dione. To a solution of 4-bromo-2-methoxyaniline (6.3 g, 31.2 mmol, 1 equiv) and Meldrum's acid (5.39 g, 37.4 mmol, 1.2 equiv) in EtOH (50 mL) was added triethyl orthoformate (5.2 mL, 31.2 mmol, 1 equiv). The reaction was stirred at 80° C. overnight. The reaction was cooled to 0° C., filtered, and washed with cold EtOH to yield the title compound (10.96 g, 30.8 mmol, 99% yield). $^1$H NMR (400 MHz, Chloroform-d) δ 11.46 (s, 1H), 8.61 (d, J=14.6 Hz, 1H), 7.23-7.14 (m, 2H), 7.12 (d, J=1.7 Hz, 1H), 3.96 (s, 4H), 1.75 (s, 6H).

Step B. Preparation of 6-Bromo-8-methoxyquinolin-4-ol. 5-((4-Bromo-2-methoxyphenyl)amino)methylene)-2,2-dimethyl-1,3-dioxane-4,6-dione (10.96 g, 30.8 mmol, 1 equiv) was added portionwise to Dowtherm A (20 mL) at 260° C. and stirred for 30 min. The reaction was cooled to room temperature, and hexanes were added. The resulting mixture was filtered, and solid was washed with hexanes to yield the title compound (7.20 g, 28.3 mmol, 92% yield). $^1$H NMR (400 MHz, DMSO-$d_6$) δ 11.50 (s, 1H), 7.77 (t, J=6.7 Hz, 1H), 7.73 (d, J=2.0 Hz, 1H), 7.38 (d, J=2.1 Hz, 1H), 6.08 (d, J=7.4 Hz, 1H), 4.01 (s, 3H).

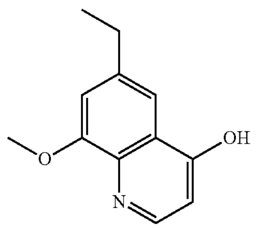

Intermediate 16

6-Ethyl-8-methoxyquinolin-4-ol

A mixture of 6-Bromo-8-methoxyquinolin-4-ol (215 mg, 0.85 mmol, 1 equiv), triethylborane (2 mL, 1.7 mmol, 2 equiv, 1 M THF), cesium carbonate (551 mg, 1.7 mmol, 2 equiv), and Pd(dppf)$Cl_2$ (31.0 mg, 42.3 mol, 0.05 equiv) in THF (3 mL) was stirred for 3 h at 60° C. under Ar in a sealed tube. The reaction was cooled to 0° C. and quenched by 10% aq. NaOH and 30% aq. $H_2O_2$. The resulting mixture was warmed to 23° C., brine was added, and the mixture was extracted with EtOAc (3×20 mL). The combined organic layers were dried over $MgSO_4$ and concentrated tinder reduced pressure. The residue was purified by flash chromatography (Combi-flash Rf, Hex/EtOAc=0-100% gradient followed by DCM/MeOH=0-10% gradient) to afford the title compound (173 mg, 0.85 mmol, quant.). $^1$H NMR (400 MHz, DMSO-$d_6$) δ 11.28 (s, 1H), 7.46 (d, J=1.7 Hz, 1H), 7.11 (d, J=1.7 Hz, 1H), 6.00 (d, J=7.3 Hz, 1H), 5.75 (s, 1H), 3.98 (s, 3H), 2.70 (q, J=7.6 Hz, 2H), 1.23 (t, J=7.6 Hz, 3H); LCMS (ESI): Method 2: $R_T$=1.185 min, m/z=204.1 [M+H]$^+$.

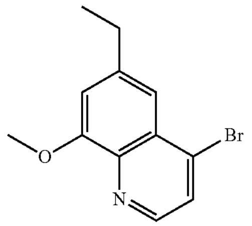

Intermediate 17

4-Bromo-6-ethyl-8-methoxyquinoline

To a solution of 6-ethyl-8-methoxyquinolin-4-ol (170 mg, 0.84 mmol, 1 equiv) in DMF (5 mL) was added $PBr_3$ (0.16 mL, 1.67 mmol, 2 equiv) dropwise at 0° C., The reaction mixture was warmed to room temperature and stirred overnight. The reaction was quenched with ice, and the pH was adjusted to 7 with $NaHCO_3$. The solid was filtered, washed with water, and dried to yield the title compound (169 mg, 0.64 mmol, 76% yield). $^1$H NMR (400 MHz, Chloroform-d) δ 8.46 (d, J=4.6 Hz, 1H), 7.53 (d, J=4.6 Hz, 1H), 7.39 (dt, J=1.8, 0.9 Hz, 1H), 6.81 (d, J=1.7 Hz, 1H), 3.96 (s, 3H), 2.70 (q, J=7.5 Hz, 2H), 1.23 (t, J=7.6 Hz, 3H); LCMS (ESI): Method 2: $R_T$=1.231 min, m/z=266.0 [M+H]$^+$.

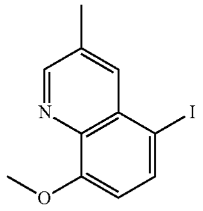

Intermediate 18

5-Iodo-8-methoxy-3-methylquinoline

The title compound (300 mg, quant.) was prepared following the procedure described for Intermediate 14, substituting N-iodosuccinimide (205 mg, 0.91 mmol, 1.05 equiv) for N-bromosuccinimide and was stirred at 60° C. overnight. $^1$H NMR (400 MHz, Chloroform-d) δ 8.76 (d, J=2.0 Hz, 1H), 8.10 (dd, J=2.1, 1.1 Hz, 1H), 7.98 (d, J=8.3 Hz, 1H), 6.79 (d, J=8.3 Hz, 1H), 4.08 (s, 3H), 2.58 (s, 3H); LCMS (ESI): Method 2: $R_T$=1.393 min, m/z=300.0 [M+H]$^+$.

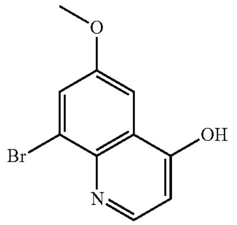

Intermediate 19

8-Bromo-6-methoxyquinolin-4-ol

The title compound (3.2 g, 12.7 mmol, 84% yield) was prepared following the synthetic sequence described in Intermediate 15, substituting 2-bromo-4-methoxyaniline (5.4 g, 15.1 mmol, 1 equiv) for 4-bromo-2-methoxyaniline in Step A $^1$H NMR (400 MHz, Chloroform-d) δ 8.97-8.53 (m, 1H), 7.76 (d, J=2.8 Hz, 1H), 7.68 (d, J=7.5 Hz, 1H), 7.52 (d, J=2.8 Hz, 1H), 6.32 (d, J=7.5 Hz, 1H), 3.91 (s, 3H).

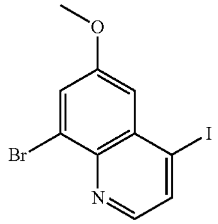

Intermediate 20

8-Bromo-4-iodo-6-methoxyquinoline

Step A. Preparation of 8-bromo-4-chloro-6-methoxyquinoline. 8-Bromo-6-methoxyquinolin-4-ol (Intermediate 19, 400 mg, 1.6 mmol, 1 equiv) was dissolved in $POCl_3$ (3.7 mL) and stirred at 100° C. for 2 h. The reaction was quenched with ice and $NaHCO_3$ was added to adjust to pH 7. The solid was filtered, washed with water, and dried to yield the title compound (430 mg, 1.6 mmol, quant.). $^1H$ NMR (400 MHz, Chloroform-d) δ 8.76 (d, J=4.7 Hz, 1H), 7.81 (d, J=2.7 Hz, 1H), 7.52 (d, J=4.7 Hz, 1H), 7.46 (d, J=2.7 Hz, 1H), 3.98 (s, 3H); LCMS (ESI): Method 2: $R_T$=1.706 min, m/z=272.0 $[M+H]^+$.

Step B. Preparation of 8-Bromo-4-iodo-6-methoxyquinoline. 8-Bromo-4-chloro-6-methoxyquinoline (430 mg, 1.6 mmol, 1 equiv) was dissolved in 4 M HCl dioxane and stirred at room temperature for 1 h. The reaction mixture was concentrated under reduced pressure. The HCl salt was dissolved in MeCN (9 mL) and potassium iodide (1.5 g, 8.9 mmol, 5 equiv) was added and reaction was stirred at 90° C. overnight. The reaction mixture was cooled to 23° C., water was added to the mixture and extracted with EtOAc (3×20 mL). The organic layer was washed with 10% sodium thiosultate, and brine. The residue was purified by flash chromatography (Combi-flash Rf, Hex/EtOAc=0-1000 gradient) to afford the title compound (325 mg, 0.89 mmol, 57% yield). $^1H$ NMR (400 MHz, Chloroform-d) δ 8.43 (d, J=4.6 Hz, 1H), 8.00 (d, J=4.5 Hz, 1H), 7.80 (d, J=2.7 Hz, 1H), 7.32 (d, J=2.7 Hz, 1H), 3.98 (s, 3H); LCMS (ESI): Method 2: $R_T$=1.783 min, m/z=363.9 $[M+H]^+$.

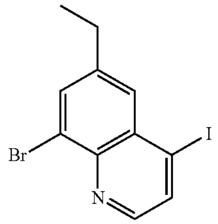

Intermediate 21

8-Bromo-6-ethyl-4-iodoquinoline

The title compound (484 mg, 1.3 mmol) was prepared following the synthetic sequence described in Intermediate 15 followed by Intermediate 20 substituting 2-bromo-4-ethylaniline for 4-bromo-2-methoxyaniline in Intermediate 15 Step A. $^1H$ NMR (400 MHz, Chloroform-d) δ 8.51 (d, J=4.5 Hz, 1H), 8.02 (d, J=4.5 Hz, 1H), 8.00 (d, J=1.9 Hz, 1H), 7.79 (s, 1H), 2.87 (q, J=7.6 Hz, 2H), 1.37 (t, J=7.6 Hz, 3H); LCMS (ESI): Method 2: $R_T$=1.983 min, m/z=361.1 $[M+H]^+$.

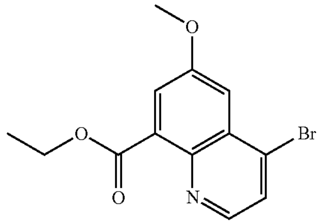 [SMILES: CCOC(=O)c1cc(OC)cc2c(Br)ccnc12]

Intermediate 22

Ethyl 4-bromo-6-methoxyquinoline-8-carboxylate

The title compound (430 mg, 1.39 mmol) was prepared following the synthetic sequence described in Intermediate 15 followed by Intermediate 17 substituting ethyl 2-amino-5-methoxybenzoate for 4-bromo-2-methoxyaniline in Intermediate 15 Step A. $^1H$ NMR (400 MHz, Chloroform-d) δ 8.63 (d, J=4.7 Hz, 1H), 7.70 (d, J=4.6 Hz, 1H), 7.66 (d, J=2.8 Hz, 1H), 7.56 (d, J=2.8 Hz, 1H), 4.52 (q, J=7.1 Hz, 2H), 4.00 (s, 3H), 1.44 (t, J=7.1 Hz, 3H), LCMS (ESI): Method 2: $R_T$=1.284 min, m/z=310.0 $[M+H]^+$.

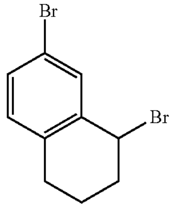 [SMILES: Brc1ccc2c(c1)C(Br)CCC2]

Intermediate 23

1,7-Dibromo-1,2,3,4-tetrahydronaphthalene

To a solution of 7-bromo-3,4-dihydronaphthalen-1(2H)-one (200 mg, 0.90 mmol, 1 equiv) in EtOH (4 mL) was added sodium borohydride (50.4 mg, 1.33 mmol, 1.5 equiv) was added in one portion and stirred at room temperature. Progress of the reaction was monitored by TLC. Upon completion, the reaction mixture was concentrated, dissolved in EtOAc, and washed with water. The organic layer was dried over $MgSO_4$ and concentrated. The residue was dissolved in $CH_2Cl_2$ (4 mL) and cooled to 0° C. $PBr_3$ (481 mg, 1.78 mmol, 2 equiv) was added dropwise to the reaction mixture. The reaction was warmed to room temperature and followed by TLC $NaHCO_3$ (sat.) was added and the mixture was extracted with EtOAc. The combined organic layers were dried over $MgSO_4$ and concentrated to give the title compound (263 mg, 0.90 mmol, quant.), which was used in the next step without further purification. $^1H$ NMR (400 MHz, Chloroform-d) δ 7.49 (d, J=2.1 Hz, 1H), 7.28 (dd, J=8.2, 2.1 Hz, 1H), 6.94 (d, J=8.2 Hz, 1H), 5.48 (t, J=3.8 Hz, 1H), 3.06-2.70 (m, 4H), 2.38 (d, J=14.4 Hz, 1H), 2.29-2.03 (m, 3H), 1.97-1.81 (m, 2H).

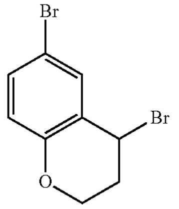 [SMILES: Brc1ccc2c(c1)C(Br)CCO2]

Intermediate 24

4,6-Dibromochromane

The title compound (120 mg, 0.41 mmol, 93% yield) was prepared following the procedure described for Intermediate 23, using 6-bromochroman-4-one (100 mg, 0.44 mmol, 1 equiv). $^{1}$H NMR (400 MHz, Chloroform-d) δ 7.41 (d, J=2.4 Hz, 1H), 7.28 (dd, J=8.8, 2.4 Hz, 1H), 6.71 (d, J=8.8 Hz, 1H), 5.42-5.35 (m, 1H), 4.57 (td, J=11.7, 2.3 Hz, 1H), 4.44-4.37 (m, 1H), 2.51 (ddt, J=16.0, 120, 4.0 Hz, 1H), 2.38 (dq, J=15.3, 2.6 Hz, 1H).

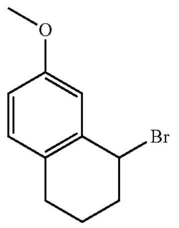

Intermediate 25

1-Bromo-7-methoxy-1,2,3,4-tetrahydronaphthalene

The title compound (140 mg, 0.57 mmol, quant.) was prepared following the procedure described for Intermediate 23, using 7-methoxy-3,4-dihydronaphthalen-1(2M-one (100 mg, 0.57 mmol, 1 equiv). $^{1}$H NMR (400 MHz, Chloroform-d) δ 6.99 (d, J=8.5 Hz, 1H), 6.88 (d, J=2.7 Hz, 1H), 6.79 (dd, J=8.4, 2.7 Hz, 1H), 5.56 (t, J=3.7 Hz, 1H), 3.80 (s, 3H), 2.94-2.69 (m, 2H), 2.44-2.06 (m, 3H), 1.93-1.86 (m, 1H).

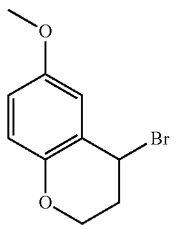

Intermediate 26

4-Bromo-6-methoxychromane

The title compound (13 mg, 0.56 mmol, quant.) was prepared following the procedure described for Intermediate 23, using 6-methoxychroman-4-one (100 mg, 0.56 mmol, 1 equiv). $^{1}$H NMR (400 MHz, Chloroform-d) δ 6.81-6.75 (m, 2H), 6.74-6.70 (m, 1H), 5.43 (p, J=1.8 Hz, 1H), 4.52 (ddd, J=12.1, 11.1, 2.1 Hz, 1H), 4.32 (dddd, J=11.2, 4.1, 2.9, 1.5 Hz, 1H), 3.76 (s, 3H), 2.52 (ddt, J=15.2, 12.1, 4.0 Hz, 1H), 2.36 (d, J=15.2, 2.6 Hz, 1H).

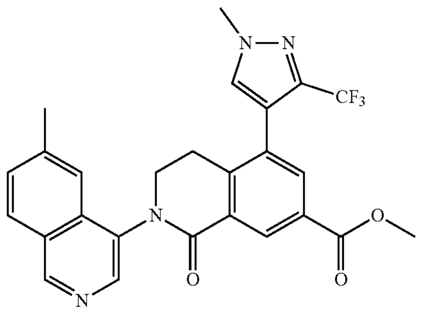 [SMILES: COC(=O)c1cc2c(c(-c3cn(C)nc3C(F)(F)F)c1)CCN(c1cncc3ccc(C)cc13)C2=O]

Intermediate 27

Methyl 6'-methyl-5-(1-methyl-3-(trifluoromethyl)-1H-pyrazol-4-yl)-1-oxo-3,4-dihydro-1H-[2,4'-biisoquinoline]-7-carboxylate The title compound (2.9 g, 62%) was prepared following the Buchwald coupling procedure described for Example 2, using methyl 5-(1-methyl-3-(trifluoromethyl)-1H-pyrazol-4-yl)-1-oxo-1,2,3,4-tetrahydroisoquinoline-7-carboxylate (Intermediate 4, 3.4 g, 9.5 mmol) and 4-bromo-6-methylisoquinoline (4.2 g, 19.0 mmol) according to the standard Buchwald coupling procedure from Example 2.

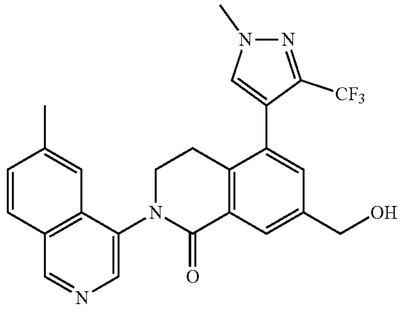 [SMILES: Cc1ccc2cncc(N3CCc4c(cc(CO)cc4-c4cn(C)nc4C(F)(F)F)C3=O)c2c1]

Intermediate 28

7-(Hydroxymethyl)-6'-methyl-5-(1-methyl-3-(trifluoromethyl)-1H-pyrazol-4-yl)-3,4-dihydro-1H-[2,4'-biisoquinoline]-1-one The title compound (2.1 g, 77%) was prepared following the standard methyl ester reduction procedure described for Intermediate 5 using methyl 6-methyl-5-(1-methyl-3-(trifluoromethyl)-1H-pyrazol-4-yl)-1-oxo-3,4-dihydro-1H-[2,4'-biisoquinoline]-7-carboxylate (Intermediate 27, 2.9 g, 5.9 mmol).

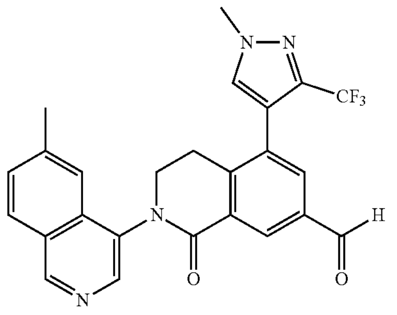 [SMILES: Cc1ccc2cncc(N3CCc4c(cc(C=O)cc4-c4cn(C)nc4C(F)(F)F)C3=O)c2c1]

Intermediate 29

6'-Methyl-5-(1-methyl-3-(trifluoromethyl)-1H-pyrazol-4-yl)-1-oxo-3,4-dihydro-1H-[2,4'-biisoquinoline]-7-carbaldehyde To a solution of 7-(hydroxymethyl)-6'-methyl-5-(1-methyl-3-(trifluoromethyl)-1H-pyrazol-4-yl)-3,4-dihydro-1H-[2,4'-biisoquinolin]-1-one (Intermediate 28, 2.1 g, 4.5 mmol) in $CH_2Cl_2$ (45 mL) was added Dess-Martin periodinane (1.92 g, 4.5 mmol, 1 eq.). The reaction was stirred at RT for 20 h then concentrated. The residue was purified by flash chromatography (Combi-flash Rf, DCM/MeOH=0-10% gradient) to afford the title compound (1.7 g, 82% yield).

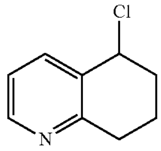 [SMILES: ClC1CCCc2ncccc21]

Intermediate 30

5-Chloro-5,6,7,8-tetrahydroquinoline

Step A. Preparation of 5,6,7,8-Tetrahydroquinolin-5-ol. To a solution of 7,8-dihydroquinolin-5(6H)-one (188.0 mg, 1.28 mmol, 1 equiv) in MeOH (6 mL) at 0° C. was added $NaBH_4$ (72.5 mg, 1.92 mmol, 1.5 equiv). The mixture was stirred for 1 h, then concentrated. The residue was dissolved in $Et_2O$, and the solution was wash with brine, dried ($Na_2SO_4$) and concentrated to provide the title compound (121 mg, 0.81 mmol, 63% yield): $^1$H NMR (400 MHz, Chloroform-d) δ 8.34 (dd, J=1.6, 4.8 Hz, 1H), 7.78 (d, J=8.0 Hz, 1H), 7.14 (dd, =4.8, 7.6 Hz, 1H), 4.76 (m, 1H), 2.90 (m, 2H), 2.05 (m, 2H), 1.81 (m, 2H); LCMS (ESI): m/z=150.4 $[M+H]^+$.

Step B. Preparation of 5-chloro-5,6,7,8-tetrahydroquinoline. To a solution of 5,6,7,8-tetrahydroquinolin-5-ol (25.6 mg, 0.17 mmol, 1 equiv) in dichloromethane (2 mL) at 0° C. was added $Et_3N$ (58 μl, 0.41 mmol, 2.4 equiv), methanesulfonyl chloride (28 μL, 0.36 mmol, 2.1 equiv). The mixture was warmed to room temperature and stirred overnight, Sat. aq. $NH_4C$ was added, and the mixture was extracted with EtOAc. The combined organic layers were dried ($Na_2SO_4$) and concentrated. The residue was purified by flash chromatography (Combi-flash Rf, Hex/EtOAc=0-40% gradient) to afford the title compound (16 mg, 0.17 mmol, 56% yield). $^1$H NMR (400 MHz, Chloroform-d) δ 8.46 (dd, J=1.6, 4.8 Hz, 1H), 7.69 (dd, J=1.6, 8.0 Hz, 1H), 7.14 (dd, J=4.8, 8.0 Hz, 1H), 5.27 (t, J=4.0 Hz, 1H), 3.08 (m, 1H), 2.91 (m, 1H), 2.26 (m, 3H), 1.97 (m, 1H); LCMS (ESI): m/z=168.3 $[M+H]^+$.

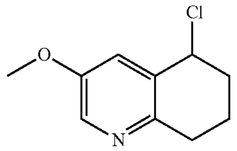

Intermediate 31

5-Chloro-3-methoxy-5,6,7,8-tetrahydroquinoline

Step A. Preparation of 3-methoxy-5,6,7,8-tetrahydroquinolin-5-ol. The title compound (81 mg, 0.45 mmol, quant.) was prepared following the procedure described for Intermediate 30 step A, substituting 3-methoxy-7,8-dihydroquinolin-5(6H)-one (80.3 mg, 0.45 mmol, 1 equiv) for 7,8-dihydroquinolin-5(6H)-one. $^1$H NMR (400 MHz, Chloroform-d) δ 8.18 (d, J=2.8 Hz, 1H), 7.35 (d, J=2.4 Hz, 1H), 4.81 (m, 1H), 3.86 (s, 3H), 2.90 (m, 2H), 2.08 (m, 2H), 1.85 (m, 2H); LCMS (ESI): m/z=180.4 $[M+H]^+$.

Step B. Preparation of 5-chloro-3-methoxy-5,6,7,8-tetrahydroquinoline. To a solution of 3-methoxy-5,6,7,8-tetrahydroquinolin-5-ol (81.2 mg, 0.45 mmol, 1 equiv) in dichloromethane (4.5 mL) at 0° C. was added thionyl chloride (43 μL, 0.59 mmol, 1.3 equiv). The reaction was warmed to room temperature slowly and stirred for 5 h, then quenched with sat. aq. $NaHCO_3$. The mixture was extracted with $Et_2O$, and the combined organic layers were dried ($Na_2SO_4$) and concentrated. The residue was purified by flash chromatography (Combi-flash Rf, Hex/EtOAc=0-50% gradient) to afford the title compound (76 mg, 0.38 mmol, 85% yield). $^1$H NMR (400 MHz, Chloroform-d) δ 8.20 (d, J=2.8 Hz, 1H), 7.20 (d, J=2.8 Hz, 1H), 5.24 (t, J=4.0 Hz, 1H), 3.85 (s, 3H), 2.99 (m, 1H), 2.85 (m, 1H), 2.23 (m, 3H), 1.95 (m, 1H); LCMS (ESI): m/z=198.4 $[M+H]^+$.

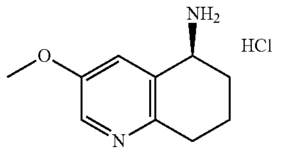

Intermediate 32

(S)-3-Methoxy-5,6,7,8-tetrahydroquinolin-5-amine hydrochloride

Step A. Preparation of (R,E)-N-(3-Methoxy-7,8-dihydroquinolin-5(6H)-ylidene)-2-methylpropane-2-sulfinamide. To a solution of 3-methoxy-7,8-dihydroquinolin-5(6H)-one (241.0 mg, 1.36 mmol, 1 equiv) in THF (9 mL) was added (R)-2-methylpropane-2-sulfinamide (164.8 mg, 1.36 mmol, 1 equiv) and tetraethoxytitanium (570 μL, 2.72 mmol, 2 equiv). The reaction was stirred at 65° C. for 24 h, then quenched with brine. The mixture was extracted with EtOAc. The combined organic layers were dried ($Na_2SO_4$)

and concentrated. The residue was purified by flash chromatography (Combi-flash Rf, Hex/EtOAc=0-90% gradient) to afford the title compound (220 mg, 0.78 mmol, 57% yield). $^1$H NMR (400 MHz, Chloroform-d) δ 8.35 (d, J=2.8 Hz, 1H), 7.97 (brs, 1H), 3.90 (s, 3H), 3.29 (m, 1H), 3.09 (m, 3H), 2.09 (m, 2H), 1.34 (s, 9H); LCMS (ESI): m/z=281.4 $[M+H]^+$.

Step B. Preparation of (R)—N—((S)-3-Methoxy-5,6,7,8-tetrahydroquinolin-5-yl)-2-methylpropane-2-sulfinamide. To a solution of (R,E)-N-(3-methoxy-7,8-dihydroquinolin-5(6H)-ylidene)-2-methylpropane-2-sulfinamide (185.0 mg, 0.66 mmol, 12/0.66 equiv) in THF (6.5 mL) at 0° C. was added L-selectride (1.0 M in THF, 2.0 mL, 2.0 mmol, 3.03 equiv). The reaction was stirred for 5 h, then quenched with sat. aq. $NaHCO_3$. The mixture was extracted with EtOAc. The combined organic layers were dried ($Na_2SO_4$) and concentrated. The residue was purified by flash chromatography (Combi-flash Rf, DCM/MeOH=0-10% gradient) to afford the title compound (185 mg, 0.66 mmol, 99% yield). $^1$H NMR (400 MHz, Chloroform-d) δ 8.17 (d, J=2.8 Hz, 1H), 7.29 (d, J=2.8 Hz, 1H), 4.48 (m, 1H), 3.83 (s, 3H), 3.40 (d, J=10.0 Hz, 1H), 2.89 (m, 2H), 2.38 (m, 1H), 2.02 (m, 1H), 1.88 (m, 2H), 1.28 (s, 9H); LCMS (ESI): m/z=283.2 $[M+H]^+$.

Step C. Preparation of (S)-3-Methoxy-5,6,7,8-tetrahydroquinolin-5-amine hydrochloride. To a solution of (R)—N—((S)-3-methoxy-5,6,7,8-tetrahydroquinolin-5-yl)-2-methylpropane-2-sulfinamide (220 mg, 0.78 mmol, 1 equiv) in THF (8 ml) at room temperature was added HCl (4 M in 1,4-dioxane, 1.95 mL, 7.8 mmol, 10 equiv). The mixture was stirred for 2 h then concentrated to provide the title compound (210 mg, 0.78 mmol, quant.), which was used without further purification. $^1$H NMR (400 MHz, Methanol-d4) δ 8.54 (s, 1H), 8.27 (s, 1H), 4.79 (m, 1H), 4.06 (s, 3H), 3.10 (m, 2H), 2.29 (m, 1H), 2.09 (m, 3H); LCMS (ESI): m/z=179.3 $[M+H]^+$.

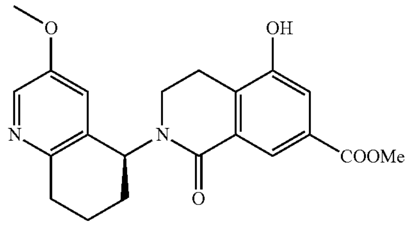 [SMILES: COC(=O)c1cc(O)c2c(c1)C(=O)N([C@H]1CCCc3ncc(OC)cc31)CC2]

Intermediate 33

Methyl (S)-5-hydroxy-2-(3-methoxy-5,6,7,8-tetrahydroquinolin-5-yl)-1-oxo-1,2,3,4-tetrahydroisoquinoline-7-carboxylate To a suspension of (S)-3-methoxy-5,6,7,8-tetrahydroquinolin-5-anine hydrochloride (595 mg, 2.36 mmol, 1.1 equiv) in dichloromethane (20 mL) at 30° C. was added DIPEA (1.12 mL, 6.42 mmol). The mixture was stirred for 15 min, then dimethyl 2-hydroxy-2,3-dihydrobenzofuran-4,6-dicarboxylate (540.0 mg, 2.14 mmol, 1 equiv) and $NaBH(OAc)_3$ (680.3 mg, 3.21 mmol, 1.5 equiv) were added sequentially. The reaction was stirred at 30° C. for 2 h, then concentrated. The residue was dissolved in 1,4-dioxane (10 ml) and heated at 90° C. for 1 h. The mixture was diluted with water and extracted with EtOAc. The combined organic layers were dried ($Na_2SO_4$) and concentrated to provide the title compound (1.1 g), which was used without further purification. $^1$H NMR (400 MHz, Chloroform-d) δ 8.30 (d, J=1.6 Hz, 1H), 8.10 (d, J=2.4 Hz, 1H), 7.52 9d, J=1.6 Hz, 1H), 7.03 (d, J=2.4 Hz, 1H), 6.07 (m, 1H), 3.91 (s, 3H), 3.75 (s, 3H), 3.35 (m, 1H), 3.15 (m, 1H), 3.00 (m, 1H), 2.89 (m, 2H), 2.79 (m, 1H), 2.12 (m, 2H), 1.94 (m, 1H), 1.80 (m, 1H); LCMS (ESI): m/z=383.4 $[M+H]^+$.

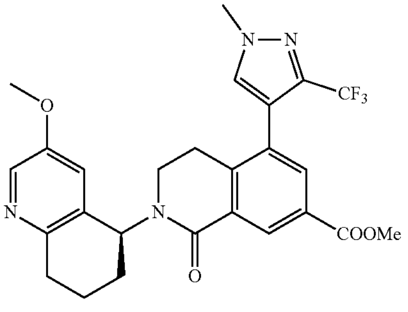 [SMILES: COC(=O)c1cc2c(c(-c3cn(C)nc3C(F)(F)F)c1)CCN([C@H]1CCCc3ncc(OC)cc31)C2=O]

Intermediate 34

Methyl (S)-2-(3-methoxy-5,6,7,8-tetrahydroquinolin-5-yl)-5-(1-methyl-3-(trifluoromethyl)-1H-pyrazol-4-yl)-1-oxo-1,2,3,4-tetrahydroisoquinoline-7-carboxylate Step A. Preparation of methyl (S)-2-(3-methoxy-5,6,7,8-tetrahydroquinolin-5-yl)-1-oxo-5-(((trifluoromethyl)sulfonyl)oxy)-1,2,3,4-tetrahydroisoquinoline-7-carboxylate. To a suspension of methyl (S)-5-hydroxy-2-(3-methoxy-5,6,7,8-tetrahydroquinolin-5-yl)-1-oxo-1,2,3,4-tetrahydroisoquinoline-7-carboxylate (1.1 g crude, 2.14 mmol, 1 equiv) in THF/acetonitrile (10 mL/10 mL) was added DIPEA (2.24 mL, 12.84 mmol, 6 equiv) and 1,1,1-trifluoro-N-phenyl-N-((trifluoromethyl)sulfonyl)methanesulfonamide (1.15 g, 3.21 mmol, 1.5 equiv). The reaction mixture was stirred at 45° C. for 2 h, then quenched with sat. aq. $NaHCO_3$ and extracted with EtOAc. The combined organic layers were dried ($Na_2SO_4$) and concentrated. The residue was purified by flash chromatography (Combi-flash Rf, Hex/EtOAc=10-90% gradient) to afford the title compound (912 mg, 1.77 mmol, 82% yield over two steps). $^1$H NMR (4001 MHz, Chloroform-d) δ 8.85 (d, J=1.6 Hz, 1H), 8.18 (d, J=2.4 Hz, 1H), 8.07 (d, J=1.6 Hz, 1H), 7.00 (d, J=2.4 Hz, 1H), 6.09 (m, 1H), 3.98 (s, 3H), 3.78 (s, 3H), 3.43 (m, 1H), 3.25 (m, 1H), 3.08 (m, 1H), 2.96 (m, 3H), 2.15 (m, 2H), 1.93 (m, 1H), 1.80 (m, 1H); LCMS (ESI): m/z=515.4 $[M+H]^+$.

Step B. methyl (S)-2-(3-methoxy-5,6,7,8-tetrahydroquinolin-5-yl)-5(1-methyl-3-(trifluoromethyl)-1H-pyrazol-4-yl)-1-oxo-1,2,3,4-tetrahydroisoquinoline-7-carboxylate. To a solution of methyl (S)-2-(3-methoxy-5,6,7,8-tetrahydroquinolin-5-yl)-1-oxo-5-(((trifluoromethyl)sulfonyl)oxy)-1,2,3,4-tetrahydroisoquinoline-7-carboxylate (310.0 mg, 0.6 mmol, 1 equiv) in 1,4-dioxane (6 mL) at room temperature was added sequentially (1-methyl-3-(trifluoromethyl)-1H-pyrazol-4-yl)boronic acid (152 mg, 0.78 mmol, 1.3 equiv), $Na_2CO_3$ (160 mg, 1.51 mmol, 2.5 equiv), $Pd(PPh_3)_4$ (41.8 mg, 0.36 mmol, 0.06 equiv), and water (0.6 mL) The resulting mixture was stirred at 80° C. for 16 h, then diluted with water. The mixture was extracted with EtOAc. The combined organic layers were dried ($Na_2SO_4$) and concentrated. The residue was purified by flash chromatography (Combi-flash Rf, DC M/MeOH=0-10% gradient) to afford the title compound (348 mg, quant.), which was used without further purification $^1$H NMR (400 MHz, Chloroform-d) δ 8.86 (d, J=2.0 Hz, 1H), 8.16 (d, J=2.4 Hz, 1H), 8.06 (d, J=1.6 Hz, 1H), 7.38 (s, 1H), 7.02 (d, J=2.0 Hz, 1H), 6.12 (m, 1H), 4.01 (s, 3H), 3.96 (s, 3H), 3.77 (s, 3H), 3.33 (m, 1H), 3.10 (m, 1H), 2.93 (m, 2H), 2.73 (m, 2H), 2.15 (m, 2H), 1.94 (m, 1H), 1.79 (m, 1H); LCMS (ESI): m/z=515.4 $[M+H]^+$.

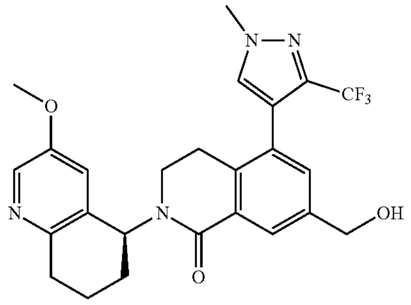 [SMILES: COc1cnc2c(c1)[C@@H](N1CCc3c(cc(CO)cc3-c3cn(C)nc3C(F)(F)F)C1=O)CCC2]

Intermediate 35

(S)-7-(Hydroxymethyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one The title compound (290 mg, 0.6 mmol, 99% yield over two steps) was prepared following the standard methylester reduction procedure described for Intermediate 5, using methyl (S)-2-(3-methoxy-5,6,7,8-tetrahydroquinolin-5-yl)-5-(1-methyl-3-(trifluoromethyl)-1H-pyrazol-4-yl)-1-oxo-1,2,3,4-tetrahydroisoquinoline-7-carboxylate (Intermediate 34, 348 mg, 0.6 mmol, 1 equiv). $^1$H NMR (400 MHz, Chloroform-d) δ 8.20 (d, J=1.6 Hz, 1H), 8.16 (d, J=2.4 Hz, 1H), 7.43 (d, J=1.6 Hz, 1H), 7.36 (s, 1H), 7.03 (d, J=2. Hz, 1H), 6.12 (m, 1H), 4.79 (d, J=6.0 Hz, 2H), 4.01 (s, 3H), 3.77 (s, 3H), 3.29 (m, 1H), 3.08 (m, 1H), 2.92 (m, 2H), 2.68 (m, 2H), 2.13 (m, 2H), 1.93 (m, 1H), 1.778 (m, 1H); LCMS (ESI): m/z=487.4 $[M+H]^+$.

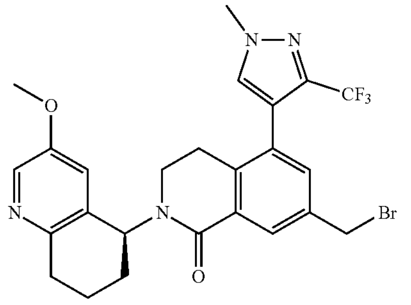 [SMILES: COc1cnc2c(c1)[C@@H](N1CCc3c(cc(CBr)cc3-c3cn(C)nc3C(F)(F)F)C1=O)CCC2]

Intermediate 36

(S)-7-(Bromomethyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one To a solution of (S)-7-(hydroxymethyl)-2-(3-methoxy-5,6,7,8-tetrahydrquinolin-5-yl)-5-(1-methyl-3-(trifluoromethyl)-1H-pyrazol-4-yl)-3,4-dihydroisoquinolin-1(2H)-one (intermediate 35, 200 mg, 0.41 mmol, 1 equiv) in dichloromethane (10 ml) at room temperature was added $CBr_4$ (272 mg, 0.82 mmol, 2 equiv) and $PPh_3$ (113 mg, 0.41 mmol, 1 equiv). The mixture was stirred for 20 min, then a second portion of $PPh_3$ (113 mg, 0.41 mmol, 1 equiv) was added. The reaction was stirred for additional 2 h then concentrated. The residue was purified by flash chromatography (Combiflash Rf, Hex/EtOAc=30-100% gradient) to afford the title compound (563 mg), which was used without further purification: LCMS (ESI): m/z=549.4 $[M+H]^+$.

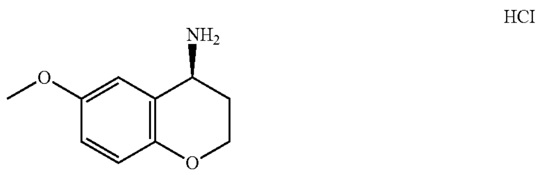

Intermediate 37

(S)-6-Methoxychroman-4-amine hydrochloride

The title compound was prepared following the synthetic sequence described in Intermediate 32, substituting 6-methoxychroman-4-one for 3-methoxy-7,8-dihydroquinolin-5(6H)-one in Step A.

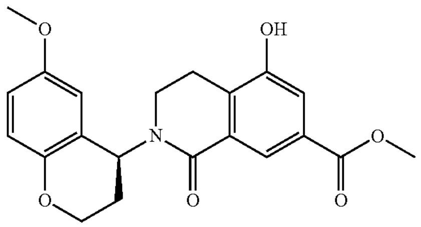 [SMILES: COC(=O)c1cc(O)c2c(c1)C(=O)N([C@H]1CCOc3ccc(OC)cc31)CC2]

Intermediate 38

Methyl (S)-5-hydroxy-2-(6-methoxychroman-4-yl)-1-oxo-1,2,3,4-tetrahydroisoquinoline-7-carboxylate The title compound (370 mg, 0.97 mmol, quant.) was prepared following the reductive amination procedure described for Intermediate 1, substituting (S)-6-methoxychroman-4-amine (172 mg, 0.96 mmol, 1 equiv). $^1$H NMR (400 MHz, Chloroform-d) δ 8.40 (s, 1H), 7.66 (s, 1H), 6.80 (d, J=8.9 Hz, 1H), 6.76 (dd, J=8.9, 2.9 Hz, 1H), 6.67 (d, J=2.9 Hz, 1H), 6.16 (t, J=8.3 Hz, 1H), 4.32 (dt, J=11.3, 4.0 Hz, 1H), 4.20 (ddd, J=11.2, 8.3, 4.6 Hz, 1H), 3.92 (s, 3H), 3.69 (s, 3H), 3.36 (td, J=11.4, 10.3, 4.6 Hz, 1H), 3.27 (dt, J=12.1, 5.5 Hz, 1H), 3.00 (dt, J=16.9, 5.3 Hz, 2H), 2.86 (ddd, J=16.4, 10.3, 5.5 Hz, 2H), 2.22-2.13 (m, 3H); LCMS (ESI) Method 2: $R_T$=1.560 min, m/z=384.0 $[M+H]^+$.

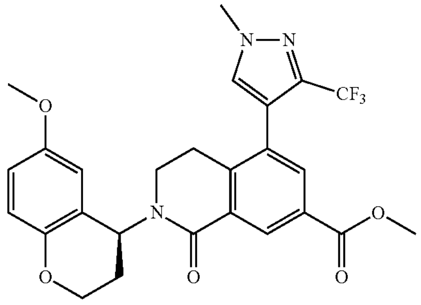 [SMILES: COC(=O)c1cc2c(c(-c3cn(C)nc3C(F)(F)F)c1)CCN([C@H]1CCOc3ccc(OC)cc31)C2=O]

Intermediate 39

Methyl (S)-2(6-methoxychroman-4-yl)-5-(1-methyl-3-(trifluoromethyl)-1H-pyrazol-4-yl)-1-oxo-1,2,3,4-tetrahydroisoquinoline-7-carboxylate The title compound (138 mg, 0.27 mmol, 48% yield, over two steps) was prepared following the synthetic sequence described in Intermediate 2 and 3, using methyl (S)-5-hydroxy-2-(6-methoxychroman-4-yl)-1-oxo-1,2,3,4-tetrahydroisoquinoline-7-carboxylate (Intermediate 38, 370 mg, 0.97 mmol) in Intermediate 2 and substituting tetrakis(triphenylphosphine)palladium(0) (0.05 equiv) for $PdCl_2$(dppf) in Intermediate 3. $^1$H NMR (400 MHz, Chloroform-d) δ 8.85 (d, J=1.9 Hz, 1H), 8.05 (d, J=1.9 Hz, 1H), 7.37 (s, 1H), 6.79 (d, J=8.8 Hz, 1H), 6.75 (dd, J=8.8, 2.7 Hz, 1H), 6.65 (d, J=2.9 Hz, 1H), 6.20-6.13 (m, 1H), 4.30 (dt, J=11.3, 4.0 Hz, 1H), 4.19 (td, J=11.2, 10.6, 3.1 Hz, 1H), 4.01 (s, 3H), 3.95 (s, 3H), 3.69 (s, 3H), 3.36-3.24 (m, 1H), 3.19 (dt, J=12.0, 5.4 Hz, 1H), 2.80-2.68 (m, 2H), 2.24-2.10 (m, 2H); LCMS (ESI) Method 2: $R_T$=1.822 min, m/z=516.0 [M+H]$^+$.

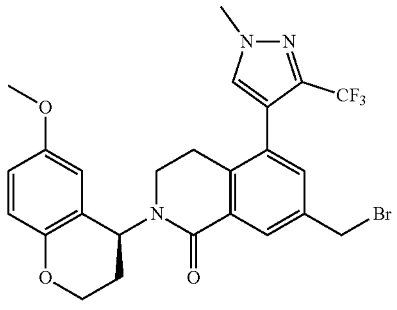 [SMILES: COc1ccc2c(c1)[C@@H](N1CCc3c(cc(CBr)cc3-c3cn(C)nc3C(F)(F)F)C1=O)CCO2]

Intermediate 40

(S)-7-(Bromomethyl)-2-(6-methoxychroman-4-yl)-5-(1-methyl-3-(trifluoromethyl)-1H-pyrazol-4-yl)-3,4-dihydroisoquinolin-1(2H)-one The title compound (151 mg, 0.27 mmol, quant., over two steps) was prepared following the methylester reduction procedure described for Intermediate 5, using Methyl (S)-2-(6-methoxychroman-4-yl)-5-(1-methyl-3-(trifluoromethyl)-1H-pyrazol-4-yl)-1-oxo-1,2,3,4-tetrahydroisoquinoline-7-carboxylate (Intermediate 39, 138 mg, 0.27 mmol, 1 equiv) followed by the bromination procedure described for Intermediate 6. $^1$H NMR (400 MHz, Chloroform-d) δ 8.23 (d, J=2.0 Hz, 1H), 7.42 (d, J=2.0 Hz, 1H), 7.37 (d, J=1.0 Hz, 1H), 6.78 (d, J=8.9 Hz, 1H), 6.74 (dd, J=8.9, 2.6 Hz, 1H), 6.65 (d, J=2.9 Hz, 1H), 6.19-6.09 (m, 1H), 4.54 (s, 2H), 4.30 (dt, J=11.3, 4.0 Hz, 1H), 4.23-4.14 (m, 1H), 4.00 (s, 3H), 3.69 (s, 3H), 3.28 (ddd, J=12.4, 10.1, 4.8 Hz, 1H), 3.23-3.11 (m, 1H), 2.75-2.57 (m, 2H), 2.21-2.10 (m, 2H); LCMS (ESI) Method 2: $R_T$=1.921 min, m/z=549.9 [M+H]$^+$.

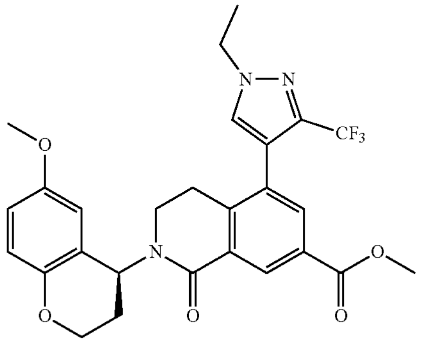 [SMILES: CCn1cc(-c2cc(C(=O)OC)cc3c2CCN([C@H]2CCOc4ccc(OC)cc42)C3=O)c(C(F)(F)F)n1]

Intermediate 41

Methyl (S)-5-(1-ethyl-3-(trifluoromethyl)-1H-pyrazol-4-yl)-2-(6-methoxychroman-4-yl)-1-oxo-1,2,3,4-tetrahydroisoquinoline-7-carboxylate The title compound (132 mg, 0.25 mmol) was prepared following the Suzuki coupling procedure described for Intermediate 3, using the synthetic sequence described in Intermediate 2 and 3, using methyl (S)-5-hydroxy-2-(6-methoxychroman-4-yl)-1-oxo-1,2,3,4-tetrahydroisoquinoline-7-carboxylate (Intermediate 38, 370 mg, 0.97 mmol) in Intermediate 2 and substituting (1-ethyl-3-(trifluoromethyl)-1H-pyrazol-4-yl)boronic acid and tetrakis(triphenylphosphine)palladium(0) (0.05 equiv) for (1-methyl-3-(trifluoromethyl)-1H-pyrazol-4-yl)boronic acid and $PdCl_2$(dppf) in Intermediate 3, respectively. $^1$H NMR (400 MHz, Chloroform-d) δ 8.85 (d, J=1.9 Hz, 1H), 8.06 (d, J=1.9 Hz, 1H), 7.40 (d, J=1.0 Hz, 1H), 6.79 (d, J=8.9 Hz, 1H), 6.74 (dd, J=8.9, 2.8 Hz, 1H), 6.66 (d, J=2.9 Hz, 1H), 6.23-6.13 (m, 1H), 4.37-4.15 (m, 4H), 3.95 (s, 3H), 3.69 (s, 3H), 3.38-3.25 (m, 1H), 3.24-3.13 (m, 1H), 2.80-2.68 (m, 2H), 2.23-2.10 (m, 2H), 1.57 (t, J=7.3 Hz, 3H); LCMS (ESI) Method 2: $R_T$=1.934 min, m/z=529.9 [M+H]$^+$.

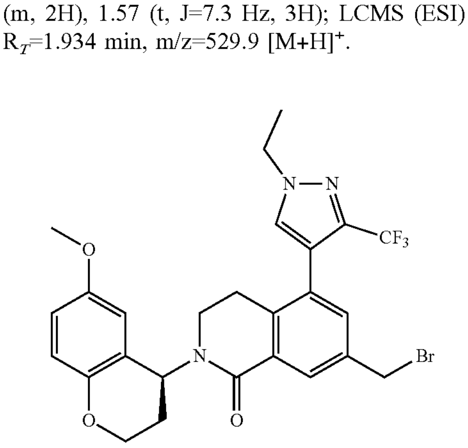

Intermediate 42

(S)-7-(Bromomethyl)-5-(1-ethyl-3-(trifluoromethyl)-1H-pyrazol-4-yl)-2-(6-methoxychroman-4-yl)-3,4-dihydroisoquinolin-1(2H)-one The title compound (131 mg, 0.23 mmol, 93% yield, over two steps) was prepared following the methylester reduction procedure described for Intermediate 5, using methyl (S)-5-(1-ethyl-3-(trifluoromethyl)-1H-pyrazol-4-yl)-2-(6-methoxychroman-4-yl)-1-oxo-1,2,3,4-tetrahydroisoquinoline-7-carboxylate (Intermediate 41, 132 mg, 0.25 mmol) followed by the bromination procedure described for Intermediate 6. $^{1}$H NMR (400 MHz, Chloroform-d) δ 8.23 (d, J=2.0 Hz, 1H), 7.43 (d, J=2.1 Hz, 1H), 7.39 (d, J=1.0 Hz, 1H), 6.78 (d, J=8.9 Hz, 1H), 6.76-6.72 (m, 1H), 6.66 (d, J=2.8 Hz, 1H), 6.20-6.10 (m, 1H), 4.54 (s, 2H), 4.33-4.15 (m, 4H), 3.69 (s, 3H), 3.34-3.23 (m, 1H), 3.23-3.10 (m, 1H), 2.77-2.60 (m, 2H), 2.18-2.12 (m, 2H), 1.56 (t, J=8.0 Hz, 3H); LCMS (ESI) Method 2: $R_T$=1.994 min, m/z=563.8 $[M+H]^+$.

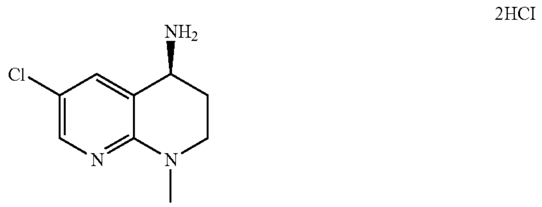

Intermediate 43

(S)-6-Chloro-1-methyl-1,2,3,4-tetrahydro-1,8-naphthyridin-4-amine hydrochloride

Step A. Preparation of (S)—N—((S)-1-(2,5-Dichloropyridin-3-yl)-3-(methylamino)propyl)-2-methylpropane-2-sulfinamide. Ozone was bubbled through a solution of (S)—N—((S)-1-(2,5-dichloropyridin-3-yl)but-3-en-1-yl)-2-methylpropane-2-sulfinamide (Intermediate 46 Step B, 610.0 mg, 1.9 mmol, 1 equiv) in dichloromethane (50 mL) at −78° C., and the reaction was monitored by LCMS. After the starting material was consumed, nitrogen gas was bubbled through the reaction mixture for 5 min to remove the excess ozone. Then TBAF (1.0 M in THF, 2.1 ml, 2.09 mmol, 1.1 equiv) was added, and the mixture was warmed to 0° C. and stirred for 1.5 h until the ozonides were decomposed. The organic phase was washed with water, dried ($Na_2SO_4$), and concentrated. The residue was dissolved in MeOH (10 mL). To this solution was added methylamine hydrochloride (641.0 mg, 9.49 mmol, 5 equiv) and DIPEA (1.3 mL, 7.60 mmol, 4 equiv). The mixture was stirred at room temperature for 5 min then dichloromethane (10 mL) was added followed by addition of $NaBH_3CN$ (418.0 mg, 6.65 mmol, 3.5 equiv). The resulting mixture was stirred at room temperature for 16 h then concentrated. The residue was dissolved in EOAc and washed with water. The combined organic layers were dried ($Na_2SO_4$) and concentrated. The residue was purified by flash chromatography (Combi-flash Rf, Hex/EtOAc=0-100% gradient) to afford the title compound (1.0 g). LCMS (ESI): m/z=338.4 $[M+H]^+$.

Step B. Preparation of (S)—N—((S)-6-Chloro-1-methyl-1,2,3,4-tetrahydro-1,8-naphthyridin-4-yl)-2-methylpropane-2-sulfinamide. To a solution of (S)—N—((S)-1-(2,5-dichloropyridin-3-yl)-3-(methylamino)propyl)-2-methylpropane-2-sulfinamide (1.0 g, 1.9 mmol, 1 equiv) in 1,4-dioxane (20 mL) was added DIPEA (1.0 mL, 5.7 mmol, 3 equiv). The mixture was stirred at 90° C. for 16 h, then concentrated. The residue was dissolved in EtAOc and washed with water. The organic layer was dried ($Na_2SO_4$) and concentrated. The residue was purified by flash chromatography (Combi-flash Rf, Hex/EtOAc=0-80% gradient) to afford the title compound (112 mg, 0.37 mmol, 20% yield over two steps). $^{1}$H NMR (400 MHz, Chloroform-d) δ 8.00 (d, J=2.8 Hz, 1H), 7.43 (d, J=2.8 Hz, 1H), 4.51 (m, 1H), 3.46 (td, J=3.6, 11.6 Hz, 1H), 3.30 (m, 1H), 3.11 (s, 3H), 2.09 (m, 1H), 1.97 (m, 1H), 1.23 (s, 9H); LCMS (ESI): m/z=302.4 $[M+H]^+$.

Step C. Preparation of (S)-6-Chloro-1-methyl-1,2,3,4-tetrahydro-1,8-naphthyridin-4-amine hydrochloride. To a solution of (S)—N—((S)-6-chloro-1-methyl-1,2,3,4-tetrahydro-1,8-naphthyridin-4-yl)-2-methylpropane-2-sulfinamide (112 mg, 0.37 mmol, 1 equiv) in 1,4-dioxane (4 mL) at room temperature was added potassium tert-butoxide (90 mg, 0.74 mmol, 2 equiv). The mixture was warmed up to 50-55° C. and stirred for 1 h. The reaction was quenched with saturated aqueous $NH_4Cl$, and the mixture was extracted with EtOAc. The combined organic layers were dried ($Na_2SO_4$) and concentrated. The residue was purified on ISCO (10-95% EtOAc in hexane) to provide the desired product (110 mg, 0.37 mmol, quant.). LCMS (ESI): m/z=198.3 $[M+H]^+$.

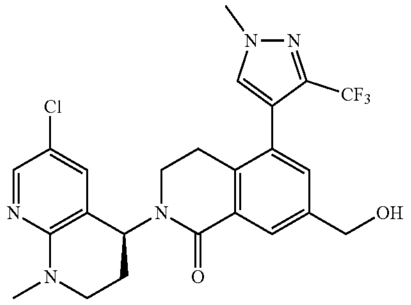 [SMILES: CN1CC[C@H](N2CCc3c(cc(CO)cc3-c3cn(C)nc3C(F)(F)F)C2=O)c2cc(Cl)cnc21]

Intermediate 44

(S)-2-(6-Chloro-1-methyl-1,2,3,4-tetrahydro-1,8-naphthyridin-4-yl)-7-(hydroxymethyl)-5-(1-methyl-3-(trifluoromethyl)-1H-pyrazol-4-yl)-3,4-dihydroisoquinolin-1(2H)-one The title compound was prepared following the synthetic sequence described in Intermediate 33-35, substituting (S)-6-chloro-1-methyl-1,2,3,4-tetrahydro-1,8-naphthyridin-4-amine hydrochloride (Intermediate 43) for (S)-3-methoxy-5,6,7,8-tetrahydroquinolin-5-amine hydrochloride in Intermediate 33. LCMS (ESI): m/z 506.4 $[M+H]^+$.

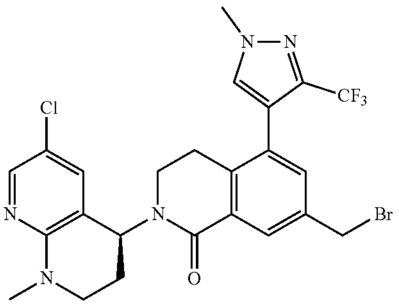 [SMILES: CN1CC[C@H](N2CCc3c(cc(CBr)cc3-c3cn(C)nc3C(F)(F)F)C2=O)c2cc(Cl)cnc21]

Intermediate 45

(S)-7-(Bromomethyl)-2-(6-chloro-1-methyl-1,2,3,4-tetrahydro-1,8-naphthyridin-4-yl)-5-(1-methyl-3-(trifluoromethyl)-1H-pyrazol-4-yl)-3,4-dihydroisoquinolin-1(2H)-one To a solution of (S)-2-(6-chloro-1-methyl-1,2,3,4-tetrahydro-1,8-naphthyridin-4-yl)-7-(hydroxymethyl)-5-(1-methyl-3-(trifluoromethyl)-1H-pyrazol-4-yl)-3,4-dihydroisoquinolin-1(2H)-one (Intermediate 44, 35.0 mg, 0.069 mmol, 1 equiv) in dichloromethane (2 mL) at 0° C. was added $PBr_3$ (1.0 M in dichloromethane, 0.14 mL, 0.14 mmol, 2 equiv). The mixture was stirred at 0° C. for 30 min then warmed to 40° C. The reaction mixture was stirred for additional 1 h then quenched with sat. aq. $NaHCO_3$ and extracted with EtOAc. The combined organic layers were dried ($Na_2SO_4$) and concentrated to provide the title compound (38 mg, 0,069 mmol, quant.), which was used without further purification. LCMS (ESI): m/z=568.4 $[M+H]^+$.

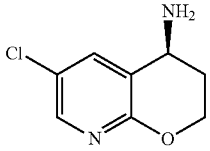

2HCl

Intermediate 46

(S)-6-Chloro-3,4-dihydro-2H-pyrano[2,3-b]pyridin-4-amine hydrochloride

Step A. Preparation of (S,E)-N-((2,5-dichloropyridin-3-yl)methylene)-2-methylpropane-2-sulfinamide To a solution of 2,5-dichloronicotinaldehyde (1.15 g, 6.53 mmol, 1 equiv) in dichloromethane (25 mL) at room temperature was added (S)-2-methylpropane-2-sulfinamide (792.0 mg, 6.53 mmol, 1 equiv) and $Cs_2CO_3$ (3.19 g, 9.80 mmol, 1.5 equiv). The mixture was stirred for 16 h then filtered. The filtrate was concentrated and the residue was purified by flash chromatography (Combi-flash Rf, Hex/EtOAc=0-20% gradient) to afford the title compound (1.7 g, 6.09 mmol, 93% yield). $^1H$ NMR (400 MHz, Chloroform-d) δ 8.92 (s, 1H), 8.48 (d, J=2.8 Hz, 1H), 8.32 (d, J=2.8 Hz, 1H), 1.30 (s, 9H); LCMS (ESI): m/z=279.1 $[M+H]^+$.

Step B. Preparation of (S)—N—((S)-1-(2,5-dichloropyridin-3-yl)but-3-en-1-yl)-2-methylpropane-2-sulfinamide To a solution of allylmagnesium bromide (1.0 M in diethyl ether, 5.2 mL, 5.2 mmol, 1.8 equiv) in THF (15 mL) at room temperature was added dropwise dimethylzinc (1.0 M in heptane, 5.7 mL, 5.7 mmol, 2.0 equiv). The mixture was stirred at room temperature for 30 min then was added slowly to a solution of (S,E)-N-((2,5-dichloropyridin-3-yl)methylene)-2-methylpropane-2-sulfinamide (800.0 mg, 2.9 mmol, 1 equiv) in THF (15 mL) at −78° C. The resulting mixture was stirred for 1.5 h then quenched with sat. aq. $NH_4Cl$. The mixture was extracted with EtOAc. The combined organic layers were dried ($Na_2SO_4$) and concentrated. The residue was purified by flash chromatography (Combi-flash Rf, Hex/EtOAc=0-90% gradient) to afford the title compound (600 mg, 1.87 mmol, 65% yield). $^1H$ NMR (400 MHz, Chloroform-d) δ 8.29 (d, J=2.4 Hz, 1H), 7.77 (d, J=2.4 Hz, 1H), 5.65 (m, 1H), 5.16 (m, 2H), 4.82 (q, J=6.4 Hz, 1H), 3.84 (brd, J=6.8 Hz, 1H), 2.64 (m, 2H), 1.23 (s, 9H); LCMS (ESI): m/z=321.2 $[M+H]^+$.

Step C. Preparation of (S)—N—((S)-1-(2,5-dichloropyridin-3-yl)-3-hydroxypropyl)-2-methylpropane-2-sulfinamide Ozone was bubbled through a solution of (S)—N—((S)-1-(2,5-dichloropyridin-3-yl)but-3-en-1-yl)-2-methylpropane-2-sulfinamide (520.0 mg, 1.62 mmol, 1 equiv) in dichloromethane (50 mL) at −78° C. while monitored the reaction by LCMS, After the starting material was consumed, nitrogen gas was bubbled through the reaction mixture for 5 mi to remove the excess ozone. Then TBAF (1.0 M in THF, 2.05 mL, 2.05 mmol, 1.26 equiv) was added, and the mixture was allowed to warm to 0° C. and stirred for 1.5 h until the ozonides were decomposed. Then MeOH (4 mL) was added and followed by addition of $NaBH_4$ (200.0 mg, 5.29 mmol). The resulting mixture was stirred for 30 min then quenched with water. The mixture was extracted with EtOAc. The combined organic layers were dried ($Na_2SO_4$) and concentrated. The residue was purified by flash chromatography (Combi-flash Rf, Hex/EtOAc=45-95% gradient) to afford the title compound (322 mg, 0.99 mmol, 61% yield). $^1H$ NMR (400 MHz, Chloroform-d) δ 8.29 (d, J=2.4 Hz, 1H), 7.90 (d, J=2.4 Hz, 1H), 4.96 (m, 1H), 4.79 (d, J=7.6 Hz, 1H), 3.78 (dd, J=4.4, 6.8 Hz, 2H), 2.13 (m, 1H), 1.95 (m, 1H), 1.18 (s, 9H); LCMS (ESI): m/z 325.2 $[M+H]^+$.

Step D. Preparation of (S)—N—((S)-6-chloro-3,4-dihydro-2H-pyrano[2,3-b]pyridin-4-yl)-2-methylpropane-2-sulfinamide To a solution of (S—N—((S)-1-(2,5-dichloropyridin-3-yl)-3-hydroxypropyl)-2-methylpropane-2-sulfinamide (250.0 mg, 0.77 mmol, 1 equiv) in 1,4-dioxane (8 mL) at room temperature was added potassium tert-butoxide (172.0 mg, 1.54 mmol, 2 equiv). The mixture was warmed to 50-55° C. and stirred for 1 h. The reaction was quenched with saturated aqueous $NH_4Cl$ and extracted with EtOAc. The combined organic layers were dried ($Na_2SO_4$) and concentrated. The residue was purified by flash chromatography (Combi-flash Rf, Hex/EtOAc=10-95% gradient) to afford the title compound (169 mg, 0.58 mmol, 76%). $^1H$ NMR (400 MHz, Chloroform-d) δ 8.14 (d, J=2.4 Hz, 1H), 7.82 (d, J=2.4 Hz, 1H), 4.61 (q, J=4.4 Hz, 1H), 4.41 (m, 2H), 3.33 (brd, J=4.0 Hz, 1H), 2.14 (m, 2H), 1.25 (s, 9H); LCMS (ESI): m/z=289.2 $[M+H]^+$.

Step E. Preparation of (S)-6-chloro-3,4-dihydro-2H-pyrano[2,3-b]pyridin-4-amine hydrochloride. The title compound (169 mg, 0.63 mmol, quant.) was prepared following the procedure described for Intermediate 43 Step C using (S)—N—((S)-6-Chloro-3,4-dihydro-2H-pyrano[2,3-b]pyridin-4-yl)-2-methylpropane-2-sulfinamide (183.0 mg, 0.63 mmol, 1 equiv). $^1H$ NMR (400 MHz, Methanol-d4) δ 8.22 (d, J=2.4 Hz, 1H), 7.93 (d, J=2.4 Hz, 1H), 4.67 (t, J=6.0 Hz, 1H), 4.48 (m, 2H), 2.43 (m, 1H), 2.18 (m 1H); LCMS (ESI): m/z=185.3 $[M+H]^+$.

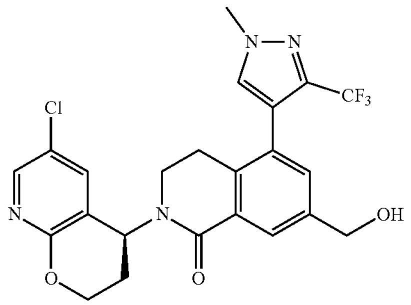 [SMILES: Cn1cc(-c2cc(CO)cc3c2CCN([C@H]2CCOc4ncc(Cl)cc42)C3=O)c(C(F)(F)F)n1]

Intermediate 47

(S)-2-(6-Chloro-3,4-dihydro-2H-pyrano[2,3-b]pyridin-4-yl)-7-(hydroxymethyl)-5-(1-methyl-3-(trifluoromethyl)-1H-pyrazol-4-yl)-3,4-dihydroisoquinolin-1(2H)-one The title compound (37 mg, 0.075 mmol) was prepared following the synthetic sequence described in Intermediates 33-35, substituting (S)-6-chloro-3,4-dihydro-2H-pyrano[2,3-b]pyridin-4-amine hydrochloride (Intermediate 46) for (S)-3-methoxy-5,6,7,8-tetrahydroquinolin-5-amine hydrochloride in Intermediate 33. $^1$H NMR (400 MHz, Chloroform-d) δ 8.19 (d, J=1.6 Hz, 1H), 8.09 (d, J=2.0 Hz, 1H), 7.47 (m, 2H), 7.37 (s, 1H), 6.23 (m, 1H), 4.78 (d, J=3.2 Hz, 2H), 4.57 (m, 1H), 4.38 (m, 1H), 4.01 (s, 3H), 3.29 (m, 1H), 3.11 (m, 1H), 2.72 (m, 2H), 2.19 (m, 2H); LCMS (ESI): m/z 493.4 [M+H]$^+$.

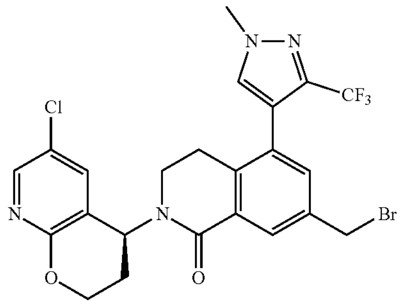 [SMILES: Cn1cc(-c2cc(CBr)cc3c2CCN([C@H]2CCOc4ncc(Cl)cc42)C3=O)c(C(F)(F)F)n1]

Intermediate 48

(S)-7-(Bromoethyl)-2-(6-chloro-3,4-dihydro-2H-pyrano[2,3-b]pyridin-4-yl)-5-(1-methyl-3-(trifluoromethyl)-1H-pyrazol-4-yl)-3,4-dihydroisoquinolin-1(2H)-one The title compound (45 mg crude) was prepared following the bromination procedure described for Intermediate 6, substituting (S)-2-(6-chloro-3,4-dihydro-2H-pyrano[2,3-b]pyridin-4-yl)-7-(hydroxymethyl)-5-(1-methyl-3-(trifluoromethyl)-1H-pyrazol-4-yl)-3,4-dihydroisoquinolin-1(2H)-one (Intermediate 47, 37 mg, 0.075 mmol, 1 equiv) for 7-(hydroxymethyl)-5-(1-methyl-3-(trifluoromethyl)-1H-pyrazol-4-yl)-3,4-dihydroisoquinolin-1(2H)-one. LCMS (ESI): m/z=555.4 [M+H]$^+$.

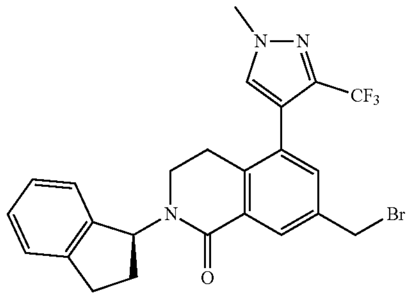 [SMILES: Cn1cc(-c2cc(CBr)cc3c2CCN([C@H]2CCc4ccccc42)C3=O)c(C(F)(F)F)n1]

Intermediate 49

(S)-7-(Bromomethyl)-2-(2,3-dihydro-1H-inden-1-yl)-5-(1-methyl-3-(trifluoromethyl)-1H-pyrazol-4-yl)-3,4-dihydroisoquinolin-1(2H)-one The title compound (160 mg, 0.32 mmol) was prepared following the synthetic sequence described in Intermediates 1-3, 5 and 6, substituting (S)-2,3-Dihydro-1H-linden-1-amine for (2,4-dimethoxyphenyl)methanamine in Intermediate 1. LCMS (ESI): m/z=504.4 [M+H]$^+$.

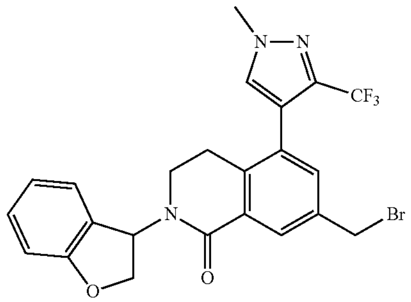 [SMILES: Cn1cc(-c2cc(CBr)cc3c2CCN(C2COc4ccccc42)C3=O)c(C(F)(F)F)n1]

Intermediate 50

7-(Bromomethyl)-2-(2,3-dihydrobenzofuran-3-yl)-5-(1-methyl-3-(trifluoromethyl)-1H-pyrazol-4-yl)-3,4-dihydroisoquinolin-1(2H)-one The title compound (91.3 mg, 0.15 mmol) was prepared following the synthetic sequence described in Intermediates 1-3, 5 and 6, substituting 2,3-dihydrobenzofuran-3-amine for (2,4-dimethoxyphenyl)methanamine in Intermediate 1. LCMS (ESI): m/z=506.4 [M+H]$^+$.

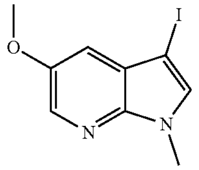

Intermediate 51

3-Iodo-5-methoxy-1-methyl-1H-pyrrolo[2,3-b]pyridine

Step A. Preparation of 3-Iodo-5-methoxy-1H-pyrrolo[2,3-b]pyridine. To a suspension of 5-methoxy-1H-pyrrolo[2, 3-b]pyridine (200.0 mg, 1.35 mmol, 1 equiv) in EtOH (8 mL) at room temperature was added KI (336 mg, 2.03 mmol, 1.5 equiv), iodine (514 mg, 2.03 mmol, 1.5 equiv), and 1 M NaOH (2 mL, 2.0 mmol, 1.5 equiv). The resulting mixture was stirred for 4 h then diluted with EtOAc, washed with saturated aqueous $Na_2S_2O_3$. The organic layer was dried ($Na_2SO_4$) and concentrated. The residue was purified by flash chromatography (Combi-flash Rf, Hex/EtOAc=0-25% gradient) to afford the title compound (301 mg, 1.1 mmol, 81%). LCMS (ESI): m/z=275.2 $[M+H]^+$.

Step B. Preparation of 3-Iodo-5-methoxy-1-methyl-1H-pyrrolo[2,3-b]pyridine. To a solution of 3-iodo-5-methoxy-1H-pyrrolo[2,3-b]pyridine (370 mg, 1.35 mmol, 1 equiv) in DMF (6.5 mL) at 0° C. was added NaH (60% in mineral oil, 81 mg, 2.03 mmol, 1.5 equiv). The mixture was stirred for 20 min then iodomethane (109 μL, 1.76 mmol, 1.3 equiv) was added. The mixture was warmed to room temperature and stirred overnight. The reaction was quenched with saturated aqueous $NH_4Cl$ and extracted with EtOAc. The combined organic layers were dried ($Na_2SO_4$) and concentrated. The residue was purified by flash chromatography (Combi-flash Rf, Hex/EtOAc=0-25% gradient) to afford the title compound (350 mg, 1.21 mmol, 90%). $^1H$ NMR (400 MHz, Chloroform-d) δ 8.11 (d, J=2.8 Hz, 1H), 7.26 (s, 1H), 7.18 (d, J=2.8 Hz, 1H), 3.92 (s, 3H), 3.88 (s, 3H); LCMS (ESI): m/z=289.1 $[M+H]^+$.

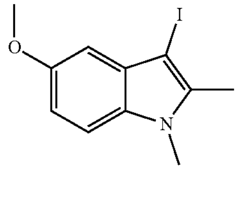

Intermediate 52

3-Iodo-5-methoxy-1,2-dimethyl-1H-indole

The title compound (51 mg, 0.17 mmol, 14% yield) was prepared following the procedure described for Intermediate 51, substituting 5-methoxy-2-methyl-1H-indole (200 mg, 1.24 mmol, 1 equiv) for 5-methoxy-1H-pyrrolo[2,3-b]pyridine in Step A. LCMS (ESI): m/z=302.2 $[M+H]^+$.

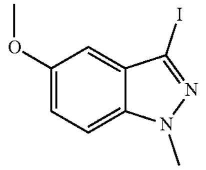

Intermediate 53

3-Iodo-5-methoxy-1-methyl-1H-indazole

The title compound (54 mg, 0.19 mmol, 62% yield) was prepared following the procedure described for Intermediate 51 Step B, substituting 3-iodo-5-methoxy-1H-indazole (83 mg, 0.30 mmol, 1 equiv) for 3-iodo-5-methoxy-1H-pyrrolo[2,3-b]pyridine. LCMS (ESI): m/z=29.0 $[M+H]^+$.

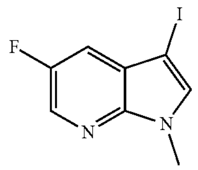

Intermediate 54

5-Fluoro-3-iodo-1-methyl-1H-pyrrolo[2,3-b]pyridine

The title compound (300 mg, 1.09 mmol, 74% yield) was prepared following the procedure described for Intermediate 51, substituting 5-fluoro-1H-pyrrolo[2,3-b]pyridine (200 mg, 1.47 mmol, 1 equiv) for 5-methoxy-1H-pyrrolo[2,3-b]pyridine in Step A. $^1H$ NMR (400 MHz, Chloroform-d) δ 8.21 (s, 1H), 7.42 (dd, J=2.4, 8.4 Hz, 1H), 7.34 (s, 1H), 3.89 (s, 3H); LCMS (ESI): m/z=277.1 $[M+H]^+$.

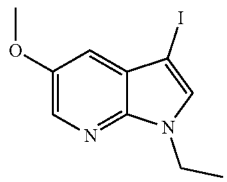

Intermediate 55

1-Ethyl-3-iodo-5-methoxy-1H-pyrrolo[2,3-b]pyridine

The title compound (71 mg, 0.24 mmol, 81% yield) was prepared following the procedure described for Intermediate 51 Step B, substituting bromoethane (43 μL, 0.58 mmol, 2 equiv) for iodomethane. LCMS (ESI): m/z=303.2 $[M+H]^+$.

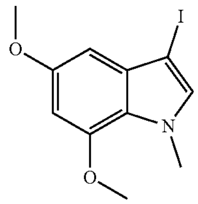

Intermediate 56

3-Iodo-5,7-dimethoxy-1-methyl-1H-indole

The title compound (100 mg, 0.31 mmol, 71% yield) was prepared following the procedure described for Intermediate 51, substituting 5,7-dimethoxy-1H-indole (108 mg, 0.61 mmol, 1 equiv) for 5-methoxy-1H-pyrrolo[2,3-b]pyridine in Step A. LCMS (ESI): m/z=318.0 $[M+H]^+$.

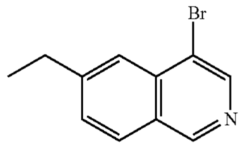

Intermediate 57

4-Bromo-6-ethylisoquinoline

To a solution of 6-ethylisoquinoline (100 mg, 0.64 mmol) in dichloromethane (2 mL) was added N-bromosuccinimide (1.2 eq). The reaction was stirred at room temperature for 24 h then concentrated. The residue was purified by flash chromatography (Combi-flash Rf, Hex/EtOAc=0-15% gradient) to afford the title compound (75 mg, 50% yield). $^1$H NMR (400 MHz, Chloroform-d) δ 9.10 (s, 1H), 8.68 (s, 1H), 7.93 (s, 1H), 7.89 (d, J=8.4 Hz, 1H), 7.54 (dd, J=8.4, 1.54 Hz, 1H), 2.91 (q, J=7.6 Hz, 2H), 1.37 (t, J=7.6 Hz, 3H).

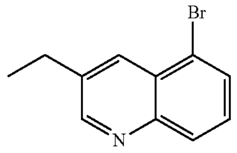

Intermediate 58

5-Bromo-3-ethylquinoline

To a solution of 2-amino-6-bromobenzaldehyde (200 mg, 1.0 mmol) in ethanol (2 ml) was added butyraldehyde (1.2 eq) and 1M aq. NaOH solution (2.0 eq). The reaction was heated under the microwave at 110° C. for 30 min. The reaction was cooled to room temperature, poured into dichlorourethane and washed with brine. The layers were separated and the organic layer was concentrated. The residue was purified by flash chromatography (Combi-flash Rf, Hex/EtOAc=0-15% gradient) to afford the title compound (157 mg, 67% yield). $^1$H NMR (400 MHz, Chloroform-d) δ 8.79 (d, J=2.4 Hz, 1H), 8.28 (d, J=2.4 Hz, 1H), 8.05 (d, J=8.4 Hz, 1H), 7.80 (d, J=8.4 Hz, 1H), 7.49 (dd, J=8.4, 8.4 Hz, 1H), 2.90 (q, J=7.6 Hz, 2H), 1.38 (t, J=7.6 Hz, 3H).

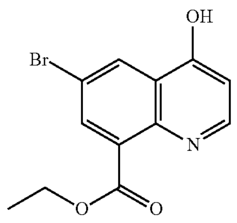 [SMILES: CCOC(=O)c1cc(Br)cc2c(O)ccnc12]

Intermediate 59

Ethyl 6-bromo-4-hydroxyquinoline-8-carboxylate

The title compound (3.70 g, 12.5 mmol, 79.9% yield in two steps) was prepared following the procedure described for Intermediate 15, substituting ethyl 2-amino-5-bromobenzoate (5.0 g, 16.6 mmol) for 4-bromo-2-methoxyaniline in Step A. $^1$H NMR (400 MHz, Chloroform-d) δ 8.75 (d, J=2.2 Hz 1H), 8.45 (d, J=2.3 Hz, 1H), 7.69-7.65 (m, 1H), 6.35 (dd, J=1.1 Hz, 1H), 4.46 (q, J=7.0 2H), 1.46 (t, J=7.1 3H); LCMS (ESI): m/z=295.9 $[M+H]^+$.

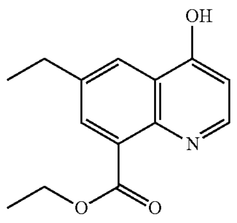

Intermediate 60

Ethyl 6-ethyl-4-hydroxyquinoline-8-carboxylate

The title compound (700 mg, 2.85 mmol, 57% yield) was prepared following the procedure described for Intermediate 16, substituting ethyl 6-bromo-4-hydroxyquinoline-8-carboxylate (Intermediate 59, 1.49 g, 5.03 mmol) for 6-bromo-8-methoxyquinolin-4-ol. $^1$H NMR (400 MHz, Chloroform-d) δ 8.49 (s, 1H), 8.25 (s, 1H), 7.69 (t, J=7.7 Hz, 1H), 6.35 (d, J=4.1 Hz, 1H), 4.48 (q, J=7.1 Hz, 2H), 2.80 (q, J=7.6 Hz, 2H), 1.47 (t, J=7.1 3H), 1.35 (t, J=7.6 3H); LCMS (ESI): m/z=246.1 $[M+H]^+$.

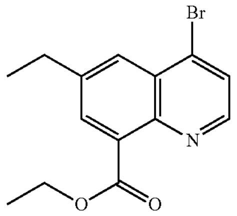 [SMILES: CCOC(=O)c1cc(CC)cc2c(Br)ccnc12]

Intermediate 61

Ethyl 4-bromo-6-ethylquinoline-8-carboxylate

The title compound (630 mg, 2.04 mmol, 82.2% yield) was prepared following the procedure described for Intermediate 17, substituting ethyl 6-ethyl-4-hydroxyquinoline-8-carboxylate (Intermediate 60, 610 mg, 2.49 mmol) for 6-ethyl-8-methoxyquinolin-4-ol, $^1$H NMR (400 MHz, Chloroform-d) δ 8.48 (s, 1H), 8.35 (s, 1H), 8.27 (t, J=7.0 Hz, 1H), 7.04 (d, J=7.0 Hz, 1H), 4.50 (q, J=7.1 Hz, 2H), 2.80 (q, J=7.6 Hz, 2H), 1.49 (t, J=7.4 3H), 1.33 (t, J=7.6 3H); LCMS (ESI): m/z=309.1 $[M+H]^+$.

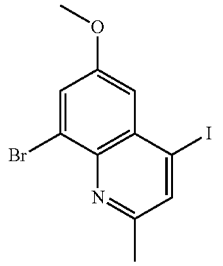

Intermediate 62

8-Bromo-4-iodo-6-methoxy-2-methylquinoline

Step A. Preparation of 5-(1-((2-bromo-4-methoxyphenyl) amino)ethylidene)-2,2-dimethyl-1,3-dioxane-4,6-dione. In round bottom flask, Meldrum's acid (15 g, 104 mmol, 2 equiv) and trimethyl orthoacetate (20 mL, 160 mmol, 3 equiv) were mixed together neat at 110° C. for 15 min. The reaction was cooled to room temperature and 2-bromo-4-methoxyaniline (10.5 g, 52 mmol, 1 equiv) was added portionwise. The reaction was heated at 110° C. for 3 h and cooled to room temperature. The precipitate was filtered and washed with ethanol to afford the title compound (18.5 g, 50 mmol, 96% yield), which was used in the next step without further purification. $^1$H NMR (400 MHz, Chloroform-d) δ 7.22 (d, J=2.8 Hz, 1H), 7.15 (d, J=8.8 Hz, 1H), 6.92 (dd, J=8.8, 2.8 Hz, 1H), 3.84 (s, 3H), 2.46 (s, 3H), 1.74 (s, 6H).

Step B. Preparation of 8-bromo-6-methoxy-2-methylquinolin-4-ol. 5-(1-((2-Bromo-4-methoxyphenyl)amino)ethylidene)-2,2-dimethyl-1,3-dioxane-4,6-dione (18.5 g, 50 mmol, 1 equiv) in Dowtherm A (15 mL) at was heated to 250° C. and stirred for 30 min. The reaction was cooled to room temperature. Hexanes were added and precipitate was filtered and washed with hexanes to afford the title compound (9.8 g, 37 mmol, 73% yield). $^1$H NMR (400 MHz, Chloroform-d) δ 8.22 (s, 1H), 7.73 (d, J=2.8 Hz, 1H), 7.48 (d, J=2.8 Hz, 1H), 6.14 (dd, J=1.7, 0.8 Hz, 1H), 3.90 (s, 3H), 2.45 (s, 3H); LCMS (ESI): Method 2: $R_T$=1.135 min, m/z=268.0 $[M+H]^+$.

Step C. Preparation of 8-bromo-6-methoxy-2-methylquinolin-4-yl trifluoromethanesulfonate. 8-Bromo-6-methoxy-2-methylquinolin-4-ol (9.8 g, 36.6 mmol) was dissolved in THF:$CH_2Cl_2$ (4:1, 125 mL) and stirred at room temperature, 1,1,1-trifluoro-N-phenyl-N-((trifluoromethyl)sulfonyl) methanesulfonamide (19.6 g, 54.8 mmol, 1.5 equiv) followed by N,N-diisoproplyethylamine (16 mL, 91.4 mmol, 2.5 equiv) were added and reaction was stirred at 50° C. overnight. The reaction was diluted with $CH_2Cl_2$ and sat. $NaHCO_3$ and extracted with $CH_2Cl_2$ (3×20 ml). The organic layer was dried over $MgSO_4$, filtered, and concentrated under reduced pressure. The residue was purified by flash chromatography (Combi-flash Rf, Hex/EtOAc=0-100% gradient) to afford the title compound (17.7 g, 44.2 mmol, quant.). $^1$H NMR (400 MHz, Chloroform-d) δ 7.81 (d, J=2.6 Hz, 1H), 7.30 (s, 1H), 7.21 (d, J=2.7 Hz, 1H), 3.94 (s, 3H), 2.82 (s, 3H); LCMS (ESI): Method 2: $R_T$=2.026 min, m/z=399.9 $[M+H]^+$.

Step D. Preparation of 8-Bromo-4-iodo-6-methoxy-2-methylquinoline. Triflic acid (3.9 mL 44.2 mmol, 1 equiv) was added to a solution of 8-bromo-6-methoxy-2-methylquinolin-4-yl trifluoromethanesulfonate (17.7 g, 44.2 mmol, 1 equiv) and potassium iodide (22.0 g, 133 mmol, 3 equiv) in acetonitrile (100 mL). The reaction mixture was stirred at 25° C. and stirred for 20 min. The reaction mixture was diluted with EtOAc and extracted with a sat. sodium thiosulfate solution. The combined organic layer was washed with brine, dried over $MgSO_4$, and concentrated. The residue was purified by flash chromatography (Combi-flash Rf, Hex/EtOAc=0-100% gradient) to afford the title compound (11.2 g, 29.7 mmol, 67% yield). $^1$H NMR (400 MHz, Chloroform-d) δ 7.89 (s, 1H), 7.74 (d, J=2.7 Hz, 1H), 7.28 (d, J=1.5 Hz, 1H), 3.96 (s, 3H), 2.71 (s, 3H); LCMS (ESI): Method 2: $R_T$=1.885 min, m/z=377.9 $[M+H]^+$.

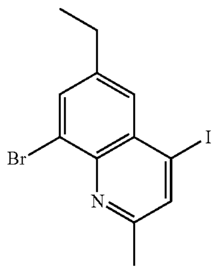

Intermediate 63

8-Bromo-6-ethyl-4-iodo-2-methylquinoline

Step A. Preparation of 8-bromo-6-ethyl-2-methylquinolin-4-ol. In a round bottom flask, 2-bromo-4-ethylaniline (10 g, 50 mmol, 1 equiv), ethyl 3-oxobutanoate (13 ml, 0.10 mol, 2 equiv), AcOH (1.4 mL, 25 mmol, 0.5 equiv), were dissolved in EtOH (30 mL) and heated at 90° C. overnight to form the imine intermediate, Dowtherm A (10 mL) was added to the reaction mixture and the temperature was increased to 250° C. The reaction was kept at 250° C. for 30 min. The reaction was cooled to room temperature and poured into hexane. The precipitate was filtered and washed with hexanes. The title compound (13 g, 20 mmol, 40% yield) was used without further purification. $^1$H NMR (400 MHz, DMSO-$d_6$) δ 10.36 (s, 1H), 7.89 (s, 1H), 7.84 (s, 1H), 5.96 (s, 1H), 2.69 (q, J=7.5 Hz, 2H), 2.42 (s, 3H), 1.21 (t, J=7.6 Hz, 3H); LCMS (ESI): Method 2: $R_T$=1.267 min, m/z 266.1 $[M+H]^+$.

Step B. Preparation of 8-bromo-6-ethyl-2-methylquinolin-4-yl trifluoromethanesulfonate. The title compound (4.71 g, 11.8 mmol, 24% yield) was prepared following the synthetic procedure described for Intermediate 62 Step C using 8-bromo-6-ethyl-2-methylquinolin-4-ol (13 g, 20 mmol). $^1$H NMR (400 MHz, Chloroform-d) δ 8.01 (d, J=1.8 Hz, 1H), 7.78-7.72 (m, 1H), 7.10 (d, J=1.2 Hz, 1H), 2.88-2.81 (m, 4H), 1.34 (t, J=7.6 Hz, 3H); LCMS (ESI): Method 2: $R_T$=2.018 min, m/z=384.0 $[M+H]^+$.

Step C. Preparation of 8-bromo-6-ethyl-4-iodo-2-methylquinoline. Acetic anhydride (1.68 mL, 17.7 mmol, 1.5 equiv) was added to a solution of 8-bromo-6-ethyl-2-methylquinolin-4-yl trifluoromethanesulfonate (4.71 g, 11.8 mmol, 1 equiv) and potassium iodide (19.6 g, 118 mmol, 10 equiv) in DMF (50 mL). The reaction mixture was stirred for 2 h at 110° C. then diluted with EtOAc and extracted with a sat. sodium thiosulfate solution. The combined organic layer was washed with brine, dried over $MgSO_4$, and concentrated. The residue was purified by flash chromatography (Combi-flash Rf, Hex/EtOAc=0-100% gradient) to afford the title compound (1.78 g, 4.73 mmol, 40% yield).

$^1$H NMR (400 MHz, Chloroform-d) δ 7.93 (d, J=1.9 Hz, 1H), 7.91 (s, 1H), 7.72 (dt, J=1.8, 0.9 Hz, 1H), 2.83 (q, J=7.6 Hz, 2H), 2.73 (s, 3H), 1.35 (t, J=7.6 Hz, 3H); LCMS (ESI): Method 2: $R_T$=2.089 min, m/z=375.9 $[M+H]^+$.

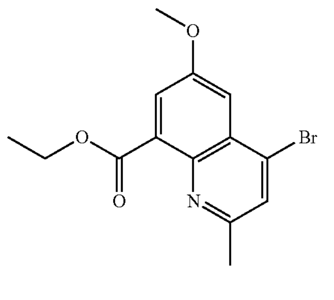 [SMILES: CCOC(=O)c1cc(OC)cc2c(Br)cc(C)nc12]

Intermediate 64

Ethyl 4-bromo-6-methoxy-2-methylquinoline-8-carboxylate

Step A. Preparation of ethyl 2-((1-(2,2-dimethyl-4,6-dioxo-1,3-dioxan-5-ylidene)ethyl)amino)-5-methoxybenzoate. The title compound (18.5 g, 50.9 mmol, 82% yield) was prepared following the procedure described for Intermediate 62 Step A using, ethyl 2-amino-5-methoxybenzoate (12.2 g, 62.5 mmol). $^1$H NMR (400 MHz, Chloroform-d) δ 7.57 (t, J=1.7 Hz, 1H), 7.12 (d, J=1.7 Hz, 2H), 4.34 (q, J=7.1 Hz, 2H), 3.89 (s, 3H), 2.47 (s, 3H), 1.74 (s, 6H), 1.33 (t, J=7.1 Hz, 3H).

Step B. Preparation of ethyl 4-hydroxy-6-methoxy-2-methylquinoline-8-carboxylate. The title compound (10.3 g, 39.4 mmol, 77% yield) was prepared following the procedure described for Intermediate 62 Step B using ethyl 2-((1-(2,2-dimethyl-4,6-dioxo-1,3-dioxan-5-ylidene)ethyl) amino)-5-methoxybenzoate (18.5 g, 50.9 mmol). $^1$H NMR (400 MHz, Chloroform-d) δ 11.44 (s, 1H), 8.05 (d, J=3.1 Hz, 1H), 7.98 (dd, J=3.0, 1.3 Hz, 1H), 6.20-6.15 (m, 1H), 4.45 (q, J=7.1 Hz, 2H), 3.93 (s, 3H), 2.43 (s, 3H), 1.45 (t, J=7.1 Hz, 3H); LCMS (ESI): Method 2: $R_T$=1.306 min, m/z 262.2 $[M+H]^+$.

Step C. Preparation of ethyl 4-bromo-6-methoxy-2-methylquinoline-8-carboxylate. The title compound (4.10 g, 12.6 mmol, 32% yield) was prepared following the procedure described for Intermediate 17 using ethyl 4-hydroxy-6-methoxy-2-methylquinoline-8-carboxylate (10.3 g, 39.4 mmol). $^1$H NMR (400 MHz, Chloroform-d) δ 7.61-7.56 (m, 2H), 7.51 (d, J=2.9 Hz, 1H), 4.51 (q, J=7.1 Hz, 2H), 3.97 (s, 3H), 2.67 (s, 3H), 1.45 (t, J=7.1 Hz, 3H); LCMS (ESI): Method 2: $R_T$=1.249 min, m/z=324.1 $[M+H]^+$.

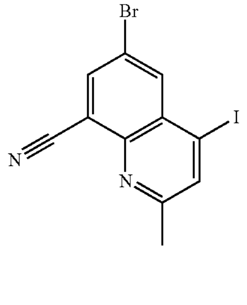

Intermediate 65

6-Bromo-4-iodo-2-methylquinoline-8-carbonitrile

Step A. Preparation of 5-bromo-2-((1-(2,2-dimethyl-4,6-dioxo-1,3-dioxan-5-ylidene)ethyl)amino)benzonitrile. The title compound (14.1 g, 38.6 mmol, 63% yield) was prepared following the procedure described for Intermediate 62 Step A using ethyl 2-amino-5-methoxybenzoate (12 g, 60.9 mmol). $^1$H NMR (400 MHz, Chloroform-d) δ 7.91 (d, J=2.2 Hz, 1H), 7.84 (dd, J=8.6, 2.3 Hz, 1H), 7.24 (d, J=8.7 Hz, 1H), 2.56 (s, 3H), 1.75 (s, 6H).

Step B. Preparation of 6-bromo-4-hydroxy-2-methylquinoline-8-carbonitrile. The title compound (10.2 g, 38.8 mmol, quant.) was prepared following the procedure described for Intermediate 62 Step B using 5-bromo-2-(1-(2,2-dimethyl-4,6-dioxo-1,3-dioxan-5-ylidene)ethyl)amino) benzonitrile (14.1 g, 33.8 mmol). $^1$H NMR (400 MHz, Chloroform-d) δ 8.67 (d, J=2.3 Hz, 1H), 8.30 (brs, 1H), 7.98 (d, J=2.3 Hz, 1H), 6.22 (s, 1H), 2.47 (s, 3H); LCMS (ESI): Method 2: $R_T$=1.168 min, m/z 263.1 $[M+H]^+$.

Step C. Preparation of 6-bromo-4-iodo-2-methylquinoline-8-carbonitrile. A round-bottom flask was charge with 6-bromo-4-hydroxy-2-methylquinoline-8-carbonitrile (10.2 g, 38.8 mmol) and pyridine (3.61 mL, 44.6 mmol, 1.15 equiv) was dissolved in MeCN (100 mL) and cooled to 0° C. Then trifluoromethanesulfonic anhydride (7.20 mL, 42.6 mmol, 1.1 equiv) was added dropwise. After complete triflate formation, sodium iodide (29.1 g, 194 mmol, 5 equiv) was added portionwise. Then trifluoromethanesulfonic acid (3.44 mL, 38.8 mmol, 1 equiv) was added dropwise. The reaction was diluted with water and $NaHCO_3$ was added to adjust pH 7-9. The reaction mixture was diluted with $CH_2Cl_2$ and extracted (3×20 mL). The organic layer was dried over $MgSO_4$, filtered, and concentrated under reduced pressure. The residue was purified by flash chromatography (Combi-flash Rf, Hex/EtOAc=0-50% gradient) to afford the title compound (3.87 g 10.36 mmol, 27% yield). $^1$H NMR (400 MHz, DMSO-$d_6$) δ 8.61 (d, J=2.1 Hz, 1H), 8.31 (d, J=2.1 Hz, 1H), 8.30 (s, 1H), 2.66 (s, 3H); LCMS (ESI): Method 2: $R_T$=1.868 min, m/z=372.9 $[M+H]^+$.

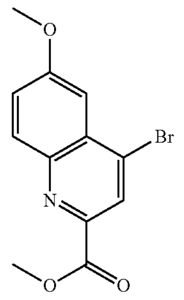 [SMILES: COC(=O)c1cc(Br)c2cc(OC)ccc2n1]

Intermediate 66

Methyl 4-bromo-6-methoxyquinoline-2-carboxylate

Step A. Preparation of dimethyl 2-((4-methoxyphenyl) amino)fumarate. Dimethyl acetylenedicarboxylate (5.5 mL, 45 mmol, 1.1 equiv) was added dropwise to a solution of 4-methoxyaniline (5.0 g, 41 mmol, 1 equiv) in MeOH (120 mL) at 0° C. (reaction is exothermic). The reaction was stirred at room temperature overnight. More dimethyl acetylenedicarboxylate (1 mL) was added at room temperature and the reaction was heated at 50° C. for 1 h. The mixture was cooled to room temperature and concentrated. The residue was purified by flash chromatography (Combi-flash Rf, Hex/EtOAc=0-100%) to afford the title compound (10 g, 38 mmol, 93% yield). LCMS (ESI): Method 2: $R_T$=1.785 min, m/z=266.1 $[M+H]^+$.

Step B. Preparation of methyl 6-methoxy-4-oxo-1,4-dihydroquinoline-2-carboxylate. The title compound (5.53 g, 23.7 mmol, 63% yield) was prepared following the procedure described for Intermediate 62 Step B using dimethyl 2-((4-methoxyphenyl)amino)fumarate (10 g, 38 mmol), $^1$H NMR (400 MHz, DMSO-$d_6$) δ 7.91 (d, J=9.1 Hz, 1H), 7.47 (s, J=2.9 Hz, 1H), 7.37 (dd, J=9.2 Hz, 2.91 Hz, 1H), 6.60 (d, J=1.7 Hz, 1H), 3.96 (s, 3H), 3.84 (s, 3H); LCMS (ESI): Method 2: $R_T$=1.134 min, m/z=234.1 $[M+H]^+$.

Step C. Preparation of methyl 4-bromo-6-methoxyquinoline-2-carboxylate Methyl 6-methoxy-4-oxo-1,4-dihydroquinoline-2-carboxylate (1.0 g, 4.3 mmol, 1 equiv) was dissolved in acetonitrile (20 mL) and stirred at room temperature. Potassium carbonate (1.8 g, 12.9 mmol, 3 equiv) and phosphorus oxybromide (3.7 g, 12.9 mmol, 3 equiv) were added and the reaction was stirred at 80° C. The reaction was quenched with addition of ice and water and sat. aq. $NaHCO_3$ was added to adjust the pH to 7-9. The aqueous layer was extracted with $CH_2Cl_2$ (3×20 mL). The combined organic layers were dried over $MgSO_4$ and concentrated. The residue was purified by flash chromatography (Combi-flash Rf, Hex/EtOAc=0-100%) to afford the title compound (1.03 g, 3.5 mmol, 81% yield). $^1$H NMR (400 MHz, Chloroform-d) δ 8.46 (s, 1H), 8.19 (d, J=8.7 Hz, 1H), 7.46-7.45 (m, 2H), 4.07 (s, 3H), 4.01 (s, 3H); LCMS (ESI): Method 2: $R_T$=1.761 min, m/z=295.9 $[M+H]^+$.

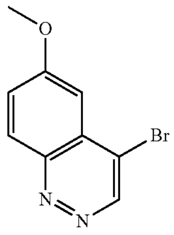

Intermediate 67

4-Bromo-6-methoxycinnoline

Step A. Preparation of 1-(2-amino-5-methoxyphenyl)ethan-1-one. A 3.4 M solution of methylmagnesium bromide in 2-MeTHF (6.0 ml, 20.3 mmol, 3 equiv) in dry THF (6 mL) was cooled to 0° C. Then a solution of 2-amino-5-methoxybenzonitrile (1.0 g, 6.75 mmol, 1 equiv) in THF was added dropwise. The reaction was allowed to warm to room temperature and stirred overnight. The suspension was cooled to 0° C., sat. aq. $NH_4Cl$ was added and the resulting mixture was vigorously stirred until complete hydrolysis of the corresponding imine. The reaction mixture was diluted with $CH_2Cl_2$ and extracted (3×20 mL). The combined organic layers were dried over $MgSO_4$ and concentrated. The residue was purified by flash chromatography (Combi-flash Rf, Hex/EtOAc=0-100% gradient followed by MeOH/$CH_2Cl_2$=0-10% gradient) to afford the title compound (138 mg, 0.084 mmol, 12% yield). $^1$H NMR (400 MHz, Chloroform-d) δ 7.19 (d, J=2.9 Hz, 1H), 6.97 (dd, J=9.4, 2.9 Hz, 1H), 6.63 (d, J=8.9 Hz, 1H), 5.95 (brs, 2H), 3.78 (s, 3H), 2.57 (s, 3H); LCMS (ESI): Method 2: $R_T$=0.406 min, m/z=166.2 $[M+H]^+$.

Step B. Preparation of 6-methoxycinnolin-4-ol. 1-(2-Amino-5-methoxyphenyl)ethan-1-one (130 mg, 0.78 mmol) was taken up in conc. HCl (2.08 mL) and stirred at 0° C. A solution of sodium nitrite (81 mg, 1.18 mmol, 1.5 equiv) in water (1 mL) was added dropwise at 0° C. The reaction was stirred for 1 h at 0° C. and allowed to warm to room temperature. The pH was adjusted to pH 7-9 by addition of $NaHCO_3$. The reaction mixture was extracted with $CH_2Cl_2$ (3×20 mL). The combined organic layers were dried over $MgSO_4$ and concentrated. The residue was purified by flash chromatography (Combi-flash Rf, Hex/EtOAc=0-100% gradient followed by MeOH/$CH_2Cl_2$=0-10% gradient) to afford the title compound (84 mg, 0.048 mmol, 61% yield). $^1$H NMR (400 MHz, DMSO-$d_6$) δ 7.70 (s, 1H), 7.61 (d, J=9.1 Hz, 1H), 7.46 (dd, J=9.3, 2.9 Hz, 1H), 7.38 (d, =2.8 Hz, 1H), 3.87 (s, 3H); LCMS (ESI): Method 2: $R_T$=1.074 min, m/z=177.1 $[M+H]^+$.

Step C. Preparation of 4-bromo-6-methoxycinnoline. 6-Methoxycinnolin-4-ol (84.0 mg, 0.4 mmol, 1 equiv) was dissolved in acetonitrile (4 mL) and stirred at room temperature. Potassium carbonate (198 mg, 1.43 mmol, 3 equiv) and phosphorus oxybromide (410 mg, 143 mmol, 3 equiv) were added, and the reaction was stirred at 60° C. The reaction was quenched with addition of ice and water. Sat. aq. $NaHCO_3$ was added to adjust the pH to 7-9. The aqueous layer was extracted with $CH_2Cl_2$ (3×20 mL). The combined organic layers were dried over $MgSO_4$ and concentrated. The residue was purified by flash chromatography (Combi-flash Rf, Hex/EtOAc=0-100% gradient) to afford the title compound (38 mg, 0.016 mmol, 33% yield). $^1$H NMR (400 MHz, Chloroform-d) δ 9.34 (s, 1H), 8.39 (d, J=9.3 Hz, 1H), 7.51 (dd, J=9.4, 2.4 Hz, 1H), 7.24 (d, J=2.5 Hz, 1H), 4.04 (s, 3H); LCMS (ESI): Method 2: $R_T$=1.429 min, m/z=239.1 $[M+H]^+$.

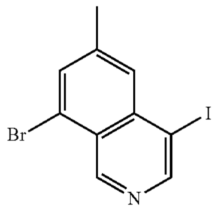

Intermediate 68

8-Bromo-4-iodo-6-methylisoquinoline

Step A. Preparation of N-(2-bromo-4-methylbenzyl)-2,2-dimethoxyethan-1-amine. A solution of 2-bromo-4-methylbenzaldehyde (8.16 g, 41.0 mmol, 1 equiv) and 2,2-dimethoxyethan-1-amine (5.17 g, 49.2 mmol, 1.2 equiv) in toluene 80 mL was heated under reflux with Dean Stark trap for 3 h then concentrated. The residue was dissolved in EtOH (80 mL), and $NaBH_4$ (2.33 g, 61.5 mmol, 1.5 equiv) was added. The resulting reaction mixture was stirred at room temperature for 2.5 h then concentrated. The residue was dissolved in EtOAc, washed with sat. aq. $NaHCO_3$, dried ($NaSO_4$), filtered and concentrated. The residue was purified by flash chromatography (Combi-flash Rf, Hex/EtOAc=10-70% gradient) to afford the title compound (10.1 g, 35 mmol, 85% yield).

Step B. Preparation of N-(2-bromo-4-methylbenzyl)-N-(2,2-dimethoxyethyl)-4-methylbenzenesulfonamide. To a solution of N-(2-bromo-4-methylbenzyl)-2,2-dimethoxy-ethan-1-amine (10.1 g, 35.0 mmol, 1 equiv) in dichloromethane (350 mL) at room temperature were added pyridine (8.5 mL, 105 mmol, 3 equiv) and p-toluenesulfonyl chloride (8.02 g, 42.1 mmol, 1.2 equiv). The mixture was stirred for 16 h, and then washed with sat. aq. $NaHCO_3$ and brine. The organic layer was dried ($Na_2SO_4$), filtered, and concentrated. The residue was purified by flash chromatography (Combi-flash Rf, Hex/EtOAc=10-60% gradient) to afford the title compound (15.4 g, 34.8 mmol, quantitative yield). $^1$H NMR (400 MHz, Chloroform-d) δ 7.73 (d, J=84 Hz, 2H), 7.33 (m, 4H), 7.09 (d, J=8.0 Hz, 1H), 4.51 (s, 2H), 4.36 (t, J=5.2 Hz, 1H), 3.29 (d, J=5.2 Hz, 2H), 3.21 (s, 6H), 2.44 (s, 3H), 2.30 (s, 3H).

Step C. Preparation of 8-bromo-6-methylisoquinoline. To a solution of N-(2-bromo-4-methylbenzyl)-N-(2,2-dimethoxyethyl)-4-methylbenzenesulfonamide (14.7 g, 33.2 mmol, 1 equiv) in dichloromethane (333 mL) at room temperature was added $AlCl_3$ (26.5 g, 199.0 mmol, 6 equiv). The mixture was stirred for 16 h then quenched with water. The mixture was extracted with EtOAc. The combined organic layers were dried ($Na_2SO_4$), filtered, and concentrated. The residue was purified by flash chromatography (Combi-flash Rf, Hex/EtOAc=10-60% gradient) to afford the title compound (3.57 g, 16.1 mmol, 48% yield). $^1$H NMR (400 MHz, Chloroform-d) δ 9.54 (s, 1H), 8.56 (d, J=5.6 Hz, 1H), 7.71 (s, 1H), 7.56 (s, 1H), 7.53 (d, J=5.6 Hz, 1H), 2.54 (s, 3H).

Step D. Preparation of 8-bromo-4-iodo-6-methylisoquinoline. To a solution of 8-bromo-6-methylisoquinoline (2.0 g, 9.0 mmol, 1 equiv) in AcOH (60 mL) was added NIS (3.04 g, 13.5 mmol, 1.5 equiv). The mixture was stirred at 80° C. for 16 h. An aliquot of reaction mixture was taken and analyzed by LCMS, which showed presence of the starting material. Additional NIS (1.01 g, 4.5 mmol, 0.5 equiv) was added and the reaction was stirred for additional 5 h then concentrated. The residue was dissolved in EtOAc and washed with sat. aq. $NaHCO_3$, dried ($Na_2SO_4$), filtered, and concentrated. The residue was purified by flash chromatography (Combi-flash Rf, Hex/EtOAc=10-50% gradient) to afford the title compound (1.88 g, 5.4 mmol, 60% yield). $^1$H NMR (400 MHz, Chloroform-d) δ 9.45 (s, 1H), 8.97 (s, 1H), 7.78 (m, 2H), 2.60 (s, 3H).

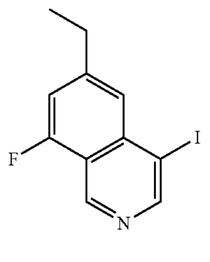

Intermediate 69

6-Ethyl-8-fluoro-4-iodoisoquinoline

Step A. Preparation of N-(4-bromo-2-fluorobenzyl)-2,2-dimethoxyethan-1-amine. The title compound (10.05 g, 34.4 mmol, 85% yield) was prepared following the procedure described for Intermediate 68 Step A, substituting 2-bromo-4-methylbenzaldehyde for 4-bromo-2-fluorobenzaldehyde (8.19 g, 40.3 mmol, 1 equiv). $^1$H NMR (400 MHz, Chloroform-d) δ 7.24 (m, 3H), 4.47 (t, J=5.6 Hz, 1H), 3.82 (s, 2H), 3.37 (s, 6H), 2.73 (d, J=5.6 Hz, 2H).

Step B. Preparation of N-(4-bromo-2-fluorobenzyl)-N-(2,2-dimethoxyethyl)-4-methylbenzenesulfonamide. The title compound (14.0 g, 31.4 mmol, 91% yield) was prepared following the procedure described for Intermediate 68 Step B, using N-(4-bromo-2-fluorobenzyl)-2,2-dimethoxyethan-1-amine (10.05 g, 34.4 mmol, 1 equiv). $^1$H NMR (400 MHz, Chloroform-d) δ 7.67 (d, J=8.0 Hz, 2H), 7.29 (m, 4H), 7.16 (dd, J=1.6, 9.6 Hz, 1H), 4.46 (s, 2H), 4.39 (t, J=5.2 Hz, 1H), 3.26 (s, 6H), 3.25 (d, J=5.2 Hz, 2H), 2.44 (s, 3H).

Step C. Preparation of 6-bromo-8-fluoroisoquinoline. The title compound (0.59 g, 2.6 mmol, 53% yield) was prepared following the procedure described for Intermediate 68 Step C, using N-(4-bromo-2-fluorobenzyl)-N-(2,2-dimethoxyethyl)-4-methylbenzenesulfonamide (2.2 g, 4.9 mmol, 1 equiv). $^1$H NMR (400 MHz, Chloroform-d) δ 9.50 (s, 1H), 8.63 (d, J=6.0 Hz, 1H), 7.82 (s, 1H), 7.59 (d, J=5.6 Hz, 1H), 7.40 (dd, J=1.6, 9.2 Hz, 1H).

Step D. Preparation of 8-fluoro-6-vinylisoquinoline. To a solution of 6-bromo-8-fluoroisoquinoline (1.17 g, 5.17 mmol, 1 equiv) in EtOH (35 mL) was added potassium trifluoro(vinyl)borate (970.0 mg, 7.24 mmol, 1.5 equiv), $PdCl_2$(dppf) (171.0 mg, 0.21 mmol, 0.04 equiv), and $Et_3N$ (1.8 mL, 12.9 mmol, 2.5 equiv). The mixture was stirred at 80° C. for 16 h then concentrated. The residue was dissolved in EtOAc and washed with brine/water, dried ($Na_2SO_4$), filtered, and concentrated. The residue was purified by flash chromatography (Combi-flash Rf, Hex/EtOAc=0-40% gradient) to afford the title compound (800 mg, 4.6 mmol, 89% yield). $^1$H NMR (400 MHz, Chloroform-d) δ 9.47 (s, 1H), 8.58 (d, J=5.6 Hz, 1H), 7.62 (d, J=6.0 Hz, 1H), 7.51 (s, 1H), 7.39 (dd, J=1.2, 11.6 Hz, 1H), 6.86 (dd, =10.8, 17.6 Hz, 1H), 5.93 (d, J=17.6 Hz, 1H), 5.50 (d, J=10.8 Hz, 1H).

Step C. Preparation of 6-ethyl-8-fluoroisoquinoline. To a solution of 8-fluoro-6-vinylisoquinoline (800.0 mg, 4.62 mmol, 1 equiv) in EtOH (35 mL) was added 10% Pd/C (246.0 mg, 0.23 mmol, 0.05 equiv). The resulting mixture was stirred under $H_2$ atmosphere for 2 h then filtered. The filtrate was concentrated, and the residue was purified by flash chromatography (Combi-flash Rf, Hex/EtOAc=0-60% gradient) to afford the title compound (667.0 mg, 3.61 mmol, 77%). $^1$H NMR (400 MHz, Chloroform-d) δ 9.47 (s, 1H), 8.55 (d, J=6.0 Hz, 1H), 7.59 (d, J=5.6 Hz, 1H), 7.40 (s, 1H), 7.12 (dd, J=1.2, 11.2 Hz, 1H), 2.84 (q, J=7.6 Hz, 2H), 1.34 (t, J=7.6 Hz, 3H).

Step D. Preparation of 6-ethyl-8-fluoro-4-iodoisoquinoline. The title compound (763.0 mg, 2.53 mmol, 66% yield) was prepared following the procedure described for Intermediate 68 Step D, using 6-ethyl-8-fluoroisoquinoline (667.0 mg, 3.61 mmol, 1 equiv). $^1$H NMR (400 MHz, Chloroform-d) δ 9.37 (s, 1H), 8.99 (s, 1H), 7.61 (s, 1H), 7.23 (d, J=10.8 Hz, 1H), 2.91 (q, J=7.6 Hz, 2H), 1.39 (t, J=7.6 Hz, 3H).

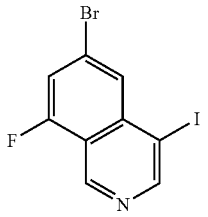 [SMILES: Fc1cc(Br)cc2c(I)cncc12]

Intermediate 70

6-Ethyl-8-fluoro-4-iodoisoquinoline

The title compound (997.0 mg, 2.83 mmol, 69% yield) was prepared following the procedure described for Intermediate 68 Step D, using 6-bromo-8-fluoroisoquinoline (Intermediate 69 Step C, 920 mg, 4.07 mmol, 1 equiv). $^1$H NMR (400 MHz, Chloroform-d) δ 9.39 (s, 1H), 9.04 (s, 1H), 8.04 (s, 1H), 7.49 (dd, J=1.6, 9.2 Hz, 1H).

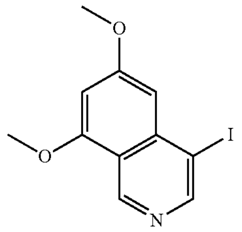

Intermediate 71

6-Ethyl-8-fluoro-4-iodoisoquinoline

To a solution of 6-bromo-8-fluoro-4-iodoisoquinoline (23.8 mg, 65.4 μmol, 1 equiv) in NMP (0.3 mL) at room temperature was added 5.4 M MeONa in MeOH (49 μL, 0.26 mmol, 4 equiv). The resulting mixture was stirred at 60° C. for 2 h then quenched with sat. aq. $NH_4Cl$. The mixture was extracted with EtOAc. The combined organic layers were dried ($Na_2SO_4$), filtered, and concentrated. The residue was purified by flash chromatography (Combi-flash Rf, Hex/EtOAc=0-40% gradient) to afford the title compound (20.0 mg, 54.9 μmol, 93% yield). $^1$H NMR (400 MHz, Chloroform-d) δ 9.34 (s, 1H), 8.87 (s, 1H), 6.85 (d, J=2.0 Hz, 1H), 6.58 (d, J=2.0 Hz, 1H), 4.01 (s, 3H), 4.00 (s, 3H).

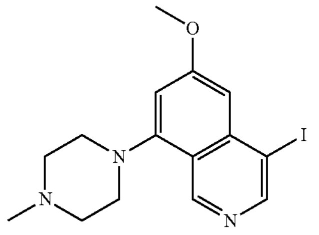 [SMILES: COc1cc(N2CCN(C)CC2)c2cncc(I)c2c1]

Intermediate 72

4-Iodo-6-methoxy-8-(4-methylpiperazin-1-yl)isoquinoline

Step A. Preparation of 6-bromo-4-iodo-8-(4-methylpiperazin-1-yl)isoquinoline. To a solution of 6-bromo-8-fluoro-4-iodoisoquinoline (Intermediate 70, 27.0 mug, 77 μmol, 1 equiv) in NMP (0.5 ml) were added 1-methylpiperazine (25.6 μL, 0.23 mmol, 3 equiv) and DIPEA (40.3 μL, 0.23 mmol, 3 equiv). The mixture was stirred in a sealed tube at 130° C. for 3.5 h then diluted with EtOAc. The organic layer was washed with water, dried ($Na_2SO_4$), filtered, and concentrated. The residue was purified by flash chromatography (Combi-flash Rf, DCM/MeOH 0-20% gradient) to afford the title compound (31.0 mg, 71 μmmol, 93% yield, contaminated with small amount of byproduct). $^1$H NMR (400 MHz, Chloroform-d) δ 9.38 (s, 1H), 8.91 (s, 1H), 7.86 (s, 1H), 7.23 (d, J=1.6 Hz, 1H), 3.20 (brs, 4H), 2.72 (brs, 4H), 2.42 (s, 3H).

Step B. Preparation of 4-iodo-6-methoxy-8-(4-methylpiperazin-1-yl)isoquinoline. To a solution of 6-bromo-4-iodo-8-(4-methylpiperazin-1-yl)isoquinoline (47.0 mg, 110 μmol, 1 equiv) in NMP (0.3 mL) was added 5.4 M MeONa in MeOH (50 μL, 270 μmol, 2.5 eq). The mixture was stirred in a sealed tube at 55° C. for 3 h then quenched with sat. aq. $NH_4Cl$. The mixture was extracted with EtOAc and the combined organic layer was dried ($Na_2SO_4$), filtered, and concentrated. The residue was purified by flash chromatography (Combi-flash Rf, DCM/MeOH=0-10% gradient) to afford the title compound (31.0 mg, 81 μmol, 74% yield). $^1$H NMR (400 Hz, Chloroform-d) δ 9.27 (s, 1H), 8.83 (s, 1H), 6.97 (d, J=1.6 Hz, 1H), 6.80 (d, J=1.6 Hz, 1H), 3.98 (s, 3H), 3.18 (brs, 4H), 2.74 (brs, 4H), 2.42 (s, 3H).

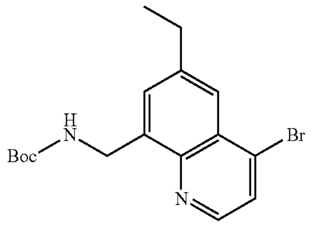 [SMILES: CCc1cc(CNC(=O)OC(C)(C)C)c2nccc(Br)c2c1]

Intermediate 73 tert-Butyl ((4-bromo-6-ethylquinolin-8-yl)methyl)carbamate

Step A. Preparation of 8-(azidomethyl)-4-bromo-6-ethylquinoline. To a solution of (4-bromo-6-ethylquinolin-8-yl)methanol (510 mg, 1.92 mmol, 1 equiv) in THF (10 mL) at 0° C. were added diphenylphosphinyl azide (0.51 mL, 2.68 mmol, 1.4 equiv) and 2,3,4,6,7,8,9,10-octahydropyrimido[1,2-a]azepine (0.4 mL, 2.68 mmol, 1.4 equiv). The mixture was allowed to warm to room temperature slowly and stirred overnight. The reaction mixture was concentrated, and the residue was dissolved in EtOAc and washed with brine/water. The organic layer was dried ($Na_2SO_4$), filtered, and concentrated. The residue was purified by flash chromatography (Combi-flash Rf, Hex/EtOAc=0-30% gradient) to afford the title compound (478 mg, 164 mmol, 85% yield). $^1$H NMR (400 MHz, Chloroform-d) δ 8.63 (d, J=4.8 Hz, 1H), 7.97 (s, 1H), 7.71 (d, J=6.4 Hz, 1H), 7.66 (s, 1H), 5.03 (s, 2H), 2.90 (q, J=7.2 Hz, 2H), 1.38 (t, J=7.2 Hz, 3H).

Step B. Preparation of tert-butyl ((4-bromo-6-ethylquinolin-8-yl)methyl)carbamate. To a solution of 8-(azidomethyl)-4-bromo-6-ethylquinoline (488.7 mg, 1.68 mmol, 1 equiv) in a mixture of THF (9 mL) and water (0.9 mL) was added $PPh_3$ (575.0 mg, 2.18 mmol, 1.3 equiv). The mixture was stirred at 45° C. for 16 h. Then water (1 mL), $NaHCO_3$ (282 mg, 3.36 mmol, 2 equiv), and $(Boc)_2O$ (495 mg, 2.27 mmol, 1.35 equiv) were added. The resulting mixture was stirred at room temperature for 4 h. Then water was added, and the mixture was extracted with EtOAc. The combined organic layers were dried ($Na_2SO_4$), filtered, and concentrated. The residue was purified by flash chromatography (Combi-flash Rf, Hex/EtOAc 0-20% gradient) to afford the title compound (1.11 g, 3.03 mmol, 91% yield). $^1$H LCMS (ESI): >95%, m/z 365.3 [M+H]$^+$.

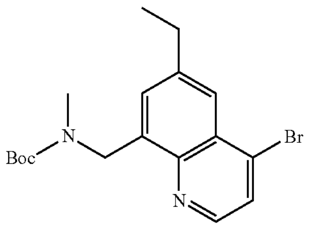

Intermediate 74 tert-Butyl ((4-bromo-6-ethylquinolin-8-yl)methyl)(methyl)carbamate

To a solution of tert-butyl ((4-bromo-6-ethylquinolin-8-yl)methyl)carbamate (Intermediate 73, 388.7 mg, 1.06 mmol, 1 equiv) in DMF (3 mL) at 0° C. was added 60% NaH in mineral oil (63.8 mg, 1.6 mmol, 1.5 equiv). The mixture was stirred for 40 min, and then iodomethane (100 μL, 1.6 mmol, 1.5 equiv) was added. The mixture was allowed to warm to room temperature and stirred overnight. The reaction was quenched with saturated aqueous $NH_4Cl$ and the mixture was extracted with EtOAc. The combined organic layers were dried ($Na_2SO_4$), filtered, and concentrated. The residue was purified by flash chromatography (Combi-flash Rf, Hex/EtOAc=0-20% gradient) to afford the title compound (392 mg, 1.03 mmol, 97% yield). $^1$H NMR (400 MHz, Chloroform-d) δ 8.59 (d, J=4.8 Hz, 1H), 7.89 (s, 1H), 7.69 (s, 1H), 7.45 (m, 1H), 5.11 (s, 2H), 2.95 (m, 2H), 2.87 (q, J=7.6 Hz, 2H), 1.48 (m, 9H), 1.35 (t, J=7.6 Hz, 3H).

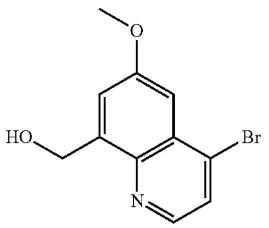

Intermediate 75

(4-Bromo-6-methoxyquinolin-8-yl)methanol

A solution of diisobutylaluminum hydride (247 mg, 1.74 mL, 1.00 molar, 2.00 equiv, 1.74 mmol) in toluene was added drop wise to a stirring solution of ethyl 4-bromo-6-methoxyquinoline-8-carboxylate (Intermediate 22, 270 mg, 1.00 equiv, 0.870 mmol) in anhydrous THF (3.00 mL) at 0° C. The reaction was stirred for 30 min, then it was quenched with sat. aq. $NaHCO_3$ (2 mL). The mixture was extracted with EtOAc (10 ml×2). The combined organic layers were dried over sodium sulfate, and concentrated. The residue was purified by flash chromatography (Combi-flash Rf, Hex/EtOAc 0-100% gradient) to afford the title compound (177 mg, 660 μmol, 75.9%). $^1$H NMR (400 MHz, Chloroform-d) δ 8.48 (d, J=4.7 Hz, 1H), 7.70 (d, J=4.7 Hz, 1H), 7.35 (d, J=2.7 Hz, 1H), 7.31 (d, J=2.7 Hz, 1H), 5.13 (d, J=5.4 Hz, 2H), 4.70 (t, J=5.6 Hz, 1H), 3.98 (s, 3H); LCMS (ESI): m/z=269.1 [M+H]$^+$.

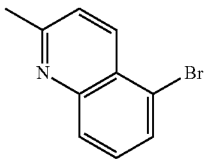

Intermediate 76

5-Bromo-2-methylquinoline

The title compound was prepared following the procedure described for Intermediate 58 substituting acetone for butyraldehyde.

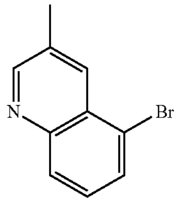

Intermediate 77

5-Bromo-3-methylquinoline

The title compound was prepared following the procedure described for Intermediate 58 substituting propionaldehyde for butyraldehyde.

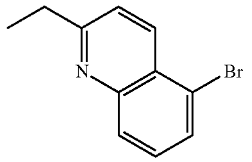

Intermediate 78

5-Bromo-2-ethylquinoline

The title compound was prepared following the procedure described for Intermediate 58 substituting 2-butanone for butyraldehyde. This reaction yielded a mixture of 5-bromo-2-ethylquinoline and 5-bromo-2,3-dimethylquinoline. The title compound was obtained by flash chromatography (Combi-flash Rf, Hex/EtOAc=0-100% gradient). $^1$H NMR (400 MHz, Chloroform-d) δ 8.44 (d, J=8.7 Hz, 1H), 8.01 (d, J=8.4 Hz, 1H), 7.75 (dd, J=7.5, 0.9 Hz, 1H), 7.55-7.51 (m, 1H), 7.41 (d, J=8.7 Hz, 1H), 3.03 (q, J=7.6 Hz, 2H), 1.40 (t, J=7.6 Hz, 3H).

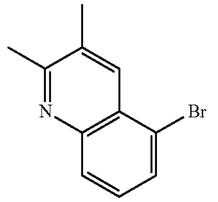

Intermediate 79

5-Bromo-2-ethylquinoline

The title compound was prepared following the procedure described for Intermediate 58 substituting 2-butanone for butyraldehyde. This reaction yielded a mixture of 5-bromo-2-ethylquinoline and 5-bromo-2,3-dimethylquinoline. The title compound was obtained by flash chromatography (Combi-flash Rf, Hex/EtOAc=0-100% gradient). $^1$H NMR (400 MHz, Chloroform-d) δ 8.19 (s, 1H), 7.96 (d, J=8.4 Hz, 1H), 7.72 (dd, J=7.5, 0.8 Hz, 1H), 7.48-7.44 (m, 2H), 2.71 (s, 3H), 2.51 (s, 3H).

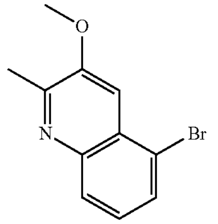

Intermediate 80

5-Bromo-3-methoxy-2-methylquinoline

The title compound was prepared following the procedure described for Intermediate 58 substituting methoxyacetone for butyraldehyde. $^1$H NMR (400 MHz, Chloroform-d) δ 7.94 (d, J=8.4 Hz, 1H), 7.73 (dd, J=7.6, 0.8 Hz, 1H), 7.62 (s, 1H), 7.40-7.36 (m, 1H), 4.01 (s, 3H), 2.67 (s, 3H).

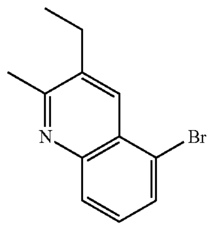

Intermediate 81

5-Bromo-3-ethyl-2-methylquinoline

The title compound was prepared following the procedure described for Intermediate 58 substituting 2-pentanone for butyraldehyde. $^1$H NMR (400 MHz, Chloroform-d) δ 8.20 (s, 1H), 7.96 (d, J=84 Hz, 1H), 7.73 (d, J=6.8 Hz, 1H), 7.49-7.45 (m, 1H), 2.86 (q, J=7.4 Hz, 2H), 2.74 (s, 3H), 1.38 (t, J=7.4 Hz, 3H).

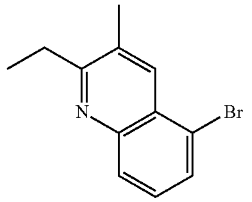

Intermediate 82

5-Bromo-2-ethyl-3-methylquinoline

The title compound was prepared following the procedure described for Intermediate 58 substituting diethyl ketone for butyraldehyde. $^1$H NMR (400 MHz, Chloroform-d) δ 8.18 (s, 1H), 7.99 (d, J=8.4 Hz, 1H), 7.71 (dd, J=7.5, 0.8 Hz, 1H), 7.47-7.43 (m, 1H), 3.01 (q, J=7.5 Hz, 2H), 2.54 (s, 3H), 1.38 (t, J=7.5 Hz, 3H),

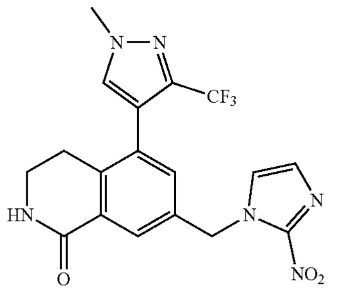 [SMILES: Cn1cc(-c2cc(Cn3ccnc3[N+](=O)[O-])cc3c2CCNC3=O)c(C(F)(F)F)n1]

Intermediate 83

5-(1-Methyl-3-(trifluoromethyl)-1H-pyrazol-4-yl)-7-((2-nitro-1H-imidazol-1-yl)methyl)-3,4-dihydroisoquinolin-1(2H)-one The title compound was prepared following the procedure described for Intermediate 7 substituting 2-nitro-1H-imidazole for 2-methyl-1H-imidazole. $^1$H NMR (400 MHz, Chloroform-d) δ 8.01 (d, J=1.9 Hz, 1H), 7.36 (s, 1H), 7.20-7.19 (m, 2H), 7.16 (d, J=0.9 Hz, 1H), 6.04 (bs, 1H), 5.64 (s, 2H), 4.01 (s, 3H), 3.50-3.46 (m, 2H), 2.80 (t, J=6.6 Hz, 2H).

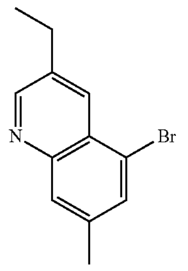

Intermediate 84

5-Bromo-3-ethyl-7-methylquinoline

Step A. Preparation of 2,6-dibromo)-4-methylbenzaldehyde. To a solution of 1,3-dibromo-5-methylbenzene (21.0 g, 84 mmol) in anhydrous THF (200 mL) was added 2.0 M lithium diisopropylamide solution (58.8 mL, 1.4 eq) was drop-wise at =78° C. The reaction mixture was stirred for 30 minutes then DMF (7.8 mL, 1.2 eq) was added. The reaction was stirred for 1 h at −78° C. then quenched with 1N HCl and EtOAc. The quenched mixture was extracted with EtOAc (2×200 mL), and the organic layer was washed with brine, dried over $MgSO_4$, filtered, and concentrated to give the title compound (23.0 g, 98%). $^1H$ NMR (400 MHz, Chloroform-d) δ 10.26 (s, 1H), 7.49 (s, 2H), 2.39 (s, 3H).

Step B. Preparation of 2-(2,6-dibromo-4-methylphenyl)-1,3-dioxolane. A mixture of 2,6-dibromo-4-methylbenzaldehyde (23.0 g, 83 mmol), ethane-1,2-diol (11 mL, 2.3 eq), and p-toluenesulfonic acid monohydrate (7.9 g, 0.5 eq) in anhydrous toluene (200 mL) was refluxed using a DeanStark trap until TLC showed no starting material. The reaction mixture was cooled to room temperature and concentrated. The residue was dissolved in DCM (200 mL), washed with 1N aq NaOH (50 mL) and concentrated. The residue was purified by flash chromatography (Combi-flash Rf, Hex/EtOAc=0-5% gradient) to afford the title compound (15.7 g, 59%). $^1H$ NMR (400 MHz, Chloroform-d) δ 7.39 (s, 2H), 6.36 (s, 1H), 4.35-4.31 (m, 2H), 4.08-4.05 (m, 2H), 2.29 (s, 3).

Step C. Preparation of N-(3-bromo-2-(1,3-dioxolan-2-yl)-5-methylphenyl)-1,1-diphenylmethanimine. A mixture of 2-(2,6-dibromo-4-methylphenyl)-1,3-dioxolane (15.7 g, 48.8 mmol), benzophenone imine (8.2 mL, 10 eq), cesium carbonate (31.8 g, 2.0 eq), BINAP (3.0 g, 0.1 eq), and palladium(II) acetate (0.55 g, 0.05 eq) in anhydrous toluene (200 mL) was purged with Ar then stirred for 16 h at 80° C. The reaction mixture was cooled to ambient temperature and quenched with $H_2O$ (200 mL). The layers were separated, and the aqueous layer was extracted with EtOAc. The combined organic layer was washed with brine, dried over $MgSO_4$, filtered, and concentrated. The residue was triturated with DCM (200 mL) The solid was filtered to give the title compound. The filtrate was concentrated, and the residue was purified by flash chromatography (Combi-flash Rf, Hex/EtOAc=0-10% gradient) to afford the additional title compound (17.1 g, 83% yield). $^1H$ NMR (400 MHz, DMSO-d6) δ 7.67-7.62 (m, 2H), 7.57-7.46 (m, 3H), 7.34 (bs, 3H), 7.24 (bs, 2H), 7.00 (s, 1H), 6.16 (s, 1H), 6.14 (s, 1H), 4.02-3.98 (m, 2H), 3.88-3.84 (m, 2H), 2.01 (s, 3H).

Step D. Preparation of 2-amino-6-bromo-4-methylbenzaldehyde. To a solution of N-(3-bromo-2-(1,3-dioxolan-2-yl)-5-methylphenyl)-1,1-diphenylmethanimine (17.1 g, 40.5 mmol) in THF (100 mL) was added aq. 1N HCl (100 mL, 2.5 eq). The reaction mixture stirred for 2 h at 80° C. than cooled to ambient temperature. The mixture was neutralized with aq. 6N NaOH. The mixture was extracted with EtOAc, and the combined organic layer was washed with brine, dried over $MgSO_4$, filtered, and concentrated. The residue was purified by flash chromatography (Combiflash Rf, Hex/EtOAc=0-10% gradient) to afford the title compound (6.3 g, 73%) as a yellow oil. $^1H$ NMR (400 MHz, Chloroform-d) δ 10.30 (s, 1H), 6.73 (s, 1H), 6.38 (s, 1H), 2.23 (s, 3H); LCMS Method 2: >95% purity 254 nm, $R_T$=1.74 min, MS (ESI) 214.0 $[M+H]^+$.

Step E. Preparation of 5-bromo-3-ethyl-7-methylquinoline. The title compound was prepared following the procedure described for Intermediate 58 utilizing 2-amino-6-bromo-4-methylbenzaldehyde and butyraldehyde. $^1H$ NMR (400 MHz, Chloroform-d) δ 8.74 (s, 1H), 8.21 (s, 1H), 7.81 (s, 1H), 8.21 (s, 1H), 7.66 (s, 1H), 2.87 (q, J=7.6 Hz, 2H), 2.53 (s, 3H), 1.37 (q, J=76 Hz, 2H).

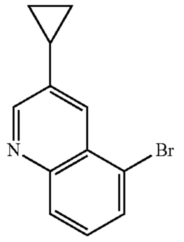 [SMILES: Brc1cccc2ncc(C3CC3)cc12]

Intermediate 85

5-Bromo-3-cyclopropylquinoline

The title compound was prepared following the procedure described for Intermediate 58 substituting 2-cyclopropylacetaldehyde for butyraldehyde. $^1H$ NMR (400 MHz, Chloroform-d) δ 8.74 (d, J=2.2 Hz, 1H), 8.08 (d, J=2.2 Hz, 1H), 8.03 (s, 1H), 8.01 (s, 1H), 7.79 (d, J=0.9 Hz, 1H), 7.77 (d, J=0.9 Hz, 1H), 2.16-2.10 (m, 1H), 1.18-1.13 (m, 2H), 0.93-0.89 (m, 2H).

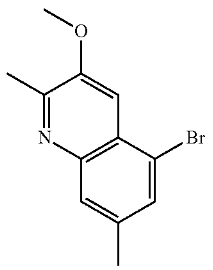

Intermediate 86

5-Bromo-3-methoxy-2,7-dimethylquinoline

The title compound was prepared following the procedure described for Intermediate 58 utilizing 2-amino-6-bromo-4-methylbenzaldehyde (intermediate 84 Step D) and methoxyacetone. $^1H$ NMR (400 MHz, Chloroform-d) δ 7.72 (s, 1H), 7.59 (s, 1H), 7.56 (s, 1H), 3.99 (s, 3H), 2.64 (s, 3H), 2.49 (s, 3H).

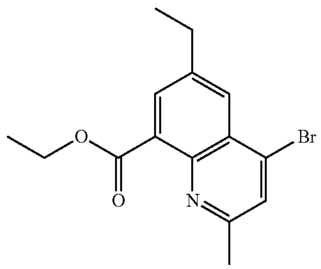 [SMILES: CCOC(=O)c1cc(CC)cc2c(Br)cc(C)nc12]

Intermediate 87

5-Bromo-3-methoxy-2,7-dimethylquinoline

The title compound was prepared following the procedures described for Intermediates 15 through 17, substituting ethyl 2-amino-5-bromobenzoate for 4-bromo-2-methoxyaniline and trimethylorthoacetate for triethyl orthoformate in the procedures for Intermediate 15. $^1$H NMR (400 MHz, Chloroform-d) δ 8.01 (s, 1H), 7.80 (s, 1H), 7.59 (s, 1H), 4.52 (q, J=7.6 Hz, 2H), 2.87 (q, J=7.6 Hz, 2H), 2.69 (s, 3H), 1.46 (t, J=7.1 Hz, 3H), 1.46 (t, J=7.6 Hz, 3H).

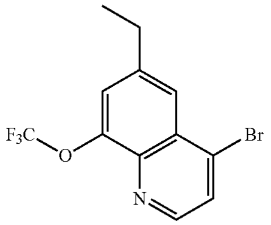

Intermediate 88

4-Bromo-6-ethyl-8-(trifluoromethoxy)quinoline

The title compound was prepared following the procedures described for Intermediates 15 through 17, substituting 4-bromo-2-(trifluoromethoxy)aniline for 4-bromo-2-methoxyaniline. $^1$H NMR (400 MHz, Chloroform-d) δ 8.71 (d, J=4.6 Hz, 1H), 7.94-7.93 (m, 1H), 7.75 (d, J=4.6 Hz, 1H), 7.56-7.55 (m, 1H), 2.90 (q, J=7.6 Hz, 2H), 1.37 (t, J=7.6 Hz, 3H).

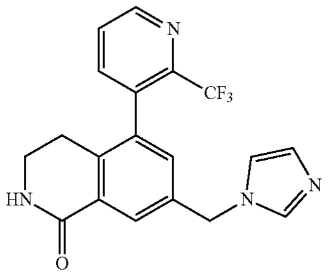 [SMILES: O=C1NCCc2c1cc(Cn1ccnc1)cc2-c1cccnc1C(F)(F)F]

Intermediate 89

7-((1H-Imidazol-1-yl)methyl)-5-(2-(trifluoromethyl)pyridin-3-yl)-3,4-dihydroisoquinolin-1(2H)-one The title compound was prepared according to the procedures for Intermediates 3-7 substituting (2-(trifluoromethyl)pyridin-3-yl)boronic acid for (1-methyl-3-(trifluoromethyl)-1H-pyrazol-4-yl)boronic acid in the procedure for Intermediate 3 and imidazole for 2-methylimidazole in the procedure for Intermediate 7.

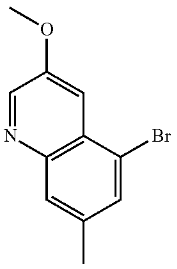

Intermediate 90

5-Bromo-3-methoxy-7-methylquinoline

The title compound was prepared following the procedure described for Intermediate 58 utilizing 2-amino-6-bromo-4-methylbenzaldehyde (intermediate 84 Step D) and methoxyacetaldehyde. $^1$H NMR (400 MHz, Chloroform-d) δ 8.63 (d, J=2.7 Hz, 1H), 7.80 (s, 1H), 7.68-7.66 (m, 2H), 3.99 (s, 3H), 2.51 (s, 3H).

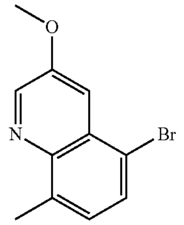

Intermediate 91

5-Bromo-3-methoxy-8-methylquinoline

Step A. Preparation of 2-amino-3-methylbenzaldehyde. To a solution of 2-amino-3-methylbenzyl alcohol (1.0 g, 7.6 mmol) in dichloromethane (20 mL) was added manganese dioxide. The reaction was stirred at RT for 16 h then filtered through celite. The filtrate was concentrated, and the residue was purified by flash chromatography (Combi-flash Rf, Hex/EtOAc=0-25% gradient) to afford the title compound, $^1$H NMR (400 MHz, Chloroform-d) δ 9.87 (s, 1H), 7.37 (d, J=7.8 Hz, 1H), 7.23 (d, J=7.8, 1H), 6.72-7.68 (m, 1H), 6.20 (bs, 2H), 2.17 (s, 3H).

Step B. Preparation of 3-methoxy-8-methylquinoline. The title compound was prepared following the procedure described for Intermediate 58 utilizing 2-amino-3-methylbenzaldehyde and methoxyacetaldehyde. $^1$H NMR (400 MHz, Chloroform-d) δ 8.70 (d, J=2.9 Hz, 1H), 7.58 (t, J=5.6 Hz, 1H), 7.41 (s, 1H), 7.39 (d, J=2.0 Hz, 1H), 7.37 (d, J=2.9 Hz, 1H), 3.95 (s, 3H), 2.79 (s, 3H).

Step C. Preparation of 5-bromo-3-methoxy-8-methylquinoline. To a solution of 3-methoxy-8-methylquinoline (114 mg, 0.66 mmol) and silver sulfate (103 mg, 0.5 eq) in sulfuric acid (1.0 mL) was added bromine (34 μL, 1.0 eq). The reaction was stirred at RT for 1 h then quenched with ice. The mixture was basified with 6.0 N aq. NaOH and extracted with dichloromethane. The organic layer was concentrated, and the residue was purified by flash chromatography (Combi-flash Rf, Hex/EtOAc=0-10% gradient) to afford the title compound. $^1$H NMR (400 MHz, Chloroform-d) δ 8.69 (d, J=2.8 Hz, 1H), 7.73 (d, J=2.8 Hz, 1H), 7.68 (d, J=7.7 Hz, 1H), 7.29-7.27 (m, 2H), 4.01 (s, 3H), 2.74 (s, 3H).

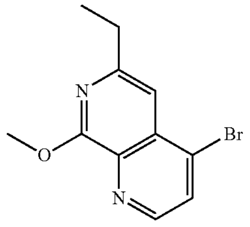

Intermediate 92

4-Bromo-6-ethyl-8-methoxy-1,7-naphthyridine

Step A. Preparation of 6-ethyl-2-methoxypyridin-3-amine. The title compound was prepared from 6-bromo-2-methoxypyridin-3-amine and triethylborane according to the procedure for Intermediate 16. $^1$H NMR (400 MHz, Chloroform-d) δ 6.84 (d, J=7.6 Hz, 1H), 6.57 (d, J=7.6 Hz, 1H), 4.00 (s, 3H), 2.65 (q, J=7.5 Hz, 2H), 1.26 (t, J=7.5 Hz, 3H).

Step B. Preparation of 6-ethyl-8-methoxy-1,7-naphthyridin-4(1H)-one. The title compound was prepared from 6-ethyl-2-methoxypyridin-3-amine according to the procedures for Intermediate 15. $^1$H NMR (400 MHz, Chloroform-d) δ 7.66 (d, J=7.4 Hz, 1H), 7.52 (s, 1H), 7.39 (d, J=7.4 Hz, 1H), 4.12 (s, 3H), 2.87 (q, J=7.5 Hz, 2H), 1.38 (t, J=7.5 Hz, 3H).

Step C. Preparation of 4-bromo-6-ethyl-8-methoxy-1,7-naphthyridine. The title compound was prepared from 6-ethyl-8-methoxy-1,7-naphthyridin-4(1H)-one according to the procedure for Intermediate 17. $^1$H NMR (400 MHz, Chloroform-d) δ 8.63 (d, J=4.6 Hz, 1H), 7.80 (d, J=4.6 Hz, 1H), 7.31 (s, 1H), 4.22 (s, 3H), 2.80 (q, J=7.5 Hz, 2H), 1.31 (t, J=7.5 Hz, 3H).

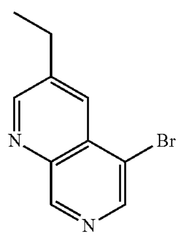

Intermediate 93

5-Bromo-3-ethyl-1,7-naphthyridine

Step A. Preparation of 3-amino-5-bromoisonicotinaldehyde. The title compound was prepared from 3,5-dibromopyridine according to the procedures for intermediate 84 from Step A to Step D. $^1$H NMR (400 MHz, Chloroform-d) δ 10.39 (s, 1H), 8.12 (s, 1H), 8.05 (s, 1H), 6.36 (bs, 2H).

Step B. Preparation of 5-bromo-3-ethyl-1,7-naphthyridine. The title compound was prepared following the procedure described for Intermediate 58 utilizing 3-amino-5-bromoisonicotinaldehyde and butyraldehyde. $^1$H NMR (400 MHz, Chloroform-d) δ 9.38 (s, 1H), 8.91 (d, J=1.8 Hz, 1H), 8.76 (s, 1H), 8.20 (d, J=1.8 Hz, 1H), 2.94 (q, J=7.5 Hz, 2H), 1.40 (t, J=7.5 Hz, 3H).

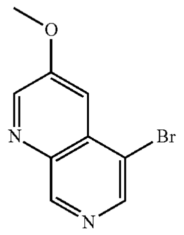

Intermediate 94

5-Bromo-3-methoxy-1,7-naphthyridine

The title compound was prepared following the procedure described for Intermediate 58 utilizing 3-amino-5-bromoisonicotinaldehyde (intermediate 93 Step A) and methoxyacetaldehyde. $^1$H NMR (400 MHz, Chloroform-d) δ 9.30 (s, 1H), 8.74-8.73 (m, 2H), 7.56 (d, J=2.6 Hz, 1H), 4.05 (s, 3H).

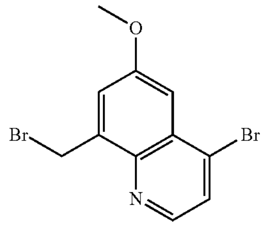

Intermediate 95

4-Bromo-8-(bromomethyl)-6-methoxyquinoline

To a solution of (4-bromo-6-methoxyquinolin-8-yl) methanol (Intermediate 75, 536 mg, 2.00 mmol, 1 equiv) in DCM (10 mL) at 0° C., $PBr_3$ (650 mg, 226 μL, 1.2 eq, 2.40 mmol) was added dropwise. The reaction mixture was stirred for 40 min, then quenched with slow addition of sat. aq. sodium carbonate solution (5 mL). The mixture was extracted with EtOAc (10 mL×2), and the combined organic layer was dried over sodium sulfate, filtered and concentrated. The residue was purified by flash chromatography (Combi-flash Rf, Hex/EtOAc=0-50% gradient) to afford the title compound (490 mg, 1.48 mmol, 74.0%). $^1$H NMR (400 MHz, Chloroform-d) δ 8.59 (d, J=4.7 Hz, 1H), 7.70 (d, J=4.7 Hz, 1H), 7.54 (d, J=2.8 Hz, 1H), 7.42 (d, J=2.8 Hz, 1H), 5.15 (s, 2H), 3.98 (s, 3H); LCMS (ESI): m/z=332.1 $[M+H]^+$.

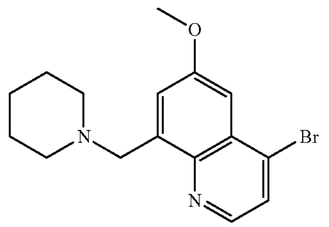 [SMILES: COc1cc(CN2CCCCC2)c2nccc(Br)c2c1]

Intermediate 96

4-Bromo-6-methoxy-8-(piperidin-1-ylmethyl)quinoline

To a solution of 4-bromo-8-(bromomethyl)-6-methoxyquinoline (99.3 mg, 0.300 mmol, 1 equiv) in acetonitrile (3 mL), piperidine (76.6 mg, 900 μmol, 3 equiv) was added and stirred for 2 h at 50° C. The reaction mixture was concentrated, and the residue was purified by flash chromatography (Combi-flash Rf, DCM/MeOH=0-15% gradient) to afford the title compound (55.00 mg, 164.1 μmol, 54.7%). $^1$H NMR (400 MHz, Chloroform-d) δ 8.50 (d, J=4.6 Hz, 1H), 7.68 (s, 1H), 7.65 (d, J=4.6 Hz, 1H), 7.34 (d, J=2.8 Hz, 1H), 4.19 (s, 2H), 3.98 (s, 3H), 2.57 (s, 4H), 1.66 (t, J=5.0 Hz, 4H), 1.49 (d, J=5.0 Hz, 2H); LCMS (ESI): m/z=336.2 $[M+H]^+$.

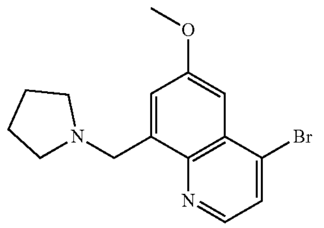 [SMILES: COc1cc(CN2CCCC2)c2nccc(Br)c2c1]

Intermediate 97

4-Bromo-6-methoxy-8-(pyrrolidin-1-ylmethyl)quinoline

The title compound (51 mg, 0.16 mmol, 53%) was prepared following the procedure described for Intermediate 96 substituting pyrrolidine for piperidine. $^1$H NMR (400 MHz, Chloroform-d) δ 8.52 (d, J=4.6 Hz, 1H), 7.70 (d, J=4.4 Hz, 1H), 7.66 (d, J=4.6 Hz, 1H), 7.37 (d, J=2.7 Hz, 1H), 4.41 (s, 2H), 3.99 (s, 3H), 2.78 (s, 4H), 1.88 (s, 4H); LCMS (ESI): m/z=322.1 $[M+H]^+$.

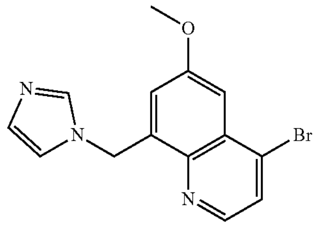 [SMILES: COc1cc(Cn2ccnc2)c2nccc(Br)c2c1]

Intermediate 98

8-((1H-Imidazol-1-yl)methyl)-4-bromo-6-methoxyquinoline

The title compound (47 mg, 0.15 mmol, 49%) was prepared following the procedure described for Intermediate 96 substituting 1H-imidazole for piperidine $^1$H NMR (400 MHz, Chloroform-d) δ 8.54 (d, J=4.7 Hz, 1H), 7.76 (s, 1H), 7.72 (d, J=4.7 Hz, 1H), 7.39 (d, J=2.7 Hz, 1H), 7.10 (s, 1H), 7.04 (t, J=5.4 Hz, 1H), 5.75 (s, 2H), 3.994 (s, 3H); LCMS (ESI): m/z=319.2 $[M+H]^+$.

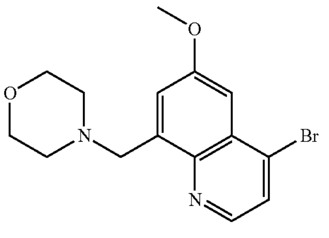 [SMILES: COc1cc(CN2CCOCC2)c2nccc(Br)c2c1]

Intermediate 99

4-((4-Bromo-6-methoxyquinolin-8-yl)methyl)morpholine

The title compound (53 mg, 0.16 mmol, 52%) was prepared following the procedure described for Intermediate 96 substituting morpholine for piperidine. $^1$H NMR (400 MHz, Chloroform-d) δ 8.51 (d, J=4.6 Hz, 1H), 7.67 (d, J=4.6 Hz, 2H), 7.37 (s, 1H), 4.24 (s, 2H), 3.99 (s, 3H), 3.80 (s, 4H), 2.65 (s, 4H); LCMS (ESI): m/z=338.2 $[M+H]^+$.

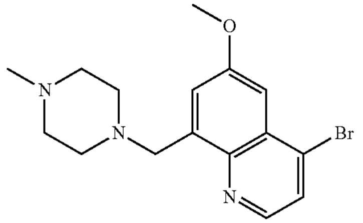 [SMILES: COc1cc(CN2CCN(C)CC2)c2nccc(Br)c2c1]

Intermediate 100

4-Bromo-6-methoxy-8-((4-methylpiperazin-1-yl)methyl)quinoline

The title compound (56 mg, 0.16 mmol, 53%) was prepared following the procedure described for Intermediate 96 substituting 1-methylpiperazine for piperidine. $^1$H NMR (400 MHz, Chloroform-d) δ 8.51 (d, J=4.6 Hz, 1H), 7.66 (d, J=4.6 Hz, 1H), 7.60 (s, 1H), 7.35 (d, J=2.8 Hz, 1H), 4.27 (s, 2-1), 3.98 (s, 3H), 2.74 (d, J=33.0 Hz, 8H), 2.42 (s, 3H); LCMS (ESI): m/z=351.1 $[M+H]^+$.

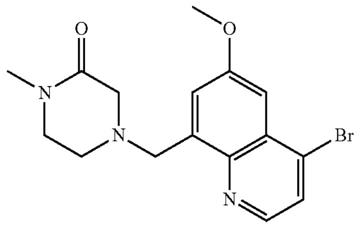 [SMILES: COc1cc(CN2CCN(C)C(=O)C2)c2nccc(Br)c2c1]

Intermediate 101

4(4-Bromo-6-methoxyquinolin-8-yl)methyl)-methylpiperazin-2-one

The title compound (37 mg, 0.10 mmol, 34%) was prepared following the procedure described for Intermediate 96 substituting 1-methylpiperazin-2-one for piperidine. LCMS (ESI): m/z=365.2 $[M+H]^+$.

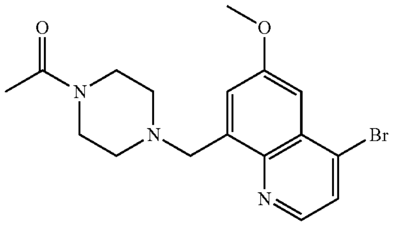 [SMILES: COc1cc(CN2CCN(C(C)=O)CC2)c2nccc(Br)c2c1]

Intermediate 102

1-(4-((4-Bromo-6-methoxyquinolin-8-yl)methyl)piperazin-1-yl)ethan-1-one

The title compound (42 mg, 0.11 mmol, 37%) was prepared following the procedure described for Intermediate 96 substituting 1-(piperazin-1-yl)ethan-1-one for piperidine. LCMS (ESI): m/z=379.2 $[M+H]^+$.

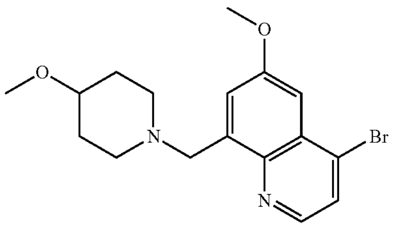 [SMILES: COc1cc(CN2CCC(OC)CC2)c2nccc(Br)c2c1]

Intermediate 103

4-Bromo-6-methoxy-8-((4-methoxyl)quinoline

The title compound (47 mg, 0.13 mmol, 51%) was prepared following the procedure described for Intermediate 96 substituting 4-methoxypiperidine for piperidine. LCMS (ESI): m/z=366.2 $[M+H]^+$.

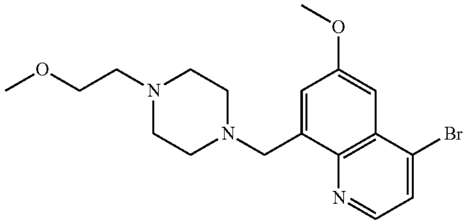 [SMILES: COCCN1CCN(Cc2cc(OC)cc3c(Br)ccnc23)CC1]

Intermediate 104

4-Bromo-6-methoxy-8-((4-(2-methoxyethyl)piperazin-1-yl)methyl)quinoline

The title compound (43 mg, 0.11 mmol, 44%) was prepared following the procedure described for Intermediate 96 substituting 1-(2-methoxyethyl)piperazine for piperidine. $^1$H NMR (400 MHz, Chloroform-d) δ 8.50 (d, J=4.6 Hz, 1H), 7.66 (d, J=4.6 Hz, 2H), 7.35 (d, J=2.8 Hz, 1H), 4.29 (s, 2H), 3.98 (s, 3H), 3.55 (t, J=5.5 Hz, 2H), 3.34 (s, 3H), 2.77 (s, 4H), 2.68 (q, J=6.4 Hz, 6H); LCMS (ESI): m/z=395.2 $[M+H]^+$.

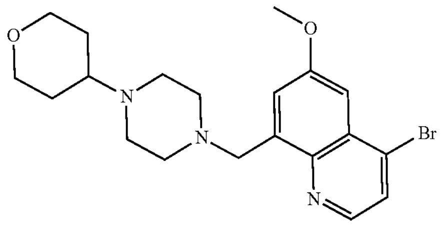 [SMILES: COc1cc(CN2CCN(C3CCOCC3)CC2)c2nccc(Br)c2c1]

Intermediate 105

4-Bromo-6-methoxy-8-((4-(tetrahydro-2H-pyran-4-yl)piperazin-1-yl)methyl)quinoline The title compound (49 mg, 0.12 mmol, 47%) was prepared following the procedure described for Intermediate 96 substituting 1-(tetrahydro-21H-pyran-4-yl)piperazine for piperidine. $^1$H NMR (400 MHz, Chloroform-d) δ 8.51 (d, J=4.6 Hz, 1H), 7.66 (d, J=4.6 Hz, 1H), 7.62 (s, 1H), 7.35 (d, J=2.8 Hz, 1H), 4.25 (s, 2H), 4.03 (t, J=5.6 Hz, 2H), 3.98 (s, 3H), 3.38 (m, J=5.0 Hz, 2H), 2.71 (s, 8H), 2.48 (s, 1H), 1.80 (d, J=11.9 Hz, 2H), 1.60 (m, J=5.8 Hz, 2H); LCMS (ESI): m/z=421.2 $[M+H]^+$.

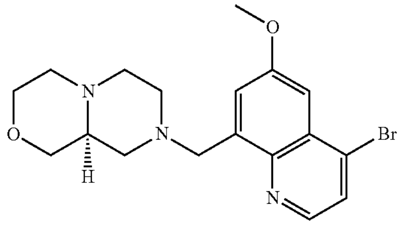 [SMILES: COc1cc(CN2CCN3CCOC[C@@H]3C2)c2nccc(Br)c2c1]

Intermediate 106

(S)-8-((4-Bromo-6-methoxyquinolin-8-yl)methyl)octahydropyrazino[2,1-c][1,4]oxazine The title compound (47 mg, 0.12 mmol, 48%) was prepared following the procedure described for Intermediate 96 substituting (S)-octahydropyrazino[2,1-c][1,4]oxazine for piperidine. $^1$H NMR (400 MHz, Chloroform-d) δ 8.50 (d, J=4.6 Hz, 1H), 7.67 (d, J=4.6 Hz, 1H), 7.39 (s, 1H), 7.26 (s, 1H), 3.99 (s, 3H), 3.85 (d, J=10.9 Hz, 1H), 3.68 (m, J=6.6 Hz, 3H), 3.12 (q, J=7.3 Hz, 1H), 2.80 (s, 1H), 2.48 (d, J=11.6 Hz, 1H), 1.58 (q, J=6.9 Hz, 4H), 1.47 (d, J=6.6 Hz, 4H); LCMS (ESI): m/z=393.2 $[M+H]^+$.

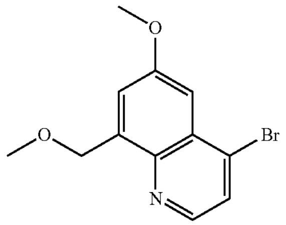 [SMILES: COCc1cc(OC)cc2c(Br)ccnc12]

Intermediate 107

4-Bromo-6-methoxy-8-(methoxymethyl)quinoline

To a solution of (4-bromo-6-methoxyquinolin-8-yl) methanol (Intermediate 75, 67 mg, 0.25 mmol, 1 equiv) and iodomethane (141.9 mg, 1.0 mmol, 4 equiv) in N,N-dimethylformamide (2 mL) at 0° C., sodium hydride (12 mg, 500 μmol, 2 equiv) was added. The reaction mixture was stirred for 1 min then quenched with water. The mixture was extracted with ethyl acetate (10 mL×2). The combined organic layer was dried over sodium sulfate, filtered and concentrated. The residue was purified by flash chromatography (Combi-flash Rf, Hex/EtOAc=0-70% gradient) to afford the title compound (47 mg, 0.17 mmol, 67%). $^1$H NMR (400 MHz, Chloroform-d) δ 8.52 (d, J=4.7 Hz, 1H), 7.68 (d, J=4.7 Hz, 1H), 7.55 (t, J=1.4 Hz, 1H), 7.36 (d, J=2.8 Hz, 1H), 5.13 (s, 2H), 3.98 (s, 3H), 3.57 (s, 3H); LCMS (ESI): m/z=283.1 [M+H]$^+$.

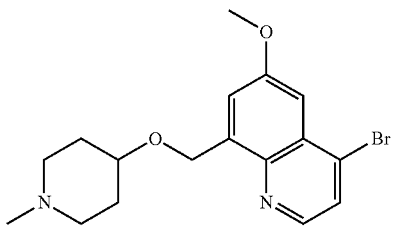 [SMILES: COc1cc(COC2CCN(C)CC2)c2nccc(Br)c2c1]

Intermediate 108

4-Bromo-6-methoxy-8-(((1-methylpiperidin-4-yl)oxy)methyl)quinoline

The title compound (35 mg, 96 μmol, 38%) was prepared following the procedure described for Intermediate 107 utilizing 4-bromo-8-(bromomethyl)-6-methoxyquinoline (Intermediate 95, 83 mg, 0.25 mmol) and 1-methylpiperidin-4-ol (29 mg, 0.25 mmol). $^1$H NMR (400 MHz, $CDCl_3$). $^1$H NMR (400 MHz, Chloroform-d) δ 8.48 (d, J=4.7 Hz, 1H), 7.68 (d, J=4.7 Hz, 1H), 7.56 (s, 1H), 7.36 (d, J=2.8 Hz, 1H), 5.18 (s, 2H), 3.99 (s, 3H), 3.74 (d, J=27.8 Hz, 1H), 2.97 (s, 2H), 2.51 (s, 2H), 2.25 (s, 2H), 2.04 (s, 2H), 1.57 (s, 2H); LCMS (ESI): m/z=366.2 [M+H]$^+$.

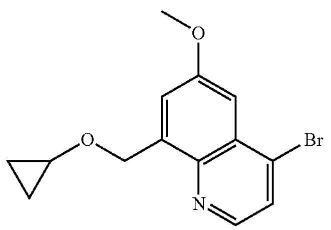 [SMILES: COc1cc(COC2CC2)c2nccc(Br)c2c1]

Intermediate 109

4-Bromo-8-(cyclopropoxymethyl)-6-methoxyquinoline

The title compound (35 mg, 0.11 mmol, 60%) was prepared following the procedure described for Intermediate 107 utilizing 4-bromo-8-(bromomethyl)-6-methoxyquinoline (Intermediate 95, 83 mg, 0.25 mmol) and cyclopropanol (33 mg, 0.75 mmol). $^1$H NMR (400 MHz, $CDCl_3$). $^1$H NMR (400 MHz, Chloroform-d) δ 8.51 (d, J=4.7 Hz, 1H), 7.67 (d, J=4.7 Hz, 1H), 7.53 (t, J=1.4 Hz, 1H), 7.34 (d, J=2.8 Hz, 1H), 5.23 (s, 2H), 3.97 (s, 3H), 3.54 (m, J=3.0 Hz, 1H), 0.72 (m, J=2.3 Hz, 2H), 0.54 (m, J=3.1 Hz, 2H); LCMS (ESI): m/z=309.2 [M+H]$^+$.

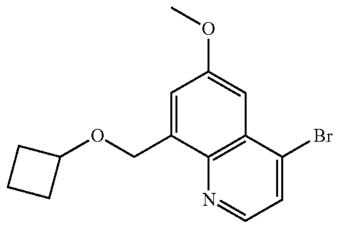 [SMILES: COc1cc(COC2CCC2)c2nccc(Br)c2c1]

Intermediate 110

4-Bromo-8-(cyclobutoxymethyl)-6-methoxyquinoline

The title compound (49 mg, 0.15 mmol, 61%) was prepared following the procedure described for Intermediate 107 utilizing 4-bromo-8-(bromomethyl)-6-methoxyquinoline (Intermediate 95, 83 mg, 0.25 mmol) and cyclobutanol (54 mg, 0.75 mmol). $^1$H NMR (400 MHz, $CDCl_3$). $^1$H NMR (400 MHz, Chloroform-d) δ 8.49 (d, J=4.7 Hz, 1H), 7.66 (d, J=4.7 Hz, 1H), 7.59 (t, J=1.4 Hz, 1H), 7.34 (d, J=2.8 Hz, 1H), 5.08 (s, 2H), 4.19 (m, J=7.3 Hz, 1H), 3.98 (s, 3H), 2.29 (m, J=3.2 Hz, 2H), 2.07 (m, J=4.0 Hz, 2H), 1.74 (q, J=10.1 Hz, 1H), 1.55 (m, J=3.9 Hz, 1H); LCMS (ESI): m/z=323.2 [M+H]$^+$.

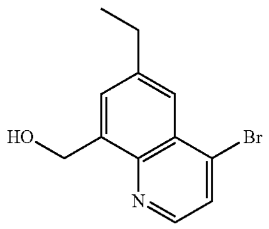

Intermediate 111

(4-Bromo-6-ethylquinolin-8-yl)methanol

The title compound (0.98 g, 3.7 mmol, 74%) was prepared following the procedure described for Intermediate 75 utilizing ethyl 4-bromo-6-ethylquinoline-8-carboxylate (Intermediate 61, 1.54 g, 5.0 mmol). $^1$H NMR (400 MHz, Chloroform-d) δ 8.60 (d, J=4.8 Hz, 1H), 7.93 (s, 1H), 7.77 (d, J=4.8 Hz, 1H), 7.57 (s, 1H), 5.18 (s, 2H), 2.88 (q, J=7.5 Hz, 2H), 1.36 (t, J=7.6 Hz, 3); LCMS(ESI): m/z=267.2 [M+H]$^+$.

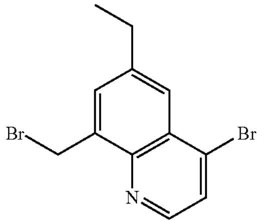

Intermediate 112

4-Bromo-8-(bromomethyl)-6-ethylquinoline

The title compound (410 mg, 1.25 mmol, 79.0%) was prepared following the procedure described for Intermediate 95 utilizing (4-bromo-6-ethylquinolin-8-yl)methanol (Intermediate 111, 0.42 g, 1.58 mmol). $^1$H NMR (400 MHz, Chloroform-d) δ 8.75 (d, J=4.8 Hz, 1H), 7.99 (t, J=0.8 Hz, 1H), 7.79 (q, J=2.7 Hz, 2H), 5.24 (s, 2H), 2.89 (q, J=7.6 Hz, 2H), 1.38 (t, J=7.6 Hz, 3H); LCMS (ESI): m/z=330.2 $[M+H]^+$.

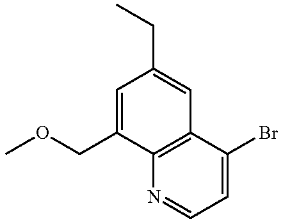 [SMILES: CCc1cc(COC)c2nccc(Br)c2c1]

Intermediate 113

4-Bromo-6-ethyl-8-(methoxymethyl)quinoline

The title compound (43 mg, 0.15 mmol, 80%) was prepared following the procedure described for Intermediate 107 utilizing 4-bromo-8-(bromomethyl)-6-ethylquinoline (Intermediate 112, 63 mg, 191 μmol) and methanol (6.1 mg, 191 μmol). LCMS (ESI): m/z=281.2 $[M+H]^+$.

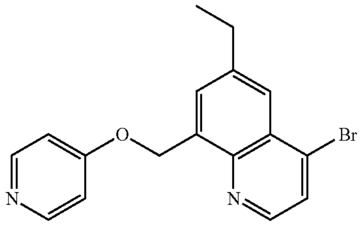 [SMILES: CCc1cc(COc2ccncc2)c2nccc(Br)c2c1]

Intermediate 114

4-Bromo-6-ethyl-8-((pyridin-4-yloxy)methyl)quinoline

The title compound (42 mg, 0.12 mmol, 64%) was prepared following the procedure described for Intermediate 107 utilizing 4-bromo-8-(bromoethyl)-6-ethylquinoline (Intermediate 112, 63 mg, 191 μmol) and pyridin-4-ol (54.4 mg, 572 μmol). $^1$H NMR (400 MHz, Chloroform-d) δ 8.62 (d, J=4.7 Hz, 1H), 8.02 (s, 1H), 7.75 (d, J=4.6 Hz, 1H), 7.70 (d, J=7.4 Hz, 2H), 7.49 (d, J=1.1 Hz, 1H), 6.51 (d, J=7.2 Hz, 1H), 5.60 (s, 2H), 2.88 (q, J=7.6 Hz, 2H), 1.36 (t, J=7.6 Hz, 3H); LCMS (ESI): m/z=344.2 $[M+H]^+$.

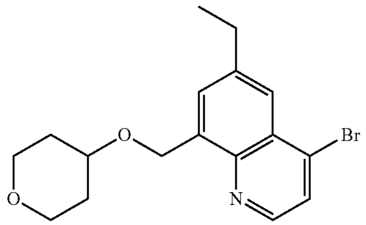 [SMILES: CCc1cc(COC2CCOCC2)c2nccc(Br)c2c1]

Intermediate 115

4-Bromo-6-ethyl-8-(((tetrahydro-2H-pyran-4-yl)oxy)methyl)quinoline

The title compound (49 mg, 0.14 mmol, 73%) was prepared following the procedure described for Intermediate 197 utilizing 4-bromo-8-(bromomethyl)-6-ethylquinoline (Intermediate 112, 64 mg, 191 μmol)) and tetrahydro-2H-pyran-4-ol (58 mg, 572 μmol). LCMS (ESI): m/z=351.2 $[M+H]^+$.

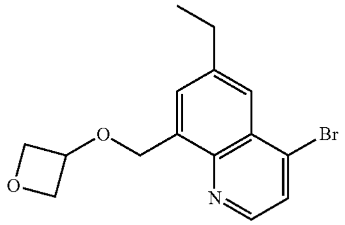 [SMILES: CCc1cc(COC2COC2)c2nccc(Br)c2c1]

Intermediate 116

4-Bromo-6-ethyl-8-((oxetan-3-yloxy)methyl)quinoline

The title compound (42 mg, 0.13 mmol, 68%) was prepared following the procedure described for Intermediate 107 utilizing 4-bromo-8-(bromomethyl)-6-ethylquinoline (Intermediate 112, 64 mg, 191 μmol)) and oxetan-3-ol (42 mg, 572 μmol). $^1$H NMR (400 MHz, Chloroform-d) δ 8.58 (d, J=4.6 Hz, 1H), 7.92 (s, 1H), 7.7 (s, 1H), 7.69 (d, J=4.6 Hz, 1H), 5.13 (s, 2H), 4.81 (m, J=4.8 Hz, 3H), 4.73 (q, J=3.8 Hz, 2H), 2.89 (m, J=5.6 Hz, 2H), 1.38 (t, J=7.5 Hz, 3H); LCMS (ESI): m/z=323.2 $[M+H]^+$.

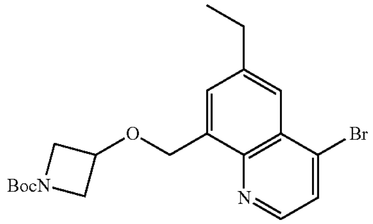 [SMILES: CCc1cc(COC2CN(C(=O)OC(C)(C)C)C2)c2nccc(Br)c2c1]

Intermediate 117 tert-Butyl 3-((4-bromo-6-ethylquinolin-8-yl)methoxy)azetidine-1-carboxylate

The title compound (57 mg, 0.14 mmol, 45%4) was prepared following the procedure described for Intermediate 107 utilizing 4-bromo-8-(bromomethyl)-6-ethylquinoline (Intermediate 112, 99 mg, 300 μmol) and tert-butyl 3-hydroxyazetidine-1-carboxylate (156 mg, 900 μmol). LCMS (ESI): m/z=422.2 [M+H]$^+$.

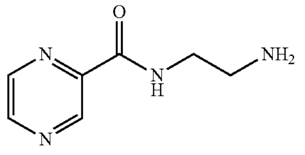 [SMILES: NCCNC(=O)c1cnccn1]

Intermediate 118

N-(2-Aminoethyl)pyrazine-2-carboxamide

Step A. Preparation of tert-butyl (2-(pyrazine-2-carboxamido)ethyl)carbamate. To a stirring solution of pyrazine-2-carboxylic acid (248 mg, 2.0 mmol, 1.0 equiv) in anhydrous DMF (5 mL), N-ethyl-N-isopropylpropan-2-amine (776 mg, 1.1 mL, 6.0 mmol, 3.0 equiv), and the reaction is cooled to 0° C. under Ar. 1-(1-(11-Oxidaneyl)-3H-114-[1,2,3]triazolo[4,5-b]pyridin-3-yl)-1-(dimethylamino)-N-(hexafluoro-17-phosphaneyl)-N,N-dimethylmethanideaminium (760 mg, 2.0 mmol, 1.0 equiv) was added, and the reaction mixture was stirred at 0° C. for another 20 min then tert-butyl (2-aminoethyl)carbamate (961 mg, 0.80 mL, 6.0 mmol, 3.0 equiv) was added. The resulting mixture was warmed to room temperature and stirred for 7 h. The reaction was quenched by addition of 5 mL sat, aq. sodium bicarbonate then extracted with dichloromethane (10 mL×2) The combined organic layer was washed with water followed by brine, dried over sodium sulfate, and concentrated. The residue was purified by flash chromatography (Combiflash Rf, Hex/EtOAc=0-100% gradient) to afford the title compound.

Step B. Preparation of N-(2-Aminoethyl)pyrazine-2-carboxamide. tert-Butyl (2-(pyrazine-2-carboxamido)ethyl) carbamate was dissolved in DCM (10 mL) and trifluoroacetic acid (2 mL) was added. The reaction mixture was stirred for 30 min then concentrated. The residue was dissolved in DCM (10 mL), washed successively with sat. aq. sodium bicarbonate (10 ml×2) and water, dried over sodium sulfate and concentrated to obtain the title compound (150 mg, 903 μmol, 45.1%). LCMS (ESI): m/z=167.2 [M+H]$^+$.

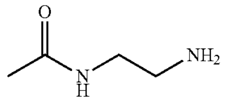

Intermediate 119

N-(2-Aminoethyl)acetamide

The title compound (125 mg, 1.2 mmol, 61%) was prepared following the procedure described for Intermediate 118 Step A and B substituting acetic acid (120 mg, 2.0 mmol) for pyrazine-2-carboxylic acid. LCMS (ESI): m/z=103.2 [M+H]$^+$.

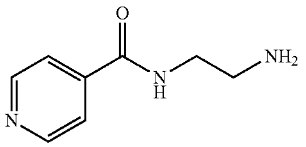 [SMILES: NCCNC(=O)c1ccncc1]

Intermediate 120

N-(2-Aminoethyl)isonicotinamide

The title compound (165 mg, 1.0 mmol, 50%) was prepared following the procedure described for Intermediate 118 Step A and B substituting isonicotinic acid (246 mg, 2.0 mmol) for pyrazine-2-carboxylic acid. LCMS (ESI): m/z=166.2 [M+H]$^+$.

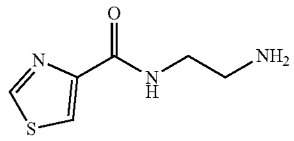 [SMILES: NCCNC(=O)c1cscn1]

Intermediate 121

N-(2-Aminoethyl)thiazole-4-carboxamide

The title compound (140 mg, 818 μmol, 401%) was prepared following the procedure described for Intermediate 118 Step A and B substituting thiazole-4-carboxylic acid (258 mg, 2.0 mmol) for pyrazine-2-carboxylic acid. LCMS (ESI): m/z=172.2 [M+H]$^+$.

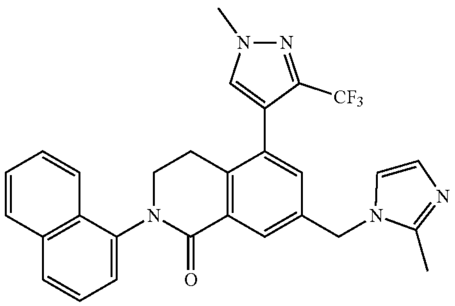 [SMILES: Cc1nccn1Cc1cc2c(c(-c3cn(C)nc3C(F)(F)F)c1)CCN(c1cccc3ccccc13)C2=O]

Example 1

7-((2-Methyl-1H-imidazol-1-yl)methyl)-5-(1-methyl-3-(trifluoromethyl)-1H-pyrazol-4-yl)-2-(naphthalen-1-yl)-3,4-dihydroisoquinolin-1(2H)-one Step A. Preparation of methyl 5-hydroxy-2-(naphthalen-1-yl)-1-oxo-1,2,3,4-tetrahydroisoquinoline-7-carboxylate. Dimethyl 2-hydroxy-2,3-dihydrobenzofuran-4,6-dicarboxylate (400 mg, 1.59 mmol, 1 equiv) and naphthalen-1-amine (454 mg, 3.17 mmol, 2 equiv) were dissolved in DCE (10 mL) and stirred at 80° C. for 1 h under Ar. Sodium triacetoxyborohydride (1.01 g, 4.76 mmol, 3 equiv) was then added to the reaction mixture and stirred at 80° C. overnight under Ar. Sat. aq. $NaHCO_3$ was added and the mixture was extracted with $CH_2Cl_2$ (3×30 mL). The combined organic phases were dried over $MgSO_4$ and concentrated under reduced pressure. The residue was purified by flash chromatography (Combi-flash Rf, Hex/EtOAc=0-100% gradient) to afford the title compound (578 mg, 1.60 mmol, quant.). $^1$H NMR (400 MHz, Chloroform-d) δ 8.38 (d, J=1.6 Hz, 1H), 7.93 7.78 (m, 3H), 7.60 (d, J=1.6 Hz, 1H), 7.55-7.43 (m, 4H), 3.99 (dt, J=12.4, 7.4 Hz, 1H), 3.90 (s, 3H), 3.87 (dd, J=12.4, 5.9 Hz, 1H), 3.18 (dd, J=7.5, 5.8 Hz, 2H); LCMS (ESI): m/z=349.0 [M+H]$^+$.

Step B. Preparation of methyl 2-(naphthalen-1-yl)-1-oxo-5-(((trifluoromethyl)sulfonyl)oxy)-1,2,3,4-tetrahydroisoquinoline-7-carboxylate. The title compound (506 mg, 1.06 mmol, 63% yield) was prepared following the triflation procedure described for Intermediate 2, using methyl 5-hydroxy-2-(naphthalen-1-yl)-1-oxo-1,2,3,4-tetrahydroisoquinoline-7-carboxylate (580 mg, 1.67 mmol, 1 equiv). $^1$H NMR (400 MHz, Chloroform-d) δ 8.89 (d, J=1.6 Hz, 1H), 8.15 (d, J=1.6 Hz, 1H), 7.98-7.93 (m, 1H), 7.90 (dt, J=8.4, 1.1 Hz, 1H), 7.85-7.79 (m, 1H), 7.58-7.51 (m, 3H), 7.47 (dd, J=7.3, 1.2 Hz, 1H), 4.10 (ddd, J=12.7, 9.4, 5.1 Hz, 1H), 4.04-3.99 (m, 1H), 3.98 (s, 3H), 3.51-3.33 (m, 2H); LCMS (ESI): m/z=479.9 [M+H]$^+$.

Step C. Preparation of methyl 5-(1-methyl-3-(trifluoromethyl)-1H-pyrazol-4-yl)-2-(naphthalen-1-yl)-1-oxo-1,2,3,4-tetrahydroisoquinoline-7-carboxylate. The title compound (80.4 mg, 0.17 mmol, 32% yield) was prepared following the Suzuki coupling procedure described for Intermediate 3, using methyl 2-(naphthalen-1-yl)-1-oxo-5-(((trifluoromethyl)sulfonyl)oxy)-1,2,3,4-tetrahydroisoquinoline-7-carboxylate (250 mg, 0.52 mmol, 1 equiv). $^1$H NMR (400 MHz, Chloroform-d) δ 8.88 (d, J=1.9 Hz, 1H), 8.12 (d, J=1.9 Hz, 1H), 7.93-7.87 (m, 1H), 7.86-7.82 (m, 2H), 7.54-7.47 (m, 4H), 7.46-7.43 (m, 3H), 3.99 (s, 3H), 3.98-3.94 (m, 1H), 3.92 (s, 3H), 3.89-3.80 (m, 1H), 3.18 (ddd, J=16.5, 9.8, 5.2 Hz, 1H), 3.03 (ddd, J=16.6, 6.3, 4.7 Hz, 1H); LCMS (ESI): m/z=480.0 [M+H]$^+$.

Step D. Preparation of 7-(hydroxymethyl)-5-(1-methyl-3-(trifluoromethyl)-1H-pyrazol-4-yl)-2-(naphthalen-1-yl)-3,4-dihydroisoquinolin-1(2H)-one. Sodium borohydride (127 mg, 3.35 mmol, 20 equiv) was added to a solution of methyl 5-(1-methyl-3-(trifluoromethyl)-1H-pyrazol-4-yl)-2-(naphthalen-1-yl)-1-oxo-1,2,3,4-tetrahydroisoquinoline-7-carboxylate (80 mg, 0.17 mmol, 1 equiv) in ethanol (4 mL) at 23° C. The reaction mixture was stirred for 12 h at 80° C. then concentrated. Water was added to the resultant residue and extracted with ethyl acetate (3×20 mL). The combined organic layers were dried over $MgSO_4$ and concentrated under reduced pressure. The residue was used without further purification. LCMS (ESI): m/z=451.0 [M+H]$^+$.

Step E. Preparation of 7-(bromomethyl)-5-(1-methyl-3-(trifluoromethyl)-1H-pyrazol-4-yl)-2-(naphthalen-1-yl)-3,4-dihydroisoquinolin-1(2H)-one. The residue from Step D was dissolved in $CH_2Cl_2$ (2 mL) and cooled to 0° C. $PBr_3$ (31.6 μL, 0.34 mmol, 2 equiv) was added dropwise and reaction mixture was warmed to room temperature and stirred overnight. The reaction was quenched with sat. aq. $NaHCO_3$ and extracted with EtOAc (3×20 mL). The combined organic layers were dried over $MgSO_4$ and concentrated under reduced pressure to afford the crude title compound, which was used without further purification. LCMS (ESI): m/z=515.8 [M+H]$^+$.

Step F. Preparation of 7-((2-methyl-1H-imidazol-1-yl)methyl)-5-(1-methyl-3-(trifluoromethyl)-1H-pyrazol-4-yl)-2-(naphthalen-1-yl)-3,4-dihydroisoquinolin-1(2H)-one. The title compound (10.3 mg, 0.020 mmol, 34% yield) was prepared following the bromide displacement procedure described for Intermediate 7, using 7-(bromoethyl)-5-(1-methyl-3-(trifluoromethyl)-1H-pyrazol-4-yl)-2-(naphthalen-1-yl)-3,4-dihydroisoquinolin-1(2H)-one (30 mg, 0.058 mmol, 1 equiv). $^1$H NMR (400 MHz, Chloroform-d) δ 8.14 (d, J=2.0 Hz, 1H), 7.92 (dt, J=6.9, 3.4 Hz, 1H), 7.86 (ddd, =7.6, 6.4, 2.3 Hz, 2H), 7.57-7.48 (m, 3H), 7.45 (dd, J=7.3, 1.2 Hz, 1H), 7.38 (d, J=1.1 Hz, 1H), 6.99 (d, J=2.0 Hz, 1H), 6.95 (d, J=1.4 Hz, 1H), 6.88 (d, J=1.4 Hz, 1H), 5.11 (s, 2H), 4.01 (s, 3H), 4.00-3.93 (m, 1H), 3.83 (dt, J=12.4, 5.6 Hz, 1H), 3.14 (ddd, =J=15.7, 10.1, 5.2 Hz, 1H), 3.03-2.92 (m, 1H), 2.36 (s, 3H); $^{19}$F NMR (376 MHz, $CDCl_3$) δ −63.12; LCMS (ESI): >95%, m/z=516.0 [M+H]$^+$.

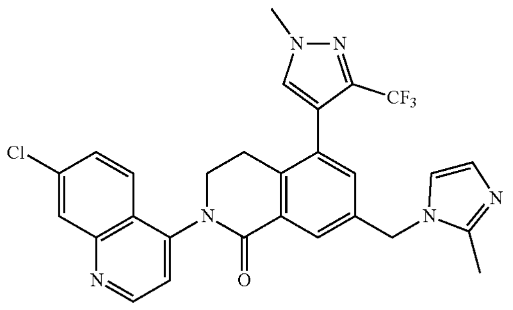 [SMILES: Cc1nccn1Cc1cc2c(c(-c3cn(C)nc3C(F)(F)F)c1)CCN(c1ccnc3cc(Cl)ccc13)C2=O]

Example 2

2-(7-Chloroquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one Standard Buchwald Coupling Procedure: 7-((2-Methyl-1H-imidazol-1-yl)methyl)-5-(1-methyl-3-(trifluoromethyl)-1H-pyrazol-4-yl)-3,4-dihydroisoquinolin-1(2H)-one (20 mg, 0.051 mmol, 1 equiv), 7-chloro-4-iodoquinoline (30 mg, 0.10 mmol, 2 equiv), cesium carbonate (33 mg, 0.10 mmol, 2 equiv), Xantphos (5.9 mg, 10 μmol, 0.2 equiv), and $Pd_2(dba)_3$ (4.7 mg, 5.1 μmol, 0.1 equiv) were dissolved in 1,4-dioxane (1 mL) under an Ar. The reaction mixture was stirred for 14 h at 110° C. then cooled to 23° C. Brine was added to the mixture and extracted with EtOAc (3×20 mL). The combined organic layers were dried over $MgSO_4$ and concentrated under reduced pressure. The residue was purified by reverse phase HPLC (Phenomenex Gemini C18, $H_2O/CH_3CN$ gradient from 15-85% $CH_3CN$, 0.1% TFA) followed by neutralization with sat. aq. $NaHCO_3$ to yield the title compound (25.1 mg, 0.046 mmol, 89% yield). $^1$H NMR (400 MHz, Chloroform-d) δ 8.97 (d, J=4.7 Hz, 1H), 8.16 (d, J=2.0 Hz, 1H), 8.09 (d, J=2.0 Hz, 1H), 7.78 (d, J=8.9 Hz, 1H), 7.50 (dd, J=9.0, 2.1 Hz, 1H), 7.38 (s, 1H), 7.32 (d, J=4.7 Hz, 1H), 7.03 (d, J=2.0 Hz, 1H), 6.94 (d, J=1.4 Hz, 1H), 6.86 (d, J=1.4 Hz, 1H), 5.11 (s, 2H), 4.10-4.02 (m, 1H), 4.01 (s, 3H), 3.80 (dt, J=12.1, 5.2 Hz, 1H), 3.14 (ddd, 3=16.2, 10.9, 5.2 Hz, 1H), 2.96 (dt, J=16.4, 4.7 Hz, 1H), 2.34 (s, 3H); LCMS (ESI) Method 2: >95%, $R_T$=1.252 min, m/z=550.9 [M+H]$^+$.

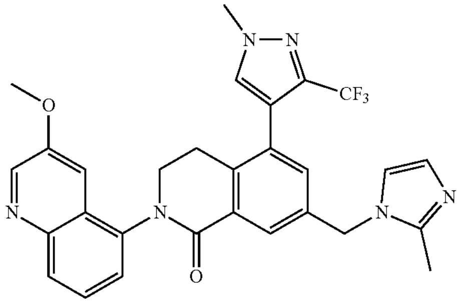 [SMILES: COc1cnc2cccc(N3CCc4c(cc(Cn5ccnc5C)cc4-c4cn(C)nc4C(F)(F)F)C3=O)c2c1]

Example 3

2-(3-Methoxyquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (21 mg, 0.039 mmol, 60% yield) was prepared following the Buchwald coupling procedure described for Example 2, substituting 5-bromo-3-methoxyquinoline (31 mg, 0.13 mmol, 2 equiv) for 7-chloro-4-iodoquinoline. $^1$H NMR (400 MHz, Chloroform-d) δ 8.70 (d, J=2.8 Hz, 1H), 8.11 (d, J=2.0 Hz, 1H), 8.07 (d, J=8.4 Hz, 1H), 7.59 (dd, J=8.4, 7.4 Hz, 1H), 7.47 (dd, J=7.4, 1.2 Hz, 1H), 7.39 (s, 1H), 7.31 (d, J=2.8 Hz, 1H), 7.01 (d, J=2.0 Hz, 1H), 6.94 (d, J=1.4 Hz, 1H), 6.87 (d, J=1.3 Hz, 1H), 5.12 (s, 2H), 4.04-3.97 (m, 4H), 3.88 (s, 3H), 3.76 (dt, J=12.4, 5.3 Hz, 1H), 3.11 (ddd, J=16.0, 10.7, 5.3 Hz, 1H), 2.97 (dt, J=16.3, 4.9 Hz, 1H), 2.36 (s, 3H); LCMS (ESI) Method 2: >95%, $R_T$=1.27 min, m/z=546.9 $[M+H]^+$.

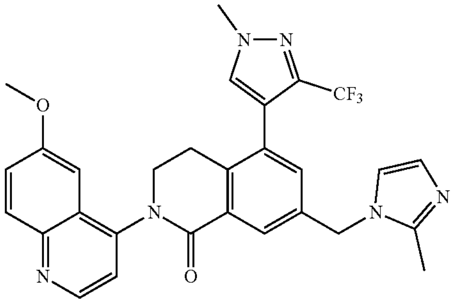 [SMILES: COc1ccc2nccc(N3CCc4c(cc(Cn5ccnc5C)cc4-c4cn(C)nc4C(F)(F)F)C3=O)c2c1]

Example 4

2-(6-Methoxyquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (27 mg, 0.050 mmol, 78% yield) was prepared following the Buchwald coupling procedure described for Example 2, substituting 4-bromo-6-methoxyquinoline (31 mg, 0.13 mmol, 2 equiv) for 7-chloro-4-iodoquinoline. $^1$H NMR (400 MHz, Chloroform-d) δ 8.82 (d, J=4.6 Hz, 1H), 8.11 (d, J=2.0 Hz, 1H), 8.07 (d, J=9.2 Hz, 1H), 7.42-7.37 (m, 2H), 7.31 (d, J=4.6 Hz, 1H), 7.06 (d, J=2.8 Hz, 1H), 7.02 (d, J=2.0 Hz, 1H), 6.94 (d, J=1.4 Hz, 1H), 6.87 (d, J=1.4 Hz, 1H), 5.12 (s, 2H), 4.01 (s, 3H), 4.00-3.94 (m, 1H), 3.86 (s, 3H), 3.80 (dt, J=12.2, 5.2 Hz, 1H), 3.14 (ddd, J=16.2, 10.9, 5.2 Hz, 1H), 2.96 (dt, J=16.4, 4.7 Hz, 1H), 2.35 (s, 3H); LCMS (ESI) Method 2: >95%, $R_T$=1.182 min, m/z=546.9 $[M+H]^+$.

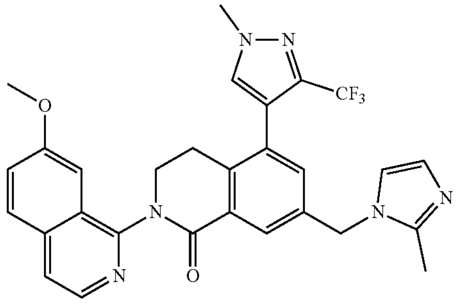

Example 5

7-Methoxy-7'-((2-methyl-1H-imidazol-1-yl)methyl)-5-(1-methyl-3-(trifluoromethyl)-1H-pyrazol-4-yl)-3',4-dihydro-1'H-[1,2'-biisoquinolin]-1'-one The title compound (19 mg, 0.035 mmol, 55% yield) was prepared following the Buchwald coupling procedure described for Example 2, substituting 1-chloro-7-methoxyisoquinoline (25 mg, 0.13 mmol, 2 equiv) for 7-chloro-4-iodoquinoline. $^1$H NMR (400 MHz, Chloroform-d) δ 8.32 (d, J=5.6 Hz, 1H), 8.13 (d, J=2.0 Hz, 1H), 7.79 (d, J=9.0 Hz, 1H), 7.60 (d, J=5.6 Hz, 1H), 7.41-7.35 (m, 2H), 7.15 (d, J=2.5 Hz, 1H), 6.99 (d, J=2.0 Hz, 1H), 6.95 (d, J=1.4 Hz, 1H), 6.87 (d, J=1.4 Hz, 1H), 5.11 (s, 2H), 4.33-4.28 (m, 1H), 4.02 (s, 3H), 3.86 (s, 3H), 3.83-3.76 (m, 1H), 3.15-3.08 (d, J=12.3 Hz, 1H), 3.00-2.96 (m, 1H), 2.36 (s, 3H); $^{19}$F NMR (376 MHz, $CDCl_3$) δ −60.17; LCMS (ESI): >95%. m/z=546.9 $[M+H]^+$.

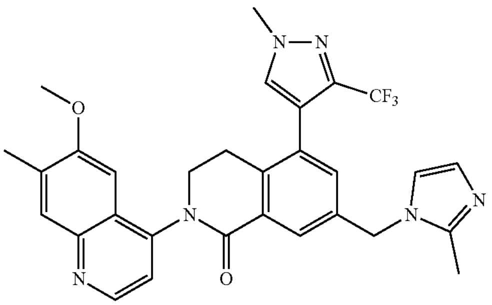 [SMILES: COc1cc2c(N3CCc4c(cc(Cn5ccnc5C)cc4-c4cn(C)nc4C(F)(F)F)C3=O)ccnc2cc1C]

Example 6

2-(6-Methoxy-7-methylquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (12 mg, 0.021 mmol, 42% yield) was prepared following the Buchwald coupling procedure described for Example 2, substituting 4-bromo-6-methoxy-7-methylquinoline (26 mg, 0.10 mmol, 2 equiv) for 7-chloro-4-iodoquinoline. $^1$H NMR (400 MHz, Chloroform-d) δ 8.77 (d, J=4.7 Hz, 1H), 8.12 (d, J=2.0 Hz, 1H), 7.89 (d, J=1.2 Hz, 1H), 7.39 (d, J=z 1.1 Hz, 1H), 7.25 (d, J=4.6 Hz, 1H), 7.02 (d, J=2.0 Hz, 1H), 6.95 (s, 1H), 6.95 (d, J=1.3 Hz, 1H), 6.87 (d, J=1.3 Hz, 1H), 5.12 (s, 2H), 4.01 (s, 3H), 4.00-3.93 (m, 1H), 3.86 (s, 3H), 3.79 (dt, J=12.3, 5.2 Hz, 1H), 3.13 (ddd, J=16.2, 10.9, 5.2 Hz, 1H), 2.96 (dt, J=16.3, 4.7 Hz, 1H), 2.40 (s, 3H), 2.35 (s, 3H); $^{19}$F NMR (376 MHz, $CDCl_3$) δ −60.16; LCMS (ESI) Method 2: >95%, $R_T$=1.29 min, m/z=561.0 $[M+H]^+$.

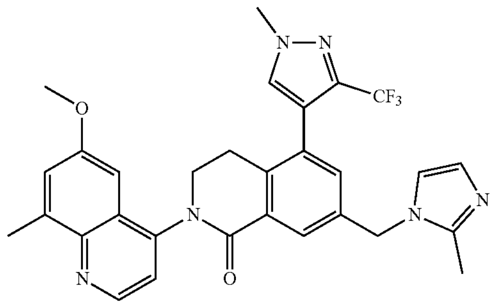 [SMILES: COc1cc(C)c2nccc(N3CCc4c(cc(Cn5ccnc5C)cc4-c4cn(C)nc4C(F)(F)F)C3=O)c2c1]

Example 7

2-(6-Methoxy-8-methylquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (36 mg, 0.064 mmol, 63% yield) was prepared following the Buchwald coupling procedure described for Example 2, substituting 4-bromo-6-methoxy-8-methylquinoline (52 mg, 0.21 mmol, 2 equiv) for 7-chloro-4-iodoquinoline. $^1$H NMR (400 MHz, Chloroform-d) δ 8.5 (d, J=4.6 Hz, 1H), 8.13 (d, J=2.0 Hz, 1H), 7.39 (d, J=1.1 Hz, 1H), 7.32 (d, J=4.6 Hz, 1H), 7.28 (d, J=2.8, 1.2 Hz, 1H), 7.01 (d, J=2.0 Hz, 1H), 6.96 (d, J=1.4 Hz, 1H), 6.93 (d, J=2.8 Hz, 1H), 6.88 (d, J=1.3 Hz, 1H), 5.13 (s, 2H), 4.02 (s, 3H), 3.97 (ddd, J=12.2, 10.9, 4.3 Hz, 1H), 3.85 (s, 3H), 3.79 (dt, J=12.3, 5.2 Hz, 1H), 3.14 (ddd, J=16.2, 10.9, 5. Hz, 1H), 2.96 (dt, J=16.4, 4.7 Hz, 1H), 2.80 (s, 3H), 2.36 (s, 3H); $^{19}$F NMR (376 MHz, $CDCl_3$) δ −60.16; LCMS (ESI): >95%, m/z=561.0 $[M+H]^+$.

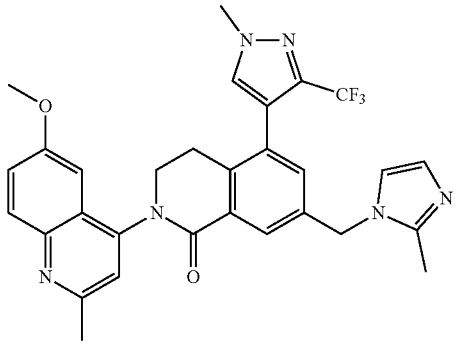 [SMILES: COc1ccc2nc(C)cc(N3CCc4c(cc(Cn5ccnc5C)cc4-c4cn(C)nc4C(F)(F)F)C3=O)c2c1]

Example 8

2-(6-Methoxy-2-methylquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (12 mg, 0.022 mmol, 43% yield) was prepared following the Buchwald coupling procedure described for Example 2, substituting 4-bromo-6-methoxy-2-methylquinoline (26 mg, 0.10 mmol, 2 equiv) for 7-chloro-4-iodoquinoline. $^1$H NMR (400 MHz, Chloroform-d) δ 8.12 (d, J=2.0 Hz, 1H), 8.00 (d, J=9.2 Hz, 1H), 7.40-7.35 (m, 2H), 7.23 (s, 1H), 7.03 (d, J=2.7 Hz, 1H), 7.02 (d, J=2.0 Hz, 1H), 6.96 (d, J=1.3 Hz, 1H), 6.88 (d, J=1.4 Hz, 1H), 5.13 (s, 2H), 4.02 (s, 3H), 3.96 (ddd, J=12.3, 10.9, 4.4 Hz, 1H), 3.85 (s, 3H), 3.84-3.74 (m, 1H), 3.13 (ddd, J=16.2, 10.9, 5.3 Hz, 1H), 2.96 (dt, J=16.3, 4.7 Hz, 1H), 2.72 (s, 3H), 2.36 (s, 3H); $^{19}$F NMR (376 MHz, $CDCl_3$) δ −60.16; LCMS (ESI) Method 2: >95%, $R_T$=1.114 min, m/z=561.0 $[M+H]^+$.

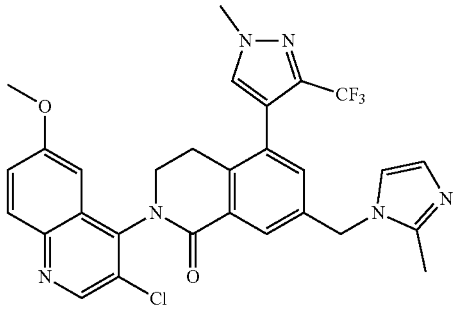 [SMILES: COc1ccc2ncc(Cl)c(N3CCc4c(cc(Cn5ccnc5C)cc4-c4cn(C)nc4C(F)(F)F)C3=O)c2c1]

Example 9

2-(3-Chloro-6-methoxyquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (21 mg, 0.036 mmol, 69% yield) was prepared following the Buchwald coupling procedure described for Example 2, substituting 4-bromo-3-chloro-6-methoxyquinoline (28 mg, 0.10 mmol, 2 equiv) for 7-chloro-4-iodoquinoline. $^1$H NMR (400 MHz, Chloroform-d) δ 8.81 (s, 1H), 8.13 (d, J=2.0 Hz, 1H), 8.06 (d, J=9.2 Hz, 1H), 7.43-7.37 (m, 2H), 7.04 (d, J=27 Hz, 1H), 7.02 (d, J=2.0 Hz, 1H), 6.96 (d, J=1.3 Hz, 1H), 6.88 (d, J=1.3 Hz, 1H), 5.13 (s, 2H), 4.02 (s, 3H), 3.93 (ddd, J=12.3, 7.8, 5.8 Hz, 1H), 3.87 (s, 3H), 3.74 (dt, J=12.2, 6.0 Hz, 1H), 3.13-3.07 (m, 2H), 2.37 (s, 3H); $^{19}$F NMR (376 MHz, $CDCl_3$) δ −60.13; LCMS (ESI) Method 2: >95%, $R_T$=1.411 min, m/z=580.9 $[M+H]^+$.

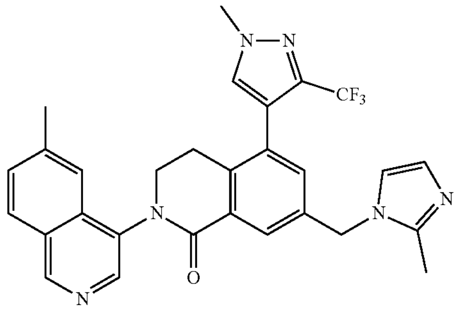 [SMILES: Cc1ccc2cncc(N3CCc4c(cc(Cn5ccnc5C)cc4-c4cn(C)nc4C(F)(F)F)C3=O)c2c1]

Example 10

6'-Methyl-7-((2-methyl-1H-imidazol-1-yl)methyl)-5-(1-methyl-3-(trifluoromethyl)-1H-pyrazol-4-yl)-3,4-dihydro-1H-[2,4'-biisoquinolin]-1-one The title compound (19 mg, 0.036 mmol, 57% yield) was prepared following the Buchwald coupling procedure described for Example 2, substituting 4-bromo-6-methylisoquinoline (29 mg, 0.13 mmol, 2 equiv) for 7-chloro-4-iodoquinoline. $^{1}$H NMR (400 MHz, Chloroform-d) δ 9.17 (s, 1H), 8.46 (s, 1H), 8.12 (d, J=2.0 Hz, 1H), 7.95 (d, J=8.3 Hz, 1H), 7.55 (d, J=1.8 Hz, 1H), 7.52-7.45 (m, 1H), 7.39 (d, J=1.3 Hz, 1H), 7.01 (d, J=2.0 Hz, 1H), 6.94 (d, J=1.4 Hz, 1H), 6.87 (d, J=1.3 Hz, 1H), 5.12 (s, 2H), 4.05-3.95 (m, 5H), 3.89-3.80 (m, 1H), 3.12 (ddd, J=15.1, 9.5, 5.2 Hz, 1H), 3.06-2.96 (m, 1H), 2.54 (s, 3H), 2.36 (s, 3H); $^{19}$F NMR (376 MHz, $CDCl_3$) δ −60.05; LCMS (ESI) Method 2: >95%, $R_T$=1.202 min, m/z=531.0 [M+H]$^+$.

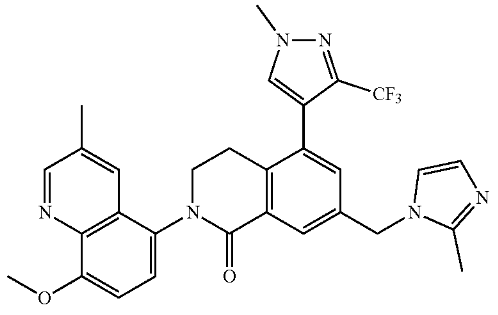 [SMILES: COc1ccc(N2CCc3c(cc(Cn4ccnc4C)cc3-c3cn(C)nc3C(F)(F)F)C2=O)c2cc(C)cnc12]

Example 11

2-(8-Methoxy-3-methylquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (4.5 mg, 8.0 μmol 16%) was prepared following the Buchwald coupling procedure described for Example 2, substituting 5-bromo-8-methoxy-3-methylquinoline (Intermediate 14, 26 mg, 0.10 mmol, 2 equiv) and BrettPhos (5.5 mg, 10 μmol, 0.2 equiv) for 7-chloro-4-iodoquinoline and Xantphos, respectively. $^{1}$H NMR (400 MHz, Chloroform-d) δ 8.79 (d, J=2.2 Hz, 1H), 8.11 (d, J=2.0 Hz, 1H), 7.93 (d, J=2.1 Hz, 1H), 7.54 (d, J=8.7 Hz, 1H), 7.48 (d, J=8.7 Hz, 1H), 7.38 (s, 1H), 6.99 (d, J=2.0 Hz, 1H), 6.96 (s, 1H), 6.88 (d, J=1.4 Hz, 1H), 5.12 (s, 2H), 4.13 (s, 3H), 4.02 (s, 3H), 3.89 (d, J=15.8 Hz, 2H), 3.00 (t, J=6.3 Hz, 2H), 2.53 (s, 3H), 2.37 (s, 3H); $^{19}$F NMR (376 MHz, $CDCl_3$) δ −60.07; LCMS (ESI) Method 2: >95%, $R_T$=1.193 min, m/z 561.0 [M+H]$^+$.

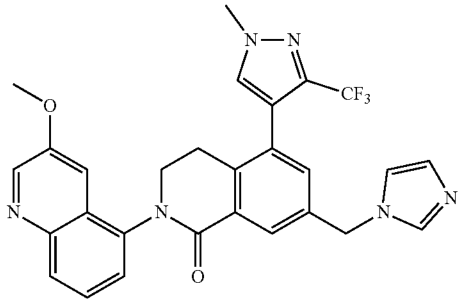 [SMILES: COc1cnc2cccc(N3CCc4c(cc(Cn5ccnc5)cc4-c4cn(C)nc4C(F)(F)F)C3=O)c2c1]

Example 12

7-((1H-Imidazol-1-yl)methyl)-2-(3-methoxyquinolin-5-yl)-5-(1-methyl-3-(trifluoromethyl)-1H-pyrazol-4-yl)-3,4-dihydroisoquinolin-1(2H)-one The title compound (195 mg, 0.16 mmol, 55% yield) was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 250 mg, 0.66 mmol, 1 equiv), 5-bromo-3-methoxyquinoline (317 mg, 1.33 mmol, 2 equiv), and Xantphos (116 mg, 0.20 mmol, 0.3 equiv) at 115° C. $^{1}$H NMR (400 MHz, Chloroform-d) δ 8.71 (d, J=2.9 Hz, 1H), 8.17 (d, J=2.0 Hz, 1H), 8.08 (dt, J=8.5, 1.0 Hz, 1H), 7.64-7.58 (m, 2H), 7.48 (dd, J=7.4, 1.2 Hz, 1H), 7.41 (d, J=1.1 Hz, 1H), 7.31 (d, J=2.91 Hz, 1H), 7.17 (d, J=2.0 Hz, 1H), 7.11 (t, J=1.1 Hz, 1H), 6.96 (t, J=1.3 Hz, 1H), 5.20 (s, 2H), 4.05-3.98 (s, 4H), 3.89 (s, 3H), 3.77 (dt, J=12.4, 5.3 Hz, 1H), 3.12 (ddd, J=16.0, 10.6, 5.2 Hz, 1H), 2.99 (dt, J=16.3, 4.9 Hz, 1H); LCMS (ESI) Method 2: >95%, $R_T$=1.310 min, m/z=532.9 [M+H]$^+$.

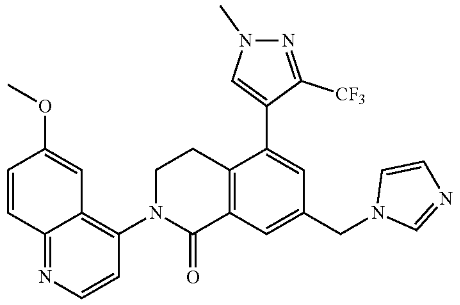

Example 13

7-((1H-Imidazol-1-yl)methyl)-2-(6-methoxyquinolin-4-yl)-5-(1-methyl-3-(trifluoromethyl)-1H-pyrazol-4-yl)-3,4-dihydroisoquinolin-1(2H)-one The title compound (23 mg, 0.043 mmol, 54% yield) was prepared following the Buchwald coupling procedure described for Example 12, substituting 4-bromo-6-methoxyquinoline (38 mg, 0.16 mmol, 2 equiv) for 5-bromo-3-methoxyquinoline. $^1$H NMR (400 MHz, Chloroform-d) δ 8.81 (d, J=4.6 Hz, 1H), 8.14 (d, J=2.0 Hz, 1H), 8.06 (d, J=9.2 Hz, 1H), 7.55 (s, 1H), 7.42-7.37 (m, 2H), 7.30 (d, J=4.6 Hz, 1H), 7.17 (d, J=2.0 Hz, 1H), 7.08 (s, 1H), 7.05 (d, J=27 Hz, 1H), 6.93 (d, J=1.7 Hz, 1H), 5.17 (s, 2H), 4.00 (s, 3H), 3.99-3.95 (m, 1H), 3.85 (s, 3H), 3.79 (dt, J=12.3, 5.2 Hz, 1H), 3.13 (ddd, J=16.2, 10.9, 5.2 Hz, 1H), 2.96 (dt, J=16.4, 4.8 Hz, 1H); LCMS (ESI) Method 2: >95%, $R_T$=1.223 min, m/z 532.9 [M+H]$^+$.

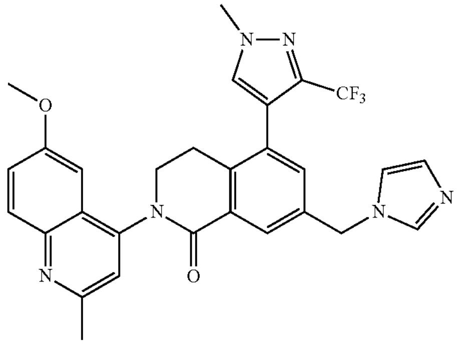

Example 14

7-((1H-Imidazol-1-yl)methyl)-2-(6-methoxy-2-methylquinolin-4-yl)-5-(1-methyl-3-(trifluoromethyl)-1H-pyrazol-4-yl)-3,4-dihydroisoquinolin-1(2H)-one The title compound (30 mg, 0.054 mmol, 68% yield) was prepared following the Buchwald coupling procedure described for Example 12, substituting 4-bromo-6-methoxy-2-methylquinoline (40 mg, 0.16 mmol, 2 equiv) for 5-bromo-3-methoxyquinoline. $^1$H NMR (400 MHz, Chloroform-d) δ 8.14 (d, J=2.0 Hz, 1H), 7.97 (d, J=9.2 Hz, 1H), 7.55 (s, 1H), 7.40 (s, 1H), 7.35 (dd, J=9.1, 2.8 Hz, 1H), 7.21 (s, 1H), 7.16 (d, J=2.0 Hz, 1H), 7.07 (s, 1H), 7.01 (d, J=2.8 Hz, 1H), 6.93 (s, 1H), 5.17 (s, 2H), 4.00 (s, 3H), 3.99-3.91 (m, 1H), 3.83 (s, 3H), 3.78 (dt, J=12.2, 5.2 Hz, 1H), 3.12 (ddd, J=16.0, 10.7, 5.2 Hz, 1H), 2.95 (dt, J=16.4, 4.8 Hz, 1H), 2.70 (s, 3H); LCMS (ESI) Method 2: >95%, $R_T$=1.178 min, m/z=546.9 [M+H]$^+$.

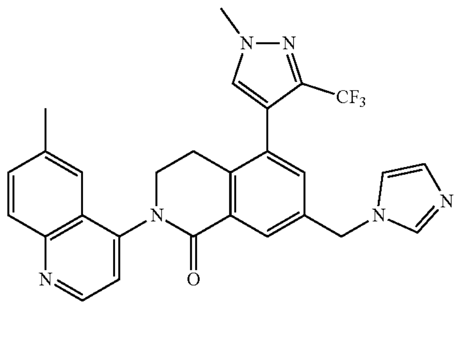 [SMILES: Cc1ccc2nccc(N3CCc4c(cc(Cn5ccnc5)cc4-c4cn(C)nc4C(F)(F)F)C3=O)c2c1]

Example 15

7-((1H-Imidazol-1-yl)methyl)-5-(1-methyl-3-(trifluoromethyl)-1H-pyrazol-4-yl)-2-(6-methylquinolin-4-yl)-3,4-dihydroisoquinolin-1(2H)-one The title compound (45 mg, 0.087 mmol, 82% yield) was prepared following the Buchwald coupling procedure described for Example 12, substituting 4-bromo-6-methylquinoline (47 mg, 0.21 mmol, 2 equiv) for 5-bromo-3-methoxyquinoline. $^1$H NMR (400 MHz Chloroform-d) δ 8.89 (d, J=4.6 Hz, 1H), 8.15 (d, J=2.0 Hz, 1H), 8.09-8.02 (m, 1H), 7.59-7.53 (m, 3H), 7.40 (d, J=1.1 Hz, 1H), 7.30 (d, J=4.6 Hz, 1H), 7.18 (d, J=2.0 Hz, 1H), 7.08 (s, 1H), 6.93 (s, 1H), 5.18 (s, 2H), 4.03-4.96 (m, 4H), 3.82 (dt, J=12.2, 5.4 Hz, 1H), 3.15 (ddd, J=15.9, 10.5, 5.2 Hz, 1H), 2.97 (dt, J=163, 4.9 Hz, 1H), 2.51 (s, 3H); $^{19}$F NMR (376 MHz, $CDCl_3$) δ −60.04; LCMS (ESI) Method 2: >95%, $R_T$=1.116 min, m/z=517.0 [M+H]$^+$.

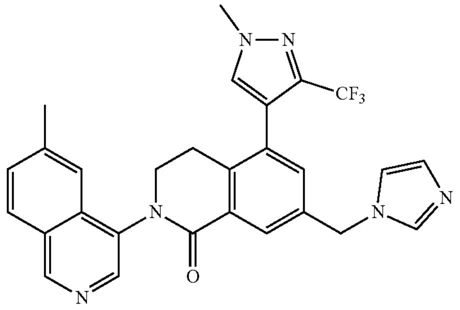

Example 16

7-((1H-Imidazol-1-yl)methyl)-6'-methyl-5-(1-methyl-3-(trifluoromethyl)-1H-pyrazol-4-yl)-3,4-dihydro-1-[2,4'-biisoquinolin]-1-one The title compound (22 mg, 0.043 mmol, 53% yield) was prepared following the Buchwald coupling procedure described for Example 12, substituting 4-bromo-6-methylisoquinoline (36 mg, 0.16 mmol, 2 equiv) for 5-bromo-3-methoxyquinoline. $^1$H NMR (400 MHz, Chloroform-d) δ 9.19-9.17 (m, 1H), 8.46 (s, 1H), 8.16 (d, J=2.0 Hz, 1H), 7.95 (d, J=8.4 Hz, 1H), 7.56 (s, 1H), 7.56-7.53 (m, 1H), 7.48 (dd, J=8.4, 16 Hz, 1H), 7.41 (d, J=1.1 Hz, 1H), 7.17 (d, J=2.0 Hz, 1H), 7.09 (s, 1H), 6.94 (d, J=1.4 Hz, 1H), 5.19 (s, 2H), 4.01 (s. 3H), 4.00-3.94 (m, 1H), 3.85 (ddd, J=12.1, 6.5, 5.2 Hz, 1H), 3.12 (ddd, J=163, 9.5, 5.1 Hz, 1H), 3.01 (ddd, J=16.3, 6.5, 4.8 Hz, 1H), 2.54 (s, 3H); LCMS (ESI) Method 2: >95%, $R_T$=1.229 min, m/z=517.0 [M+H]$^+$.

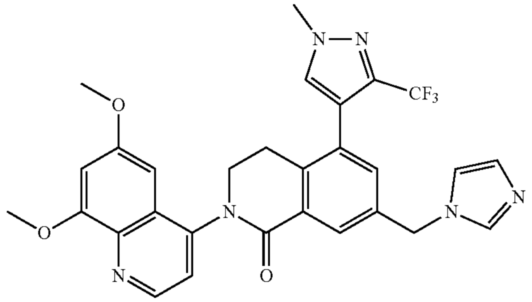 [SMILES: COc1cc(OC)c2nccc(N3CCc4c(cc(Cn5ccnc5)cc4-c4cn(C)nc4C(F)(F)F)C3=O)c2c1]

Example 17

7-((1H-Imidazol-1-yl)methyl)-2-(6,8-dimethoxyquinolin-4-yl)-5-(1-methyl-3-(trifluoromethyl)-1H-pyrazol-4-yl)-3,4-dihydroisoquinolin-1(2H)-one The title compound (30 mg, 0.053 mmol, 50% yield) was prepared following the Buchwald coupling procedure described for Example 12, substituting 4-bromo-6,8-dimethoxyquinoline (57 mg, 0.21 mmol, 2 equiv) for 5-bromo-3-methoxyquinoline. $^1$H NMR (400 MHz, Chloroform-d) δ 881 (dd, J=4.6, 1.2 Hz, 1H), 8.16 (d, J=1.9 Hz, 1H), 7.56 (s, 1H), 7.40 (s, 1H), 7.34 (dd, J=4.7, 1.2 Hz, 1H), 7.17 (d, J=1.9 Hz, 1H), 7.09 (s, 1H), 6.94 (d, J=1.6 Hz, 1H), 6.74 (t, J=1.8 Hz, 1H), 6.63 (dd, J=2.5, 1.3 Hz, 1H), 5.18 (s, 2H), 4.06 (s, 3H), 4.01 (s, 3H), 3.99-3.91 (m, 1H), 3.84 (d, J=1.3 Hz, 3H), 3.79 (td, J=11.6, 10.3, 4.6 Hz, 1H), 3.13 (ddd, J=16.3, 10.9, 5.3 Hz, 1H), 2.96 (dt, J=16.4, 4.9 Hz, 1H); $^{19}$F NMR (376 MHz, $CDCl_3$) δ −60.16; LCMS (ESI) Method 2: >95%, $R_T$=1.162 min, m/z=562.9 $[M+H]^+$.

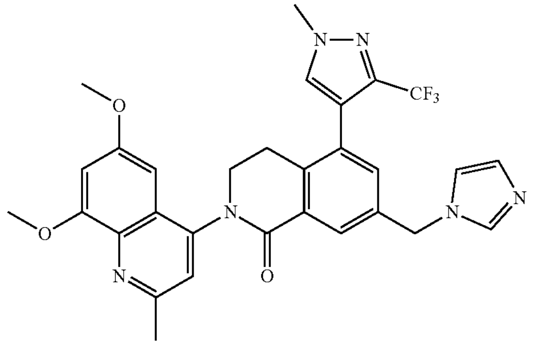 [SMILES: COc1cc(OC)c2nc(C)cc(N3CCc4c(cc(Cn5ccnc5)cc4-c4cn(C)nc4C(F)(F)F)C3=O)c2c1]

Example 18

7-((1H-Imidazol-1-yl)methyl)-2-(6,8-dimethoxy-2-methylquinolin-4-yl)-5-(1-methyl-3-(trifluoromethyl)-1H-pyrazol-4-yl)-3,4-dihydroisoquinolin-1(2H)-one The title compound (22 mg, 0.038 mmol, 36% yield) was prepared following the Buchwald coupling procedure described for Example 12, substituting 4-bromo-6,8-dimethoxy-2-methylquinoline (60 mg, 0.21 mmol, 2 equiv) for 5-bromo-3-methoxyquinoline. $^1$H NMR (400 MHz, Chloroform-d) δ 8.14 (d, J=2.0 Hz, 1H), 7.56 (s, 1H), 7.40 (d, J=1.0 Hz, 1H), 7.25 (1H), 7.16 (d, J=2.0 Hz, 1H), 7.08 (t, J=1.1 Hz, 1H), 6.94 (d, J=1.3 Hz, 1H), 6.72 (d, J=2.5 Hz, 1H), 6.60 (d, J=2.5 Hz, 1H), 5.18 (s, 2H), 4.04 (s, 3H), 4.01 (s, 3H), 3.97-3.88 (m, 1H), 3.82 (s, 3H), 3.77 (dt, J=12.3, 5.3 Hz, 1H), 3.12 (ddd, J=16.2, 10.8, 5.3 Hz, 1H), 2.94 (dt, J=16.4, 4.8 Hz, 1H), 2.75 (s, 3H); $^{19}$F NMR (376 MHz, $CDCl_3$) δ −60.2; LCMS (ESI) Method 2: >95%, $R_T$=1.440 min, m/z=576.9 $[M+H]^+$.

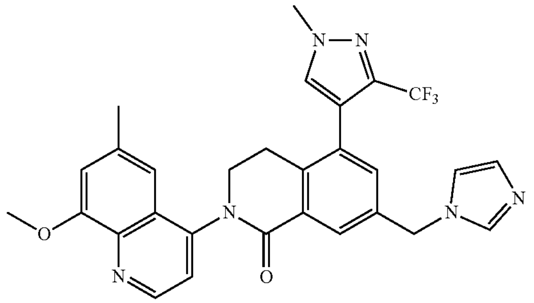 [SMILES: COc1cc(C)cc2c(N3CCc4c(cc(Cn5ccnc5)cc4-c4cn(C)nc4C(F)(F)F)C3=O)ccnc12]

Example 19

7-((1H-Imidazol-1-yl)methyl)-2-(8-methoxy-6-methylquinolin-4-yl)-5-(1-methyl-3-(trifluoromethyl)-1H-pyrazol-4-yl)-3,4-dihydroisoquinolin-1(2H)-one The title compound (32 mg, 0.059 mmol, 55% yield) was prepared following the Buchwald coupling procedure described for Example 12, substituting 4-bromo-8-methoxy-6-methylquinoline (54 mg, 0.21 mmol, 2 equiv) for 5-bromo-3-methoxyquinoline. $^1$H NMR (400 MHz, Chloroform-d) δ 8.89 (d, J=4.6 Hz, 1H), 8.14 (d, J=2.0 Hz, 1H), 7.55 (s, 1H), 7.40 (s, 1H), 7.32 (d, J=4.6 Hz, 1H), 7.16 (d, J=2.0 Hz, 1H), 7.14 (d, J=1.4 Hz, 1H), 7.08 (s, 1H), 6.93 (d, J=1.5 Hz, 1H), 6.90 (d, J=1.6 Hz, 1H), 5.17 (s, 2H), 4.07 (s, 3H), 4.00 (s, 3H), 3.99-3.91 (m, 1H), 3.80 (dt, J=11.7, 5.4 Hz, 1H), 3.14 (ddd, J=15.9, 10.5, 5.2 Hz, 1H), 2.96 (dt, J=16.5, 4.9 Hz, 1H), 2.49 (s, 3H); $^{19}$F NMR (376 MHz, $CDCl_3$) δ −60.04; LCMS (ESI) Method 2: >95%, $R_T$=1.097 min, m/z=546.9 $[M+H]^+$.

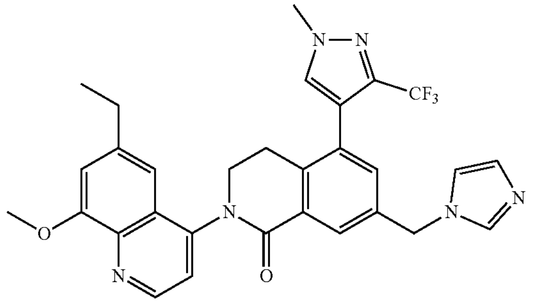 [SMILES: CCc1cc(OC)c2nccc(N3CCc4c(cc(Cn5ccnc5)cc4-c4cn(C)nc4C(F)(F)F)C3=O)c2c1]

Example 20

7-((1H-Imidazol-1-yl)methyl)-2-(6-ethyl-8-methoxyquinolin-4-yl)-5-(1-methyl-3-(trifluoromethyl)-1H-pyrazol-4-yl)-3,4-dihydroisoquinolin-1(2H)-one Step A. Preparation of 5-(((4-bromo-2-methoxyphenyl)amino)methylene)-2,2-dimethyl-1,3-dioxane-4,6-dione. To a solution of 4-bromo-2-methoxyaniline (6.3 g, 31.2 mmol, 1 equiv) and Meldrum's acid (5.39 g, 37.4 mmol, 1.2 equiv) in EtOH (50 mL) was added triethyl orthoformate (5.2 mL, 31.2 mmol, 1 equiv). The reaction was stirred at 80° C. overnight. The reaction was cooled to 0° C., filtered, and washed with cold EtOH to yield the title compound (10.96 g, 30.8 mmol, 99% yield). $^1$H NMR (400 MHz, Chloroform-d) δ 11.46 (s, 1H), 8.61 (d, J=14.6 Hz, 1H), 7.23-7.14 (m, 2H), 7.12 (d, J=1.7 Hz, 1H), 3.96 (s, 4H), 1.75 (s, 6H).

Step B. Preparation of 6-bromo-8-methoxyquinolin-4-ol. 5-((4-Bromo-2-methoxyphenyl)amino)methylene)-2,2-dimethyl-1,3-dioxane-4,6-dione (10.96 g, 30.8 mmol, 1 equiv) was added portionwise to Dowtherm A (20 mL) at 260° C. and stirred for 30 min. The reaction was cooled to room temperature, and hexanes were added. The resulting mixture was filtered, and solid was washed with hexanes to yield the title compound (7.20 g, 28.3 mmol, 92% yield). $^1$H NMR (40 MHz, DMSO-$d_6$) δ 11.50 (s, 1H), 7.77 (t, J=6.7 Hz, 1H), 7.73 (d, J=2.0 Hz, 1H), 7.38 (d, J=2.1 Hz, 1H), 6.08 (d, J=7.4 Hz, 1H), 4.01 (s, 3H).

Step C. Preparation of 6-ethyl-8-methoxyquinolin-4-ol. A mixture of 6-bromo-8-methoxyquinolin-4-ol (215 mg, 0.85 mmol, 1 equiv), triethylborane (2 mL, 1.7 mmol, 2 equiv, 1 M THF), cesium carbonate (551 mg, 1.7 mmol, 2 equiv), and Pd(dppf)$Cl_2$ (31.0 mg, 42.3 μmol, 0.05 equiv) in THF (3 mL) was stirred for 3 h at 60° C. under Ar in a sealed tube. The reaction was cooled to 0° C. and quenched by 10% aq. NaOH and 30% aq. $H_2O_2$. The resulting mixture was warmed to 23° C., brine was added, and the mixture was extracted with EtOAc (3×20 mL). The combined organic layers were dried over $MgSO_4$ and concentrated under reduced pressure. The residue was purified by flash chromatography (Combi-flash Rf, Hex/EtOAc=0-100% gradient followed by DCM/MeOH=0-10% gradient) to afford the title compound (173 mg, 0.85 mmol, quant.). $^1$H NMR (400 MHz, DMSO-d) δ 11.28 (s, 1H), 7.46 (d, J=1.7 Hz, 1H), 7.11 (d, J=1.7 Hz, 1H), 6.00 (d, J=7.3 Hz, 1H), 5.75 (s, 1H), 3.98 (s, 3H), 2.70 (q, J=7.6 Hz, 2H), 1.23 (t, J=7.6 Hz, 3H); LCMS (ESI): Method 2: $R_T$=1.185 min, m/z=204.1 [M+H]$^+$.

Step D. Preparation of 4-bromo-6-ethyl-8-methoxyquinoline. To a solution of 6-ethyl-8-methoxyquinolin-4-ol (170 mg, 0.84 mmol, 1 equiv) in DMF (5 mL) was added $PBr_3$ (0.16 mL, 1.67 mmol, 2 equiv) dropwise at 0° C. The reaction mixture was warmed to room temperature and stirred overnight. The reaction was quenched with ice, and the pH was adjusted to 7 with $NaHCO_3$. The solid was filtered, washed with water, and dried to yield the title compound (169 mg, 0.64 mmol, 76% yield). $^1$H NMR (400 MHz, Chloroform-d) δ 8.46 (d, J=4.6 Hz, 1H), 7.53 (d, J=4.6 Hz, 1H), 7.39 (dt, J=1.8, 0.9 Hz, 1H), 6.81 (d, J=1.7 Hz, 1H), 3.96 (s, 3H), 2.70 (q, J=7.5 Hz, 2H), 1.23 (t, J=7.6 Hz, 3H); LCMS (ESI): Method 2: $R_T$=1.231 min, m/z=266.0 [M+H]$^+$.

Step E. Preparation of 7-((1H-Imidazol-1-yl)methyl)-2-(6-ethyl-8-methoxyquinolin-4-yl)-5-(1-methyl-3-(trifluoromethyl)-1H-pyrazol-4-yl)-3,4-dihydroisoquinolin-(2H)-one. 7-((1H-Imidazol-1-yl)methyl)-5-(1-methyl-3-(trifluoromethyl)-1H-pyrazol-4-yl)-3,4-dihydroisoquinolin-1(2H)-one (Intermediate 8, 1.0 equiv), 4-bromo-6-ethyl-8-methoxyquinoline (Intermediate 17, 57 mg, 0.21 mmol, 2 equiv), cesium carbonate (2.0 equiv), Xantphos (0.2 equiv), and $Pd_2(dba)_3$ (0.1 equiv) were dissolved in 1,4-dioxane under an Ar. The reaction mixture was stirred for 14 h at 110° C. then cooled to 23° C. Brine was added to the mixture and extracted with EtOAc (3×50 mL). The combined organic layers were dried over $MgSO_4$ and concentrated under reduced pressure. The residue was purified by reverse phase 1-PLC (Phenomenex Gemini C18, $H_2O/CH_3CN$ gradient from 10-70% $CH_3CN$, 0.1% TFA) followed by neutralization with sat. aq. $NaHCO_3$ to yield the title compound (30 mg, 0.054 mmol, 50% yield). $^1$H NMR (400 MHz, Chloroform-d) δ 8.92 (d, J=4.6 Hz, 1H), 8.17 (d, J=2.0 Hz, 1H), 7.59 (s, 1H), 7.41 (d, J=1.1 Hz, 1H), 7.35 (d, J=4.6 Hz, 1H), 7.18 (t, J=2.2 Hz, 2H), 7.10 (d, J=1.3 Hz, 1H), 6.95 (d, J=1.6 Hz, 2H), 5.20 (s, 2H), 4.10 (s, 3H), 4.02 (s, 3H), 3.96 (ddd, J=12.2, 10.6, 4.4 Hz, 1H), 3.82 (dt, J=12.3, 5.3 Hz, 1H), 3.15 (ddd, J=16.0, 10.6, 5.2 Hz, 1H), 2.97 (dt, J=16.3, 4.9 Hz, 1H), 2.80 (q, J=7.6 Hz, 2H), 1.30 (t, J=7.6 Hz, 3H); $^1$H NMR (376 MHz, Chloroform-d) δ −60.11. LCMS (ESI) Method 3: >95%, $R_T$=1.849 min, m/z=561.1 [M+H]$^+$.

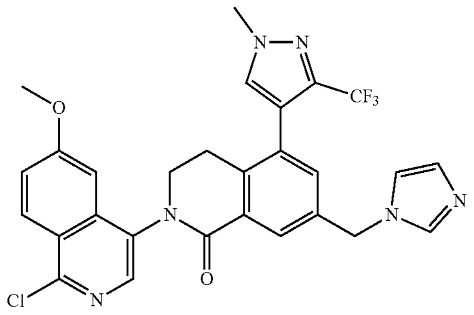 [SMILES: COc1ccc2c(Cl)ncc(N3CCc4c(cc(Cn5ccnc5)cc4-c4cn(C)nc4C(F)(F)F)C3=O)c2c1]

Example 21

7-((1H-Imidazol-1-yl)methyl)-1'-chloro-6'-methoxy-5-(1-methyl-3-(trifluoromethyl)-1H-pyrazol-4-yl)-3,4-dihydro-1H-[2,4'-biisoquinolin]-1-one The title compound (52 mg, 0.092 mmol, 75% yield) was prepared following the procedures described in Example 12, substituting 1-chloro-4-iodo-6-methoxyisoquinoline (78 mg, 0.25 mmol, 2 equiv) for 5-bromo-3-methoxyquinoline. LCMS (ESI) Method 2: >95%, $R_T$=1.300 min, m/z=566.8 [M+H]$^+$.

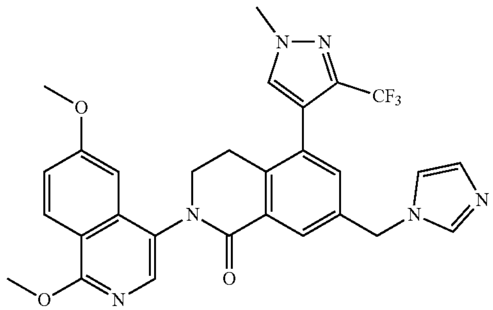 [SMILES: COc1ccc2c(OC)ncc(N3CCc4c(cc(Cn5ccnc5)cc4-c4cn(C)nc4C(F)(F)F)C3=O)c2c1]

Example 22

7-((1H-imidazol-1-yl)methyl)-1',6'-dimethoxy-5-(1-methyl-3-(trifluoromethyl)-1H-pyrazol-4-yl)-3,4-dihydro-1H-[2,4'-biisoquinolin]-one To a solution of 7-((1H-imidazol-1-yl)methyl)-1'-chloro-6'-methoxy-5-(1-methyl-3-(trifluoromethyl)-1H-pyrazol-4-yl)-3,4-dihydro-1H-[2,4'-biisoquinolin]-1-one (Example 21, 25 mg, 0.044 mmol, 1 equiv) in MeOH (0.6 mL) was added sodium methoxide (15 μL, 0.066 mmol, 1.5 equiv) dropwise at 23° C. The reaction mixture was stirred for 12 h at 23° C. then concentrated under reduced pressure. The residue was dissolved in EtOAc and washed with water and brine. The organic layer was dried over $MgSO_4$, filtered, and concentrated under reduced pressure. The residue was purified by reverse phase HPLC (Phenomenex Gemini C18, $H_2O/CH_3CN$ gradient from 10-80% $CH_3CN$, 0.1% TFA) to yield the title compound (3.0 mg, 0.005 mmol, 12% yield). $^1H$ NMR (400 MHz, Chloroform-d) δ 8.22 (d, J=9.1 Hz, 1H), 8.17 (d, J=2.0 Hz, 1H), 7.96 (s, 1H), 7.60 (s, 1H), 7.40 (d, J=1.1 Hz, 1H), 7.19 (dd, J=9.1, 2.5 Hz, 1H), 7.15 (d, J=2.0 Hz, 1H), 7.11 (s, 1H), 6.96 (s, 1H), 6.94 (d, J=2.5 Hz, 1H), 5.20 (s, 2H), 4.12 (s, 3H), 4.02 (s, 3H), 3.93 (ddd, J=12.4, 9.7, 4.6 Hz, 1H), 3.87 (s, 3H), 3.79 (dt, J=12.2, 5.5 Hz, 1H), 3.09 (ddd, J=15.3, 9.8, 5.2 Hz, 1H), 2.98 (dt, J=16.3, 5.4 Hz, 1H); $^{19}F$ NMR (376 MHz, $CDCl_3$) δ −60.14; LCMS (ESI) Method 2: >95%, $R_T$=1.422 min, m/z=562.9 $[M+H]^+$.

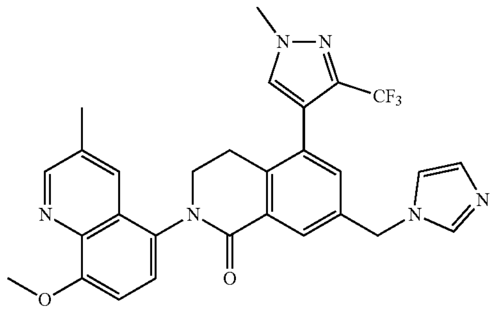 [SMILES: COc1ccc(N2CCc3c(cc(Cn4ccnc4)cc3-c3cn(C)nc3C(F)(F)F)C2=O)c2cc(C)cnc12]

Example 23

7-((1H-Imidazol-1-yl)methyl)-2-(8-methoxy-3-methylquinolin-5-yl)-5-(1-methyl-3-(trifluoromethyl)-1H-pyrazol-4-yl)-3,4-dihydroisoquinolin-1(2H)-one 7-((1H-Imidazol-1-yl)methyl)-5-(1-methyl-3-(trifluoromethyl)-1H-pyrazol-4-yl)-3,4-dihydroisoquinolin-1(2H)-one (Intermediate 8, 20 mg, 0.053 mmol, 1 equiv), 5-iodo-8-methoxy-3-methylquinoline (Intermediate 18, 32 mg, 0.11 mmol, 2 equiv), potassium phosphate tribasic (23 mg, 0.11 mmol, 2 equiv), (1S,2S)—N1,N2-methylcyclohexane-1,2-diamine (0.76 mg, 0.84 μL, 5.3 μmol, 0.1 equiv), and copper(I) iodide (1.0 mg, 5.3 μmol, 0.1 equiv) were dissolved in 1,4-dioxane (1 mL) under Ar. The reaction mixture was stirred for 14 h at 115° C. then cooled to 23° C. Brine was added to the mixture and extracted with EtOAc. The combined organic layers were dried over $MgSO_4$ and concentrated under reduced pressure. The residue was purified by reverse phase HPLC (Phenomenex Gemini C18, $H_2O$/$CH_3CN$ gradient from 15-80% $CH_3CN$, 0.1% TFA) followed by neutralization with sat. aq. $NaHCO_3$ to yield the title compound (14 mg, 0.025 mmol, 47% yield). $^1H$ NMR (400 MHz, Chloroform-d) δ 8.80 (d, J=2.1 Hz, 1H), 8.15 (d, J=2.0 Hz, 1H), 7.82 (dd, J=2.2, 1.2 Hz, 1H), 7.58 (s, 1H), 7.39 (d, J=8.2 Hz, 2H), 7.16 (d, J=2.0 Hz, 1H), 7.10 (s, 1H), 7.00 (d, J=8.2 Hz, 1H), 6.95 (s, 1H), 5.18 (s, 2H), 4.10 (s, 3H), 4.01 (s, 3H), 3.96 (ddd, J=12.3, 9.8, 4.5 Hz, 1H), 3.76 (dt, J=12.0, 5.6 Hz, 1H), 3.11 (ddd, J=15.5, 10.0, 5.2 Hz, 1H), 2.98 (dt, J=16.3, 5.3 Hz, 1H), 2.50 (s, 3H); $^{19}F$ NMR (376 MHz, $CDCl_3$) δ −60.07; LCMS (ESI) Method 3: >95%, $R_T$=1.824 min, m/z=547.2 $[M+H]^+$.

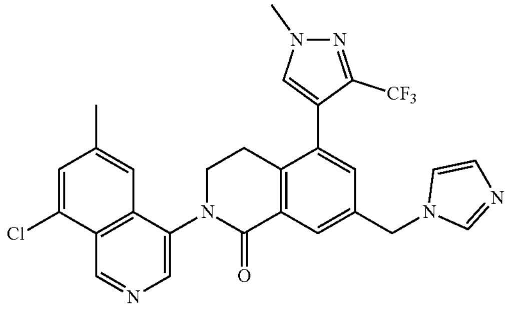 [SMILES: Cc1cc(Cl)c2cncc(N3CCc4c(cc(Cn5ccnc5)cc4-c4cn(C)nc4C(F)(F)F)C3=O)c2c1]

Example 24

7-((1H-Imidazol-1-yl)methyl)-8'-chloro-6'-methyl-5-(1-methyl-3-(trifluoromethyl)-1H-pyrazol-4-yl)-3,4-dihydro-1H-[2,4'-biisoquinolin]-1-one The title compound (35 mg, 0.064 mmol, 79% yield) was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (30 mg, 080 mmol, 1 equiv) and 4-bromo-8-chloro-6-methylisoquinoline (41 mg, 0.16 mmol, 2 equiv). $^1H$ NMR (400 MHz, Chloroform-d) δ 9.60 (s, 1H), 8.55 (s, 1H), 8.16 (s, 1H), 7.57 (s, 1H), 7.54 (d, J=2.0 Hz, 1H), 7.48 (s, 1H), 7.41 (s, 1H), 7.19 (d, J=2.0 Hz, 1H), 7.10 (s, 1H), 6.95 (s, 1H), 5.20 (s, 2H), 4.04 (s, 3H), 4.02 (m, 1H), 3.83 (m, 1H), 3.12 (m, 1H), 3.04 (m, 1H), 2.52 (s, 3H); LCMS (ESI): >88%, m/z=551.4 $[M+H]^+$.

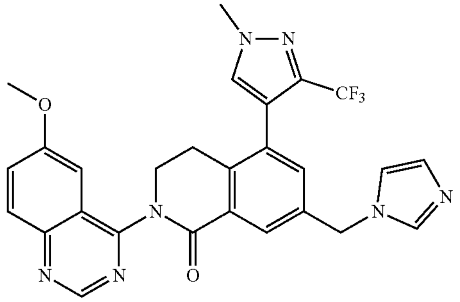

Example 25

7-((1H-Imidazol-1-yl)methyl)-2-(6-methoxyquinazolin-4-yl)-5-(1-methyl-3-(trifluoromethyl)-1H-pyrazol-4-yl)-3,4-dihydroisoquinolin-1(2)-one The title compound (11 mg, 0.021 mmol, 13% yield) was prepared following the Buchwald coupling procedure described for Example 12, substituting 4-chloro-6-methoxyquinazoline (62 mg, 0.32 mmol, 2 equiv) for 5-bromo-3-methoxyquinoline. $^1H$ NMR (400 MHz, Chloroform-d) δ 9.09 (s, 1H), 8.17 (d, J=2.0 Hz, 1H), 8.00 (d, J=9.2 Hz, 1H), 7.57 (dd, J=9.2, 2.8 Hz, 2H), 7.41 (d, J=1.1 Hz, 1H), 7.19 (d, J=2.0 Hz, 1H), 7.11 (s, 1H), 7.04 (d, J=2.8 Hz, 1H), 6.95 (s, 1H), 5.20 (s, 2H), 4.16 (s, 2H), 4.03 (s, 3H), 3.88 (s, 3H), 3.06 (t, J=6.3 Hz, 2H); $^{19}F$ NMR (376 MHz, $CDCl_3$) δ −60.10; LCMS (ESI) Method 2: >95%, $R_T$=1.305 min, m/z=534.0 $[M+H]^+$.

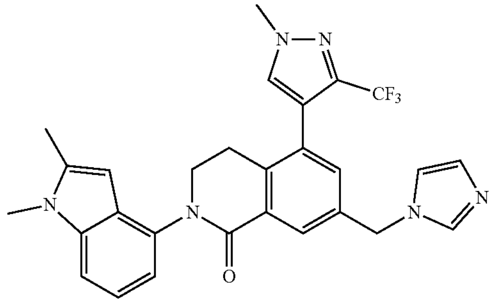 [SMILES: Cc1cc2c(N3CCc4c(cc(Cn5ccnc5)cc4-c4cn(C)nc4C(F)(F)F)C3=O)cccc2n1C]

Example 26

7-((1H-Imidazol-1-yl)methyl)-2-(1,2-dimethyl-1H-indol-4-yl)-5-(1-methyl-3-(trifluoromethyl)-1H-pyrazol-4-yl)-3,4-dihydroisoquinolin-1(2H)-one The title compound (8 mg, 0.016 mmol, 24% yield) was prepared following the Buchwald coupling procedure described for Example 12, substituting 4-bromo-1,2-dimethyl-1H-indole (30 mg, 0.13 mmol, 2 equiv) for 5-bromo-3-methoxyquinoline. $^{1}H$ NMR (400 MHz, Chloroform-d) δ 8.19 (d, J=2.0 Hz, 1H), 7.58 (s, 1H), 7.37 (s, 1H), 7.22 (d, J=8.1 Hz, 1H), 7.17 (t, J=7.7 Hz, 1H), 7.11 (d, J=2.0 Hz, 1H), 7.09 (s, 1H), 7.01 (dd, J=7.3, 1.1 Hz, 1H), 6.94 (s, 1H), 6.12 (s, 1H), 5.17 (s, 2H), 4.01 (s, 3H), 3.98-3.91 (m, 2H), 3.67 (s, 3H), 2.97 (t, J=6.4 Hz, 2H), 2.41 (d, J=0.9 Hz, 3H); $^{19}F$ NMR (376 MHz, $CDCl_3$) δ −60.09; LCMS (ESI) Method 2: >95%, $R_T$=1.501 min, m/z=519.0 $[M+H]^+$.

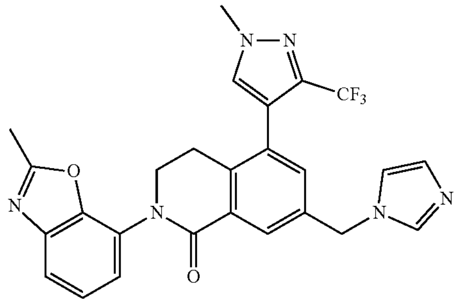 [SMILES: Cc1nc2cccc(N3CCc4c(cc(Cn5ccnc5)cc4-c4cn(C)nc4C(F)(F)F)C3=O)c2o1]

Example 27

7-((1H-Imidazol-1-yl)methyl)-5-(1-methyl-3-(trifluoromethyl)-1H-pyrazol-4-yl)-2-(2-methylbenzo[d]oxazol-7-yl)-3,4-dihydroisoquinolin-1(2H)-one The title compound (5 mg, 0.01 mmol, 20% yield) was prepared following the Buchwald coupling procedure described in Example 12, substituting 7-bromo-2-methylbenzo[d]oxazole (23 mg, 0.11 mmol, 2 equiv) for 5-bromo-3-methoxyquinoline. $^{1}H$ NMR (400 MHz, Chloroform-d) δ 8.11 (d, J=2.0 Hz, 1H), 7.59 (d, J=8.6 Hz, 2H), 7.37 (s, 1H), 7.17 (d, J=2.0 Hz, 1H), 7.11 (d, J=1.1 Hz, 1H), 6.95-6.90 (m, 2H), 6.86 (t, J=8.0 Hz, 1H), 5.20 (s, 2H), 4.02 (s, 3H), 3.93 (t, J=6.5 Hz, 2H), 2.97 (t, J=6.5 Hz, 2H), 2.17 (s, 3H); $^{19}F$ NMR (376 MHz, $CDCl_3$) δ −60.06; LCMS (ESI) Method 2: >95%, $R_T$=1.226 min, m/z=507.0 $[M+H]^+$.

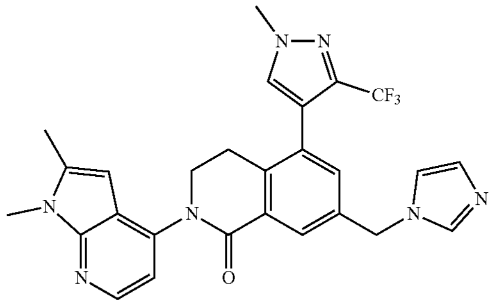

Example 28

7-((1H-Imidazol-1-yl)methyl)-2-(1,2-dimethyl-1H-pyrrolo[2,3-b]pyridin-4-yl)-5-(1-methyl-3-(trifluoromethyl)-1H-pyrazol-4-yl)-3,4-dihydroisoquinolin-1(2H)-one The title compound (23 mg, 0.044 mmol, 65% yield) was prepared following the Buchwald coupling procedure described in Example 12, substituting 4-bromo-1,2-dimethyl-1H-pyrrolo[2,3-b]pyridine (30 mg, 0.13 mmol, 2 equiv) for 5-bromo-3-methoxyquinoline. $^{1}H$ NMR (400 MHz, Chloroform-d) δ 8.26 (d, J=5.2 Hz, 1H), 8.17 (d, J=2.0 Hz, 1H), 7.55 (s, 1H), 7.37 (s, 1H), 7.13 (d, J=2.0 Hz, 1H), 7.08 (s, 1H), 6.97 (d, J=5.2 Hz, 1H), 6.93 (s, 1H), 6.10 (d, J=1.2 Hz, 1H), 5.17 (s, 2H), 4.02-3.99 (m, 5H), 3.79 (s, 3H), 2.97 (t, J=6.3 Hz, 2H), 2.44 (d, J=1.0 Hz, 3H), LCMS (ESI) Method 2: >95%, $R_T$=1.204 min, m/z=520.0 $[M+H]^+$.

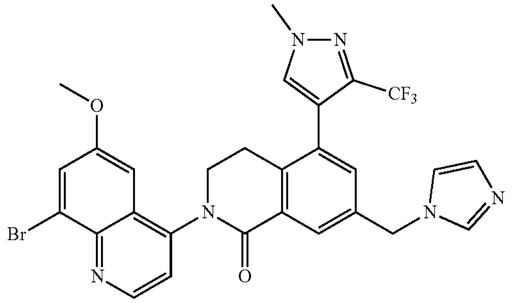

Example 29

7-((1H-Imidazol-1-yl)methyl)-2-(8-bromo-6-methoxyquinolin-4-yl)-5-(1-methyl-3-(trifluoromethyl)-1H-pyrazol-4-yl)-3,4-dihydroisoquinolin-1(2H)-one The title compound (1.01 g, 1.66 mmol, 96% yield) was prepared following the Buchwald coupling procedure described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 650 mg, 1.73 mmol, 1 equiv) and 8-bromo-4-iodo-6-methoxyquinoline (Intermediate 20, 1.07 g, 2.94 mmol, 1.7 equiv). $^{1}H$ NMR (400 MHz, Chloroform-d) δ 8.96 (d, J=4.6 Hz, 1H), 8.16 (d, J=2.0 Hz, 1H), 7.81 (d, J=2.7 Hz, 1H), 7.57 (s, 1H), 7.41 (s, 1H), 7.38 (d, J=4.6 Hz, 1H), 7.18 (d, J=2.0 Hz, 1H), 7.11 (d, J=1.4 Hz, 1H), 7.07 (d, J=2.7 Hz, 1H), 6.95 (t, J=1.3

Hz, 1H), 5.20 (s, 2H), 4.03 (s, 3H), 3.99 (dd, J=11.5, 4.3 Hz, 1H), 3.87 (s, 3H), 3.82-3.75 (m, 1H), 3.15 (ddd, J=16.2, 11.0, 5.3 Hz, 1H), 3.03-2.93 (m, 1H); LCMS (ESI) Method 2: >95%, $R_T$=1.204 min, m/z=611.0 $[M+H]^+$.

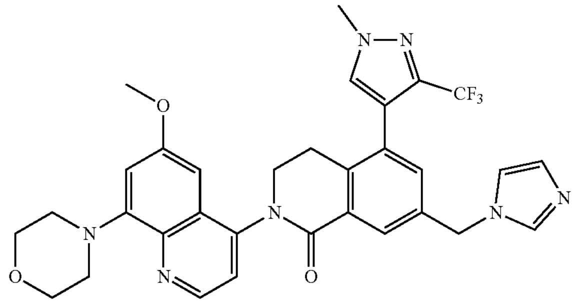 [SMILES: COc1cc(N2CCOCC2)c2nccc(N3CCc4c(cc(Cn5ccnc5)cc4-c4cn(C)nc4C(F)(F)F)C3=O)c2c1]

Example 30

7-((1H-Imidazol-1-yl)methyl)-2-(6-methoxy-8-morpholinoquinolin-4-yl)-5-(1-methyl-3-(trifluoromethyl)-1H-pyrazol-4-yl)-3,4-dihydroisoquinolin-1(2H)-one The title compound (12 mg, 0.019 mmol, 30% yield) was prepared following the Buchwald coupling procedure described in Example 12, using 7-((1H-Imidazol-1-yl)methyl)-2-(8-bromo-6-methoxyquinolin-4-yl)-5-(1-methyl-3-(trifluoromethyl)-1H-pyrazol-4-yl)-3,4-dihydroisoquinolin-1(2H)-one (Example 29, 40 mg, 0.065 mmol, 1 equiv) and morpholine (11 mg, 0.13 mmol, 2 equiv). $^1$H NMR (400 MHz, Chloroform-d) δ 8.77 (d, J=4.6 Hz, 1H), 8.16 (d, J=2.0 Hz, 1H), 7.59 (s, 1H), 7.40 (d, J=1.0 Hz, 1H), 7.30 (d, J=4.61 Hz, 1H), 7.17 (d, J=2.0 Hz, 1H), 7.10 (s, 1H), 6.95 (s, 1H), 6.81 (d, J=2.6 Hz, 1H), 6.72 (d, J=2.6 Hz, 1H), 5.20 (s, 2H), 4.05-4.00 (m, 7H), 4.00-3.91 (s, 1H), 3.84 (s, 3H), 3.78 (dt, J==12.4, 5.2 Hz, 1H), 3.58-3.48 (m, 2H), 3.30 (dd, J=10.9, 5.3 Hz, 2H), 3.13 (ddd, J=16.3, 11.0, 5.2 Hz, 1H), 2.96 (dt, J=16.3, 4.7 Hz, 1H); $^{19}$F NMR (376 MHz, $CDCl_3$) δ −60.18; LCMS (ESI) Method 2: >95%, $R_T$=1.204 min, m/z=618.1 $[M+H]^+$.

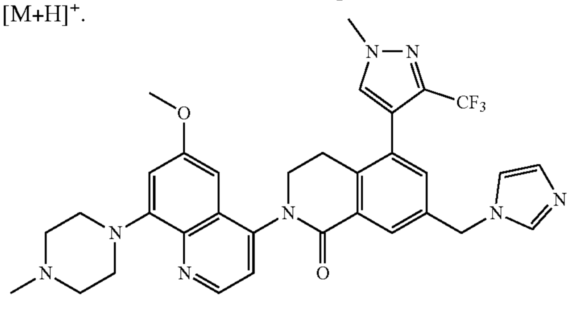

Example 31

7-((1H-Imidazol-1-yl)methyl)-2-(6-methoxy-8-(4-methylpiperazin-1-yl)quinolin-4-yl)-5-(1-methyl-3-(trifluoromethyl)-1H-pyrazol-4-yl)-3,4-dihydroisoquinolin-1(2H)-one The title compound (28 mg, 0.045 mmol, 34% yield) was prepared following the Buchwald coupling procedure described in Example 12, using 7-((1H-Imidazol-1-yl)methyl)-2-(8-bromo-6-methoxyquinolin-4-yl)-5-(1-methyl-3-(trifluoromethyl)-1H-pyrazol-4-yl)-3,4-dihydroisoquinolin-1(2H)-one (Example 29, 80 mg, 0.13 mmol, 1 equiv), 1-methylpiperazine (26 mg, 0.26 mmol, 2 equiv), and sodium tert-butoxide (31 mg, 0.33 mmol, 2.5 equiv) at a reaction temperature of 100° C. $^1$H NMR (400 MHz, Chloroform-d) δ 8.76 (d, J=4.6 Hz, 1H), 8.15 (d, J=2.0 Hz, 1H), 7.55 (d, J=1.1 Hz, 1H), 7.39 (d, J=1.1 Hz, 1H), 7.28 (d, J=4.5 Hz, 1H), 7.15 (d, J=2.0 Hz, 1H), 7.08 (d, J=1.1 Hz, 1H), 6.93 (t, J=1.3 Hz, 1H), 6.81 (d, J=2.6 Hz, 1H), 6.69 (d, J=2.6 Hz, 1H), 5.18 (s, 2H), 4.01 (s, 3H), 3.94 (ddd, 3=12.3, 10.9, 4.3 Hz, 1H), 3.82 (s, 3H), 3.77 (dt, J=12.4, 5.2 Hz, 1H), 3.51 (brs, 2H), 3.34 (brs, 2H), 3.12 (ddd, J=16.3, 11.0, 5.2 Hz, 1H), 2.94 (dt, J=163, 4.7 Hz, 1H), 2.76 (brs, 4H), 2.40 (s, 3H); LCMS (ESI) Method 2: >95%, $R_T$=1.471 min, m/z=631.1 $[M+H]^+$.

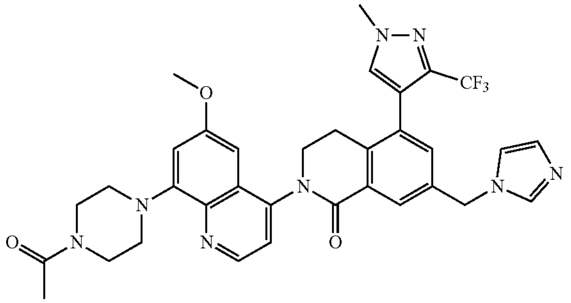 [SMILES: COc1cc(N2CCN(C(C)=O)CC2)c2nccc(N3CCc4c(cc(Cn5ccnc5)cc4-c4cn(C)nc4C(F)(F)F)C3=O)c2c1]

Example 32

7-((1H-imidazol-1-yl)methyl)-2-(8-(4-acetylpiperazin-1-yl)-6-methoxyquinolin-4-yl)-5-(1-methyl-3-(trifluoromethyl)-1H-pyrazol-4-yl)-3,4-dihydroisoquinolin-1(2H)-one The title compound (28 mg, 0.042 mmol, 32% yield) was prepared following the Buchwald coupling procedure described in Example 31, substituting 1-acetylpiperazine (34 mg, 0.26 mmol, 2 equiv) for 1-methylpiperazine. $^1$H NMR (400 MHz, Chloroform-d) δ 8.78 (d, J=4.6 Hz, 1H), 8.14 (d, J=2.0 Hz, 1H), 7.55 (s, 1H), 7.40 (d, J=1.1 Hz, 1H), 7.30 (d, J=4.6 Hz, 1H), 7.17 (d, J=2.0 Hz, 1H), 7.08 (d, J=1.3 Hz, 1H), 6.94 (d, J=1.3 Hz, 1H), 6.78 (d, J=2.6 Hz, 1H), 6.73 (d, J=2.5 Hz, 1H), 5.18 (s, 2H), 4.05-3.99 (s, 4H), 3.99-3.92 (m, 1H), 3.86-3.75 (m, 7H), 3.58 (dt, J=10.2, 4.7 Hz, 1H), 3.36 (ddd, J=10.9, 7.3, 3.3 Hz, 1H), 3.31-3.19 (m, 2H), 3.13 (ddd, J=16.3, 11.0, 5.2 Hz, 1H), 2.95 (dt, J=16.3, 4.7 Hz, 1H), 2.15 (s, 3H); $^{19}$F NMR (376 MHz, $CDCl_3$) δ −60.16; LCMS (ESI) Method 2: >95%, $R_T$=1.142 min, m/z=659.2 $[M+H]^+$.

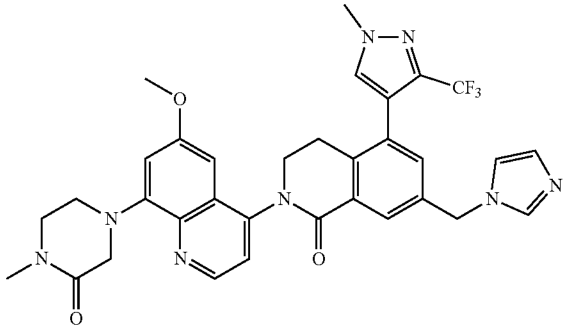 [SMILES: COc1cc(N2CCN(C)C(=O)C2)c2nccc(N3CCc4c(cc(Cn5ccnc5)cc4-c4cn(C)nc4C(F)(F)F)C3=O)c2c1]

Example 33

7-((1H-Imidazol-1-yl)methyl)-2-(6-methoxy-8-(4-methyl-3-oxopiperazin-1-yl)quinolin-4-yl)-5-(1-methyl-3-(trifluoromethyl)-1H-pyrazol-4-yl)-3,4-dihydroisoquinolin-1(2H)-one The title compound (19 mg, 0.029 mmol, 23% yield) was prepared following the Buchwald coupling procedure described in Example 31, substituting 1-methylpiperazin-2-one (30 mg, 0.26 mmol, 2 equiv) for 1-methylpiperazine. $^{1}$H NMR (400 MHz, Chloroform-d) δ 8.77 (d, J=4.6 Hz, 1H), 8.15 (d, J=2.0 Hz, 1H), 7.56 (s, 1H), 7.40 (s, 1H), 7.32 (d, J=4.6 Hz, 1H), 7.17 (d, J=2.0 Hz, 1H), 7.09 (s, 1H), 6.94 (s, 1H), 6.77 (d, J=25 Hz, 1H), 6.74 (d, J=2.5 Hz, 1H), 5.19 (s, 2H), 4.05 (s, 2H), 4.02 (s, 3H), 4.00-3.89 (m, 2H), 3.83 (s, 3H), 3.78 (dt, J=12.3, 5.1 Hz, 1H), 3.63 (tt, J=10.6, 5.3 Hz, 2H), 3.56-3.47 (m, 1H), 3.13 (ddd, J=16.2, 10.9, 5.2 Hz, 1H), 3.05 (s, 3H), 2.96 (dt, J=16.3, 4.7 Hz, 1H); $^{19}$F NMR (376 MHz, $CDCl_3$) δ −60.16; LCMS (ESI) Method 2: >95%, $R_T$=1.135 min, m/z=645.2 [M+H]$^+$.

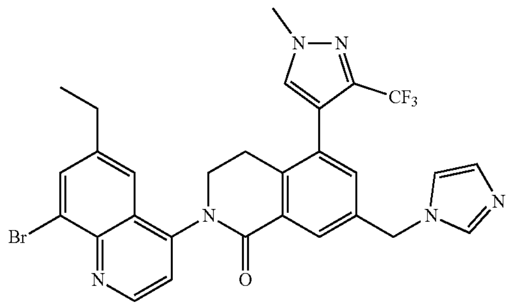

Example 34

7-((1H-Imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one The title compound (398 mg, 0.65 mmol, 98% yield) was prepared following the Buchwald coupling procedure described for Example 29, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 250 mg, 0.66 mmol, 1 equiv) and 8-bromo-6-ethyl-4-iodoquinoline (Intermediate 21, 482 mg, 1.33 mmol, 2 equiv). LCMS (ESI): m/z=609.0 [M+H]$^+$.

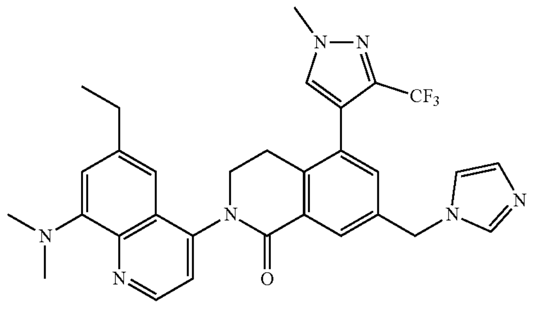

Example 35

7-((1H-Imidazol-1-yl)methyl)-2-(8-(dimethylamino)-6-ethylquinolin-4-yl)-5-(1-methyl-3-(trifluoromethyl)-1H-pyrazol-4-yl)-3,4-dihydroisoquinolin-1(2H)-one The title compound (28 mg, 0.048 mmol, 29% yield) was prepared following the Buchwald coupling procedure described in Example 31, using 7-((1H-Imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 100 mg, 0.16 mmol, 1 equiv) and dimethylamine hydrochloride (27 mg, 0.33 mmol, 2 equiv) at 115° C. $^{1}$H NMR (400 MHz, Chloroform-d) δ 8.87 (d, J=4.5 Hz, 1H), 8.16 (d, J=2.0 Hz, 1H), 7.56 (s, 1H), 7.40 (s, 1H), 7.29 (d, J=4.5 Hz, 1), 7.19 (d, J=1.7 Hz, 1H), 7.16 (d, J=2.0 Hz, 1H), 7.09 (s, 1H), 7.00 (d, J=1.8 Hz, 1H), 6.94 (s, 1H), 5.18 (s, 2H), 4.01 (s, 3H), 3.95 (ddd, J=12.3, 10.6, 4.4 Hz, 1H), 3.81 (dt, J=12.3, 5.3 Hz, 1H), 3.14 (ddd, J=16.0, 10.6, 5.2 Hz, 1H), 3.08 (s, 6H), 2.95 (dt, J=16.3, 4.9 Hz, 1H), 2.75 (q, J=7.5 Hz, 2H), 1.28 (t, J=7.6 Hz, 3H); $^{19}$F NMR (376 MHz, $CDCl_3$) δ −60.09, LCMS (ESI): >95, m/z=574.2 [M+H]$^+$.

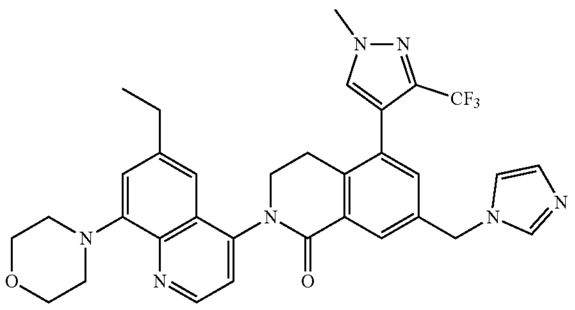

Example 36

7-((1H-Imidazol-1-yl)methyl)-2-(6-ethyl-8-morpholinoquinolin-4-yl)-5-(1-methyl-3-(trifluoromethyl)-1H-pyrazol-4-yl)-3,4-dihydroisoquinolin-1(2H)-one The title compound (14 mg, 0.022 mmol, 22% yield) was prepared following the Buchwald coupling procedure described in Example 35, substituting morpholine (17 mg, 0.20 mmol, 2 equiv) for dimethylamine hydrochloride. $^{1}$H NMR (400 MHz, Chloroform-d) δ 8.87 (d, J=4.6 Hz, 1H), 8.16 (d, J=2.0 Hz, 1H), 7.57 (s, 1H), 7.40 (s, 1H), 7.30 (d, J=4.5 Hz, 1H), 7.25 (s, 1H), 7.17 (d, J=2.0 Hz, 1H), 7.10 (s, 1H), 7.02 (d, J=1.7 Hz, 1H), 6.95 (s, 1H), 5.19 (s, 2H), 4.09-4.03 (m, 4H), 4.02 (s, 3H), 3.96 (ddd, J=12.2, 10.6, 4.3 Hz, 1H), 3.80 (dt, J=12.3, 5.3 Hz, 1H), 3.57-3.47 (m, 2H), 3.34-3.23 (m, 2H), 3.15 (ddd, J=16.1, 10.7, 5.3 Hz, 1H), 2.96 (dt, J=16.3, 4.8 Hz, 1H), 2.77 (q, J=7. Hz, 2H), 1.28 (t, J=7.6 Hz, 3H); $^{19}$F NMR (376 MHz, $CDCl_3$) δ −60.11; LCMS (ESI) Method 2: >95%, $R_T$=1.204 min, m/z=616.2 [M+H]$^+$.

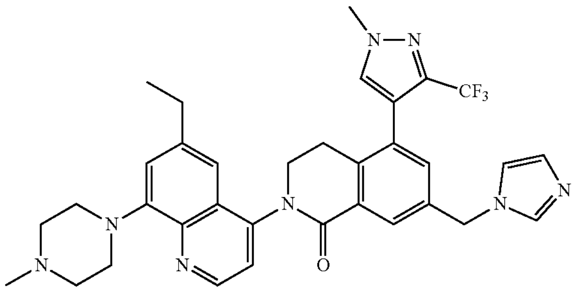

Example 37

7-((1H-Imidazol-1-yl)methyl)-2-(6-ethyl-8-(4-methylpiperazin-1-yl)quinolin-4-yl)-5-(1-methyl-3-(trifluoromethyl)-1H-pyrazol-4-yl)-3,4-dihydroisoquinolin-1(2H)-one The title compound (23 mg, 0.036 mmol, 28% yield) was prepared following the Buchwald coupling procedure described in Example 35, substituting 1-methylpiperazine (26 mg, 0.26 mmol, 2 equiv) for dimethylamine hydrochloride. $^{1}$H NMR (400 MHz, $CDCl_3$) δ 8.86 (d, J=4.6 Hz, 1H), 8.15 (d, J=2.0 Hz, 1H), 7.56 (s, 1H), 7.40 (s, 1H), 7.28 (d, J=4.5 Hz, 1H), 7.23 (d, J=1.6 Hz, 1H), 7.16 (d, J=2.0 Hz, 1H), 7.09 (d, J=1.1 Hz, 1H), 7.02 (d, J=1.9 Hz, 1H), 6.94 (d, J=1.4 Hz, 1H), 5.18 (s, 2H), 4.01 (s, 3H), 3.94 (ddd, J=12.3, 10.7, 4.3 Hz, 1H), 3.80 (dt, J=12.3, 5.3 Hz, 1H), 3.52 (s, 2H), 3.34 (s, 2H), 3.14 (ddd, J=16.0, 10.6, 5.2 Hz, 1H), 2.95 (dt, J=16.3, 4.9 Hz, 1H), 2.83-2.70 (m, 6H), 2.42 (s, 3H), 1.27 (t, J=7.6 Hz, 3H); $^{19}$F NMR (376 MHz, $CDCl_3$) δ −60.10; LCMS (ESI) Method 2: >95%, $R_T$=1.083 min, m/z=629.2 $[M+H]^+$.

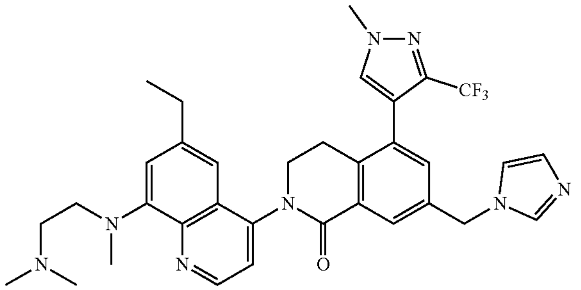

Example 38

7-((1H-Imidazol-1-yl)methyl)-2-(8-((2-(dimethylamino)ethyl)(methyl)amino)-6-ethylquinolin-4-yl)-5-(1-methyl-3-(trifluoromethyl)-1H-pyrazol-4-yl)-3,4-dihydroisoquinolin-1(2H)-one The title compound (22 mg, 0.034 mmol, 28% yield) was prepared following the Buchwald coupling procedure described in Example 31, using 7-((1H-Imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 74 mg, 0.12 mmol, 1 equiv) and N, N, N'-trimethylethylenediamine (25 mg, 0.24 mmol, 2 equiv). $^{1}$H NMR (400 MHz, Chloroform-d) δ 8.84 (d, J=4.5 Hz, 1H), 8.15 (d, J=2.0 Hz, 1H), 7.56 (d, J=1.1 Hz, 1H), 7.40 (d, J=1.1 Hz, 1H), 7.28 (d, J=4.5 Hz, 1), 7.16 (d, J=1.9 Hz, 2H), 7.09 (t, J=1.1 Hz, 1H), 7.00 (d, J=1.8 Hz, 1H), 6.94 (t, J=1.3 Hz, 1), 5.19 (s, 2H), 4.01 (s, 3H), 3.94 (ddd, J=12.3, 10.5, 4.3 Hz, 1H), 3.80 (dt, J=12.2, 5.3 Hz, 1H), 3.69-3.58 (m, 2H), 3.14 (ddd, J=16.0, 11.8, 5.2 Hz, 1H), 3.06 (s, 3H), 2.95 (dt, J=16.3, 4.9 Hz, 1H), 2.74 (q, J=7.5 Hz, 2H), 2.68 (dt, J=8.0, 5.4 Hz, 2H), 2.28 (s, 6H), 1.27 (t, J=7.6 Hz, 3H); $^{19}$F NMR (376 MHz, $CDCl_3$) δ −60.09; LCMS (ESI) Method 2: >95%, $R_T$=1.461 min, m/z=631.2 $[M+H]^+$.

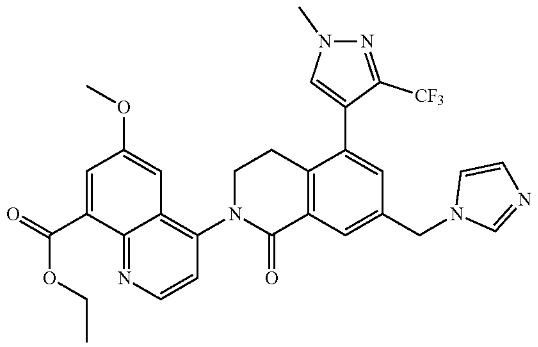 [SMILES: CCOC(=O)c1cc(OC)cc2c(N3CCc4c(cc(Cn5ccnc5)cc4-c4cn(C)nc4C(F)(F)F)C3=O)ccnc12]

Example 39

Ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylate The title compound (1.91 g, 3.16 mmol, 99% yield) was prepared following the Buchwald coupling procedure described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and ethyl 4-bromo-6-methoxyquinoline-8-carboxylate (Intermediate 22, 1.88 g, 6.07 mmol, 1.9 equiv). $^{1}$H NMR (400 MHz, Chloroform-d) δ 8.90 (dd, J=4.6, 1.3 Hz, 1H), 8.11 (d, J=2.0 Hz, 1H), 7.64 (d, J=2.8 Hz, 1H), 7.57 (s, 1H), 7.43 (s, 1H), 7.32 (d, J=4.6 Hz, 1H), 7.18 (d, J=2.0 Hz, 1H), 7.16 (d, J=2.8 Hz, 1H), 7.06 (s, 1H), 6.92 (t, J=1.3 Hz, 1H), 5.16 (s, 2H), 4.50 (q, J=71 Hz, 2H), 4.04-3.93 (m, 4H), 3.85 (s, 3H), 3.74 (dt, J=12.3, 5.1 Hz, 1H), 3.12 (ddd, J=16.3, 10.9, 5.2 Hz, 1H), 2.96 (dt, J=16.4, 4.7 Hz, 1H), 1.42 (t, J=7.1 Hz, 3H); LCMS (ESI) Method 2: >95%, $R_T$=1.190 min, m/z=605.4 $[M+H]^+$.

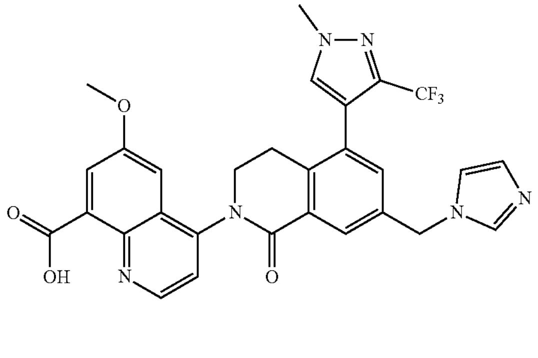 [SMILES: COc1cc(C(=O)O)c2nccc(N3CCc4c(cc(Cn5ccnc5)cc4-c4cn(C)nc4C(F)(F)F)C3=O)c2c1]

Example 40

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylic acid Ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylate (Example 39, 1.9123 g, 3.16 mmol) was dissolved in THF (12 mL) at room temperature. Water (4.0 mL) and LiOH (151.5 mg, 6.33 mml) were added and the reaction mixture was stirred overnight. The reaction was concentrated and was purified by silica gel chromatography (0-10% MeOH:$CH_2Cl_2$) to yield Example 41 (1.54 g, 2.67 mmol, 85% yield). LCMS (ESI) Method 2: >95%, $R_T$=1.180 min, m/z=577.2 $[M+H]^+$.

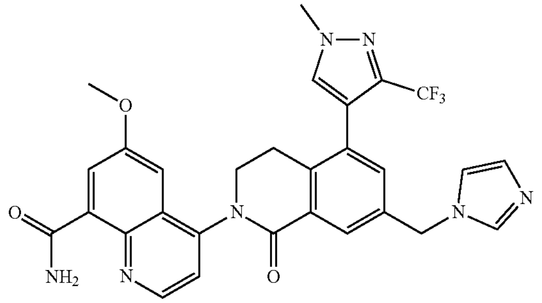 [SMILES: COc1cc(C(N)=O)c2nccc(N3CCc4c(cc(Cn5ccnc5)cc4-c4cn(C)nc4C(F)(F)F)C3=O)c2c1]

Example 41

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxamide To a solution of 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylic acid (60 mg, 0.10 mmol, 1 equiv) in 1,4-dioxane (1 mL) was added EDC.HCl (47 mg, 0.21 mmol, 2 equiv), HOBt (32 mg, 0.21 mmol, 2 equiv), and N,N-diisopropylethylamine (54 mg, 0.42 mmol, 4 equiv). The reaction mixture was stirred at room temperature for 10 min then ammonium chloride (45 mg, 0.83 mmol, S equiv) was added After stirring for 14 h at 90° C., the reaction mixture was diluted with EtOAc and washed with 1 M HCl, water, and brine in sequence. The organic layer was dried ($MgSO_4$), filtered and concentrated. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (23.7 mg, 0.041 mmol, 40% yield). $^1H$ NMR (400 MHz, Chloroform-d) δ 10.93 (d, J=5.1 Hz, 1H), 8.84 (d, J=4.6 Hz, 1H), 8.60 (d, J=3.0 Hz, 1H), 8.15 (d, J=2.0 Hz, 1H), 7.57 (s, 1H), 7.40 (d, J=4.5 Hz, 2H), 7.30 (d, J=3.0 Hz, 1H), 7.19 (d, J=2.0 Hz, 1H), 7.11 (d, J=1.1 Hz, 1H), 6.95 (t, J=1.3 Hz, 1H), 6.11 (d, J=5.1 Hz, 1H), 5.20 (s, 2H), 4.05-3.98 (nu, 4H), 3.93 (s, 3H), 3.81 (dt, J=12.2, 5.2 Hz, 1H), 3.17 (ddd, J=16.3, 11.0, 5.2 Hz, 1), 2.99 (dt, J=16.4, 4.7 Hz, 1H); $^{19}F$ NMR (376 MHz, $CDCl_3$) δ −60.13; LCMS, >95%, m/z=576.2 $[M+H]^+$.

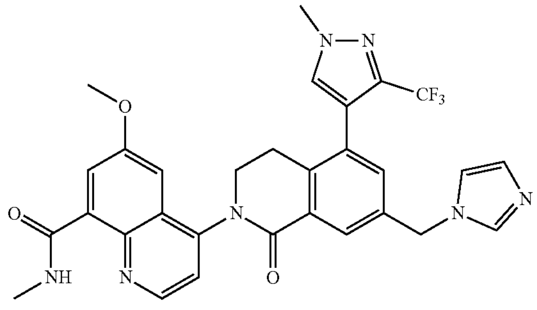 [SMILES: CNC(=O)c1cc(OC)cc2c(N3CCc4c(cc(Cn5ccnc5)cc4-c4cn(C)nc4C(F)(F)F)C3=O)ccnc12]

Example 42

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-methylquinoline-8-carboxamide Step A. Preparation of ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylate (Example 39). 7-((1H-Imidazol-1-yl)methyl)-5-(1-methyl-3-(trifluoromethyl)-1H-pyrazol-4-yl)-3,4-dihydroisoquinolin-1(2l)-one (Intermediate 8 3.2 mmol, 1.0 equiv), ethyl 4-bromo-6-methoxyquinoline-8-carboxylate (Intermediate 22, 1.88 g, 6.1 mmol, 1.9 equiv), cesium carbonate (6.1 mmol, 2 equiv), Xantphos (0.64 mmol, 0.2 equiv), and $Pd_2(dba)_3$ (0.32 mmol, 0.1 equiv) were dissolved in 1,4-dioxane (40 mL) under an Ar. The reaction mixture was stirred for 14 h at 110° C. then cooled to 23° C. Brine was added to the mixture and extracted with EtOAc (3×50 mL). The combined organic layers were dried over $MgSO_4$ and concentrated under reduced pressure. The residue was purified by reverse phase HPLC (Phenomenex Gemini C18, $H_2O/CH_3CN$ gradient from 15-85% $CH_3CN$, 0.1% TFA) followed by neutralization with sat. aq. $NaHCO_3$ to yield the title compound (1.91 g, 3.16 mmol, 99% yield). $^1H$ NMR (400 MHz, Chloroform-d) δ 8.90 (dd, J=4.6, 1.3 Hz, 1H), 8.11 (d, J=2.0 Hz, 1H), 7.64 (d, J=2.8 Hz, 1H), 7.57 (s, 1H), 7.43 (s, 1H), 7.32 (d, J=4.6 Hz, 1H), 7.18 (d, J=2.0 Hz, 1H), 7.16 (d, J=2.8 Hz, 1H), 7.06 (s, 1H), 6.92 (t, J=1.3 Hz, 1H), 5.16 (s, 2H), 4.50 (q, J=7.1 Hz, 2H), 4.04-3.93 (m, 4H), 3.85 (s, 3H), 3.74 (dt, J=12.3, 5.1 Hz, 1H), 3.12 (ddd, J=16.3, 10.9, 5.2 Hz, 1H), 2.96 (dt, J=16.4, 4.7 Hz, 1H), 1.42 (t, J=7.1 Hz, 3H); LCMS (ESI) Method 2: >95%, $R_T$=1.190 min, m/z=605.4 $[M+H]^+$.

Step B. Preparation of 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylic acid (Example 40). Ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylate (Example 39, 1.9123 g, 3.16 mmol) was dissolved in THF (12 mL) at room temperature. Water (4.0 mL) and LiOH (151.5 mg, 6.33 mmol) were added and the reaction mixture was stirred overnight. The reaction was concentrated and was purified by silica gel chromatography (0-10% MeOH:$CH_2Cl_2$) to yield Example 40 (1.54 g, 2.67 mmol, 85% yield). LCMS (ESI) Method 2: >95%, $R_T$=1.180 min, m/z=577.2 $[M+H]^+$.

Step C. Preparation of 4-(7-((1H-imidazol-1-yl)methyl)-5-(1-methyl-3-(trifluoromethyl)-1H-pyrazol-4-yl)-1-oxo-3,4-dihydroisoquinolin-2(1)-yl)-6-methoxy-N-methylquinoline-8-carboxamide. To a solution of 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylic acid (3.9 g, 6.8 mmol, 1 equiv) in DMF (10 mL) was added HATU (3.5 g, 10 mmol, 1.5 equiv). After stirring at room temperature for 10 min, the reaction was cooled to 0° C. Methylamine hydrochloride (4.6 g, 68 mmol, 10 equiv) and N,N-diisopropylethylamine (5.9 mL, 34 mmol, 5 equiv). were added then stirred for additional 2 h at 0° C. and allowed to warm to room temperature. The reaction mixture was diluted with EtOAc (50 mL) and washed with 1 M HCl (50 mL), sat. $NaHCO_3$ (50 mL), water (50 mL), and brine (50 ml). The organic layer was then dried ($MgSO_4$), filtered and concentrated. The residue was purified by reverse phase HI-PLC (Phenomenex Gemini C18, $H_2O/CH_3CN$ gradient from 15-80% $CH_3CN$, 0.1% TFA) followed by neutralization with sat. aq. $NaHCO_3$ to yield the title compound (2.7 g, 4.6 mmol, 68% yield). $^1H$ NMR (400 MHz, Chloroform-d) δ 11.09 (d, J=5.1 Hz, 1H), 8.83 (d, J=4.7 Hz, 1H), 8.62 (d, J=3.0 Hz, 1H), 8.15 (d, J=2.0 Hz, 1H), 7.57 (s, 1H), 7.41 (s, 1H), 7.39 (d, J=4.6 Hz, 1H), 7.25 (d, J=3.1 Hz, 1H), 7.19 (d, J=2.0 Hz, 1H), 7.10 (s, 1H), 6.94 (t, J=1.3 Hz, 1H), 5.20 (s, 2H), 4.03 (s, 3H), 3.99 (dd, J=11.4, 4.3 Hz, 1H), 3.92 (s, 3H), 3.80 (dt, J=11.6, 5.1 Hz, 1H), 3.21-3.10 (m, 4H), 2.98 (dt, J=16.4, 4.7 Hz, 1H); $^{19}F$ NMR (376 MHz, Chloroform-d) δ −60.13; LCMS (ESI) Method 2: >95%, $R_T$=1.214 min, m/z=589.9 [M+H]$^+$.

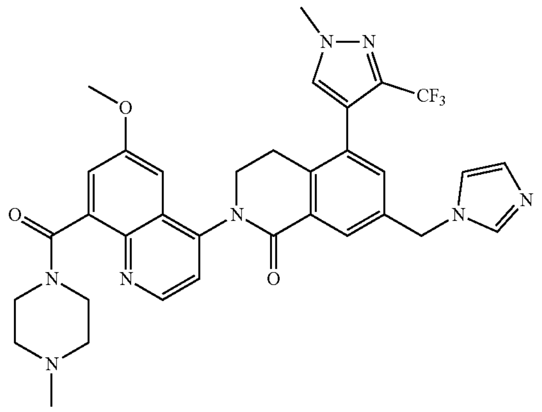 [SMILES: COc1cc(C(=O)N2CCN(C)CC2)c2nccc(N3CCc4c(cc(Cn5ccnc5)cc4-c4cn(C)nc4C(F)(F)F)C3=O)c2c1]

Example 43

7-((1H-Imidazol-1-yl)methyl)-2-(6-methoxy-8-(4-methylpiperazine-1-carbonyl)quinolin-4-yl)-5-(1-methyl-3-(trifluoromethyl)-1H-pyrazol-4-yl)-3,4-dihydroisoquinolin-1(2H)-one The title compound (25 mg, 0.037 mmol, 54% yield) was prepared following the procedure described in Example 42, substituting 1-methylpiperazine (14 mg, 0.14 mmol, 2 equiv) for methylamine hydrochloride. $^1H$ NMR (400 MHz, Chloroform-d) δ 8.82 (t, J=4.4 Hz, 1H), 8.13 (dd, J=10.1, 2.0 Hz, 1H), 7.57 (s, 1H), 7.43-7.38 (m, 1H), 7.34 (d, J=2.6 Hz, 1H), 7.32 (d, J=4.5 Hz, 1H), 7.18 (dd, J=16.1, 2.0 Hz, 1H), 7.08 (t, J=3.4 Hz, 2H), 6.95 (s, 1H), 5.18 (d, J=7.0 Hz, 2H), 4.01 (s, 3H), 3.99-3.89 (m, 3H), 3.85 (s, 3H), 3.76 (tt, J=12.3, 5.2 Hz, 1H), 3.29-3.19 (m, 2H), 3.13 (ddd, J=16.2, 11.1, 5.5 Hz, 1H), 2.97 (dt, J=16.4, 4.8 Hz, 1H), 2.67 (dt, J=10.8, 5.0 Hz, 1H), 2.51 (dt, J=10.9, 5.1 Hz, 1H), 2.45-2.37 (m, 1H), 2.32 (d, J=4.6 Hz, 3H), 2.23 (ddt, J=9.4, 6.9, 3.6

Hz, 1H); $^{19}F$ NMR (376 MHz, $CDCl_3$) δ −60.09; LCMS (ESI) Method 2: >95%, $R_T$=1.072 min, m/z=659.2 [M+H]$^+$.

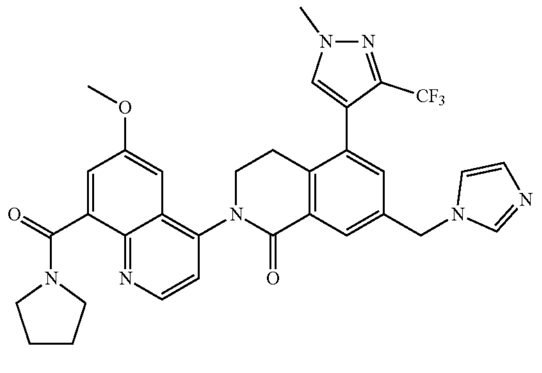 [SMILES: COc1cc(C(=O)N2CCCC2)c2nccc(N3CCc4c(cc(Cn5ccnc5)cc4-c4cn(C)nc4C(F)(F)F)C3=O)c2c1]

Example 44

7-((1H-Imidazol-1-yl)methyl)-2-(6-methoxy-8-(pyrrolidine-1-carbonyl)quinolin-4-yl)-5-(1-methyl-3-(trifluoromethyl)-1H-pyrazol-4-yl)-3,4-dihydroisoquinolin-1(2H)-one The title compound (19 mg, 0.030 mmol, 44% yield) was prepared following the procedure described in Example 42, substituting pyrrolidine (9.9 mg, 0.14 mmol, 2 equiv) for methylamine hydrochloride. $^1H$ NMR (400 MHz, Chloroform-d) δ 8.83 (d, J=4.6 Hz, 1H), 8.14 (d, J=2.0 Hz, 1H), 7.63 (s, 1H), 7.42 (d, J=1.0 Hz, 1H), 7.39 (d, J=2.7 Hz, 1H), 7.31 (d, J=4.6 Hz, 1H), 7.22-7.17 (m, 1H), 7.11-7.06 (m, 2H), 6.95 (d, J=1.3 Hz, 1H), 5.20 (s, 2H), 4.01 (s, 3H), 3.95-3.92 (m, 2H), 3.86 (s, 4H), 3.81-3.65 (m, 2H), 3.18-3.09 (m, 3H), 2.97 (dt, J=16.4, 4.7 Hz, 1H), 2.06-1.93 (m, 2H), 1.89-1.82 (m, 2H); $^{19}F$ NMR (376 MHz, $CDCl_3$) δ −60.09; LCMS (ESI) Method 2: >95%, $R_T$=1.258 min, m/z=630.1 [M+H]$^+$.

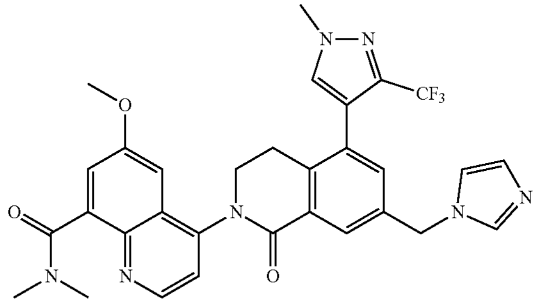 [SMILES: COc1cc(C(=O)N(C)C)c2nccc(N3CCc4c(cc(Cn5ccnc5)cc4-c4cn(C)nc4C(F)(F)F)C3=O)c2c1]

Example 45

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N,N-dimethylquinoline-8-carboxamide The title compound (18 mg, 0.029 mmol, 42% yield) was prepared following the procedure described in Example 42, substituting dimethylamine hydrochloride (11 mg, 0.14 mmol, 2 equiv) for methylamine hydrochloride, $^1H$ NMR (400 MHz, Chloroform-d) δ 8.84 (d, J=4.6 Hz, 1H), 8.20-

8.10 (m, 1H), 7.67 (d, J=14.5 Hz, 1H), 7.42 (s, 1H), 7.36 (d, J=2.7 Hz, 1H), 7.32 (d, J=4.6 Hz, 1H), 7.19 (dd, J=10.9, 2.8 Hz, 1H), 7.11 (s, 1H), 7.08 (d, J=2.8 Hz, 1H), 6.96 (s, 1H), 5.20 (d, J=10.0 Hz, 2H), 4.02 (s, 3H), 3.99-3.90 (m, 1H), 3.86 (s, 3H), 3.74 (dt, J=11.9, 5.2 Hz, 1H), 3.25 (s, 3H), 3.13 (ddt, =17.8, 12.1, 6.1 Hz, 1H), 2.97 (dt, J=16.4, 4.8 Hz, 1H), 2.82 (d, J=18.9 Hz, 3H); $^{19}$F NMR (376 MHz, $CDCl_3$) δ −60.09; LCMS (ESI) Method 2: >95%, $R_T$=1.200 min, m/z=604.2 [M+H]$^+$.

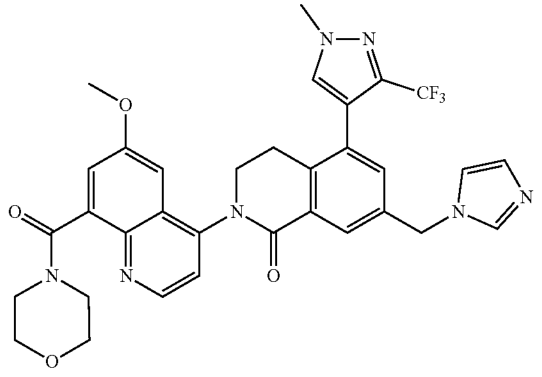 [SMILES: COc1cc(C(=O)N2CCOCC2)c2nccc(N3CCc4c(cc(Cn5ccnc5)cc4-c4cn(C)nc4C(F)(F)F)C3=O)c2c1]

Example 46

7-((1H-Imidazol-1-yl)methyl)-2-(6-methoxy-8-(morpholine-4-carbonyl)quinolin-4-yl)-5-(1-methyl-3-(trifluoromethyl)-1H-pyrazol-4-yl)-3,4-dihydroisoquinolin-1(2H)-one The title compound (25 mg, 0.039 mmol, 57% yield) was prepared following the procedure described in Example 42, substituting morpholine (12 mg, 0.14 mmol, 2 equiv) for methylamine hydrochloride. $^1$H NMR (400 MHz, Chloroform-d) δ 8.82 (t, J=5.0 Hz, 1H), 8.13 (dd, J=11.4, 2.0 Hz, 1H), 7.60 (s, 1H), 7.42 (s, 1H), 7.36 (d, J=2.7 Hz, 1H), 7.33 (d, J=4.5 Hz, 1H), 7.19 (dd, J=13.4, 2.0 Hz, 1H), 7.08 (d, J=2.8 Hz, 2H), 6.95 (s, 1H), 5.19 (d, J=7.6 Hz, 2H), 4.07-4.02 (m, 1H), 4.01 (s, 3H), 3.99-3.88 (m, 3H), 3.86 (s, 3H), 3.82-3.70 (m, 2H), 3.64 (tdt, J=8.8, 5.7, 3.3 Hz, 1H), 3.56-3.45 (m, 1H), 3.28-3.07 (s, 3H), 2.97 (dq, J=16.4, 4.4 Hz, 1H); $^{19}$F NMR (376 MHz, $CDCl_3$) δ −60.08; LCMS (ESI) Method 2: >95%, $R_T$=1.199 min, m/z=646.2 [M+H]$^+$.

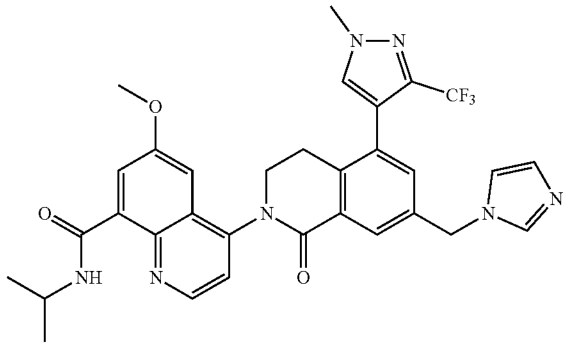 [SMILES: COc1cc(C(=O)NC(C)C)c2nccc(N3CCc4c(cc(Cn5ccnc5)cc4-c4cn(C)nc4C(F)(F)F)C3=O)c2c1]

Example 47

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-isopropyl-6-methoxyquinoline-8-carboxamide The title compound (26 mg, 0.042 mmol, 40% yield) was prepared following the procedure described in Example 42, substituting isopropylamine (12 mg, 0.21 mmol, 2 equiv) for methylamine hydrochloride. $^1$H NMR (400 MHz, Chloroform-d) δ 11.12 (d, J=7.5 Hz, 1H), 8.82 (d, J=4.6 Hz, 1H), 8.58 (d, J=3.0 Hz, 1H), 8.13 (d, J=2.0 Hz, 1H), 7.55 (s, 1H), 7.42 (s, 1H), 7.38 (d, J=4.7 Hz, 1H), 7.23 (d, J=3.0 Hz, 1H), 7.18 (d, J=2.0 Hz, 1H), 7.08 (s, 1H), 6.93 (s, 1H), 5.18 (s, 2H), 4.44-4.29 (m, J=6.6 Hz, 1H), 4.01-3.96 (m, 4H), 3.89 (s, 3H), 3.79 (dt, J=12.2, 5.1 Hz, 1H), 3.15 (ddd, J=16.3, 11.0, 5.3 Hz, 1H), 2.97 (dt, J=16.5, 4.7 Hz, 1H), 1.35 (d, J=6.6 Hz, 6H); LCMS (ESI) Method 2: >95%, $R_T$=1.385 min, m/z 618.1 [M+H]$^+$.

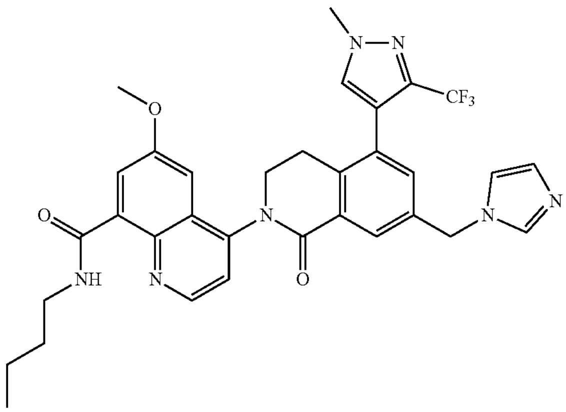 [SMILES: CCCCNC(=O)c1cc(OC)cc2c(N3CCc4c(cc(Cn5ccnc5)cc4-c4cn(C)nc4C(F)(F)F)C3=O)ccnc12]

Example 48

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-butyl-6-methoxyquinoline-8-carboxamide The title compound (6.1 mg, 0.010 mmol, 9% yield) was prepared following the procedure described in Example 42, substituting butylamine (15 mg, 0.21 mmol, 2 equiv) for methylamine hydrochloride. $^1$H NMR (400 MHz, Chloroform-d) δ 11.20 (t, J=5.6 Hz, 1H), 8.83 (d, J=4.7 Hz, 1H), 8.61 (d, J=3.0 Hz, 1H), 8.15 (d, J=2.0 Hz, 1H), 7.57 (s, 1H), 7.41 (s, 1H), 7.39 (d, J=4.7 Hz, 1H), 7.24 (d, J=3.0 Hz, 1H), 7.19 (d, J=2.0 Hz, 1H), 7.10 (s, 1H), 6.94 (s, 1H), 5.20 (s, 2H), 4.02-3.97 (m, 4H), 3.92 (s, 3H), 3.80 (dt, J=12.2, 5.1 Hz, 1H), 3.60 (q, 3=6.6 Hz, 2H), 3.16 (ddd, J=16.2, 11.0, 5.2 Hz, 1H), 2.98 (dt, 3=16.4, 4.6 Hz, 1H), 1.75-1.67 (m, 2H), 1.56-1.43 (m, 2H), 0.99 (t, J=7.3 Hz, 3H); LCMS (ESI) Method 2: >95%, $R_T$=1.425 min, m/z=632.2 [M+H]$^+$.

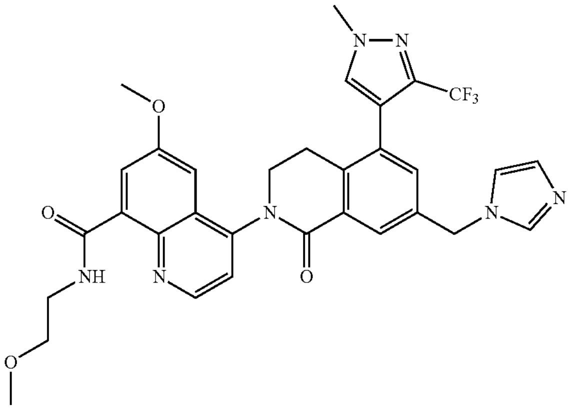 [SMILES: COCCNC(=O)c1cc(OC)cc2c(N3CCc4c(cc(Cn5ccnc5)cc4-c4cn(C)nc4C(F)(F)F)C3=O)ccnc12]

Example 49

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-(2-methoxyethyl)quinoline-8-carboxamide The title compound (8.1 mg, 0.013 mmol, 12% yield) was prepared following the procedure described in Example 42, substituting 2-methoxyethylamine (16 mg, 0.21 mmol, 2 equiv) for methylamine hydrochloride. $^{1}H$ NMR (400 MHz, Chloroform-d) δ 11.42 (t, J=5.6 Hz, 1H), 8.85 (d, J=4.7 Hz, 1H), 8.59 (d, J=3.0 Hz, 1H), 8.15 (d, J=2.0 Hz, 1H), 7.57 (s, 1H), 7.41 (s, 1H), 7.39 (d, J=4.7 Hz, 1H), 7.25 (d, J=3.1 Hz, 1H), 7.19 (d, J=2.0 Hz, 1H), 7.10 (s, 1H), 6.94 (s, 1H), 5.19 (s, 2H), 4.02-3.97 (m, 4H), 3.91 (s, 3H), 3.85-3.75 (m, 3H), 3.71-3.62 (m, 2H), 3.44 (s, 3H), 3.16 (ddd, J=16.3, 11.0, 5.2 Hz, 1H), 2.98 (dt, J=16.4, 4.7 Hz, 1H); LCMS (ESI) Method 2: >95%, $R_T$=1.305 min, m/z 634.2 $[M+H]^+$.

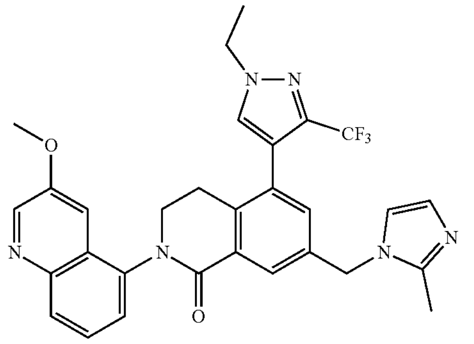 [SMILES: CCn1cc(-c2cc(Cn3ccnc3C)cc3c2CCN(c2cccc4ncc(OC)cc24)C3=O)c(C(F)(F)F)n1]

Example 50

5-(1-Ethyl-3-(trifluoromethyl)-1H-pyrazol-4-yl)-2-(3-methoxyquinolin-5-yl)-7-((2-methyl-1H-imidazol-1-yl)methyl)-3,4-dihydroisoquinolin-1(2H)-one The title compound (31 mg, 0.056 mmol, 56% yield) was prepared following the Buchwald coupling procedure described for Example 2, using 5-(1-ethyl-3-(trifluoromethyl)-1H-pyrazol-4-yl)-7-((2-methyl-1H-imidazol-1-yl)methyl)-3,4-dihydroisoquinolin-1(2H)-one (Intermediate 12, 40 mg, 0.10 mmol, 1 equiv) and 5-bromo-3-methoxyquinoline (47 mg, 0.20 mmol, 2 equiv). $^{1}H$ NMR (400 MHz, Chloroform-d) δ 8.69 (d, J=2.8 Hz, 1H), 8.10 (d, J=2.0 Hz, 1H), 8.05 (d, J=8.4 Hz, 1H), 7.58 (dd, J=8.4, 7.4 Hz, 1H), 7.46 (dd, J=7.4, 1.2 Hz, 1H), 7.41 (s, 1H), 7.30 (d, J=2.8 Hz, 1H), 7.03 (d, J=2.0 Hz, 1H), 6.94 (d, J=1.3 Hz, 1H), 6.87 (d, J=1.3 Hz, 1H), 5.11 (s, 2H), 4.26 (q, J=7.3 Hz, 2H), 4.00 (ddd, J=12.3, 10.6, 4.4 Hz, 1H), 3.87 (s, 3H), 3.75 (dt, J=12.4, 5.3 Hz, 1H), 3.11 (ddd, J=16.1, 10.7, 5.2 Hz, 1H), 2.97 (dt, J=16.4, 5.0 Hz, 1H), 2.35 (s, 3H), 1.57 (t, J=7.3 Hz, 3H); $^{19}F$ NMR (376 MHz, $CDCl_3$) δ −60.04; LCMS (ESI) Method 2: >95%, $R_T$=1.332 min, m/z=561.0 $[M+H]^+$.

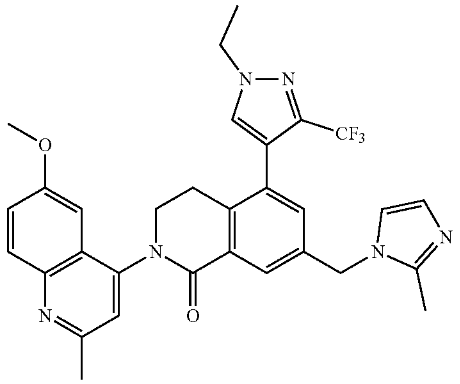 [SMILES: CCn1cc(-c2cc(Cn3ccnc3C)cc3c2CCN(c2cc(C)nc4ccc(OC)cc24)C3=O)c(C(F)(F)F)n1]

Example 51

5-(1-Ethyl-3-(trifluoromethyl)-1H-pyrazol-4-yl)-2-(6-methoxy-2-methylquinolin-4-yl)-7-((2-methyl-1H-imidazol-1-yl)methyl)-3,4-dihydroisoquinolin-1(2H)-one The title compound (36 mg, 0.063 mmol, 64% yield) was prepared following the Buchwald coupling procedure described for Example 2, using 5-(1-ethyl-3-(trifluoromethyl)-1H-pyrazol-4-yl)-7-((2-methyl-1H-imidazol-1-yl)methyl)-3,4-dihydroisoquinolin-1(2H)-one (Intermediate 12, 40 mg, 0.10 mmol, 1 equiv) and 4-bromo-6-methoxy-2-methylquinoline (50 mg, 0.20 mmol, 2 equiv). $^{1}H$ NMR (400 MHz, Chloroform-d) δ 8.13 (d, J=2.0 Hz, 1H), 8.00 (d, J=9.2 Hz, 1H), 7.42 (s, 1H), 7.38 (dd, J=9.2, 2.8 Hz, 1H), 7.23 (s, 1H), 7.04 (d, J=2.4 Hz, 2H), 6.97 (d, J=1.4 Hz, 1H), 6.89 (d, J=1.4 Hz, 1H), 5.14 (s, 2H), 4.28 (q, J=7.4 Hz, 2H), 3.96 (td, J=11.7, 11.3, 4.3 Hz, 1H), 3.86 (s, 3H), 3.79 (dt, J=11.7, 5.2 Hz, 1H), 3.14 (ddd, J=16.1, 10.8, 5.2 Hz, 1H), 2.96 (dt, J=16.4, 4.8 Hz, 1H), 2.73 (s, 3H), 2.37 (s, 3H), 1.59 (t, J=14.7 Hz, 3H); $^{19}F$ NMR (376 MHz, $CDCl_3$) δ −60.08; LCMS (ESI) Method 2: >95%, $R_T$=1.156 min, m/z=574.9 $[M+H]^+$.

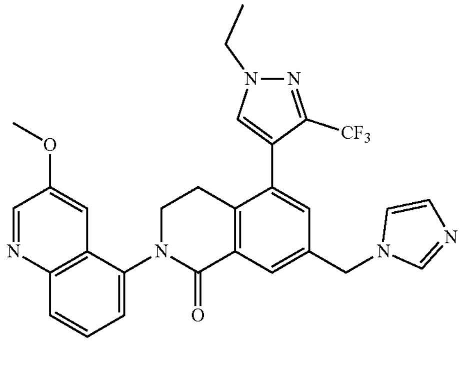 [SMILES: CCn1cc(-c2cc(Cn3ccnc3)cc3c2CCN(c2cccc4ncc(OC)cc24)C3=O)c(C(F)(F)F)n1]

Example 52

7-((1H-Imidazol-1-yl)methyl)-5-(1-ethyl-3-(trifluoromethyl)-1H-pyrazol-4-yl)-2-(3-methoxyquinolin-5-yl)-3,4-dihydroisoquinolin-1(2H)-one The title compound (13 mg, 0.024 mmol, 37% yield) was prepared following the Buchwald coupling procedure described for Example 2, using 7-((1H-imidazol-1-yl)methyl)-5-(1-ethyl-3-(trifluoromethyl)-1H-pyrazol-4-yl)-3,4-dihydroisoquinolin-1(2H)-one (Intermediate 13, 25 mg, 0.064 mmol, 1 equiv) and 5-bromo-3-methoxyquinoline (31 mg, 0.13 mmol, 2 equiv). $^1$H NMR (400 MHz, Chloroform-d) δ 8.71 (d, J=2.9 Hz, 1H), 8.16 (d, J=2.0 Hz, 1H), 8.07 (dt, J=8.5, 1.0 Hz, 1H), 7.60 (dd, J=8.4, 7.4 Hz, 1H), 7.57 (t, J=1.1 Hz, 1H), 7.47 (dd, J=7.4, 1.2 Hz, 1H), 7.43 (d, J=1.0 Hz, 1H), 7.31 (dd, J=2.9, 0.8 Hz, 1H), 7.25 (s, 1H), 7.19 (d, J=2.0 Hz, 1H), 7.09 (t, J=1.1 Hz, 1H), 6.95 (t, =1.3 Hz, 1H), 5.19 (s, 2H), 4.28 (q, J=7.3 Hz, 2H), 4.06-3.96 (m, 1H), 3.89 (s, 3H), 3.77 (dt, J=12.4, 5.3 Hz, 1H), 3.12 (ddd, J=16.0, 10.6, 5.2 Hz, 1H), 2.98 (dt, J=16.4, 4.9 Hz, 1H), 1.58 (t, J=7.4 Hz, 3H); $^{19}$F NMR (376 MHz, $CDCl_3$) δ −60.06; LCMS (ESI) Method 2: >95% $R_T$=1.379 min, m/z=546.9 $[M+H]^+$.

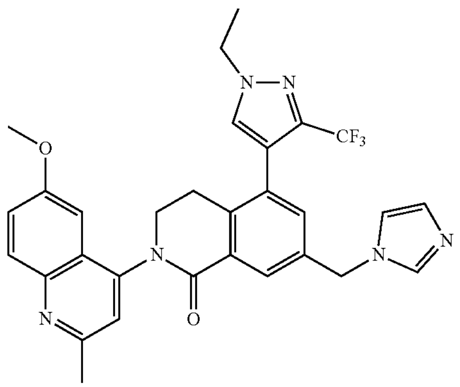 [SMILES: CCn1cc(-c2cc(Cn3ccnc3)cc3c2CCN(c2cc(C)nc4ccc(OC)cc24)C3=O)c(C(F)(F)F)n1]

Example 53

7-((1H-Imidazol-1-yl)methyl)-5-(1-ethyl-3-(trifluoromethyl)-1H-pyrazol-4-yl)-2-(6-methoxy-2-methylquinolin-4-yl)-3,4-dihydroisoquinolin-1(2H)-one The title compound (18 mg, 0.033 mmol, 51% yield) was prepared following the Buchwald coupling procedure described for Example 2, using 7-((1H-imidazol-1-yl)methyl)-5-(1-ethyl-3-(trifluoromethyl)-1H-pyrazol-4-yl)-3,4-dihydroisoquinolin-1(2H)-one (Intermediate 13, 25 mg, 0.064 mmol, 1 equiv) and 4-bromo-6-methoxy-2-methylquinoline (32 mg, 0.13 mmol, 2 equiv). $^1$H NMR (400 MHz, Chloroform-d) δ 8.16 (d, J=2.0 Hz, 1H), 7.99 (d, J=9.2 Hz, 1H), 7.57 (d, J=1.2 Hz, 1H), 7.43 (d, J=1.1 Hz, 1H), 7.37 (dd, J=9.2, 2.8 Hz, 1H), 7.22 (s, 1H), 7.19 (d, J=2.0 Hz, 1H), 7.10 (d, J=1.2 Hz, 1H), 7.03 (d, J=2.8 Hz, 1H), 6.95 (d, J=1.3 Hz, 1H), 5.19 (s, 2H), 4.27 (q, J=7.3 Hz, 2H), 3.96 (ddd, J=12.4, 10.9, 4.3 Hz, 1H), 3.85 (s, 3H), 3.79 (dt, J=12.3, 5.2 Hz, 1H), 3.13 (ddd, J=16.1, 10.8, 5.2 Hz, 1H), 2.96 (dt, J=16.4, 4.8 Hz, 1H), 2.72 (s, 3H), 1.58 (t, J=7.3 Hz, 3H); $^{19}$F NMR (376 MHz, $CDCl_3$) δ −60.07; LCMS (ESI) Method 2: >95%, $R_T$=1.252 min, m/z=561.0 $[M+H]^+$.

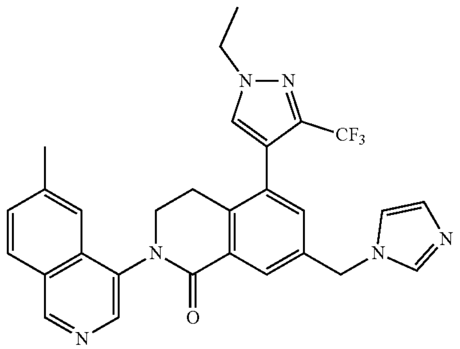 [SMILES: CCn1cc(-c2cc(Cn3ccnc3)cc3c2CCN(c2cncc4ccc(C)cc24)C3=O)c(C(F)(F)F)n1]

Example 54

7-((1H-Imidazol-1-yl)methyl)-5-(1-ethyl-3-(trifluoromethyl)-1H-pyrazol-4-yl)-6'-methyl-3,4-dihydro-1H-[2,4'-biisoquinolin]-1-one The title compound (31 mg, 0.058 mmol, 57% yield) was prepared following the Buchwald coupling procedure described for Example 2, using 7-((1H-imidazol-1-yl)methyl)-5-(1-ethyl-3-(trifluoromethyl)-1H-pyrazol-4-yl)-3,4-dihydroisoquinolin-1(2H)-one (Intermediate 13, 25 mg, 0.064 mmol, 1 equiv) and 4-bromo-6-methylisoquinoline (46 mg, 0.21 mmol, 2 equiv). $^1$H NMR (400 MHz, Chloroform-d) δ 9.17 (d, J=0.8 Hz, 1H), 8.46 (s, 1H), 8.16 (d, J=2.0 Hz, 1H), 7.95 (d, J=8.4 Hz, 1H), 7.59-7.53 (m, 2H), 7.48 (dd, J=8.5, 1.6 Hz, 1H), 7.43 (d, J=1.0 Hz, 1H), 7.19 (d, J=2.0 Hz, 1H), 7.09 (t, J=1.1 Hz, 1H), 6.94 (d, J=1.3 Hz, 1H), 5.18 (s, 2H), 4.27 (q, J=73 Hz, 2H), 3.99 (ddd, J=12.3, 9.4, 4.7 Hz, 1H), 3.85 (ddd, J=12.1, 6.5, 5.2 Hz, 1H), 3.12 (ddd, J=16.2, 9.4, 5.1 Hz, 1H), 3.01 (ddd, J=16.3, 6.5, 4.8 Hz, 1H), 2.54 (s, 3H), 1.57 (t, J=7.3 Hz, 3H); LCMS (ESI) Method 2: >95%, $R_T$=1.183 min, m/z 531.0 $[M+H]^+$.

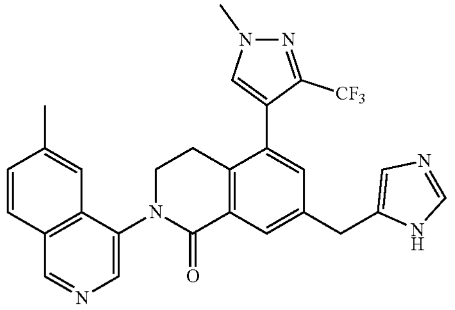 [SMILES: Cc1ccc2cncc(N3CCc4c(cc(Cc5cnc[nH]5)cc4-c4cn(C)nc4C(F)(F)F)C3=O)c2c1]

Example 55

7-((1H-imidazol-5-yl)methyl)-6'-methyl-5-(1-methyl-3-(trifluoromethyl)-1H-pyrazol-4-yl)-3,4-dihydro-1H-[2,4'-biisoquinolin]-1-one Step A. Preparation of 7-(hydroxy(1-trityl-1H-imidazol-5-yl)methyl)-6'-methyl-5-(1-methyl-3-(trifluoromethyl)-1H-pyrazol-4-yl)-3,4-dihydro-1H-[2,4'-biisoquinolin]-1-one. To a solution of 5-iodo-1-trityl-1H-imidazole (0.75 g, 17 mmol) in anhydrous $CH_2Cl_2$ (10 mL) was added 3.0 M ethyl magnesium bromide solution (0.6 mL, 17 mmol) at room temperature. The reaction mixture was stirred at RT for 20 h. A solution of 6'-methyl-5-(1-methyl-3-(trifluoromethyl)-1H-pyrazol-4-yl)-1-oxo-3,4-dihydro-1H-[2,4'-biisoquinoline]-7-carbaldehyde (Intermediate 29, 400 mg, 0.85 mmol) in $CH_2Cl_2$ (10 mL) was added. The resulting mixture was stirred at RT for additional 1 h then quenched with sat. aq. $NH_4Cl$. The organic layer was separated and concentrated. The residue was purified by flash chromatography (Combi-flash Rf, DCM/MeOH=0-10% gradient) to afford the title compound (0.45 g, 67% yield).

Step B. Preparation of 7-((1H-imidazol-5-yl)methyl)-6'-methyl-5-(1-methyl-3-(trifluoromethyl)-1H-pyrazol-4-yl)-3,4-dihydro-1H-[2,4'-biisoquinolin]-1-one. To a sealable pressure flask was added 7-(hydroxy(1 trityl-1H-imidazol-5-yl)methyl)-6'-methyl-5-(1-methyl-3-(trifluoromethyl)-1H-pyrazol-4-yl)-3,4-dihydro-1H-[2,4'-biisoquinolin]-1-one (450 mg, 0.58 mmol), 1,2-dichloroethane (2 mL), TFA (20.0 eq), and triethylsilane (10.0 eq). The flask was sealed and heated at 110° C. for 48 h. The reaction was cooled and concentrated. The residue was dissolved in EtOAc and washed with 1N NaOH. The organic layer was concentrated. The residue was purified by reverse phase HPLC (Phenomenex Gemini C18, $H_2O/CH_3CN$ gradient from 5-95% $CH_3CN$, 0.1% TFA) followed by neutralization with sat. aq. $NaHCO_3$ to yield the title compound (0.11 g, 37% yield). $^1H$ NMR (400 MHz, Chloroform-d) δ 9.16 (s, 1H), 8.45 (s, 1H), 8.11 (d, J=1.4 Hz, 1H), 7.95 (d, J=8.2 Hz, 1H), 7.57 (s, 1H), 7.50-7.46 (m, 2H), 7.42 (s, 1H), 7.37 (s, 1H), 6.79 (s, 1H), 4.02 (s, 2H), 4.01 (s, 3H), 3.99-3.94 (m, 1H), 3.85-3.80 (m, 1H), 3.14-3.06 (m, 1H), 3.02-2.95 (m, 1H), 2.54 (s, 3H). LCMS Method 2: >95% 254 nm, $R_T$=1.13 min, MS (ESI) 517.2 $[M+H]^+$.

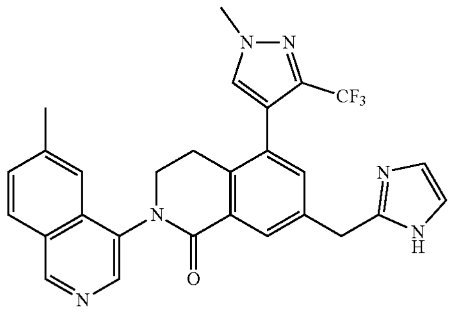 [SMILES: Cc1ccc2cncc(N3CCc4c(cc(Cc5ncc[nH]5)cc4-c4cn(C)nc4C(F)(F)F)C3=O)c2c1]

Example 56

7-((1H-Imidazol-2-yl)methyl)-6'-methyl-5-(1-methyl-3-(trifluoromethyl)-1H-pyrazol-4-yl)-3,4-dihydro-1H-[2,4'-biisoquinolin]-1-one The title compound (120 mg) was prepared following the procedures described in Example 55 substituting 2-iodo-1-trityl-1H-imidazole for 5-iodo-1-trityl-1H-imidazole in Step A. $^1H$ NMR (400 MHz, Methanol-d4) δ 9.21 (s, 1H), 8.47 (s, 1H), 8.15 (d, J=8.4 Hz, 1H), 8.04 (d, J=1.7 Hz, 1H), 7.83 (s, 1H), 7.66 (s, 1H), 7.63 (dd, =8.4, 1.7 Hz, 1H), 7.41 (d, J=1.7 Hz, 1H), 6.97 (s, 2H), 4.18 (s, 2H), 4.07-400 (m, 1H), 4.03 (s, 3H), 3.94-3.88 (m, 1H), 3.23-3.15 (m, 1H), 3.10-3.03 (m, 1H), 2.58 (s, 3H). LCMS Method 2: >95% 254 nm, $R_T$=1.13 min, MS (ESI) 517.2 $[M+H]^+$

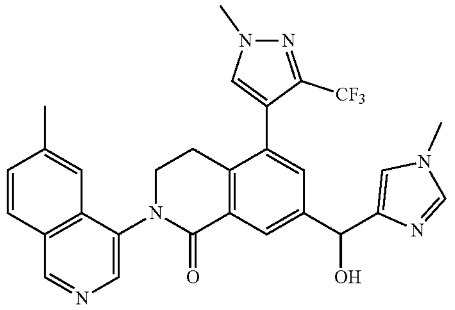 [SMILES: Cc1ccc2cncc(N3CCc4c(cc(C(O)c5cn(C)cn5)cc4-c4cn(C)nc4C(F)(F)F)C3=O)c2c1]

Example 57

7-(Hydroxy(1-methyl-1H-imidazol-4-yl)methyl)-6'-methyl-5-(1-methyl-3-(trifluoromethyl)-1H-pyrazol-4-yl)-3,4-dihydro-1H-[2,4'-biisoquinolin]-1-one The title compound (36 mg, 0.067 mmol, 87%) was prepared following the procedures described in Example 55 Step A, substituting 4-iodo-1-methyl-1H-imidazole for 5-iodo-1-trityl-1H-imidazole. LCMS Method 2: >95% 254 nm, $R_T$=1.14 min, MS (ESI) 547.2 $[M+H]^+$

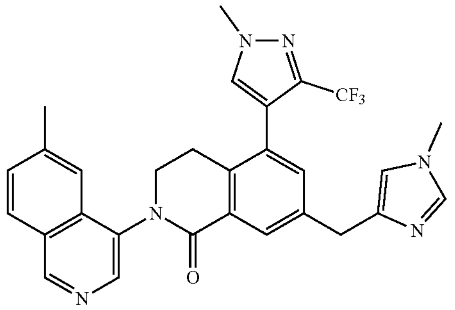 [SMILES: Cc1ccc2cncc(N3CCc4c(cc(Cc5cn(C)cn5)cc4-c4cn(C)nc4C(F)(F)F)C3=O)c2c1]

Example 58

6'-Methyl-7-((1-methyl-1H-imidazol-4-yl)methyl)-5-(1-methyl-3-(trifluoromethyl)-1H-pyrazol-4-yl)-3,4-dihydro-1H-[2,4'-biisoquinolin]-1-one The title compound (84 mg, 69%) was prepared following the procedures described in Example 55 Step B, using 7-(Hydroxy(1-methyl-1H-imidazol-4-yl)methyl)-6'-methyl-5-(1-methyl-3-(trifluoromethyl)-1H-pyrazol-4-yl)-3,4-dihydro-1H-[2,4'-biisoquinolin]-1-one (Example 57, 125 mg, 0.23 mmol). LC-MS Method 2: >95% (254 nm), $R_T$=1.212 min, MS (ESI) 531.2$[M+H]^+$.

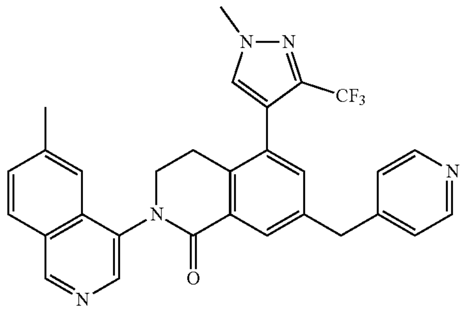 [SMILES: Cc1ccc2cncc(N3CCc4c(cc(Cc5ccncc5)cc4-c4cn(C)nc4C(F)(F)F)C3=O)c2c1]

Example 59

6'-Methyl-5-(1-methyl-3-(trifluoromethyl)-1H-pyrazol-4-yl)-7-(pyridin-4-ylmethyl)-3,4-dihydro-1H-[2,4'-biisoquinolin]-1-one Step A. Preparation of 7-(hydroxy(pyridin-4-yl)methyl)-6'-methyl-5-(1-methyl-3-(trifluoromethyl)-1H-pyrazol-4-yl)-3,4-dihydro-1H-[2,4'-biisoquinolin]-1-one. The title compound was prepared from the procedure described in Example 55 Step A, substituting 4-iodopyridine for 5-iodo-1-trityl-1H-imidazole. LCMS Method 2: >95% 254 nm, $R_T$1.14 min, MS (ESI) 547.2 $[M+H]^+$.

Step B. Preparation of 6'-methyl-5-(1-methyl-3-(trifluoromethyl)-1H-pyrazol-4-yl)-7-(pyridin-4-ylmethyl)-3,4-dihydro-1H-[2,4'-biisoquinolin]-1-one. To a sealable pressure flask was added 7-(hydroxy(pyridin-4-yl)methyl)-6'-methyl-5-(1-methyl-3-(trifluoromethyl)-1H-pyrazol-4-yl)-3,4-dihydro-1H-[2,4'-biisoquinolin]-1-one (50 mg, 0.09 mmol) and phosphorous tribromide (3.0 eq) in THF (1 mL). The flask was, sealed, stirred at room temperature for 30 min then at 80° C. for 2 h. The reaction was cooled to room temperature and concentrated. The residue was dissolved in EtOAc and washed with 1N NaOH, and the organic layer was concentrated. The residue was purified by reverse phase HPLC (Phenomenex Gemini C18, $H_2O/CH_3CN$ gradient from 5-95% $CH_3CN$, 0.1% TFA) followed by neutralization with sat. aq. $NaHCO_3$ to yield the title compound (8 mg, 17% yield). LCMS Method 2: >95% 254 nm, $R_T$=1.54 min, MS (ESI) 528.1 $[M+H]^+$

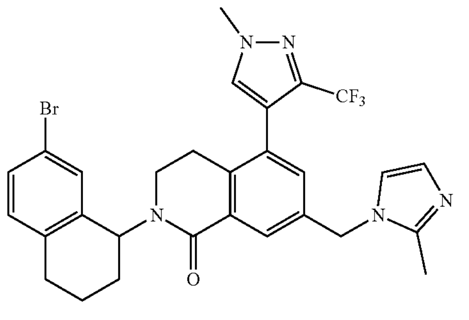 [SMILES: Cc1nccn1Cc1cc2c(c(-c3cn(C)nc3C(F)(F)F)c1)CCN(C1CCCc3ccc(Br)cc31)C2=O]

Example 60

2-(7-Bromo-1,2,3,4-tetrahydronaphthalen-1-yl)-7-((2-methyl-1H-imidazol-1-yl)methyl)-6-(1-methyl-3-(trifluoromethyl)-1H-pyrazol-4-yl)-3,4-dihydroisoquinolin-1(2H)-one To a solution of 7-((2-Methyl-1H-imidazol-1-yl)methyl)-5-(1-methyl-3-(trifluoromethyl)-1H-pyrazol-4-yl)-3,4-dihydroisoquinolin-1(2H)-one (Intermediate 7, 60 mg, 0.15 mmol, 1 equiv) in DMF (0.7 mL) at 0° C. was added sodium hydride (6.2 mg, 0.23 mmol, 1.5 equiv). The reaction mixture was stirred at 0° C. for 20 min, then solution of 1,7-dibromo-1,2,3,4-tetrahydronaphthalene (Intermediate 23, 89 mg, 0.31 mmol, 2 equiv) was in DMF (0.7 mL) was added dropwise. The reaction mixture was warmed slowly to room temperature then quenched by addition of water. The resulting mixture was extracted with $CH_2Cl_2$, dried over $MgSO_4$, and concentrated. The residue was purified by reverse phase HPLC (Phenomenex Gemini C18, $H_2O/CH_3CN$ gradient from 10-95% $CH_3CN$, 0.1% TFA) to yield the title compound (60 mg, 0.1 mmol, 65% yield). $^1H$ NMR (400 MHz, Chloroform-d) δ 8.08 (d, J=2.0 Hz, 1H), 7.35-7.29 (m, 2H), 7.29-7.24 (m, 1H), 6.99 (d, J=8.2 Hz, 1H), 6.94 (d, J=1.5 Hz, 2H), 6.87 (d, J=1.3 Hz, 1H), 6.03 (dd, J=10.3, 6.0 Hz, 1H), 5.11 (s, 2H), 3.97 (s, 3H), 3.27 (ddd, J=12.5, 9.6, 5.2 Hz, 1H), 3.10 (dt, J=12.4, 5.4 Hz, 1H), 2.74 (dd, J=8.1, 4.3 Hz, 2H), 2.70-2.58 (m, 1H), 2.15-2.06 (m, 1H), 2.06-1.93 (m, 2H), 1.91-1.68 (m, 2H); LCMS (ESI) Method 2: >95%, $R_T$=1.570 min, m/z=598.8 $[M+H]^+$.

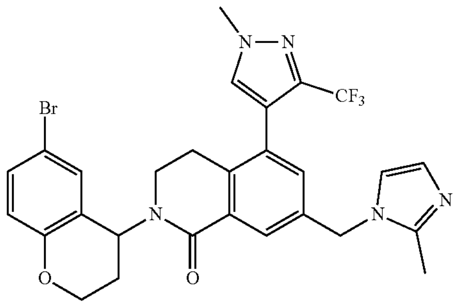 [SMILES: Cc1nccn1Cc1cc2c(c(-c3cn(C)nc3C(F)(F)F)c1)CCN(C1CCOc3ccc(Br)cc31)C2=O]

Example 61

2-(6-Bromochroman-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (33 mg, 0.055 mmol, 61% yield) was prepared following the procedure described for Example 60, substituting 4,6-dibromochromane (Intermediate 24, 52 mg, 0.18 mmol, 2 equiv) for 1,7-dibromo-1,2,3,4-tetrahydronaphthalene (Intermediate 23). $^1H$ NMR (400 MHz, Chloroform-d) δ 8.07 (d, J=2.0 Hz, 1H), 7.32 (s, 1H), 7.26-7.23 (m, 2H), 6.97 (t, J=1.5 Hz, 2H), 6.87 (d, J=1.4 Hz, 1H), 6.75-6.71 (m, 1H), 6.14 (t, J=8.3 Hz, 1H), 5.11 (d, J=2.7 Hz, 2H), 4.35 (dt, J=11.4, 3.9 Hz, 1H), 4.29-4.17 (m, 1H), 3.98 (s, 3H), 3.28 (ddd, J=12.4, 9.3, 5.5 Hz, 1H), 3.15 (dt, J=11.9, 5.4 Hz, 1H), 2.69 (dq, J=10.4, 5.7, 5.1 Hz, 2H), 2.37 (s, 3H), 2.20-2.10 (m, 2H); $^{19}F$ NMR (376 MHz, $CDCl_3$) δ -63.15; LCMS (ESI): >95%, m/z=599.8 $[M+H]^+$.

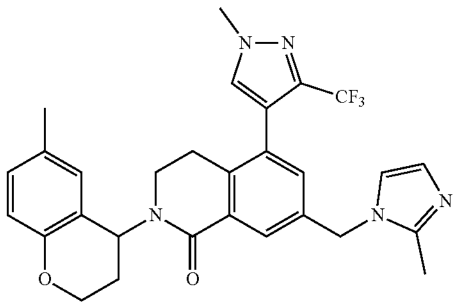 [SMILES: Cc1ccc2c(c1)C(N1CCc3c(cc(Cn4ccnc4C)cc3-c3cn(C)nc3C(F)(F)F)C1=O)CCO2]

Example 62

7-((2-Methyl-1H-imidazol-1-yl)methyl)-5-(1-methyl-3-(trifluoromethyl)-1H-pyrazol-4-yl)-2-(6-methylchroman-4-yl)-3,4-dihydroisoquinolin-1(2H)-one 2-(6-Bromochroman-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (Example 62, 130 mg, 0.22 mmol, 1 equiv), methylboronic acid (26 mg, 0.43 mmol, 2 equiv), cesium carbonate (176 mg, 0.54 mmol, 2.5 equiv), SPhos (17.8 mg, 0.043 mmol, 0.2 equiv), and $Pd(OAc)_2$ (4.0 mg, 0.022 mmol, 0.1 equiv) were dissolved in 1,4-dioxane (2 mL) under Ar. The reaction mixture was stirred for 14 h at 110° C. then cooled to 23° C. Brine was added to the mixture and extracted with EtOAc (3×20 mL). The combined organic layers were dried over $MgSO_4$ and concentrated under reduced pressure. The residue was purified by reverse phase HPLC (Phenomenex Gemini C18, $H_2O/CH_3CN$ gradient from 10-95% $CH_3CN$, 0.1% TFA) followed by neutralization with sat. aq. $NaHCO_3$ to yield the title compound (4 mg, 0.008 mmol, 4% yield). $^1H$ NMR (400 MHz, Chloroform-d) δ 8.08 (d, J=2.0 Hz, 1H), 7.29 (s, 1H), 6.97-6.94 (m, 3H), 6.91 (d, J=2.1 Hz, 1H), 6.87 (d, J=1.4 Hz, 1H), 6.74 (d, J=8.3 Hz, 1H), 6.12 (t, J=8.2 Hz, 1H), 5.11 (s, 2H), 4.31 (dt, J=11.3, 4.1 Hz, 1H), 4.20 (ddd, J=11.4, 8.0, 5.0 Hz, 1H), 3.97 (s, 3H), 3.26 (ddd, J=12.5, 9.0, 5.4 Hz, 1H), 3.15 (dt, J=12.1, 5.6 Hz, 1H), 2.72-2.58 (m, 2H), 2.36 (s, 3H), 2.21 (s, 3H), 2.18-2.11 (m, 2H); $^{19}F$ NMR (376 MHz, $CDCl_3$) δ −60.16; LCMS (ESI): >95%, m/z=535.9 $[M+H]^+$.

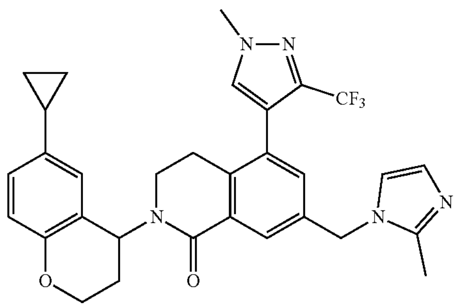 [SMILES: Cc1nccn1Cc1cc2c(c(-c3cn(C)nc3C(F)(F)F)c1)CCN(C1CCOc3ccc(C4CC4)cc31)C2=O]

Example 63

2-(6-Cyclopropylchroman-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (4 mg, 0.006 mmol, 26% yield) was prepared following the procedure described for Example 62, substituting cyclopropylboronic acid (4 mg, 0.050 mmol, 2 equiv) for methylboronic acid. $^1H$ NMR (400 MHz, Chloroform-d) δ 8.08 (d, J=2.0 Hz, 1H), 7.30 (s, 1H), 6.96-6.95 (m, 2H), 6.89-6.85 (m, 2H), 6.84 (d, J=2.2 Hz, 1H), 6.74 (d, J=8.4 Hz, 1H), 6.15-6.07 (m, 1H), 5.11 (s, 2H), 4.30 (dt, J=11.4, 4.1 Hz, 1H), 4.25-4.14 (m, 1H), 3.98 (s, 3H), 3.26 (ddd, J=12.5, 9.4, 5.3 Hz, 1H), 3.14 (dt, J=12.1, 5.4 Hz, 1H), 2.66 (qt, J=10.7, 4.9 Hz, 2H), 2.37 (s, 3H), 2.14 (td, J=9.7, 9.2, 4.0 Hz, 2H), 1.80-1.74 (m, 1H), 0.93-0.80 (m, 2H), 0.61-0.45 (m, 2H); $^{19}F$ NMR (376 MHz, $CDCl_3$) δ −60.19; LCMS (ESI) Method 2: >95%, $R_T$=1.506 min, m/z=562.0 $[M+H]^+$.

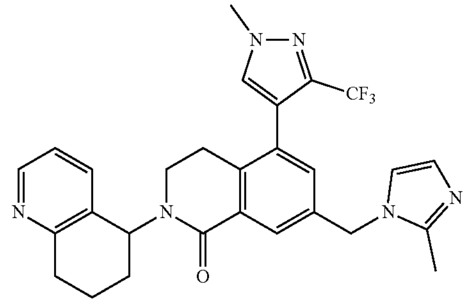 [SMILES: Cc1nccn1Cc1cc2c(c(-c3cn(C)nc3C(F)(F)F)c1)CCN(C1CCCc3ncccc31)C2=O]

Example 64

7-((2-Methyl-1H-imidazol-1-yl)methyl)-5-(1-methyl-3-(trifluoromethyl)-1H-pyrazol-4-yl)-2-(5,6,7,8-tetrahydroquinolin-5-yl)-3,4-dihydroisoquinolin-1(2H)-one To a solution of 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 7, 12.6 mg, 32.4 μmol, 1 equiv) in DMF (1.0 mL) at 0° C. was added NaI (60% in mineral oil, 3.2 mg, 80.9 μmol, 2.5 equiv). After stirring for 15 min, a solution of 5-chloro-5,6,7,8-tetrahydroquinoline (Intermediate 30, 13.6 mg, 80.9 μmol, 2.5 equiv) in DMF (0.5 mL) was added at 0° C. The mixture was stirred for 20 min then warmed to room temperature and stirred for another 30 min. The reaction was quenched by addition of sat. aq. $NH_4Cl$, and the mixture was extracted with EtAOc. The combined organic layers were dried ($Na_2SO_4$) and concentrated. The residue was purified by flash chromatography (Combi-flash Rf, DCM/MeOH=0-10% gradient) to afford the title compound (6 mg, 12 μmol, 36% yield). $^1H$ NMR (400 MHz, Chloroform-d) δ 8.44 (d, J=4.4 Hz, 1H), 8.09 (d, J=1.2 Hz, 1H), 7.50 (d, J=8.0 Hz, 1H), 7.31 (s, 1H), 7.10 (dd, J=4.8, 7.6 Hz, 1H), 6.97 (s, 2H), 6.89 (s, 1H), 6.13 (dd, J=5.2, 10.4 Hz, 1H), 5.12 (s, 2H), 3.98 (s, 3H), 3.29 (m, 1H), 3.08 (m, 1H), 3.00 (m, 2H), 2.68 (m, 2H), 2.37 (s, 3H), 2.15 (m, 2H), 1.94 (m, 1H), 1.2 (m, 1H); LCMS (ESI): >92%, m/z=521.4 $[M+H]^+$.

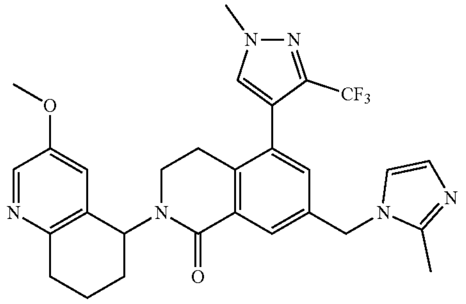 [SMILES: COc1cnc2c(c1)C(N1CCc3c(cc(Cn4ccnc4C)cc3-c3cn(C)nc3C(F)(F)F)C1=O)CCC2]

Example 65

2-(3-Methoxy-5,6,7,8-tetrahydroquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (5.1 mg, 9.3 μmol, 18% yield) was prepared following the procedure described for Example 64, substituting 5-chloro-3-methoxy-5,6,7,8-tetrahydroquinoline (Intermediate 31, 20.3 mg, 103 μmol, 2 equiv) for 5-chloro-5,6,7,8-tetrahydroquinoline (Intermediate 30). $^{1}$H NMR (400 MHz, Chloroform-d) δ 8.16 (d, J=2.4 Hz, 1H), 8.09 (d, J=2.0 Hz, 1H), 7.30 (s, 1H), 7.01 (d, J=2.4 Hz, 1H), 6.96 (m, 2H), 6.88 (s, 1H), 6.09 (m, 1H), 5.12 (s, 2H), 3.98 (s, 3H), 3.77 (s, 3H), 3.29 (m, 1H), 3.08 (m, 1H), 2.90 (m, 2H), 2.67 (m, 2H), 2.36 (s, 3H), 2.13 (m, 2H), 1.93 (m, 1H), 1.78 (m, 1H); LCMS (ESI): >93%, m/z=551.5 $[M+H]^+$.

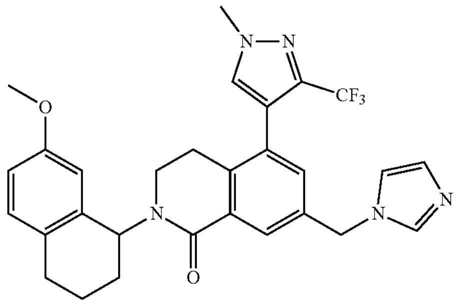

Example 66

7-((1H-Imidazol-1-yl)methyl)-2-(7-methoxy-1,2,3,4-tetrahydronaphthalen-1-yl)-5-(1-methyl-3-(trifluoromethyl)-1H-pyrazol-4-yl)-3,4-dihydroisoquinolin-1(2H)-one The title compound (23 mg, 0.043 mmol, 64% yield) was prepared following the procedure described for Example 60, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 25 mg, 0.067 mmol, 1 equiv) and 1-bromo-7-methoxy-1,2,3,4-tetrahydronaphthalene (Intermediate 25, 48 mg, 0.20 mmol, 3 equiv). $^{1}$H NMR (400 MHz, Chloroform-d) δ 8.13 (d, J=2.0 Hz, 1H), 7.60 (s, 1H), 7.31 (d, J=1.1 Hz, 1H), 7.12-7.07 (m, 2H), 7.03 (d, J=8.2 Hz, 1H), 6.94 (s, 1H), 6.76-6.70 (m, 2H), 6.02 (dd, J=10.1 6.0 Hz, 1H), 5.17 (s, 2H), 3.96 (s, 3H), 3.70 (s, 3H), 3.27 (ddd, J=12.5, 10.2, 4.7 Hz, 1H), 3.13 (dt, J=12.5, 5.4 Hz, 1H), 2.75-2.58 (m, 4H), 2.14-2.08 (m, 1H), 2.00-1.94 (m, 1H), 1.89-1.69 (in 2H); $^{19}$F NMR (376 MHz, $CDCl_3$) δ -60.15; LCMS (ESI) Method 2: >95%, $R_T$=1.570 min, m/z=535.9 $[M+H]^+$.

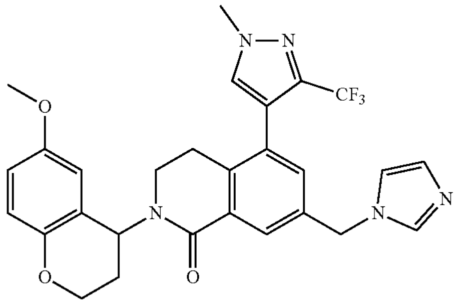

Example 67

7-((1H-Imidazol-1-yl)methyl)-2-(6-methoxychroman-4-yl)-5-(1-methyl-3-(trifluoromethyl)-1H-pyrazol-4-yl)-3,4-dihydroisoquinolin-1(2H)-one The title compound (27 mg, 0.050 mmol, 63% yield) was prepared following the procedure described for Example 60, using 7-((1H-imidazol-1-yl)methyl)-5-(1-methyl-3-(trifluoromethyl)-1H-pyrazol-4-yl)-3,4-dihydroisoquinolin-1(2l)-one (Intermediate 8, 25 mg, 0.067 mmol, 1 equiv) and 4-bromo-6-ethoxychromane (Intermediate 26, 58 mg, 0.24 mmol, 3 equiv). $^{1}$H NMR (400 MHz, Chloroform-d) δ 8.11 (d, J=2.0 Hz, 1H), 7.56 (s, 1H), 7.30 (d, J=1.1 Hz, 1H), 7.10 (d, J=2.0 Hz, 1H), 7.08 (d, J=1.1 Hz, 1H), 6.93 (d, J=1.3 Hz, 1H), 6.77 (d, J=8.9 Hz, 1H), 6.73 (dd, J=8.9, 2.9 Hz, 1H), 6.64 (d, J=2.8 Hz, 1H), 6.12 (dd, J=9.3, 7.2 Hz, 1H), 5.17 (s, 2H), 4.29 (dt, J=11.3, 4.0 Hz, 1H), 4.17 (ddd, J=11.3, 9.3, 3.7 Hz, 1H), 3.96 (s, 3H), 3.68 (s, 3H), 3.27 (ddd, J=12.4, 9.9, 4.8 Hz, 1H), 3.22-3.13 (m, 1H), 2.74-2.60 (m, 2H), 2.21-2.09 (m, 2H); $^{19}$F NMR (376 MHz, $CDCl_3$) δ -60.1; LCMS (ESI) Method 2: >95%, $R_T$=1.423 min, m/z=538.0 $[M+H]^+$.

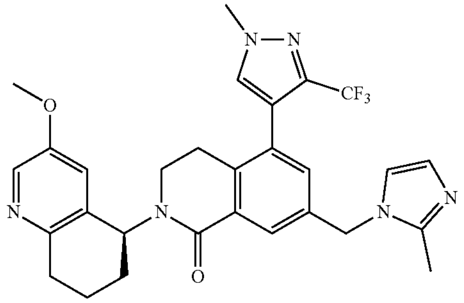 [SMILES: COc1cnc2c(c1)[C@@H](N1CCc3c(cc(Cn4ccnc4C)cc3-c3cn(C)nc3C(F)(F)F)C1=O)CCC2]

Example 68

(S)-2-(3-Methoxy-5,6,7,8-tetrahydroquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (18 mg, 0.033 mmol, 40% yield) was prepared following the bromide displacement procedure described for Intermediate 7, using (S)-7-(bromomethyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one (Intermediate 36, 45 mg, 0.082 mmol, 1 equiv) and 2-methyl-1H-imidazole. $^{1}$H NMR (400 MHz, Chloroform-d) δ 8.16 (d, J=2.4 Hz, 1H), 8.09 (d, J=2.0 Hz, 1H), 7.30 (s, 1H), 7.01 (d, J=2.4 Hz, 1H), 6.96 (m, 2H), 6.88 (s, 1H), 6.09 (m, 1H), 5.12 (s, 2H), 3.98 (s, 3H), 3.77 (s, 3H), 3.29 (m, 1H), 3.08 (m, 1H), 2.90 (m, 2H), 2.67 (m, 2H), 2.36 (s, 3H), 2.13 (m, 2H), 1.93 (m, 1H), 1.78 (m, 1H); LCMS (ESI): >95%, m/z=551.5 $[M+H]^+$.

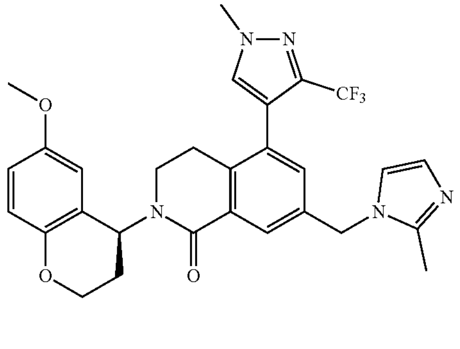

Example 69

(S)-2-(6-Methoxychroman-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (23 mg, 0.041 mmol, 45% yield) was prepared following the bromide displacement procedure described for Intermediate 7, using (S)-7-(bromomethyl)-2-(6-methoxy chroman-4-yl)-5-(1-methyl-3-(trifluoromethyl)-1H-pyrazol-4-yl)-3,4-dihydroisoquinolin-1(2H)-one (Intermediate 40, 50 mg, 0.091 mmol, 1 equiv) and 2-methyl-1H-imidazole. $^1$H NMR (400 MHz, Chloroform-d) δ 8.06 (d, J=2.0 Hz, 1H), 7.29 (d, J=1.0 Hz, 1H), 6.95 (d, J=2.0 Hz, 1H), 6.94 (d, J=1.3 Hz, 1H), 6.86 (d, J=1.4 Hz, 1H), 6.78 (d, J=8.9 Hz, 1H), 6.73 (ddd, J=8.9, 2.9, 0.7 Hz, 1H), 6.64 (dt, J=2.9, 0.7 Hz, 1H), 6.12 (dd, J=9.3, 7.2 Hz, 1H), 5.10 (s, 2H), 4.29 (dt, J=11.3, 4.0 Hz, 1H), 4.17 (ddd, J=11.3, 9.3, 3.7 Hz, 1H), 3.96 (s, 3H), 3.68 (s, 3H), 3.27 (ddd, J=12.4, 10.0, 4.8 Hz, 1H), 3.16 (dt, J=12.5, 5.4 Hz, 1H), 2.66 (tp, J=16.1, 5.1 Hz, 2H), 2.35 (s, 3H), 2.20-2.06 (m, 2H); $^{19}$F NMR (376 MHz, $CDCl_3$) δ −60.15; LCMS (ESI) Method 2: >95%, $R_T$=1.490 min, m/z=552.0 $[M+H]^+$.

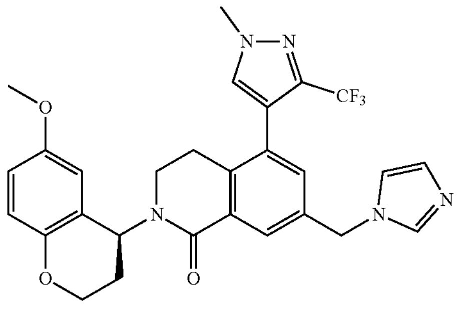

Example 70

(S)-7-((1H-Imidazol-1-yl)methyl)-2-(6-methoxychroman-4-yl)-5-(1-methyl-3-(trifluoromethyl)-1H-pyrazol-4-yl)-3,4-dihydroisoquinolin-1(2H)-one The title compound (25 mg, 0.046 mmol, 51% yield) was prepared following the bromide displacement procedure described for Intermediate 7, using (S)-7-(bromomethyl)-2-(6-methoxychroman-4-yl)-5-(1-methyl-3-(trifluromethyl)-1H-pyrazol-4-yl)-3,4-dihydroisoquinolin-1(2H)-one (Intermediate 40, 50 mg, 0.091 mmol, 1 equiv) and 1H-imidazole (19 mg, 0.27 mmol, 3 equiv). $^1$H NMR (400 MHz, Chloroform-d) δ 8.11 (d, J=2.0 Hz, 1H), 7.55 (d, J=1.2 Hz, 1H), 7.30 (d, J=1.1 Hz, 1H), 7.10 (d, J=2.0 Hz, 1H), 7.08 (d, J=1.1 Hz, 1H), 6.93 (d, J=1.3 Hz, 1H), 6.77 (d, J=8.9 Hz, 1H), 6.73 (ddd, J=8.9, 2.9, 0.7 Hz, 1H), 6.64 (dt, J=2.9, 0.7 Hz, 1H), 6.12 (dd, J=9.3, 7.1 Hz, 1H), 5.17 (s, 2H), 4.29 (dt, J=11.2, 3.9 Hz, 1H), 4.17 (ddd, J=11.3, 9.4, 3.7 Hz, 1H), 3.97 (s, 3H), 3.68 (s, 3H), 3.27 (ddd, J=12.4, 10.0, 4.8 Hz, 1H), 3.16 (dt, J=12.5, 5.4 Hz, 1H), 2.75-2.60 (m, 2H), 2.23-2.07 (m, 2H); $^{19}$F NMR (376 MHz, $CDCl_3$) δ −60.14; LCMS (ESI) Method 2: >95%, $R_T$=1.420 min, m/z=537.9 $[M+H]^+$.

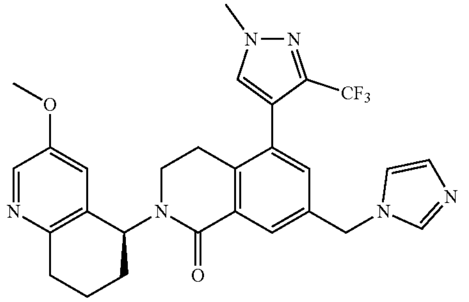 [SMILES: COc1cnc2c(c1)[C@@H](N1CCc3c(cc(Cn4ccnc4)cc3-c3cn(C)nc3C(F)(F)F)C1=O)CCC2]

Example 71

(S)-7-((1H-Imidazol-1-yl)methyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one Step A. Preparation of (R,E)-N-(3-Methoxy-7,8-dihydroquinolin-5(6H)-ylidene)-2-methylpropane-2-sulfinamide. To a solution of 3-methoxy-7,8-dihydroquinolin-5(6-1)-one (241.0 mg, 1.36 mmol, 1 equiv) in THF (9 mL) was added (1)-2-methylpropane-2-sulfinamide (164.8 mg, 1.36 mmol, 1 equiv) and tetraethoxytitanium (570 μL, 2.72 mmol, 2 equiv). The reaction was stirred at 65° C. for 24 h, then quenched with brine. The mixture was extracted with EtOAc. The combined organic layers were dried ($Na_2SO_4$) and concentrated. The residue was purified by flash chromatography (Combi-flash Rf I-ex/EtOAc=0-90% gradient) to afford the title compound (220 mg, 0.78 mmol, 57% yield). $^1$H NMR (400 MHz, Chloroform-d) δ 8.35 (d, J=2.8 Hz, 1H), 7.97 (brs, 1H), 3.90 (s, 3H), 3.29 (m, 1H), 3.09 (m, 3H), 2.09 (m, 2H), 1.34 (s, 9H); LCMS (ESI): m/z=281.4 $[M+H]^+$.

Step B. Preparation of (R)—N—((S)-3-Methoxy-5,6,7,8-tetrahydroquinolin-5-yl)-2-methylpropane-2-sulfinamide. To a solution of (R,E)-N-(3-methoxy-7,8-dihydroquinolin-5(6H)-ylidene)-2-methylpropane-2-sulfinamide (185.0 mg, 0.66 mmol, 1.0 equiv) in THF (6.5 mL) at 0° C. was added L-selectride (1.0 M in THF, 2.0 mL, 2.0 mmol, 3.03 equiv). The reaction was stirred for 5 h, then quenched with sat. aq. $NaHCO_1$. The mixture was extracted with EtOAc. The combined organic layers were dried ($Na_2SO_4$) and concentrated. The residue was purified by flash chromatography (Combi-flash Rf, DCM/MeOH=0-10% gradient) to afford the title compound (185 mg, 0.66 mmol, 99% yield), $^1$H NMR (400 MHz, Chloroform-d) δ 8.17 (d, J=2.8 Hz, 1H), 7.29 (d, J=2.8 Hz, 1H), 4.48 (m, 1H), 3.83 (s, 3H), 3.40 (d, J=10.0 Hz, 1H), 2.89 (m, 2H), 2.38 (m, 1H), 2.02 (m, 1H), 1.88 (m, 2H), 1.28 (s, 9H); LCMS (ESI): m/z=283.2 $[M+H]^+$.

Step C. Preparation of (S)-3-Methoxy-5,6,7,8-tetrahydroquinolin-5-anine hydrochloride. To a solution of (R)—N—((S-3-methoxy-5,6,7,8-tetrahydroquinolin-5-yl)-2-methylpropane-2-sulfinamide (220 mg, 0.78 mmol, 1 equiv) in THF (8 mL) at room temperature was added HCl (4 M in 1,4-dioxane, 1.95 mL, 7.8 mmol, 10 equiv). The mixture was stirred for 2 h then concentrated to provide the title compound (210 mg, 0.78 mmol, quant.), which was used without further purification. $^1$H NMR (400 MHz, Methanol-d4) δ 8.54 (s, 1H), 8.27 (s, 1H), 4.79 (m, 1H), 4.06 (s, 3H), 3.10 (m, 2H), 2.29 (m, 1H), 2.09 (m, 3H); LCMS (ESI): m/z=179.3 $[M+H]^+$.

Step D. Preparation of methyl (S)-5-hydroxy-2-(3-methoxy-5,6,7,8-tetrahydroquinolin-5-yl)-1-oxo-1,2,3,4-tetrahydroisoquinoline-7-carboxylate. To a suspension of (S)-3-methoxy-5,6,7,8-tetrahydroquinolin-5-amine hydrochloride (595 mg, 2.36 mmol, 1.1 equiv) in dichloromethane (20 mL) at 30° C. was added DIPEA (1.12 mL, 6.42 mmol). The mixture was stirred for 15 min, then dimethyl 2-hydroxy-2,3-dihydrobenzofuran-4,6-dicarboxylate (540.0 mg, 2.14 mmol, 1 equiv) and $NaBH(OAc)_3$ (680.3 mg, 3.21 mmol, 1.5 equiv) were added sequentially. The reaction was stirred at 30° C. for 2 h, then concentrated. The residue was dissolved in 1,4-dioxane (10 mL) and heated at 90° C. for 1 h. The mixture was diluted with water and extracted with EtOAc. The combined organic layers were dried ($Na_2SO_4$) and concentrated to provide the title compound (1.1 g), which was used without further purification. $^1$H NMR (400 MHz, Chloroform-d) δ 8.30 (d, J=1.6 Hz, 1H), 8.10 (d, J=2.4 Hz, 1H), 7.52 9d, J=1.6 Hz, 1H), 7.03 (d, J=2.4 Hz, 1H), 6.07 (m, 1H), 3.91 (s, 3H), 3.75 (s, 3H), 3.35 (m, 1H), 3.15 (m, 1H), 3.00 (m, 1H), 2.89 (m, 2H), 2.79 (m, 1H), 2.12 (m, 2H), 1.94 (m, 1H), 1.80 (m, 1H); LCMS (ESI): m/z=383.4 $[M+H]^+$.

Step E. Preparation of methyl (S)-2-(3-methoxy-5,6,7,8-tetrahydroquinolin-5-yl)-1-oxo-5-(((trifluoromethyl)sulfonyl)oxy)-1,2,3,4-tetrahydroisoquinoline-7-carboxylate. To a suspension of methyl (S)-5-hydroxy-2-(3-methoxy-5,6,7,8-tetrahdroquinolin-5-yl)-1-oxo-1,2,3,4-tetrahydroisoquinoline-7-carboxylate (1.1 g crude, 2.14 mmol, 1 equiv) in THF/acetonitrile (10 mL/10 mL) was added DIPEA (2.24 mL, 12.84 mmol, 6 equiv) and 1,1,1-trifluoro-N-phenyl-N-((trifluoromethyl)sulfonyl)methanesulfonamide (1.15 g, 3.21 mmol, 1.5 equiv). The reaction mixture was stirred at 45° C. for 2 h, then quenched with sat. aq. $NaHCO_3$ and extracted with EtOAc. The combined organic layers were dried ($Na_2SO_4$) and concentrated. The residue was purified by flash chromatography (Combi-flash Rf, Hex/EtOAc=10-90% gradient) to afford the title compound (912 mg, 1.77 mmol, 82% yield over two steps). $^1$H NMR (400 MHz, Chloroform-d) δ 8.85 (d, J=1.6 Hz, 1H), 8.18 (d, J=2.4 Hz, 1H), 8.07 (d, J=1.6 Hz, 1H), 7.00 (d, J=2.4 Hz, 1H), 6.09 (m, 1H), 3.98 (s, 3H), 3.78 (s, 3H), 3.43 (m, 1H), 3.25 (m, 1H), 3.08 (m, 1H), 2.96 (m, 3H), 2.15 (m, 2H), 1.93 (m, 1H), 1.80 (m, 1H); LCMS (ESI): m/z=515.4 $[M+H]^+$.

Step F. Preparation of methyl (S)-2-(3-methoxy-5,6,7,8-tetrahydroquinolin-5-yl)-5-(1-methyl-3-(trifluoromethyl)-1H-pyrazol-4-yl)-1-oxo-1,2,3,4-tetrahydroisoquinoline-7-carboxylate (Intermediate 34). To a solution of methyl (S)-2-(3-methoxy-5,6,7,8-tetrahydroquinolin-5-yl)-1-oxo-5-(((trifluoromethyl)sulfonyl)oxy)-1,2,3,4-tetrahydroisoquinoline-7-carboxylate (310.0 mg, 0.6 mmol, 1 equiv) in 1,4-dioxane (6 mL) at room temperature was added sequentially (1-methyl-3-(trifluoromethyl)-1H-pyrazol-4-yl)boronic acid (152 mg, 0.78 mmol, 1.3 equiv), $Na_2CO_3$ (160 mg, 1.51 mmol, 2.5 equiv), $Pd(PPh_3)_4$ (41.8 mg, 0.36 mmol, 0.06 equiv), and water (0.6 mL). The resulting mixture was stirred at 80° C. for 16 h, then diluted with water. The mixture was extracted with EtOAc. The combined organic layers were dried ($Na_2SO_4$) and concentrated. The residue was purified by flash chromatography (Combi-flash R, DCM/MeOH=0-10% gradient) to afford the title compound (348 mg, quant.), which was used without further purification, $^1$H NMR (400 MHz, Chloroform-d) δ 8.86 (d, J=2.0 Hz, 1H), 8.16 (d, J=2.4 Hz, 1H), 8.06 (d, J=1.6 Hz, 1H), 7.38 (s, 1H), 7.02 (d, J=2.0 Hz, 1H), 6.12 (m, 1H), 4.01 (s, 3H), 3.96 (s, 3H), 3.77 (s, 3H), 3.33 (m, 1H), 3.10 (m, 1H), 2.93 (m, 2H), 2.73 (m, 2H), 2.15 (m, 2H), 1.94 (m, 1H), 1.79 (m, 1H); LCMS (ESI): m/z=515.4 $[M+H]^+$.

Step G. Preparation of (S)-7-(Hydroxymethyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one. Lithium triethylborohydride (3 equiv) was added dropwise to a solution of methyl (S)-2-(3-methoxy-5,6,7,8-tetrahydroquinolin-5-yl)-5-(1-methyl-3-(trifluoromethyl)-1H-pyrazol-4-yl)-1-oxo-1,2,3,4-tetrahydroisoquinoline-7-carboxylate (Intermediate 34, 348 mg, 0.6 mmol, 1 equiv) in THF at 0° C. The reaction was stirred for 40 min then quenched with sat. aq. $NaHCO_3$. The mixture was extracted with EtOAc. The combined organic layer was dried over $MgSO_4$, concentrated, and dried under reduced pressure to provide the title compound (290 mg, 0.6 mmol, 99%), which was used without further purification. $^1$H NMR (400 MHz, Chloroform-d) δ 8.20 (d, J=1.6 Hz, 1H), 8.16 (d, J=2.4 Hz, 1H), 7.43 (d, J=1.6 Hz, 1H), 7.36 (s, 1H), 7.03 (d, J=2.0 Hz, 1H), 6.12 (m, 1H), 4.79 (d, J=6.0 Hz, 2H), 4.01 (s, 3H), 3.77 (s, 3H), 3.29 (m, 1H), 3.08 (m, 1H), 2.92 (m, 2H), 2.68 (m, 2H), 2.13 (m, 2H), 1.93 (m, 1H), 1.778 (m, 1H); LCMS (ESI): m/z 487.4 $[M+H]^+$.

Step 11. Preparation of (S)-7-(bromoethyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one. To a solution of (S)-7-(hydroxymethyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one (200 mg, 0.41 mmol, 1 equiv) in dichloromethane (10 mL) at room temperature was added carbon tetrabromide (272 mg, 0.82 mmol, 2 equiv) and $PPh_3$ (113 mg, 0.41 mmol, 1 equiv). The mixture was stirred for 20 min then another batch of $PPh_3$ (113 mg, 0.41 mmol, 1 equiv) was added. The reaction was allowed to stir for another 2 h then concentrated. The residue was purified by flash chromatography (Combi-flash Rf, DCM/MeOH=0-10% gradient) to afford the title compound (563 mg). LCMS (ESI): m/z=549.4 $[M+H]^+$.

Step L Preparation of (S)-7-((1H-Imidazol-1-yl)methyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one. 1H-Imidazole (33 mg, 0.48 mmol, 3 equiv) was added to a solution of (S)-7-(bromoethyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one (45 mg, 0.082 mmol, 1 equiv) in acetonitrile (1.0 mL) at 23° C. The reaction mixture was stirred for 12 h at 50° C., then cooled to ambient temperature, filtered and concentrated. The residue was purified by reverse phase 1-PLC (Phenomenex Gemini C18, $H_2O$/$CH_3CN$ gradient from 15-85% $CH_3CN$, 0.1% TFA) followed by neutralization with sat. aq. $NaHCO_3$ to yield the title compound (35 mg, 0.065 mmol, 40% yield). $^1$H NMR (400 MHz, Chloroform-d) δ 8.16 (d, J=2.8 Hz, 1H), 8.14 (d, J=2.0 Hz, 1H), 7.57 (s, 1H), 7.31 (s, 1H), 7.10 (s, 2H), 7.01 (d, J=2.4 Hz, 1H), 6.95 (s, 1H), 6.09 (m, 1H), 5.19 (s, 2H), 3.99 (s, 3H), 3.77 (s, 3H), 3.30 (m, 1H), 3.08 (m, 1H), 2.93 9m, 2H), 2.69 (m, 2H), 2.14 (m, 2H), 2.93 (m, 1H), 1.78 (m, 1H); LCMS (ESI): >95%, m/z=537.5 $[M+H]^+$.

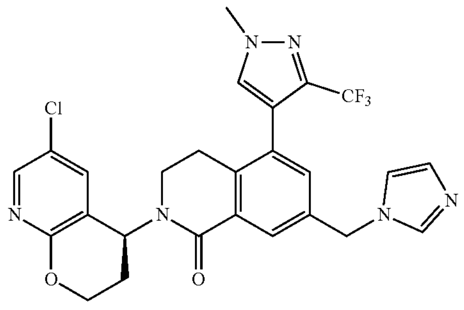 [SMILES: Cn1cc(-c2cc(Cn3ccnc3)cc3c2CCN([C@H]2CCOc4ncc(Cl)cc42)C3=O)c(C(F)(F)F)n1]

Example 72

((S)-7-((1H-Imidazol-1-yl)methyl)-2-(6-chloro-3,4-dihydro-2H-pyrano[2,3-b]pyridin-4-yl)-5-(1-methyl-3-(trifluoromethyl)-1H-pyrazol-4-yl)-3,4-dihydroisoquinolin-1(2H)-one The title compound (23 mg, 0.042 mmol, 56% yield) was prepared following the displacement procedure described for Intermediate 7, substituting (S)-7-(bromomethyl)-2-(6-chloro-3,4-dihydro-2H-pyrano[2,3-b]pyridin-4-yl)-5-(1-methyl-3-(trifluoromethyl)-1H-pyrazol-4-yl)-3,4-dihydroisoquinolin-1(2H)-one (Intermediate 48, 45 mg, 0.075 mmol, 1 equiv). $^1$H NMR (400 MHz, Chloroform-d) δ 8.11 (m, 2H), 7.57 (s, 1H), 7.47 (m, 1H), 7.33 (s, 1H), 7.15 (d, J=2.0 Hz, 1H), 7.11 (s, 1H), 6.94 (s, 1H), 6.22 (t, J=8.8 Hz, 1H), 5.19 (s, 2H), 4.56 (m, 1H), 4.39 (m, 1H), 4.00 (s, 3H), 3.31 (m, 1H), 3.12 (m, 1H), 2.73 (m, 2H), 2.19 (m, 2H); LCMS (ESI): >95%, m/z=543.4 $[M+H]^+$.

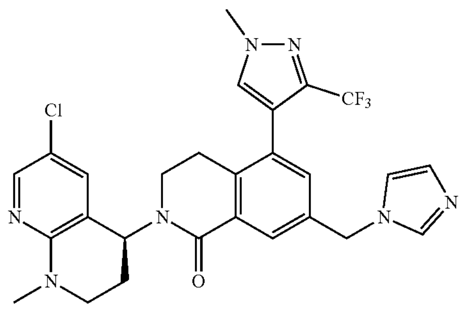 [SMILES: CN1CC[C@H](N2CCc3c(cc(Cn4ccnc4)cc3-c3cn(C)nc3C(F)(F)F)C2=O)c2cc(Cl)cnc21]

Example 73

(S)-7-((1H-Imidazol-1-yl)methyl)-2-(6-chloro-1-methyl-1,2,3,4-tetrahydro-1,8-naphthyridin-4-yl)-5-(1-methyl-3-(trifluoromethyl)-1H-pyrazol-4-yl)-3,4-dihydroisoquinolin-1(2H)-one The title compound (30 mg, 0.054 mmol, 79% yield) was prepared following the displacement procedure described for Intermediate 7, using (S)-7-(bromoethyl)-2-(6-chloro-1-methyl-1,2,3,4-tetrahydro-1,8-naphthyridin-4-yl)-5-(1-methyl-3-(trifluoromethyl)-1H-pyrazol-4-yl)-3,4-dihydroisoquinolin-1(2H)-one (Intermediate 45, 39 mg, 0.069 mmol, 1 equiv) and 1H-Imidazole (33 mg, 0.48 mmol, 3 equiv). $^1$H NMR (400 MHz, Chloroform-d) δ 8.11 (d, J=1.6 Hz, 1H), 7.98 (m, 1H), 7.56 (s, 1H), 7.34 (s, 1H), 7.16 (m, 1H), 7.13 (d, J=1.6 Hz, 1H), 7.10 (s, 1H), 6.93 (s, 1H), 6.05 (dd, J=6.4, 10.4 Hz, 1H), 5.18 (s, 2H), 4.00 (s, 3H), 3.55 (m, 1H), 3.33 (m, 2H), 3.19 (m, 1H), 3.09 (s, 3H), 2.74 (m, 2H), 2.13 (m, 2H); LCMS (ESI): >95%, m/z=556.4 $[M+H]^+$.

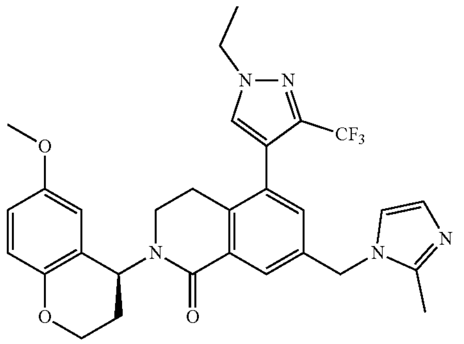 [SMILES: CCn1cc(-c2cc(Cn3ccnc3C)cc3c2CCN([C@H]2CCOc4ccc(OC)cc42)C3=O)c(C(F)(F)F)n1]

Example 74

(S)-5-(1-Ethyl-3-(trifluoromethyl)-1H-pyrazol-4-yl)-2-(6-methoxychroman-4-yl)-7-((2-methyl-1H-imidazol-1-yl)methyl)-3,4-dihydroisoquinolin-1(2H)-one The title compound (31 mg, 0.055 mmol, 61% yield) was prepared following the bromide displacement procedure described for Intermediate 7, using (S)-7-(bromomethyl)-5-(1 ethyl-3-(trifluoromethyl)-1H-pyrazol-4-yl)-2-(6-methoxychroman-4-yl)-3,4-dihydroisoquinolin-1(2H)-one (Intermediate 42, 50 mg, 0.089 mmol, 1 equiv) and 2-methyl-1H-imidazole (20 mg, 0.27 mmol, 3 equiv). $^1$H NMR (400 MHz, Chloroform-d) δ 8.06 (d, J=2.0 Hz, 1H), 7.31 (d, J=1.3 Hz, 1H), 6.97 (d, J=2.0 Hz, 1H), 6.94 (d, J=1.3 Hz, 1H), 6.86 (d, J=1.3 Hz, 1H), 6.77 (d, J=8.9 Hz, 1), 6.73 (dd, J=8.9, 2.9 Hz, 1H), 6.64 (d, J=2.8 Hz, 1H), 6.18-6.08 (m, 1H), 5.10 (s, 2H), 4.33-4.10 (m, 4H), 3.68 (s, 3H), 3.27 (ddd, J=12.4, 10.0, 4.8 Hz, 1), 3.16 (dt, J=12.4, 5.4 Hz, 1H), 2.74-2.59 (m, 2H), 2.35 (s, 3H), 2.21-2.05 (m, 2H), 1.53 (t, J=7.3 Hz, 3H); $^{19}$F NMR (376 MHz, $CDCl_3$) δ −60.06; LCMS (ESI) Method 2: >95%, $R_T$=1.517 min, m/z=565.9 $[M+H]^+$.

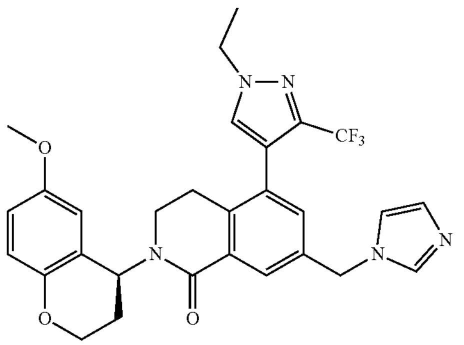 [SMILES: CCn1cc(-c2cc(Cn3ccnc3)cc3c2CCN([C@H]2CCOc4ccc(OC)cc42)C3=O)c(C(F)(F)F)n1]

Example 75

(S)-7-((1H-Imidazol-1-yl)methyl)-5-(1-ethyl-3-(trifluoromethyl)-1H-pyrazol-4-yl)-2-(6-methoxychroman-4-yl)-3,4-dihydroisoquinolin-1(2H)-one The title compound (19 mg, 0.035 mmol, 40% yield) was prepared following the bromide displacement procedure described for Intermediate 7, using (S)-7-(bromomethyl)-5-(1-ethyl-3-(trifluoromethyl)-1H-pyrazol-4-yl)-2-(6-methoxychroman-4-yl)-3,4-dihydroisoquinolin-1(2H)-one (Intermediate 42, 50 mg, 0.089 mmol, 1 equiv) and 1H-imidazole (18 mg, 0.27 mmol, 3 equiv). $^1$H NMR (400 MHz, Chloroform-d) δ 8.11 (d, J=2.0 Hz, 1H), 7.56 (d, J=1.2 Hz, 1H), 7.33 (d, J=1.0 Hz, 1H), 7.12 (d, J=2.0 Hz, 1H), 7.08 (t, J=1.1 Hz, 1H), 6.93 (d, J=1.3 Hz, 1H), 6.78 (d, J=8.9 Hz, 1H), 6.73 (ddd, =8.9, 2.9, 0.7 Hz, 1H), 6.64 (d, J=2.8 Hz, 1H), 6.13 (dd, J=9.3, 7.1 Hz, 1H), 5.17 (s, 2H), 4.35-4.13 (m, 4H), 3.68 (s, 3H), 3.28 (ddd, J=12.4, 10.0, 4.8 Hz, 1H), 3.16 (dt, J=12.4, 5.4 Hz, 1H), 2.75-2.60 (m, 2H), 2.20-2.09 (m, 2H), 1.54 (t, J=7.3 Hz, 3H); $^{19}$F NMR (376 MHz $CDCl_3$) δ −60.06; LCMS (ESI) Method 2: >95%, $R_T$=1.482 min, m/z=552.0 [M+H]$^+$.

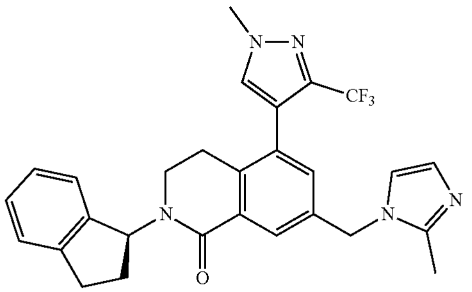 [SMILES: Cc1nccn1Cc1cc2c(c(-c3cn(C)nc3C(F)(F)F)c1)CCN([C@H]1CCc3ccccc31)C2=O]

Example 76

(S)-2-(2,3-Dihydro-1H-inden-1-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one To a solution of (S)-7-(bromoethyl)-2-(2,3-dihydro-1H-inden-1-yl)-5-(1-methyl-3-(trifluoromethyl)-1H-pyrazol-4-yl)-3,4-dihydroisoquinolin-1(2H)-one (Intermediate 49, 32.0 mg, 63 μmol) in acetonitrile (3 mL) was added 2-methyl-1H-imidazole (16.0 mg, 0.19 mmol, 3 equiv). The mixture was stirred at 80° C. for 30 min, then concentrated. The residue was purified by flash chromatography (Combiflash Rf, DCM/MeOH=0-10% gradient) to afford the title compound (15 mg, 0.30 mmol, 47% yield). $^1$H NMR (400 MHz, Chloroform-d) δ 8.10 (d, J=2.0 Hz, 1H), 7.27 (m, 3H), 7.20 (m, 2H), 6.95 (m, 2H), 7.87 (s, 1H), 6.46 (t, J=8.0 Hz, 1H), 5.11 (s, 2H), 3.97 (s, 3H), 3.22 (m, 1H), 3.13 (m, 1), 2.98 (m, 2H), 2.67 (m, 2H), 2.54 (m, 1H), 2.36 (s, 3H), 1.97 (m, 1H); LCMS (ESI): >95%, m/z=506.5 [M+H]$^+$.

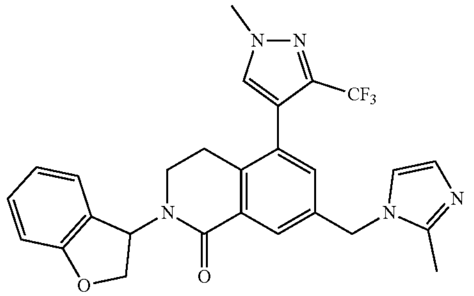 [SMILES: Cc1nccn1Cc1cc2c(c(-c3cn(C)nc3C(F)(F)F)c1)CCN(C1COc3ccccc31)C2=O]

Example 77

2-(2,3-Dihydrobenzofuran-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (14 mg, 27.6 μmol, 44% yield) was prepared following the procedures described in Example 76 using 7-(bromomethyl)-2-(2,3-dihydrobenzofuran-3-yl)-5-(1-methyl-3-(trifluoromethyl)-1H-pyrazol-4-yl)-3,4-dihydroisoquinolin-1(2H)-one (Intermediate 50, 32 mg, 63 μmol, 1 equiv) and 2-methyl-1H-imidazole (16.0 mg, 0.19 mmol, 3 equiv). $^1$H NMR (400 MHz, Chloroform-d) δ 8.05 (d, J=1.6 Hz, 1H), 7.28 (m, 3H), 6.90 (m, 5H), 6.58 (dd, J=3.6, 8.8 Hz, 1H), 5.10 (s, 2H), 4.74 (dd, J=8.8, 10.4 Hz, 1H), 4.41 (dd, J=3.6, 10.4 Hz, 1H), 3.96 (s, 3H), 3.24 (m, 1H), 3.01 (m, 1H), 2.64 (m, 2H), 2.35 (s, 3H); LCMS (ESI): >95%, m/z=508.4 [M+H]$^+$.

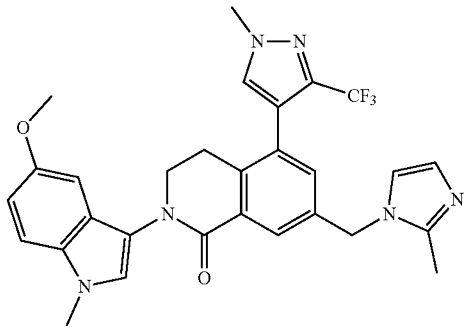

Example 78

2-(5-Methoxy-1-methyl-1H-indol-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one In a sealed tube, 7-((2-methyl-1H-imidazol-1-yl)methyl)-5-(1-methyl-3-(trifluoromethyl)-1H-pyrazol-4-yl)-3,4-dihydroisoquinolin-1(2)-one (Intermediate 7, 40 mg, 0.10 mmol, 1 equiv), 3-iodo-5-methoxy-1-methyl-1H-indole (59 mg, 0.21 mmol, 2 equiv), potassium carbonate (28 mg, 0.21 mmol, 2 equiv), and copper(I) iodide (39 mg, 0.21 mmol, 2 equiv) were dissolved in DMF (1 mL) and placed under Ar. The reaction mixture was stirred for 14 h at 150° C. then cooled to 23° C. Brine was added to the mixture and extracted with EtOAc (3×20 mL). The combined organic layers were dried over $MgSO_4$ and concentrated. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (30 mg, 0.055 moil, 45% yield). $^1H$ NMR (400 MHz, Chloroform-d) δ 8.12 (d, J=2.0 Hz, 1H), 7.35 (d, J=1.2 Hz, 1H), 7.24-7.19 (m, 1H), 7.15 (s, 1H), 6.95 (d, J=2.0 Hz, 1H), 6.93 (d, J=1.3 Hz, 1H), 6.92-6.88 (m, 2H), 6.86 (d, J=1.3 Hz, 1H), 5.10 (s, 2H), 3.99 (s, 3H), 3.92 (t, J=6.4 Hz, 2H), 3.82 (s, 3H), 3.75 (s, 3H), 2.97 (t, J=6.4 Hz, 2H), 2.35 (s, 3H); $^{19}F$ NMR (376 MHz, $CDCl_3$) δ −60.06; LCMS (ESI) Method 2: >95%, $R_T$=1.451 min, m/z=549.0 $[M+H]^+$.

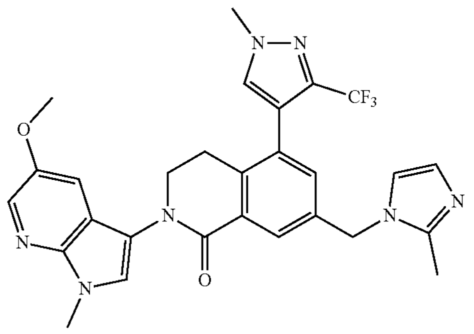

Example 79

2-(5-Methoxy-1-methyl-1H-pyrrolo[2,3-b]pyridin-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (14 mg, 25 μmol, 65% yield) was prepared following the procedure described for Example 12, using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 7, 1 equiv) and 3-iodo-5-methoxy-1-methyl-1H-pyrrolo[2,3-b]pyridine (intermediate 51, 22.6 mg, 78.6 μmol, 2 equiv). $^1H$ NMR (400 MHz, Chloroform-d) δ 8.15 (d, J=2.8 Hz, 1H), 8.12 (d, J=1.0 Hz, 1H), 7.36 (s, 1H), 7.28 (m, 2H), 6.97 (m, 2H), 6.88 (s, 1H), 5.12 (s, 2H), 4.02 (s, 3H), 3.94 (t, J=6.4 Hz, 2H), 3.88 (s, 3H), 3.87 (s, 3H), 2.98 (t, J=6.4 Hz, 2H), 2.37 (s, 3H); LCMS (ESI): >95%, m/z=550.5 $[M+H]^+$.

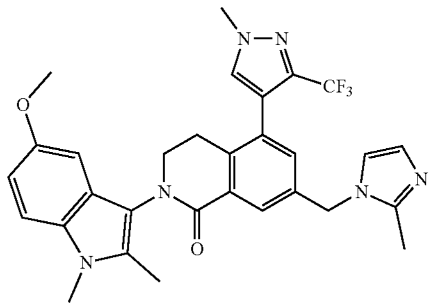 [SMILES: COc1ccc2c(c1)c(N1CCc3c(cc(Cn4ccnc4C)cc3-c3cn(C)nc3C(F)(F)F)C1=O)c(C)n2C]

Example 80

2-(5-Methoxy-1,2-dimethyl-1H-indol-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (3.8 mg, 0.17 mmol, 17% yield) was prepared following the procedure described for Example 12, using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 7, 1 equiv) and 3-iodo-5-methoxy-1,2-dimethyl-1H-indole (Intermediate 52, 23.5 mg, 78 μmol, 2 equiv). $^1H$ NMR (400 MHz, Chloroform-d) δ 8.16 (d, J=1.6 Hz, 1H), 7.36 (s, 1H), 7.20 (d, J=8.4 Hz, 1H), 6.98 (s, 2H), 6.90 (s, 1H), 6.84 (m, 2H), 5.13 (s, 2H), 4.02 (s, 3H), 3.96 (m, 1H), 3.85 (s, 3H), 3.75 (m, 1H), 3.68 (s, 3H), 3.00 (m, 2H), 2.40 (s, 3H), 2.33 (s, 3H); LCMS (ESI): >95%, m/z=563.6 $[M+H]^+$.

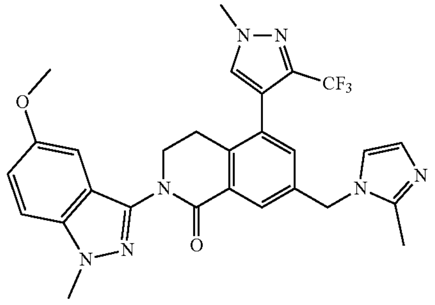 [SMILES: COc1ccc2c(c1)c(N1CCc3c(cc(Cn4ccnc4C)cc3-c3cn(C)nc3C(F)(F)F)C1=O)nn2C]

Example 81

2-(5-Methoxy-1-methyl-1H-indazol-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (8.5 mg, 15 μmol, 40% yield) was prepared following the procedure described for Example 12, using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 7, 1 equiv) and 3-iodo-5-methoxy-1-methyl-1H-indazole (Intermediate 53, 22.2 mg, 77 μmol, 2 equiv). $^1H$ NMR (400 MHz, Chloroform-d) δ 8.16 (d, J=1.6 Hz, 1H), 7.37 (s, 1H), 7.25 (s, 1H), 7.09 (dd, J=2.4, 8.4 Hz, 1H), 7.00 (m, 3H), 6.89 (brs, 1H), 5.13 (s, 2H), 4.11 (t, J=6.4 Hz, 2H), 4.02 (s, 3H), 4.00 (s, 3H), 3.85 (s, 3H), 2.99 (t, J=6.4 Hz, 2H), 2.38 (s, 3H); LCMS (ESI): >95%, m/z=550.4 $[M+H]^+$.

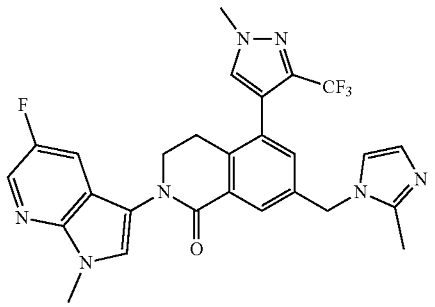 [SMILES: Cc1nccn1Cc1cc2c(c(-c3cn(C)nc3C(F)(F)F)c1)CCN(c1cn(C)c3ncc(F)cc13)C2=O]

Example 82

2-(5-Fluoro-1-methyl-1H-pyrrolo[2,3-b]pyridin-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (7.5 mg, 14 μmol, 40% yield) was prepared following the procedure described for Example 12, using 7-((2-methyl-1H-imidazol-1-yl)methyl)-5-(1-methyl-3-(trifluoromethyl)-1H-pyrazol-4-yl)-3,4-dihydroisoquinolin-(2H)-one (Intermediate 7, 1 equiv) and 5-fluoro-3-iodo-1-methyl-1-pyrrolo[2,3-b]pyridine (Intermediate 54, 19.3 mg, 70 μmol, 2 equiv). $^1$H NMR (400 MHz, Chloroform-d) δ 8.24 (m, 1H), 8.11 (d, J=2.0 Hz, 1H), 7.54 (dd, J=2.4, 8.8 Hz, 1H), 7.37 (s, 1H), 7.36 (s, 1H), 6.98 (m, 2H), 6.89 (s, 1H), 5.13 (s, 2H), 4.02 (s, 3H), 3.93 (t, J=6.4 Hz, 2H), 3.90 (s, 3H), 2.98 (t, J=6.4 Hz, 2H), 2.37 (s, 3H); LCMS (ESI): >95%, m/z=538.4 [M+H]$^+$.

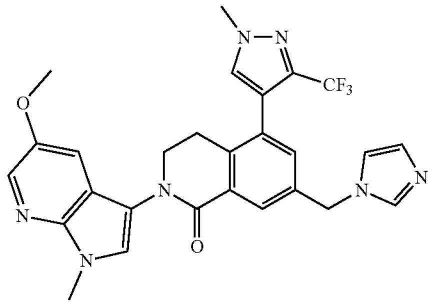 [SMILES: COc1cnc2c(c1)c(N1CCc3c(cc(Cn4ccnc4)cc3-c3cn(C)nc3C(F)(F)F)C1=O)cn2C]

Example 83

7-((1H-Imidazol-1-yl)methyl)-2-(5-methoxy-1-methyl-1H-pyrrolo[2,3-b]pyridin-3-yl)-5-(1-methyl-3-(trifluoroethyl)-1H-pyrazol-4-yl)-3,4-dihydroisoquinolin-1(2H)-one The title compound (35 mg, 65 μmol, 31% yield) was prepared following the procedure described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 80 mg, 0.21 mmol, 1 equiv) and 3-iodo-5-methoxy-1-methyl-1H-pyrrolo[2,3-b]pyridine (Intermediate 51, 123 mg, 0.42 mmol, 2 equiv). $^1$H NMR (400 MHz, Chloroform-d) δ 8.17 (d, J=1.6 Hz, 1H), 8.15 (d, J=2.4 Hz, 1H), 7.57 (s, 1H), 7.37 (s, 1H), 7.28 (m, 2H), 7.13 (d, J=2.0 Hz, 1H), 7.10 (s, 1H), 6.95 (s, 1H), 5.19 (S, 2H), 4.02 (S, 3h), 3.95 (t, J=6.4 Hz, 2H), 3.88 (s, 3H), 3.87 (s, 3H), 2.99 (t, J=6.4 Hz, 2H); LCMS (ESI): >95%, m/z=536.4 [M+H]$^+$.

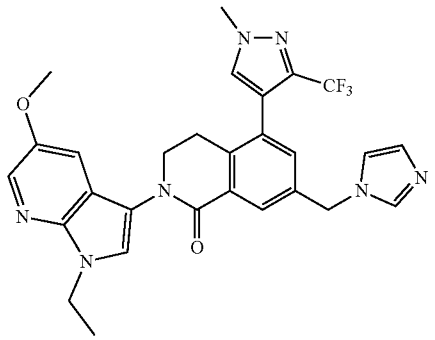 [SMILES: CCn1cc(N2CCc3c(cc(Cn4ccnc4)cc3-c3cn(C)nc3C(F)(F)F)C2=O)c2cc(OC)cnc21]

Example 84

7-((1H-Imidazol-1-yl)methyl)-2-(1-ethyl-5-methoxy-1H-pyrrolo[2,3-b]pyridin-3-yl)-5-(1-methyl-3-(trifluoromethyl)-1H-pyrazol-4-yl)-3,4-dihydroisoquinolin-1(2H)-one The title compound (16 mg, 0.12 mmol, 25% yield) was prepared following the procedure described for Example 12, using 7-((1H-imidazol-1-yl)methyl)-5-(1-methyl-3-(trifluoromethyl)-1H-pyrazol-4-yl)-3,4-dihydroisoquinolin-1(2)-one (Intermediate 8, 1 equiv) and 1-ethyl-3-iodo-5-methoxy-1H-pyrrolo[2,3-b]pyridine (Intermediate 55, 71 mg, 0.24 mmol, 2 equiv). $^1$H NMR (400 MHz, Chloroform-d) δ 8.16 (s, 1H), 8.13 (d, J=2.4 Hz, 1H), 7.59 (brs, 1H), 7.38 (s, 1H), 7.31 (s, 1H), 7.29 (d, J=2.4 Hz, 1H), 7.13 (m, 2H), 6.96 (brs, 1H), 5.19 (s, 2H), 4.32 (q, 0.1=7.2 Hz, 2H), 4.02 (s, 3H), 3.96 (t, J=6.4 Hz, 2H), 3.87 (s, 3H), 2.98 (t, J=6.4 Hz, 2H), 1.50 (t, J=7.2 Hz, 3H); LCMS (ESI): >95%, m/z=550.5 [M+H]$^+$.

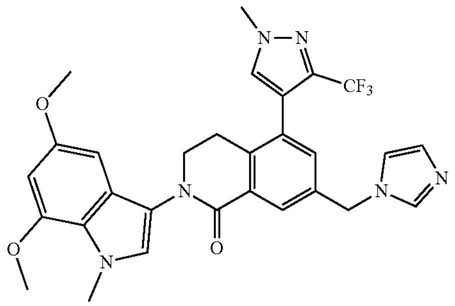 [SMILES: COc1cc(OC)c2c(c1)c(N1CCc3c(cc(Cn4ccnc4)cc3-c3cn(C)nc3C(F)(F)F)C1=O)cn2C]

Example 85

7-((1H-Imidazol-1-yl)methyl)-2-(5,7-dimethoxy-1-methyl-1H-indol-3-yl)-5-(1-methyl-3-(trifluoromethyl)-1H-pyrazol-4-yl)-3,4-dihydroisoquinolin-1(2H)-one The title compound (10 mg, 18 μmol, 16% yield) was prepared following the procedures described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 1 equiv) and 3-iodo-5,7-dimethoxy-1-methyl-1H-indole (Intermediate 56, 69 mg, 0.22 mmol, 2 equiv). $^1$H NMR (400 MHz, Chloroform-d) δ 8.18 (d, J=1.6 Hz, 1H), 7.57 (s, 1H), 7.37 (s, 1H), 7.11 (m, 2H), 7.01 (s, 1H), 6.94 (s, 1H), 6.41 (d, J=2.0 Hz, 1H), 6.32 (d, J=2.0 Hz, 1H), 5.18 (s, 2H), 4.02 (s, 3H), 3.99 (s, 3H), 3.89 (m, 5H), 3.81 (s, 3H), 2.97 (t, J=6.4 Hz, 2H); LCMS (ESI): >95%, m/z=565.4 [M+H]$^+$.

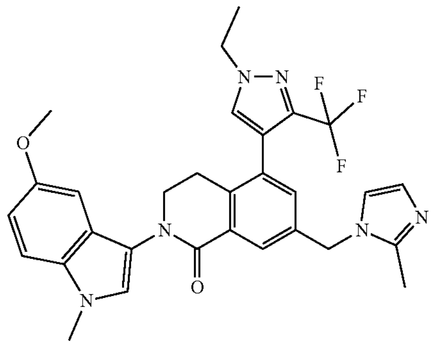 [SMILES: CCn1cc(-c2cc(Cn3ccnc3C)cc3c2CCN(c2cn(C)c4ccc(OC)cc24)C3=O)c(C(F)(F)F)n1]

Example 86

5-(1-Ethyl-3-(trifluoromethyl)-1H-pyrazol-4-yl)-2-(5-methoxy-1-methyl-1H-indol-3-yl)-7-((2-methyl-1H-imidazol-1-yl)methyl)-3,4-dihydroisoquinolin-1(2H)-one The title compound (23 mg, 0.043 mmol, 64% yield) was prepared following the procedure described for Example 78, substituting 5-(1-ethyl-3-(trifluoromethyl)-1H-pyrazol-4-yl)-7-((2-methyl-1H-imidazol-1-yl)methyl)-3,4-dihydroisoquinolin-1(2H)-one (Intermediate 12, 40 mg, 0.10 mmol, 1 equiv). $^1$H NMR (400 MHz, Chloroform-d) δ 8.13 (d, J=2.0 Hz, 1H), 7.38 (d, J=1.2 Hz, 1H), 7.25-7.20 (m, 1H), 7.16 (s, 1H), 6.97 (d, J=2.0 Hz, 1H), 6.94 (d, J=1.3 Hz, 1H), 6.90 (d, J=7.5 Hz, 2H), 6.87 (d, J=1.3 Hz, 1H), 5.10 (s, 2H), 4.26 (q, J=7.3 Hz, 2H), 3.92 (t, J=6.4 Hz, 2H), 3.82 (s, 3H), 3.76 (s, 3H), 2.97 (t, J=6.4 Hz, 2H), 2.35 (s, 3H), 1.57 (t, J=7.3 Hz, 3H); $^{19}$F NMR (376 MHz, $CDCl_3$) δ −59.98.

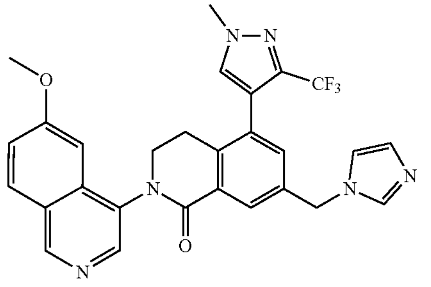

Example 87

7-((1H-imidazol-1-yl)methyl)-6'-methoxy-5-(1-methyl-3-(trifluoromethyl)-1H-pyrazol-4-yl)-3,4-dihydro-1H-[2,4'-biisoquinolin]-1-one To a solution of 7-((1H-imidazol-1-yl)methyl)-1'-chloro-6'-methoxy-5-(1-methyl-3-(trifluoromethyl)-1H-pyrazol-4-yl)-3,4-dihydro-1H-[2,4-biisoquinolin]-1-one (Example 21, 50 mg, 0.09 mmol) in 2 mL of methanol was added 50 mg of 10% Palladium on Carbon. The reaction was degassed and stirred under an atmosphere of hydrogen for 48 h. The reaction mixture was filtered off and the filtrate was concentrated to dryness. The residue was purified by flash chromatography (Combi-flash Rf, DCM/MeOH=0-10% gradient) followed by reverse phase HPLC (Phenomenex Gemini C18, $H_2O/CH_3CN$ gradient from 5-95% $CH_3CN$, 0.1% TFA) to afford the title compound (8 mg, 17% yield). $^1$H NMR (400 MHz, Methanol-d4) δ 9.11 (s, 1H), 8.43 (s, 1H), 8.13 (d, J=9.0 Hz, 1H), 8.07 (d, J=1.7 Hz, 1H), 7.85 (s, 1H), 7.80 (s, 1H), 7.41 (d, J=1.7 Hz, 1H), 7.38 (dd, J=9.0, 2.2 Hz, 1H), 7.16 (s, 1H), 7.10 (d, J=2.2 Hz, 1H), 7.00 (s, 1H), 5.34 (s, 2H), 4.07-4.02 (m, 1H), 4.02 (s, 3H), 3.93-3.87 (m, 1H), 3.91 (s, 3H), 3.25-3.16 (m, 1H), 3.12-3.05 (m, 1H). LCMS Method 2: >95% 254 nm, $R_T$=1.10 min, MS (ESI) 533.2 [M+H]$^+$.

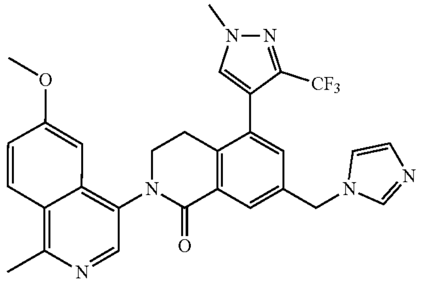 [SMILES: COc1ccc2c(C)ncc(N3CCc4c(cc(Cn5ccnc5)cc4-c4cn(C)nc4C(F)(F)F)C3=O)c2c1]

Example 88

7-((1H-imidazol-1-yl)methy)-6'-methoxy-1'-methyl-5-(1-methyl-3-(trifluoromethyl)-1H-pyrazol-4-yl)-3,4-dihydro-1H-[2,4'-biisoquinolin]-1-one 7-((1H-Imidazol-1-yl)methyl)-1'-chloro-6'-methoxy-5-(1-methyl-3-(trifluoromethyl)-1H-pyrazol-4-yl)-3,4-dihydro-1H-[2,4'-biisoquinolin]-1-one (Example 21, 60 mg, 0.11 mmol), methylboronic acid (2.0 eq), potassium carbonate (3.0 eq), $PdCl_2(dppf)-CH_2Cl_2$ adduct (0.1 eq), and dioxane (2 mL) were combined in a vial. The vial was degassed with Ar and heated under the microwave at 140° C. for 30 min. The reaction was cooled to room temperature, diluted with EtOAc, and filtered through celite. The filtrate was washed with brine and concentrated. The residue was purified by flash chromatography (Combi-flash Rf, DCM/MeOH=0-10% gradient) followed by reverse phase HPLC (Phenomenex Gemini C18, $H_2O/CH_3CN$ gradient from 5-95% $CH_3CN$, 0.1% TFA) to afford the title compound (10 mg, 17% yield). LCMS Method 2: >95% 254 nm, $R_T$=1.13 min, MS (ESI) 547.2 [M+H]$^+$.

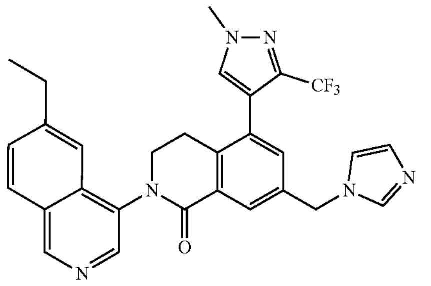 [SMILES: CCc1ccc2cncc(N3CCc4c(cc(Cn5ccnc5)cc4-c4cn(C)nc4C(F)(F)F)C3=O)c2c1]

Example 89

7-((1H-Imidazol-1-yl)methyl)-6'-ethyl-5-(1-methyl-3-(trifluoromethyl)-1H-pyrazol-4-yl)-3,4-dihydro-1H-[2,4'-biisoquinolin]-1-one The title compound was prepared following the Buchwald coupling procedure described for Example 2, using 7-((1H- imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-ethylisoquinoline (Intermediate 57). LCMS Method 2: >95% 254 nm, $R_T$=1.17 min, MS (ESI) 531.2 $[M+H]^+$.

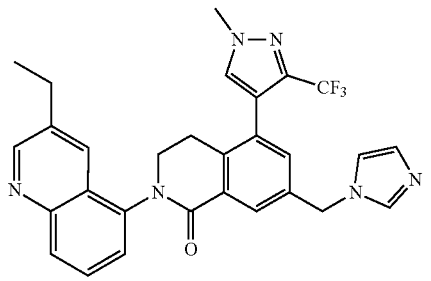 [SMILES: CCc1cnc2cccc(N3CCc4c(cc(Cn5ccnc5)cc4-c4cn(C)nc4C(F)(F)F)C3=O)c2c1]

Example 90

7-((1H-Imidazol-1-yl)methyl)-2-(3-ethylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-ethylquinoline (Intermediate 58). LCMS Method 2: >95% 254 nm, $R_T$=1.14 min, MS (ESI) 531.2 $[M+H]^+$.

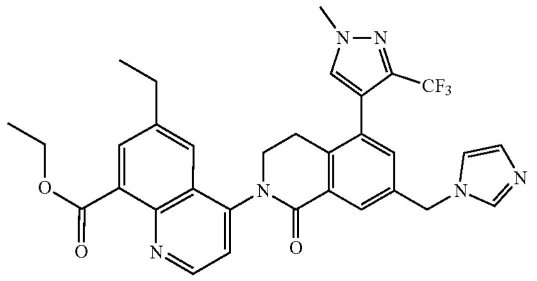 [SMILES: CCOC(=O)c1cc(CC)cc2c(N3CCc4c(cc(Cn5ccnc5)cc4-c4cn(C)nc4C(F)(F)F)C3=O)ccnc12]

Example 91

Ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylate The title compound (712 mg, 1.21 mmol, 80% yield) was prepared following the Buchwald coupling procedure described for Example 12, substituting ethyl 4-bromo-6-ethylquinoline-8-carboxylate (Intermediate 61, 750 mg, 2.43 mmol) for 4-bromo-6-methoxy-2-methylquinoline. $^1$H NMR (400 MHz, Chloroform-d) δ 9.03 (d, J=4.6 Hz, 1H), 8.16 (d, J=1.8 Hz, 1H), 7.88 (d, J=1.9 Hz, 1H), 7.71 (d, J=0.9 Hz, 1H), 7.57 (s, 1H), 7.41 (s, 1H), 7.35 (dd, J=9.1, 2.8 Hz, 1H), 7.18 (d, J=1.8 Hz, 1H), 7.10 (s, 1H), 6.95 (s, 1H), 5.19 (s, 2H), 4.02 (s, 3H), 4.00-3.93 (m, 1H), 3.81-3.75 (m 1H), 3.19-3.11 (m, 1H), 3.00-2.94 (m, 1H), 2.84 (q, J=7.6, 2H), 1.45 (t, J=7.1, 3H), 1.31 (=t, 7.6, 3H); LCMS (ESI): m/z=603.2 $[M+H]^+$.

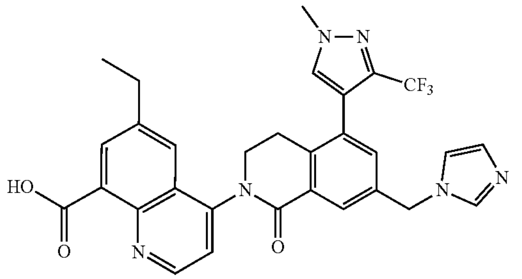 [SMILES: CCc1cc(C(=O)O)c2nccc(N3CCc4c(cc(Cn5ccnc5)cc4-c4cn(C)nc4C(F)(F)F)C3=O)c2c1]

Example 92

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid The title compound (250 mg, 1.21 mmol, 75% yield) was prepared following the procedure described for Example 40, substituting ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylate (Example 91, 350 mg, 0.581 mmol) for ethyl 4-(7-((1H-imidazol-1-yl)methyl)-5-(1H-methyl-3-(trifluoromethyl)-1H-pyrazol-4-yl)-1-oxo-3,4-dihydroisoquinolin-2(1H)-yl)-6-methoxyquinoline-8-carboxylate (Example 39). $^1$H NMR (400 MHz, Chloroform-d) δ 8.92 (d, J=4.9 Hz, 1H), 8.75 (d, J=2.0 Hz, 1H), 8.15 (d, J=1.8 Hz, 1H), 7.84 (d, J=1.9 Hz, 1H), 7.57 (s, 1H), 7.51 (d, J=4.9 Hz, 1H), 7.41 (s, 1H), 7.22 (d, J=1.8 Hz, 1H), 7.10 (s, 1H), 6.94 (s, 1H), 5.20 (s, 2H), 4.12 (dd, J=7.9 Hz, 1H), 4.05 (s, 31H), 3.87 (q, J=5.1 Hz, 1H), 3.23-3.15 (m, 1H), 3.04-2.98 (m, 1H), 2.84 (q, J=7.6, 2H), 1.33 (t, J=7.6, 3H); LCMS (ESI): m/z=575.2 $[M+H]^+$.

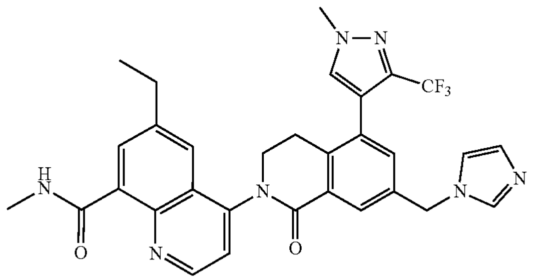 [SMILES: CCc1cc(C(=O)NC)c2nccc(N3CCc4c(cc(Cn5ccnc5)cc4-c4cn(C)nc4C(F)(F)F)C3=O)c2c1]

Example 93

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-methylquinoline-8-carboxamide Step A. Preparation of ethyl 5-bromo-2-((2,2-dimethyl-4,6-dioxo-1,3-dioxan-5-ylidene)methyl)amino)benzoate. To a solution of ethyl 2-amino-5-bromobenzoate (5.00 g, 20.5 mmol, 1.0 equiv) and 2,2-dimethyl-1,3-dioxane-4,6-dione (3.55 g, 24.6 mmol, 1.2 equiv) in anhydrous ethanol (50 mL), triethoxymethane (3.04 g, 3.41 mL, 20.5 mmol, 1.0 equiv) was added and the mixture was stirred under argon atmosphere at 80° C. for 14 h. It was then cooled to 0° C., filtered, washed with ice-cold ethanol and dried to obtain the title compound (7.7 g, 94%) as a white solid. $^1$H NMR (400 MHz, Chloroform-d) δ 8.08 (d, J=3.1 Hz, 1H), 8.03 (d, J=3.1 Hz, 1H), 7.66 (dd, J=7.4, 6.1 Hz, 1H), 6.34 (dd, J=7.4, 1.6 Hz, 1H), 4.46 (q, J=7.1 Hz, 2H), 3.95 (s, 6H), 1.45 (t, J=7.1 Hz, 3H)

Step B. Preparation of ethyl 6-bromo-4-hydroxyquinoline-8-carboxylate. Ethyl 5-bromo-2-(((2,2-dimethyl-4,6-dioxo-1,3-dioxan-5-ylidene)methyl)amino)benzoate (6.60 g, 16.6 mmol) was added portionwise to Dowtherm A (50 mL) at 250° C. and stirred for 45 min. The reaction was cooled to room temperature. Hexanes (50 mL) were added and a precipitate was formed. The mixture was filtered and the filtered solid was washed with hexanes to obtain the title compound (3.70 g, 75.4%). $^1$H NMR (400 MHz, Chloroform-d) δ 8.75 (d, J=2.2 Hz 1H), 8.45 (d, J=2.3 Hz, 1H), 7.69-7.65 (m, 1H), 6.35 (dd, J=1.1 Hz, 1H), 4.46 (q, J=7.0 2H), 1.46 (t, J=7.1 3H); LCMS (ESI): m/z=295.9 $[M+H]^+$.

Step C. Preparation of ethyl 6-ethyl-4-hydroxyquinoline-8-carboxylate. To a solution of methyl 6-bromo-4-hydroxyquinoline-8-carboxylate (3.808 g, 13.5 mmol, 1.0 equiv) and triethylborane (2.646 g 27.0 mL 27 mmol, 2.0 equiv) in THF (10 ml) under argon atmosphere, cesium carbonate (8.797 g, 27. Mmol, 2.0 equiv), and Pd(dppf)$Cl_2$ (493.9 mg, 0.050 Eq, 675.0 μmol) were added. The reaction mixture was stirred at 60° C. for 3 h. It was cooled to 0° C. and quenched by slow addition of an acetic acid and water mixture (1:1, 3 mL), then stirred at room temperature for 30 min followed by refluxing for 30 min. The resulting mixture was cooled to 0° C., basified using sat. aq. $NaHCO_3$, extracted with $CH_2Cl_2$ (35 mL×2). The combined organic layer was dried over $Na_2SO_4$, filtered and concentrated. The residue was purified by flash chromatography (Combi-flash Rf, 1-ex/EtOAc=0-100% gradient) to afford the title compound (1.70 g, 69.4%) as a greenish solid. $^1$H NMR (400 MHz, Chloroform-d) δ 8.49 (s, 1H), 8.25 (s, 1H), 7.69 (t, =7.7 Hz, 1H), 6.35 (d, J=4.1 Hz, 1H), 4.48 (q, J=7.1 Hz, 2H), 2.80 (q, J=7.6 Hz, 2H), 1.47 (t, J=7.1 3H), 1.35 (t, J=7.6 3H); LCMS (ESI): m/z=246.1 $[M+H]^+$.

Step D. Preparation of ethyl 4-bromo-6-ethylquinoline-8-carboxylate. To a solution of methyl 6-ethyl-4-hydroxyquinoline-8-carboxylate (3.01 g, 13.0 mmol, 1.0 equiv) in DMF at 0° C., $PBr_3$ (4.40 g, 1.53 mL, 16.3 mmol, 1.25 equiv) was added dropwise. The reaction mixture was stirred for 40 min then quenched by slow addition of sat. aq. $NaHCO_3$. The mixture was extracted with EtOAc (35 mL×2), and the combined organic layer was washed with brine (35 mL×1), dried over $Na_2SO_4$, filtered and concentrated. The residue was purified by flash chromatography (Combi-flash Rf, DCM/MeOH=0-10% gradient) to afford the title compound (3.21 g, 83.8%). $^1$H NMR (400 MHz, Chloroform-d) δ 8.48 (s, 1H), 8.35 (s, 1H), 8.27 (t, J=7.0 Hz, 1H), 7.04 (d, J=7.0 Hz, 1H), 4.50 (q, J=7.1 Hz, 2H), 2.80 (q, J=7.6 Hz, 2H), 1.49 (t, J=7.4 3H), 1.33 (t, J=7.6 3H); LCMS (ESI): m/z=309.1 $[M+H]^+$.

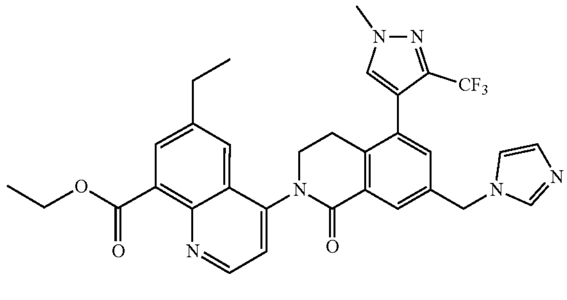 [SMILES: CCOC(=O)c1cc(CC)cc2c(N3CCc4c(cc(Cn5ccnc5)cc4-c4cn(C)nc4C(F)(F)F)C3=O)ccnc12]

Step E. Preparation of ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylate. A solution of ethyl 4-bromo-6-ethylquinoline-8-carboxylate (4.52 g, 14.7 mmol, 1.1 equiv) and 7-((1H-imidazol-1-yl)methyl)-5-(1-methyl-3-(trifluoromethyl)-1H-pyrazol-4-yl)-3,4-dihydroisoquinolin-1(2H)-one (5.00 g, 133 mmol, 1.0 equiv) in anhydrous dioxane (200 mL) was degassed and tris(dibenzylideneacetone)dipalladium(0) (1.22 g, 1.33 mmol, 0.1 equiv), cesium carbonate (8.68 g, 26.6 mmol, 2.0 equiv) and (9,9-dimethyl-9H-xanthene-4,5-diyl)bis(diphenylphosphane) (2.31 g, 4.00 mmol, 0.3 equiv) were added. The reaction mixture was stirred at 115° C. for 15 h, cooled to room temperature then concentrated under reduced pressure. Water (50 mL) was added to the residue and the mixture was extracted with ethyl acetate (50 mL×3). The combined organic layers were washed with brine (50 mL×1), dried over sodium sulfate, and concentrated. The residue was purified by flash chromatography (Combi-flash Rf, DCM/MeOH 0-10% gradient) to afford the title compound (7.00 g, 87.2%). $^1$H NMR (400 MHz, Chloroform-d) δ 9.03 (d, J=4.6 Hz, 1H), 8.16 (d, J=1.8 Hz, 1H), 7.88 (d, J=1.9 Hz, 1H), 7.71 (d, J=0.9 Hz, 1H), 7.57 (s, 1H), 7.41 (s, 1H), 7.35 (dd, J=9.1, 2.8 Hz, 1H), 7.18 (d, J=1.8 Hz, 1H), 7.10 (s, 1H), 6.95 (s, 1H), 5.19 (s, 2H), 4.02 (s, 3H), 4.00-3.93 (m, 1H), 3.81-3.75 (m, 1H), 3.19-3.11 (m, 1H), 3.00-2.94 (m, 1H), 2.84 (q, J=7.6, 2H), 1.45 (t, J=7.1, 3H), 1.31 (t, J=7.6, 3H); LCMS (ESI): m/z=603.2 $[M+H]^+$.

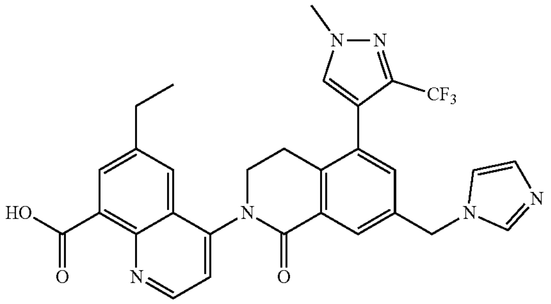 [SMILES: CCc1cc(C(=O)O)c2nccc(N3CCc4c(cc(Cn5ccnc5)cc4-c4cn(C)nc4C(F)(F)F)C3=O)c2c1]

Step F. Preparation of 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid. To a solution of ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylate (2.02 g, 3.35 mmol, 1.0 equiv) in THF (20.0 mL), lithium hydroxide (241 mg, 5.0 mL, 10.0 mmol, 3.0 equiv) aq. solution was added. The reaction mixture was stirred at room temperature for 14 h then diluted with EtOAc (50 mL). The resulting mixture was washed with sat. aq. $NH_4Cl$ (35 mL) and brine (35 mL), dried over sodium sulfate, and concentrated. The residue was purified by flash chromatography (Combi-flash Rf, DCM/MeOH=0-15% gradient) to afford the title compound (1.77 g, 92.0%). $^1$H NMR (400 MHz, Chloroform-d) δ 8.92 (d, J=4.9 Hz, 1H), 8.75 (d, =2.0 Hz, 1H), 8.15 (d, J=1.8 Hz, 1H), 7.84 (d, J=1.9 Hz, 1H), 7.57 (s, 1H), 7.51 (d, J=4.9 Hz, 1H), 7.41 (s, 1H), 7.22 (d, J=1.8 Hz, 1H), 7.10 (s, 1H), 6.94 (s, 1H), 5.20 (s, 2H), 4.12 (dd, J=7.9 Hz, 1H), 4.05 (s, 3H), 3.87 (q, J=5.1 Hz, 1H), 3.23-3.15 (m, 1H), 3.04-2.98 (m, 1H), 2.84 (q, J=76, 2H), 1.33 (t, J=7.6, 3H); LCMS (ESI): m/z=575.2 $[M+H]^+$.

Step G. Preparation of 4-(7-((1H-imidazol-1-yl)methyl)-5-(1-methyl-3-(trifluoromethyl)-1H-pyrazol-4-yl)-1-oxo-3, 4-dihydroisoquinolin-2(1H)-yl)-6-ethyl-N-methylquinoline-8-carboxamide. 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid (1.700 g, 3.0 mmol, 1.0 equiv) was mixed with sulfurous dichloride (7.040 g, 4.29 mL, 59. Mmol, 20 equiv) under Ar and stirred at 70° C. for 30 min then concentrated. The residue was dissolved in toluene (10 mL) and concentrated. The process was repeated three times to remove excess sulfurous dichloride. The residue was dissolved in $CH_2Cl_2$ (25 mL), and methylamine hydrochloride (998.9 mg, 14.8 mmol, 5.0 equiv) was added. The reaction mixture was cooled to 0° C., and N-ethyl-N-isopropylpropan-2-amine (3.824 g, 10 Eq, 29.59 mmol) was added. The resulting mixture was stirred for 1 h at 0° C. $CH_2Cl_2$ (50 mL) was added, and the resulting mixture was washed with water (35 mL), sat. aq. $NaHCO_3$ (35 mL) and brine (35 mL), dried over sodium sulfate, filtered and concentrated. The residue was purified by reverse phase HPLC (Phenomenex Gemini C18, $H_2O/CH_3CN$ gradient from 5-55% $CH_3CN$, 0.1% TFA). Desired fractions were combined and concentrated. The residue was treated with sat. aq. $NaHCO_3$, and the resulting mixture was extracted with $CH_2Cl_2$ (25 mL×2). The combined organic phase was washed with sat. aq. $NaHCO_3$ (35 mL) and brine (35 mL), dried over sodium sulfate and concentrated to obtain the title compound (1.10 g, 63.3%). $^1$H NMR (400 MHz, Chloroform-d) δ 11.04 (d, J=4.7 Hz, 1H), 8.92 (d, J=4.7 Hz, 1H), 8.80 (d, J=2.1 Hz, 1H), 8.16 (d, J=1.8 Hz, 1H), 7.74 (d, J=2.0 Hz, 1H), 7.57 (s, 1H), 7.41 (d, J=2.6 Hz, 1H), 7.19 (d, J=1.8 Hz, 1H), 7.10 (s, 1H), 6.95 (s, 1H), 5.20 (s, 2H), 4.02 (s, 3H), 3.98-3.95 (m, 1H), 3.85-3.79 (m, 1H), 3.19-3.17 (m, 1H), 3.16 (d, J=7.7, 3H), 3.01-2.97 (m, 1H), 1.31 (t, J=7.6, 3H); LCMS (ESI): m/z=588.5 [M+H]$^+$.

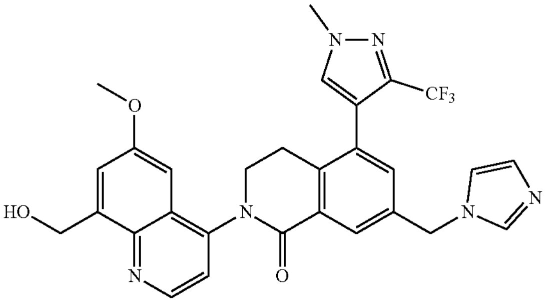 [SMILES: COc1cc(CO)c2nccc(N3CCc4c(cc(Cn5ccnc5)cc4-c4cn(C)nc4C(F)(F)F)C3=O)c2c1]

Example 94

7-((1H-Imidazol-1-yl)methyl)-2-(8-(hydroxymethyl)-6-methoxyquinolin-4-yl)-5-(1-methyl-3-(trifluoromethyl)-1H-pyrazol-4-yl)-3,4-dihydroisoquinolin-1(2H)-one The title compound (35 mg, 62 μmol, 62% yield) was prepared following the Buchwald coupling procedure described for Example 12, substituting (4-bromo-6-methoxyquinolin-8-yl)methanol (32 mg, 0.12 mmol) for 5-bromo-3-methoxyquinoline for. $^1$H NMR (400 MHz, Chloroform-d) δ 8.79 (d, J=4.7 Hz, 1H), 8.17 (d, J=1.8 Hz, 1H), 7.57 (s, 1H), 7.40 (s, 1H), 7.36 (d, J=4.6 Hz, 1H), 7.31 (d, J=2.7 Hz, 1H), 7.18 (d, J=1.8 Hz, 1H), 7.10 (s, 1H), 6.99 (d, J=2.7 Hz, 1H), 6.95 (s, 1H), 5.20 (m, 4H), 4.80 (s, 1H), 4.03 (m, 4H), 3.86 (m, 4H), 3.14 (m, J=5.4 Hz, 1H), 2.98 (m, J=5.3 Hz, 1H); LCMS (ESI): m/z=563.21 [M+H]$^+$.

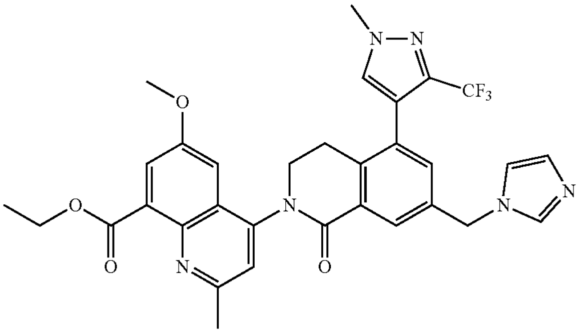 [SMILES: CCOC(=O)c1cc(OC)cc2c(N3CCc4c(cc(Cn5ccnc5)cc4-c4cn(C)nc4C(F)(F)F)C3=O)cc(C)nc12]

Example 95

Ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylate The title compound (1.407 g, 2.28 mmol, 85% yield) was prepared following the Buchwald coupling procedure described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 1.00 g, 2.66 mmol, 1 equiv) and ethyl 4-bromo-6-methoxy-2-methylquinoline-8-carboxylate (Intermediate 64, 1.73 g, 5.33 mmol, 2 equiv). $^1$H NMR (400 MHz, Chloroform-d) δ 8.16 (d, J=2.0 Hz, 1H), 7.60 (d, J=2.8 Hz, 1H), 7.57 (s, 1H), 7.40 (s, 1H), 7.24 (s, 1H), 7.17 (d, J=2.0 Hz, 1H), 7.14 (d, J=2.9 Hz, 1H), 7.10 (s, 1H), 6.94 (s, 1H), 5.19 (s, 2H), 4.52 (q, J=7.1 Hz, 2H), 4.02 (s, 3H), 4.01-3.90 (m, 1H), 3.86 (s, 3H), 3.79-3.69 (m, 1H), 3.13 (ddd, J=16.2, 10.9, 5.2 Hz, 1H), 2.96 (dt, J=16.4, 4.7 Hz, 1H), 2.72 (s, 3H), 1.46 (t, J=7.1 Hz, 3H); LCMS (ESI): Method 2: $R_T$=1.282 min m/z=619.2 [M+H]$^+$.

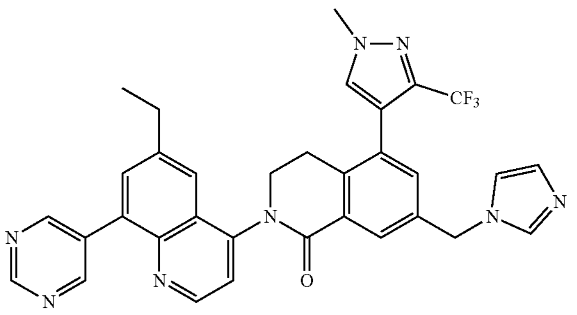 [SMILES: CCc1cc(-c2cncnc2)c2nccc(N3CCc4c(cc(Cn5ccnc5)cc4-c4cn(C)nc4C(F)(F)F)C3=O)c2c1]

Example 96

7-((1H-Imidazol-1-yl)methyl)-2-(6-ethyl-8-(pyrimidin-5-yl)quinolin-4-yl)-5-(1-methyl-3-(trifluoromethyl)-1H-pyrazol-4-yl)-3,4-dihydroisoquinolin-1(2H)-one 7-((1H-Imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 80 mg, 0.13 mmol), 5-(4,4,5,5-tetramethyl-1,3,2-dioxaborolan-2-yl)pyrimidine (54 mg, 0.26 mmol, 2 equiv), potassium carbonate (36 mg, 0.26 mmol, 2 equiv), $Ad_2PBu$ (4.7 mg, 0.013 mmol, 0.1 equiv), $Pd_2(dba)_3$ (3.6 mg, 0.004 mmol, 0.03 equiv) were dissolved in 1,4-dioxane:water (4:1, 1.3 mL) under Ar in a sealed tube. The reaction mixture was stirred for 14 h at 60° C. then cooled to 23° C. Brine was added to the mixture and extracted with EtOAc (3×20 mL). The combined organic layers were dried over $MgSO_4$ and concentrated under reduced pressure. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (49 mg, 0.081 mmol, 61% yield). $^1H$ NMR (400 MHz, Chloroform-d) δ 9.26 (s, 1H), 9.10 (s, 2H), 8.94 (d, J=4.6 Hz, 1H), 8.18 (d, J=2.0 Hz, 1H), 7.71 (d, J=1.9 Hz, 1H), 7.67 (d, J=1.9 Hz, 1H), 7.58 (s, 1H), 7.42 (s, 1H), 7.39 (d, J=4.6 Hz, 1H), 7.20 (d, J=2.0 Hz, 1H), 7.11 (d, J=1.2 Hz, 1H), 6.96 (d, J=1.4 Hz, 1H), 5.21 (s, 2H), 4.09-4.02 (m, 4H), 3.94-3.76 (m, 1H), 3.20 (ddd, 1=16.1, 10.7, 5.2 Hz, 1H), 3.01 (dt, J=16.3, 4.8 Hz, 1H), 2.90 (q, J=7.6 Hz, 2H), 1.35 (t, J=7.6 Hz, 3H); LCMS (ESI): Method 2: $R_T$=1.367 min, m/z=609.2 $[M+H]^+$.

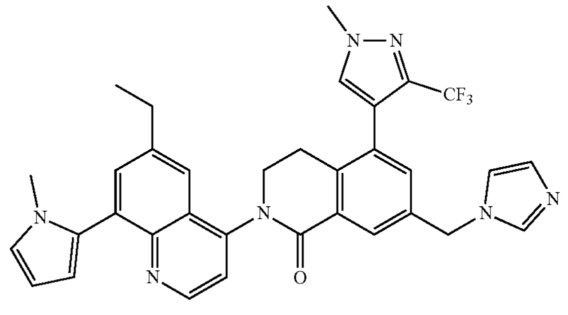 [SMILES: CCc1cc(-c2cccn2C)c2nccc(N3CCc4c(cc(Cn5ccnc5)cc4-c4cn(C)nc4C(F)(F)F)C3=O)c2c1]

Example 9

7-((1H-Imidazol-1-yl)methyl)-2-(6-ethyl-8-(1-methyl-1H-pyrrol-2-yl)quinolin-4-yl)-5-(1-methyl-3-(trifluoromethyl)-1H-pyrazol-4-yl)-3,4-dihydroisoquinolin-1(2H)-one The title compound (26 mg, 0.13 mmol, 32% yield) was prepared following the procedures described for Example 96, using 7-((1H-Imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 80 mg, 0.13 mmol) and 1-methyl-2-(4,4,5,5-tetra-ethyl-1,3,2-dioxaborolan-2-yl)-1H-pyrrole (54 mg, 0.26 mmol, 2 equiv). $^1H$ NMR (400 MHz, Chloroform-d) δ 8.95 (d, J=4.6 Hz, 1H), 8.18 (d, J=2.0 Hz, 1H), 7.64 (d, J=n 2.0 Hz, 1H), 7.62 (d, J=2.0 Hz, 1H), 7.58 (s, 1H), 7.42 (s, 1H), 7.31 (d, J=4.6 Hz, 1H), 7.19 (d, J=2.0 Hz, 1H), 7.11 (d, J=1.1 Hz, 1H), 6.96 (t, J=1.3 Hz, 1H), 6.84 (t, J=2.3 Hz, 1H), 6.29 (d, J=2.2 Hz, 2H), 5.21 (s, 2H), 4.03 (s, 3H), 3.99 (dd, J=11.1, 4.4 Hz, 1H), 3.85 (dt, J=11.7, 5.3 Hz, 1H), 3.50 (s, 3H), 3.18 (ddd, J=16.1, 10.6, 5.2 Hz, 1H), 2.99 (dt, J=16.5, 4.9 Hz, 1H), 2.83 (q, J=7.6 Hz, 2H), 1.31 (t, J=7.6 Hz, 3H); LCMS (ESI): Method 2: $R_T$=1.379 min, m/z=610.2 $[M+H]^+$.

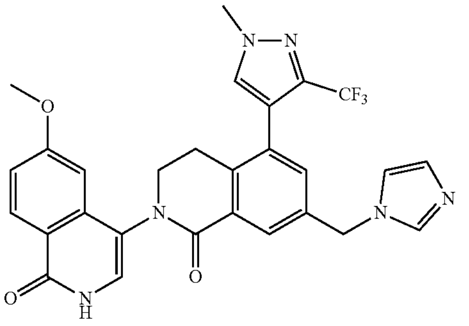 [SMILES: COc1ccc2c(=O)[nH]cc(N3CCc4c(cc(Cn5ccnc5)cc4-c4cn(C)nc4C(F)(F)F)C3=O)c2c1]

Example 98

7-((1H-imidazol-1-yl)methyl)-6'-methoxy-5-(1-methyl-3-(trifluoromethyl)-1H-pyrazol-4-yl)-3,4-dihydro-1H-[2,4'-biisoquinoline]-1,1'(2'H)-dione A solution of 7-((1H-Imidazol-1-yl)methyl)-1'-chloro-6'-methoxy-5-(1-methyl-3-(trifluoromethyl)-1H-pyrazol-4-yl)-3,4-dihydro-1H-[2,4'-biisoquinolin]-1-one (Example 21, 65 mg, 0.12 mmol) was dissolved in 1 mL of 6N aqueous HCl. The reaction was heated in a capped vial at 110° C. for 24 h. The reaction was cooled to ambient temperature and neutralized with 6N aq. NaOH solution. The aqueous layer was extracted with EtOAc. The combined organic layers were washed with brine, dried over $MgSO_4$, filtered, and concentrated. The residue was purified by flash chromatography (Combi-flash Rf, DCM/MeOH=0-10% gradient) to afford the title compound (11 mg, 0.02 mmol, 17% yield) as a white solid. LCMS (ESI) Method 2: >95%, $R_T$=1.22 min, m/z=549.1 $[M+H]^+$.

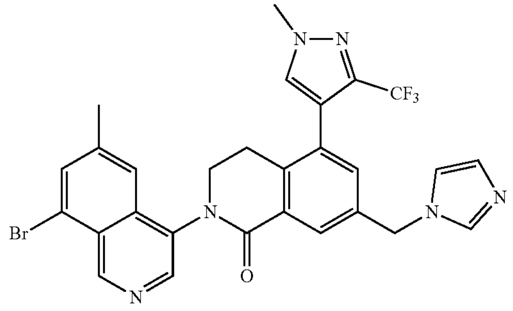 [SMILES: Cc1cc(Br)c2cncc(N3CCc4c(cc(Cn5ccnc5)cc4-c4cn(C)nc4C(F)(F)F)C3=O)c2c1]

Example 99

7-((1H-imidazol-1-yl)methyl)-8'-bromo-6'-methyl-5-(1-methyl-3-(trifluoromethyl)-1H-pyrazol-4-yl)-3,4-dihydro-1H-[2,4'-biisoquinolin]-1-one The title compound (120.0 mg, 0.2 mmol, 75% yield) was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 100.0 mg, 0.27 mmol, 1 equiv) and 8-bromo-4-iodo-6-methylisoquinoline (139.1 mg, 0.4 mmol, 1.5 equiv). $^1H$ NMR (400 MHz, Chloroform-d) δ 9.56 (s, 1H), 8.55 (s, 1H), 8.16 (d, J=1.6 Hz, 1H), 7.75 (s, 1H), 7.57 (s, 1H), 7.52 (s, 114H), 7.42 (s, 1H), 7.19 (d, J=2.0 Hz, 1H), 7.10 (s, 1H), 6.95 (s, 1H), 5.20 (s, 2H), 4.03 (s, 3H), 4.00 (m, 1H), 3.83 (m, 1H), 3.13 (m, 1H), 3.02 (m, 1H), 2.52 (s, 3H).

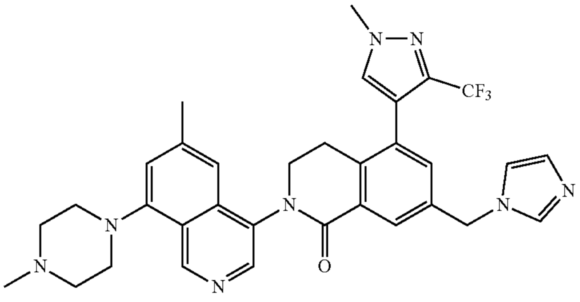 [SMILES: Cc1cc(N2CCN(C)CC2)c2cncc(N3CCc4c(cc(Cn5ccnc5)cc4-c4cn(C)nc4C(F)(F)F)C3=O)c2c1]

Example 100

7-((1H-Imidazol-1-yl)methyl)-6'-methyl-5-(1-methyl-3-(trifluoromethyl)-1H-pyrazol-4-yl)-8'-(4-methylpiperazin-1-yl)-3,4-dihydro-1H-[2,4'-biisoquinolin]-1-one To a solution of 7-((1H-imidazol-1-yl)methyl)-8'-bromo-6'-methyl-5-(1-methyl-3-(trifluoromethyl)-1H-pyrazol-4-yl)-3,4-dihydro-1H-[2,4'-biisoquinolin]-1-one (Example 99, 70.0 mg, 118 μmol, 1 equiv) in 1,4-dioxane (3 mL) were added 1-methylpiperazine (33 μL, 294 μmol, 2.5 equiv), Xantphos (13.6 mg, 23.5 μmol, 0.2 equiv), and $Pd_2(dba)_3$ (10.8 mg, 11.8 μmol, 0.1 equiv). The mixture was degassed with Ar then sodium tert-butoxide (33.9 mg, 353 μmol, 3 equiv) was added. The mixture was stirred in a sealed tube at 110° C. for 16 h. Brine was added, and the mixture was extracted with EtOAc. The combined organic layers were dried ($Na_2SO_4$), filtered, and concentrated. The residue was purified by reverse phase HPLC (Phenomenex Gemini C18, $H_2O/CH_3CN$ gradient from 5-50% $CH_3CN$, 0.1% TFA) to yield the title compound (35 mg, 57 μmol, 48% yield). $^1H$ NMR (400 MHz, Chloroform-d) δ 9.50 (s, 1H), 8.45 (s, 1H), 8.17 (d, J=1.6 Hz, 1H), 7.58 (s, 1H), 7.41 (s, 1H), 7.22 (s, 1H), 7.17 (d, J=1.6 Hz, 1H), 7.11 (s, 1H), 6.98 (s, 1H), 6.96 (s, 1H), 5.20 (s, 2H), 4.03 (s, 3H), 3.96 (m, 1H), 3.83 (m, 1H), 3.25 (brs, 2H), 3.18 (brs, 2H), 3.09 (m, 1H), 3.00 (m, 1H), 2.74 (brs, 4H), 2.49 (s, 3H), 2.44 (s, 3H); LCMS (ESI): >95%, m/z=615.5 $[M+H]^+$.

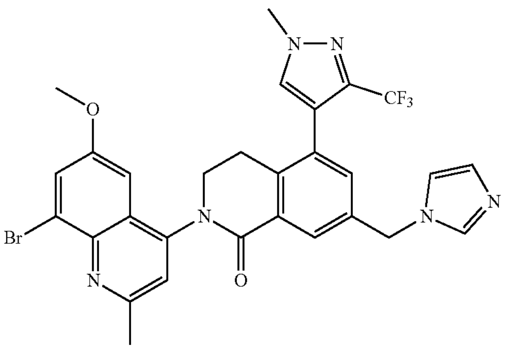 [SMILES: COc1cc(Br)c2nc(C)cc(N3CCc4c(cc(Cn5ccnc5)cc4-c4cn(C)nc4C(F)(F)F)C3=O)c2c1]

Example 101

7-((1H-Imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one The title compound (3.68 g, 5.88 mmol, 85% yield) was prepared following the Buchwald coupling procedure described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 2.60 g, 6.93 mmol, 1 equiv) and 8-bromo-4-iodo-6-methoxyquinoline (Intermediate 62, 5.24 g, 13.85 mmol, 2 equiv). $^1H$ NMR (400 MHz, Chloroform-d) δ 8.15 (d, J=2.0 Hz, 1H), 7.76 (d, J=2.7 Hz, 1H), 7.57 (d, J=1.2 Hz, 1H), 7.40 (d, J=1.1 Hz, 1H), 7.26 (s, 1H), 7.17 (d, J=2.0 Hz, 1H), 7.10 (t, J=1.1 Hz, 1H), 7.03 (d, J=2.7 Hz, 1H), 6.94 (t, J=1.3 Hz, 1H), 5.20 (s, 2H), 4.03 (s, 3H), 3.96 (td, J=11.7, 11.3, 4.3 Hz, 1H), 3.84 (s, 3H), 3.80-3.70 (m, 1H), 3.13 (ddd, J=16.2, 10.9, 5.2 Hz, 1H), 2.96 (dt, J=16.2, 4.7 Hz, 1H), 2.79 (s, 3H); LCMS (ESI): Method 2: $R_T$=1.465 min, m/z=625.1 $[M+H]^+$.

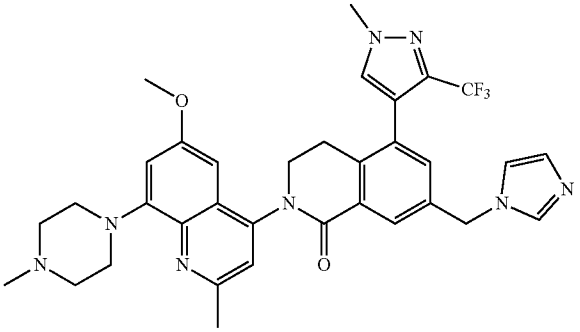 [SMILES: COc1cc(N2CCN(C)CC2)c2nc(C)cc(N3CCc4c(cc(Cn5ccnc5)cc4-c4cn(C)nc4C(F)(F)F)C3=O)c2c1]

Example 102

7-((1H-Imidazol-1-yl)methyl)-2-(6-methoxy-2-methyl-8-(4-methylpiperazin-1-yl)quinolin-4-yl)-5-(1-methyl-3-(trifluoromethyl)-1H-pyrazol-4-yl)-3,4-dihydroisoquinolin-1(2H)-one 7-((1H-Imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 80 mg, 0.13 mmol), 1-methylpiperazine (26 mg, 0.26 mmol, 2 equiv), sodium tert-butoxide (12 mg, 0.13 mmol, 1 equiv), Xantphos (22 mg, 0.038 mmol, 0.3 equiv), $Pd_2(dba)_3$ (12 mg, 0.013 mmol, 0.1 equiv) were dissolved in 1,4-dioxane (1 mL) under Ar in a sealed tube. The reaction mixture was stirred for 14 h at 90° C. then cooled to 23° C. Brine was added to the mixture and extracted with $CH_2Cl_2$ (3×20 mL). The combined organic layers were dried over $MgSO_4$ and concentrated under reduced pressure. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (8 mg, 0.012 mmol, 10% yield). $^1H$ NMR (400 MHz, Chloroform-d) δ 8.16 (d, J=2.0 Hz, 1H), 7.56 (t, J=1.1 Hz, 1H), 7.39 (d, J=1.1 Hz, 1H), 7.18 (s, 1H), 7.15 (d, J=2.0 Hz, 1H), 7.09 (d, J=1.1 Hz, 1H), 6.94 (d, J=1.3 Hz, 1H), 6.78 (d, J=2.6 Hz, 1H), 6.66 (d, J=2.6 Hz, 1H), 5.19 (s, 2H), 4.02 (s, 3H), 3.97-3.84 (m, 1H), 3.81 (s, 3H), 3.76 (dt, J=12.4, 5.2 Hz, 1H), 3.60 (brs, 2H), 3.34 (brs, 2H), 3.11 (ddd, 3=16.2, 10.9, 5.3 Hz, 1H), 2.94 (dt, J=16.3, 4.7 Hz, 1H), 2.76 (s, 3H), 2.70 (s, 3H), 2.41 (s, 3H); LCMS (ESI): Method 2: $R_T$=1.073 min, m/z=645.3 $[M+H]^+$.

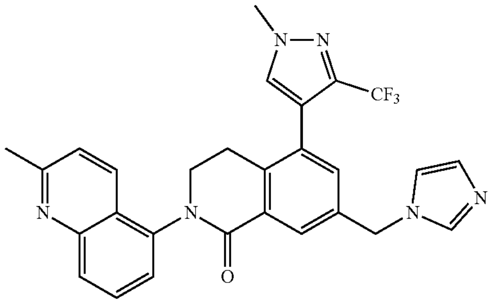 [SMILES: Cc1ccc2c(N3CCc4c(cc(Cn5ccnc5)cc4-c4cn(C)nc4C(F)(F)F)C3=O)cccc2n1]

Example 103

7-((1H-Imidazol-1-yl)methyl)-5-(1-methyl-3-(trifluoromethyl)-1H-pyrazol-4-yl)-2-(2-methylquinolin-5-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-2-methylquinoline (Intermediate 76). $^1$H NMR (400 MHz, methanol-4) δ 8.20 (d, J=8.7 Hz, 1H), 8.13 (s, 1H), 8.06 (d, J=1.8 Hz, 1H), 8.01 (d, J=8.5 Hz, 1H), 7.84-7.80 (m, 2H), 7.59-7.57 (m, 1H), 7.48 (d, J=8.7 Hz, 1H), 7.46-7.45 (m, 1H), 7.29 (t, J=1.3 Hz, 1H), 7.16 (t, J=1.3 Hz, 1H), 5.40 (s, 2H), 4.11-4.04 (m, 1H), 4.02 (s, 3H), 3.89-3.83 (m, 1H), 3.25-3.17 (m, 1H), 3.09-3.02 (m, 1H), 2.74 (s, 3H); LCMS Method 2: >95%, $R_T$=1.05 min, MS (ESI) 517.2 $[M+H]^+$.

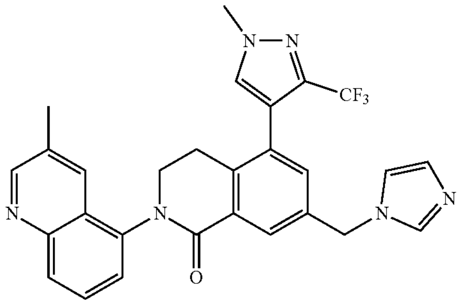 [SMILES: Cc1cnc2cccc(N3CCc4c(cc(Cn5ccnc5)cc4-c4cn(C)nc4C(F)(F)F)C3=O)c2c1]

Example 104

7-((1H-Imidazol-1-yl)methyl)-5-(1-methyl-3-(trifluoromethyl)-1H-pyrazol-4-yl)-2-(3-methylquinolin-5-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-methylquinoline (Intermediate 77). $^1$H NMR (400 MHz, methanol-d4) δ 8.77 (d, J=2.0 Hz, 1H), 8.06-8.03 (m, 3H), 7.83 (s, 1H), 7.79-7.75 (m, 2H), 7.63-7.60 (m, 1H), 7.40 (d, J=1.6 Hz, 1H), 7.15 (t, J=1.2 Hz, 1H), 6.99 (t, J=1.2 Hz, 1H), 5.33 (s, 2H), 4.09-4.03 (m, 1H), 4.01 (s, 3H), 3.89-3.82 (m, 1H), 3.25-3.15 (m, 1H), 3.08-3.08 (m, 1H), 2.52 (s, 3H); LCMS Method 2: >95%, $R_T$=1.09 min, MS (ESI) 517.2 $[M+H]^+$.

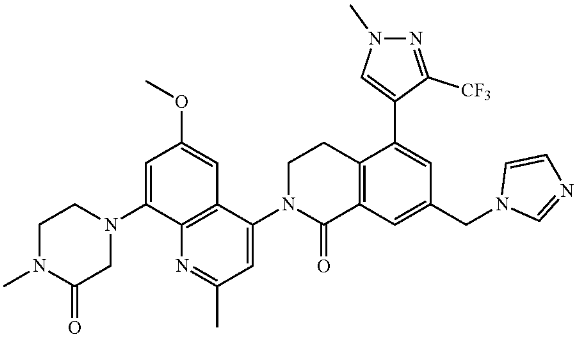 [SMILES: COc1cc(N2CCN(C)C(=O)C2)c2nc(C)cc(N3CCc4c(cc(Cn5ccnc5)cc4-c4cn(C)nc4C(F)(F)F)C3=O)c2c1]

Example 105

7-((1H-Imidazol-1-yl)methyl)-2-(6-methoxy-2-methyl-8-(4-methyl-3-oxopiperazin-1-yl)quinolin-4-yl)-5-(1-methyl-3-(trifluoromethyl)-1H-pyrazol-4-yl)-3,4-dihydroisoquinolin-1(2H)-one The title compound (30.7 mg, 0.047 mmol, 36% yield) was prepared following the Buchwald coupling procedure described for Example 102, using 7-((1H-imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1 (2H)-one (Example 101, 80 mg, 0.13 mmol), and 1-methylpiperazin-2-one (29 mg, 0.26 mmol, 2 equiv). $^1$H NMR (400 MHz, Chloroform-d) δ 8.15 (d, J=2.0 Hz, 1H), 7.57 (s, 1H), 7.40 (s, 1H), 7.22 (s, 1H), 7.17 (d, J=2.0 Hz, 1H), 7.10 (t, J=1.1 Hz, 1H), 6.95 (t, J=1.3 Hz, 1H), 6.74 (d, J=2.6 Hz, 1H), 6.71 (d, J=2.5 Hz, 1H), 5.20 (s, 2H), 4.04 (s, 2H), 4.03 (s, 3H), 4.02-3.90 (m, 3H), 3.82 (s, 3H), 3.80-3.57 (m, 2H), 3.52 (dt, J=10.0, 4.7 Hz, 1H), 3.13 (ddd, J=16.4, 11.1, 5.5 Hz, 1H), 3.06 (s, 3H), 2.95 (dt, J=16.4, 4.7 Hz, 1H), 2.72 (s, 3H); LCMS (ESI): Method 2: $R_T$=1.159 min, m/z=659.2 $[M+H]^+$.

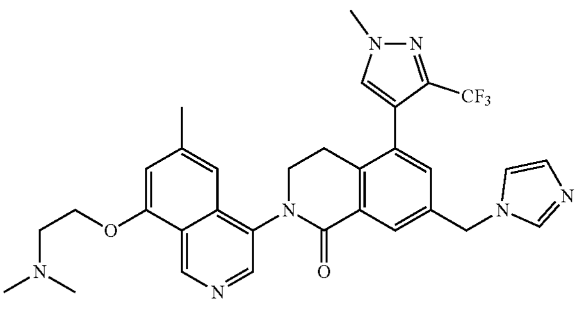 [SMILES: Cc1cc(OCCN(C)C)c2cncc(N3CCc4c(cc(Cn5ccnc5)cc4-c4cn(C)nc4C(F)(F)F)C3=O)c2c1]

Example 106

7-((1H-Imidazol-1-yl)methyl)-8'-(2-(dimethylamino) ethoxy)-6'-methyl-5-(1-methyl-3-(trifluoromethyl)-1H-pyrazol-4-yl)-3,4-dihydro-1H-[2,4'-biisoquinolin]-1-one To a solution of 7-((1H-imidazol-1-yl)methyl)-8'-bromo-6'-methyl-5-(1-ethyl-3-(trifluoromethyl)-1H-pyrazol-4-yl)-3,4-dihydro-1H-[2,4-biisoquinolin]-1-one (Example 99, 50.8 mg, 92.2 μmol, 1 equiv) in 1,4-dioxane (3 mL) were added 2-(dimethylamino)ethan-1-ol (55 μL, 553 μmol, 6 equiv), Xantphos (10.7 mg, 18.4 μmol, 0.2 equiv), and $Pd_2(dba)_3$ (8.4 mg, 9.2 μmol, 0.1 equiv). The mixture was degassed with Ar then sodium tert-butoxide (53.2 mg, 553 μmol, 6 equiv) was added. The mixture was stirred in a sealed tube at 100° C. for 16 h. Brine was added and the mixture was extracted with EtOAc. The combined organic layers were dried ($Na_2SO_4$), filtered, and concentrated. The residue was purified by reverse phase HPLC (Phenomenex Gemini C18, $H_2O/CH_3CN$ gradient from 5-50% $CH_3CN$, 0.1% TFA) followed by neutralization with sat. aq. $NaHCO_3$ to yield the title compound (2.8 mg, 4.6 μmol, 5% yield). $^1H$ NMR (400 MHz, Chloroform-d) δ 9.56 (s, 1H), 8.48 (s, 1H), 8.17 (d, J=1.6 Hz, 1H), 7.58 (s, 1H), 7.41 (s, 1H), 7.17 (d, J=1.6 Hz, 1H), 7.10 (s, 2H), 6.95 (s, 1H), 6.76 (s, 1H), 5.20 (s, 2H), 4.30 (t, J=5.6 Hz, 2H), 4.03 (s, 3H), 3.96 (m, 1H), 3.84 (m, 1H), 3.12 (m, 1H), 3.02 (m, 1H), 2.92 (m, 2H), 2.50 (s, 3H), 2.43 (s, 6H); LCMS (ESI): >95%, m/z=604.5 $[M+H]^+$.

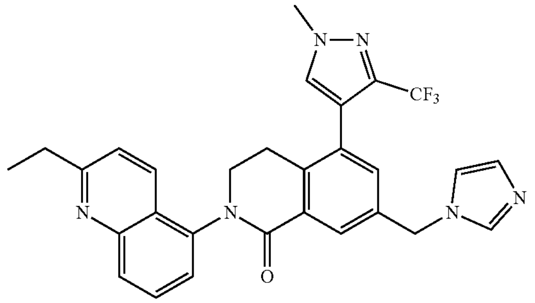

Example 107

7-((1H-Imidazol-1-yl) methyl)-2-(2-ethylquinolin-5-yl)-5-(1-methyl-3-(trifluoromethyl-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1 (2H)-one (Intermediate 8) and 5-bromo-2-ethylquinoline (Intermediate 78). $^1H$ NMR (400 MHz, methanol-d4) δ 8.23 (d, J=8.7 Hz, 1H), 8.04-8.02 (m, 2H), 7.83-7.78 (m, 3H), 7.58 (dd, J=7.4, 1.0 Hz, 1H), 7.51 (d, J=8.7 Hz, 1H), 7.41 (d, J=1.7 Hz, 1H), 7.15 (bs, 1H), 7.00 (bs, 1H), 5.33 (s, 2H), 4.1.0-4.04 (m, 1H), 4.02 (s, 3H), 3.88-3.82 (m, 1H), 3.24-3.17 (m, 1H), 3.08-2.99 (m, 3H), 1.39 (t, J=7.6 Hz, 3H); LCMS Method 2: >95%, $R_T$=1.09 min, MS (ESI) 531.2 $[M+H]^+$.

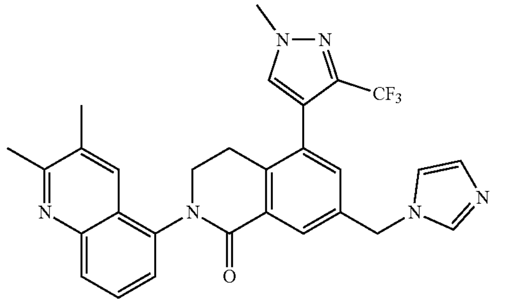 [SMILES: Cc1cc2c(N3CCc4c(cc(Cn5ccnc5)cc4-c4cn(C)nc4C(F)(F)F)C3=O)cccc2nc1C]

Example 108

7-((1H-imidazol-1-yl)methy)-2-(2,3-dimethylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-2,3-dimethylquinoline (intermediate 79). $^1H$ NMR (400 MHz, chloroform-d) δ 8.18 (d, J=1.8 Hz, 1H), 8.04 (d, J=8.4 Hz, 1H), 7.81 (s, 1H), 7.70-7.66 (m, 1H), 7.60 (s, 1H), 7.43-7.39 (m, 2H), 7.19 (d, J=1.8 Hz, 1H), 7.12 (bs, 1H), 6.97 (bs, 1H), 5.22 (s, 2H), 4.07-4.00 (m, 1H), 4.05 (s, 3H), 3.84-3.78 (m, 1H), 3.19-3.11 (m, 1H), 3.04-2.97 (m, 1H), 2.71 (s, 3H), 2.46 (s, 3H); LCMS Method 2: >95%, $R_T$=1.11 min, MS (ESI) 531.1 $[M+H]^+$.

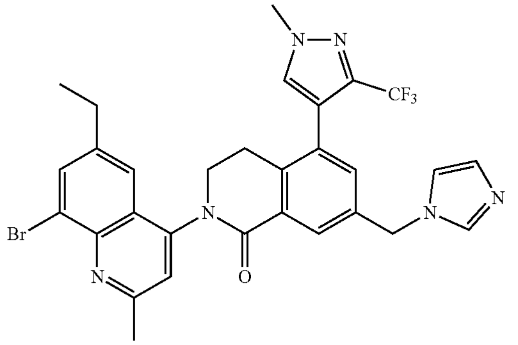 [SMILES: CCc1cc(Br)c2nc(C)cc(N3CCc4c(cc(Cn5ccnc5)cc4-c4cn(C)nc4C(F)(F)F)C3=O)c2c1]

Example 109

7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1 (2H)-one The title compound (1.68 g, 2.69 mmol, quant.) was prepared following the Buchwald coupling procedure described for Example 12, using 7-((1H-imidazol-1-yl) methyl)-5-(1-methyl-3-(trifluoromethyl)-1H-pyrazol-4-yl)-3,4-dihydroisoquinolin-1(2H)-one (Intermediate 8, 900 mg, 2.40 mmol, 1 equiv) and 8-bromo-6-ethyl-4-iodo-2-methylquinoline (Intermediate 63, 1.78 g, 4.72 mmol, 2 equiv). $^1H$ NMR (400 MHz, Chloroform-d) δ 8.15 (d, J=2.0 Hz, 1H), 7.94 (d, J=1.8 Hz, 1H), 7.57 (d, J=1.2 Hz, 1H), 7.51 (d, J=1.8 Hz, 1H), 7.40 (d, J=1.1 Hz, 1H), 7.27 (s, 1H), 7.18 (d, J=2.0 I-z, 1H), 7.10 (t, J=1.1 Hz, 1H), 6.95 (t, J=1.3 Hz, 1H), 5.20 (s, 2H), 4.03 (s, 3H), 3.96 (ddd, 3=12.3, 10.7, 4.3 Hz, 1H), 3.78 (dt, J=12.3, 5.3 Hz, 1H), 3.14 (ddd, J=16.1, 10.7, 5.2 Hz, 1H), 2.97 (dt, J=16.3, 4.9 Hz, 1H), 2.80 (s, 3H), 2.77 (q, J=7.7 Hz, 2H), 1.28 (t, J=7.6 Hz, 3H); LCMS (ESI): Method 2: $R_T$1.561 min, m/z=623.1 [M+H]$^+$.

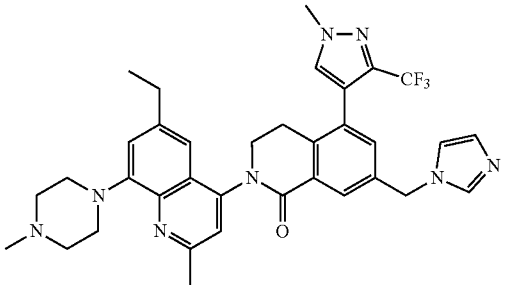 [SMILES: CCc1cc(N2CCN(C)CC2)c2nc(C)cc(N3CCc4c(cc(Cn5ccnc5)cc4-c4cn(C)nc4C(F)(F)F)C3=O)c2c1]

Example 110

7-((1H-imidazol-1-yl)methyl)-2-(6-ethyl-2-methyl-8-(4-methylpiperazin-1-yl)quinolin-4-yl)-5-(1-methyl-3-(trifluoromethyl)-1H-pyrazol-4-yl)-3,4-dihydroisoquinolin-1(2H)-one The title compound (10 mg, 0.016 mmol, 12% yield) was prepared following the Buchwald coupling procedure described for Example 102, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 80 mg, 0.13 mmol), and 1-methylpiperazine (26 mg, 0.26 mmol, 2 equiv). $^1$H NMR (400 MHz, Chloroform-d) δ 8.15 (d, J=2.0 Hz, 1H), 7.56 (d, J=1.2 Hz, 1H), 7.40 (d J=1.1 Hz, 1H), 7.26 (s, 1H), 7.18 (s, 1H), 7.18-7.16 (m, 1H), 7.15 (d, J=2.0 Hz, 1H), 7.09 (d, J=1.1 Hz, 1H), 6.98 (d, J=1.8 Hz, 1H), 6.96-6.93 (m, 1H), 5.19 (s, 2H), 4.02 (s, 3H), 3.90 (ddd, J=12.3, 10.5, 4.4 Hz, 1H), 3.78 (dt, J=12.3, 5.3 Hz, 1H), 3.57 (brs, 2H), 3.34 (brs, 2H), 3.13 (ddd, J=16.0, 10.6, 5.2 Hz, 1H), 2.94 (dt, J=16.4, 4.9 Hz, 1H), 2.80-2.76 (m, 4H), 2.73 (d, J=8.6 Hz, 5H), 2.42 (s, 3H), 1.26 (t, J=7.6 Hz, 3H); LCMS (ESI): Method 2: $R_T$1.121 min, m/z=643.2 [M+H]$^+$.

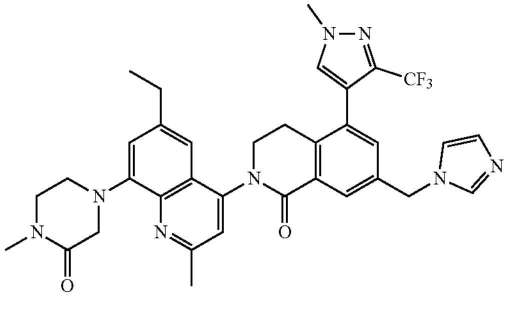 [SMILES: CCc1cc(N2CCN(C)C(=O)C2)c2nc(C)cc(N3CCc4c(cc(Cn5ccnc5)cc4-c4cn(C)nc4C(F)(F)F)C3=O)c2c1]

Example 111

7-((1H-Imidazol-1-yl)methyl)-2-(6-ethyl-2-methyl-8-(4-methyl-3-oxopiperazin-1-yl)quinolin-4-yl)-5-(1-methyl-3-(trifluoromethyl)-1H-pyrazol-4-yl)-3,4-dihydroisoquinolin-1(2H)-one The title compound (33.4 mg, 0.051 mmol, 40% yield) was prepared following the Buchwald coupling procedure described for Example 102, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 80 mg, 0.13 mmol), and 1-methylpiperazin-2-one (29 mg, 0.26 mmol, 2 equiv). $^1$H NMR (400 MHz, Chloroform-d) δ 8.15 (d, J=2.0 Hz, 1H), 7.57 (s, 1H), 7.43-7.38 (m, 1H), 7.22 (s, 2H), 7.17 (d, J=2.0 Hz, 1H), 7.10 (t, J=1.1 Hz, 1H), 6.97-6.91 (m, 2H), 5.20 (s, 2H), 4.05 (s, 2H), 4.03 (s, 3H), 4.01-3.96 (m, 2H), 3.93 (dd, J=11.6, 4.2 Hz, 1H), 3.79 (dt, J=11.8, 5.4 Hz, 1H), 3.66 (dtd, J=22.8, 11.4, 7.2 Hz, 2H), 3.52 (dd, J=11.2, 5.7 Hz, 1H), 3.14 (ddd, J=16.1, 10.7, 5.2 Hz, 1H), 3.07 (s, 3H), 3.01-2.90 (m, 1H), 2.78-2.70 (m, 5H), 1.26 (t, J=7.6 Hz, 3H); LCMS (ESI): Method 2: $R_T$=1.15 mm, m/z=657.3 [M+H]$^+$.

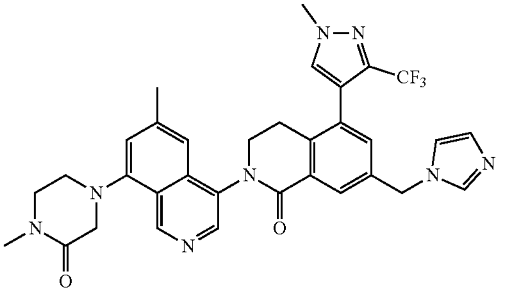 [SMILES: Cc1cc(N2CCN(C)C(=O)C2)c2cncc(N3CCc4c(cc(Cn5ccnc5)cc4-c4cn(C)nc4C(F)(F)F)C3=O)c2c1]

Example 112

7-((1H-Imidazol-1-yl)methyl)-6'-methyl-5-(1-methyl-3-(trifluoromethyl)-1H-pyrazol-4-yl)-8'-(4-methyl-3-oxopiperazin-1-yl)-3,4-dihydro-1H-[2,4'-biisoquinolin]-1-one The title compound (35.0 mg, 56 μmol, 44% yield) was prepared following the procedure described for Example 100, using 7-((1H-imidazol-1-yl)methyl)-8'-bromo-6'-methyl-5-(1-methyl-3-(trifluoromethyl)-1H-pyrazol-4-yl)-3,4-dihydro-1H-[2,4'-biisoquinolin]-1-one (Example 99, 75.0 mg, 126 μmol, 1 equiv) and 1-methylpiperazin-2-one (35.9 mg, 315 μmol, 2.5 equiv). $^1$H NMR (400 MHz, Chloroform-d) δ 9.41 (s, 1H), 8.43 (s, 1H), 8.10 (d, J=1.6 Hz, 1H), 7.52 (s, 1H), 7.36 (s, 1H), 7.23 (s, 1H), 7.12 (d, J=1.6 Hz, 1H), 7.04 (s, 1H), 6.90 (s, 2H), 5.14 (s, 2H), 3.97 (s, 3H), 3.92 (m, 1H), 3.82 (s, 2H), 3.77 (m, 1H), 3.61 (m, 1H), 3.49 (m, 2H), 3.33 (m, 1H), 3.07 (m, 1H), 3.05 (s, 3H), 2.96 (m, 1H), 2.44 (s, 3H); LCMS (ESI): >95%, m/Z=629.4 [M+H]$^+$.

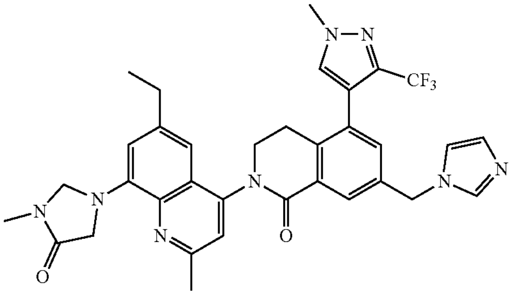 [SMILES: CCc1cc(N2CC(=O)N(C)C2)c2nc(C)cc(N3CCc4c(cc(Cn5ccnc5)cc4-c4cn(C)nc4C(F)(F)F)C3=O)c2c1]

Example 113

7-((1H-Imidazol-1-yl)methyl)-2-(6-ethyl-2-methyl-8-(3-methyl-4-oxoimidazolidin-1-yl)quinolin-4-yl)-5-(1-methyl-3-(trifluoromethyl)-1H-pyrazol-4-yl)-3,4-dihydroisoquinolin-1(2H)-one The title compound (25 mg, 0.040 mmol, 31% yield) was prepared following the Buchwald coupling procedure described for Example 102, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 80 mg, 0.13 mmol), and 3-methylimidazolidin-4-one hydrochloride (35 mg, 0.26 mmol, 2 equiv). $^1$H NMR (400 MHz, Chloroform-d) δ 8.16 (d, J=2.0 Hz, 1H), 7.58 (s, 1H), 7.41 (s, 1H), 7.20 (s, 1H), 7.17 (d, J=2.0 Hz, 1H), 7.11 (t, J=1.1 Hz, 1H), 7.06-7.01 (m, 1H), 6.95 (d, J=1.3 Hz, 1H), 6.57 (d, J=1.5 Hz, 1H), 5.58 (d, J=6.2 Hz, 1H), 5.40 (d, J=6.3 Hz, 1H), 5.20 (s, 2H), 4.39-4.17 (m, 2H), 4.03 (s, 3H), 3.97-3.86 (m, 1H), 3.80 (dt, J=11.8, 5.3 Hz, 1H), 3.15 (ddt, J=15.6, 10.4, 5.1 Hz, 1H), 3.05 (s, 3H), 2.95 (dt, J=16.2, 4.9 Hz, 1H), 2.77-2.70 (m, 2H), 2.70 (s, 3H), 1.27 (t, J=7.6 Hz, 3H); LCMS (ESI): Method 2: $R_T$=1.349 min, m/z=643.3 [M+H]$^+$.

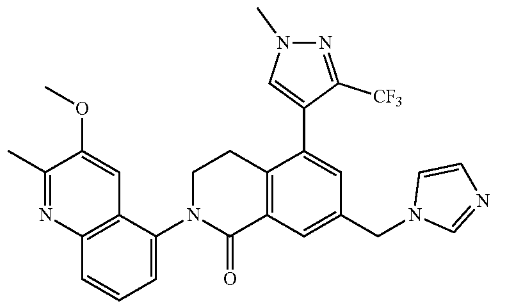 [SMILES: COc1cc2c(N3CCc4c(cc(Cn5ccnc5)cc4-c4cn(C)nc4C(F)(F)F)C3=O)cccc2nc1C]

Example 114

7-((1H-Imidazol-1-yl)methyl)-2-(3-methoxy-2-methylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-methoxy-2-methylquinoline (Intermediate 80). $^1$H NMR (400 MHz, Chloroform-d) δ 8.17 (d, J=1.8 Hz, 1H), 7.99 (d, J=84 Hz, 1H), 7.58-7.54 (m, 2H), 7.41-7.39 (m, 2H), 7.20 (s, 1H), 7.16 (d, J=1.8 Hz, 1H), 7.10 (bs, 1H), 6.95 (bs, 1H), 5.20 (s, 2H), 4.04-3.97 (m, 1H), 4.02 (s, 3H), 3.87 (s, 3H), 3.79-3.73 (m, 1H), 3.15-3.07 (m, 1H), 3.01-2.94 (m, 1H), 2.65 (s, 3H); LCMS Method 2: >95%. $R_T$=1.16 min, MS (ESI) 547.2 [M+H]$^+$.

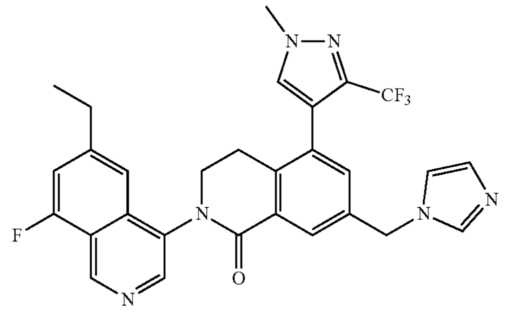 [SMILES: CCc1cc(F)c2cncc(N3CCc4c(cc(Cn5ccnc5)cc4-c4cn(C)nc4C(F)(F)F)C3=O)c2c1]

Example 115

7-((1H-Imidazol-1-yl)methyl)-6'-ethyl-8'-fluoro-5-(1-methyl-3-(trifluoromethyl)-1H-pyrazol-4-yl)-3,4-dihydro-1H-[2,4'-biisoquinolin]-1-one The title compound (33.6 mg, 61.3 μmol, 76% yield) was prepared following the procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 80 μmol, 1 equiv) and 6-ethyl-8-fluoro-4-iodoisoquinoline (Intermediate 69, 36.1 mg, 120 μmol, 1.5 equiv). $^1$H NMR (400 MHz, Chloroform-d) δ 9.46 (s, 1H), 8.55 (s, 1H), 8.16 (d, J=1.6 Hz, 1H), 7.58 (s, 1H), 7.42 (s, 1H), 7.36 (s, 1H), 7.18 (m, 2H), 7.10 (s, 1H), 6.95 (s, 1H), 5.20 (s, 2H), 3.98 (m, 1H), 3.83 (m, 1H), 3.13 (m, 1H), 3.01 (m, 1H), 2.82 (q, J=7.6 Hz, 2H), 1.30 (t, J=7.6 Hz, 3H); LCMS (ESI): >90%, m/z=549.4 [M+H]$^+$.

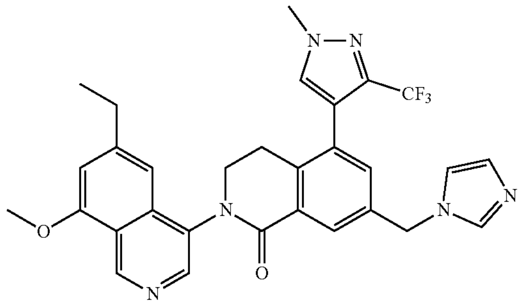 [SMILES: CCc1cc(OC)c2cncc(N3CCc4c(cc(Cn5ccnc5)cc4-c4cn(C)nc4C(F)(F)F)C3=O)c2c1]

Example 116

7-((1H-Imidazol-1-yl)methy)-6'-ethyl-8-methoxy-5-(1-methyl-3-(trifluoromethyl)-1H-pyrazol-4-yl)-3,4-dihydro-1H-[2,4'-biisoquinolin]-one To a solution of 7-((1H-imidazol-1-yl)methyl)-6'-ethyl-8'-fluoro-5-(1-methyl-3-(trifluoromethyl)-1H-pyrazol-4-yl)-3,4-dihydro-1H-[2,4'-biisoquinolin]-1-one (Example 115, 31.0 mg, 57 μmol, 1 equiv) in NMP (0.3 mL) at room temperature was added 5.4 M MeONa in MeOH (42 μL, 0.23 mmol, 4 equiv). The mixture was stirred for 16 h then quenched with brine. The mixture was extracted with EtOAc and the combined organic layer was dried ($Na_2SO_4$), filtered, and concentrated. The residue was purified by reverse phase HPLC (Phenomenex Gemini C18, $H_2O/CH_3CN$ gradient from 10-75% $CH_3CN$, 0.1% TFA) followed by neutralization with sat. aq. $NaHCO_3$ to yield the title compound (20.7 mg, 36.9 μmol, 65% yield). $^1$H NMR (400 MHz, Chloroform-d) δ 9.56 (s, 1H), 8.49 (s, 1H), 8.18 (d, J=1.6 Hz, 1H), 7.59 (brs, 1H), 7.41 (s, 1H), 7.17 (d, J=1.6 Hz, 1H), 7.12 (m, 2H), 6.97 (brs, 1H), 6.80 (s, 1H), 5.20 (s, 2H), 4.05 (s, 3H), 4.03 (s, 3H), 3.96 (m, 1H), 3.83 (m, 1H), 3.12 (m, 1H), 3.01 (m, 1H), 2.80 (q, J=7.6 Hz, 2H), 1.31 (t, J=7.6 Hz, 3H); LCMS (ESI): >95%, m/z=561.4 $[M+H]^+$.

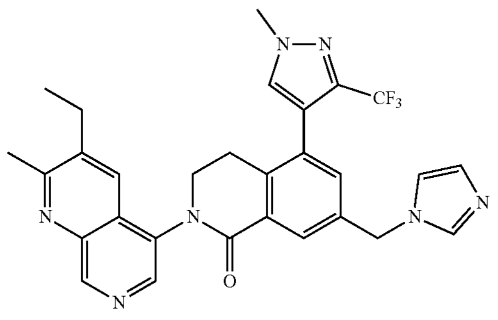 [SMILES: CCc1cc2c(N3CCc4c(cc(Cn5ccnc5)cc4-c4cn(C)nc4C(F)(F)F)C3=O)cncc2nc1C]

Example 117

7-((1H-Imidazol-1-yl)methyl)-2-(3-ethyl-2-methylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1 (2H)-one (Intermediate 8) and 5-bromo-3-ethyl-2-methylquinoline (Intermediate 81). $^1$H NMR (400 MHz, Chloroform-d) δ 8.19 (d, J=1.8 Hz, 1H), 8.04 (d, J=8.5 Hz, 1H), 7.83 (s, 1H), 7.70-7.67 (m, 1H), 7.60 (s, 1H), 7.44-7.42 (m, 2H), 7.18 (d, J=1.8 Hz, 1H), 7.12 (bs, 1H), 6.98 (bs, 1H), 5.22 (s, 2H), 4.05 (s, 3H), 4.05-3.99 (m, 11H), 3.83-3.77 (m, 1H), 3.19-3.11 (m, 1H), 3.03-2.97 (m, 2H), 2.82 (q, J=7.4 Hz, 2H), 2.75 (s, 3H), 1.30 (t, J=7.4 Hz, 3H); LCMS Method 2: >95%, $R_T$=1.11 min, MS (ESI) 545.2 $[M+H]^+$.

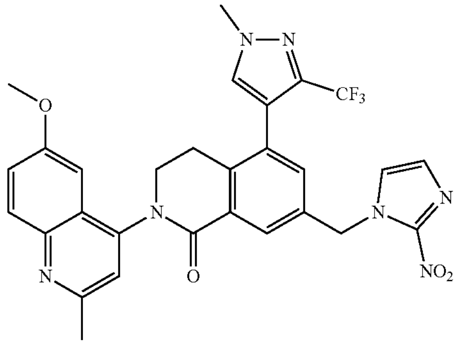

Example 118

2-(6-Methoxy-2-methylquinolin-4-yl)-5-(1-methyl-3-(trifluoromethyl)-1H-pyrazol-4-yl)-7-((2-nitro-1H-imidazol-1-yl)methyl)-3,4-dihydroisoquinolin-1(2)-one The title compound was prepared following the Buchwald coupling procedure described for Example 2, using 5-(1-methyl-3-(trifluoromethyl)-1H-pyrazol-4-yl)-7-((2-nitro-1H-imidazol-1-yl)methyl)-3,4-dihydroisoquinolin-1(2H)-one (Intermediate 83) and 4-bromo-6-methoxy-2-methylquinoline LCMS Method 2: >95%, $R_T$=1.38 min, MS (ESI) 592.2 $[M+H]^+$.

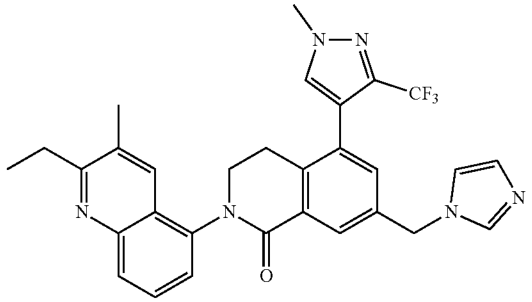 [SMILES: CCc1nc2cccc(N3CCc4c(cc(Cn5ccnc5)cc4-c4cn(C)nc4C(F)(F)F)C3=O)c2cc1C]

Example 119

7-((1H-Imidazol-1-yl)methyl)-2-(2-ethyl-3-methylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-2-ethyl-3-methylquinoline (Intermediate 82). LCMS Method 2: >95%, $R_T$=1.18 min, MS (ESI) 545.2 $[M+H]^+$.

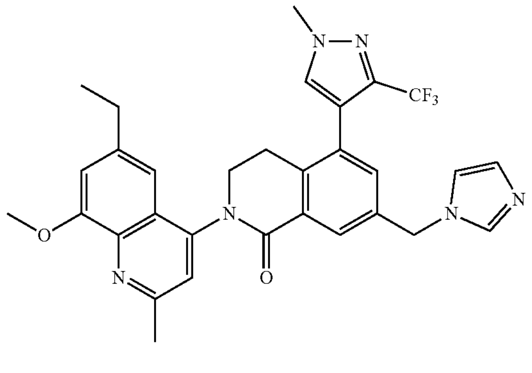 [SMILES: CCc1cc(OC)c2nc(C)cc(N3CCc4c(cc(Cn5ccnc5)cc4-c4cn(C)nc4C(F)(F)F)C3=O)c2c1]

Example 120

7-((1H-Imidazol-1-yl)methyl)-2-(6-ethyl-8-methoxy-2-methylquinolin-4-yl)-5-(1-methyl-3-(trifluoromethyl)-1H-pyrazol-4-yl)-3,4-dihydroisoquinolin-1(2H)-one 7-((1H-Imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 80 mg, 0.13 mmol), methanol (10 mg, 0.32 mmol, 5 equiv), cesium carbonate (31 mg, 0.096 mmol, 1.5 equiv), RockPhos (3 mg, 0.006 mmol, 0.1 equiv), $Pd_2(dba)_3$ (1.5 mg, 0.002 mmol, 0.025 equiv) were dissolved in 1,4-dioxane (1 mL) under Ar in a sealed tube. The reaction mixture was stirred for 5 h at 80° C. then cooled to 23° C.

Brine was added to the mixture and extracted with $CH_2Cl_2$ (3×20 mL). The combined organic layers were dried over $MgSO_4$ and concentrated under reduced pressure. The residue was purified by reverse phase 1-PLC (Phenomenex Gemini C18, $H_2O/CH_3CN$ gradient from 15-80% $CH_3CN$, 0.1% TFA) followed by neutralization with sat. aq. $NaHCO_3$ to yield the title compound (13 mg, 0.023 mmol, 35% yield). $^1H$ NMR (400 MHz, Chloroform-d) δ 8.16 (d, J=2.0 Hz, 1H), 7.57 (s, 1H), 7.40 (d, J=1.1 Hz, 1H), 7.25 (s, 1H), 7.16 (d, J=2.0 Hz, 1H), 7.13 (d, J=1.5 Hz, 1H), 7.10 (t, J=1.1 Hz, 1H), 6.94 (d, J=1.3 Hz, 1H), 6.92 (d, J=1.6 Hz, 1H), 5.19 (s, 2H), 4.08 (s, 3H), 4.02 (s, 3H), 3.93 (ddd, J=12.3, 10.5, 4.4 Hz, 1H), 3.81 (dt, J=12.3, 5.4 Hz, 1H), 3.14 (ddd, J=15.9, 10.5, 5.2 Hz, 1H), 2.95 (dt, J=16.3, 4.9 Hz, 1H), 2.78 (s, 3-1), 2.82-2.69 (m, 2H), 1.29 (t, J=7.6 Hz, 3H); LCMS (ESI): Method 2: $R_T$=1.246 min, m/z=575.2 $[M+H]^+$.

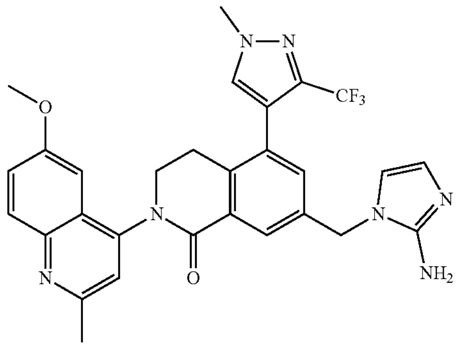

Example 121

7-((2-Amino-1H-imidazol-1-yl)methyl)-2-(6-methoxy-2-methylquinolin-4-yl)-5-(1-methyl-3-(trifluoromethyl)-1-1H-pyrazol-4-yl)-3,4-dihydroisoquinolin-1(2H)-one 2-(6-Methoxy-2-methylquinolin-4-yl)-5-(1-methyl-3-(trifluoromethyl)-1H-pyrazol-4-yl)-7-((2-nitro-1H-imidazol-1-yl)methyl)-3,4-dihydroisoquinolin-1(2H)-one (Example 118, 55 mg, 0.093 mmol) and 10% Pd/C (40 mg) were combined in MeOH (1 mL). The reaction mixture was stirred under 1-2 at room temperature until all starting material was consumed. The reaction mixture was filtered, and the filtrate was concentrated. The residue was purified by reverse phase HPLC (Phenomenex Gemini C18, $H_2O/CH_3CN$ gradient from 5-95% $CH_3CN$, 0.1% TFA) followed by neutralization with sat. aq. $NaHCO_3$ to yield the title compound (3.0 mg, 0.005 mmol, 6% yield). $^1H$ NMR (400 MHz, methanol-d4) δ 8.03 (d, J=1.7 Hz, 1H), 7.94 (d, J=9.2 Hz, 1H), 7.83 (s, 1H), 7.46 (s, 1H), 7.45-7.42 (m, 1H), 7.35 (d, J=1.7 Hz, 1H), 7.09 (d, J=2.7 Hz, 1H), 6.62 (d, J=1.6 Hz, 1H), 6.53 (d, J=1.6 Hz, 1H), 5.09 (s, 2H), 4.11-3.99 (m, 1H), 4.02 (s, 3H), 3.90-3.82 (m, 1H), 3.85 (s, 3H), 3.25-3.17 (m, 1), 3.06-3.00 (m, 1H), 2.71 (s, 3H); LCMS Method 2: >95%, $R_T$=1.17 min, MS (ESI) 562.2 $[M+H]^+$.

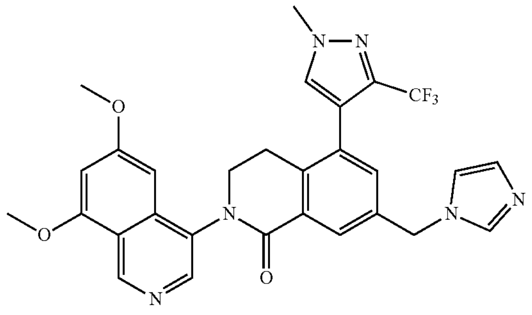

Example 122

7-((1H-Imidazol-1-yl)methyl)-6',8'-dimethoxy-5-(1-methyl-3-(trifluoromethyl)-1H-pyrazol-4-yl)-3,4-dihydro-1H-[2,4'-biisoquinolin]-1-one The title compound (4.0 mg, 7.1 μmol, 17% yield) was prepared following the procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 42 μmol, 1 equiv) and 4-iodo-6,8-dimethoxyisoquinoline (20.1 mg, 63.9 μmol, 1.5 equiv). $^1H$ NMR (400 MHz, Chloroform-d) δ 9.44 (s, 1H), 8.46 (s, 1H), 8.18 (s, 1H), 7.58 (s, 1H), 7.41 (s, 1H), 7.16 (s, 1H), 7.11 (s, 1H), 6.96 (s, 1H), 6.58 (d, J=4.8 Hz, 2H), 5.20 (s, 2H), 4.03 (s, 3H), 4.02 (s, 3H), 3.93 (m, 1H), 3.87 (s, 3H), 3.79 (m, 1H), 3.11 (m, 1H), 3.00 (m, 1H); LCMS (ESI): >95%, m/z=563.5 $[M+H]^+$.

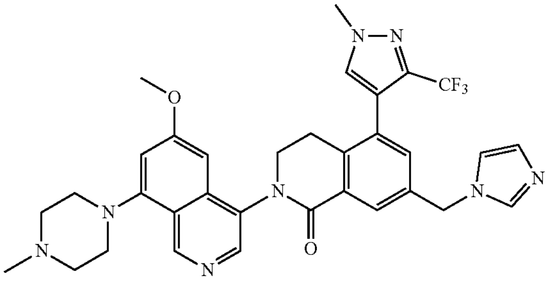 [SMILES: COc1cc(N2CCN(C)CC2)c2cncc(N3CCc4c(cc(Cn5ccnc5)cc4-c4cn(C)nc4C(F)(F)F)C3=O)c2c1]

Example 123

7-((1H-Imidazol-1-yl)methyl)-6'-methoxy-5-(1-methyl-3-(trifluoromethyl)-1H-pyrazol-4-yl)-8'-(4-methylpiperazin-1-yl)-3,4-dihydro-1H-[2,4'-biisoquinolin]-1-one The title compound (7.0 mg, 11 μmol, 31% yield) was prepared following the procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 35 μmol, 1 equiv) and 4-iodo-6-methoxy-8-(4-methylpiperazin-1-yl)isoquinoline (20.0 mg, 53.3 μmol, 1.5 equiv). $^1H$ NMR (400 MHz, Chloroform-d) δ 9.44 (s, 1H), 8.46 (s, 1H), 8.18 (s, 1H), 7.58 (s, 1H), 7.41 (s, 1H), 7.16 (s, 1H), 7.11 (s, 1H), 6.96 (s, 1H), 6.58 (d, J=4.8 Hz, 2H), 5.20 (s, 2H), 4.03 (s, 3H), 4.02 (s, 3H), 3.93 (m, 1H), 3.87 (s, 3H), 3.79 (m, 1H), 3.11 (m, 1H), 3.00 (m, 1H); LCMS (ESI): >95% m/z=563.5 $[M+H]^+$.

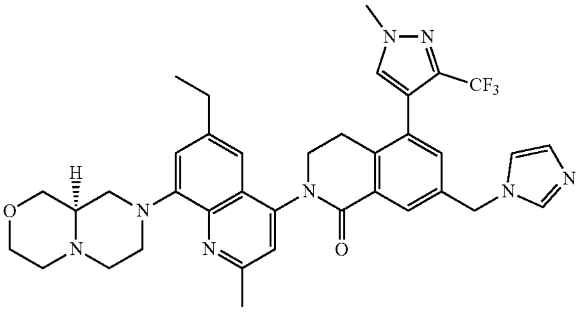 [SMILES: CCc1cc(N2CCN3CCOC[C@H]3C2)c2nc(C)cc(N3CCc4c(cc(Cn5ccnc5)cc4-c4cn(C)nc4C(F)(F)F)C3=O)c2c1]

Example 124

(R)-7-((1H-Imidazol-1-yl)methyl)-2-(6-ethyl-8-(hexahydropyrazino[2,1-c][1,4]oxazin-8(1H)-yl)-2-methylquinolin-4-yl)-5-(1-methyl-3-(trifluoromethyl)-1H-pyrazol-4-yl)-3,4-dihydroisoquinolin-1(2H)-one The title compound (23 mg, 0.033 mmol, 41% yield) was prepared following the Buchwald coupling procedure described for Example 102, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 50 mg, 0.08 mmol), (9aR)-octahydropyrazino[2,1-c][1,4]oxazine dihydrochloride (51 mg, 0.24 mmol, 3 equiv), sodium tert-butoxide (58 mg, 0.60 mmol, 7.5 equiv), BINAP (15 mg, 0.024 mmol, 0.3 equiv), and $Pd_2(dba)_3$ (7.3 mg, 0.008 mmol, 0.1 equiv) at 100° C. $^1$H NMR (400 MHz, Chloroform-d) δ 8.15 (d, J=2.0 Hz, 1H), 7.57 (s, 1H), 7.40 (d, J=1.1 Hz, 1H), 7.18 (d, J=2.8 Hz, 2H), 7.16 (d, J=2.0 Hz, 1H), 7.10 (s, 1H), 6.98-6.92 (m, 2H), 5.19 (s, 2H), 4.16 (d, J=11.0 Hz, 1H), 4.02 (s, 3H), 3.96-3.83 (m, 1H), 3.78 (td, J=9.7, 4.7 Hz, 3H), 3.63 (d, J=10.4 Hz, 1H), 3.37 (dt, J=18.2, 10.6 Hz, 1H), 3.13 (td, J=10.4, 5.3 Hz, 1H), 2.93 (dq, J=15.6, 5.1 Hz, 2H), 2.84 (d, J=11.2 Hz, 1H), 2.78-2.69 (m, 5H), 2.67-2.42 (m, 2H), 1.26 (t, J=7.6 Hz, 3H); LCMS (ESI): Method 2: $R_T$=1.152 min, m/z=685.3 [M+H]$^+$.

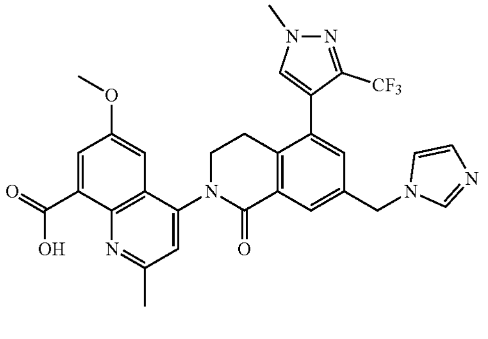 [SMILES: COc1cc(C(=O)O)c2nc(C)cc(N3CCc4c(cc(Cn5ccnc5)cc4-c4cn(C)nc4C(F)(F)F)C3=O)c2c1]

Example 125

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylic acid The title compound (0.76 g, 1.29 mmol, 80% yield) was prepared following the procedure described for Example 40, using ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylate (Example 95, 1.0 g, 1.62 mmol). $^1$H NMR (400 MHz, Chloroform-d) δ 8.41 (d, J=2.9 Hz, 1H), 8.12 (d, J=1.9 Hz, 1H), 7.57 (s, 1H), 7.43 (s, 1H), 7.36 (s, 1H), 7.28 (d, J=2.9 Hz, 1H), 7.21 (d, J=1.9 Hz, 1H), 7.10 (s, 1H), 6.94 (s, 1H), 5.20 (s, 2H), 4.09-4.01 (m, 1H), 3.91 (s, 3H), 3.82 (dt, J=12.2, 5.1 Hz, 1H), 3.22-3.13 (m, 1H), 3.00 (dt, J=16.5, 4.5 Hz, 1H), 2.80 (s, 3H); LCMS (ESI): Method 2: $R_T$=1.276 min, m/z=591.1 [M+H]$^+$.

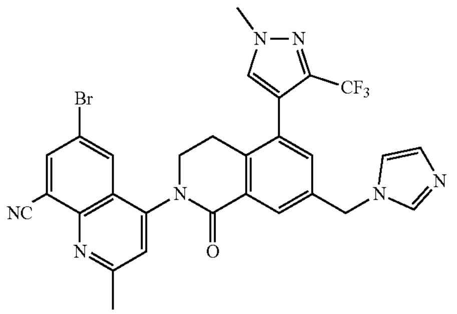

Example 126

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-bromo-2-methylquinoline-8-carbonitrile The title compound (629 mg, 1.01 mmol, 89% yield) was prepared following the Buchwald coupling procedure described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 427 mg, 1.14 mmol) and 6-bromo-4-iodo-2-methylquinoline-8-carbonitrile (Intermediate 65, 849 mg, 2.28 mmol, 2 equiv). $^1$H NMR (400 MHz, Chloroform-d) δ 8.16 (t, J=1.8 Hz, 1H), 8.11-8.10 (m, 2H), 7.58 (s, 1H), 7.42 (s, 1H), 7.34 (s, 1H), 7.20 (d, J=1.8 Hz, 1H), 7.10 (s, 1H), 6.94 (d, J=1.1 Hz, 1), 5.20 (s, 2H), 4.08 (td, J=11.7, 4.2 Hz, 1), 4.03 (s, 3H), 3.77 (dt, J=12.0, 5.1 Hz, 1H), 3.21-3.12 (m, 1H), 2.99 (dt, J=16.5, 4.5 Hz, 1H), 2.81 (s, 3H); LCMS (ESI): Method 2: $R_T$=1.435 min, m/z=620.1 [M+H]$^+$.

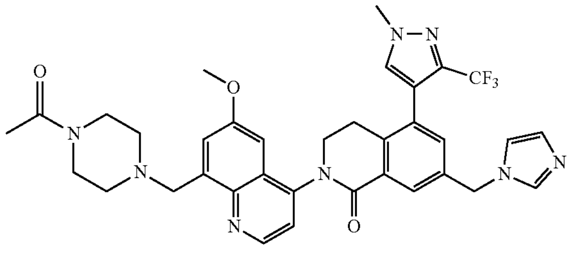 [SMILES: COc1cc(CN2CCN(C(C)=O)CC2)c2nccc(N3CCc4c(cc(Cn5ccnc5)cc4-c4cn(C)nc4C(F)(F)F)C3=O)c2c1]

Example 127

7-((1H-Imidazol-1-yl)methyl)-2-(8-((4-acetylpiperazin-1-yl)methyl)-6-methoxyquinolin-4-yl)-5-(1-methyl-3-(trifluoromethyl)-1H-pyrazol-4-yl)-3,4-dihydroisoquinolin-1(2H)-one The title compound (35 mg, 52 μmol, 52%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2E)-one (Intermediate 8) and 1-(4-((4-bromo-6-methoxyquinolin-8-yl)methyl)piperazin-1-yl)ethan-1-one (Intermediate 102). $^{1}$H NMR (400 MHz, Chloroform-d) δ 8.82 (d, J=4.6 Hz, 1H), 8.16 (d, J=1.8 Hz, 1H), 7.60 (d, J=2.8 Hz, 1H), 7.57 (s, 1H), 7.40 (s, 1H), 7.33 (d, J=4.6 Hz, 1H), 7.18 (d, J=1.8 Hz, 1H), 7.10 (s, 1H), 6.99 (d, J=2.8 Hz, 1H), 6.95 (s, 1H), 5.20 (s, 2H), 4.27 (s, 2H), 4.03 (s, 3H), 3.98 (m, J=5.9 Hz, 1H), 3.87 (s, 3H), 3.78 (m, J=5.3 Hz, 2H), 3.57 (m, J=6.4 Hz, 1H), 3.42 (m, 2H), 3.15 (m, J=5.41 Hz, 1H), 2.98 (m, J=5.1 Hz, 1H), 2.60 (m, J=4.6 Hz, 4H), 2.09 (s, 3H); LCMS (ESI): m/z 673.3 [M+H]$^{+}$.

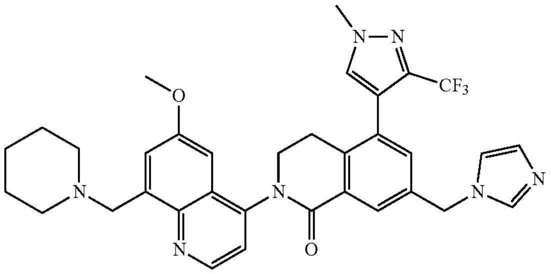 [SMILES: COc1cc(CN2CCCCC2)c2nccc(N3CCc4c(cc(Cn5ccnc5)cc4-c4cn(C)nc4C(F)(F)F)C3=O)c2c1]

Example 128

7-((1H-imidazol-1-yl))methyl)-2-(6-methoxy-8-(piperidin-1-ylmethyl)quinolin-4-yl)-5-(1-methyl-3-(trifluoromethyl)-1H-pyrazol-4-yl)-3,4-dihydroisoquinolin-1(2H)-one The title compound (55 mg, 87 μmol, 87%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-methoxy-8-(piperidin-1-ylmethyl)quinoline (Intermediate 96). $^{1}$H NMR (400 MHz, Chloroform-d) δ 8.82 (d, =4.6 Hz, 1H), 8.17 (d, J=1.8 Hz, 1H), 7.65 (d, J=2.6 Hz, 1H), 7.57 (s, 1H), 7.40 (s, 1H), 7.31 (d, J=4.6 Hz, 1H), 7.26 (s, 1H), 7.17 (d, J=1.9 Hz, 1H), 7.10 (s, 1H), 6.96 (q, J=2.7 Hz, 2H), 5.20 (s, 2H), 4.20 (s, 1H), 4.02 (s, 3H), 3.97 (m, J=5.5 Hz, 1H), 3.87 (s, 3H), 3.80 (m, J=5.7 Hz, 1H), 3.14 (m, J=5.5 Hz, 1H), 2.97 (m, J=5.2 Hz, 1H), 2.56 (s, 4H), 1.64 (t, J=6.9 Hz, 4H), 1.49 (d, J=4.8 Hz, 2H); LCMS (ESI): m/z=630.3 [M+H]$^{+}$.

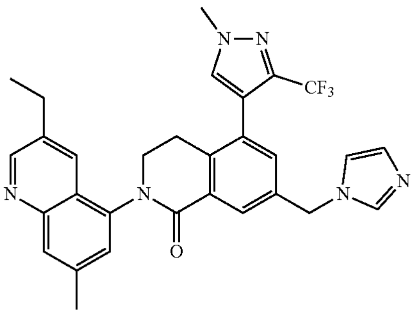 [SMILES: CCc1cnc2cc(C)cc(N3CCc4c(cc(Cn5ccnc5)cc4-c4cn(C)nc4C(F)(F)F)C3=O)c2c1]

Example 129

7-((1H-Imidazol-1-yl)methyl)-2-(3-ethyl-7-methylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-ethyl-7-methylquinoline (Intermediate 84). $^{1}$H NMR (400 MHz, methanol-4) δ 8.75 (d, J=2 Hz, 1H), 8.05 (d, J=1.8 Hz, 1H), 7.99 (d, J=1.2 Hz, 1H), 7.84 (s, 2H), 7.80 (s, 1H), 7.51 (d, J=1.4 Hz, 1H), 7.41 (d, J=1.4 Hz, 1H), 7.16 (s, 1H), 7.00 (s, 1H), 5.35 (s, 2H), 4.10-4.03 (m, 1H), 4.02 (s, 3H), 3.87-3.81 (m, 1H), 3.25-3.16 (m, 1H), 3.08-3.01 (m, 1H), 2.85 (q, J=7.6 Hz, 2H), 2.58 (s, 3H), 1.30 (q, J=7.6 Hz, 2H); LCMS Method 2: >95%, $R_T$=1.20 min, MS (ESI) 545.2 [M+H]$^{+}$.

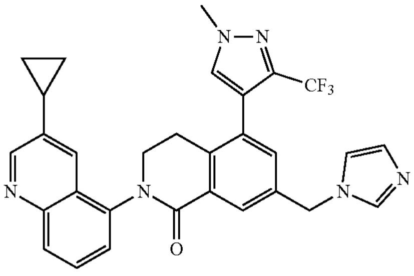 [SMILES: Cn1cc(-c2cc(Cn3ccnc3)cc3c2CCN(c2cccc4ncc(C5CC5)cc24)C3=O)c(C(F)(F)F)n1]

Example 130

7-((1H-Imidazol-1-yl)methyl)-2-(3-cyclopropylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-cyclopropylquinoline (Intermediate 85). LCMS Method 2: >95%, $R_T$=1.21 min, MS (ESI) 543.1 [M+H]$^{+}$.

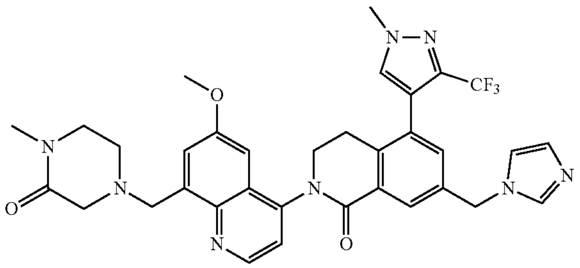 [SMILES: COc1cc(CN2CCN(C)C(=O)C2)c2nccc(N3CCc4c(cc(Cn5ccnc5)cc4-c4cn(C)nc4C(F)(F)F)C3=O)c2c1]

Example 131

7-((1H-Imidazol-1-yl)methyl)-2-(6-methoxy-8-((4-methyl-3-oxopiperazin-1-yl)methyl)quinolin-4-yl)-5-(1-methyl-3-(trifluoromethyl)-1H-pyrazol-4-yl)-3,4-dihydroisoquinolin-1(2H)-one The title compound (37 mg, 56 μmol, 56%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-((4-bromo-6-methoxyquinolin-8-yl)methyl)-1-methylpiperazin-2-one (Intermediate 101). $^1$H NMR (400 MHz, Chloroform-d) δ 8.83 (d, J=4.6 Hz, 1H), 8.16 (d, J=1.8 Hz, 1H), 7.56 (d, J=3.6 Hz, 1H), 7.41 (s, 1H), 7.33 (d, J=4.6 Hz, 1H), 7.18 (d, J=1.8 Hz, 1H), 7.10 (s, 1H), 7.00 (d, J=2.8 Hz, 1H), 6.95 (s, 1H), 5.20 (s, 2H), 4.29 (q, J=18.9 Hz, 2H), 4.03 (s, 3H), 3.98 (m, J=5.9 Hz, 2H), 3.86 (s, 3H), 3.80 (m, J=5.7 Hz, 1H), 3.35 (m, J=6.0 Hz, 4H), 3.15 (m, J=5.41 Hz, 1H), 3.00 (t, J=4.7 Hz, 1H), 2.97 (s, 3H), 2.86 (m, J=4.91 Hz, 2H); LCMS (ESI): m/z=659.2 [M+H]$^+$.

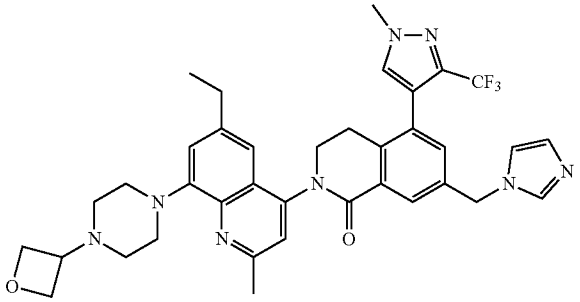 [SMILES: CCc1cc(N2CCN(C3COC3)CC2)c2nc(C)cc(N3CCc4c(cc(Cn5ccnc5)cc4-c4cn(C)nc4C(F)(F)F)C3=O)c2c1]

Example 132

7-((1H-Imidazol-1-yl)methyl)-2-(6-ethyl-2-methyl-8-(4-(oxetan-3-yl)piperazin-1-yl)quinolin-4-yl)-5-(1-methyl-3-(trifluoromethyl)-1H-pyrazol-4-yl)-3,4-dihydroisoquinolin-1(2H)-one The title compound (23 mg, 0.034 mmol, 42% yield) was prepared following the Buchwald coupling procedure described for Example 124, using 7(1H-imidazol-1-yl) methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 50 mg, 0.08 mmol), and 1-(oxetan-3-yl)piperazine (34 mg, 0.24 mmol, 3 equiv). $^1$H NMR (400 MHz, Chloroform-d) δ 8.15 (d, J=2.0 Hz, 1H), 7.57 (d, J=1.2 Hz, 1H), 7.40 (d, J=1.1 Hz, 1H), 7.19 (d, J=1.6 Hz, 2H), 7.16 (d, J=2.0 Hz, 1H), 7.10 (t, J=1.1 Hz, 1H), 6.99 (d, J=1.7 Hz, 1H), 6.94 (t, J=1.3 Hz, 1H), 5.19 (s, 2H), 4.78-4.68 (m, 4H), 4.02 (s, 3H), 3.97-3.86 (m, 1H), 3.78 (dt, J=11.8, 5.4 Hz, 1H), 3.67 (p, J=6.4 Hz, 1H), 3.60 (brs, 2H), 3.36 (brs, 2H), 3.13 (ddd, J=16.0, 10.6, 5.3 Hz, 1H), 2.94 (dt, J=16.4, 4.9 Hz, 1H), 2.77-2.70 (m, 9H), 1.27 (t, J=7.6 Hz, 3H); LCMS (ESI): Method 2: $R_T$=1.126 min, m/z=685.3 [M+H]$^+$.

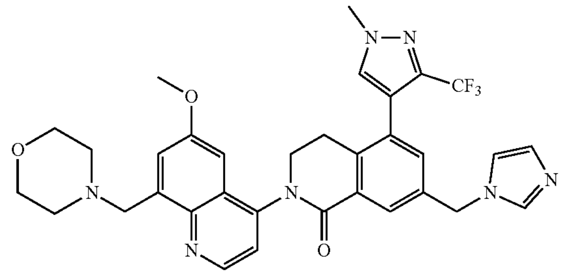 [SMILES: COc1cc(CN2CCOCC2)c2nccc(N3CCc4c(cc(Cn5ccnc5)cc4-c4cn(C)nc4C(F)(F)F)C3=O)c2c1]

Example 133

7-((1H-Imidazol-1-yl)methyl)-2-(6-methoxy-8-(morpholinomethyl)quinolin-4-yl)-5-(1-methyl-3-(trifluoromethyl)-1H-pyrazol-4-yl)-3,4-dihydroisoquinolin-1(2H)-one The title compound (40 mg, 63 μmol, 63%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-((4-bromo-6-methoxyquinolin-8-yl)methyl)morpholine (Intermediate 99). $^1$H NMR (400 MHz, Chloroform-d) δ 8.83 (d, J=4.6 Hz, 1H), 8.16 (d, J=1.8 Hz, 1H), 7.63 (d, J=2.8 Hz, 1H), 7.57 (s, 1H), 7.40 (s, 1H), 7.32 (d, J=4.6 Hz, 1H), 7.17 (d, J=1.8 Hz, 1H), 7.10 (s, 1H), 6.98 (d, J=2.8 Hz, 1H), 6.95 (s, 1H), 5.20 (s, 2H), 4.24 (s, 2H), 4.03 (s, 3H), 3.97 (m, J=5.8 Hz, 1H), 3.87 (s, 3H), 3.78 (t, J=4.6 Hz, 4H), 3.15 (m, J=5.4 Hz, 1H), 2.97 (m, J=5.2 Hz, 1H), 2.64 (d, J=3.6 Hz, 4H); LCMS (ESI): m/z=632.2 [M+H]$^+$.

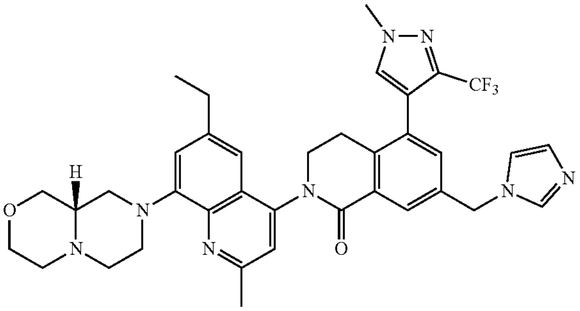 [SMILES: CCc1cc(N2CCN3CCOC[C@@H]3C2)c2nc(C)cc(N3CCc4c(cc(Cn5ccnc5)cc4-c4cn(C)nc4C(F)(F)F)C3=O)c2c1]

Example 134

(S)-7-((1H-imidazol-1-yl)methyl)-2-(6-ethyl-8-(hexahydropyrazino[2,1-c][1,4]oxazin-8(1H)-yl)-2-methylquinolin-4-yl)-5-(1-methyl-3-(trifluoromethyl)-1H-pyrazol-4-yl)-3,4-dihydroisoquinolin-1(2H)-one The title compound (24 mg, 0.035 mmol, 44% yield) was prepared following the Buchwald coupling procedure described for Example 124, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 50 mg, 0.08 mmol), and (9aS)-octahydropyrazino[2,1-c][1,4]oxazine dihydrochloride (51 mg, 0.24 mmol, 3 equiv). $^1$H NMR (400 MHz, Chloroform-d) δ 8.15 (d, J=2.0 Hz, 1H), 7.57 (s, 1H), 7.40 (s, 1H), 7.18 (d, J=2.9 Hz, 2H), 7.16 (d, J=2.0 Hz, 1H), 7.10 (d, J=1.3 Hz, 2H), 6.98-6.92 (m, 2H), 5.19 (s, 2H), 4.16 (d, J=11.0 Hz, 1H), 4.02 (s, 3H), 3.99-3.86 (m, 2H), 3.78 (ddd, J=12.0, 7.6, 3.7 Hz, 4H), 3.63 (d, J=10.6 Hz, 1H), 3.36 (dt, J=18.2, 10.61 Hz, 1H), 3.13 (ddd, J=16.0, 10.1, 5.3 Hz, 2H), 2.93 (dq, J=15.5, 5.2 Hz, 2H), 2.88-2.78 (m, 1H), 2.73 (d, J=7.8 Hz, 5H), 2.66-2.39 (m, J=2H), 1.26 (t, J=7.6 Hz, 3H); LCMS (ESI): Method 2: $R_T$=1.151 min, m/z=685.3 [M+H]$^+$.

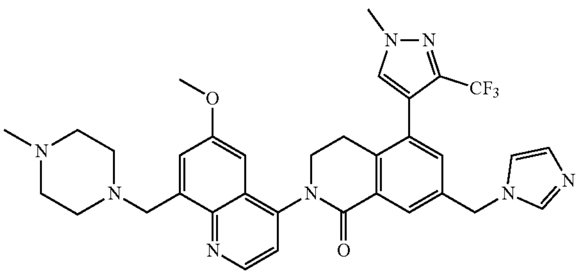 [SMILES: COc1cc(CN2CCN(C)CC2)c2nccc(N3CCc4c(cc(Cn5ccnc5)cc4-c4cn(C)nc4C(F)(F)F)C3=O)c2c1]

Example 135

7-((1H-Imidazol-1-yl)methyl)-2-(6-methoxy-8-((4-methylpiperazin-1-yl)methyl)quinolin-4-yl)-5-(1-methyl-3-(trifluoromethyl)-1H-pyrazol-4-yl)-3,4-dihydroisoquinolin-1(2H)-one The title compound (51 mg, 79 μmol, 79%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) 4-bromo-6-methoxy-8-((4-methylpiperazin-1-yl)methyl)quinoline (Intermediate 100). $^1$H NMR (400 MHz, Chloroform-d) δ 8.83 (d, J=4.6 Hz, 1H), 8.17 (d, J=1.9 Hz, 1H), 7.63 (d, J=2.8 Hz, 1H), 7.57 (s, 1H), 7.40 (s, 1H), 7.32 (d, J=4.6 Hz, 1H), 7.17 (d, J=1.9 Hz, 1H), 7.10 (s, 1H), 6.97 (d, J=2.8 Hz, 1H), 6.95 (t, J=1.2 Hz, 1H), 5.20 (s, 2H), 4.25 (d, J=4.4 Hz, 2H), 4.03 (s, 3H), 3.97 (m, J=4.3 Hz, 2H), 3.87 (s, 3H), 3.80 (m, J=5.7 Hz, 1H), 3.15 (m, J=5.4 Hz, 1H), 2.97 (m, J=5.1 Hz, 1H), 2.60 (d, J=62.3 Hz, 7H), 2.32 (s, 3H); LCMS (ESI): m/z=645.3 [M+H]$^+$.

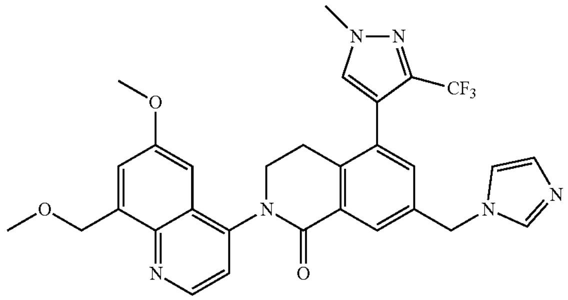 [SMILES: COCc1cc(OC)cc2c(N3CCc4c(cc(Cn5ccnc5)cc4-c4cn(C)nc4C(F)(F)F)C3=O)ccnc12]

Example 136

7-((1H-Imidazol-1-yl)methyl)-2-(6-methoxy-8-(methoxymethyl)quinolin-4-yl)-5-(1-methyl-3-(trifluoromethyl)-1H-pyrazol-4-yl)-3,4-dihydroisoquinolin-1(2H)-one The title compound (42 mg, 73 μmol, 73%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-methoxy-8-(methoxymethyl)quinoline (Intermediate 107). $^1$H NMR (400 MHz, Chloroform-d) δ 8.82 (d, J=4.6 Hz, 1H), 8.17 (d, J=1.8 Hz, 1H), 7.57 (s, 1H), 7.55 (t, J=1.4 Hz, 1H), 7.40 (s, 1H), 7.33 (d, J=4.6 Hz, 1H), 7.17 (d, J=1.9 Hz, 1H), 7.10 (s, 1H), 7.00 (d, J=2.8 Hz, 1H), 6.95 (s, 1H), 5.17 (d, J=22.9 Hz, 4H), 4.02 (s, 3H), 3.97 (m, J=5.5 Hz, 1H), 3.88 (s, 3H), 3.80 (m, J=4.6 Hz, 1H), 3.58 (s, 3H), 3.15 (m, J=5.4 Hz, 1H), 2.97 (m, J=5.1 Hz, 1H); LCMS (ESI): m/z=577.2 [M+H]$^+$.

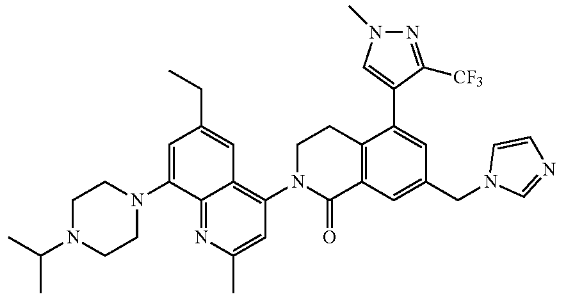 [SMILES: CCc1cc(N2CCN(C(C)C)CC2)c2nc(C)cc(N3CCc4c(cc(Cn5ccnc5)cc4-c4cn(C)nc4C(F)(F)F)C3=O)c2c1]

Example 137

7-((1H-Imidazol-1-yl)methyl)-2-(6-ethyl-8-(4-isopropylpiperazin-1-yl)-2-methylquinolin-4-yl)-5-(1-methyl-3-(trifluoromethyl)-1H-pyrazol-4-yl)-3,4-dihydroisoquinolin-1(2H)-one The title compound (22 mg, 0.033 mmol, 41% yield) was prepared following the Buchwald coupling procedure described for Example 124, using 7-((1H-imidazol-1-yl)methyl)-2-(8-bromo-6-ethyl-2-methylquinolin-4-yl)-5-methyl-3-(trifluoromethyl)-1H-pyrazol-4-yl)-3,4-dihydroisoquinolin-1 (2H)-one (Example 109, 50 mg, 0.08 mmol), and 1H-isopropylpiperazine (31 mg, 0.24 mmol, 3 equiv). $^1$H NMR (400 MHz, Chloroform-d) δ 8.16 (d, J=2.0 Hz, 1H), 7.57 (t, J=1.1 Hz, 1H), 7.40 (d, J=1.1 Hz, 1H), 7.18 (s, 1H), 7.17-7.16 (m, 2H), 7.16 (d, J=2.0 Hz, 1H), 7.10 (t, J=1.1 Hz, 1H), 6.99 (d, J=1.8 Hz, 1H), 6.94 (t, J=1.3 Hz, 1H), 5.19 (s, 2H), 4.02 (s, 3H), 3.96-3.85 (m, 1H), 3.78 (dt, J=11.8, 5.4 Hz, 1H), 3.57 (brs, 2H), 3.33 (brs, 2H), 3.13 (ddd, J=16.0, 10.5, 5.2 Hz, 1H), 2.99-2.90 (m, 1H), 2.88 (s, 5H), 2.74 (d, J=5.9 Hz, 5H), 1.26 (t, J=7.6 Hz, 3H), 1.15 (d, J=6.5 Hz, 6H); LCMS (ESI): Method 2: $R_T$=1.154 min, m/z=671.3 [M+H]$^+$.

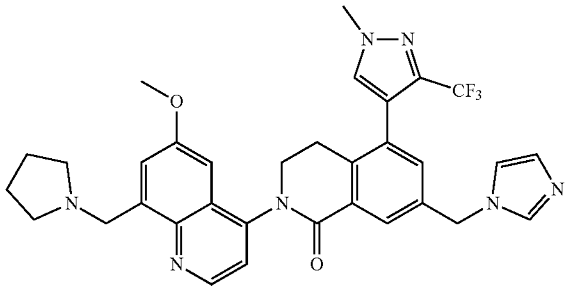 [SMILES: COc1cc(CN2CCCC2)c2nccc(N3CCc4c(cc(Cn5ccnc5)cc4-c4cn(C)nc4C(F)(F)F)C3=O)c2c1]

Example 138

7-((1H-Imidazol-1-yl)methyl)-2-(6-methoxy-8-(pyrrolidin-1-ylmethyl)quinolin-4-yl)-5-(1-methyl-3-(trifluoromethyl)-1H-pyrazol-4-yl)-3,4-dihydroisoquinolin-1(2H)-one The title compound (49 mg, 80 μmol, 80%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-methoxy-8-(pyrrolidin-1-ylmethyl)quinoline (Intermediate 97). $^1$H NMR (400 MHz, Chloroform-d) δ 8.83 (d, J=4.6 Hz, 1H), 8.17 (d, J=1.9 Hz, 1H), 7.60 (d, J=2.5 Hz, 1H), 7.57 (s, 1H), 7.40 (s, 1H), 7.31 (d, =4.6 Hz, 1H), 7.17 (d, J=1.8 Hz, 1H), 7.10 (s, 1H), 6.97 (d, J=2.8 Hz, 1H), 6.95 (s, 1H), 5.20 (s, 2H), 4.36 (q, J=18.8 Hz, 2H), 4.02 (s, 3H), 3.96 (m, J=5.0 Hz, 1H), 3.87 (s, 3H), 3.80 (q, J=5.9 Hz, 1H), 3.14 (m, J=5.4 Hz, 1H), 2.97 (m, J=5.2 Hz, 1H), 2.71 (d, J=2.9 Hz, 4H), 1.84 (m, J=3.2 Hz, 4H); LCMS (ESI): m/z=616.2 [M+H]$^+$.

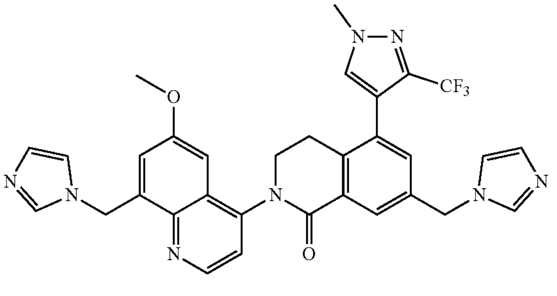 [SMILES: COc1cc(Cn2ccnc2)c2nccc(N3CCc4c(cc(Cn5ccnc5)cc4-c4cn(C)nc4C(F)(F)F)C3=O)c2c1]

Example 139

7-((1H-imidazol-1-yl)methyl)-2-(8-((1H-imidazol-1-yl)methyl)-6-methoxyquinolin-4-yl)-5-(1-methyl-3-(trifluoromethyl)-1H-pyrazol-4-yl)-3,4-dihydroisoquinolin-1(2H)-one The title compound (35 mg, 57 μmol, 57%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 8-((1H-imidazol-1-yl)methyl)-4-bromo-6-methoxyquinoline (Intermediate 98). $^1$H NMR (400 MHz, Chloroform-d) δ 8.86 (d, J=4.6 Hz, 1H), 8.15 (d, J=1.8 Hz, 1H), 7.70 (s, 1H), 7.57 (s, 1H), 7.40 (s, 1H), 7.37 (d, J=4.6 Hz, 1H), 7.18 (d, J=1.8 Hz, 1H), 7.09 (d, J=6.5 Hz, 2H), 7.05 (s, 1H), 7.00 (q3=3.2 Hz, 2H), 6.95 (s, 1H), 5.79 (q, J=34.9 Hz, 2H), 5.20 (s, 2H), 4.02 (m, 4H), 3.81 (m, 4H), 3.14 (m, J=5.4 Hz, 1H), 2.98 (m, J=5.1 Hz, 1H); LCMS (ESI): m/z=613.2 [M+H]$^+$.

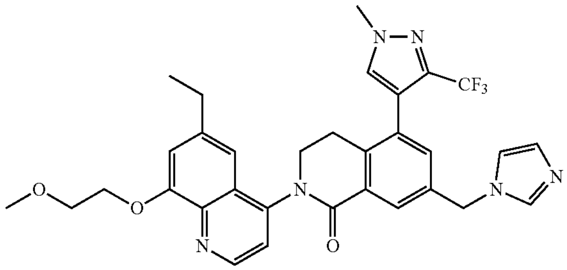 [SMILES: CCc1cc(OCCOC)c2nccc(N3CCc4c(cc(Cn5ccnc5)cc4-c4cn(C)nc4C(F)(F)F)C3=O)c2c1]

Example 140

7-((1H-Imidazol-1-yl)methyl)-2-(6-ethyl-8-(2-methoxyethoxy)quinolin-4-yl)-5-(1-methyl-3-(trifluoromethyl)-1H-pyrazol-4-yl)-3,4-dihydroisoquinolin-1(2H)-one The title compound (10 mg, 0.017 mmol, 25% yield) was prepared following the Buchwald coupling procedure described for Example 120, using 7-((1H-imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 40 mg, 0.066 mmol), 2-methoxyethanol (15 mg, 0.20 mmol, 3 equiv), sodium tert-butoxide (9.5 mg, 0.098 mmol, 1.5 equiv), RockPhos (6 mg, 0.013 mmol, 0.2 equiv), and $Pd_2(dba)_3$ (3 mg, 0.003 mmol, 0.05 equiv) at 40° C. $^1$H NMR (400 MHz, Chloroform-d) δ 8.93 (d, J=4.6 Hz, 1H), 8.16 (d, J=2.0 Hz, 1H), 7.57 (s, 1H), 7.40 (s, 1H), 7.34 (d, J=4.6 Hz, 1H), 7.19 (s, 1H), 7.17 (d, J=2.0 Hz, 1H), 7.10 (s, 1H), 7.02 (d, J=1.7 Hz, 1H), 6.94 (s, 1H), 5.19 (s, 2H), 4.42 (t, J=5.2 Hz, 2H), 4.02 (s, 3H), 3.99-3.91 (m, 3H), 3.81 (dt, J=11.7, 5.4 Hz, 1H), 3.48 (s, 3H), 3.15 (ddd, J=16.1, 10.6, 5.2 Hz, 1H), 2.96 (dt, J=16.5, 5.0 Hz, 1H), 2.78 (q, =7.5 Hz, 2H), 1.28 (t, J=7.6 Hz, 3H).

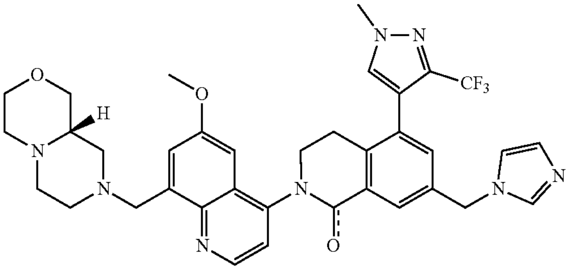

Example 141

(S)-7-((1H-Imidazol-1-yl)methyl)-2-(8-((hexahydropyrazino[2,1-c][1,4]oxazin-8(1H)-yl)methyl)-6-methoxyquinolin-4-yl)-5-(1-methyl-3-(trifluoromethyl)-1H-pyrazol-4-yl)-3,4-dihydroisoquinolin-1(2H)-one The title compound (28 mg, 41 μmol, 41%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and (S)-8-((4-bromo-6-methoxyquinolin-8-yl)methyl)octahydropyrazino[2,1-c][1,4]oxazine (Intermediate 106). $^1$H NMR (400 MHz, Chloroform-d) δ 8.82 (d, J=4.6 Hz, 1H), 8.17 (d, J=1.7 Hz, 1H), 7.61 (d, J=2.3 Hz, 1H), 7.57 (s, 1H), 7.40 (s, 1H), 7.32 (d, J=4.6 Hz, 1H), 7.17 (s, 1H), 7.10 (s, 1H), 6.98 (d, J=2.7 Hz, 1H), 6.95 (s, 1H), 5.20 (s, 2H), 4.25 (d, J=4.9 Hz, 2H), 4.03 (s, 3H), 3.97 (m, J=5.4 Hz, 1H), 3.87 (s, 3H), 3.80 (m, J=6.0 Hz, 2H), 3.68 (m, 0.1=4.5 Hz, 2H), 3.25 (t, 3=10.6 Hz, 1H), 3.14 (m, J=5.4 Hz, 1H), 2.97 (m, J=5.1 Hz, 2H), 2.76 (t, J=4.5 Hz, 2H), 2.68 (d, J=11.7 Hz, 1H), 2.46 (m, J=6.9 Hz, 4H), 2.00 (q, J=11.1 Hz, 1H); LCMS (ESI): m/z=687.2 $[M+H]^+$.

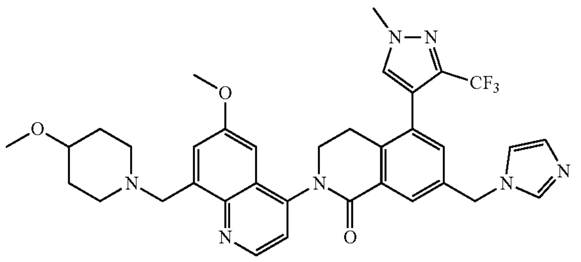 [SMILES: COc1cc(CN2CCC(OC)CC2)c2nccc(N3CCc4c(cc(Cn5ccnc5)cc4-c4cn(C)nc4C(F)(F)F)C3=O)c2c1]

Example 142

7-((1H-Imidazol-1-yl)methyl)-2-(6-methoxy-8-((4-methoxypiperidin-1-yl)methyl)quinolin-4-yl)-5-(1-methyl-3-(trifluoromethyl)-1H-pyrazol-4-yl)-3,4-dihydroisoquinolin-1(2H)-one The title compound (42 mg, 64 μmol, 64%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-methoxy-8-((4-methoxypiperidin-1-yl)methyl)quinoline (Intermediate 103). $^1$H NMR (400 MHz, Chloroform-d) δ 8.82 (d, J=4.6 Hz, 1H), 8.17 (d, J=1.8 Hz, 1H), 7.64 (s, 1H), 7.57 (s, 1H), 7.40 (s, 1H), 7.31 (d, J=4.6 Hz, 1H), 7.17 (d, J=1.9 Hz, 1H), 7.10 (s, 1H), 6.97 (d, J=2.7 Hz, 1H), 6.95 (s, 1H), 5.20 (s, 2H), 4.24 (s, 2H), 4.02 (s, 3H), 3.96 (m, J=5.3 Hz, 1H), 3.87 (s, 3H), 3.80 (m, J=5.7 Hz, 1H), 3.35 (s, 3H), 3.26 (m, J=4.4 Hz, 1H), 3.14 (m, J=5.4 Hz, 1H), 2.96 (m, J=5.7 Hz, 3H), 2.34 (d, J=11.1 Hz, 2H), 1.95 (s, 2H), 1.65 (s, 2H); LCMS (ESI): m/z=660.3 $[M+H]^+$.

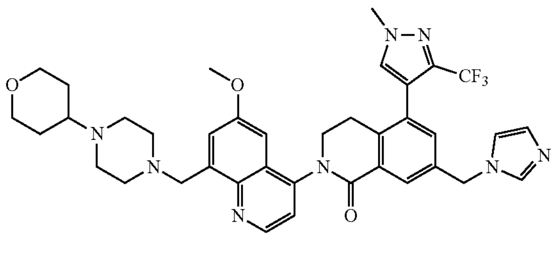 [SMILES: COc1cc(CN2CCN(C3CCOCC3)CC2)c2nccc(N3CCc4c(cc(Cn5ccnc5)cc4-c4cn(C)nc4C(F)(F)F)C3=O)c2c1]

Example 143

7-((1H-Imidazol-1-yl)methyl)-2-(6-methoxy-8-((4-(tetrahydro-2H-pyran-4-yl)piperazin-1-yl)methyl)quinolin-4-yl)-5-(1-methyl-3-(trifluoromethyl)-1H-pyrazol-4-yl)-3,4-dihydroisoquinolin-1(2H)-one The title compound (33 mg, 46 μmol, 46%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-methoxy-8-((4-(tetrahydro-2H-pyran-4-yl)piperazin-1-yl)methyl)quinoline (Intermediate 105). $^1$H NMR (400 MHz, Chloroform-d) δ 8.83 (d, J=4.6 Hz, 1H), 8.16 (d, J=1.6 Hz, 1H), 7.59 (s, 1H), 7.57 (s, 1H), 7.40 (s, 1H), 7.32 (d, J=4.6 Hz, 1H), 7.17 (d, J=1.7 Hz, 1H), 7.10 (s, 1H), 6.97 (d, J=2.8 Hz, 1H), 6.95 (s, 1H), 5.20 (s, 2H), 4.64 (q, J=5.9 Hz, 4H), 4.28 (s, 2H), 4.02 (s, 3H), 3.96 (m, J=5.9 Hz, 1H), 3.86 (s, 3H), 3.79 (m, J=5.7 Hz, 1H), 3.54 (t, J=6.5 Hz, 1H), 3.14 (m, J=5.4 Hz, 1H), 2.97 (m, J=5.1 Hz, 1H), 2.71 (s, 4H), 2.44 (s, 4H), 1.69 (s, 3H); LCMS (ESI): m/z 715.2 $[M+H]^+$.

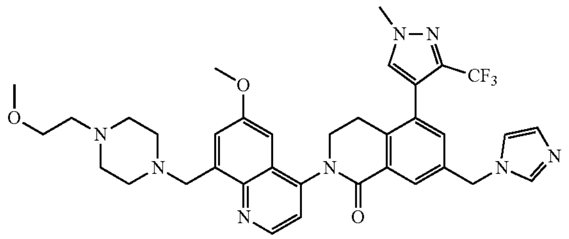 [SMILES: COCCN1CCN(Cc2cc(OC)cc3c(N4CCc5c(cc(Cn6ccnc6)cc5-c5cn(C)nc5C(F)(F)F)C4=O)ccnc23)CC1]

Example 144

7-((1H-Imidazol-1-yl)methyl)-2-(6-methoxy-8-((4-(2-methoxyethyl)piperazin-1-yl)methyl)quinolin-4-yl)-5-(1-methyl-3-(trifluoromethyl)-1H-pyrazol-4-yl)-3,4-dihydroisoquinolin-1(2H)-one The title compound (37 mg, 54 μmol, 54%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-methoxy-8-((4-(2-methoxyethyl)piperazin-1-yl)methyl)quinoline (Intermediate 104). $^1$H NMR (400 MHz, Chloroform-d) δ 8.82 (d, J=4.6 Hz, 1H), 8.17 (d, J=1.7 Hz, 1H), 7.62 (d, J=2.3 Hz, 1H), 7.57 (s, 1H), 7.40 (s, 1H), 7.31 (d, J=4.6 Hz, 1H), 7.17 (d, J=1.7 Hz, 1H), 7.10 (s, 1H), 6.96 (t, J=4.5 Hz, 1H), 5.20 (s, 2H), 4.26 (q, J=13.4 Hz, 2H), 4.02 (s, 3H), 3.96 (m, J=4.9 Hz, 1H), 3.87 (s, 3H), 3.79 (m, J=5.7 Hz, 1H), 3.53 (t, J=5.7 Hz, 2H), 3.35 (s, 3H), 3.14 (m, J=5.4 Hz, 1H), 2.97 (m, J=5.1 Hz, 1H), 2.70 (s, 4H), 2.61 (t, J=5.7 Hz, 6H); LCMS (ESI): m/z=689.2 $[M+H]^+$.

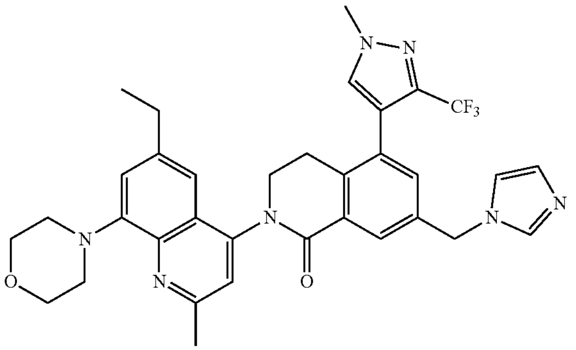 [SMILES: CCc1cc(N2CCOCC2)c2nc(C)cc(N3CCc4c(cc(Cn5ccnc5)cc4-c4cn(C)nc4C(F)(F)F)C3=O)c2c1]

Example 145

7-((1H-Imidazol-1-yl)methyl)-2-(6-ethyl-2-methyl-8-morpholinoquinolin-4-yl)-5-(1-methyl-3-(trifluoromethyl)-1H-pyrazol-4-yl)-3,4-dihydroisoquinolin-1(2H)-one The title compound (27 mg, 0.042 mmol, 44% yield) was prepared following the Buchwald coupling procedure described for Example 124, using 7-((1H-imidazol-1-yl) methyl)-2-(8-bromo-6-ethyl-2-methylquinolin-4-yl)-5-(1-methyl-3-(trifluoromethyl)-1H-pyrazol-4-yl)-3,4-dihydroisoquinolin-1 (2H)-one (Example 109, 60 mg, 0.096 mmol), and morpholine (25 mg, 0.29 mmol, 3 equiv). $^1$H NMR (400 MHz, Chloroform-d) δ 8.16 (d, J=2.0 Hz, 1H), 7.57 (s, 1H), 7.40 (s, 1H), 7.20 (d, J=2.2 Hz, 2H), 7.16 (d, J=2.0 Hz, 1H), 7.10 (t, J=1.1 Hz, 1H), 6.97 (d, J=1.7 Hz, 1H), 6.95 (t, J=1.3 Hz, 1H), 5.20 (s, 2H), 4.09-4.00 (m, 7H), 3.98-3.86 (m, 1H), 3.79 (dt, J=11.9, 5.4 Hz, 1H), 3.57 (d, J=11.4 Hz, 2H), 3.35-3.20 (m, 2H), 3.13 (ddd, J=15.9, 10.5, 5.2 Hz, 1H), 2.95 (dt, J=16.3, 4.8 Hz, 1H), 2.80-2.70 (m, 5H), 1.28 (t, J=7.6 Hz, 3H); LCMS (ESI): Method 2: $R_T$=1.291 min, m/z=630.3 [M+H]$^+$.

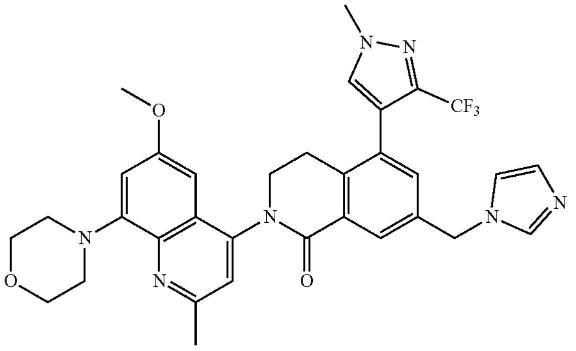 [SMILES: COc1cc(N2CCOCC2)c2nc(C)cc(N3CCc4c(cc(Cn5ccnc5)cc4-c4cn(C)nc4C(F)(F)F)C3=O)c2c1]

Example 146

7-((1H-Imidazol-1-yl)methyl)-2-(6-methoxy-2-methyl-8-morpholinoquinolin-4-yl)-5-(1-methyl-3-(trifluoromethyl)-1H-pyrazol-4-yl)-3,4-dihydroisoquinolin-1(2H)-one The title compound (27 mg, 0.043 mmol, 44% yield) was prepared following the Buchwald coupling procedure described for Example 124, using 7-((1H-imidazol-1-yl) methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 60 mg, 0.096 mmol), and morpholine (25 mg, 0.29 mmol, 3 equiv). $^1$H NMR (400 MHz, Chloroform-d) δ 8.16 (d, J=2.0 Hz, 1H), 7.57 (s, 1H), 7.40 (d, J=1.1 Hz, 1H), 7.20 (s, 1H), 7.16 (d, J=2.0 Hz, 1H), 7.10 (s, 1H), 6.95 (s, 1H), 6.77 (d, J=2.6 Hz, 1H), 6.68 (d, J=2.6 Hz, 1H), 5.20 (s, 2H), 4.07-3.98 (m, 7H), 3.96-3.87 (m, 1H), 3.82 (s, 3H), 3.81-3.71 (m, 1H), 3.60-3.53 (m, 2H), 3.32-3.24 (m, 2H), 3.12 (ddd, J=16.3, 10.8, 5.2 Hz, 1H), 2.94 (dt, J=16.5, 4.9 Hz, 1H), 2.70 (s, 3H); LCMS (ESI): Method 2: $R_T$=1.253 min, m/z=632.2 [M+H]$^+$.

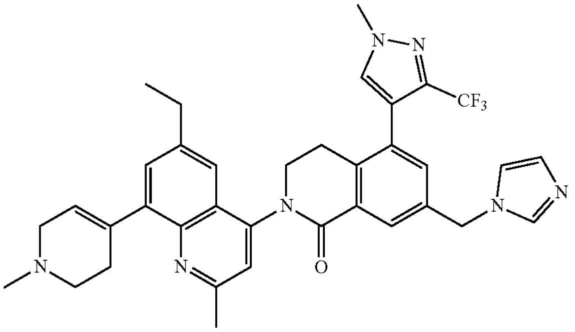 [SMILES: CCc1cc(C2=CCN(C)CC2)c2nc(C)cc(N3CCc4c(cc(Cn5ccnc5)cc4-c4cn(C)nc4C(F)(F)F)C3=O)c2c1]

Example 147

7-((1H-imidazol-1-yl)methyl)-2-(6-ethyl-2-methyl-8-(1-methyl-1,2,3,6-tetrahydropyridin-4-yl)quinolin-4-yl)-5-(1-methyl-3-(trifluoromethyl)-1H-pyrazol-4-yl)-3,4-dihydroisoquinolin-1(2H)-one 7-((1H-Imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 200 mg, 0.32 mmol), 1-methyl-4-(4,4,5,5-tetramethyl-1,3,2-dioxaborolan-2-yl)-1,2,3,6-tetrahydropyridine (143 mug, 0.64 mmol, 2 equiv), potassium carbonate (89 mg, 0.64 mmol, 2 equiv), $Ad_2PBu$ (11 mg, 0.032 mmol, 0.1 equiv), and $Pd_2(dba)_3$ (9 mg, 9.62 μmol, 0.03 equiv) were dissolved in DMLA:$H_2O$ (4:1, 1.3 mL) and placed under an argon atmosphere. The reaction mixture was then placed in a preheated heating block and stirred for 14 h at 100° C. At 23° C., brine was added to the mixture and extracted with $CH_2Cl_2$ (3×20 mL). The combined organic layers were dried over $MgSO_4$ and concentrated under reduced pressure. The residue was purified by flash chromatography (Combi-flash Rf, Hex/EtOAc=0-100% gradient followed by MeOH/$CH_2Cl_2$=0-10% gradient) to provide the title compound (180 mg, 0.28 mmol, 88% yield), $^1$H NMR (400 MHz, Chloroform-d) mixture of isomers δ 8.19-8.11 (m, 1H), 7.57 (s, 1H), 7.47-7.38 (m, 2H), 7.25-7.14 (m, 2H), 7.10 (s, 1H), 6.95 (d, J=1.6 Hz, 1H), 5.82 (d, J=42.5 Hz, 1H), 5.20 (s, 2H), 4.10-4.00 (m, 3H), 3.99-3.88 (m, 1H), 3.77 (dd, J=14.5, 7.6 Hz, 2H), 3.21 (s, 1H), 3.12 (dt, J=10.9, 6.01 Hz, 1H), 2.97 (ddt, J=16.2, 10.0, 5.1 Hz, 1H), 2.84-2.61 (m, 7H), 2.47 (s, 2H), 1.27 (t, J=7.6 Hz, 3H); LCMS (ESI): Method 2: $R_T$=1.198 min, m/z=640.2 [M+H]$^+$.

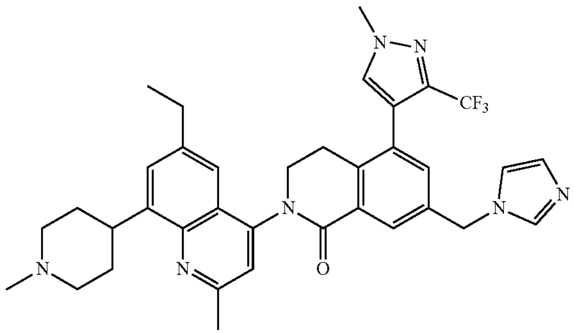 [SMILES: CCc1cc(C2CCN(C)CC2)c2nc(C)cc(N3CCc4c(cc(Cn5ccnc5)cc4-c4cn(C)nc4C(F)(F)F)C3=O)c2c1]

Example 148

7-((1H-Imidazol-1-yl)methyl)-2-(6-ethyl-2-methyl-8-(1-methylpiperidin-4-yl)quinolin-4-yl)-5-(1-methyl-3-(trifluoromethyl)-1H-pyrazol-4-yl)-3,4-dihydroisoquinolin-1(2H)-one 7-((1H-Imidazol-1-yl)methyl)-2-(6-ethyl-2-methyl-8-(1-methyl-1,2,3,6-tetrahydropyridin-4-yl)quinolin-4-yl)-5-(1-methyl-3-(trifluoromethyl)-1H-pyrazol-4-yl)-3,4-dihydroisoquinolin-1(2H)-one (Example 147, 180 mg, 0.28 mmol) was dissolved in EtOH (1 mL) and placed under an argon atmosphere. Then $Pd(OH)_2$/C (39 mg, 0.056 mmol, 0.2 equiv, 20 wt. %) and Pd/C (30 mg, 0.028 mmol, 0.1 equiv, 10 wt. %) were added and the mixture was degassed and placed under a hydrogen atmosphere with balloon. The reaction mixture was then placed in a preheated heating block and stirred for 2 days at 50° C. At 23° C., the reaction mixture was filtered through celite and concentrated under reduced pressure. Brine was added to the mixture and extracted with $CH_2Cl_2$ (3×20 mL). The combined organic layers were dried over $MgSO_4$ and concentrated under reduced pressure. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (71 mg, 0.11 mmol, 39% yield). $^1H$ NMR (400 MHz, Chloroform-d) δ 8.16 (d, J=2.0 Hz, 1H), 7.57 (t, J=1.1 Hz, 1H), 7.47 (d, J=1.9 Hz, 1H), 7.42-7.4.0 (m, 1H), 7.39 (d, J=1.8 Hz, 1H), 7.19 (s, 1H), 7.16 (d, J=2.0 Hz, 1H), 7.10 (t, J=1.1 Hz, 1H), 6.95 (t, J=1.3 Hz, 1H), 5.19 (s, 2H), 4.06-4.00 (m, 4H), 3.92 (ddd, J=12.3, 10.5, 4.4 Hz, 1H), 3.79 (dt, J=12.3, 5.4 Hz, 1H), 3.13 (ddd, J=15.9, 10.5, 5.2 Hz, 1H), 3.02 (d, J=11.2 Hz, 2H), 2.95 (dt, J=16.3, 4.9 Hz, 1H), 2.82-2.70 (m, 5H), 2.38 (s, 3H), 2.26 (td, J=11.6, 2.9 Hz, 2H), 2.04-1.93 (m, 1H), 1.93-1.80 (m, 2H), 1.26 (t, J=7.6 Hz, 3H); LCMS (ESI): Method 2: $R_T$=1.223 min, m/z 642.3 $[M+H]^+$.

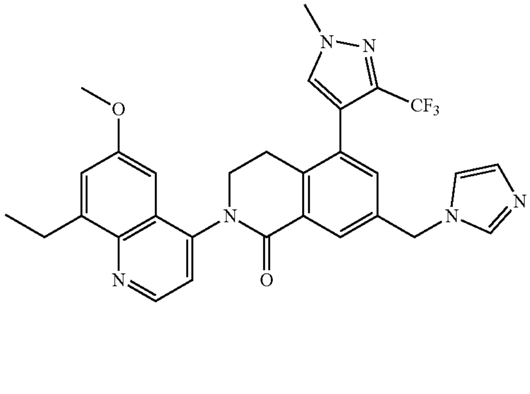 [SMILES: CCc1cc(OC)cc2c(N3CCc4c(cc(Cn5ccnc5)cc4-c4cn(C)nc4C(F)(F)F)C3=O)ccnc12]

Example 149

7-((1H-Imidazol-1-yl)methyl)-2-(8-ethyl-6-methoxyquinolin-4-yl)-5-(1-methyl-3-(trifluoromethyl)-1H-pyrazol-4-yl)-3,4-dihydroisoquinolin-1(2H)-one 7-((1H-Imidazol-1-yl)methyl)-2-(8-bromo-6-methoxyquinolin-4-yl)-5-(1-methyl-3-(trifluoromethyl)-1H-pyrazol-4-yl)-3,4-dihydroisoquinolin-1(2H)-one (Example 29, 100 mg, 0.164 mmol), triethylborane (0.25 mL, 0.25 mmol, 1.5 equiv, 1 M THF), cesium carbonate (107 mg, 0.33 mmol, 2 equiv), and $Pd(dppf)Cl_2$ (6 mg, 8.2 μmol, 0.05 equiv) in THF (1 mL) was stirred for 3 h at 60° C. under Ar in a sealed tube. The reaction was cooled to 0° C. and quenched by addition of $AcOH:H_2O$ (1:1, 10 mL). The resulting mixture was warmed to 23° C., brine was added, and the mixture was extracted with EtOAc (3×20 mL). The combined organic layers were dried over $MgSO_4$ and concentrated under reduced pressure. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (42 mg, 0.075 mmol, 46% yield). $^1H$ NMR (400 MHz, Chloroform-d) δ 8.85 (d, J=4.6 Hz, 1H), 8.17 (d, J=2.0 Hz, 1H), 7.58 (s, 1H), 7.40 (s, 1H), 7.31 (d, J=4.6 Hz, 1H), 7.27 (d, J=3.0 Hz, 1H), 7.17 (d, J=2.0 Hz, 1H), 7.11 (s, 1H), 6.95 (d, J=1.3 Hz, 1H), 6.93 (s, 1H), 5.20 (s, 2H), 4.03 (s, 3H), 3.97 (td, J=11.7, 4.4 Hz, 1H), 3.86 (s, 3H), 3.84-3.75 (m, 1H), 3.29 (hept, J=7.1 Hz, 2H), 3.14 (ddd, J=16.1, 10.8, 5.2 Hz, 1H), 2.97 (dt, J=16.4, 4.8 Hz, 1H), 1.39 (t, J=7.5 Hz, 3H); LCMS (ESI): Method 2: $R_T$=1.31 min, m/z=561.2 $[M+H]^+$.

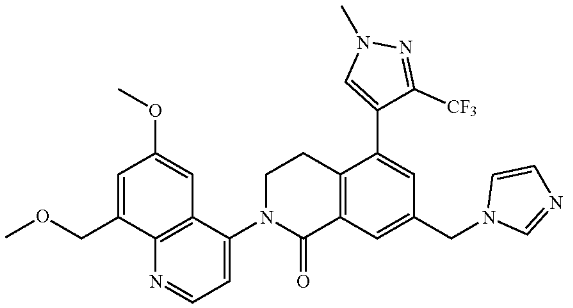 [SMILES: COCc1cc(OC)cc2c(N3CCc4c(cc(Cn5ccnc5)cc4-c4cn(C)nc4C(F)(F)F)C3=O)ccnc12]

Example 150

7-((1H-Imidazol-1-yl)methyl)-2-(6-methoxy-8-(methoxymethyl)quinolin-4-yl)-5-(1-methyl-3-(trifluoromethyl)-1H-pyrazol-4-yl)-3,4-dihydroisoquinolin-1(2H)-one The title compound (19 mg, 0.032 mmol, 20% yield) was prepared following the Suzuki coupling procedure described for Example 147, using 7-((1H-imidazol-1-yl)methyl)-2-(8-bromo-6-methoxyquinolin-4-yl)-5-(1-methyl-3-(trifluoromethyl)-1H-pyrazol-4-yl)-3,4-dihydroisoquinolin-1(2H)-one (Example 29, 100 mg, 0.16 mmol), and potassium trifluoro(methoxymethyl)borate (49 mg, 0.32 mmol, 2 equiv). $^1H$ NMR (400 MHz, Chloroform-d) δ 8.16 (d, J=20 Hz, 1H), 7.57 (s, 1H), 7.51 (d, J=2.8 Hz, 1H), 7.40 (s, 1H), 7.21 (s, 1H), 7.16 (d, J=2.0 Hz, 1H), 7.10 (s, 1H), 6.98-6.92 (m, 2H), 5.27 (d, J=24.2 Hz, 1H), 5.20 (d, J=0.4 Hz, 3H), 5.11 (d, J=14.2 Hz, 1H), 4.02 (s, 3H), 4.00-3.90 (m, 1H), 3.86 (s, 3H), 3.83-3.73 (m, 1H), 3.58 (s, 3H), 3.13 (ddd, J=16.2, 10.8, 5.3 Hz, 1H), 2.96 (dt, J=16.3, 4.8 Hz, 1H), 2.70 (s, 3H); LCMS (ESI): Method 2: $R_T$=1.282 min, m/z=591.2 $[M+H]^+$.

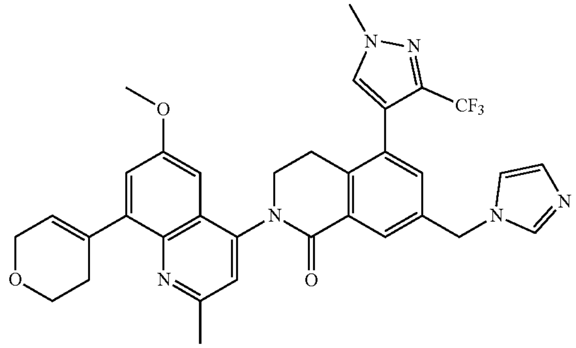 [SMILES: COc1cc(C2=CCOCC2)c2nc(C)cc(N3CCc4c(cc(Cn5ccnc5)cc4-c4cn(C)nc4C(F)(F)F)C3=O)c2c1]

Example 151

7-((1H-imidazol-1-yl)methyl)-2-(8-(3,6-dihydro-2H-pyran-4-yl)-6-methoxy-2-methylquinolin-4-yl)-5-(1-methyl-3-(trifluoromethyl)-1H-pyrazol-4-yl)-3,4-dihydroisoquinolin-1(2H)-one The title compound (151 mg, 0.24 mmol) was prepared following the Suzuki coupling procedure described for Example 147, using 7-(1H-imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 150 mg, 0.24 mmol), and 2-(3,6-dihydro-2H-pyran-4-yl)-4,4,5,5-tetramethyl-1,3,2-dioxaborolane (101 mg, 0.48 mmol, 2 equiv). $^1$H NMR (400 MHz, Chloroform-d) δ 8.16 (d, J=2.0 Hz, 1H), 7.57 (s, 1H), 7.40 (s, 1H), 7.24 (d, J=2.9 Hz, 1H), 7.19 (s, 1H), 7.17 (d, J=2.0 Hz, 1H), 7.11 (s, 1H), 6.97 (d, J=2.9 Hz, 1H), 6.95 (s, 1H), 6.02 (s, 1H), 5.20 (s, 2H), 4.41 (d, J=2.8 Hz, 2H), 4.07-3.99 (m, 5H), 3.95 (td, J=12.0, 4.7 Hz, 1H), 3.85 (s, 3H), 3.82-3.72 (m, 1H), 3.13 (ddd, J=16.1, 10.7, 5.2 Hz, 1H), 2.96 (dt, J=16.2, 4.7 Hz, 2H), 2.74 (d, J=19.8 Hz, 1H), 2.69 (s, 3H); LCMS (ESI): Method 2: $R_T$=1.260 min, m/z=629.2 $[M+H]^+$.

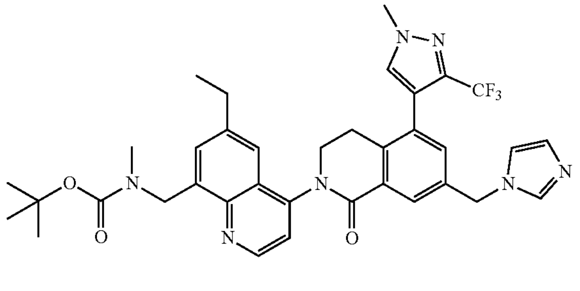 [SMILES: CCc1cc(CN(C)C(=O)OC(C)(C)C)c2nccc(N3CCc4c(cc(Cn5ccnc5)cc4-c4cn(C)nc4C(F)(F)F)C3=O)c2c1]

Example 152 tert-Butyl ((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)(methyl)carbamate The title compound (40.0 mg, 59 μmol, 74% yield) was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 80 μmol, 1 equiv) and tert-butyl ((4-bromo-6-ethylquinolin-8-yl)methyl)(methyl)carbamate (Intermediate 74, 51.5 mg, 136 μmol, 1.7 equiv). $^1$H NMR (400 MHz, Chloroform-d) δ 8.91 (d, J=4.8 Hz, 1H), 8.17 (s, 1H), 7.60 (s, 1H), 7.52 (s, 1H), 7.47 (m, 1H), 7.42 (s, 1H), 7.34 (brs, 1H), 7.19 (s, 1H), 7.12 (s, 1H), 6.96 (s, 1H), 5.21 (s, 2H), 5.15 (m, 2H), 4.03 (s, 3H), 3.98 (m, 1H), 3.84 (m, 1H), 3.18 (m, 1H), 2.98 (m, 4H), 2.80 (q, J=7.6 Hz, 2H), 1.49 (n 9H), 1.28 (t, J=7.6 Hz, 3H).

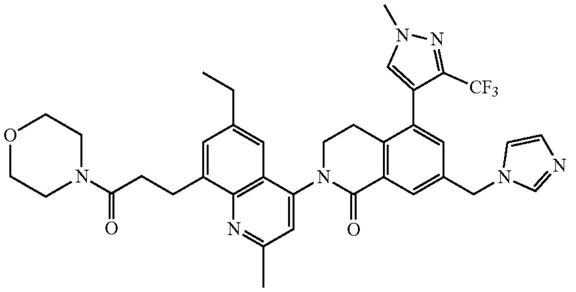 [SMILES: CCc1cc(CCC(=O)N2CCOCC2)c2nc(C)cc(N3CCc4c(cc(Cn5ccnc5)cc4-c4cn(C)nc4C(F)(F)F)C3=O)c2c1]

Example 153

7-((1H-Imidazol-1-yl)methyl)-2-(6-ethyl-2-methyl-8-(3-morpholino-3-oxopropyl)quinolin-4-yl)-5-(1b-methyl-3-(trifluoromethyl)-1H-pyrazol-4-yl)-3,4-dihydroisoquinolin-1(2H)-one The title compound (41 mg, 0.06 mmol, 37% yield) was prepared following the Suzuki coupling procedure described for Example 147, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1 (2H)-one (Example 109, 100 mg, 0.16 mmol), and potassium trifluoro(3-morpholino-3-oxopropyl)borate (80 mg, 0.32 mmol, 2 equiv). $^1$H NMR (400 MHz, Chloroform-d) δ 8.16 (d, J=2.0 Hz, 1H), 7.57 (s, 1H), 7.48 (d, J=1.9 Hz, 1H), 7.42 (d, J=1.9 Hz, 1H), 7.41 (s, 1H), 7.21 (s, 1H), 7.17 (d, J=2.0 Hz, 1H), 7.11 (t, J=1.1 Hz, 1H), 6.97-6.92 (m, 1H), 5.20 (s, 2H), 4.03 (s, 3H), 3.99-3.33 (m, 1H), 3.79 (dt, J=11.8, 5.4 Hz, 1H), 3.75-3.52 (m, 91H), 3.41 (td, J=12.3, 11.7, 5.7 Hz, 1H), 3.14 (ddd, J=16.0, 10.6, 5.3 Hz, 1H), 3.02-2.70 (m, 5H), 2.69 (s, 3H), 1.27 (t, J=7.6 Hz, 3H); LCMS (ESI): Method 2: $R_T$=1.399 min, m/z 686.2 $[M+H]^+$.

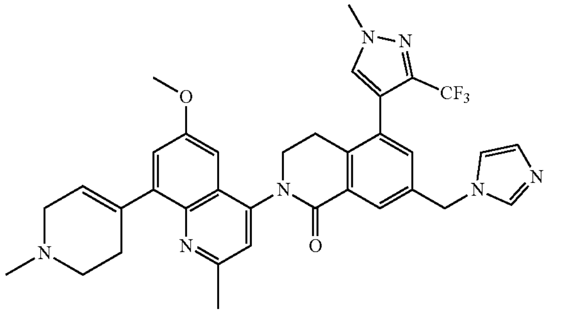 [SMILES: COc1cc(C2=CCN(C)CC2)c2nc(C)cc(N3CCc4c(cc(Cn5ccnc5)cc4-c4cn(C)nc4C(F)(F)F)C3=O)c2c1]

Example 154

7-((1H-Imidazol-1-yl)methyl)-2(6-methoxy-2-methyl-8-(1-methyl-1,2,3,6-tetrahydropyridin-4-yl)quinolin-4-yl)-5-(1-methyl-3-(trifluoromethyl)-1H-pyrazol-4-yl)-3,4-dihydroisoquinolin-1(2H)-one The title compound (200 mg, 0.31 mmol, 97% yield) was prepared following the Suzuki coupling procedure described for Example 147, using 7-((1H-imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 200 mg, 0.32 mmol), and 1-methyl-4-(4,4,5,5-tetramethyl-1,3,2-dioxaborolan-2-yl)-1,2,3,6-tetrahydropyridine (143 mg, 0.64 mmol, 2 equiv). $^1$H NMR (400 MHz, Chloroform-d) mixture of isomers δ 8.19-8.11 (m, 1H), 7.57 (s, 1H), 7.40 (d, J=5.5 Hz, 1H), 7.25-7.14 (m, 3H), 7.10 (q, J=1.4 Hz, 1H), 7.02-6.93 (m, 2H), 6.38-6.05 (m, 1), 5.84 (d, J=64.0 Hz, 1H), 5.20 (s, 2H), 4.03 (d, J=3.3 Hz, 3H), 4.01-3.88 (m, 1), 3.89-3.69 (m, 5H), 3.20 (s, 1H), 3.12 (dq, J=11.0, 5.2 Hz, 1H), 2.98 (tt, J=11.6, 6.1 Hz, 1H), 2.87-2.72 (m, 1H), 2.66 (d, J=19.8 Hz, 3H), 2.46 (s, 2H); LCMS (ESI): Method 2: $R_T$=1.266 min, m/z=642.3 [M+H]$^+$.

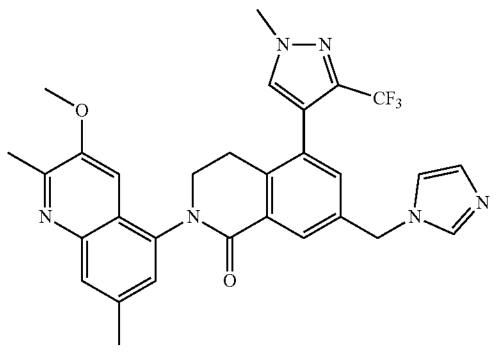 [SMILES: COc1cc2c(N3CCc4c(cc(Cn5ccnc5)cc4-c4cn(C)nc4C(F)(F)F)C3=O)cc(C)cc2nc1C]

Example 155

7-((1H-Imidazol-1-yl)methyl)-2-(3-methoxy-2,7-dimethylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-methoxy-2,7-dimethylquinoline (Intermediate 86). (400 MHz, Chloroform-d) δ 8.17 (d, J=1.8 Hz, 1H), 7.79 (s, 1H), 7.57 (s, 1H), 7.40 (s, 1H), 7.15 (s, 2H), 7.10 (s, 1H), 6.95 (s, 1H), 5.20 (s, 2H), 4.03 (s, 3H), 4.01-3.94 (m, 1H), 3.86 (s, 3H), 3.77-3.72 (m, 1H), 3.14-3.07 (m, 1H), 2.63 (s, 3H), 2.52 (s, 3H); LCMS Method 2: >95%, $R_T$=1.31 min, MS (ESI) 561.2 [M+H]$^+$.

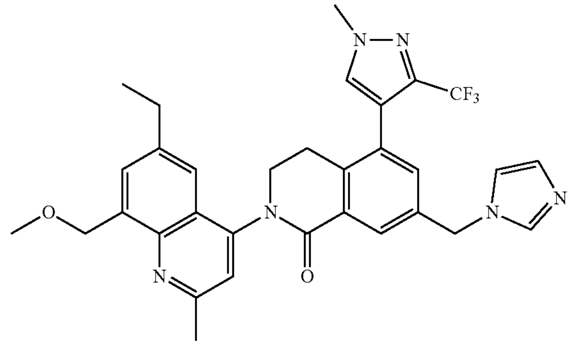 [SMILES: CCc1cc(COC)c2nc(C)cc(N3CCc4c(cc(Cn5ccnc5)cc4-c4cn(C)nc4C(F)(F)F)C3=O)c2c1]

Example 156

7-((1H-Imidazol-1-yl)methyl)-2-(6-ethyl-8-(methoxymethyl)-2-methylquinolin-4-yl)-5-(1-methyl-3-(trifluoromethyl)-1H-pyrazol-4-yl)-3,4-dihydroisoquinolin-1(2H)-one The title compound (43 mg, 0.073 mmol, 46% yield) was prepared following the Suzuki coupling procedure described for Example 147, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 100 mg, 0.16 mmol), and potassium trifluoro(methoxymethyl)borate (49 mg, 0.32 mmi-ol, 2 equiv). $^1$H NMR (400 MHz, Chloroform-d) δ 8.17 (d, J=2.0 Hz, 1H), 7.69 (d, J=1.9 Hz, 1H), 7.57 (s, 1H), 7.46 (d, J=1.8 Hz, 1H), 7.40 (s, 1H), 7.21 (s, 1H), 7.17 (d, J=2.0 Hz, 1H), 7.10 (t, J=1.1 Hz, 1H), 6.95 (t, J=1.3 Hz, 1H), 5.33-5.22 (m, 1H), 5.20 (s, 2H), 5.12 (d, J=13.7 Hz, 1H), 4.03 (s, 3H), 3.99-3.88 (m, 1H), 3.80 (dt, J=120, 5.5 Hz, 1H), 3.59 (s, 3H), 3.15 (ddd, J=15.9, 10.5, 5.3 Hz, 1H), 2.96 (dt, J=16.4, 5.0 Hz, 1H), 2.79 (q, J=7.6 Hz, 2H), 2.73 (s, 3H), 1.29 (t, J=7.6 Hz, 3H); LCMS (ESI): Method 2: $R_T$=1.402 min, m/z=589.2 [M+H]$^+$.

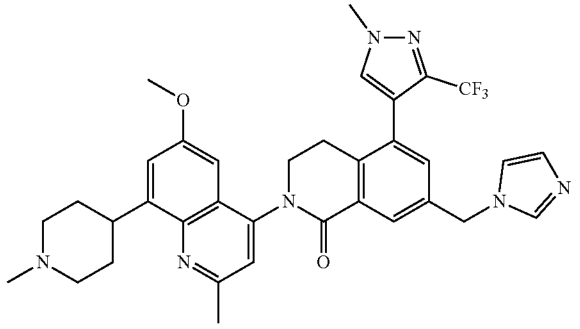 [SMILES: COc1cc(C2CCN(C)CC2)c2nc(C)cc(N3CCc4c(cc(Cn5ccnc5)cc4-c4cn(C)nc4C(F)(F)F)C3=O)c2c1]

Example 157

7-((1H-Imidazol-1-yl)methyl)-2-(6-methoxy-2-methyl-8-(1-methylpiperidin-4-yl)quinolin-4-yl)-5-(1-methyl-3-(trifluoromethyl)-1H-pyrazol-4-yl)-3,4-dihydroisoquinolin-1(2H)-one 7-((1H-Imidazol-1-yl)methyl)-2-(6-methoxy-2-methyl-8-(1-methyl-1,2,3,6-tetrahydropyridin-4-yl)quinolin-4-yl)-5-(1-methyl-3-(trifluoromethyl)-1H-pyrazol-4-yl)-3,4-dihydroisoquinolin-1(2H)-one (Example 154, 55 mg, 0.086 mmol) was dissolved in MeOH (1 mL) and placed under Ar. Then Pd/C (55 mg, 0.028 mmol, 0.6 equiv, 10 wt. %) were added and the mixture was degassed and placed under $H_2$ with balloon. The reaction mixture was stirred for overnight at room temperature. The reaction mixture was filtered through celite and concentrated. Brine was added to the residue and extracted with $CH_2Cl_2$ (3×20 mL). The combined organic layers were dried over $MgSO_4$ and concentrated. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (10 mg, 0.016 mmol, 18% yield). $^1$H NMR (400 MHz, Chloroform-d) δ 8.16 (d, J=2.0 Hz, 1H), 7.57 (s, 1H), 7.40 (s, 1H), 7.26 (s, 1H), 7.20 (s, 1H), 7.16 (d, J=2.0 Hz, 1H), 7.10 (t, J=1.1 Hz, 1H), 6.95 (t, J=1.3 Hz, 1H), 6.89 (d, J=2.7 Hz, 1H), 5.20 (s, 2H), 4.03-4.01 (m, 4H), 4.00-3.87 (m, 1H), 3.83 (s, 3H), 3.81-3.72 (m, 1H), 3.12 (ddd, J=16.1, 10.8, 5.3 Hz, 1H), 3.03 (d, J=11.1 Hz, 2H), 2.95 (dt, J=16.3, 4.8 Hz, 1H), 2.71 (s, 3H), 2.38 (s, 2H), 2.26 (t, J=11.5 Hz, 2H), 1.97 (d, J=9.9 Hz, 2H), 1.93-1.75 (m, 2H); LCMS (ESI): Method 2: $R_T$=1.183 min, m/z=644.2 [M+H]$^+$.

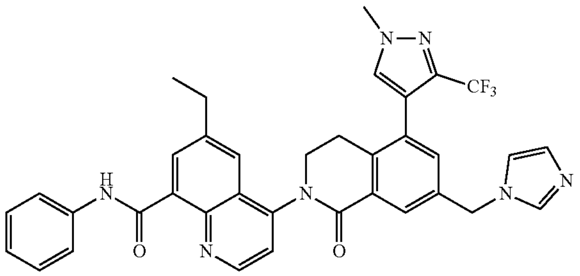 [SMILES: CCc1cc(C(=O)Nc2ccccc2)c2nccc(N3CCc4c(cc(Cn5ccnc5)cc4-c4cn(C)nc4C(F)(F)F)C3=O)c2c1]

Example 158

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(pyridin-4-yl) quinoline-8-carboxamide 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid (Example 92, 40 mg, 0.070 mmol, 1.0 equiv) was dissolved in neat sulfurous dichloride (0.33 g, 0.20 mL, 2.8 mmol, 40 equiv), and the solution was stirred at 70° C. for 1 h. The reaction mixture was cooled to room temperature and concentrated. The residue was dissolved in DCM (2.0 mL), cooled to 0° C. then pyridin-4-amine (7.9 mg, 84 μmol, 1.2 equiv) and N-ethyl-N-isopropylpropan-2-amine (45 mg, 61 μL, 0.35 mmol) were added. The mixture was warmed to room temperature, stirred for 1 h and concentrated. The residue was purified by reverse phase HPLC (Phenomenex Gemini C18, $H_2O/CH_3CN$ gradient from 5-70% $CH_3CN$, 0.1% TFA) followed by neutralization with sat. aq. $NaHCO_3$ to yield the title compound (31 mg, 48 μmol, 68%). $^1$H NMR (400 MHz, Chloroform-d) δ9.03 (d, J=4.7 Hz, 1H), 8.87 (d, J=2.0 Hz, 1H), 8.58 (d, J=6.3 Hz, 1H), 8.16 (d, J=1.8 Hz, 1H), 7.84 (d, J=1.9 Hz, 1H), 7.80 (q, J=2.1 Hz, 1H), 7.58 (s, 1H), 7.49 (d, J=4.7 Hz, 1H), 7.42 (s, 1H), 7.21 (d, J=1.8 Hz, 1H), 7.11 (s, 1H), 6.95 (s, 1H), 5.21 (s, 2H), 4.08 (q, J=5.4 Hz, 1H), 4.04 (s, 3H), 3.85 (m, J=5.6 Hz, 1H), 3.20 (m, J=5.4 Hz, 1H), 3.01 (m, J=5.1 Hz, 1H), 2.91 (q, J=7.61 Hz, 2H), 1.35 (t, J=7.6 Hz, 3H); LCMS (ESI): m/z=651.2 [M+H]$^+$.

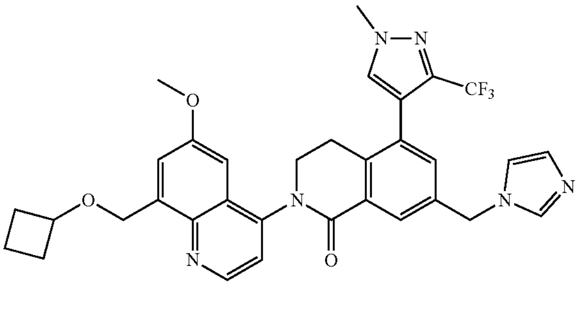 [SMILES: COc1cc(COC2CCC2)c2nccc(N3CCc4c(cc(Cn5ccnc5)cc4-c4cn(C)nc4C(F)(F)F)C3=O)c2c1]

Example 159

7-((1H-Imidazol-1-yl)methyl)-2-(8-(cyclobutoxymethyl)-6-methoxyquinolin-4-yl)-5-(1-methyl-3-(trifluoromethyl)-1H-pyrazol-4-yl)-3,4-dihydroisoquinolin-1(2H)-one The title compound (37 mg, 60 μmol, 64%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-8-(cyclobutoxymethyl)-6-methoxyquinoline (Intermediate 110). $^1$H NMR (400 MHz, Chloroform-d) δ 8.81 (d, J=4.6 Hz, 1H), 8.17 (d, J=1.8 Hz, 1H), 7.60 (t, J=1.4 Hz, 1H), 7.57 (s, 1H), 7.40 (s, 1H), 7.32 (d, J=4.6 Hz, 1H), 7.17 (d, J===1.9 Hz, 1H), 7.10 (s, 1H), 6.98 (d, J=2.8 Hz, 1H), 6.95 (t, J=1.2 Hz, 1H), 5.20 (s, 2H), 5.12 (q, J=15.6 Hz, 2H), 4.19 (q, J=7.21 Hz, 1H), 4.02 (s, 3H), 3.97 (m, J=5.5 Hz, 1H), 3.88 (s, 3H), 3.80 (m, J=5.7 Hz, 1H), 3.15 (m, J=5.4 Hz, 1H), 2.97 (m, J=5.2 Hz, 1H), 2.30 (m, J=2.9 Hz, 2H), 2.08 (m, J=4.0 Hz, 2H), 1.75 (q, J=10.0 Hz, 1H), 1.54 (m, J=3.4 Hz, 1H); LCMS (ESI): m/z=617.2 [M+H]$^+$.

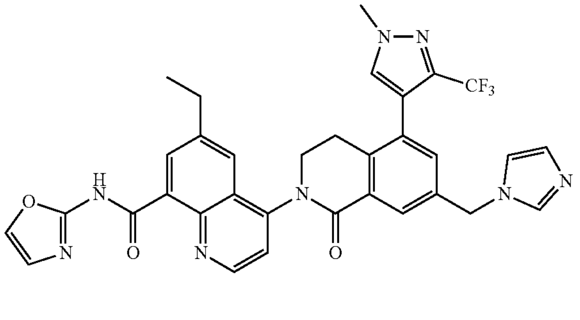 [SMILES: CCc1cc(C(=O)Nc2ncco2)c2nccc(N3CCc4c(cc(Cn5ccnc5)cc4-c4cn(C)nc4C(F)(F)F)C3=O)c2c1]

Example 160

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(oxazol-2-yl) quinoline-8-carboxamide To a stirring solution of 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid (Example 92, 57.5 mg, 1 eq, 100 μmol) in anhydrous DMF (2 mL) at 0° C. under Ar was added N-ethyl-N-isopropylpropan-2-amine (91 mg, 0.12 mL, 700 μmol, 7.0 equiv) and the reaction mixture was stirred for 10 min. 1-(1-(l1-Oxidaneyl)-3H-1l4-[1,2,3]triazolo[4,5-b]pyridin-3-yl)-1-(dimethylamino)-N-(hexafluoro-l1-phosphaneyl)-N,N-dimethylmethanideaminium (45.6 mg, 120 μmol, 1.2 equiv) was added and stirred for additional 20 min at 0° C. Oxazol-2-amine (10.1 mg, 1.2 eq, 120 μmol) was added, and the reaction mixture was stirred at 0° C. for 3 h. The reaction mixture was then slowly warmed to ambient temperature and stirred for additional 14 h. The reaction was quenched by addition of water (10 mL) and extracted with dichloromethane (5 mL×2). The combined organic layer was washed with sat. aq. sodium bicarbonate (5 mL), water (5 mL), and brine (5 mL) successively, dried over sodium sulfate, and concentrated. The residue was purified by reverse phase HPLC (Phenomenex Gemini C18, $H_2O$/$CH_3CN$ gradient from 5-70% $CH_3CN$, 0.1% TFA) followed by neutralization with sat. aq. $NaHCO_3$ to yield the title compound (49 mg, 76 μmol, 76%) $^1H$ NMR (400 MHz, Chloroform-d) δ 9.03 (d, J=4.7 Hz, 1H), 8.88 (d, J=2.0 Hz, 1H), 8.16 (d, J=1.8 Hz, 1H), 7.85 (d, J=1.9 Hz, 1H), 7.58 (s, 1H), 7.54 (d, J=0.7 Hz, 1H), 7.48 (d, J=4.8 Hz, 1H), 7.42 (s, 1H), 7.21 (d, J=1.8 Hz, 1H), 7.11 (d, J=0.7 Hz, 1H), 6.95 (s, 1H), 5.21 (s, 2H), 4.08 (q, J=5.4 Hz, 1H), 4.03 (s, 3H), 3.84 (m, J=5.6 Hz, 1H), 3.19 (m, J=5.4 Hz, 1H), 3.01 (m, J=5.1 Hz, 1H), 2.91 (q, J=7.6 Hz, 2H), 1.34 (t, J=7.6 Hz, 3H); LCMS (ESI): m/z=641.2 $[M+H]^+$.

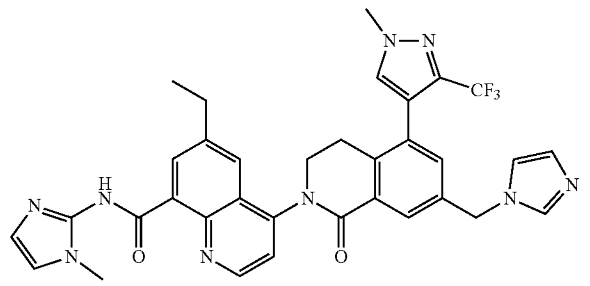 [SMILES: CCc1cc(C(=O)Nc2nccn2C)c2nccc(N3CCc4c(cc(Cn5ccnc5)cc4-c4cn(C)nc4C(F)(F)F)C3=O)c2c1]

Example 161

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-methyl-1H-imidazol-2-yl)quinoline-8-carboxamide The title compound (51 mg, 78 μmol, 78%) was prepared following the procedure described for Example 160, substituting 1-methyl-1H-imidazol-2-amine (9.7 mg, 100.0 μmol, 1.0 equiv) for oxazol-2-amine. $^1H$ NMR (400 MHz, Chloroform-d) δ 8.96 (d, J=4.7 Hz, 1H), 8.82 (d, J=1.7 Hz, 1H), 8.16 (d, J=1.8 Hz, 1H), 7.83 (d, J=1.3 Hz, 1H), 7.57 (s, 1H), 7.45 (s, 1H), 7.42 (s, 1H), 7.21 (d, J=1.8 Hz, 1H), 7.11 (s, 1H), 7.00 (d, J=1.0 Hz, 1H), 6.95 (s, 1H), 6.90 (s, 1H), 5.21 (s, 2H), 4.08 (q, J=5.2 Hz, 1H), 4.03 (s, 3H), 3.85 (m, J=5.6 Hz, 1H), 3.65 (s, 3H), 3.19 (m, J=5.4 Hz, 1H), 3.01 (r, J=5.1 Hz), 2.89 (q, J=7.6 Hz, 2H), 1.33 (t, J=7.6 Hz, 3H); LCMS (ESI): m/z=654.2 $[M+H]^+$.

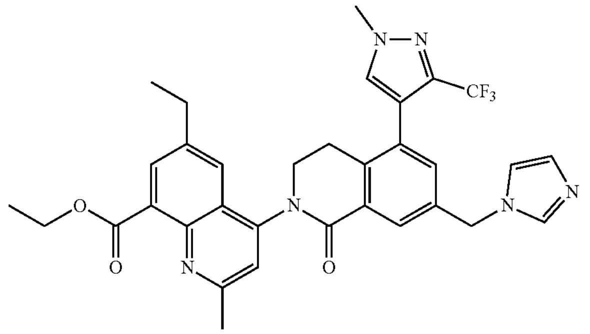 [SMILES: CCOC(=O)c1cc(CC)cc2c(N3CCc4c(cc(Cn5ccnc5)cc4-c4cn(C)nc4C(F)(F)F)C3=O)cc(C)nc12]

Example 162

Ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-2-methylquinoline-8-carboxylate The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and ethyl 4-bromo-6-ethyl-2-methylquinoline-8-carboxylate (Intermediate 87). $^1H$ NMR (400 MHz, Chloroform-d) δ 8.16 (d, J=1.8 Hz, 1H), 7.80 (d, J=1.9 Hz, 1H), 7.64 (d, J=1.6 Hz, 1H), 7.60 (s, 1H), 7.41 (s, 1H), 7.24 (s, 1H), 7.18 (d, J=1. Hz, 1H), 7.11 (s, 1H), 6.95 (s, 1H), 5.19 (s, 2H), 4.53 (q, J=7.2 Hz, 2H), 4.02 (s, 3H), 3.99-3.92 (m, 1H), 3.79-3.73 (m, 1H), 3.18-3.10 (m, 1H), 3.00-2.93 (m, 1H), 2.80 (q, J=7.6 Hz, 2H), 2.74 (s, 3H), 1.46 (t, J=7.2 Hz, 3H), 1.29 (t, J=7.6 Hz, 3H); LCMS Method 2: >95%, $R_T$=1.31 min, MS (ESI): m/z=617.2 $[M+H]^+$.

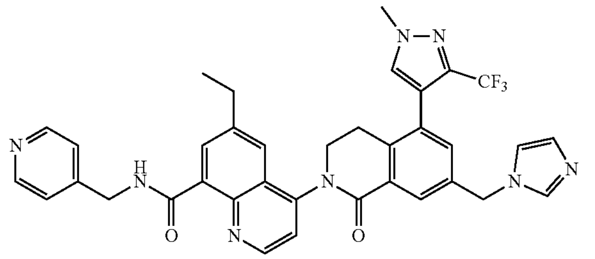 [SMILES: CCc1cc(C(=O)NCc2ccncc2)c2nccc(N3CCc4c(cc(Cn5ccnc5)cc4-c4cn(C)nc4C(F)(F)F)C3=O)c2c1]

Example 163

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(pyridin-4-ylmethyl)quinoline-8-carboxamide The title compound (35 mg, 53 μmol, 53%) was prepared following the procedure described for Example 158, substituting pyridin-4-ylmethanamine (13 mg, 120 μmol, 1.2 equiv) for pyridin-4-amine. $^1H$ NMR (400 MHz, Chloroform-d) δ 8.92 (d, J=4.7 Hz, 1H), 8.83 (d, J=2.0 Hz, 1H), 8.56 (q, J=2.0 Hz, 1H), 8.16 (d, J=1.8 Hz, 1H), 7.79 (d, J=2.0 Hz, 1H), 7.58 (s, 1H), 7.43 (d, J=4.9 Hz, 1H), 7.35 (d, J=5.9 Hz, 1H), 7.20 (d, J=1.8 Hz, 1H), 7.11 (s, 1H), 6.95 (s, 1H), 5.20 (s, 2H), 4.86 (q, J=2.8 Hz, 2H), 4.03 (m, 4H), 3.83 (m, J=5.6 Hz, 1H), 3.19 (m, J=5.4 Hz, 1H), 3.00 (m, J=5.1 Hz, 1H), 2.88 (q, J=7.6 Hz, 2H), 1.33 (t, 3=7.6 Hz, 3H); LCMS (ESI): m/z=665.3 $[M+H]^+$.

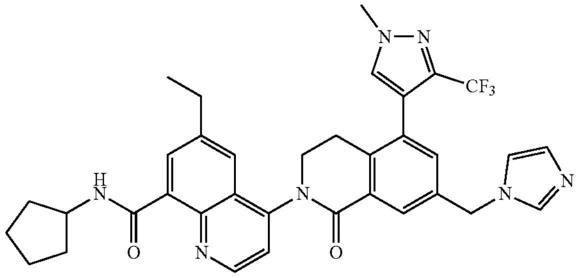 [SMILES: CCc1cc(C(=O)NC2CCCC2)c2nccc(N3CCc4c(cc(Cn5ccnc5)cc4-c4cn(C)nc4C(F)(F)F)C3=O)c2c1]

Example 164

4-(7-((1H-Imidazol-1-yl)methyl)-5-(1-methyl-3-(trifluoromethyl)-1H-pyrazol-4-yl)-1-oxo-3,4-dihydroisoquinolin-2(1)-yl)-N-cyclopentyl-6-ethylquinoline-8-carboxamide The title compound (35 mg, 55 μmol, 55%) was prepared following the procedure described for Example 158, substituting cyclopentylamine (10 mg, 120 μmol, 1.2 equiv) for pyridin-4-amine. $^1$H NMR (400 MHz, Chloroform-d) δ 11.22 (d, J=7.5 Hz, 1H), 8.91 (d, J=4.8 Hz, 1H), 8.79 (d, J=2.2 Hz, 1H), 8.16 (d, J=2.2 Hz, 1H), 7.73 (s, 1H), 7.57 (s, 1H), 7.41 (s, 1H), 7.39 (d, J=4.7 Hz, 1H), 7.19 (d, J=2.0 Hz, 1H), 7.10 (s, 1H), 6.95 (s, 1H), 5.20 (s, 2H), 4.54 (q, J=6.2 Hz, 1H), 4.03 (s, 3H), 3.99 (q, J=5.3 Hz, 1H), 3.18 (m, J=5.5 Hz, 1H), 3.18 (m, J=5.6 Hz, 1H), 2.99 (m, J=5.3 Hz, 1H), 2.86 (q, J=7.6 Hz, 2H), 2.12 (m, J=4.5 Hz, 2H), 1.82 (m, J=3.3 Hz, 2H), 1.70 (m, J=6.4 Hz, 4H), 1.31 (t, J=7.3 Hz, 3H); LCMS (ESI): m/z=642.3 $[M+H]^+$.

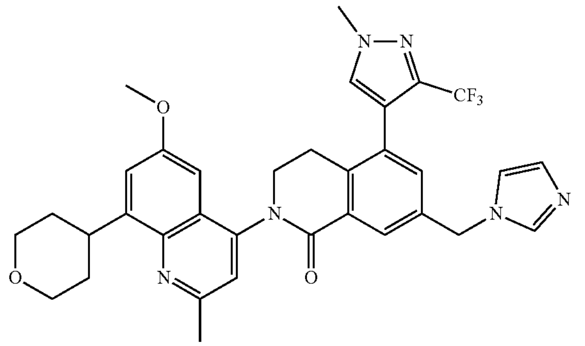 [SMILES: COc1cc(C2CCOCC2)c2nc(C)cc(N3CCc4c(cc(Cn5ccnc5)cc4-c4cn(C)nc4C(F)(F)F)C3=O)c2c1]

Example 165

7-((1H-Imidazol-1-yl)methy)-2-(6-methoxy-2-methyl-8-(tetrahydro-2H-pyran-4-yl)quinolin-4-yl)-5-(1-methyl-3-(trifluoromethyl)-1H-pyrazol-4-yl)-3,4-dihydroisoquinolin-1(2H)-one The title compound (3 mg, 0.004 mmol, 3% yield) was prepared following the procedure described for Example 157, using 7-((1H-imidazol-1-yl)methyl)-2-(8-(3,6-dihydro-2H-pyran-4-yl)-6-methoxy-2-methylquinolin-4-yl)-5(1-methyl-3-(trifluoromethyl)-1H-pyrazol-4-yl)-3,4-dihydroisoquinolin-1(2H)-one (Example 151, 100 mg, 0.16 mmol). $^1$H NMR (400 MHz, Chloroform-d) δ 8.16 (d, J=1.7 Hz, 1H), 7.58 (s, 1H), 7.40 (s, 1H), 7.23 (d, J=2.7 Hz, 1H), 7.21 (s, 1H), 7.16 (d, J=1.7 Hz, 1H), 7.11 (s, 1H), 6.95 (s, 1H), 6.89 (d, =2.7 Hz, 1H), 5.20 (s, 2H), 4.29-4.21 (m, 1H), 4.12 (d, J=10.2 Hz, 2H), 4.02 (s, 3H), 3.97-3.90 (m, 1H), 3.84 (s, 3H), 3.80-3.70 (m, 3H), 3.17-3.09 (m, 1H), 2.99-2.92 (m, 1H), 2.71 (s, 3H), 1.95-1.80 (m, 4H); LCMS (ESI): Method 2: $R_T$=1.346 min, m/z=631.3 $[M+H]^+$.

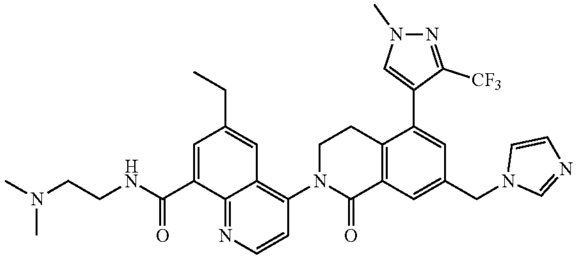 [SMILES: CCc1cc(C(=O)NCCN(C)C)c2nccc(N3CCc4c(cc(Cn5ccnc5)cc4-c4cn(C)nc4C(F)(F)F)C3=O)c2c1]

Example 166

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(2-(dimethylamino)ethyl)-6-ethylquinoline-8-carboxamide The title compound (39 mg, 60 μmol, 60%) was prepared following the procedure described for Example 158, substituting N1,N1-dimethylethane-1,2-diamine (11 mg, 120 μmol, 1.2 equiv) for pyridin-4-amine. $^1$H NMR (400 MHz, Chloroform-d) δ 11.26 (s, 1H), 8.93 (d, J=4.6 Hz, 1H), 8.78 (d, J=2.1 Hz, 1H), 8.16 (s, 1H), 7.74 (s, 1H), 7.57 (s, 1H), 7.40 (t, J=4.9 Hz, 1H), 7.20 (s, 1H), 7.11 (s, 1H), 6.95 (s, 1H), 5.20 (s, 2H), 4.03 (m, 4H), 3.82 (m, J=5.2 Hz, 1H), 3.72 (q, J=5.9 Hz, 2H), 3.17 (m, J=5.5 Hz, 1H), 2.99 (m, J=5.1 Hz, 1H), 2.85 (t, J=7.9 Hz, 2H), 2.64 (t, J=7.2 Hz, 2H), 2.36 (s, 6H), 1.30 (d, J=7.2 Hz, 3H); LCMS (ESI): m/z=645.3 $[M+H]^+$.

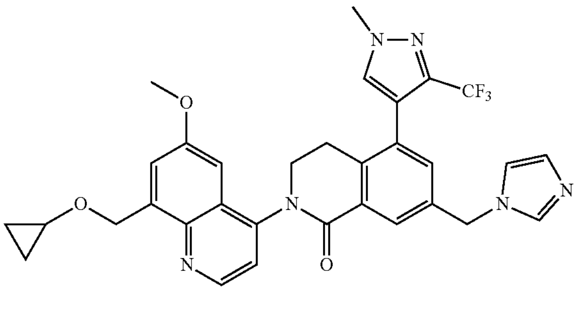 [SMILES: COc1cc(COC2CC2)c2nccc(N3CCc4c(cc(Cn5ccnc5)cc4-c4cn(C)nc4C(F)(F)F)C3=O)c2c1]

Example 167

7-((1H-Imidazol-1-yl)methyl)-2-(8-(cyclopropoxymethyl)-6-methoxyquinolin-4-yl)-5-(1-methyl-3-(trifluoromethyl)-1H-pyrazol-4-yl)-3,4-dihydroisoquinolin-1(2H)-one The title compound (42 mg, 70 μmol, 75%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-8-(cyclopropoxymethyl)-6-methoxyquinoline (Intermediate 109). $^{1}$H NMR (400 MHz, Chloroform-d) δ 8.82 (d, J=4.6 Hz, 1H), 8.17 (d, J=1.8 Hz, 1H), 7.57 (s, 1H), 7.54 (t, J=1.4 Hz, 1H), 7.40 (s, 1H), 7.33 (d, J=4.6 Hz, 1H), 7.17 (d, J=1.8 Hz, 1H), 7.10 (s, 1H), 6.98 (d, J=2.8 Hz, 1H), 6.95 (s, 1H), 5.30 (q, J=12.1 Hz, 2H), 5.20 (s, 2H), 4.02 (s, 3H), 3.97 (m, J=5.5 Hz, 1H), 3.87 (s, 3H), 3.79 (m, J=5.7 Hz, 1H), 3.56 (m, J=3.0 Hz, 1H), 3.15 (m, J=5.4 Hz, 1H), 2.97 (m, J=5.1 Hz, 1H), 0.74 (m, J=2.9 Hz, 2H), 0.55 (m, J=3.6 Hz, 2H); LCMS (ESI): m/z=603.2 [M+H]$^{+}$.

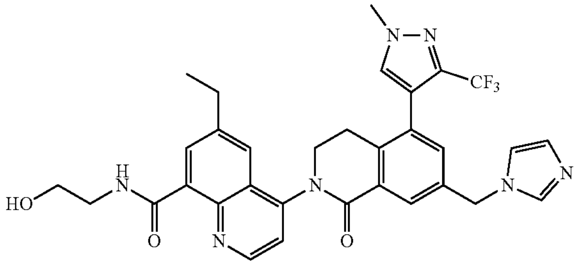 [SMILES: CCc1cc(C(=O)NCCO)c2nccc(N3CCc4c(cc(Cn5ccnc5)cc4-c4cn(C)nc4C(F)(F)F)C3=O)c2c1]

Example 168

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-hydroxyethyl)quinoline-8-carboxamide Step A. Preparation of 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(2-((tert-butyldimethylsilyl)oxy)ethyl)-6-ethylquinoline-8-carboxamide. The title compound was prepared following the procedure described for Example 160, substituting 2-((tert-butyldimethylsilyl)oxy)ethan-1-amine (26.3 mg, 150 μmol, 1.2 equiv) for oxazol-2-amine.

Step B. Preparation of 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-hydroxyethyl)quinoline-8-carboxamide. 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(2-((tert-butyldimethylsilyl)oxy)ethyl)-6-ethylquinoline-8-carboxamide was dissolved in DCM (5.0 mL) and trifluoroacetic acid (2.0 mL) and stirred for 1 h at room temperature then concentrated. The residue was dissolved in methanol (5.0 mL) and stirred for 20 min then concentrated. The residue was purified by reverse phase HPLC (Phenomenex Gemini C18, $H_2O/CH_3CN$ gradient from 5-70% $CH_3CN$, 0.1% TFA) followed by neutralization with sat. aq. $NaHCO_3$ to yield the title compound (63 mg, 0.10 mmol, 82%). $^{1}$H NMR (400 MHz, Chloroform-d) δ 8.93 (d, J=4.7 Hz, 1H), 8.78 (d, J=2.0 Hz, 1H), 8.17 (d, J=1.8 Hz, 1H), 7.77 (d, J=1.9 Hz, 1H), 7.56 (s, 1H), 7.41 (d, J=4.5 Hz, 1H), 7.19 (d, J=1.8 Hz, 1H), 7.10 (s, 1H), 6.94 (s, 1H), 5.19 (s, 2H), 4.03 (m, 4H), 3.92 (d, J=4.5 Hz, 2H), 3.81 (m, J=5.6 Hz, 3H), 3.54 (s, 1H), 3.18 (m, J=5.4 Hz, 1H), 2.99 (m, J=5.2 Hz, 1H), 2.87 (q, J=7.6 Hz, 2H), 1.32 (t, J=7.6 Hz, 3H); LCMS Method 2: >95%, $R_T$=1.31 min, MS (ESI) 618.2 [M+H]$^{+}$.

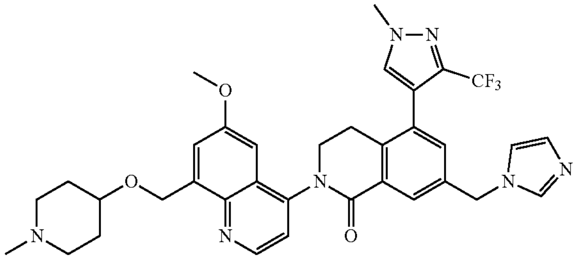 [SMILES: COc1cc(COC2CCN(C)CC2)c2nccc(N3CCc4c(cc(Cn5ccnc5)cc4-c4cn(C)nc4C(F)(F)F)C3=O)c2c1]

Example 169

7-((1H-Imidazol-1-yl)methyl)-2-(6-methoxy-8-(((1-methylpiperidin-4-yl)oxy)methyl)quinolin-4-yl)-5-(1-methyl-3-(trifluoromethyl)-1H-pyrazol-4-yl)-3,4-dihydroisoquinolin-1(2H)-one The title compound (28.0 mg, 42.4 μmol, 45.5%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-methoxy-8-(((1-methylpiperidin-4-yl)oxy)methyl) quinoline (Intermediate 108). $^{1}$H NMR (400 MHz, Chloroform-d) δ 8.80 (d, J=4.6 Hz, 1H), 8.17 (d, J=1.8 Hz, 1H), 7.63 (t, J=1.4 Hz, 1H), 7.57 (s, 1H), 7.40 (s, 1H), 7.33 (d, J=4.6 Hz, 1H), 7.17 (d, J=1.8 Hz, 1H), 7.10 (s, 1H), 6.97 (d, J=2.8 Hz, 1H), 6.95 (s, 1H), 5.27 (q, J=8.0 Hz, 2H), 5.20 (s, 2H), 4.03 (s, 3H), 3.97 (m, J=5.5 Hz, 1H), 3.88 (s, 3H), 3.80 (m, J=5.6 Hz, 1H), 3.59 (m, J=4.1 Hz, 1H), 3.15 (m, J=5.4 Hz, 1H), 2.97 (m, J=5.1 Hz, 1H), 2.75 (t, J=5.0 Hz, 2H), 2.28 (s, 3H), 2.18 (d, J=11.1 Hz, 2H), 2.04 (q, J=4.5 Hz, 2H), 1.83 (m, J=4.2 Hz, 2H); LCMS (ESI): m/z=660.2 [M+H]$^{+}$.

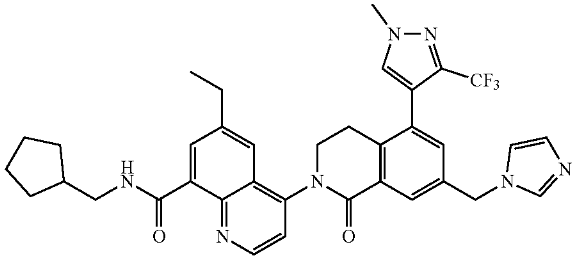 [SMILES: CCc1cc(C(=O)NCC2CCCC2)c2nccc(N3CCc4c(cc(Cn5ccnc5)cc4-c4cn(C)nc4C(F)(F)F)C3=O)c2c1]

Example 170

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(cyclopentylmethyl)-6-ethylquinoline-8-carboxamide The title compound (42 mg, 64 μmol, 64%) was prepared following the procedure described for Example 158, substituting cyclopentylmethanamine (12 mg, 120 μmol, 1.2 equiv) for pyridin-4-amine. $^{1}$H NMR (400 MHz, Chloroform-d) δ 11.25 (s, 1H), 8.93 (d, J=4.6 Hz, 1H), 8.80 (d, J=2.1 Hz, 1H), 8.16 (s, 1H), 7.74 (s, 1H), 7.57 (s, 1H), 7.41 (t, J=3.6 Hz, 1H), 7.20 (s, 1H), 7.10 (s, 1H), 6.95 (s, 1H), 5.20 (s, 2H), 4.03 (m, 4H), 3.84 (s, 1H), 3.56 (m, 2H), 3.18 (m, 1H), 3.01 (m, 1H), 2.87 (d, J=7.6 Hz, 2H), 2.29 (m, 1H), 1.86 (m, 2H), 1.69 (m, 2H), 1.62 (m, 2H), 1.42 (m, 2H), 1.31 (t, J=7.6 Hz, 3H); LCMS (ESI): m/z 656.2 [M+H]+.

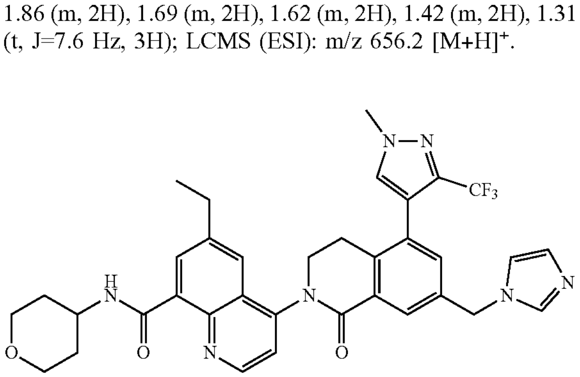

Example 171

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(tetrahydro-2H-pyran-4-yl)quinoline-8-carboxamide The title compound (39 mg, 59 μmol, 59%) was prepared following the procedure described for Example 160, substituting tetrahydro-2H-pyran-4-amine (10 mg, 100 μmol, 1.0 equiv) for oxazol-2-amine. $^1$H NMR (400 MHz, Chloroform-d) δ 11.37 (d, J=8.6 Hz, 1H), 8.93 (d, J=4.7 Hz, 1H), 8.79 (d, J=2.1 Hz, 1H), 8.16 (s, 1H), 7.75 (s, 1H), 7.57 (s, 1H), 7.41 (t, J=2.3 Hz, 2H), 7.20 (s, 1H), 7.11 (s, 1H), 6.95 (s, 1H), 5.20 (s, 2H), 4.38 (m, J=5.0 Hz, 1H), 4.03 (d, J=2.1 Hz, 4H), 4.00 (t, J=5.91 Hz, 2H), 3.82 (m, J=6.0 Hz, 1H), 3.65 (t, J=10.3 Hz, 2H), 3.18 (m, J=5.7 Hz, 1H), 2.99 (m, J=5.0 Hz, 1H), 2.87 (q, J=7.5 Hz, 2H), 2.12 (d, J=13.7 Hz, 2H), 1.76 (m, J=3.4 Hz, 2H), 1.32 (t, J=7.6 Hz, 3H); LCMS (ESI): m/z 658.2 [M+H]+.

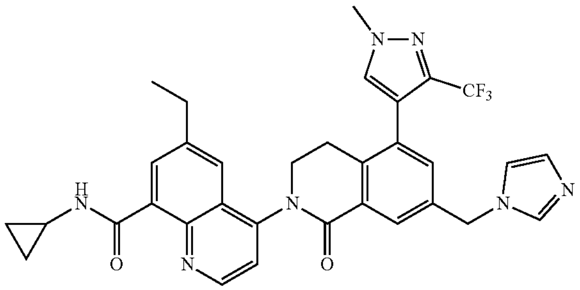 [SMILES: CCc1cc(C(=O)NC2CC2)c2nccc(N3CCc4c(cc(Cn5ccnc5)cc4-c4cn(C)nc4C(F)(F)F)C3=O)c2c1]

Example 172

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-cyclopropyl-6-ethylquinoline-8-carboxamide The title compound (44 mug, 72 μmol, 72%) was prepared following the procedure described for Example 160, substituting cyclopropanamine (5.7 mg, 100 μmol, 1.0 equiv) for oxazol-2-amine. $^1$H NMR (400 MHz, Chloroform-d) δ 11.19 (s, 1H), 8.90 (d, J=4.7 Hz, 1H), 8.80 (d, J=2.1 Hz, 1H), 8.15 (s, 1H), 7.74 (s, 1H), 7.57 (s, 1H), 7.41 (s, 1H), 7.39 (d, J=4.7 Hz, 1H), 7.19 (d, J=2.2 Hz, 1H), 7.10 (s, 1H), 6.95 (s, 1H), 5.20 (s, 2H), 4.03 (s, 3H), 3.99 (q, =5.8 Hz, 1H), 3.82 (m, J=4.5 Hz, 1H), 3.18 (m, J=5.4 Hz, 1H), 3.09 (m, J=3.8 Hz, 1H), 2.99 (m, J=5.2 Hz, 1H), 2.87 (q, J=7.0 Hz, 2H), 1.31 (t, J=7.6 Hz, 3H), 0.91 (m, J=2.5 Hz, 2H), 0.72 (m, J=3.1 Hz, 2H); LCMS (ESI): m/z=614.2 [M+H]+.

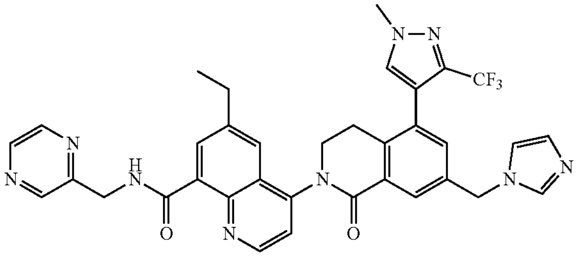 [SMILES: CCc1cc(C(=O)NCc2cnccn2)c2nccc(N3CCc4c(cc(Cn5ccnc5)cc4-c4cn(C)nc4C(F)(F)F)C3=O)c2c1]

Example 173

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(pyrazin-2-ylmethyl)quinoline-8-carboxamide The title compound (37 mg, 56 μmol, 56%) was prepared following the procedure described for Example 158, substituting pyrazin-2-ylmethanamine (13 mg, 120 μmol, 1.2 equiv) for pyridin-4-amine. $^1$H NMR (400 MHz, Chloroform-d) δ 8.95 (d, J=4.7 Hz, 1H), 8.81 (d, J=2.0 Hz, 1H), 8.77 (d, J=1.3 Hz, 1H), 8.56 (q, J=1.3 Hz, 1H), 8.49 (d, J=2.5 Hz, 1H), 8.16 (d, J=1.8 Hz, 1H), 7.78 (d, J=2.0 Hz, 1H), 7.58 (s, 1H), 7.42 (d, J=4.6 Hz, 1H), 7.20 (d, J=1.8 Hz, 1H), 7.11 (s, 1H), 6.95 (s, 1H), 5.20 (s, 2H), 5.00 (m, J=6.7 Hz, 2H), 4.03 (m, 4H), 3.82 (m, J=5.7 Hz, 1H), 3.18 (m, J=5.4 Hz, 1H), 2.99 (m, J=5.2 Hz, 1H), 2.88 (q, J=7.6 Hz, 2H), 1.32 (t, J=7.6 Hz, 3H); LCMS (ESI): m/z=666.3 [M+H]+.

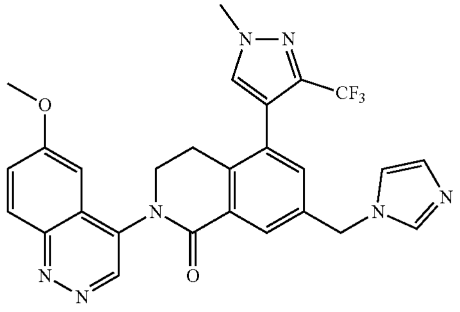

Example 174

7-((1H-Imidazol-1-yl)methyl)-2-(6-methoxycinnolin-4-yl)-5-(1-methyl-3-(trifluoromethyl)-1H-pyrazol-4-yl)-3,4-dihydroisoquinolin-1(2H)-one The title compound (34 mg, 0.064 mmol, 60% yield) was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 40 mg, 0.11 m mol, 1 equiv) and 4-bromo-6-methoxycinnoline (Intermediate 67, 39 mg, 0.16 mmol, 1.5 equiv). $^1$H NMR (400 MHz, Chloroform-d) δ 9.13 (s, 1H), 8.48 (d, J=9.4 Hz, 1H), 8.16 (d, J=1.9 Hz, 1H), 7.57 (s, 1H), 7.51 (dd, J=9.2, 2.6 Hz, 1H), 7.41 (s, 1H), 7.20 (s, 1H), 7.10 (s, 1H), 6.95 (t, J=1.2 Hz, 1H), 6.91 (d, J=2.6 Hz, 1H), 5.21 (s, 2H), 4.10 (td, J=11.4, 4.2 Hz, 1H), 4.03 (s, 3H), 3.92 (s, 3H), 3.85 (dt, J=12.2, 5.3 Hz, 1H), 3.18-3.10 (m, 1H), 3.02 (dt, J=16.3, 4.8 Hz, 1H); LCMS (ESI): Method 2: $R_T$=1.335 min, m/z=534.0 $[M+H]^+$.

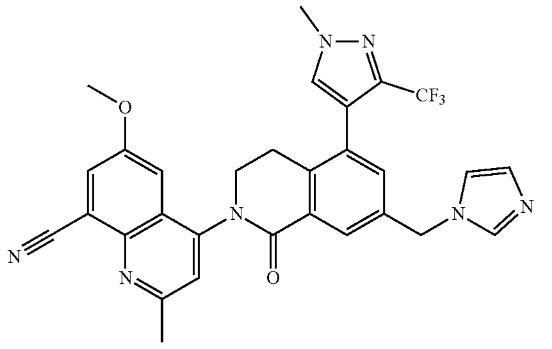 [SMILES: COc1cc(C#N)c2nc(C)cc(N3CCc4c(cc(Cn5ccnc5)cc4-c4cn(C)nc4C(F)(F)F)C3=O)c2c1]

Example 175

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carbonitrile 7-((1H-Imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 400 mg, 0.64 mmol), zinc cyanide (150 mg, 1.28 mmol, 2 equiv), $Ad_2PBu$ (23 mg, 0.064 mmol, 0.1 equiv), and $Pd_2(dba)_3$ (18 mg, 19.2 μmol, 0.03 equiv) were dissolved in DMF (4 mL) and placed under an argon atmosphere. The reaction mixture was stirred at 115° C. until completion. At 23° C., brine was added to the mixture and extracted with $CH_2Cl_2$ (3×20 mL). The combined organic layers were dried over $MgSO_4$ and concentrated under reduced pressure. The residue was purified by flash chromatography (Combi-flash Rf, Hex/EtOAc=0-100% gradient followed by MeOH/$CH_2Cl_2$=0-10% gradient) to provide the title compound (375 mg, 0.66 mmol, quant.). $^1$H NMR (400 MHz, Chloroform-d) δ 8.13 (d, J=2.0 Hz, 1H), 7.76 (d, J=2.8 Hz, 1H), 7.57 (s, 1H), 7.40 (s, 1H), 7.30 (s, 1H), 7.25 (s, 1H), 7.19 (d, J=2.0 Hz, 1H), 7.11 (s, 1H), 6.95 (s, 1H), 5.20 (s, 2H), 4.07-4.00 (m, 4H), 3.88 (s, 3H), 3.82-3.71 (m, 1H), 3.13 (ddd, J=16.3, 11.0, 5.2 Hz, 1H), 3.03-2.94 (m, 1H), 2.79 (s, 3H); LCMS (ESI): Method 2: $R_T$=1.448 min, m/z=572.2 $[M+H]^+$.

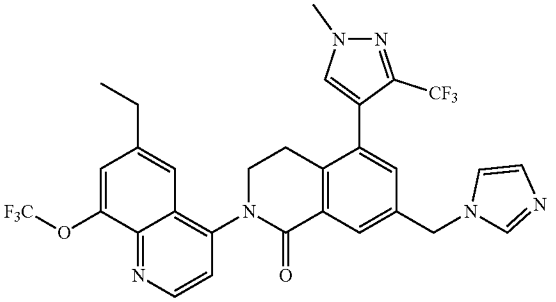 [SMILES: CCc1cc(OC(F)(F)F)c2nccc(N3CCc4c(cc(Cn5ccnc5)cc4-c4cn(C)nc4C(F)(F)F)C3=O)c2c1]

Example 176

7-((1H-imidazol-1-yl)methyl)-2-(6-ethyl-8-(trifluoromethoxy)quinolin-4-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-ethyl-8-(trifluoromethoxy) quinolone (Intermediate 88). $^1$H NMR (400 MHz, Chloroform-d) δ 9.05 (d, J=4.6 Hz, 1H), 8.19 (s, 1H), 7.68 (s, 1H), 7.58 (s, 1H), 7.57 (s, 1H), 7.44 (s, 1H), 7.43 (d, J=4.6 Hz, 1H), 7.23 (s, 1H), 7.15 (s, 1H), 6.99 (s, 1H), 5.24 (s, 2H), 4.09-4.02 (m, 1H), 4.05 (s, 3H), 3.87-3.82 (m, 1H), 3.23-3.15 (m, 1H), 3.05-2.85 (m, 1H), 2.86 (q, J=7.6 Hz, 2H), 1.33 (t, J=7.6 Hz, 3H); LCMS Method 2: >95%, $R_T$=1.54 min, MS (ESI) 615.1 $[M+H]^+$.

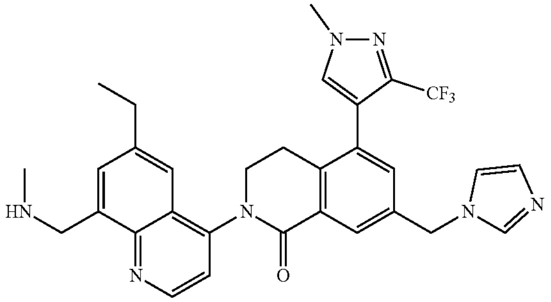 [SMILES: CCc1cc(CNC)c2nccc(N3CCc4c(cc(Cn5ccnc5)cc4-c4cn(C)nc4C(F)(F)F)C3=O)c2c1]

Example 177

7-((1H-Imidazol-1-yl)methyl)-2-(6-ethyl-8-((methylamino)methyl)quinolin-4-yl)-5-(1-methyl-3-(trifluoromethyl)-1H-pyrazol-4-yl)-3,4-dihydroisoquinolin-1(2H)-one To a solution of tert-butyl ((4-(7-((1H-imidazo-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)(methyl)carbamate (Example 152, 40.0 mg, 59.4 μmol, 1 equiv) in dichloromethane (1 mL) at 0° C. was added TFA (1 mL). The mixture was allowed to warm to room temperature and stirred overnight. The solvent was removed under reduced pressure and the residue was dissolved in EtOAc and washed with saturated aqueous $NaHCO_3$. The organic layer was dried ($Na_2SO_4$), filtered, and concentrated to provide the desired product. LCMS (ESI): >95%, m/z=574.6 $[M+H]^+$.

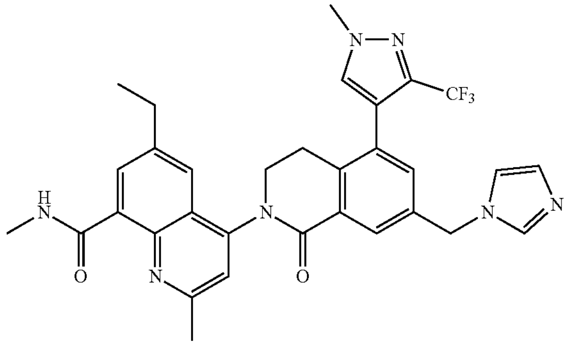

Example 178

4-(7-((1H-Imidazol-1-yl)methyl)-5-(1-methyl-3-(trichloromethyl)-1H-pyrazol-4-yl)-1-oxo-3,4-dihydroisoquinolin-2(1H)-yl)-6-ethyl-N,2-dimethylquinoline-8-carboxamide The title compound was prepared from ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-2-methylquinoline-8-carboxylate (Example 162) using the ester hydrolysis procedure found in Example 40 followed by the amide formation procedure found in Example 42. $^1$H NMR (400 MHz, Chloroform-d) δ 11.29 (q, J=4.8 Hz, 1H), 8.76 (d, J=1.8 Hz, 1H), 8.16 (d, J=1.8 Hz, 1H), 7.69 (s, 1H), 7.63 (s, 1H), 7.42 (s, 1H), 7.28 (s, 1H), 7.20 (d, J=1.8 Hz, 1H), 7.12 (s, 1H), 6.96 (s, 1H), 5.21 (s, 2H), 4.03 (s, 3H), 4.01-3.94 (m, 1H), 3.83-3.77 (m, 1H), 3.20-3.12 (m, 1H), 3.15 (d, J=4.8 Hz, 3H), 3.01-2.95 (m, 1H), 2.84 (d, J=7.6 Hz, 2H), 2.79 (s, 3H), 1.30 (t, J=7.6 Hz, 3H); LCMS Method 2: >95%, $R_T$=1.28 min, MS (ESI) 602.2 $[M+H]^+$.

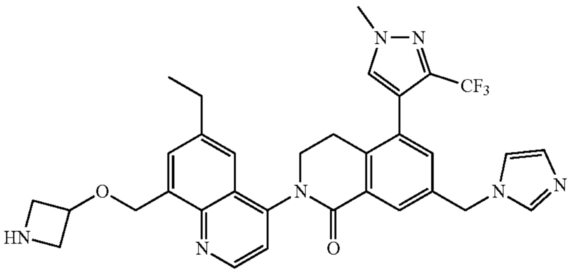 [SMILES: CCc1cc(COC2CNC2)c2nccc(N3CCc4c(cc(Cn5ccnc5)cc4-c4cn(C)nc4C(F)(F)F)C3=O)c2c1]

Example 179

7-((1H-Imidazol-1-yl)methyl)-2-(8-((azetidin-3-yloxy)methyl)-6-ethylquinolin-4-yl)-5-(1-methyl-3-(trifluoromethyl)-1H-pyrazol-4-yl)-3,4-dihydroisoquinolin-1(2H)-one Step A. Preparation of tert-butyl 3-((4-(7-((1H-imidazol-1-yl)methyl)-5-(1 methyl-3-(trifluoromethyl)-1H-pyrazol-4-yl)-1-oxo-3,4-dihydroisoquinolin-2(1H)-yl)-6-ethylquinolin-8-yl)methoxy)azetidine-1-carboxylate. The title compound (28.0 mg, 45 μmol, 49%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and tert-butyl 3-((4-bromo-6-ethylquinolin-8-yl)methoxy)azetidine-1-carboxylate (Intermediate 117, 47.1 mg, 112 μmol, 1.2 equiv).

Step B. Preparation of 7-((1H-Imidazol-1-yl)methyl)-2-(8-((azetidin-3-yloxy)methyl)-6-ethylquinolin-4-yl)-5-(1-methyl-3-(trifluoromethyl)-1H-pyrazol-4-yl)-3,4-dihydroisoquinolin-1(2H)-one. To a solution of tert-butyl 3-((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methoxy)azetidine-1-carboxylate in DCM (2.5 mL) was added TEA (2.5 mL). The reaction mixture was stirred for 30 min at room temperature then concentrated. The residue was purified by reverse phase HPLC (Phenomenex Gemini C18, $H_2O/CH_3CN$ gradient from 5-60% $CH_3CN$, 0.1% TFA) followed by neutralization with sat. aq. $NaHCO_3$ to yield the title compound (28 mg, 45 μmol, 49%). $^1$H NMR (400 MHz, Chloroform-d) δ 8 91 (s, 1H), 8.18 (s, 1H), 7.72 (s, 1H), 7.56 (s, 1H), 7.54 (d, J=6.9 Hz, 1H), 7.41 (s, 1H), 7.34 (s, 1H), 7.33 (s, 1H), 7.17 (s, 1H), 7.08 (d, J=6.9 Hz, 1H), 6.94 (d, J=8.2 Hz, 1H), 5.18 (t, J=9.3 Hz, 2H), 5.09 (d, J=13.7 Hz, 2H), 4.03 (s, 3H), 3.95 (m, J=7.6 Hz, 3H), 3.82 (m, J=5.8 Hz, 2H), 3.74 (t, J=8.6 Hz, 2H), 3.16 (m, J=6.2 Hz, 2H), 2.98 (m, J=4.9 Hz, 1H), 2.82 (q, J=8.5 Hz, 2H), 1.30 (t, J=7.9 Hz, 3H); LCMS (ESI): m/z=616.2 $[M+H]^+$.

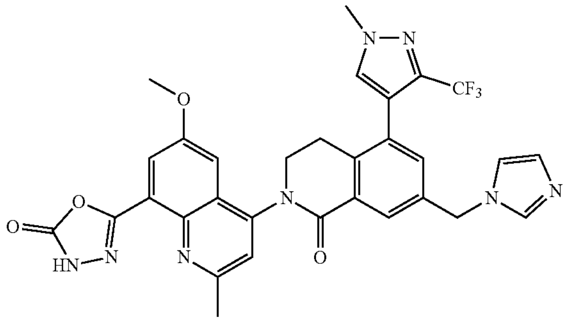 [SMILES: COc1cc(-c2n[nH]c(=O)o2)c2nc(C)cc(N3CCc4c(cc(Cn5ccnc5)cc4-c4cn(C)nc4C(F)(F)F)C3=O)c2c1]

Example 180

5-(4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinolin-8-yl)-1,3,4-oxadiazol-2(3-1)-one Ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylate (Example 95, 100 mg, 0.16 mmol) was dissolved in EtOH (1 mL) and hydrazine hydrate (249 mg, 0.24 mL, 3.23 mmol, 20 equiv, 65 wt. %) was added. The reaction mixture was stirred at 90° C. overnight. The reaction was concentrated under reduced pressure and diluted in DMF (1 mL) at room temperature. Then N,N-diisopropylethylamine (0.042 mL, 0.24 mmol, 1.5 equiv) followed by CDI (39 mg, 0.24 mmol, 1.5 equiv) were added and the reaction was stirred for 1 h. Water was added and the reaction was extracted with $CH_2Cl_2$ (3×20 mL). The combined organic layers were dried over $MgSO_4$ and concentrated under reduced pressure. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (53 mg, 0.084 mmol, 52% yield). $^1H$ NMR (400 MHz, DMSO-$d_6$) δ 8.08 (s, 1H), 7.78 (s, 1H), 7.74 (d, J=2.8 Hz, 1H), 7.58 (s, 1H), 7.42 (d, J=2.0 Hz, 1H), 7.32 (d, J=2.9 Hz, 1H), 7.21 (d, J=1.3 Hz, 1H), 6.91 (d, J=1.2 Hz, 1H), 5.31 (s, 2H), 4.04-3.97 (m, 4H), 3.87 (s, 3H), 3.85-3.77 (m, 1H), 3.23-3.11 (m, 2H), 2.97-2.85 (m, 1H), 2.64 (s, 3H); LCMS (ESI): Method 2: $R_T$=1.220 min, m/z=631.2 $[M+H]^+$.

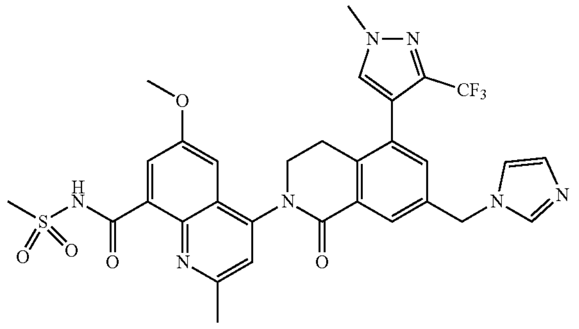 [SMILES: COc1cc(C(=O)NS(C)(=O)=O)c2nc(C)cc(N3CCc4c(cc(Cn5ccnc5)cc4-c4cn(C)nc4C(F)(F)F)C3=O)c2c1]

Example 181

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methyl-N-(methylsulfonyl)quinoline-8-carboxamide 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylic acid (Example 125, 60 mg, 0.10 mmol) was dissolved in $CH_2Cl_2$ (1 ml) and 1,1'-carbonyldiimidazole (20 mg, 0.12 mmol, 1.2 equiv) was added and stirred for 3 h at room temperature. Then methanesulfonamide (39 mg, 0.41 mmol, 4 equiv) and DBU (62 mg, 0.41 mmol, 4 equiv) were added and the reaction was stirred overnight. Water and sat. aq. $NH_4Cl$ were added and the reaction was extracted with $CH_2Cl_2$ (3×20 mL). The combined organic layers were dried over $MgSO_4$ and concentrated. The residue was purified by reverse phase HPLC (Phenomenex Gemini C18, $H_2O$/$CH_3CN$ gradient from 15-80% $CH_3CN$, 0.1% TEA) followed by neutralization with sat. aq. $NaHCO_3$ to yield the title compound (39 mg, 0.058 mmol, 57% yield). $^1H$ NMR (400 MHz, Chloroform-d) δ 8.50 (d, J=2.9 Hz, 1H), 8.13 (d, J=2.0 Hz, 1H), 7.57 (s, 1H), 7.41 (s, 1H), 7.34 (s, 1H), 7.32 (d, J=3.0 Hz, 1H), 7.20 (d, J=2.0 Hz, 1H), 7.14-7.08 (m, 1H), 6.94 (t, J=1.3 Hz, 1H), 5.20 (s, 2H), 4.06-3.99 (m, 4H), 3.91 (s, 3H), 3.87-3.73 (m, 1H), 3.45 (d, J=1.6 Hz, 3H), 3.22-3.09 (m, 1H), 3.02-2.96 (m, 1H), 2.81 (s, 3H); LCMS (ESI): Method 2: $R_T$=1.36 min, m/z=668.2 $[M+H]^+$.

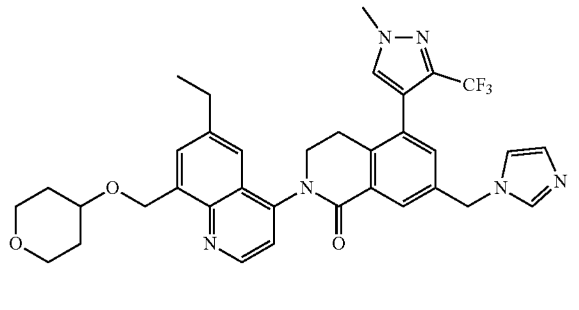 [SMILES: CCc1cc(COC2CCOCC2)c2nccc(N3CCc4c(cc(Cn5ccnc5)cc4-c4cn(C)nc4C(F)(F)F)C3=O)c2c1]

Example 182

7-((1H-Imidazol-1-yl) methyl)-2-(6-ethyl-8-(((tetrahydro-2H-pyran-4-yl)oxy)methyl)quinolin-4-yl)-5-(1-methyl-3-(trifluoromethyl)-1H-pyrazol-4-yl)-3,4-dihydroisoquinolin-1(2H)-one The title compound (43 mg, 67 μmol, 72%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-ethyl-8-(((tetrahydro-2H-pyran-4-yl)oxy)methyl)quinoline (Intermediate 115). $^1H$ NMR (400 MHz, Chloroform-d) δ 8.89 (d, J=4.6 Hz, 1H), 8.17 (d, J=1.7 Hz, 1H), 7.80 (s, 1H), 7.57 (s, 1H), 7.52 (s, 1H), 7.41 (s, 1H), 7.33 (d, J=4.6 Hz, 1H), 7.18 (d, J=1.7 Hz, 1H), 7.10 (s, 1H), 6.95 (s, 1H), 5.30 (t, J=7.2 Hz, 2H), 5.20 (s, 2H), 4.03 (s, 3H), 3.98 (m, J=4.8 Hz, 3H), 3.80 (m, J=4.9 Hz, 2H), 3.49 (m, =5.8 Hz, 2H), 3.16 (m, J=5.4 Hz, 1H), 2.97 (m, J=5.2 Hz, 1H), 2.83 (q, J=7.5 Hz, 2H), 2.06 (q, J=4.3 Hz, 2H), 1.78 (m, J=3.3 Hz, 2H), 1.30 (t, J=7.6 Hz, 3H); LCMS (ESI): m/z=645.2 $[M+H]^+$.

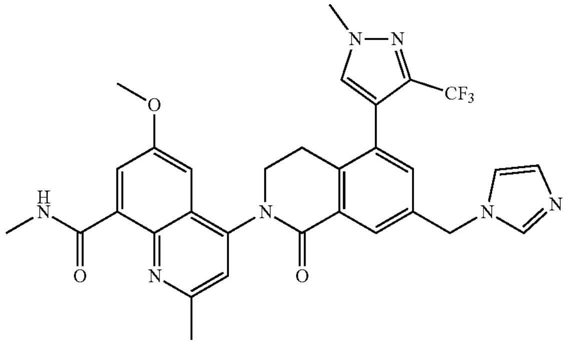 [SMILES: CNC(=O)c1cc(OC)cc2c(N3CCc4c(cc(Cn5ccnc5)cc4-c4cn(C)nc4C(F)(F)F)C3=O)cc(C)nc12]

Example 183

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N,2-dimethylquinoline-8-carboxamide The title compound (41 mg, 0.068 mmol, 67% yield) was prepared following the procedure described for Example 42, using 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylic acid (Example 125, 60 mg, 0.10 mmol) and methylamine hydrochloride (69 mg, 1.0 mmol, 10 equiv). $^1H$ NMR (400 MHz, Chloroform-d) δ 11.33 (d, J=4.9 Hz, 1H), 8.58 (d, J=3.0 Hz, 1H), 8.15 (d, J=2.1 Hz, 1H), 7.57 (t, J=1.1 Hz, 1H), 7.41 (s, 1H), 7.28 (s, 1H), 7.22 (d, J=3.0 Hz, 1H), 7.18 (d, J=2.0 Hz, 1H), 7.11 (t, J=1.1 Hz, 1H), 6.95 (d, J=1.3 Hz, 1H), 5.20 (s, 2H), 4.03 (s, 3H), 4.01-3.93 (m, 1H), 3.92 (s, 3H), 3.79 (dq, J=11.5, 5.5 Hz, 1H), 3.19-3.11 (m, 4H), 2.97 (dt, J=16.4, 4.8 Hz, 1H), 2.76 (s, 3H); LCMS (ESI): Method 2: $R_T$=1.277 min, m/z=604.2 $[M+H]^+$.

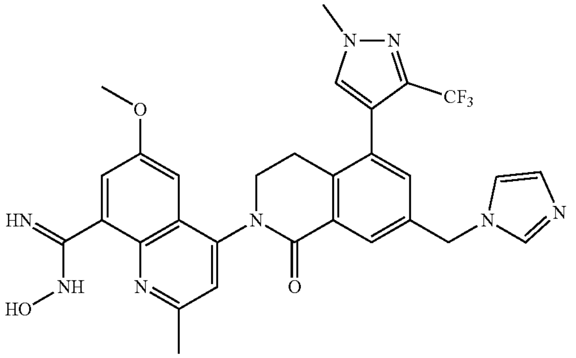 [SMILES: COc1cc(C(=N)NO)c2nc(C)cc(N3CCc4c(cc(Cn5ccnc5)cc4-c4cn(C)nc4C(F)(F)F)C3=O)c2c1]

Example 184

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-hydroxy-6-methoxy-2-methylquinoline-8-carboximidamide 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carbonitrile (Example 175, 80 mg, 0.14 mmol) was dissolved in EtOH (1 mL). A hydroxylamine solution (92 mg, 1.4 mmol, 10 equiv, 50 wt. %) was added. The reaction mixture was stirred at 80° C. overnight then concentrated. The residue was purified by flash chromatography (Combi-flash Rf, MeOH/$CH_2Cl_2$=0-10% gradient) to provide the title compound (75 mg, 0.12 mmol, 89% yield). $^1$H NMR (400 MHz, Chloroform-d) δ 8.16 (d, J=2.0 Hz, 1H), 8.01 (d, J=2.91 Hz, 1H), 7.58 (s, 1H), 7.40 (s, 1H), 7.25 (s, 2H), 7.17 (d, J=2.0 Hz, 1H), 7.14 (d, J=2.9 Hz, 1H), 7.11 (d, J=1.1 Hz, 1H), 6.95 (d, J=1.3 Hz, 1H), 6.91-6.86 (m, 2H), 5.20 (s, 2H), 4.03 (s, 3H), 3.95 (td, J=11.6, 4.3 Hz, 1H), 3.87 (s, 3H), 3.83-3.72 (m, 1H), 3.14 (ddd, J=16.3, 10.8, 5.2 Hz, 1H), 2.97 (dt, J=16.4, 4.8 Hz, 1H), 2.72 (s, 3H); LCMS (ESI): Method 2: $R_T$=1.096 min, m/z 605.2 [M+H]$^+$.

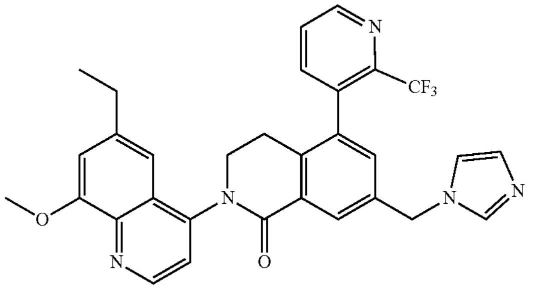 [SMILES: CCc1cc(OC)c2nccc(N3CCc4c(cc(Cn5ccnc5)cc4-c4cccnc4C(F)(F)F)C3=O)c2c1]

Example 185

7-((1H-Imidazol-1-yl)methyl)-2-(6-ethyl-8-methoxyquinolin-4-yl)-5-(2-(trifluoromethyl)pyridin-3-yl)-3,4-dihydroisoquinolin-1(2H)-one The title compound was prepared following the Buchwald coupling procedure described for Example 2, using 7-((1H-imidazol-1-yl)methyl)-5-(2-(trifluoromethyl)pyridin-3-yl)-3,4-dihydroisoquinolin-1(2H)-one (Intermediate 89) and 4-bromo-6-ethyl-8-methoxyquinoline (Intermediate 17). $^1$H NMR (400 MHz, Chloroform-d) δ 8.92 (t, J=4.6 Hz, 1H), 8.81 (d, J=4.6 Hz, 1H), 8.23 (s, 1H), 7.72-7.67 (m, 1H), 7.65 (s, 1H), 7.63-7.60 (m, 1H), 7.36 (dd, J=9.6, 4.6 Hz, 1H), 7.17-7.12 (m, 3H), 6.96 (bs, 2H), 5.24 (s, 2H), 4.10 (s, 3H), 4.03-3.73 (m, 2H), 3.09-2.93 (m, 1H), 2.83-2.65 (m, 3H), 1.30 (t, J=7.6 Hz, 3H); LCMS Method 2: >95%, $R_T$=1.21 min, MS (ESI) 558.2 [M+H]$^+$.

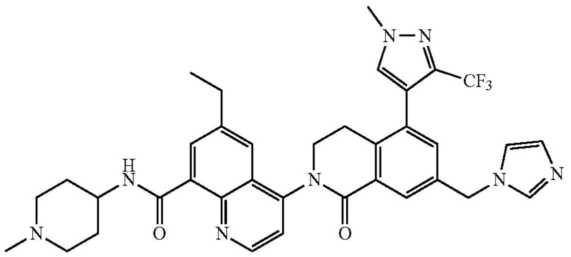 [SMILES: CCc1cc(C(=O)NC2CCN(C)CC2)c2nccc(N3CCc4c(cc(Cn5ccnc5)cc4-c4cn(C)nc4C(F)(F)F)C3=O)c2c1]

Example 186

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-methylpiperidin-4-yl)quinoline-8-carboxamide The title compound (47 mg, 70 μmol, 70%) was prepared following the procedure described for Example 160, substituting 1-methylpiperidin-4-amine (12 mg, 100.0 μmol, 1.0 equiv) for oxazol-2-amine. $^1$H NMR (400 MHz, Chloroform-d) δ δ 11.32 (d, J=10.1 Hz, 1H), 8.90 (d, J=4.7 Hz, 1H), 8.78 (d, J=2.0 Hz, 1H), 8.16 (s, 1H), 7.74 (s, 1H), 7.57 (s, 1H), 7.41 (s, 1H), 7.39 (s, 1H), 7.20 (s, 1H), 7.10 (s, 1H), 6.95 (s, 1H), 5.20 (s, 2H), 4.20 (s, 1H), 4.03 (s, 3H), 4.00 (t, J=5.8 Hz, 1H), 3.83 (t, J=8.1 Hz, 1H), 3.18 (q, J=8.5 Hz, 1H), 2.99 (d, J=16.2 Hz, 1H), 2.87 (q, J=7.6 Hz, 2H), 2.79 (d, J=7.0 Hz, 2H), 2.33 (s, 3H), 2.28 (t, J=11.6 Hz, 2H), 2.13 (m, J=8.4 Hz, 2H), 1.78 (m, J=6.1 Hz, 2H), 1.31 (t, J=7.6 Hz, 3H); LCMS (ESI): m/z=671.2 [M+H]$^+$.

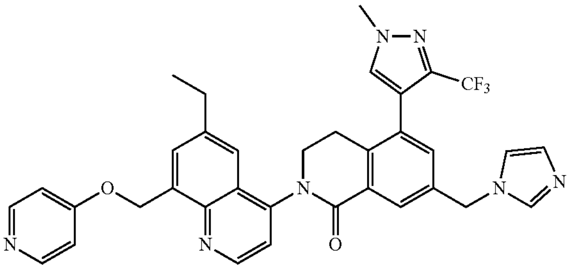 [SMILES: CCc1cc(COc2ccncc2)c2nccc(N3CCc4c(cc(Cn5ccnc5)cc4-c4cn(C)nc4C(F)(F)F)C3=O)c2c1]

Example 187

7-((1H-Imidazol-1-yl)methyl)-2-(6-ethyl-8-((pyridin-4-yloxy)methyl)quinolin-4-yl)-5-(1-methyl-3-(trifluoromethyl)-1H-pyrazol-4-yl)-3,4-dihydroisoquinolin-1(2H)-one The title compound (35 mg, 55 μmol, 59%) was prepared following the Buchwald coupling procedure described for Example 2, utilizing 7-((1H-imidazol-1-yl)methyl)-5-(1- methyl-3-(trifluoromethyl)-1H-pyrazol-4-yl)-3,4-dihydroisoquinolin-1(2H)-one (Intermediate 8) and 4-bromo-6-ethyl-8-((pyridin-4-yloxy)methyl)quinoline (Intermediate 1H). $^1$H NMR (400 MHz, Chloroform-d) δ 8.93 (d, J=4.6 Hz, 1H), 8.14 (d, J=1.8 Hz, 1H), 7.61 (q, J=4.6 Hz, 3H), 7.57 (s, 1H), 7.41 (s, 2H), 7.39 (d, J=4.6 Hz, 1H), 7.19 (d, J=1.8 Hz, 1H), 7.10 (s, 1H), 6.94 (s, 1H), 6.38 (s, 1H), 6.37 (d, J=1.7 Hz, 1H), 5.71 (d, J=14.8 Hz, 1H), 5.42 (d, J=14.9 Hz, 1H), 5.20 (s, 2H), 4.02 (s, 3H), 3.99 (d, J=4.2 Hz, 1H), 3.81 (m, J=5.7 Hz, 1H), 3.16 (m, J=5.4 Hz, 1H), 2.98 (m, J=5.1 Hz, 1H), 2.81 (q, J=7.5 Hz, 2H), 1.28 (t, J=7.6 Hz, 3H); LCMS (ESI): m/z=638.2 [M+H]$^+$.

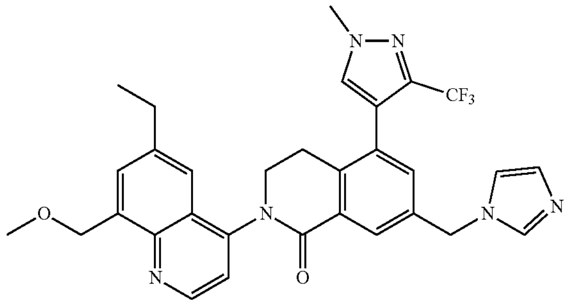 [SMILES: CCc1cc(COC)c2nccc(N3CCc4c(cc(Cn5ccnc5)cc4-c4cn(C)nc4C(F)(F)F)C3=O)c2c1]

Example 188

7-((1H-Imidazol-1-yl)methyl)-2-(6-ethyl-8-(methoxymethyl)quinolin-4-yl)-5-(1-methyl-3-(trifluoromethyl)-1H-pyrazol-4-yl)-3,4-dihydroisoquinolin-1(2H)-one The title compound (40 mg, 70 mol, 75%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-ethyl-8-(methoxymethyl)quinoline (Intermediate 113). $^1$H NMR (400 MHz, Chloroform-d) δ 8.92 (d, J=4.6 Hz, 1H), 8.17 (d, J=1.7 I-z 1H), 7.74 (s, 1H), 7.57 (s, 1H), 7.53 (s, 1H), 7.41 (s, 1H), 7.33 (d, J=4.6 Hz, 1H), 7.18 (d, J=1.7 Hz, 1), 7.10 (s, 1H), 6.95 (s, 1H), 5.21 (q, J=15.5 Hz, 4H), 4.03 (s, 3H), 3.98 (m, J=5.5 Hz, 1H), 3.82 (m, J=5.7 Hz, 1H), 3.59 (s, 3H), 3.16 (m, J=5.4 Hz, 1H), 2.97 (m, J=51 Hz, 1H), 2.82 (q, J=7.6 Hz, 2H), 1.30 (t, J=7.6 Hz, 3H); LCMS (ESI): m/z=575.2 [M+H]$^+$.

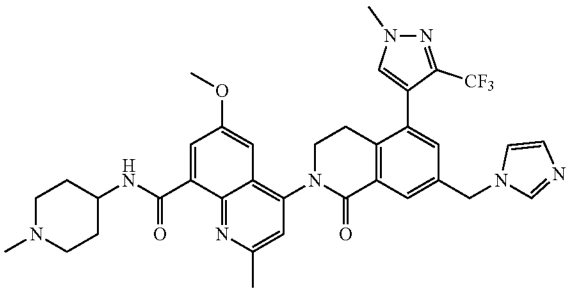 [SMILES: COc1cc(C(=O)NC2CCN(C)CC2)c2nc(C)cc(N3CCc4c(cc(Cn5ccnc5)cc4-c4cn(C)nc4C(F)(F)F)C3=O)c2c1]

Example 189

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methyl-N-(1-methylpiperidin-4-yl)quinoline-8-carboxamide The title compound (45 mg, 0.065 mmol, 64% yield) was prepared following the procedure described for Example 42, using 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylic acid (Example 125, 60 mg, 0.10 mmol) and 1-methylpiperidin-4-amine (58 mg, 0.51 mmol, 5 equiv). $^1$H NMR (400 MHz, Chloroform-d) δ 8.56 (d, J=3.0 Hz, 1H), 8.15 (d, J=2.0 Hz, 1H), 7.57 (s, 1H), 7.40 (s, 1H), 7.28 (s, 1H), 7.21 (d, J=3.0 Hz, 1H), 7.18 (d, J=2.0 Hz, 1H), 7.10 (t, J=1.1 Hz, 1H), 6.94 (d, J=1.3 Hz, 1H), 5.20 (s, 2H), 4.18 (brs, 1H), 4.03 (s, 3H), 3.96 (td, J=11.6, 4.3 Hz, 1H), 3.90 (s, 3H), 3.82-3.72 (m, 1H), 3.15 (ddd, J=16.2, 10.8, 5.2 Hz, 1H), 2.97 (dt, J=16.4, 4.7 Hz, 1H), 2.83 (brs, 2H), 2.75 (s, 3H), 2.36 (s, 3H), 2.16 (brs, 2H), 1.79 (brs, 2H), 1.60 (brs, 2H); LCMS (ESI): Method 2: $R_T$=1.164 min, m/z=687.3 [M+H]$^+$.

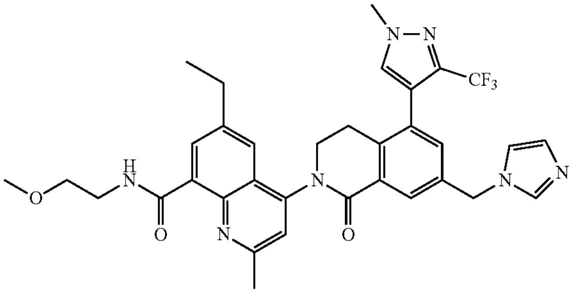 [SMILES: CCc1cc(C(=O)NCCOC)c2nc(C)cc(N3CCc4c(cc(Cn5ccnc5)cc4-c4cn(C)nc4C(F)(F)F)C3=O)c2c1]

Example 190

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-methoxyethyl)-2-methylquinoline-8-carboxamide The title compound was prepared from ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-2-methylquinoline-8-carboxylate (Example 162) using the ester hydrolysis procedure found in Example 40 followed by the amide formation procedure found in Example 42 with 2-methoxyethylamine as the amine $^1$H NMR (400 MHz, Chloroform-d) δ 8.74 (d, J=1.8 Hz, 1H), 8.16 (s, 1H), 7.68 (bs, 1H), 7.65 (Us, 1H), 7.42 (s, 1H), 7.28 (s, 1H), 7.20 (s, 1H), 7.13 (bs, 1H), 6.97 (bs, 1H), 5.21 (s, 2H), 4.03 (s, 3H), 4.01-3.94 (m, 1H), 3.86-3.77 (m, 3H), 3.71-3.66 (m, 2H), 3.48 (s, 3H), 3.20-3.12 (m, 1H), 3.01-2.95 (m, 1H), 2.84 (q, J=7.6 Hz, 2H), 2.79 (s, 3H), 1.30 (t, J=7.6 Hz, 3H); LCMS Method 2: >95%, $R_T$=1.37 min, MS (ESI) 646.3 [M+H]$^+$.

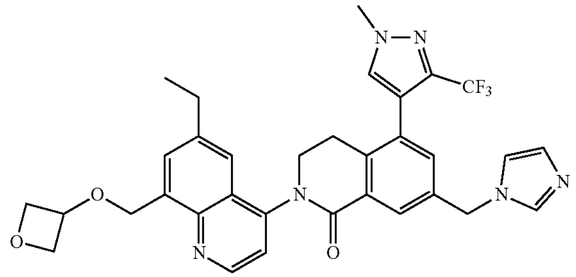 [SMILES: CCc1cc(COC2COC2)c2nccc(N3CCc4c(cc(Cn5ccnc5)cc4-c4cn(C)nc4C(F)(F)F)C3=O)c2c1]

Example 191

7-((1H-Imidazol-1-yl)methyl)-2-(6-ethyl-8-((oxetan-3-yloxy)methyl)quinolin-4-yl)-5-(1-methyl-3-(trifluoromethyl)-1H-pyrazol-4-yl)-3,4-dihydroisoquinolin-1(2H)-one The title compound (37 mg, 60 μmol, 64%) was prepared following the Buchwald coupling procedure described for Example 2, utilizing 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 4-bromo-6-ethyl-8-((oxetan-3-yloxy)methyl)quinoline (Intermediate 116). $^1$H NMR (400 MHz, Chloroform-d) δ 8.90 (d, J=4.6 Hz, 1H), 8.17 (d, J=1.8 Hz, 1H), 7.76 (s, 1H), 7.57 (s, 1H), 7.55 (s, 1H), 7.41 (s, 1H), 7.34 (d, J=4.6 Hz, 1H), 7.18 (d, J=1.8 Hz, 1H), 7.11 (s, 1H), 6.95 (s, 1H), 5.19 (q, J=16.0 Hz, 4H), 4.82 (m, J=5.1 Hz, 3H), 4.75 (m, J=3.1 Hz, 2H), 4.03 (s, 3H), 3.98 (m, J=5.8 Hz, 1H), 3.82 (m, J=5.7 Hz, 1H), 3.17 (m, J=5.4 Hz, 1H), 2.98 (m, J=5.2 Hz, 1H), 2.83 (q, J=7.6 Hz, 2H), 1.31 (t, J=7.6 Hz, 3H); LCMS (ESI): m/z=617.2 [M+H]$^+$.

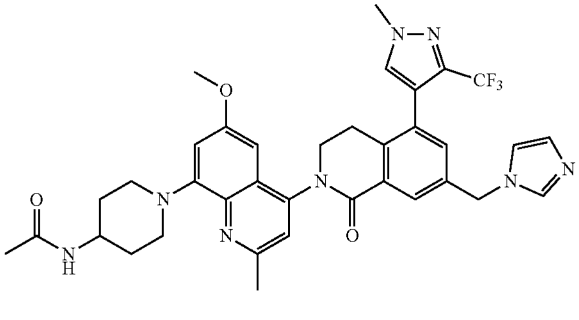 [SMILES: COc1cc(N2CCC(NC(C)=O)CC2)c2nc(C)cc(N3CCc4c(cc(Cn5ccnc5)cc4-c4cn(C)nc4C(F)(F)F)C3=O)c2c1]

Example 192

N-(1-(4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinolin-8-yl)piperidin-4-yl)acetamide The title compound (19 mg, 0.028 mmol, 29% yield) was prepared following the Buchwald coupling procedure described for Example 124, using 7-((1H-imidazol-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 60 mg, 0.096 mmol), and N-(piperidin-4-yl)acetamide (41 mg, 0.29 mmol, 3 equiv). $^1$H NMR (400 MHz, Chloroform-d) δ 8.16 (d, J=2.0 Hz, 1), 7.57 (s, 1H), 7.40 (s, 1H), 7.19 (s, 1H), 7.16 (d, J=2.0 Hz, 1H), 7.10 (d, J=1.1 Hz, 1H), 6.95 (t, J=1.3 Hz, 1H), 6.78 (d, J=2.6 Hz, 1), 6.66 (d, J=2.6 Hz, 1H), 5.42 (d, J=8.1 Hz, 1H), 5.19 (s, 2H), 4.05-3.99 (m, 5H), 3.91 (tt, J=12.5, 6.1 Hz, 1H), 3.81 (s, 3H), 3.79-3.70 (m, 1H), 3.12 (ddd, J=16.2, 10.8, 5.2 Hz, 1H), 3.01-2.89 (m, 2H), 2.89-2.78 (m, 1H), 2.71 (s, 3H), 2.12 (t, J=12.4 Hz, 2H), 2.02 (s, 3H), 1.98-1.74 (m, 2H); LCMS (ESI): Method 2: $R_T$=1.131 min, m/z=687.3 [M+H]$^+$.

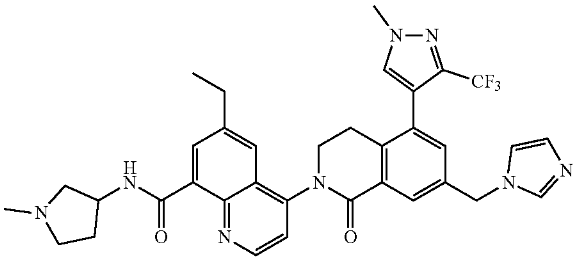 [SMILES: CCc1cc(C(=O)NC2CCN(C)C2)c2nccc(N3CCc4c(cc(Cn5ccnc5)cc4-c4cn(C)nc4C(F)(F)F)C3=O)c2c1]

Example 193

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-methylpyrrolidin-3-yl)quinoline-8-carboxamide The title compound (44 mg, 67 μmol, 67%) was prepared following the procedure described for Example 160, substituting 1-methylpyrrolidin-3-amine (12 mg, 120 μmol, 1.2 equiv) for oxazol-2-amine. $^1$H NMR (400 MHz, Chloroform-d) δ 11.38 (d, J=7.4 Hz, 1H), 8.94 (d, J=3.9 Hz, 1H), 8.77 (d, J=2.1 Hz, 1H), 8.16 (s, 1H), 7.74 (s, 1H), 7.57 (s, 1H), 7.41 (s, 1H), 7.39 (d, J=4.7 Hz, 1H), 7.20 (s, 1H), 7.10 (s, 1H), 6.95 (s, 1H), 5.20 (s, 2H), 4.76 (m, J=7.3 Hz, 1H), 4.03 (s, 3H), 4.00 (t, J=6.4 Hz, 1H), 3.81 (t, J=7.4 Hz, 1H), 3.17 (m, J=7.0 Hz, 1H), 2.98 (m, J=7.8 Hz, 1H), 2.87 (m, J=6.4 Hz, 4H), 2.74 (q, J=6.6 Hz, 1H), 2.49 (t, J=6.4 Hz, 2H), 2.42 (d, J=4.6 Hz, 3H), 1.91 (s, 1H), 1.32 (d, J=8.2 Hz, 3H); LCMS (ESI): m/z=657.2 [M+H]$^+$.

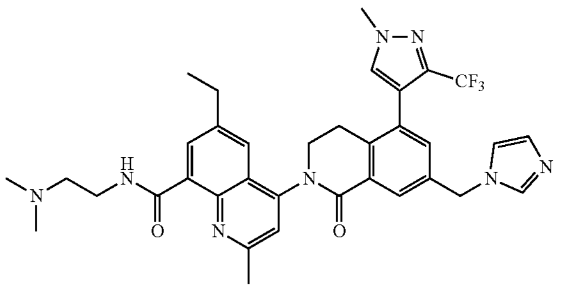 [SMILES: CCc1cc(C(=O)NCCN(C)C)c2nc(C)cc(N3CCc4c(cc(Cn5ccnc5)cc4-c4cn(C)nc4C(F)(F)F)C3=O)c2c1]

Example 194

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(2-(dimethylamino)ethyl)-6-ethyl-2-methylquinoline-8-carboxamide The title compound vas prepared from ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6- ethyl-2-methylquinoline-8-carboxylate (Example 162) using the ester hydrolysis procedure found in Example 40 followed by the amide formation procedure found in Example 42 with N,N-dimethylethylenediamine as the amine $^1$H NMR (400 MHz, Chloroform-d) δ 8.73 (s, 1H), 8.15 (s, 1H), 7.68 (s, 1H), 7.57 (s, 1H), 7.41 (s, 1H), 7.28 (s, 1H), 7.19 (s, 1H), 7.10 (s, 1H), 6.94 (s, 1H), 5.20 (s, 2H), 4.03 (s, 3H), 4.01-3.95 (m, 1H), 3.83-3.73 (m, 3H), 3.20-3.11 (m, 1H), 3.01-2.94 (m, 1H), 2.84 (q, J=7.61 Hz, 2H), 2.79 (s, 3H), 2.76-2.67 (m, 2H), 2.41 (s, 6H), 1.30 (t, J=7.6 Hz, 3H); LCMS Method 2: >95%, $R_T$=1.20 min, MS (ESI) 659.3 $[M+H]^+$.

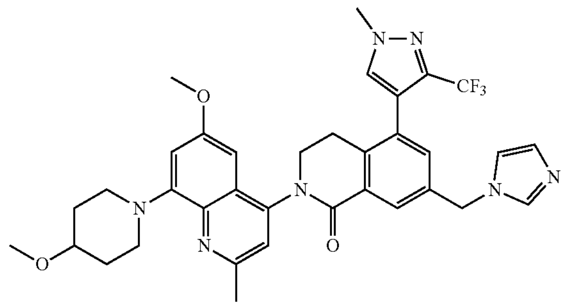 [SMILES: COc1cc(N2CCC(OC)CC2)c2nc(C)cc(N3CCc4c(cc(Cn5ccnc5)cc4-c4cn(C)nc4C(F)(F)F)C3=O)c2c1]

Example 195

7-((1H-Imidazol-1-yl)methyl)-2-(6-methoxy-8-(4-methoxypiperidin-1-yl)-2-methylquinolin-4-yl)-5-(1-methyl-3-(trifluoromethyl)-1H-pyrazol-4-yl)-3,4-dihydroisoquinolin-1(2H)-one The title compound (24 mg, 0.036 mmol, 38% yield) was prepared following the Buchwald coupling procedure described for Example 124, using 7-((1H-imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 60 mg, 0.096 mmol), and 4-methoxypiperidine (33 mg, 0.29 mmol, 3 equiv). $^1$H NMR (400 MHz, Chloroform-d) δ 8.16 (d, J=2.0 Hz, 1H), 7.57 (d, J=1.4 Hz, 1H), 7.39 (d, J=1.1 Hz, 1K), 7.18 (s, 1H), 7.15 (d, J=2.0 Hz, 1H), 7.10 (t, J=1.1 Hz, 1H), 6.94 (t, J=1.3 Hz, 1H), 6.79 (d, J=2.6 Hz, 1H), 6.65 (d, J=2.6 Hz, 1H), 5.19 (s, 2H), 4.02 (s, 3H), 3.95-3.88 (m, 2H), 3.81 (s, 3H), 3.79-3.70 (m, 1K), 3.63-3.56 (m, 1H), 3.47-3.43 (m, 1H), 3.42 (s, 3K), 3.23-3.05 (m, 2H), 3.00-2.89 (m, 2H), 2.71 (s, 3H), 2.16 (d, J=10.5 Hz, 2H), 2.00-1.89 (m, 2H); LCMS (ESI): Method 2: $R_T$=1.219 min, m/z=660.3 $[M+H]^+$.

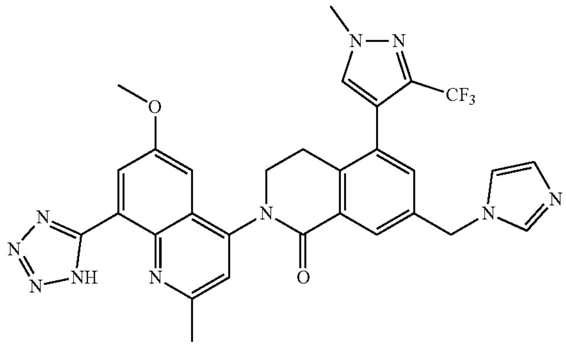 [SMILES: COc1cc(-c2nnn[nH]2)c2nc(C)cc(N3CCc4c(cc(Cn5ccnc5)cc4-c4cn(C)nc4C(F)(F)F)C3=O)c2c1]

Example 196

7-((1H-Imidazol-1-yl)methyl)-2-(6-methoxy-2-methyl-8-(1H-tetrazol-5-yl)quinolin-4-yl)-5-(1-methyl-3-(trifluoromethyl)-1H-pyrazol-4-yl)-3,4-dihydroisoquinolin-1(2H)-one 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carbonitrile (Example 175, 60 mg, 0.10 mmol), ammonium chloride (56 mg, 1.0 mmol, 10 equiv), and sodium azide (68 mg, 1.0 mmol, 10 equiv) were dissolved in DMF (1 mL) under Ar, and the reaction mixture was stirred for 14 h at 60° C. then cooled to 23° C. Brine was added to the mixture and extracted with $CH_2Cl_2$ (3×20 mL). The combined organic layers were dried over $MgSO_4$ and concentrated. The residue was purified by reverse phase HPLC (Phenomenex Gemini C18, $H_2O$/$CH_3CN$ gradient from 15-80% $CH_3CN$, 0.1% TFA) followed by neutralization with sat. aq. $NaHCO_3$ to yield the title compound (36 mg, 0,006 mmol, 6% yield). $^1$H NMR (400 MHz, Chloroform-d) δ 8.62 (d, J=2.8 Hz, 1H), 8.16 (d, =2.0 Hz, 1K), 7.58 (s, 1K), 7.42 (d, H=1.1 Hz, 1H, 7.36 (s, 1H), 7.24 (d, J=2.9 Hz, 1H), 7.21 (d, J=2.0 Hz, 1H), 7.11 (d, J=1.1 Hz, 1H), 6.95 (d, J=1.4 Hz, 1H), 5.21 (s, 2H), 4.07-4.00 (m, 4H), 3.94 (s, 3H), 3.83 (dt, J=11.4, 5.2 Hz, 1H), 3.18 (ddd, J=16.4, 11.1, 5.3 Hz, 1H), 3.01 (dt, J=16.4, 4.7 Hz, 1H), 2.85 (s, 3H); LCMS (ESI): Method 2: $R_T$=1.350 min, m/z=615.3 $[M+H]^+$.

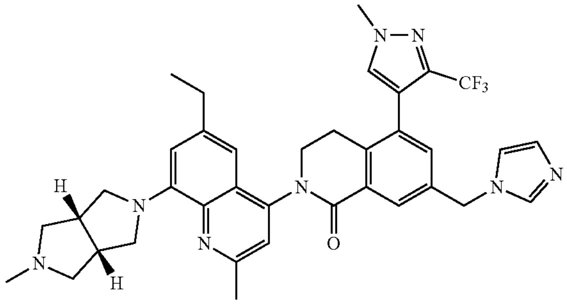 [SMILES: CCc1cc(N2C[C@H]3CN(C)C[C@H]3C2)c2nc(C)cc(N3CCc4c(cc(Cn5ccnc5)cc4-c4cn(C)nc4C(F)(F)F)C3=O)c2c1]

Example 197

7-((1H-Imidazol-1-yl)methyl)-2-(6-ethyl-2-methyl-8-((3aR,6aS)-5-methylhexahydropyrrolo[3,4-c]pyrrol-2(1H)-yl)quinolin-4-yl)-5-(1-methyl-3-(trifluoromethyl)-1H-pyrazol-4-yl)-3,4-dihydroisoquinolin-1(2H)-one The title compound (13 mg, 0.019 mmol, 15% yield) was prepared following the Buchwald coupling procedure described for Example 124, using 7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one (Example 109, 80 mg, 0.13 mmol), and (3aR,6aS)-2-methyloctahydropyrrolo[3,4-c]pyrrole dihydrochloride (51 mg, 0.26 mmol, 2 equiv). $^1$H NMR (400 MHz, Chloroform-d) δ 8.16 (d, J=2.0 Hz, 1H), 7.57 (s, 1H), 7.40 (s, 1H), 7.17 (s, 1H), 7.15 (d, J=2.0 Hz, 1H), 7.10 (d, J=1.1 Hz, 1H), 7.08 (d, J=1.6 Hz, 1H), 6.94 (t, J=1.3 Hz, 1H), 6.85 (d, J=1.8 Hz, 1H), 5.19 (s, 2H), 4.07-4.02 (m, 4H), 3.96-3.83 (m, 1H), 3.79 (q, J=6.5, 5.9 Hz, 2H), 3.48-3.41 (m, 1H), 3.25-2.99 (m, 4H), 2.93 (dt, J=16.3, 5.0 Hz, 1H), 2.76-2.58 (m, 9H), 2.39 (s, 3H), 1.25 (t, J=76 Hz, 3H); LCMS (ESI): Method 2: $R_T$=1.252 min, m/z=669.3 $[M+H]^+$.

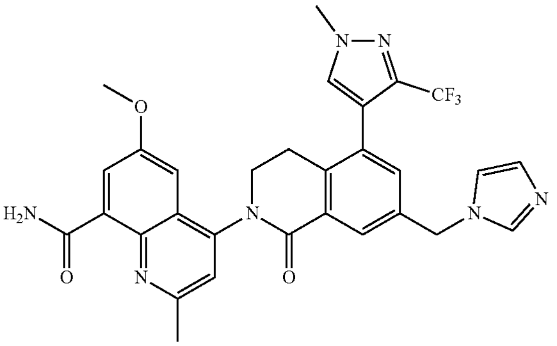 [SMILES: COc1cc(C(N)=O)c2nc(C)cc(N3CCc4c(cc(Cn5ccnc5)cc4-c4cn(C)nc4C(F)(F)F)C3=O)c2c1]

Example 198

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxamide 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylic acid (Example 125, 100 mg, 0.17 mmol) was taken up in DMF (1.5 mL) and then HATU (96.6 mg, 0.25 mmol, 1.5 equiv) was added and the reaction was cooled to 0° C. Ammonium chloride (91 mg, 1.69 mmol, 10 equiv), and N,N-diisopropylethylamine (0.89 mL, 508 μmol, 3 equiv) were added and the reaction was allowed to warm room temperature. After stirring for 14 h at room temperature the reaction was diluted with $CH_2Cl_2$ and extracted from sat. aq. $NaHCO_3$. The combined organic layers were then dried over $MgSO_4$ and concentrated. The residue was purified by reverse phase HPLC (Phenomenex Gemini C18, $1H_2O/CH_3CN$ gradient from 15-80% $CH_3CN$, 0.1% TFA) followed by neutralization with sat. aq. $NaHCO_3$ to yield the title compound (66 mg, 0.11 mmol, 66% yield). $^1H$ NMR (400 MHz, Chloroform-d) δ 11.17 (d, J=5.3 Hz, 1H), 8.56 (d, J=3.0 Hz, 1H), 8.15 (d, J=2.0 Hz, 1H), 7.57 (s, 1H), 7.40 (s, 1H), 7.29 (s, 1), 7.27 (s, 1H), 7.18 (d, J=2.0 Hz, 1H), 7.11 (s, 1H), 6.95 (s, 1H), 6.08 (d, J=5.2 Hz, 1H), 5.20 (s, 2H), 4.03 (s, 3H), 4.01-3.94 (m, 1H), 3.91 (s, 3H), 3.84-3.74 (m, 1H), 3.15 (ddd, J=16.3, 10.9, 5.2 Hz, 1H), 2.98 (dt, 3=16.5, 4.8 Hz, 1H), 2.76 (s, 3H); LCMS (ESI): Method 2: $R_T$=1.213 min, m/z=590.2 $[M+H]^+$.

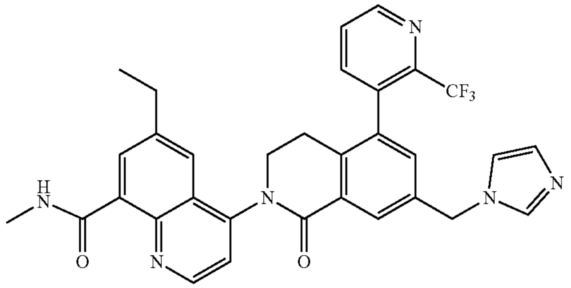 [SMILES: CCc1cc(C(=O)NC)c2nccc(N3CCc4c(cc(Cn5ccnc5)cc4-c4cccnc4C(F)(F)F)C3=O)c2c1]

Example 199

4-(7-((1H-imidazol-1-yl)methyl)-1-oxo-5-(2-(trifluoromethyl)pyridin-3-yl)-3,4-dihydroisoquinolin-2(1H)-yl)-6-ethyl-N-methylquinoline-8-carboxamide The title compound was prepared following the Buchwald coupling procedure described for Example 2, using 7-((1H-imidazol-1-yl)methyl)-5-(2-(triiodomethyl)pyridin-3-yl)-3,4-dihydroisoquinolin-1(2H)-one (Intermediate 89) and ethyl 4-bromo-6-ethylquinoline-8-carboxylate (Intermediate 61) followed by the ester hydrolysis procedure found in Example 40 and the amide formation procedure found in Example 42. LCMS Method 2: >95%, $R_T$=1.28 min, MS (ESI): 585.3$[M+H]^+$.

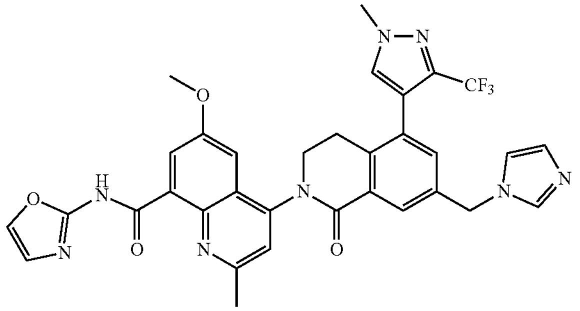 [SMILES: COc1cc(C(=O)Nc2ncco2)c2nc(C)cc(N3CCc4c(cc(Cn5ccnc5)cc4-c4cn(C)nc4C(F)(F)F)C3=O)c2c1]

Example 200

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methyl-N-(oxazol-2-yl)quinoline-8-carboxamide The title compound (42 mg, 0.064 mmol, 56% yield) was prepared following the procedure described for Example 42, using 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylic acid (Example 125, 67 mg, 0.11 mmol) and oxazol-2-amine (29 mg, 0.34 mmol, 3 equiv). $^1H$ NMR (400 MHz, Chloroform-d) δ 8.63 (d, J=3.0 Hz, 1H), 8.15 (d, J=2.0 Hz, 1H), 7.57 (s, 1H), 7.52 (d, J=1.0 Hz, 1H), 7.41 (s, 1H), 7.35 (s, 1H), 7.30 (d, J=3.0 Hz, 1H), 7.20 (d, J=2.0 Hz, 1H), 7.11 (t, J=1.1 Hz, 2H), 6.95 (d, J=1.3 Hz, 1H), 5.20 (s, 2H), 4.03-3.99 (m, 4H), 3.93 (s, 3H), 3.81 (dt, J=11.4, 5.1 Hz, 1H), 3.16 (ddd, J=16.3, 11.0, 5.2 Hz, 1H), 2.99 (dt, J=16.4, 4.6 Hz, 1H), 2.87 (s, 3H); LCMS (ESI): Method 2: $R_T$=1.406 min, m/z=657.3 $[M+H]^+$

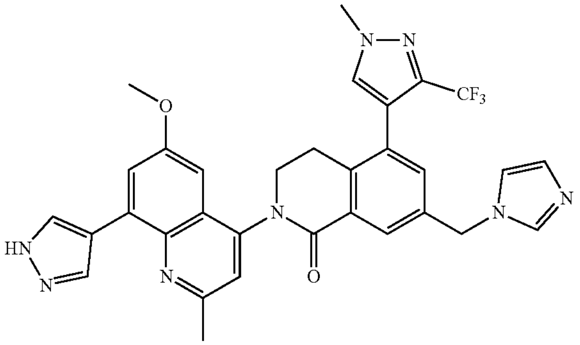 [SMILES: COc1cc(-c2cn[nH]c2)c2nc(C)cc(N3CCc4c(cc(Cn5ccnc5)cc4-c4cn(C)nc4C(F)(F)F)C3=O)c2c1]

Example 201

7-((1H-imidazol-1-yl)methyl)-2-(6-methoxy-2-methyl-8-(1H-pyrazol-4-yl)quinolin-4-yl)-5-(1-methyl-3-(trifluoromethyl)-1H-pyrazol-4-yl)-3,4-dihydroisoquinolin-1(2H)-one The title compound (46 mg, 0.075 mmol, 59% yield) was prepared following the Suzuki coupling procedure described for Example 147, using 7-((1H-imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one (Example 101, 80 mg, 0.13 mmol), and 4-(4,4,5,5-tetramethyl-1,3,2-dioxaborolan-2-yl)-1H-pyrazole (50 mg, 0.26 mmol, 2 equiv). $^1$H NMR (400 MHz, Chloroform-d) δ 8.46 (s, 2H), 8.18 (d, J=2.0 Hz, 1H), 7.60 (d, J=2.8 Hz, 1H), 7.58 (s, 1H), 7.41 (s, 1H), 7.25 (s, 1H), 7.18 (d, J=2.0 Hz, 1H), 7.11 (t, J=1.1 Hz, 1H), 6.99-6.93 (m, 2H), 5.20 (s, 2H), 4.03 (s, 3H), 3.96 (td, J=11.6, 11.1, 4.2 Hz, 1H), 3.88 (s, 3H), 3.85-3.75 (m, 1H), 3.15 (ddd, J=16.2, 10.9, 5.3 Hz, 1H), 2.97 (dt, J=16.4, 4.8 Hz, 1H), 2.74 (s, 3H); LCMS (ESI): Method 2: $R_T$1.331 min, m/z=613.2 [M+H]$^+$.

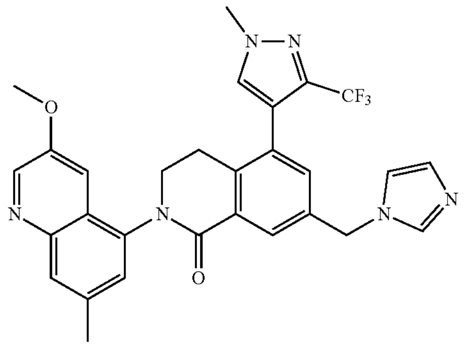

Example 202

7-((1H-Imidazol-1-yl)methyl)-2-(3-methoxy-7-methylquinolin-5-yl)-5-(1-methyl-3-(trifluoromethyl)-1H-pyrazol-4-yl)-3,4-dihydroisoquinolin-1(2H)-one Step A. Preparation of 2,6-dibromo-4-methylbenzaldehyde. To a solution of 1,3-dibromo-5-methylbenzene (21.0 g, 84 mmol) in anhydrous THF (200 mL) was added 2.0 M lithium diisopropylamide solution (58.8 mL, 1.4 eq) was drop-wise at −78° C. The reaction mixture was stirred for 30 minutes then DMF (7.8 mL, 1.2 eq) was added. The reaction was stirred for 1 h at −78° C. then quenched with 1N HCl and EtOAc. The quenched mixture was extracted with EtOAc (2×200 mL), and the organic layer was washed with brine, dried over $MgSO_4$, filtered, and concentrated to give the title compound (23.0 g, 98%). $^1$H NMR (400 MHz, Chloroform-d) δ 10.26 (s, 1H), 7.49 (s, 2H), 2.39 (s, 3H).

Step B. Preparation of 2-(2,6-dibromo-4-methylphenyl)-1,3-dioxolane. A mixture of 2,6-dibromo-4-methylbenzaldehyde (23.0 g, 83 mmol), ethane-1,2-diol (11 mL, 2.3 eq), and p-toluenesulfonic acid monohydrate (7.9 g, 0.5 eq) in anhydrous toluene (200 ml) was refluxed using a DeanStark trap until TLC showed no starting material. The reaction mixture was cooled to room temperature and concentrated. The residue was dissolved in DCM (200 mL), washed with 1N aq NaOH (50 mL) and concentrated. The residue was purified by flash chromatography (Combi-flash Rf, Hex/EtOAc=0-5% gradient) to afford the title compound (15.7 g, 59%). $^1$H NMR (400 MHz, Chloroform-d) δ 7.39 (s, 2H), 6.36 (s, 1H), 4.35-4.31 (m, 2H), 4.08-4.05 (m, 2H), 2.29 (s, 3).

Step C. Preparation of N-(3-bromo-2-(1,3-dioxolan-2-yl)-5-methylphenyl)-1,1-diphenylmethanimine. A mixture of 2-(2,6-dibromo-4-methylphenyl)-1,3-dioxolane (15.7 g, 48.8 mmol), benzophenone imine (8.2 mL, 1.0 eq), cesium carbonate (31.8 g, 2.0 eq), BINAP (3.0 g, 0.1 eq), and palladium(II) acetate (0.55 g, 0.05 eq) in anhydrous toluene (200 mL) was purged with Ar then stirred for 16 h at 80° C. The reaction mixture was cooled to ambient temperature and quenched with $H_2O$ (200 mL). The layers were separated, and the aqueous layer was extracted with EtOAc. The combined organic layer was washed with brine, dried over $MgSO_4$, filtered, and concentrated. The residue was triturated with DCM (200 mL). The solid was filtered to give the title compound. The filtrate was concentrated, and the residue was purified by flash chromatography (Combi-flash Rif, Hex EtOAc=0-10% gradient) to afford the additional title compound (17.1 g, 83% yield). $^1$H NMR (400 MHz, DMSO-$d_6$) δ 7.67-7.62 (m, 2H), 7.57-7.46 (m, 3H), 7.34 (bs, 3H), 7.24 (bs, 2H), 7.00 (s, 1H), 6.16 (s, 1H), 6.14 (s, 1H), 4.02-3.98 (m, 2H), 3.88-3.84 (m, 2H), 2.01 (s, 3H).

Step D. Preparation of 2-amino-6-bromo-4-methylbenzaldehyde. To a solution of N-(3-bromo-2-(1,3-dioxolan-2-yl)-5-methylphenyl)-1,1-diphenylmethanimine (17.1 g, 40.5 mmol) in THF (100 mL) was added aq. 1N HCl (100 mL, 2.5 eq). The reaction mixture stirred for 2 h at 80° C. than cooled to ambient temperature. The mixture was neutralized with aq. 6N NaOH. The mixture was extracted with EtOAc, and the combined organic layer was washed with brine, dried over $MgSO_4$, filtered, and concentrated. The residue was purified by flash chromatography (Combi-flash Rf, Hex/EtOAc=0-10% gradient) to afford the title compound (6.3 g, 73%) as a yellow oil. $^1$H NMR (400 MHz, Chloroform-d) δ 10.30 (s, 1H), 6.73 (s, 1H), 6.38 (s, 1H), 2.23 (s, 3H); LCMS Method 2: >95% purity 254 nm, $R_T$=74 min, MS (ESI) 214.0 [M+H]$^+$.

Step E. Preparation of 5-bromo-3-methoxy-7-methylquinoline (Intermediate 90). To a solution of 2-amino-6-bromo-4-methylbenzaldehyde (1.0 mmol) in ethanol (2 mL) was added methoxyacetaldehyde (1.2 mmol) and 1M aq. NaOH solution (2.0 eq). The reaction was heated under the microwave at 110° C. for 30 min. The reaction was cooled to room temperature, poured into dichloromethane and washed with brine. The layers were separated and the organic layer was concentrated. The residue was purified by flash chromatography (Combi-flash Rf, Hex/EtOAc=0-15% gradient) to afford the title compound (50% yield). $^1$H NMR (400 MHz, Chloroform-d) δ 8.63 (d, J=2.7 Hz, 1H), 7.80 (s, 1H), 7.68-7.66 (m, 2H), 3.99 (s, 3H), 2.51 (s, 3H).

Step F. Preparation of 7-((1H-Imidazol-1-yl)methyl)-2-(3-methoxy-7-methylquinolin-5-yl)-5-(1-methyl-3-(trifluoromethyl)-1H-pyrazol-4-yl)-3,4-dihydroisoquinolin-1(2H)-one. 7-((1H-Imidazol-1-yl)methyl)-5-(1-methyl-3-(trifluoromethyl)-1H-pyrazol-4-yl)-3,4-dihydroisoquinolin-1(2H)-one (Intermediate 8, 1.0 equiv), 5-bromo-3-methoxy-2,7-dimethylquinoline (Intermediate 90, 1.9 equiv), cesium carbonate (2.0 equiv), Xantphos (0.2 equiv), and $Pd_2(dba)_3$ (0.1 equiv) were dissolved in 1,4-dioxane under an Ar. The reaction mixture was stirred for 14 h at 110° C. then cooled to 23° C. Brine was added to the mixture and extracted with EtOAc (3×50 mL). The combined organic layers were dried over $MgSO_4$ and concentrated under reduced pressure. The residue was purified by reverse phase HPLC (Phenomenex Gemini C18, $H_2O/CH_3CN$ gradient from 15-85% $CH_3CN$, 0.1% TFA) followed by neutralization with sat. aq. $NaHCO_3$ to yield the title compound. $^1H$ NMR (400 MHz, Chloroform-d) δ 8.59 (d, J=2.7 Hz, 1H), 8.05 (d, J=1.7 Hz, 1H), 7.84 (s, 1H), 7.81 (s, 1H), 7.78 (s, 1H), 7.49 (d, J=1.2 Hz, 1H), 7.43 (d, J=27 Hz, 1H), 7.41 (d, J=1.7 Hz, 1H), 7.15 (s, 1H), 7.00 (s, 1H), 5.34 (s, 2H), 4.08-4.01 (m, 1H), 4.01 (s, 3H), 3.89 (s, 3H), 3.87-3.81 (m, 1H), 3.24-3.16 (m, 1H), 3.08-3.01 (m, 1H), 2.55 (s, 3H); LCMS Method 2: >95%, $R_T$=1.39 min, MS (ESI) 547.0 $[M+H]^+$.

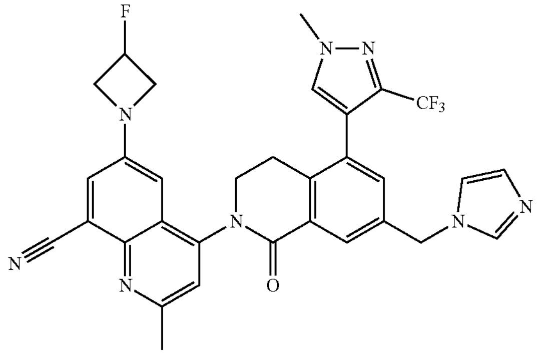 [SMILES: Cc1cc(N2CCc3c(cc(Cn4ccnc4)cc3-c3cn(C)nc3C(F)(F)F)C2=O)c2cc(N3CC(F)C3)cc(C#N)c2n1]

Example 203

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-(3-fluoroazetidin-1-yl)-2-methylquinoline-8-carbonitrile 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-bromo-2-methylquinoline-8-carbonitrile (Example 126, 80 mg, 0.13 mmol), 3-fluoroazetidine hydrochloride (29 mg, 0.26 mmol, 2 equiv), sodium tert-butoxide (37 mg, 0.39 mmol, 3 equiv), BINAP (24 mg, 0.039 mmol, 0.3 equiv), and $Pd_2(dba)_3$ (12 mg, 0.013 mmol, 0.1 equiv) were dissolved in toluene (1 mL) and placed under Ar. The reaction mixture was stirred for 14 h at 60° C. then cooled to 23° C. Brine was added to the mixture and extracted with $CH_2Cl_2$ (3×20 mL). The combined organic layers were dried over $MgSO_4$ and concentrated. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (66 mg, 0.11 mmol, 66% yield). $^1H$ NMR (400 MHz, Chloroform-d) δ 8.13 (d, J=1.7 Hz, 1H), 7.57 (s, 1H), 7.40 (s, 1H), 7.34 (d, J=2.6, 1H), 7.25 (s, 1H), 7.18 (d, J=1.7 Hz, 1H), 7.11 (s, 1H), 6.95 (s, 1H), 6.67 (d, J=26 Hz, 1H), 5.53-5.49 (m, 0.5H), 5.38-5.36 (m, 0.5H), 5.20 (s, 2H), 4.32-4.21 (m, 2H), 4.14-4.05 (m, 2H), 4.03 (s, 3H), 4.01-3.95 (m, 1H), 3.76-3.70 (m, 1H), 3.14-3.06 (m, 1H), 2.99-2.93 (m, 1H), 2.76 (s, 3H); LCMS (ESI): Method 2: $R_T$=1.502 min, m/z=615.3 $[M+H]^+$.

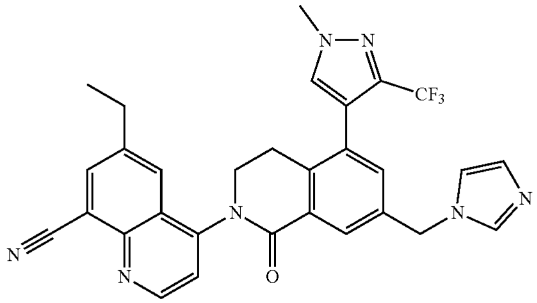 [SMILES: CCc1cc(C#N)c2nccc(N3CCc4c(cc(Cn5ccnc5)cc4-c4cn(C)nc4C(F)(F)F)C3=O)c2c1]

Example 204

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carbonitrile The title compound (99.5 mg, 0.179 mmol, 96% yield) was prepared following the Negishi coupling procedure described for Example 175, using 7-((1H-imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 113 mg, 0.186 mmol). $^1H$ NMR (400 MHz, Chloroform-d) δ 9.09 (d, J=4.6 Hz, 1H), 8.14 (d, J=1.8 Hz, 1H), 8.05 (d, J=1.8 Hz, 1H), 7.81 (s, 1H), 7.57 (s, 1H), 7.43 (d, J=4.7 Hz, 1H), 7.41 (s, 1H), 7.20 (d, J=1.8 Hz, 1), 7.11 (s, 1H), 6.95 (s, 1H), 5.20 (s, 2H), 4.09 (td, J=11.7, 4.2 Hz, 1H), 4.03 (s, 3H), 3.81 (dt, J=12.1, 5.2 Hz, 1H), 3.21-3.13 (m, 1H), 2.99 (dt, J=16.4, 4.6 Hz, 1H), 2.86 (q, J=7.6 Hz, 2H), 1.32 (t, J=7.6 Hz, 3H); LCMS (ESI): Method 2: $R_T$=1.463 min, m/z=556.2 $[M+H]^+$.

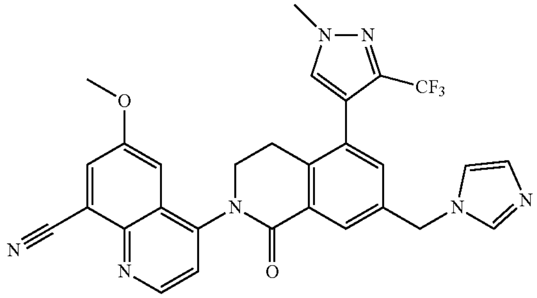 [SMILES: COc1cc(C#N)c2nccc(N3CCc4c(cc(Cn5ccnc5)cc4-c4cn(C)nc4C(F)(F)F)C3=O)c2c1]

Example 205

4-(7-((1H-Imidazol-1-yl)methyl)-5-(1-methyl-3-(trifluoromethyl)-1H-pyrazol-4-yl-1-oxo-3,4-dihydroisoquinolin-2(1H)-yl)-6-methoxyquinoline-8-carbonitrile The title compound (375 mg, 0.67 mmol, quant.) was prepared following the Negishi coupling procedure described for Example 175, using 7-((1H-imidazol-1-yl)methyl)-2-bromo-6-methoxyquinolin-4-yl)-5-(1-methyl-3-(trifluoromethyl)-1H-pyrazol-4-yl)-3,4-dihydroisoquinolin-1(2H)-one (Example 29, 400 mg, 0.65 mmol). $^1H$ NMR (400 MHz, Chloroform-d) δ 9.00 (d, J=4.7 Hz, 1H), 8.13 (d, J=1.8 Hz, 1H), 7.82 (d, J=2.8 Hz, 1H), 7.57 (s, 1H), 7.42-7.41 (m, 2H), 7.29 (d, J=2.8 Hz, 1H), 7.20 (d, J=1.8 Hz, 1H), 7.10 (s, 114H), 6.95 (s, 1H), 5.20 (s, 2H), 4.08 (td, J=12.0, 4.2 Hz, 1H), 4.03 (s, 3H), 3.90 (s, 3H), 3.79 (dt, J=12.0, 5.1 Hz, 1H), 3.19-3.11 (m, 1H), 2.99 (dt, J=16.4, 4.5 Hz, 1H); LCMS (ESI): Method 2: $R_T$=1.395 min, m/z=558.1 $[M+H]^+$.

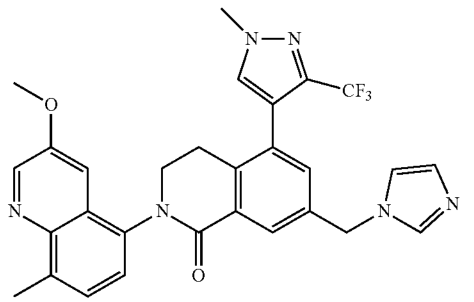 [SMILES: COc1cnc2c(C)ccc(N3CCc4c(cc(Cn5ccnc5)cc4-c4cn(C)nc4C(F)(F)F)C3=O)c2c1]

Example 206

7-((1H-Imidazol-1-yl)methyl)-2-(3-methoxy-8-methylquinolin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-methoxy-8-methylquinoline (Intermediate 91). $^1$H NMR (400 MHz, Chloroform-d) δ 8.73 (d, J=2.9 Hz, 1H), 8.17 (d, J=1.8 Hz, 1H), 7.59 (s, 1H), 7.45 (d, J=7.4 Hz, 1H), 7.40 (s, 1H), 7.37 (d, J=7.4 Hz, 1H), 7.31 (d, J=7.4 Hz, 1H), 7.16 (d, 1.9 Hz, 1H), 7.10 (s, 1H), 6.94 (s, 1H), 5.19 (s, 2H), 4.02 (s, 3H), 3.99-3.95 (m, 1H), 3.89 (s, 3H), 3.78-3.72 (m, 1H), 3.15-3.07 (m, 1H), 3.00-2.92 (m, 1H), 2.80 (s, 3H); LCMS Method 2: >95%, $R_T$=1.33 min, MS (ESI) 547.0 $[M+H]^+$.

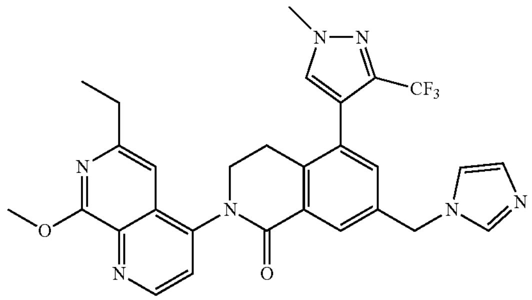 [SMILES: CCc1cc2c(N3CCc4c(cc(Cn5ccnc5)cc4-c4cn(C)nc4C(F)(F)F)C3=O)ccnc2c(OC)n1]

Example 207

7-((1H-Imidazol-1-yl)methyl)-2-(6-ethyl-8-methoxy-1,7-naphthyridin-4-yl)-5-(1-methyl-3-(trifluoromethyl)-1H-pyrazol-4-yl)-3,4-dihydroisoquinolin-1(2H)-one Step A. Preparation of 6-ethyl-2-methoxypyridin-3-amine. A mixture of 4-bromo-2-methoxyaniline (1 equiv), triethylborane (2 equiv), cesium carbonate (2 equiv), and Pd(dppf)$Cl_2$ (0.05 equiv) in THF was stirred for 3 h at 60° C. under Ar in a sealed tube. The reaction was cooled to 0° C. and quenched by 10% aq. NaOH and 30% aq. $H_2O_2$. The resulting mixture was warmed to 23° C., brine was added, and the mixture was extracted with EtOAc (3×20 ml). The combined organic layers were dried over $MgSO_4$ and concentrated under reduced pressure. The residue was purified by flash chromatography (Combi-flash Rf, Hex/EtOAc=0-100% gradient followed by DCM/MeOH=0-10% gradient) to afford the title compound. $^1$H NMR (400 MHz, Chloroform-d) δ 6.84 (d, J=7.6 Hz, 1H), 6.57 (d, J=7.6 Hz, 1H), 4.00 (s, 3H), 2.65 (q, J=7.5 Hz, 2H), 1.26 (t, J=7.5 Hz, 3H).

Step B. Preparation of 5-(((6-bromo-2-methoxypyridin-3-yl)amino)methylene)-2,2-dimethyl-1,3-dioxane-4,6-dione. To a solution of 6-ethyl-2-methoxypyridin-3-anine (1 equiv) and Meldrum's acid (1.2 equiv) in EtOH was added triethyl orthoformate (1 equiv). The reaction was stirred at 80° C. overnight. The reaction was cooled to 0° C., filtered, and washed with cold EtOH to yield the title compound.

Step C. Preparation of 6-ethyl-8-methoxy-1,7-naphthyridin-4(1H)-one. 5-(((6=Bromo-2-methoxypyridin-3-yl)amino)methylene)-2,2-dimethyl-1,3-dioxane-4,6-dione was added portionwise to Dowtherm A at 260° C. and stirred for 30 min. The reaction was cooled to room temperature, and hexanes were added. The resulting mixture was filtered, and the solid was washed with hexanes to yield the title compound. $^1$H NMR (400 MHz, Chloroform-d) δ 7.66 (d, J=7.4 Hz, 1H), 7.52 (s, 1H), 7.39 (d, J=7.4 Hz, 1H), 4.12 (s, 3), 2.87 (q, J=7.5 Hz, 2H), 1.38 (t, J=7.5 Hz, 3H).

Step D. Preparation of 4-bromo-6-ethyl-8-methoxy-1,7-naphthyridine. To a solution of 6-ethyl-8-methoxy-1,7-naphthyridin-4(1H)-one (1 equiv) in DMF was added $PBr_3$ (2 equiv) dropwise at 0° C. The reaction mixture was warmed to room temperature and stirred overnight. The reaction was quenched with ice, and the pH was adjusted to 7 with $NaHCO_3$. The solid was filtered, washed with water, and dried to yield the title compound. $^1$H NMR (400 MHz, Chloroform-d) δ 8.63 (d, J=4.6 Hz, 1H), 7.80 (d, J=4.6 Hz, 1H), 7.31 (s, 1H), 4.22 (s, 3H), 2.80 (q, J=7.5 Hz, 2H), 1.31 (t, J=7.5 Hz, 3H).

Step E. Preparation of 7-((1H-imidazol-1-yl)methyl)-2-(6-ethyl-8-methoxy-1,7-naphthyridin-4-yl)-5-(1-methyl-3-(trifluoromethyl)-1H-pyrazol-4-yl)-3,4-dihydroisoquinolin-1(2H)-one. 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 1.0 equiv), 4-bromo-6-ethyl-8-methoxy-1,7-naphthyridine (Intermediate 92, 2.0 equiv), cesium carbonate (2.0 equiv), Xantphos (0.2 equiv), and $Pd_2(dba)_3$ (0.1 equiv) were dissolved in 1,4-dioxane tinder an Ar. The reaction mixture was stirred for 14 h at 110° C. then cooled to 23° C. Brine was added to the mixture and extracted with EtOAc (3×50 mL). The combined organic layers were dried over $MgSO_4$ and concentrated tinder reduced pressure. The residue was purified by reverse phase HPLC (Phenomenex Gemini C18, $H_2O/CH_3CN$ gradient from 15-85% $CH_3CN$, 0.1% TFA) followed by neutralization with sat. aq. $NaHCO_3$ to yield the title compound. $^1$H NMR (400 MHz, Chloroform-d) δ 8.93 (d, J=46 Hz, 1H), 8.15 (s, 1H), 7.59 (s, 1H), 7.47 (d, J=4.6 Hz, 1H), 7.41 (s, 1H), 7.18 (s, 1H), 7.11 (s, 1H), 6.95 (s, 2H), 5.20 (s, 2H), 4.22 (s, 3H), 4.02 (s, 3H), 4.00-3.96 (m, 1H), 3.84-3.78 (s, 1H), 3.19-3.11 (m, 1H), 3.00-2.94 (m, 1H), 2.81 (q, J=5 Hz, 2H), 1.32 (t, J=7.5 Hz, 3H); LCMS Method 2: >95%, $R_T$=1.40 min, MS (ESI) 562.0 $[M+H]^+$.

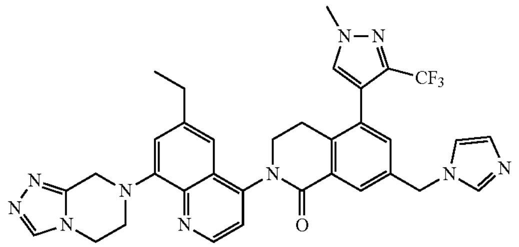 [SMILES: CCc1cc(N2CCn3cnnc3C2)c2nccc(N3CCc4c(cc(Cn5ccnc5)cc4-c4cn(C)nc4C(F)(F)F)C3=O)c2c1]

Example 208

7-((1H-Imidazol-1-yl)methyl)-2-(8-(5,6-dihydro-[1,2,4]triazolo[4,3-a]pyrazin-7(8H)-yl)-6-ethylquinolin-4-yl)-5-(1-methyl-3-(trifluoromethyl)-1H-pyrazol-4-yl)-3,4-dihydroisoquinolin-1(2H)-one The title compound (27 mg, 0.042 mmol, 32% yield) was prepared following the Buchwald coupling procedure described for Example 124, using 7-((1H-imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 80 mg, 0.13 mmol), and 5,6,7,8-tetrahydro-[1,2,4]triazolo[4,3-a]pyrazine (33 mg, 0.26 mmol, 2 equiv). $^1$H NMR (400 MHz, Chloroform-d) δ 8.90 (d, =4.6 Hz, 1H), 8.20 (s, 1H), 8.15 (d, J=1.8 Hz, 1H), 7.58 (s, 1H), 7.41 (s, 1H), 7.36 (d, J=4.6 Hz, 1H), 7.33 (s, 1H), 7.19 (d, J=1.9 Hz, 1H), 7.11 (s, 1H), 7.05 (d, J=1.5 Hz, 1H), 6.95 (s, 1H), 5.20 (s, 2H), 4.80 (s, 2H), 4.39-4.33 (m, 1H), 4.27-4.14 (m, 2H), 4.03 (s, 3H), 4.00-3.90 (m, 2H), 3.82 (dt, J=12.8, 5.3 Hz, 1H), 3.20-3.12 (m, 1), 2.98 (dt, J=16.4, 4.8 Hz, 1H), 2.76 (q, J=7.6 Hz, 2H), 1.27 (t, J=7.6 Hz, 3H); LCMS (ESI): Method 2: $R_T$=1.169 min, m/z=653.1 [M+H]$^+$.

2.99 (q, J=8.1 Hz, 1H), 2.87 (q, J=7.5 Hz, 2H), 1.31 (t, J=7.6 Hz, 3H); LCMS (ESI): m/z=723.2 [M+H]$^+$.

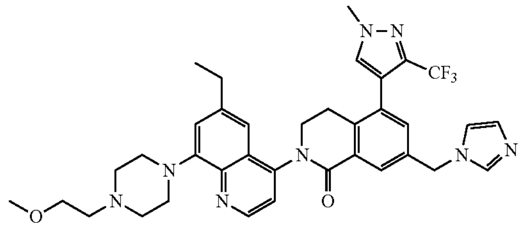 [SMILES: CCc1cc(N2CCN(CCOC)CC2)c2nccc(N3CCc4c(cc(Cn5ccnc5)cc4-c4cn(C)nc4C(F)(F)F)C3=O)c2c1]

Example 210

7-(1H-Imidazol-1-yl)methyl)-2-(6-ethyl-8-(4-(2-methoxyethyl)piperazin-1-yl)quinolin-4-yl)-5-(1-methyl-3-(trifluoromethyl)-1H-pyrazol-4-yl)-3,4-dihydroisoquinolin-1(2H)-one The title compound (50 mg, 0.075 mmol, 57% yield) was prepared following the Buchwald coupling procedure described for Example 124, using 7-((1H-imidazol-1-yl)methyl)-2-(8-bromo-6-ethylquinolin-4-yl)-5-(1-methyl-3-(rifluoromethyl)-1H-pyrazol-4-yl)-3,4-dihydroisoquinolin-1(2H)-one (Example 34, 80 mg, 0.13 mmol), 1-(2-methoxyethyl)piperazine (38 mg, 0.26 mmol, 2 equiv), and cesium carbonate (43 mg, 0.13 mmol, 1 equiv). $^1$H NMR (400 MHz, Chloroform-d) δ 8.87 (d, J=4.6 Hz, 1H), 8.16 (d, J=1.8 Hz, 1H), 7.57 (s, 1H), 7.40 (s, 1H), 7.28 (d, J=4.6 Hz, 1H), 7.23 (s, 1H), 7.16 (d, J=1.8 Hz, 1H), 7.10 (s, 1H), 7.03 (d, J=14 Hz, 1H), 6.95 (s, 1H), 5.20 (s, 2H), 4.02 (s, 3H), 3.95 (td, J=11.6, 4.4 Hz, 1H), 3.80 (dt, J=12.0, 5.3 Hz, 1H), 3.60 (t, J=5.6 Hz, 2H), 3.56 (brs, 2H), 3.39 (s, 3H), 3.36 (brs, 2H), 3.18-3.10 (m, 1H), 2.95 (dt, J=16.8, 5.0 Hz, 1H), 2.87

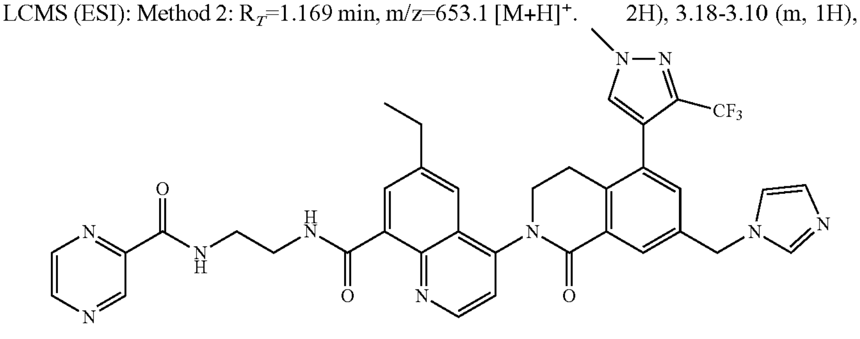

Example 209

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-(pyrazine-2-carboxamido)ethyl)quinoline-8-carboxamide The title compound (41 mg, 57 μmol, 57%) was prepared following the procedure described for Example 160, substituting N-(2-aminoethyl)pyrazine-2-carboxamide (Intermediate 118, 10 mg, 120 μmol, 1.2 equiv) for oxazol-2-amine. $^1$H NMR (400 MHz, Chloroform-d) δ 9.41 (d, J=1.4 Hz, 1H), 8.86 (d, J=4.7 Hz, 1H), 8.78 (d, J=2.1 Hz, 1H), 8.73 (d, J=2.5 Hz, 1H), 8.54 (q, J=1.3 Hz, 1H), 8.40 (s, 1H), 8.15 (d, J=1.8 Hz, 1H), 7.75 (d, J=2.0 Hz, 1H), 7.60 (s, 1H), 7.41 (s, 1H), 7.39 (d, J=4.7 Hz, 1H), 7.20 (d, J=1.8 Hz, 1H), 7.11 (s, 1H), 6.95 (s, 1H), 5.20 (s, 2H), 4.03 (s, 3H), 3.99 (d, J=4.2 Hz, 1H), 3.84 (m, J=7.3 Hz, 5H), 3.17 (q, J=7.9 Hz, 1H), (brs, 4H), 2.76 (q, J=7.5 Hz, 2H), 2.73 (t, J=5.7 Hz, 2H), 1.27 (t, J=7.6 Hz, 3H); LCMS (ESI): Method 2: $R_T$=1.112 min, m/z=673.0 [M+H]$^+$.

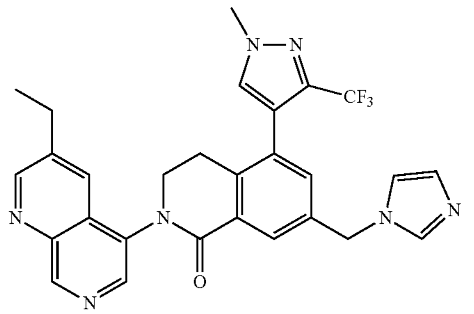 [SMILES: CCc1cnc2cncc(N3CCc4c(cc(Cn5ccnc5)cc4-c4cn(C)nc4C(F)(F)F)C3=O)c2c1]

Example 211

7-((1H-imidazol-1-yl)methyl)-2-(3-ethyl-1,7-naphthyridin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1 (2H)-one (Intermediate 8) and 5-bromo-3-ethyl-1,7-naphthyridine (intermediate 93). $^{1}$H NMR (400 MHz, Chloroform-d) δ 9.47 (s, 1H), 8.94 (d, J=2.5 Hz, 1H), 8.57 (s, 1H), 8.16 (d, J=1.9 Hz, 1H), 7.84 (d, J=1.1 Hz, 1H), 7.71 (s, 1H), 7.42 (s, 1H), 7.21 (d, J=1.9 Hz, 1H), 7.14 (s, 1H), 6.98 (bs, 1H), 5.24 (s, 2H), 4.11-4.06 (m, 1H), 4.03 (s, 3H), 3.87-3.81 (m, 1H), 3.17-3.09 (m, 1H), 3.07-2.99 (m, 1H), 2.89 (q, J=76 Hz, 2H), 1.35 (t, J=7.6 Hz, 3H); LCMS Method 2: >95% $R_T$=1.28 min, MS (ESI) 532.0 [M+H]$^+$.

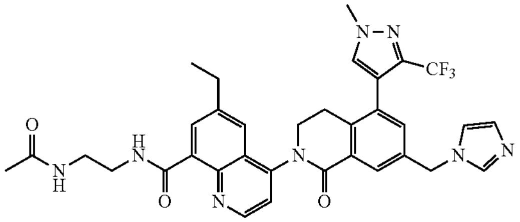 [SMILES: CCc1cc(C(=O)NCCNC(C)=O)c2nccc(N3CCc4c(cc(Cn5ccnc5)cc4-c4cn(C)nc4C(F)(F)F)C3=O)c2c1]

Example 212

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(2-acetamidoethyl)-6-ethylquinoline-8-carboxamide The title compound (51 mg, 77 μmol, 77%) was prepared following the procedure described for Example 160, substituting N-(2-aminoethyl)acetamide (Intermediate 119, 20 mg, 200 μmol, 2.0 equiv) for oxazol-2-amine. $^{1}$H NMR (400 MHz, Chloroform-d) δ 8.94 (d, J=4.7 Hz, 1H), 8.76 (d, J=2.01 Hz, 1H), 8.16 (d, =1.9 Hz, 1H), 7.77 (s, 1H), 7.59 (s, 1H), 7.41 (d, J=2.9 Hz, 2H), 7.20 (s, 1H), 7.10 (s, 1H), 6.94 (s, 1H), 6.68 (s, 1H), 5.19 (s, 2H), 4.03 (m, 4H), 3.80 (m, J=6.1 Hz, 3H), 3.58 (m, J=3.5 Hz, 2H), 3.18 (m, J=5.6 Hz, 1H), 3.00 (m, J=5.2 Hz, 1H), 2.88 (q, J=8.0 Hz, 2H), 2.00 (s, 3H), 1.32 (t, J=7.3 Hz, 3H); LCMS (ESI): m/z=659.2 [M+H]$^+$.

Example 213

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-(isonicotinamido)ethyl)quinoline-8-carboxamide The title compound (45 mg, 62 μmol, 62%) was prepared following the procedure described for Example 160, substituting N-(2-aminoethyl)isonicotinamide (Intermediate 120, 33 mg, 200 μmol, 2.0 equiv) for oxazol-2-amine. $^{1}$H NMR (4.00 MHz, Chloroform-d) δ 8.91 (d, J=4.7 Hz, 1H), 8.80 (d, J=2.0 Hz, 1H), 8.74 (d, J=6.0 Hz, 2H), 8.42 (s, 1H), 8.15 (d, J=1.7 Hz, 1H), 7.79 (d, J=1.8 Hz, 1H), 7.75 (q, J=2.0 Hz, 2H), 7.60 (s, 1H), 7.42 (d, J=4.7 Hz, 2H), 7.20 (s, 1H), 7.11 (s, 1H), 6.95 (s, 1H), 5.19 (s, 2H), 4.03 (s, 3H), 3.88 (m, J=7.2 Hz, 6H), 3.18 (m, J=5.4 Hz, 1H), 2.99 (m, J=5.1 Hz, 1H), 2.89 (q, J=7.5 Hz, 2H), 1.33 (t, J=7.6 Hz, 3H); LCMS (ESI): m/z=722.2 [M+H]$^+$.

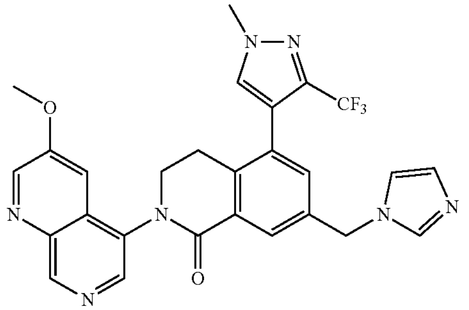

Example 214

7-((1H-imidazol-1-yl)methyl)-2-(3-methoxy-1,7-naphthyridin-5-yl)-5-(1-methyl-3-(trifluoromethyl)-1H-pyrazol-4-yl)-3,4-dihydroisoquinolin-1(2H)-one The title compound was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8) and 5-bromo-3-methoxy-1,7-naphthyridine (intermediate 94). $^{1}$H NMR (400 MHz, Chloroform-d) δ 9.39 (s, 1H), 8.77 (d, 1=2.5 Hz, 1H), 8.54 (s, 1H), 8.15 (d, J=1.9 Hz, 1H), 7.64-7.63 (m, 1H), 7.42 (s, 1H), 7.20 (d, J=1.9 Hz, 1H), 7.17 (d, J=2.7 Hz, 1H), 7.11 (s, 1H), 6.98 (bs, 1H), 5.21 (s, 2H), 4.11-4.06 (m, 1H), 4.03 (s, 3H), 3.93 (s,

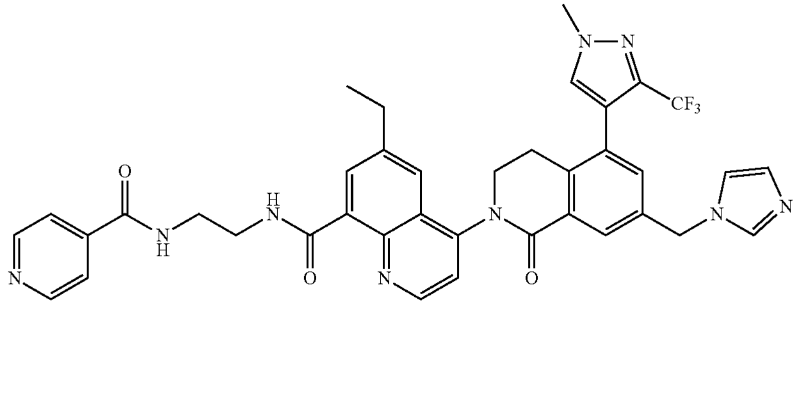 [SMILES: CCc1cc(C(=O)NCCNC(=O)c2ccncc2)c2nccc(N3CCc4c(cc(Cn5ccnc5)cc4-c4cn(C)nc4C(F)(F)F)C3=O)c2c1]

3H), 3.85-3.79 (m, 1H), 3.14-3.00 (m, 2H); LCMS Method 2: >95%, $R_T$=1.18 min, MS (ESI) 534.0 [M+H]$^+$.

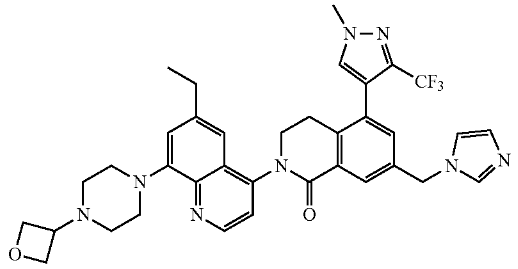 [SMILES: CCc1cc(N2CCN(C3COC3)CC2)c2nccc(N3CCc4c(cc(Cn5ccnc5)cc4-c4cn(C)nc4C(F)(F)F)C3=O)c2c1]

Example 215

7-((1H-Imidazol-1-yl)methyl)-2-(6-ethyl-8-(4-(oxetan-3-yl)piperazin-1-yl)quinolin-4-yl)-5-(1-methyl-3-(trifluoromethyl)-1H-pyrazol-4-yl)-3,4-dihydroisoquinolin-1(2H)-one The title compound (58 mg, 0.087 mmol, 66% yield) was prepared following the Buchwald coupling procedure described for Example 124, using 7-((1H-imidazo-1-yl) methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 80 mg, 0.13 mmol), 1-(oxetan-3-yl)piperazine (37 mg, 0.26 mmol, 2 equiv), and cesium carbonate (43 mg, 0.13 mmol, 1 equiv). $^1$H NMR (400 MHz, Chloroform-d) δ 8.86 (d, J=4.5 Hz, 1H), 8.16 (d, J=1.8 Hz, 1H), 7.57 (s, 1H), 7.40 (s, 1H), 7.30 (d, J=4.6 Hz, 1H), 7.25 (s, 1H), 7.17 (d, J=1.8 Hz, 1H), 7.10 (s, 1H), 7.04 (d, J=1.4 Hz, 1H), 6.95 (s, 1H), 5.20 (s, 2H), 4.74-4.69 (m, 4H), 4.02 (s, 3H), 3.95 (td, J=11.2, 4.3 Hz, 1H), 3.80 (dt, J=12.4, 5.4 Hz, 1H), 3.67 (p, J=6.5 Hz, 1H), 3.56 (brs, 2H), 3.37 (brs, 2H), 3.18-3.10 (m, 1H), 2.95 (dt, J=16.5, 4.9 Hz, 1H), 2.77 (q, J=7.5 Hz, 2H), 2.71 (brs, 4H), 1.28 (t, J=7.6 Hz, 3H); LCMS (ESI): Method 2: $R_T$=1.169 min, m/z=653.1 [M+H]$^+$.

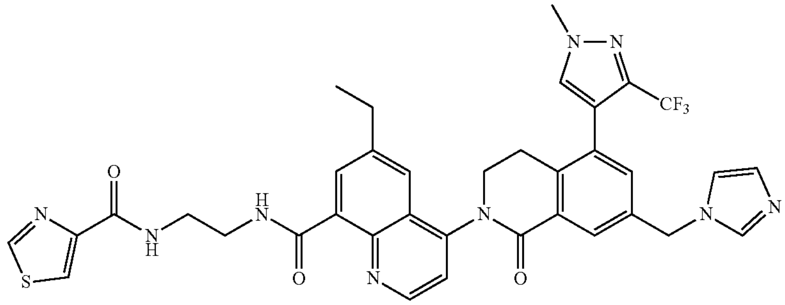 [SMILES: CCc1cc(C(=O)NCCNC(=O)c2cscn2)c2nccc(N3CCc4c(cc(Cn5ccnc5)cc4-c4cn(C)nc4C(F)(F)F)C3=O)c2c1]

Example 216

N-(2-(4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxamido)ethyl)thiazole-4-carboxamide The title compound (42 mg, 58 μmol, 58%) was prepared following the procedure described for Example 160, substituting N-(2-aminoethyl)thiazole-4-carboxamide (Intermediate 121, 34 mg, 200 μmol, 2.0 equiv) for oxazol-2-amine. $^1$H NMR (400 MHz, Chloroform-d) δ 8.87 (d, J=4.7 Hz, 1H), 8.79 (d, J=2.0 Hz, 1H), 8.76 (d, J=2.1 Hz, 1H), 8.18 (d, J=2.1 Hz, 1H), 8.15 (s, 1H), 7.98 (s, 1H), 7.75 (s, 1H), 7.61 (s, 1H), 7.42 (s, 1H), 7.38 (d, J=4.7 Hz, 1H), 7.20 (s, 1H), 7.11 (s, 1H), 6.96 (s, 1H), 5.20 (s, 2H), 4.03 (s, 3H), 3.99 (t, J=7.7 Hz, 1H), 3.82 (m, J=6.4 Hz, 5H), 3.18 (q, J=9.4 Hz, 1H), 2.99 (q, J=8.1 Hz, 1H), 2.87 (q, J=7.2 Hz, 2H), 1.31 (t, J=7.0 Hz, 3H); LCMS (ESI): m/z 728.2 [M+H]$^+$.

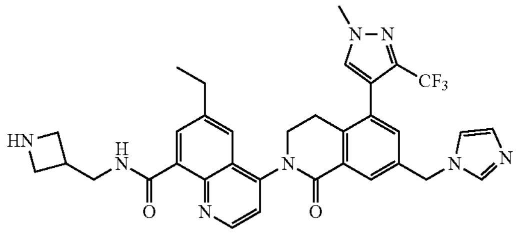 [SMILES: CCc1cc(C(=O)NCC2CNC2)c2nccc(N3CCc4c(cc(Cn5ccnc5)cc4-c4cn(C)nc4C(F)(F)F)C3=O)c2c1]

Example 217

4-(7-(1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-ylmethyl)-6-ethylquinoline-8-carboxamide The title compound (252 mg, 392 μmol, 71%) was prepared following the procedure described for Intermediate 118 Step A and B, using 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid (Example 92, 216 mg, 0.55 mmol, 1.0 equiv) and tert-butyl 3-(aminomethyl)azetidine-1-carboxylate (205 mg, 1.10 mmol, 2.0 equiv). LCMS (ESI): m/z 643.2 [M+H]$^+$.

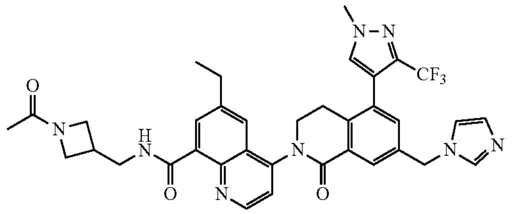 [SMILES: CCc1cc(C(=O)NCC2CN(C(C)=O)C2)c2nccc(N3CCc4c(cc(Cn5ccnc5)cc4-c4cn(C)nc4C(F)(F)F)C3=O)c2c1]

Example 218

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-((1-acetylazetidin-3-yl)methyl)-6-ethylquinoline-8-carboxamide The title compound (32 mg, 47 μmol, 47%) was prepared following the procedure described for Example 160, utilizing 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-ylmethyl)-6-ethylquinoline-8-carboxamide (Example 217, 64.3 mg, 100 μmol, 1.0 equiv) and acetic acid (12 mg, 200 μmol, 2.0 equiv). $^1$H NMR (400 MHz, Chloroform-d) δ 8.92 (q, J=2.0 Hz, 1H), 8.78 (d, J=2.0 Hz, 1H), 8.16 (d, J=1.7 Hz, 1H), 7.77 (d, J=1.6 Hz, 1H), 7.63 (s, 1H), 7.42 (s, 1H), 7.41 (s, 1H), 7.21 (s, 1H), 7.12 (s, 1H), 6.96 (s, 1H), 5.21 (s, 2H), 4.24 (m, J=4.2 Hz, 1H), 4.15 (m, J=4.4 Hz, 1H), 4.03 (s, 3H), 4.01 (t, J=4.1 Hz, 2H), 3.84 (m, J=5.4 Hz, 4H), 3.18 (m, J=5.4 Hz, 1H), 3.02 (m, J=5.5 Hz, 1H), 2.87 (q, J=7.5 Hz, 2H), 1.84 (d, J=10.5 Hz, 3H), 1.32 (t, J=7.6 Hz, 3H); LCMS (ESI): m/z=685.2 [M+H]$^+$.

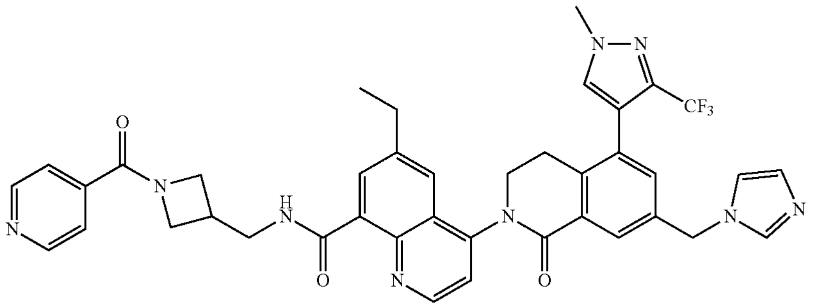 [SMILES: CCc1cc(C(=O)NCC2CN(C(=O)c3ccncc3)C2)c2nccc(N3CCc4c(cc(Cn5ccnc5)cc4-c4cn(C)nc4C(F)(F)F)C3=O)c2c1]

Example 219

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-((1-isonicotinoylazetidin-3-yl)methyl)quinoline-8-carboxamide The title compound (32 mg, 43 μmol, 43%) was prepared following the procedure described for Example 160, utilizing 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-1)-N-(azetidin-3-ylmethyl)-6-ethylquinoline-8-carboxamide (Example 217, 64.3 mg, 100 μmol, 1.0 equiv) and isonicotinic acid (25 mg, 200 mol, 2.0 equiv). $^1$H NMR (400 MHz, Chloroform-d) δ 8.90 (q, J=2.4 Hz, 1H), 8.76 (d, J=2.0 Hz, 1H), 8.67 (t, J=6.0 Hz, 2H), 8.15 (s, 1H), 7.77 (d, J=1.7 Hz, 1H), 7.60 (s, 1H), 7.41 (d, J=4.8 Hz, 4H), 7.21 (s, 1H), 7.11 (s, 1H), 6.96 (s, 1H), 5.21 (s, 2H), 4.39 (m, J=7.2 Hz, 2H), 4.17 (m, J=6.7 Hz, 2H), 4.03 (m, 4H), 3.85 (m, J=6.1 Hz, 3H), 3.18 (m, J=5.3 Hz, 2H), 3.00 (m, 3=5.0 Hz, 1H), 2.87 (q, J=7.5 Hz, 2H), 1.32 (t, J=7.6 Hz, 3H); LCMS (ESI): m/z=748.2 [M+H]$^+$.

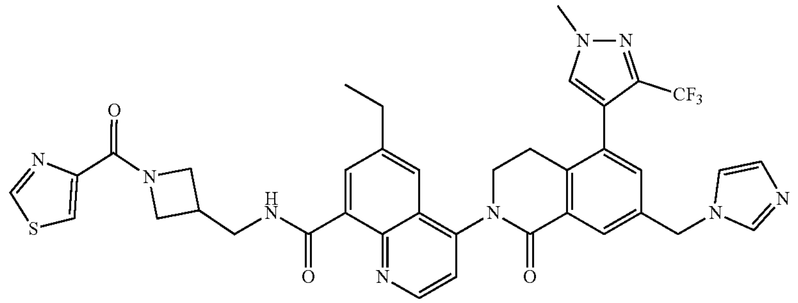 [SMILES: CCc1cc(C(=O)NCC2CN(C(=O)c3cscn3)C2)c2nccc(N3CCc4c(cc(Cn5ccnc5)cc4-c4cn(C)nc4C(F)(F)F)C3=O)c2c1]

Example 220

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-((1-(thiazole-4-carbonyl)azetidin-3-yl)methyl)quinoline-8-carboxamide The title compound (45 mg, 60 μmol, 60%) was prepared following the procedure described for Example 160, utilizing 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-ylmethyl)-6-ethylquinoline-8-carboxamide (Example 217, 64.3 mg, 100 μmol, 1.0 equiv) and thiazole-4-carboxylic acid (26 mg, 200 μmol, 2.0 equiv). $^1$H NMR (400 MHz, Chloroform-d) δ 8.88 (q, J=6.7 Hz, 1H), 8.78 (d, J=2.0 Hz, 1H), 8.75 (q, J=2.1 Hz, 1H), 8.18 (d, J=2.2 Hz, 1H), 8.15 (s, 1H), 7.75 (s, 1H), 7.61 (s, 1H), 7.42 (s, 1H), 7.39 (q, J=4.3 Hz, 1H), 7.20 (d, J=1.4 Hz, 1H), 7.11 (s, 1H), 6.96 (s, 1H), 5.20 (s, 2H), 4.79 (t, J=9.2 Hz, 1H), 4.53 (m, J=5.0 Hz, 1H), 4.36 (m, J=4.8 Hz, 1H), 4.11 (q, J=5.3 Hz, 1H), 4.03 (s, 3H), 3.98 (t, J=4.1 Hz, 1H), 3.87 (m, J=6.1 Hz, 3H), 3.18 (m, J=6.5 Hz, 2H), 2.99 (m, J=5.1 Hz, 1H), 2.87 (q, J=7.5 Hz, 2H), 1.31 (t, J=7.6 Hz, 3H); LCMS (ESI): m/z=754.2 [M+H]$^+$.

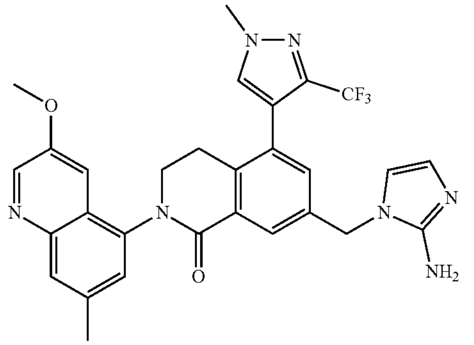 [SMILES: COc1cnc2cc(C)cc(N3CCc4c(cc(Cn5ccnc5N)cc4-c4cn(C)nc4C(F)(F)F)C3=O)c2c1]

Example 221

7-((2-Amino-1H-imidazol-1-yl)methyl)-2-(3-methoxy-7-methylquinolin-5-yl)-5-(1-methyl-3-(trifluoromethyl)-1H-pyrazol-4-yl)-3,4-dihydroisoquinolin-1(2H)-one Step A. Preparation of 2-(3-methoxy-7-methylquinolin-5-yl)-5-(1methyl-3-(trifluoromethyl)-1H-pyrazol-4-yl)-7-((2-nitro-1H-imidazol-1-yl)methyl)-3,4-dihydroisoquinolin-1(2H)-one. The title compound was prepared following the Buchwald coupling procedure described for Example 2, using 5-(1-methyl-3-(trifluoromethyl)-1H-pyrazol-4-yl)-7-((2-nitro-1H-imidazol-1-yl)methyl)-3,4-dihydroisoquinolin-1(2H)-one (Intermediate 83) and 5-bromo-3-methoxy-7-methylquinoline (Intermediate 90).

Step B. Preparation of 7-((2-amino-1H-imidazol-1-yl) methyl)-2-(3-methoxy-7-methylquinolin-5-yl)-5-(1-methyl-3-(trifluoromethyl)-1H-pyrazol-4-yl)-3,4-dihydroisoquinolin-1(2H)-one. The title compound was synthesized from 2-(3-methoxy-7-methylquinolin-5-yl)-5-(1-methyl-3-(trifluoromethyl)-1H-pyrazol-4-yl)-7-4(2-nitro-1H-imidazol-1-yl)methyl)-3,4-dihydroisoquinolin-1(2H)-one according to the hydrogenation method found in Example 121. $^1$H NMR (400 MHz, Chloroform-d) δ 8.65 (d, J=2.9 Hz, 1H), 8.14 (d, J=1.7 Hz, 1H), 7.84 (s, 1H), 7.49 (s, 1H), 7.33 (d, J=1.3 Hz, 1H), 7.27 (s, 1H), 7.20 (d, 1=1.7 Hz, 1H), 6.60 (d, J=1.8 Hz, 1H), 6.51 (d, J=1.8 Hz, 1H), 4.98 (s, 2H), 4.03 (s, 3H), 4.01-3.96 (m, 1H), 3.87 (s, 3H), 3.73-3.73 (m, 1H), 3.16-3.08 (m, 1H), 3.01-2.94 (m, 1H), 2.53 (s, 3H); LCMS Method 2: >95%, $R_T$=1.32 min, MS (ESI) 562.0 [M+H]$^+$.

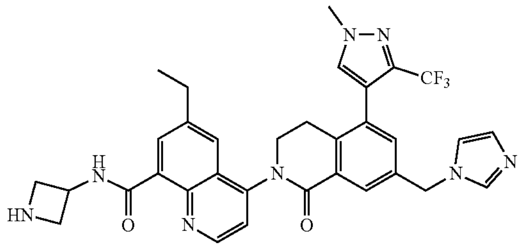

Example 222

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-ethylquinoline-8-carboxamide The title compound was prepared following the procedure described for Intermediate 118 Step A and B, using 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid (Example 92) and tert-butyl 3-aminoazetidine-1-carboxylate. LCMS (ESI): m/z=629.2 [M+H]$^+$.

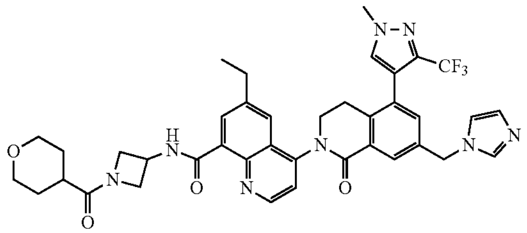 [SMILES: CCc1cc(C(=O)NC2CN(C(=O)C3CCOCC3)C2)c2nccc(N3CCc4c(cc(Cn5ccnc5)cc4-c4cn(C)nc4C(F)(F)F)C3=O)c2c1]

Example 223

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-(tetrahydro-2H-pyran-4-carbonyl)azetidin-3-yl)quinoline-8-carboxamide The title compound (19 mg, 26 μmol, 33%) was prepared following the procedure described for Example 160, utilizing 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-ethylquinoline-8-carboxamide (Example 222, 72 mg, 0.12 mmol) and tetrahydro-2H-pyran-4-carboxylic acid (10 mg, 77 μmol). $^1$H NMR (400 MHz, MeOD) δ 9.08 (q, J=3.0 Hz, 2H), 8.55 (d, J=1.9 Hz, 1H), 8.14 (d, J=1.9 Hz, 1H), 7.95 (d, J=1.8 Hz, 1H), 7.85 (s, 1H), 7.77 (d, J=5.2 Hz. H), 7.64 (t, =1.7 Hz, 1H), 7.58 (t, J=1.7 Hz, 2H), 5.55 (s, 2H), 4.67 (t, J=8.5 Hz, 1H), 4.37 (m, J=6.0 Hz, 2H), 4.20 (m, J=5.3 Hz, 1H), 4.09 (q, J=5.3 Hz, 1H), 3.99 (s, 3H), 3.93 (m, J=3.6 Hz, 3H), 3-44 (m, J=3.3 Hz, 2H), 3.24 (m, 2H), 3.05 (q, J=5.6 Hz, 1H), 2.87 (q, J=7.5 Hz, 2H), 2.59 (m, J=5.6 Hz, 1H), 1.72 (m, J=5.9 Hz, 2H), 1.61 (t, J=6.6 Hz, 2H), 1.28 (t, J=7.6 Hz, 3H); LCMS (ESI): m/z=742.0 $[M+H]^+$.

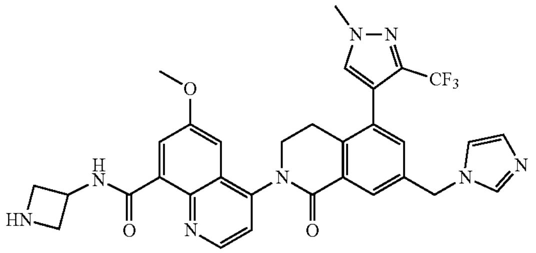 [SMILES: COc1cc(C(=O)NC2CNC2)c2nccc(N3CCc4c(cc(Cn5ccnc5)cc4-c4cn(C)nc4C(F)(F)F)C3=O)c2c1]

Example 224

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-methoxyquinoline-8-carboxamide The title compound was prepared following the procedure described for Intermediate 118 Step A and B, using 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylic acid (Example 40) and tert-butyl 3-aminoazetidine-1-carboxylate. LCMS (ESI): m/z=631.2 $[M+H]^+$.

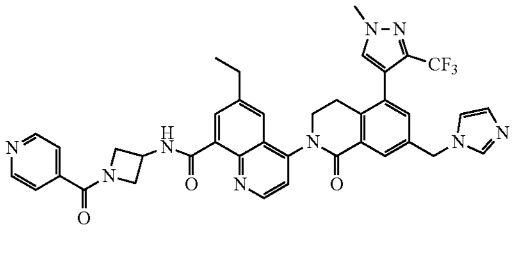 [SMILES: CCc1cc(C(=O)NC2CN(C(=O)c3ccncc3)C2)c2nccc(N3CCc4c(cc(Cn5ccnc5)cc4-c4cn(C)nc4C(F)(F)F)C3=O)c2c1]

Example 225

4-(7-((1H-Imidazol-1-yl)methyl)-5-(1-methyl-3-(trifluoromethyl)-1H-pyrazol-4-yl-1-oxo-3,4-dihydroisoquinolin-2(1H)-yl)-6-ethyl-N-(1-isonicotinoylazetidin-3-yl)quinoline-8-carboxamide The title compound (15 mg, 20 μmol, 25%) was prepared following the procedure described for Example 160, utilizing 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-ethylquinoline-8-carboxamide (Example 222, 77 mg, 0.12 mmol) and isonicotinic acid (10 mg, 81 μmol). $^1$H NMR (400 MHz, MeOD) δ 9.10 (s, 1H), 9.07 (d, J=5.0 Hz, 1H), 8.85 (d, J=5.6 Hz, 2H), 8.57 (d, J=1.9 Hz, 1H), 8.15 (d, J=1.4 Hz, 1H), 8.01 (d, J=5.1 Hz, 2H), 7.93 (s, 1H), 7.87 (s, 1H), 7.73 (d, J=4.8 Hz, 1H), 7.65 (t, J=1.7 Hz, 1H), 7.59 (q, J=1.8 Hz, 2H), 5.56 (s, 2H), 4.98 (m, J=5.4 Hz, 1H), 4.77 (t, J=8.7 Hz, 1H), 4.66 (t, J=9.6 Hz, 1H), 4.57 (q, J=4.9 Hz, 1H), 4.39 (q, J=5.5 Hz, 1H), 4.18 (q, J=7.6 Hz, 1H), 4.01 (s, 3H), 3.94 (q, J=5.6 Hz, 1H), 3.25 (d, J=5.0 Hz, 1H), 3.06 (m, J=5.2 Hz, 1H), 2.87 (q, J=7.6 Hz, 2H), 1.29 (t, J=8.0 Hz, 3H); LCMS (ESI): m/z=735.0 $[M+H]^+$.

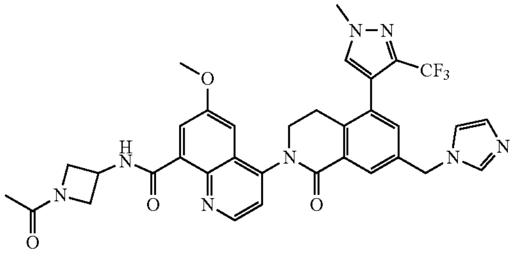 [SMILES: COc1cc(C(=O)NC2CN(C(C)=O)C2)c2nccc(N3CCc4c(cc(Cn5ccnc5)cc4-c4cn(C)nc4C(F)(F)F)C3=O)c2c1]

Example 226

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(1-acetylazetidin-3-yl)-6-methoxyquinoline-8-carboxamide The title compound (25 mg, 37 μmol, 37%) was prepared following the procedure described for Example 160, utilizing 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-methoxyquinoline-8-carboxamide (Example 224, 95 mg, 0.15 mmol) and acetic acid (6.0 mg, 5.7 μL, 0.10 mmol). $^1$H NMR (400 MHz, Chloroform-d) δ 8.87 (d, J=4.6 Hz, 1H), 8.56 (d, J=2.8 Hz, 1H), 8.15 (s, 1H), 7.58 (s, 1H), 7.45 (d, J=5.5 Hz, 2H), 7.29 (d, J=3.2 Hz, 1H), 7.22 (s, 1H), 7.11 (s, 1H), 6.96 (s, 1H), 5.21 (s, 2H), 4.96 (m, J=6.3 Hz, 1H), 4.60 (t, J=8.1 Hz, 1H), 4.48 (t, J=9.1 Hz, 1H), 4.14 (m, J=5.4 Hz, 3H), 4.04 (s, 3H), 3.93 (s, 3H), 3.85 (q, J=11.7 Hz, 1H), 3.18 (m, J=5.4 Hz, 1H), 3.01 (t, J=8.2 Hz, 1H), 1.94 (d, J=5.5 Hz, 3H); LCMS (ESI): m/z=674.0 $[M+H]^+$.

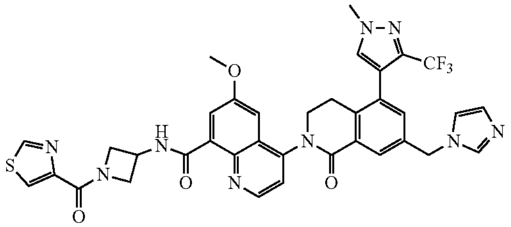 [SMILES: COc1cc(C(=O)NC2CN(C(=O)c3cscn3)C2)c2nccc(N3CCc4c(cc(Cn5ccnc5)cc4-c4cn(C)nc4C(F)(F)F)C3=O)c2c1]

Example 227

4-(7-(1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-(1-(thiazole-4-carbonyl)azetidin-3-yl)quinoline-8-carboxamide The title compound (28 mg, 38 μmol, 49%) was prepared following the procedure described for Example 160, utilizing 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-methoxyquinoline-8-carboxamide (Example 224, 73 mg, 0.12 mmol) and thiazole-4-carboxylic acid (10 mg, 77 mol). $^1$H NMR (400

MHz, Chloroform-d) δ 8.85 (d, J=4.7 Hz, 1H), 8.77 (q, J=3.1 Hz, 1H), 8.57 (d, J=3.0 Hz, 1H), 8.24 (d, J=2.2 Hz, 1H), 8.14 (s, 1H), 7.57 (s, 1H), 7.42 (d, J=4.5 Hz, 1H), 7.27 (d, J=3.6 Hz, 1H), 7.20 (s, 1H), 7.10 (s, 1H), 6.95 (s, 1H), 5.20 (s, 2H), 5.10 (m, J=5.3 Hz, 2H), 4.69 (q, J=6.4 Hz, 2H), 4.29 (m, J=5.4 Hz, 1H), 4.05 (m, J=4.2 Hz, 4H), 3.99-3.92 (s, 3H), 3.81 (m, J=5.6 Hz, 1H), 3.17 (m, J=5.4 Hz, 1), 2.99 (m, J=5.1 Hz, 1H); LCMS (ESI): m/z=742.8 [M+H]+.

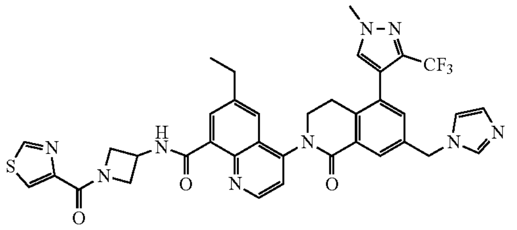 [SMILES: CCc1cc(C(=O)NC2CN(C(=O)c3cscn3)C2)c2nccc(N3CCc4c(cc(Cn5ccnc5)cc4-c4cn(C)nc4C(F)(F)F)C3=O)c2c1]

Example 228

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-(thiazole-4-carbonyl)azetidin-3-yl)quinoline-8-carboxamide The title compound (19 mg, 26 μmol, 33%) was prepared following the procedure described for Example 160, utilizing 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-ethylquinoline-8-carboxamide (Example 222, 73 mg, 0.12 mmol) and thiazole-4-carboxylic acid (10 mg, 77 μmol). $^1$H NMR (400 MHz, MeOD) δ 9.07 (d, J=5.4 Hz, 1H), 9.04 (s, 1H), 8.97 (d, J=2.0 Hz, 1H), 8.55 (d, J=1.8 Hz, JH), 8.26 (d, J=2.0 Hz, 1H), 8.14 (d, J=1.8 Hz, 1H), 7.98 (d, J=1.6 Hz, 1H), 7.84 (s, 1H), 7.82 (d, J=5.4 Hz, 1H), 7.62 (t, J=1.7 Hz, 1H), 7.56 (q, J=1.7 Hz, 2H), 5.53 (s, 2H), 5.07 (q, J=6.2 Hz, 1H), 4.93 (m, J=3.0 Hz, 1H), 4.74 (q, J=5.4 Hz, 1H), 4.57 (t, J=9.4 Hz, 1H), 4.23 (m, J=5.8 Hz, 2H), 3.98 (s, 3H), 3.95 (t, J=6.1 Hz, 1H), 3.30 (d, J=11.6 Hz, 1H), 3.03 (d, J=16.6 Hz, 1H), 2.87 (q, J=7.5 Hz, 2H), 1.28 (t, J=7.5 Hz, 3H); LCMS (ESI): m/z 740.8 [M+H]+.

Example 229

4-(7-(1H-Imidazol-1-yl)methyl)-5-(1-methyl-3-(trifluromethyl)-1H-pyrazol-4-yl)-1-oxo-3,4-dihydroisoquinolin-2(1H)-yl)-6-methoxy-N-(1-(tetrahydro-2H-pyran-4-carbonyl)azetidin-3-yl)quinoline-8-carboxamide The title compound (24 mg, 32 μmol, 42%) was prepared following the procedure described for Example 160, utilizing 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-methoxyquinoline-8-carboxamide (Example 224, 73 mg, 0.12 mmol) and tetrahydro-2H-pyran-4-carboxylic acid (10 mg, 77 μmol). LCMS (ESI): m/z=743.0 [M+H]+.

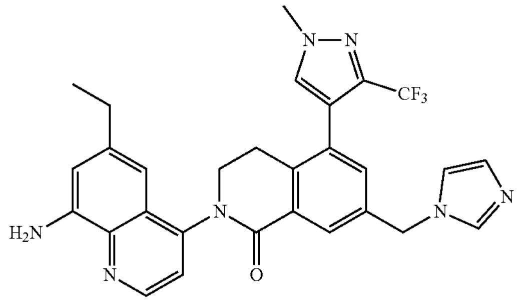

Example 230

7-((1H-Imidazol-1-yl)methyl)-2-(8-amino-6-ethylquinolin-4-yl)-5-(1-methyl-3-(trifluoromethyl)-1H-pyrazol-4-yl)-3,4-dihydroisoquinolin-1(2H)-one The title compound (70 mg, 0.13 mmol, 92%) was prepared following the procedure described for Example 177, using tert-butyl (4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)carbamate (90 mg, 0.14 mmol). $^1$H NMR (400 MHz, $CDCl_3$). $^1$H NMR (400 MHz, Chloroform-d) δ 8.74 (d, J=4.5 Hz, 1H), 8.18 (d, J=1.8 Hz, 1H), 7.62 (s, 1H), 7.41 (s, 1H), 7.30 (d, J=4.5 Hz, 1H), 7.17 (d, J=1.8 Hz, 1H), 7.11 (s, 1H), 6.94 (d, J=10.4 Hz, 2H), 6.84 (d, J=1.5 Hz, 1H), 5.19 (s, 2H), 4.02 (s, 3H), 3.88 (m, J=6.1 Hz, 2H), 3.14 (m, J=5.3 Hz, 1H), 2.95

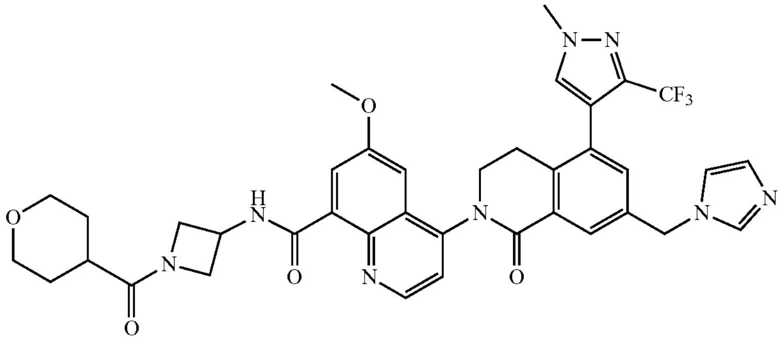 [SMILES: COc1cc(C(=O)NC2CN(C(=O)C3CCOCC3)C2)c2nccc(N3CCc4c(cc(Cn5ccnc5)cc4-c4cn(C)nc4C(F)(F)F)C3=O)c2c1]

(m, J=5.2 Hz, 1H), 2.69 (q, J=7.5 Hz, 2H), 1.25 (t, J=7.6 Hz, 3H); LCMS (ESI): m/z 546.4 [M+H]$^+$.

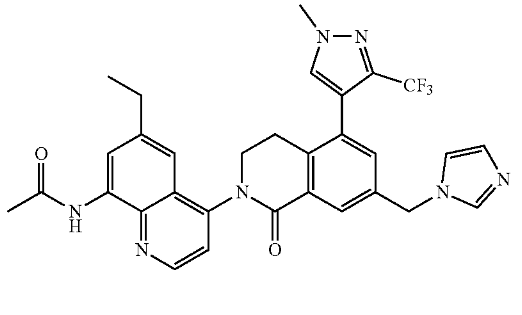 [SMILES: CCc1cc(NC(C)=O)c2nccc(N3CCc4c(cc(Cn5ccnc5)cc4-c4cn(C)nc4C(F)(F)F)C3=O)c2c1]

Example 231

N-(4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)acetamide The title compound (21 mg, 36 mol, 50%) was prepared following the procedure described for Example 160, utilizing 7-((1H-imidazol-1-yl)methyl)-2-(8-amino-6-ethylquinolin-4-yl)-5-(1-methyl-3-(trifluoromethyl)-1H-pyrazol-4-yl)-3,4-dihydroisoquinolin-1(2H)-one (Example 230, 40 mg, 0.70 mol) and acetic acid (20 mg, 0.4 mmol). $^1$H NMR (400 MHz, Chloroform-d) δ 9.79 (s, 1H), 8.79 (d, J=4.6 Hz, 1H), 8.72 (d, J=1.1 Hz, 1H), 8.17 (d, J=1.6 Hz, 1H), 7.63 (s, 1H), 7.42 (s, 1H), 7.38 (d, J=4.6 Hz, 1H), 7.27 (s, 1H), 7.19 (d, J=1.5 Hz, 1H), 7.11 (s, 1H), 6.96 (s, 1H), 5.20 (s, 2H), 4.03 (s, 1H), 3.97 (m, J=5.5 Hz, 1H), 3.83 (m, J=5.7 Hz, 1H), 3.17 (m, J=5.4 Hz, 1H), 2.97 (m, J=5.2 Hz, 1H), 2.80 (q, J=7.5 Hz, 2H), 2.35 (s, 3H), 1.29 (t, J=7.6 Hz, 3H); LCMS (ESI): m/z=588.4 [M+H]$^+$.

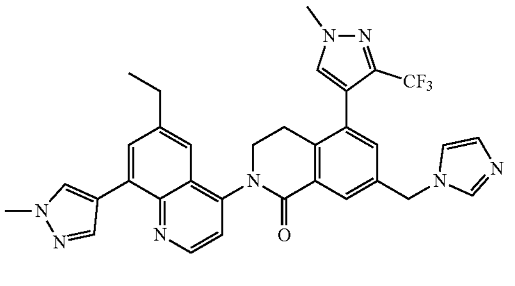 [SMILES: CCc1cc(-c2cnn(C)c2)c2nccc(N3CCc4c(cc(Cn5ccnc5)cc4-c4cn(C)nc4C(F)(F)F)C3=O)c2c1]

Example 232

7-((1H-Imidazol-1-yl)methyl)-2-(6-ethyl-8-(1-methyl-1H-pyrazol-4-yl)quinolin-4-yl)-5-(1-methyl-3-(trifluoromethyl)-1H-pyrazol-4-yl)-3,4-dihydroisoquinolin-1(2H)-one A mixture of 2.0 M aq. solution of sodium carbonate (246 μL, 4-92 prol, 3.0 equiv), 7-((1H-imidazol-yl-)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one (Example 34, 100 mg, 164 μmol, 1.0 equiv), 1-methyl-4-(4,4,5,5-tetramethyl-1,3,2-dioxaborolan-2-yl)-1H-pyrazole (41.0 mg, 197 μmol, 1.2 equiv) and $Pd(PPh_3)_4$ (9.48 mg, 8.20 μmol, 0.05 equiv) in water (250 μL) and 1,4-dioxane (750 μL) mixture was degassed and purged with Ar and stirred at 100° C. for 7 h. Solvent was removed and the residue was suspended in dichloromethane (10 mL), washed with water (10 mL) and brine (10 mL), dried over sodium sulfate then concentrated. The residue was purified by reverse phase HPLC (Phenomenex Gemini C18, $H_2O$/$CH_3CN$ gradient from 15-80% $CH_3CN$, 0.1% TFA) followed by neutralization with sat. aq. $NaHCO_3$ to yield the title compound (75 mg, 0.12 mmol, 75%). $^1$H NMR (400 MHz, Chloroform-d) δ 8.95 (d, J=4.5 Hz, 1H), 8.41 (s, 1H), 8.18 (s, 1H), 8.07 (s, 1H), 7.81 (s, 1H), 7.59 (s, 1H), 7.53 (s, 1H), 7.46 (s, 1H), 7.36 (d, J=4.4 Hz, 1H), 7.21 (s, 1H), 7.10 (s, 1H), 6.96 (s, 1H), 5.19 (s, 2H), 4.02 (s, 7H), 3.85 (m, J=5.6 Hz, 1H), 3.20 (m, J=5.3 Hz, 1H), 3.01 (q, J=5.5 Hz, 1H), 2.84 (q, J=7.5 Hz, 2H), 1.33 (t, J=7.5 Hz, 3H); LCMS (ESI): m/z=611.4 [M+H]$^+$.

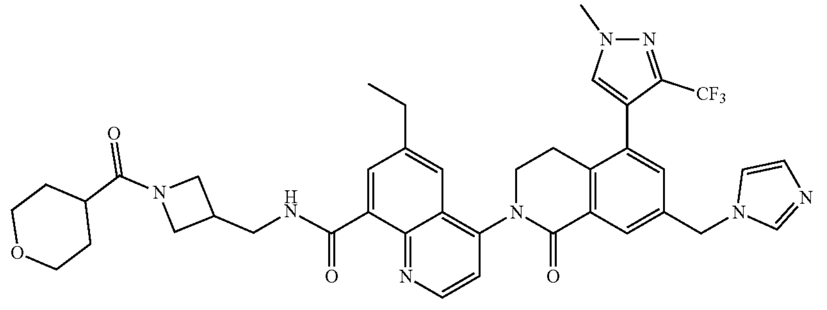 [SMILES: CCc1cc(C(=O)NCC2CN(C(=O)C3CCOCC3)C2)c2nccc(N3CCc4c(cc(Cn5ccnc5)cc4-c4cn(C)nc4C(F)(F)F)C3=O)c2c1]

Example 233

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-((1-(tetrahydro-2H-pyran-4-carbonyl)azetidin-3-yl)methyl) quinoline-8-carboxamide The title compound (45 mg, 60 μmol, 60%) was prepared following the procedure described for Example 160, utilizing 4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-ylmethyl)-6-ethylquinoline-8-carboxamide (Example 217, 64.3 mg, 100 μmol, 1.0 equiv) and tetrahydro-2H-pyran-4-carboxylic acid (30 mg, 230 μmol, 2.3 equiv). $^1$H NMR (400 MHz, Chloroform-d) δ 8.92 (t, J=3.9 Hz, 1H), 8.77 (s, 1H), 8.15 (s, 1H), 7.77 (d, J=1.5 Hz, 1H), 7.60 (s, 1H), 7.41 (d, J=4.1 Hz, 2H), 7.21 (s, 1H), 7.11 (s, 1H), 6.96 (s, 1H), 5.21 (s, 2H), 4.28 (t, J=8.3 Hz, 1H), 4.15 (q, J=6.2 Hz, 1H), 3.93 (m, J=6.5 Hz, 1H), 3.36 (m, J=5.3 Hz, 2H), 3.18 (m, J=5.4 Hz, 1H), 3.03 (m, J=6.0 Hz, 2H), 2.87 (q, J=7.6 Hz, 2H), 2.38 (m, J=41.4 Hz, 1H), 1.83 (m, J=6.1 Hz, 2H), 1.52 (q, J=13.9 Hz, 2H), 1.32 (t, J=7.6 Hz, 3H); LCMS (ESI): m/z 755.2 $[M+H]^+$.

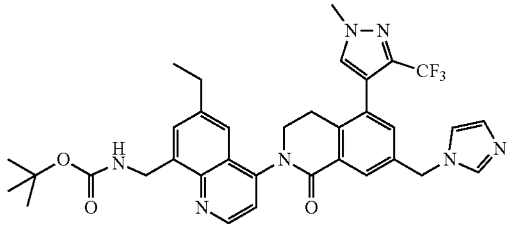 [SMILES: CCc1cc(CNC(=O)OC(C)(C)C)c2nccc(N3CCc4c(cc(Cn5ccnc5)cc4-c4cn(C)nc4C(F)(F)F)C3=O)c2c1]

Example 234 tert-Butyl ((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)carbamate The title compound (80.0 mg, 115 μmol, quantitative yield) was prepared following the Buchwald coupling procedure described for Example 2, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 115 μmol, 1 equiv) and tert-butyl ((4-bromo-6-ethylquinolin-8-yl)methyl)carbamate (Intermediate 73, 71.1 mg, 195 μmol, 1.7 equiv). $^1$H NMR (400 MHz, Chloroform-d) δ 8.91 (d, J=4.8 Hz, 1H), 8.17 (d, J=2.0 Hz, 1H), 7.62 (brs, 1H), 7.58 (s, 1H), 7.53 (s, 1H), 7.42 (s, 1H), 7.34 (d, J=4.8 Hz, 1H), 7.18 (d, J=2.0 Hz, 1H), 7.10 (s, 1H), 6.95 (s, 1H), 5.81 (brs, 1H), 5.20 (s, 2H), 4.85 (m, 2H), 4.03 (s, 3H), 3.98 (m, 1H), 3.82 (m, 1H), 3.17 (m, 1H), 2.98 (m, 1H), 2.79 (q, J=7.6 Hz, 2H), 1.44 (s, 9H), 1.28 (t, J=7.6 Hz, 3H).

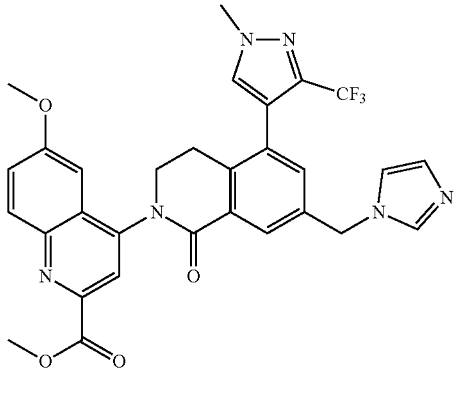 [SMILES: COC(=O)c1cc(N2CCc3c(cc(Cn4ccnc4)cc3-c3cn(C)nc3C(F)(F)F)C2=O)c2cc(OC)ccc2n1]

Example 235

Methyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl-6-methoxyquinoline-2-carboxylate The title compound (432 mg, 0.73 mmol, 92% yield) was prepared following the Buchwald coupling procedure described for Example 12, using 7-((1H-imidazol-1-yl)methyl)-5-(1-methyl-3-(trifluoromethyl)-1H-pyrazol-4-yl)-3,4-dihydroisoquinolin-1(2H)-one (Intermediate 8, 300 mg, 0.80 mmol) and methyl 4-bromo-6-methoxyquinolin-2-carboxylate (Intermediate 66, 473 mg, 1.60 mmol, 2 equiv). $^1$H NMR (400 MHz, Chloroform-d) δ 8.28 (d, J=9.2 Hz, 1H), 8.16 (s, 1H), 8.13 (s, 1H), 7.58 (s, 1H), 7.48 (d, J=8.3 Hz, 1H), 7.41, 7.18 (s, 1H), 7.10 (s, 1H), 7.07 (s, 1H), 6.95 (s, 1H), 5.21 (s, 2), 4.14-4.05 (m, 4H), 4.03 (s, 3H), 3.93-3.79 (m, 4H), 3.19-3.11 (m, 1H), 3.00 (dt, J=16.4, 4.5 Hz, 1H); LCMS (ESI): Method 2: $R_T$=1.469 min, m/z=591.0 $[M+H]^+$.

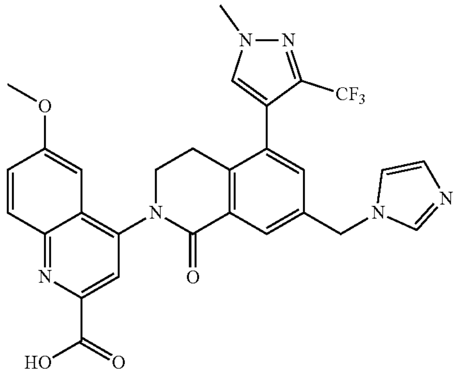 [SMILES: COc1ccc2nc(C(=O)O)cc(N3CCc4c(cc(Cn5ccnc5)cc4-c4cn(C)nc4C(F)(F)F)C3=O)c2c1]

Example 236

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-2-carboxylic acid The title compound (150 mg, 0.26 mmol, 36% yield) was prepared following the procedure described for Example 40, using ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylate (Example 235, 426 mg, 0.72 mmol). LCMS (ESI): Method 2: $R_T$=1.357 min, m/z=577.0 $[M+H]^+$.

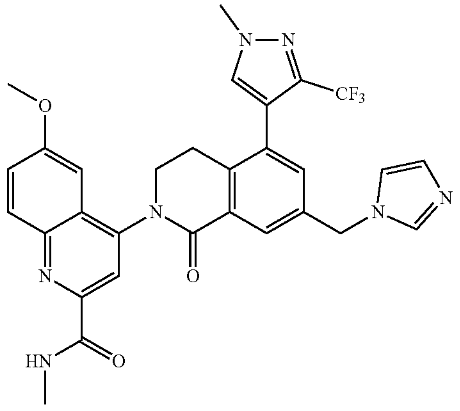 [SMILES: CNC(=O)c1cc(N2CCc3c(cc(Cn4ccnc4)cc3-c3cn(C)nc3C(F)(F)F)C2=O)c2cc(OC)ccc2n1]

Example 237

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-methylquinoline-2-carboxamide The title compound (25 mg, 0.043 mmol, 41% yield) was prepared following the procedure described for Example 42, using 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-2-carboxylic acid (Example 236, 60 mg, 0.10 mmol) and methylamine hydrochloride (70 mg, 1.0 mmol, 10 equiv), The reaction was stirred at 60° C. An additional portion of each reagent was added to drive the reaction to completion. $^1$H NMR (400 MHz, Chloroform-d) δ 8.20 (s, 1H), 8.16 (s, 1H), 8.14 (d, J=4.9 Hz, 1H), 8.05 (d, J=9.3 Hz, 1H), 7.77 (brs, 1H), 7.44 (dd, J=9.3, 2.6 Hz, 1H), 7.43 (s, 1H), 7.19 (s, 1H), 7.14 (s, 1H), 7.05 (d, J=2.4 Hz, 1H), 6.98 (s, 1H), 5.23 (s, 2H), 4.12 (td, J=11.7, 4.3 Hz, 1H), 4.03 (s, 3H), 3.88 (s, 3H), 3.81 (dt, J=12.3, 5.4 Hz, 1H), 3.18-3.08 (m, 4H), 3.01 (dt, J=16.5, 4.7 Hz, 1H); LCMS (ESI): Method 2: $R_T$=1.488 min, m/z=590.1 [M+H]$^+$.

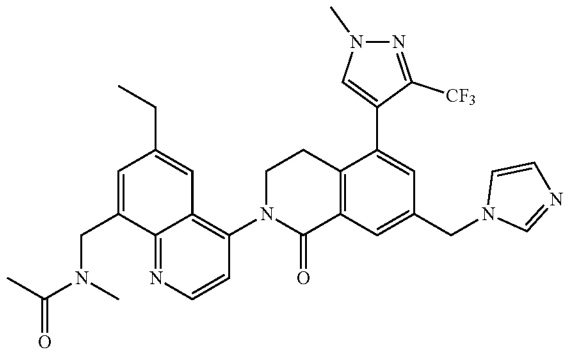 [SMILES: CCc1cc(CN(C)C(C)=O)c2nccc(N3CCc4c(cc(Cn5ccnc5)cc4-c4cn(C)nc4C(F)(F)F)C3=O)c2c1]

Example 238

N-((4-(7-((1H-Imidazol-1-yl)methyl)-5-(1-methyl-3-(trifluoromethyl)-1H-pyrazol-4-yl)-1-oxo-3,4-dihydroisoquinolin-2(1H)-(yl)-6-ethylquinolin-8-yl)methyl)-N-methylacetamide To a solution of 7-((1H-imidazol-1-yl)methyl)-2-(6-ethyl-8-((methylamino)methyl)quinolin-4-yl)-5-(1-methyl-3-(trifluoromethyl)-1H-pyrazol-4-yl)-3,4-dihydroisoquinolin-1(2H)-one (Example 177, 34.0 mg, 59.3 μmol, 1 equiv) in a mixture of THF (2 mL) and dichloromethane (2 mL) at room temperature were added pyridine (12 μL, 148 μmol, 2.5 equiv) and acetic anhydride (11.2 μL, 119 μmol, 2 equiv). The reaction was stirred overnight then quenched with sat. aq. $NaHCO_3$. The mixture was extracted with EtOAc, and the combined organic layer was dried ($Na_2SO_4$), filtered, and concentrated. The residue was purified by reverse phase HPLC (Phenomenex Gemini C18, $H_2O/CH_3CN$ gradient from 0-60% $CH_3CN$, 0.1% TFA) to yield the title compound (27.0 mg, 44 μmol, 74% yield), $^1$H NMR (400 MHz, Chloroform-d) δ 8.92 (d, J=4.8 Hz, 1H), 8.17 (s, 1H), 7.58 (s, 1H), 7.56 (brs, 1H), 7.46 (m, 1H), 7.42 (s, 1H), 7.33 (m, 1H), 7.19 (brs, 1H), 7.11 (s, 1H), 6.96 (s, 1H), 5.2 (s, 2H), 4.03 (s, 3H), 1.00 (m, 1H), 3.83 (m, 1H), 3.17 (m, 1H), 3.08 (m, 3H), 2.98 (m, 1H), 2.80 (m, 2H), 2.20 (m, 3H), 1.27 (m, 3H); LCMS (ESI): >95%, m/z=616.6 [M+H]$^+$.

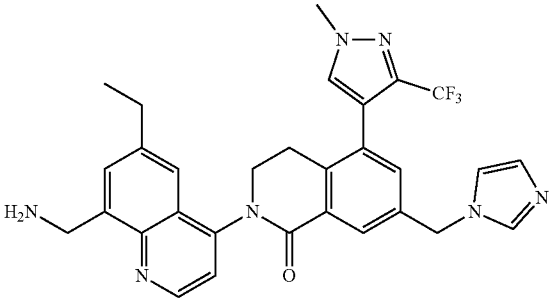

Example 239

7-((1H-Imidazol-1-yl)methyl)-2-(8-(aminomethyl)-6-ethylquinolin-4-yl)-5-(1-methyl-3-(trifluoromethyl)-1H-pyrazol-4-yl)-3,4-dihydroisoquinolin-1(2H)-one The title compound (34.0 mg, 60.6 μmol, quantitative yield) was prepared following the procedure described for Example 177, using tert-butyl ((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)carbamate (Example 234, 40.0 mg, 60.6 μmol). LCMS (ESI): >95%, m/z=560.4 [M+H]$^+$.

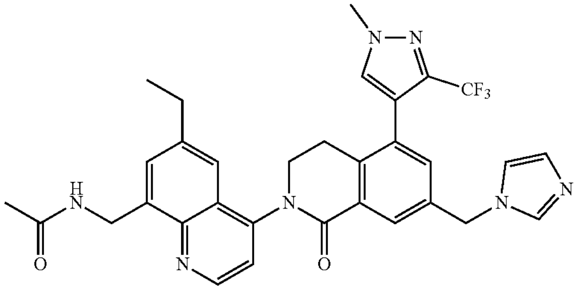 [SMILES: CCc1cc(CNC(C)=O)c2nccc(N3CCc4c(cc(Cn5ccnc5)cc4-c4cn(C)nc4C(F)(F)F)C3=O)c2c1]

Example 240

N-((4-(7-((1H-Imidazol-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)acetamide The title compound (32.0 mg, 53 μmol, 88% yield) was prepared following the procedure described for Example 238, using 7-((1H-imidazol-1-yl)methyl)-2-(8-(aminomethyl)-6-ethylquinolin-4-yl)-5-(1-methyl-3-(trifluoromethyl)-1H-pyrazol-4-yl)-3,4-dihydroisoquinolin-1(2H)-one (Example 239, 33.9 mg, 60.6 μmol, 1 equiv). $^1$H NMR (400 MHz, Chloroform-d) δ 8.92 (d, J=4.4 Hz, 1H), 8.17 (d, J=4.6 Hz, 1H), 7.64 (s, 1H), 7.58 (s, 1H), 7.55 (s, 1H), 7.42 (s, 1H), 7.36 (d, J=4.8 Hz, 1H), 7.19 (d, J=1.6 Hz, 1H), 7.11 (s, 1H), 6.95 (s, 1H), 6.90 (t, J=6.0 Hz, 1H), 5.20 (s, 2H), 4.97 (m, 2H), 4.03 (s, 3H), 3.98 (m, 1H), 3.82 (m, 1H), 3.18 (m, 1H), 2.98 (m, 1H), 2.79 (q, J=7.6 Hz, 2H), 1.97 (s, 3H), 1.29 (t, J=7.6 Hz, 3H); LCMS (ESI): >95%, m/z=602.6 [M+H]$^+$.

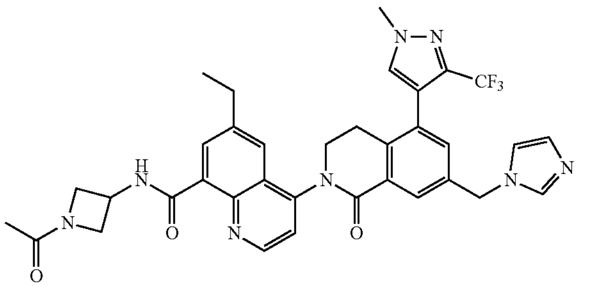 [SMILES: CCc1cc(C(=O)NC2CN(C(C)=O)C2)c2nccc(N3CCc4c(cc(Cn5ccnc5)cc4-c4cn(C)nc4C(F)(F)F)C3=O)c2c1]

Example 241

4-(7-(1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(1-acetylazetidin-3-yl)-6-ethylquinoline-8-carboxamide The title compound (12 mg, 18 μmol, 21%) was prepared following the procedure described for Example 160, utilizing 4-(7-((1H-imidazol-1-yl)methyl)-5(1-methyl-3-(trifluoromethyl)-1H-pyrazol-4-yl)-oxo-3,4-dihydroisoquinolin-2(1H)-yl)-N-(azetidin-3-yl)-6-ethylquinoline-8-carboxamide (Example 222, 79 mg, 0.12 mmol) and acetic acid (5.0 mg, 4.8 μL, 83 μmol). $^{1}$H NMR (400 MHz, MeOD) δ 9.03 (d, J=4.7 Hz, 1H), 8.55 (t, J=1.9 Hz, 1H), 8.05 (s, 1H), 7.89 (d, J=2.0 Hz, 1H), 7.84 (s, 1H), 7.77 (s, 1H), 7.62 (d, J=4.7 Hz, 1H), 7.41 (d, J=1.4 Hz, 1H), 7.14 (s, 1H), 7.00 (s, 1H), 5.48 (s, 1H), 5.33 (s, 2H), 4.88 (m, J=2.2 Hz, 1H), 4.63 (q, J=5.7 Hz, 1H), 4.41 (t, J=9.2 Hz, 1H), 4.32 (q, J=4.8 Hz, 1H), 4.11 (m, J=5.4 Hz, 2H), 4.01 (s, 3H), 3.88 (m, J=5.7 Hz, 1H), 3.24 (m, J=5.5 Hz, 1H), 3.03 (m, J=5.3 Hz, 1H), 2.87 (q, J=7.6 Hz, 2H), 1.92 (d, J=1.5 Hz, 3H), 1.29 (t, J=7.6 Hz, 3H); LCMS (ESI): m/z=671.3 [M+H]$^{+}$.

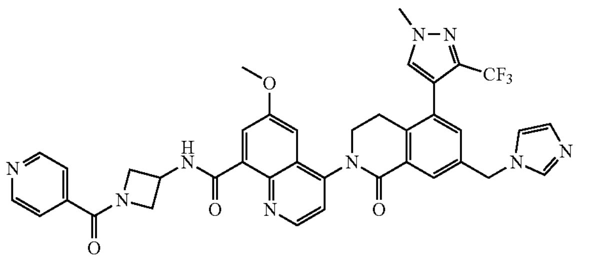 [SMILES: COc1cc(C(=O)NC2CN(C(=O)c3ccncc3)C2)c2nccc(N3CCc4c(cc(Cn5ccnc5)cc4-c4cn(C)nc4C(F)(F)F)C3=O)c2c1]

Example 242

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-(1-isonicotinoylazetidin-3-yl)-6-methoxyquinoline-8-carboxamide The title compound (21 mg, 29 μmol, 35%) was prepared following the procedure described for Example 160, utilizing 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-methoxyquinoline-8-carboxamide (Example 224, 77 mg, 0.12 mmol) and isonicotinic acid (10 mg, 1 Eq, 81 μmol). LCMS (ESI): m/z 736.5 [M+H]$^{+}$.

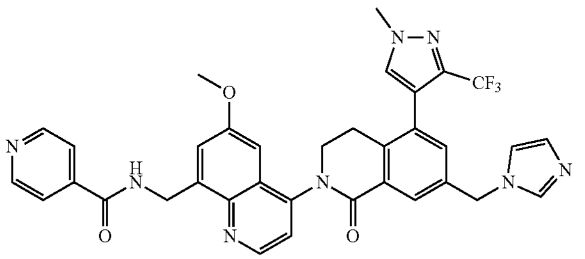 [SMILES: COc1cc(CNC(=O)c2ccncc2)c2nccc(N3CCc4c(cc(Cn5ccnc5)cc4-c4cn(C)nc4C(F)(F)F)C3=O)c2c1]

Example 243

N-((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)isonicotinamide The title compound (51 mg, 78 μmol, 78%) was prepared following the procedure described for Example 160, utilizing 7-((1H-imidazol-1-yl)methyl)-2-(8-(aminomethyl)-6-ethylquinolin-4-yl)-5-(1-methyl-3-(trifluoromethyl)-1H-pyrazol-4-yl)-3,4-dihydroisoquinolin-1(2H)-one (Example 239, 40 mg, 0.70 μmol) and isonicotinic acid (43 mg, 0.35 mmol). $^{1}$H NMR (4001 MHz, Chloroform-d) δ 10.83 (s, 1), 8.86 (m, J=3.5 Hz, 4H), 8.17 (d, J=1.8 Hz, 1H), 7.91 (q, J=2.0 Hz, 2H), 7.60 (s, 1H), 7.43 (t, J=3.4 Hz, 2H), 7.36 (t, J=0.7 Hz, 1H), 7.20 (d, J=1.8 Hz, 1H), 7.11 (s, 1H), 6.96 (s, 1H), 5.20 (s, 2H), 4.03 (s, 3H), 3.99 (q, J=5.0 Hz, 1H), 3.86 (m, J=5.7 Hz, 1H), 3.18 (m, J=54 Hz, 1H), 2.99 (m, J=5.1 Hz, 1H), 2.86 (q, J=7.5 Hz, 2H), 1.34 (t, J=7.6 Hz, 3H); LCMS (ESI): m/z=651.3 [M+H]$^{+}$.

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The routes by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, tale, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

Mixed lineage leukemia (MLL) presents a heterogeneous group of acute myeloid leukemia and acute lymphoblastic leukemia bearing features of more than one hematopoietic cell lineages. MLL accounts for about 80% of infant acute leukemia cases (Tomizava, 2007) and 10% of all acute leukemia cases (Marschalek, 2011). MLL leukemia patients have a poor prognosis with overall 5-year survival ratio around 35% (Dimartino, 1999; Pui, 2003; Tomizawa, 2007).

MLL is composited of heterogeneous cell lineages with different molecular biology, cell biology and immunology features. However, MLL does share a common feature, which involves the chromosomal rearrangement of Mixed Lineage Leukemia (MLL) gene MLL gene locates on chromosome 11q23 and the encoded MLL protein is a homolog of *Drosophila trithorax* (Trx) (Thachuk, 1992). Wild type MLL binds to regulatory regions of homeox (HOX) genes (Milne, 2005) through the amino terminal fragment while the catalytic C-terminal domain catalyzes the Histone 3 lysine 4 (H3K4) methylation via interaction with WDR5 and up regulates target genes transcription (Nakamura, 2002; Yokoyama, 2004; Milne, 2002). Wild type MLL in conjunction with WDR5 is required for maintenance HOX genes expression and is widely expressed not only during embryo development but also in adult tissues including myeloid and lymphoid cells (Butler, 1997; Yu, 1998). Reciprocal translocations of MLL gene result in-frame fusion of 5'-end MLL with the 3'-end of another partner gene. A common feature of MLL abnormality in leukemia is the preservation of one wild-type MLL1 allele. Currently, more than 80 partner genes have been identified, with MLL-AF4, MLL-AF9 and MLL-ENL being the three most frequently found fusion genes (Pui, 2003; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, 2007; Yokoyama, 2005). The numerous chromosomal translocation of MLL gene and partner genes diversity add to the complexity to MLL leukemia treatment, though HOX9 and MEIS1 overexpression are commonly observed among MLL leukemia patients, each rearrangement leading to distinct dysregulated target gene expression patterns and downstream events (Slany, 2009). Clinical studies reveal that MLL of different chromosomal translocations are associated with different prognosis and are treated differently under current protocols (Tamai, 2010; Balgobind, 2011; Pigazzi, 2011).

Intrinsic HMT activity of MLL1 is extremely low and requires a complex assembly of WDR5, RbBP5, ASH2L, and DPY30 protein partners for effective H3K4 trimethylation, so called WRAD complex. The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, et al. Molecular Cell, 2014, 53, 247-261.) In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. The molecules described herein will target this interaction and could provide an attractive therapeutic approach to develop novel drugs for leukemias with translocations of MLL gene and other leukemias with upregulation of target genes. It also appreciated that WDR5 has been implicated in other cancer types and may utilize the WIN-site for other chromatin regulatory complexes outside and/or overlapping with WRAD complex. As such the WIN-site inhibitors described herein may have utility in multiple cancer types through mechanisms of action involving both direct competitive WIN-site antagonism, or through allosteric inhibition of higher complexes wherein WDR5 is dependent for their proliferative activity and tumor formation. Examples include breast cancer (Dai, X. et al. PLoS One, 2015), MYC-driven tumor types (Thomas, et al. Molecular Cell, 2015), bladder cancer (Chen, X. et al. Nature, Scientific Reports, 2015), neuroblastoma (Sun, Y. et al. Cancer Research, 2015), and pancreatic cancer (Carugo, A. et al. Cell Reports, 2016).

The disclosed compounds and compositions may be used in methods for treatment of MLL related cancers. The methods of treatment may comprise administering to a subject in need of such treatment a composition comprising a therapeutically effective amount of the compound of formula (I).

In one aspect, disclosed is a method of treating cancer, the method comprising administration of a therapeutically effective amount of a compound of formula (I), or a pharmaceutically acceptable salt thereof to a subject in need thereof.

In certain embodiments, the cancer being treated is associated with dysfunction of MLL.

In certain embodiments, the cancer is at least one of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

In another aspect, disclosed is a method of disrupting the protein-protein interaction between WDR5 and MLL1, the method comprising administration of a therapeutically effective amount of a compound of formula (I), or a pharmaceutically acceptable salt thereof to a subject in need thereof.

The compositions can be administered to a subject in need thereof to bind WDR5 and modulate MLL to treat a variety of diverse cancers. The present disclosure is directed to methods for administering the composition to inhibit the protein-protein interaction between WDR5 its binding partners such chromatin, cognate transcription and other regulatory factors, including for example the histone methyltransferase MLL1.

The compositions may be useful for treating certain cancers in humans and animals related to MLL dysfunction. Treatment of such cancers can be effected by modulating MLL1 in a subject, by administering a compound or composition of the invention, either alone or in combination with another active agent as part of a therapeutic regimen to a subject in need thereof.

Disruption of the interaction between WDR5 and its binding partners (such as MLL1) can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, leukemia (mixed-lineage leukemia), ovarian cancer, breast cancer, colorectal cancer, pancreatic cancer, gastric cancer, stomach cancer, lung cancer, cervical cancer, uterine cancer, cancers of the blood, and cancers of the lymphatic system.

In some embodiments, the administered composition to a subject in need thereof can mediate reduction, clearance or prevention of additional growth of tumor cells by disrupting the ability of MLL1, another transcription factor, or chromatin to associate with WDR5, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

A. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

B. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula. (I). The above combinations include combinations of a compound of the present invention not only with one other active compound, but also with two or more other active compounds. For example, the compound of Formula (I) can be combined with a variety of different anti-cancer drugs such as chemotherapeutics, anti-tumor agents, and anti-proliferative agents.

Further, the compound of formula (I) can be combined with the following, but not limited to, actinomycins, alkylating agents, anthracyclines, antifolates, antiestrogen agents, anti-metabolites, anti-androgens, antimicrotubule agents, aromatase inhibitors, bleomycins, bromodomain inhibitors, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of raparycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, vitamin D3 analogs, □-radiation, DOT1L inhibitors, agents targeting epigenetic mechanisms, or an additional chemotherapeutic agent such as N-Ac-Sar-Gly-Val-D-alloIle-Thr-Nva-Ile-Arg-Pro-NHCH2CH3 or a salt thereof, actinonycin D, AG13736, 17-allylamino-17-demethoxygeldanamycin, 9-aminocamptothecin, N-(4-(3-amino-1H-indazol-4-yl)phenyl}-N'-(2-fluoro-5-methylphenyl)urea or a salt thereof, N-(4-(4-aminothieno[2,3-d]

pyrimidin-5-yl)phenyl}-N'-(2-fluoro-5-(trifluoromethyl) phenyl)urea or a salt thereof, temozolomide, nedaplatin, satraplatin, triplatin tetranitrate, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNT-1001, CNF-2024. CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phenylpyridinium, MG132, mitomycin, mitoxantrone, MLN518, MLN4924, MS-275, mycophenolic acid, mitomycin C, nitrosoureas, oprelvekin, oxaliplatin, paclitaxel, PARP inhibitors (e.g., rucaparib, niraparib, olaparib, iniparib, talazoparib, and veliparib), PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, tamoxifen, taxol, temozolamide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizunab, enzastaurin, temsirolimus, cilengitide, lapatinib, sunitinib, axitinib, pazopanib, vemurafenib, dabrafenib, JQ1 or combinations thereof.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

5. Biological Activity

The in vitro modulation of WDR5 protein was determined as follows.

MLL Peptide Binding Assay

General

Provided compounds of the present invention can be demonstrated to compete for binding with fluorescently labeled peptides derived from relevant MLL protein.

Time Resolved-Fluorescence Energy Transfer Competition Assay

A Time-Resolved Fluorescence Resonance Energy Transfer TR-FRET) assay that measures the displacement of the 10mer-Thr-FAM probe in response to compound treatment was performed for compounds wherein the $IC_{50}$ from FPA assay using 10mer-Thr-FAM was below the lower assay $IC_{50}$ limit ~1 nM. Excess 10mer-Thr-FAM probe was utilized with His-tagged WDR5 in conjunction with a commercial anti-His antibody containing a Terbium label. The LanthaScreen™ Elite Tb-anti-HIS Antibody from ThermoFisher Scientific was used for this purpose. This Tb-anti-HIS has an excitation/emission of 340 nm and 490 nm, respectively. The 10mer-Thr-FAM probe when bound to WDR5 will undergo a FRET interaction with the Tb-anti-HIS and emit at 520 nm. The ratio of the 520 and 495 signals are then utilized to generate a dose-response curve to calculate an $IC_{50}$ value. By virtue of FRET there is little to no background fluorescence interference from 10mer-Thr-FAM probe allowing an excess of the probe to be used permitting an increase in the lower limit of the calculated $K_i$ when testing against highly potent inhibitors with $K_i$<<nM. WDR5-His Tag (Δ23, residues 24-334) is expressed and purified in our lab in sufficient quantities for screening. 10mer-Thr-FAMpeptide is used at 150 nM. WDR5-His tag protein is used at 2 nM. A source plate is prepared using an Echo Liquid Handler, which distributes the compounds to the assay plate (white, flat-bottom; OptiPlate) in a 10-point, 5-fold dilution schemes with a top concentration of 5 μM, in a final volume of 20 μL. A final target (WDR5)/Tb-Ab concentration of 2 nM/1 nM is dispensed front appropriate stock solutions, respectively. The final DMSO concentration in each well of the assay plate is 1% or lower. The plate is covered, shielded from light, and incubated for 60 minutes at room temperature with rocking. 10mer-Thr-FAM and Anti-His terbium antibody fluorescence is then measured on a Biotek Cytation 3 at excitation wavelength of 340 nm, and emission wavelengths of 495 nm and 520 nm. Working buffer conditions contain 1× Phosphate Buffered Saline, 300 mM NaCl, 0.5 mM TCEP, 0.1% CHAPS, at pH 7.2. TR-FRET signal is plotted and $IC_{50}$ and $K_i$ values are calculated according to the formula of Wang Z. FEBS Lett (1996) 3, 245.

$$K_i=[I]_{50}/([L]_{50}/K_d+[P]_0/K_d+1)$$

where $[I]_{50}$ is the concentration of the free inhibitor at 50% inhibition, $[L]_{50}$ is the concentration of the free labeled ligand at 50% inhibition, $[P]_0$ is the concentration of the free protein at 0% inhibition, $K_d$ represents the dissociation constant of the FITC-MLL or 10mer-Thr-FAM probe for WDR5. Total fluorescence is also measured, to rule out compounds that are inherently fluorescent or able to act as quenchers in the assay.

TR-FRET Binding Assay

TABLE 2

$K_i$ for Exemplified Compounds for Inhibition of WDR5 by TR-FRET assay

| Example | $K_i$ (nM) |
|---|---|
| 1 | 0.46 |
| 2 | 0.05 |
| 3 | <0.02 |

TABLE 2-continued

| $K_i$ for Exemplified Compounds for Inhibition of WDR5 by TR-FRET assay | |
|---|---|
| Example | $K_i$ (nM) |
| 4 | <0.02 |
| 5 | 0.034 |
| 6 | 0.024 |
| 7 | 0.026 |
| 8 | 0.026 |
| 9 | 0.048 |
| 10 | 0.029 |
| 11 | 0.035 |
| 12 | <0.02 |
| 13 | <0.02 |
| 14 | 0.02.8 |
| 15 | 0.026 |
| 16 | 0.028 |
| 17 | 0.025 |
| 18 | <0.02 |
| 19 | 0.02 |
| 20 | <0.02 |
| 21 | <0.02 |
| 22 | 0.029 |
| 23 | <0.02 |
| 24 | 0.026 |
| 25 | 0.061 |
| 26 | 0.087 |
| 27 | 4.6 |
| 28 | 0.032 |
| 29 | <0.02 |
| 30 | <0.02 |
| 31 | <0.02 |
| 32 | 0.025 |
| 33 | 0.022 |
| 34 | 0.02 |
| 35 | <0.02 |
| 36 | <0.02 |
| 37 | <0.02 |
| 38 | <0.02 |
| 40 | 0.062 |
| 41 | 0.023 |
| 42 | <0.02 |
| 43 | 0.032 |
| 44 | <0.02 |
| 45 | 0.037 |
| 46 | 0.038 |
| 47 | 0.022 |
| 48 | 0.028 |
| 49 | <0.02 |
| 50 | <0.02 |
| 51 | <0.02 |
| 52 | 0.028 |
| 53 | <0.02 |
| 54 | 0.028 |
| 55 | <0.02 |
| 56 | 0.031 |
| 57 | 27 |
| 58 | 0.025 |
| 59 | 1.4 |
| 60 | 0.023 |
| 61 | 0.052 |
| 62 | 0.028 |
| 63 | 0.068 |
| 64 | 0.042 |
| 65 | <0.02 |
| 66 | 0.062 |
| 67 | 0.062 |
| 68 | <0.02 |
| 69 | <0.02 |
| 70 | <0.02 |
| 71 | <0.02 |
| 72 | <0.02 |
| 73 | <0.02 |
| 74 | <0.02 |
| 75 | <0.02 |
| 76 | <0.02 |
| 77 | <0.02 |
| 78 | 0.029 |
| 79 | <0.02 |

TABLE 2-continued

| $K_i$ for Exemplified Compounds for Inhibition of WDR5 by TR-FRET assay | |
|---|---|
| Example | $K_i$ (nM) |
| 80 | 0.029 |
| 81 | <0.02 |
| 82 | 0.061 |
| 83 | <0.02 |
| 84 | <0.02 |
| 85 | <0.02 |
| 86 | <0.02 |
| 87 | 0.027 |
| 88 | 0.043 |
| 89 | 0.022 |
| 90 | 0.033 |
| 91 | 0.023 |
| 92 | 0.062 |
| 93 | <0.02 |
| 94 | 0.039 |
| 95 | <0.02 |
| 96 | <0.02 |
| 97 | 0.021 |
| 98 | 0.059 |
| 100 | 0.026 |
| 101 | 0.023 |
| 102 | 0.025 |
| 103 | 0.029 |
| 104 | 0.028 |
| 105 | 0.022 |
| 106 | 0.045 |
| 107 | 0.021 |
| 108 | 0.042 |
| 109 | <0.02 |
| 110 | 0.021 |
| 111 | 0.027 |
| 112 | 0.037 |
| 113 | 0.023 |
| 114 | 0.038 |
| 115 | 0.031 |
| 116 | 0.028 |
| 117 | 0.036 |
| 118 | >33000 |
| 119 | 0.057 |
| 120 | 0.023 |
| 121 | 0.023 |
| 122 | 0.052 |
| 123 | 0.040 |
| 124 | 0.030 |
| 127 | 0.021 |
| 128 | 0.038 |
| 129 | 0.029 |
| 130 | 0.051 |
| 131 | 0.043 |
| 132 | 0.030 |
| 133 | 0.035 |
| 134 | 0.030 |
| 135 | 0.040 |
| 136 | <0.02 |
| 137 | 0.032 |
| 138 | <0.02 |
| 139 | <0.02 |
| 140 | <0.02 |
| 141 | 0.070 |
| 142 | 0.036 |
| 143 | 0.038 |
| 144 | 0.047 |
| 145 | 0.020 |
| 146 | 0.025 |
| 147 | 0.022 |
| 148 | 0.028 |
| 149 | 0.035 |
| 150 | 0.025 |
| 151 | <0.02 |
| 153 | 0.022 |
| 154 | 0.022 |
| 155 | 0.029 |
| 156 | 0.020 |
| 157 | <0.02 |
| 158 | <0.02 |

TABLE 2-continued

Ki for Exemplified Compounds for Inhibition of WDR5 by TR-FRET assay

| Example | $K_i$ (nM) |
|---|---|
| 159 | 0.027 |
| 160 | <0.02 |
| 161 | 0.026 |
| 162 | 0.026 |
| 163 | 0.024 |
| 164 | 0.028 |
| 165 | 0.042 |
| 166 | 0.029 |
| 167 | 0.034 |
| 168 | 0.028 |
| 169 | <0.02 |
| 170 | 0.023 |
| 171 | <0.02 |
| 172 | <0.02 |
| 173 | <0.02 |
| 175 | <0.02 |
| 176 | <0.02 |
| 178 | <0.02 |
| 179 | <0.02 |
| 180 | 0.023 |
| 181 | 0.040 |
| 182 | <0.02 |
| 183 | <0.02 |
| 184 | <0.02 |
| 185 | 0.028 |
| 186 | <0.02 |
| 187 | <0.02 |
| 188 | <0.02 |
| 189 | <0.02 |
| 190 | <0.02 |
| 191 | <0.02 |
| 192 | 0.021 |
| 193 | <0.02 |
| 194 | <0.02 |
| 195 | <0.02 |
| 196 | 0.366 |
| 197 | 0.020 |
| 198 | 0.023 |
| 199 | 0.035 |
| 200 | <0.02 |
| 201 | 0.023 |
| 202 | 0.020 |
| 203 | 0.025 |
| 204 | <0.02 |
| 205 | <0.02 |
| 206 | 0.022 |
| 207 | <0.02 |
| 208 | <0.02 |
| 209 | <0.02 |
| 210 | <0.02 |
| 211 | <0.02 |
| 212 | <0.02 |
| 213 | <0.02 |
| 214 | <0.02 |
| 215 | <0.02 |
| 216 | <0.02 |
| 218 | <0.02 |
| 219 | <0.02 |
| 220 | <0.02 |
| 221 | 0.024 |
| 223 | <0.02 |
| 225 | <0.02 |
| 226 | <0.02 |
| 227 | <0.02 |
| 228 | <0.02 |
| 229 | <0.02 |
| 230 | <0.02 |
| 231 | <0.02 |
| 232 | <0.02 |
| 233 | <0.02 |
| 237 | <0.02 |
| 238 | <0.02 |

TABLE 2-continued

Ki for Exemplified Compounds for Inhibition of WDR5 by TR-FRET assay

| Example | $K_i$ (nM) |
|---|---|
| 240 | <0.02 |
| 241 | <0.02 |
| 242 | <0.02 |

Among other things, these data demonstrate the utility of representative compounds as, selective inhibitors of the activity of WDR5 protein to bind peptides from relevant MLL domain.

Cellular Viability of Human Tumor Cell Lines

Anti-proliferative activity using MLL-harboring cell lines. MV-4-11 and K562 cells are grown in IMDM media supplemented with 10% FBS and 1% penicillin/streptomycin, Molm-13 cells are cultured in RPMI-1640 media supplemented with 10% FBS and 1% penicillin/streptomycin. Viability assays are performed by dispensing 200 cells at 7200 cells/mL into each well of an opaque 384-well plate and adding compounds at the indicated concentrations in a final volume, of 32 μL. and a final concentration of DMSO of 0.3% for all samples. A certain range of compound concentrations is made through a series of 2-fold dilutions starting 30 μM at the highest, total 22 dilutions. After a set incubation period, 5 day protocol, the viability of cells in each well is assessed using the CellTiter-Glo assay (Promega), read on a 96 Microplane Luminometer (Cytation 3, BioTek). Serial dilutions of each cell type are performed in all assays to generate standard curves and the final densities of cells are determined within the dynamic range of the instrument. $GI_{50}$ values are calculated based on XLfit software (IDBS, Guildford, UK) with Sigmoidal Dose-Response Model. Each compound is tested in minimum of two replicates. Data are expressed as mean.

TABLE 3

$GI_{50}$ (in μM) for representative compounds on cellular proliferation of MV4:11 human cancer cell lines

| Example | $GI_{50}$ (nM) |
|---|---|
| 1 | 1540 |
| 2 | 189 |
| 3 | 20 |
| 4 | <20 |
| 5 | 83 |
| 6 | 32 |
| 7 | 29 |
| 8 | <20 |
| 9 | 43 |
| 10 | <20 |
| 11 | 3890 |
| 12 | 34 |
| 13 | 45 |
| 14 | 44 |
| 15 | 64 |
| 16 | 42 |
| 17 | <20 |
| 18 | <20 |
| 19 | 26 |
| 20 | <20 |
| 21 | 23 |
| 22 | 111 |
| 23 | 210 |
| 24 | 92 |
| 25 | 70 |
| 26 | 369 |
| 27 | >30,000 |
| 28 | 281 |

TABLE 3-continued

GI$_{50}$ (in μM) for representative compounds on cellular proliferation of MV4:11 human cancer cell lines

| Example | GI$_{50}$ (nM) |
|---|---|
| 29 | 65 |
| 30 | <20 |
| 31 | <20 |
| 32 | <20 |
| 33 | <20 |
| 34 | <20 |
| 35 | 76 |
| 36 | 23 |
| 37 | <20 |
| 38 | 31 |
| 40 | 291 |
| 41 | 24 |
| 42 | 20 |
| 43 | 563 |
| 44 | 353 |
| 45 | 326 |
| 46 | 444 |
| 47 | 54 |
| 48 | 119 |
| 49 | 34 |
| 50 | 22 |
| 51 | <20 |
| 52 | 62 |
| 53 | 59 |
| 54 | 71 |
| 55 | 59 |
| 56 | 97 |
| 57 | 29,000 |
| 58 | 191 |
| 59 | 4381 |
| 60 | 38 |
| 61 | 31 |
| 62 | 25 |
| 63 | 87 |
| 64 | 284 |
| 65 | <20 |
| 66 | 84 |
| 67 | 35 |
| 68 | <20 |
| 69 | <20 |
| 70 | <20 |
| 71 | <20 |
| 72 | <20 |
| 73 | <20 |
| 74 | 20 |
| 75 | 23 |
| 76 | 613 |
| 77 | 583 |
| 78 | 48 |
| 79 | <20 |
| 80 | 61 |
| 81 | 38 |
| 82 | 384 |
| 83 | 45 |
| 84 | 39 |
| 85 | 92 |
| 86 | 107 |
| 87 | <20 |
| 88 | <20 |
| 89 | 22 |
| 90 | 21 |
| 91 | <20 |
| 92 | 388 |
| 93 | <20 |
| 94 | 28 |
| 95 | 23 |
| 96 | <20 |
| 97 | 83 |
| 98 | 163 |
| 100 | <20 |
| 101 | <20 |
| 102 | <20 |
| 103 | 718 |
| 104 | 24 |
| 105 | <20 |

TABLE 3-continued

GI$_{50}$ (in μM) for representative compounds on cellular proliferation of MV4:11 human cancer cell lines

| Example | GI$_{50}$ (nM) |
|---|---|
| 106 | <20 |
| 107 | 452 |
| 108 | 40 |
| 109 | 22 |
| 110 | <20 |
| 111 | <20 |
| 112 | 23 |
| 113 | <20 |
| 114 | 43 |
| 115 | 40 |
| 116 | <20 |
| 117 | 64 |
| 118 | 3968 |
| 119 | 457 |
| 120 | <20 |
| 121 | <20 |
| 122 | 27 |
| 123 | <20 |
| 124 | <20 |
| 127 | <20 |
| 128 | <20 |
| 129 | 35 |
| 130 | 218 |
| 131 | <20 |
| 132 | <20 |
| 133 | <20 |
| 134 | <20 |
| 135 | <20 |
| 136 | <20 |
| 137 | <20 |
| 138 | <20 |
| 139 | <20 |
| 140 | <20 |
| 141 | <20 |
| 142 | <20 |
| 143 | <20 |
| 144 | <20 |
| 145 | 36 |
| 146 | 26 |
| 147 | 43 |
| 148 | <20 |
| 149 | 75 |
| 150 | 27 |
| 151 | 55 |
| 153 | 47 |
| 154 | 33 |
| 155 | <20 |
| 156 | 28 |
| 157 | <20 |
| 158 | 31 |
| 159 | 159 |
| 160 | <20 |
| 161 | 59 |
| 162 | 88 |
| 163 | 56 |
| 164 | 155 |
| 165 | 129 |
| 166 | <20 |
| 167 | 106 |
| 168 | 46 |
| 169 | <20 |
| 170 | 212 |
| 171 | <20 |
| 172 | <20 |
| 173 | <20 |
| 175 | <20 |
| 176 | 33 |
| 178 | <20 |
| 179 | 33 |
| 180 | 68 |
| 181 | 856 |
| 182 | <20 |
| 183 | <20 |
| 184 | 21 |
| 185 | 55 |

TABLE 3-continued

GI$_{50}$ (in μM) for representative compounds on cellular proliferation of MV4:11 human cancer cell lines

| Example | GI$_{50}$ (nM) |
|---|---|
| 186 | <20 |
| 187 | 43 |
| 188 | <20 |
| 189 | <20 |
| 190 | <20 |
| 191 | <20 |
| 192 | <20 |
| 193 | <20 |
| 194 | <20 |
| 195 | <20 |
| 196 | >10,000 |
| 197 | <20 |
| 198 | <20 |
| 199 | 131 |
| 200 | 28 |
| 201 | 23 |
| 202 | <20 |
| 203 | 49 |
| 204 | 22 |
| 205 | <20 |
| 206 | 43 |
| 207 | <20 |
| 208 | 55 |
| 209 | <20 |
| 210 | <20 |
| 211 | 20 |
| 212 | 35 |
| 213 | <20 |
| 214 | <20 |
| 215 | <20 |
| 216 | <20 |
| 218 | 21 |
| 219 | <20 |
| 220 | <20 |
| 221 | <20 |
| 223 | <20 |
| 225 | <20 |
| 226 | 43 |
| 227 | <20 |
| 228 | <20 |
| 229 | 26 |
| 230 | 54 |
| 231 | <20 |
| 232 | 38 |
| 233 | 26 |
| 237 | 51 |
| 238 | 30 |
| 240 | 23 |
| 241 | <20 |
| 242 | 29 |

It is understood that the foregoing detailed description and accompanying examples are merely illustrative and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A compound of formula (I)

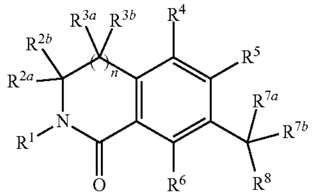

(I)

or a pharmaceutically acceptable salt thereof, wherein:

n is 0, 1, or 2;

$R^1$ is $G^1$;

$G^1$ is a 9- to 12-membered bicyclic aryl, an 8- to 12-membered bicyclic heteroaryl, an 8- to 12-membered fused bicyclic heterocyclyl, or a $C_{3-10}$carbocyclyl fused to a 6-membered arene or to a 5- to 6-membered heteroarene, wherein $G^1$ is optionally substituted with 1-5 substituents independently selected from the group consisting of halogen, $C_{1-6}$alkyl, $C_{1-6}$haloalkyl, oxo, -$L^1$-$X^1$, and -$L^1$-$G^{1a}$;

$X^1$, at each occurrence, is independently —$OR^{1a}$, —$N(R^{1a})_2$, —$SR^{1a}$, cyano, —$C(O)OR^{1a}$, —$C(O)N(R^{1a})_2$, —$C(O)N(R^{1a})SO_2R^{1b}$, —C(NH)NHOH, —C(O)H, —$C(O)R^{1b}$, —$SOR^{1b}$, —$SO_2R^{1b}$, —$SO_2N(R^{1a})_2$, —$NR^{1a}C(O)H$, —$NR^{1a}C(O)R^{1b}$, —$NR^{1a}C(O)OR^{1a}$, —$NR^{1a}C(O)N(R^{1a})_2$, —$NR^{1a}S(O)_2R^{1b}$, or —$NR^{1a}S(O)_2N(R^{1a})_2$;

$R^{1a}$, at each occurrence, is independently hydrogen, $C_{1-6}$-alkyl, $C_{1-6}$haloalkyl, —$C_{2-4}$alkylene-$OR^{1e}$—, —$C_{2-4}$alkylene-$N(R^{1e})_2$, —$C_{2-4}$alkylene-$N(R^{1e})C(O)R^{1e}$, $G^{1a}$, or —$C_{1-6}$alkylene-$G^{1a}$;

$R^{1b}$, at each occurrence, is independently $C_{1-6}$alkyl, $C_{1-6}$haloalkyl, —$C_{1-4}$alkylene-$OR^{1e}$, —$C_{1-4}$alkylene-$N(R^{1e})_2$, —$C_{1-4}$alkylene-$N(R^{1c})C(O)R^{1e}$, $G^{1a}$, or —$C_{1-6}$alkylene-$G^{1a}$;

$L^1$, at each occurrence, is independently a bond or $C_{1-3}$alkylene;

$G^{1a}$ at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, -$L^2$-$X^2$, and -$L^2$-$G^{1b}$;

$X^2$, at each occurrence, is independently —$OR^{1c}$, —$N(R^{1c})_2$, —$SR^{1c}$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NR^{1c}C(O)R^{1c}$, —$NR^{1c}C(O)OR^{1c}$, —$NR^{1c}C(O)N(R^{1c})_2$, —$NR^{1c}S(O)_2R^{1d}$, or —$NR^{1c}S(O)_2N(R^{1c})_2$;

$R^{1c}$, at each occurrence, is independently hydrogen, $C_{1-6}$alkyl, $C_{1-6}$haloalkyl, $G^{1b}$, or —$C_{1-3}$alkylene-$G^{1b}$, wherein alternatively two $R^{1c}$, together with a common nitrogen atom to which the $R^{1c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{1d}$, at each occurrence, is independently $C_{1-6}$alkyl, $C_{1-6}$haloalkyl, $G^{1b}$, or —$C_{1-3}$alkylene-$G^{1b}$;

$R^{1e}$, at each occurrence, is independently hydrogen, $C_{1-4}$alkyl, $C_{1-4}$haloalkyl, $G^{1b}$, or —$C_{1-3}$alkylene-$G^{1b}$, wherein alternatively two $R^{1e}$, together with a common nitrogen atom to which the $R^{1e}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$L^2$, at each occurrence, is independently a bond or $C_{1-3}$alkylene;

$G^{1b}$ is a $C_{3-6}$cycloalkyl, a 4- to 6-membered monocyclic heterocyclyl containing 1-2 heteroatoms independently selected from O, N, and S, a 5- to 6-membered heteroaryl containing 1-4 heteroatoms independently selected from O, N, and S, or a phenyl, wherein $G^{1b}$ is optionally substituted with 1-4 substituents independently selected from the group consisting of halogen, cyano, $C_{1-4}$alkyl, $C_{1-4}$haloalkyl, oxo, —OH, and —$OC_{1-4}$alkyl;

$R^{2a}$, $R^{2b}$, $R^{3a}$, and $R^{3b}$ are independently hydrogen, halogen, $C_{1-4}$alkyl, $C_{1-4}$haloalkyl, or —$OC_{1-4}$alkyl; or alternatively any two of $R^{2a}$, $R^{2b}$, $R^{3a}$, and $R^{3b}$ are taken together with the atom or atoms to which they attach to form a 3-8 membered saturated or partially unsaturated carbocyclic or heterocyclic ring that is optionally substituted with 1-4 substituents independently selected from the group consisting of halogen, $C_{1-4}$alkyl, $C_{1-4}$haloalkyl, and —$OC_{1-4}$alkyl;

or alternatively one $R^{3a}$ and one $R^{3b}$ are taken together to form an oxo group;

$R^4$ is hydrogen, halogen. $C_{1-6}$alkyl, $C_{1-6}$-haloalkyl, $C_{1-6}$haloalkenyl, —$OR^{4a}$, —$SR^{4a}$, —$N(R^{4a})_2$, —$S(O)R^{4b}$, —$S(O)_2R^{4b}$, —$S(O)N(R^{4a})_2$, —$C(O)N(R^{4a})_2$, —$C(O)^{4a}$, —$NR^{4a}C(O)R^{4a}$, $NR^{4a}C(O)OR^{4a}$, —$NR^{4a}C(O)N(R^{4a})_2$, —$NR^{4a}S(O)_2R^{4b}$, —$NR^{4a}S(O)_2N(R^{4a})_2$, or $G^2$;

$R^{4a}$ at each occurrence, is independently hydrogen, $C_{1-6}$alkyl, $C_{1-6}$haloalkyl, $G^2$, or —$C_{1-3}$alkylene-$G^2$;

$R^{4b}$ is $C_{1-6}$alkyl, $C_{1-6}$haloalkyl, $G^2$, or —$C_{1-3}$alkylene-$G^2$;

$G^2$, at each occurrence, is independently a $C_{3-10}$carbocyclyl, a 6- to 12-membered aryl, a 5- to 12-membered heteroaryl, or a 4- to 12-membered heterocyclyl, wherein $G^2$ is optionally substituted with 1-5 substituents independently selected from the group consisting of halogen, $C_{1-6}$alkyl, $C_{1-6}$haloalkyl, oxo, —$OR^{4c}$, —$N(R^{4c})_2$, —$SR^{4c}$, cyano, —$C(O)OR^{4c}$, —$C(O)N(R^{4c})_2$, —$C(O)R^{4c}$, —$SOR^{4d}$, —$SO_2R^{4d}$, —$SO_2N(R^{4c})_2$, —$NR^{4c}C(O)R^{4c}$, —$NR^{4c}(O)OR^{4c}$, —$NR^{4c}C(O)N(R^{4c})_2$, —$NR^{4c}S(O)_2R^{4d}$—$NR^{4c}S(O)_2N(R^{4c})_2$, $C_{3-8}$cycloalkyl, and —$C_{1-3}$alkylene-$C_{3-8}$-cycloalkyl, wherein each $C_{3-8}$cycloalkyl is optionally substituted with 1-4 substituents independently selected from the group consisting, of $C_{1-4}$alkyl and halogen;

$R^{4c}$, at each occurrence, is independently hydrogen, $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein alternatively two $R^{4c}$, together with a common nitrogen atom to which the $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{4d}$, at each occurrence, is independently $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^5$ and $R^6$ are each independently hydrogen, halogen, $C_{1-4}$alkyl, $C_{1-4}$haloalkyl, or —$OC_{1-4}$alkyl;

$R^{7a}$ and $R^{7b}$ are independently selected from the group consisting of hydrogen, halogen, hydroxy, $C_{1-4}$alkyl, and $C_{1-4}$haloalkyl, or $R^{7a}$ and $R^{7b}$ are taken together to form an oxo group; and $R^8$ is a 5- to 6-membered heterocyclic ring containing 1-3 heteroatoms and 1-3 double bonds, wherein one of the 1-3 heteroatoms is a nitrogen and the remaining heteroatoms are independently selected from nitrogen and oxygen, wherein R is optionally substituted with 1-3 substituents independently selected from the group consisting of halogen, $C_{1-4}$alkyl, $C_{1-4}$haloalkyl, imino, oxo, $NO_2$, $NH_2$, —$NH(C_{1-4}$alkyl), —$N(C_{1-4}$alkyl$)_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

Clause 2. The compound of clause 1, or a pharmaceutically acceptable salt thereof, wherein:

$G^1$ is a 9- to 12-membered bicyclic aryl, an 8- to 12-membered bicyclic heteroaryl, an 8- to 12-membered fused bicyclic heterocyclyl, or a $C_{3-10}$carbocyclyl fused to a 6-membered arene or to a 5- to 6-membered heteroarene, wherein $G^1$ is optionally substituted with 1-5 substituents independently selected from the group consisting of halogen, $C_{1-6}$alkyl, $C_{1-6}$haloalkyl, oxo, —$OR^{1a}$, —$N(R^{1a})_2$, —$SR^{1a}$, cyano, —$C(O)OR^{1a}$, —$C(O)N(R^{1a})_2$, —C(O)H, —$C(O)R^{1b}$, —$SOR^{1b}$, —$SO_2R^{1b}$, —$SO_2N(R^{1a})_2$, —$NR^{1a}C(O)H$, —$NR^{1a}C(O)R^{1b}$, —$NR^{1a}C(O)OR^{1a}$, —$NR^{1a}C(O)N(R^{1a})_2$, —$NR^{1a}S(O)_2R^{1b}$, —$NR^{1a}S(O)_2N(R^{1a})_2$, and -$L^1$-$G^{1a}$;

$R^{1a}$, at each occurrence, is independently hydrogen, $C_{1-6}$-alkyl, $C_{1-6}$haloalkyl, —$C_{2-4}$alkylene-$OR^{1e}$—, —$C_{2-4}$alkylene-$N(R^{1e})_2$, $G^{1a}$, or —$C_{1-6}$alkylene-$G^{1a}$;

$R^{1b}$, at each occurrence, is independently $C_{1-6}$alkyl, $C_{1-6}$haloalkyl, —$C_{1-4}$alkylene-$OR^{1e}$, —$C_{1-4}$alkylene-$N(R^{1e})_2$, $G^{1a}$, or —$C_{1-6}$alkylene-$G^{1a}$;

$L^1$ is a bond or $C_{1-3}$alkylene;

$G^{1a}$ at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, —$OR^{1c}$, —$N(R^{1c})_2$, —$SR^{1c}$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NR^{1c}C(O)R^{1c}$, —$NR^{1c}C(O)OR^{1c}$, —$NR^{1c}C(O)N(R^{1c})_2$, —$NR^{1c}S(O)_2R^{1d}$, —$NR^{1c}S(O)_2N(R^{1c})_2$, $C_{3-6}$cycloalkyl, and —$C_{1-3}$alkylene-$C_{3-6}$cycloalkyl;

$R^{1e}$, at each occurrence, is independently hydrogen, $C_{1-4}$alkyl, $C_{1-4}$haloalkyl, $C_{3-6}$cycloalkyl, or —$C_{1-3}$alkylene-$C_{3-6}$cycloalkyl, wherein alternatively two $R^{1e}$, together with a common nitrogen atom to which the $R^{1e}$ attach form a4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{1c}$ and $R^{4c}$, at each occurrence, are independently hydrogen, $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein alternatively two $R^{1c}$ and/or two $R^{4c}$, together with a common nitrogen atom to which the $R^{1c}$ and/or $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{1d}$ and $R^{4d}$, at each occurrence, are independently $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

and $R^8$ is 5- to 6-membered heterocyclic ring containing 1-3 heteroatoms and 1-3 double bonds, wherein one of the 1-3 heteroatoms is a nitrogen and the remaining heteroatoms are independently selected from nitrogen and oxygen, wherein BY is optionally substituted with 1-3 substituents independently selected from the group consisting of halogen, $C_{1-4}$alkyl, $C_{1-4}$haloalkyl, imino, oxo, $NH_2$, —NH($C_{1-4}$alkyl), —N($C_{1-4}$alkyl)$_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

Clause 2.1. The compound of clause 1, or a pharmaceutically acceptable salt thereof, wherein $R^8$ is an imidazolyl unsubstituted or substituted with 1-3 substituents independently selected from the group consisting of halogen, $C_{1-4}$alkyl, $C_{1-4}$haloalkyl, $NO_2$, $NH_2$, —NH($C_{1-4}$alkyl), —N($C_{1-4}$alkyl)$_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

Clause 3 The compound of any one of clauses 1-3, or a pharmaceutically acceptable salt thereof, wherein $R^8$ is

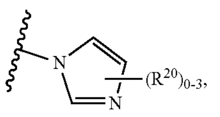
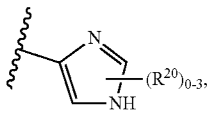
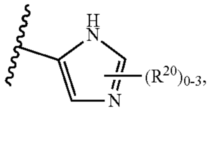
or
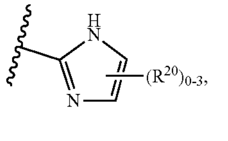

and $R^{20}$, at each occurrence, is independently halogen, $C_{1-4}$alkyl, $C_{1-4}$haloalkyl, $NH_2$, —NH($C_{1-4}$alkyl), —N($C_{1-4}$alkyl)$_2$, $C_{3-8}$cycloalkyl, or —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

Clause 4. The compound of clause 3, or a pharmaceutically acceptable salt thereof, wherein $R^8$ is

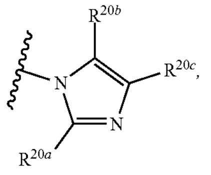
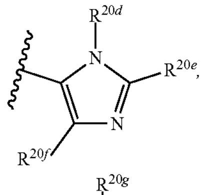
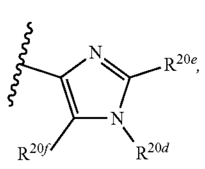
or
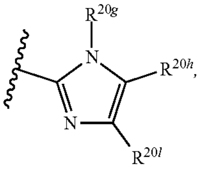

$R^{20a}$ is hydrogen, $C_{1-4}$alkyl, $NH_2$, —NH($C_{1-4}$alkyl), —N($C_{1-4}$alkyl)$_2$, or $C_{3-8}$cycloalkyl; and $R^{20b}$, $R^{20c}$, $R^{20d}$, $R^{20e}$, $R^{20f}$, $R^{20g}$, $R^{20h}$, and $R^{20i}$ are each independently hydrogen, $C_{1-4}$alkyl, or $C_{3-8}$cycloalkyl.

Clause 5. The compound of clause 4, or a pharmaceutically acceptable salt thereof, wherein $R^8$ is

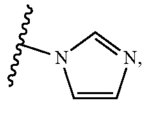
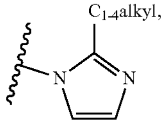
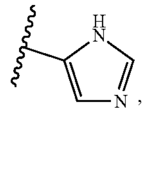
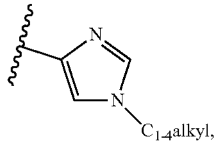
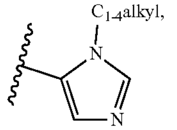
or
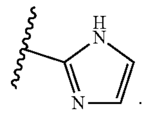

Clause 6. The compound of clause 1 or 2.1, or a pharmaceutically acceptable salt thereof, wherein $R^8$ is

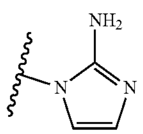
or
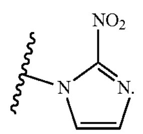

Clause 7. The compound of clause 1 or 2, or a pharmaceutically acceptable salt thereof, wherein $R^8$ is a pyridinyl.

Clause 8. The compound of any of clauses 1-7, or a pharmaceutically acceptable salt thereof, wherein $G^1$ is a naphthalenyl, an 8- to 10-membered fused bicyclic heteroaromatic ring system, a 5- to 7-membered monocyclic heterocyclyl fused to a 6-membered arene or fused to a 5- to 6-membered heteroarene, or a $C_{5-7}$-carbocyclyl fused to a 6-membered arene or fused to a 5- to 6-membered heteroarene, wherein $G^1$ is optionally substituted with 1-5 substituents independently selected from the group consisting of halogen, $C_{1-6}$alkyl, $C_{1-6}$haloalkyl, oxo, —$OR^{1a}$, —N($R^{1a}$)$_2$, —$SR^{1a}$, cyano, —C(O)$OR^{1a}$, —C(O)N($R^{1a}$)$_2$, —C(O)H, —C(O)$R^{1b}$, —$SOR^{1b}$, —$SO_2R^{1b}$, —$SO_2$N($R^{1a}$)$_2$, —$NR^{1a}C(O)H$, —$NR^{1a}C(O)R^{1b}$, —$NR^{1a}C(O)OR^{1a}$, —$NR^{13}C(O)N(R^{1a})_2$—$NR^{1a}S(O)_2R^{1b}$, —$NR^{1a}S(O)_2N(R^{1a})_2$, and -$L^1$-$G^{1a}$.

Clause 9. The compound of clause 8, or a pharmaceutically acceptable salt thereof, wherein $G^1$ is the naphthalenyl.

Clause 10. The compound of clause 9, or a pharmaceutically acceptable salt thereof, wherein $G^1$ is naphthalen-1-yl.

Clause 11. The compound of clause 8, or a pharmaceutically acceptable salt thereof, wherein $G^1$ is the 8- to 10-membered fused bicyclic heteroaromatic ring system.

Clause 12. The compound of clause 11, or a pharmaceutically acceptable salt thereof, wherein the 8- to 10-membered fused bicyclic heteroaromatic ring system has a first ring nitrogen atom and optionally a second ring heteroatom selected from nitrogen and oxygen.

Clause 13. The compound of clause 12, or a pharmaceutically acceptable salt thereof, wherein the 8- to 10-membered fused bicyclic heteroaromatic ring system is a quinolinyl, isoquinolinyl, indolyl, indazolyl, benzoxazolyl, quinazolinyl, or pyrrolo[2,3-b]pyridinyl.

Clause 14. The compound of clause 12, or a pharmaceutically acceptable salt thereof, wherein the 8- to 10-membered fused bicyclic heteroaromatic ring system is a quinolin-4-yl, quinolin-5-yl, isoquinolin-1-yl, isoquinolin-4-yl, quinazolin-4-yl, indol-3-yl, indol-4-yl, indazol-3-yl, benzo[d]oxazol-7-yl, pyrrolo[2,3-b]pyridin-3-yl, or pyrrolo[2,3-b]pyridin-4-yl.

Clause 15. The compound of any of clauses 1-14, or a pharmaceutically acceptable salt thereof, wherein $G^1$ is optionally substituted with 1-3 substituents independently selected from the group consisting of halogen, $C_{1-6}$alkyl, $C_{1-6}$haloalkyl, —$OR^{1a}$, —$N(R^{1a})_2$, —$C(O)OR^{1a}$, —$C(O)N(R^{1a})_2$, —$C(O)R^{1b}$, and $G^{1a}$, wherein $G^{1a}$ is optionally substituted with 1-4 substituents independently selected from the group consisting of halogen, $C_{1-4}$alkyl, $C_{1-4}$haloalkyl, oxo, OH, —$OC_{1-4}$alkyl, —$C(O)C_{1-4}$alkyl, —$C(O)OC_{1-4}$alkyl, $C_{3-6}$cycloalkyl, and —$C_{1-3}$alkylene-$C_{3-6}$cycloalkyl.

Clause 16. The compound of clause 15, or a pharmaceutically acceptable salt thereof, wherein $G^1$ is optionally substituted with 1-3 substituents independently selected from the group consisting of halogen, $C_{1-4}$alkyl, $C_{1-4}$haloalkyl, —$OC_{1-4}$alkyl, —$OC_{1-4}$haloalkyl, —$NH_2$, —$NHC_{1-4}$alkyl, —$N(C_{1-4}alkyl)_2$, —$N(C_{1-4}alkyl)$-$C_{2-4}$alkylene-$N(C_{1-4}alkyl)_2$, —C(O)OH, —$C(O)OC_{1-4}$alkyl, —$C(O)NH_2$, —$C(O)NH(C_{1-4}alkyl)$, —C(O)NH—$C_{2-4}$alkylene-$OC_{1-4}$alkyl, —$C(O)N(C_{1-4}alkyl)_2$, —$C(O)G^{1a}$, and $G^{1a}$, wherein $G^{1a}$ is optionally substituted with 1-4 substituents independently selected from the group consisting of halogen, $C_{1-4}$alkyl, $C_{1-4}$haloalkyl, oxo, —OH, —$O(C_{1-4}$alkyl, —$C(O)C_{1-4}$alkyl, —$(C(O)OC_{1-4}$alkyl, $C_{3-6}$cycloalkyl, and —$C_{1-3}$alkylene-$C_{3-6}$cycloalkyl.

Clause 17. The compound of any of clauses 1-8 or 11-16, or a pharmaceutically acceptable salt thereof, wherein $G^1$ is

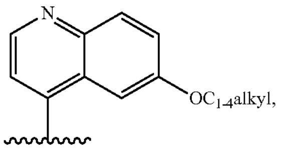

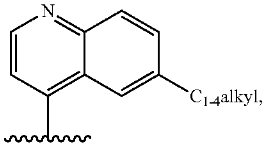

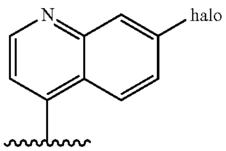

,

-continued

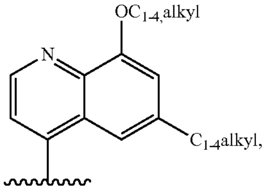

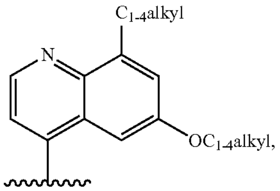

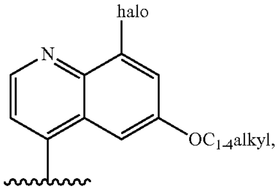

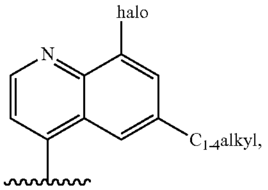

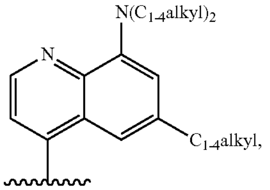

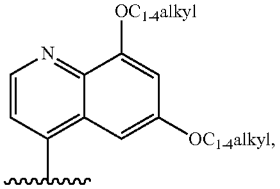

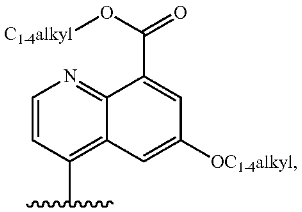

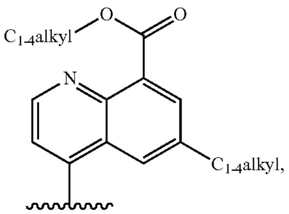

-continued
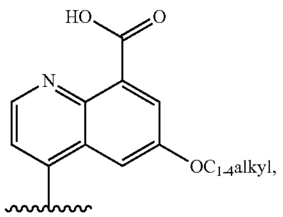
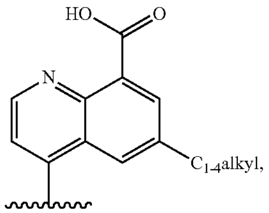
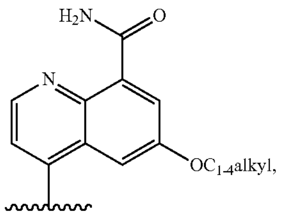
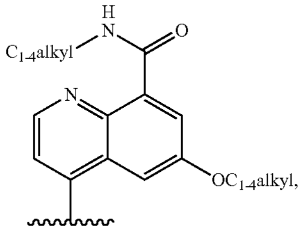
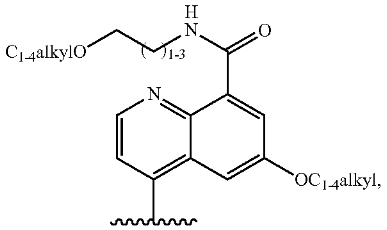
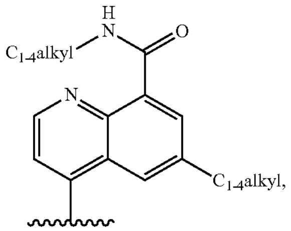
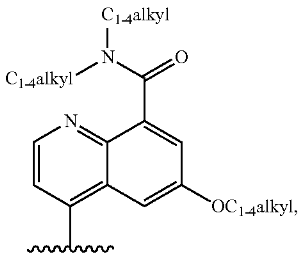
-continued
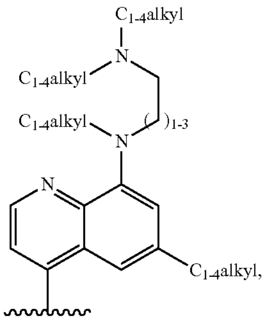
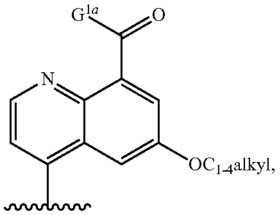
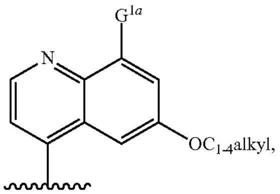
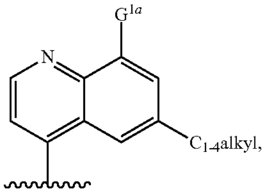
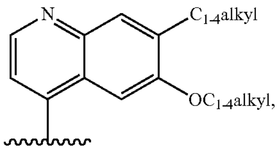
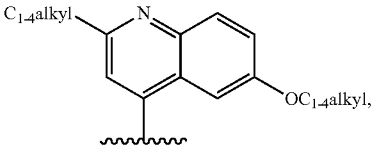
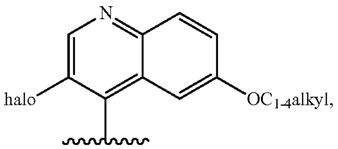
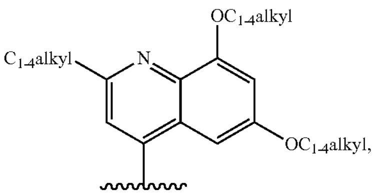
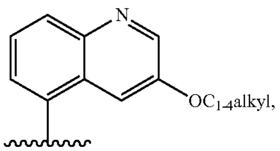

-continued

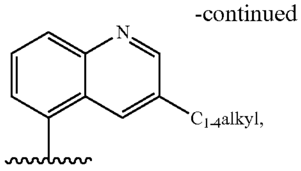

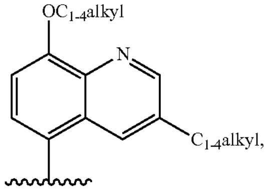

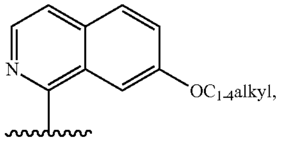

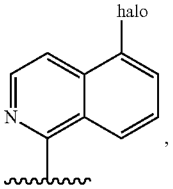

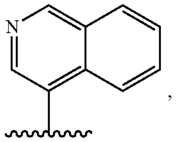

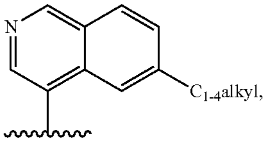

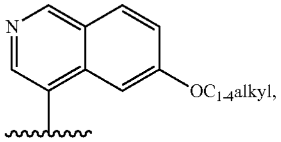

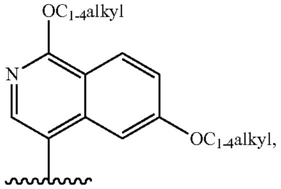

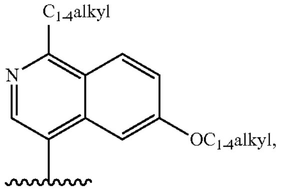

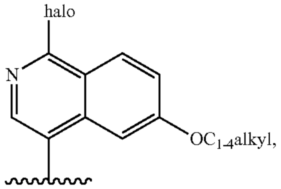

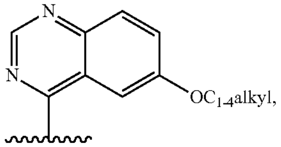

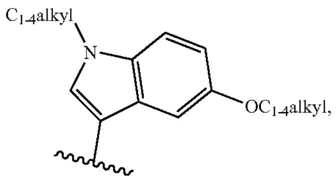

-continued

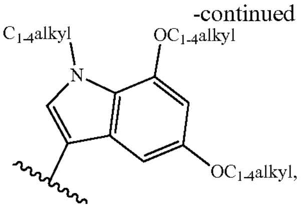

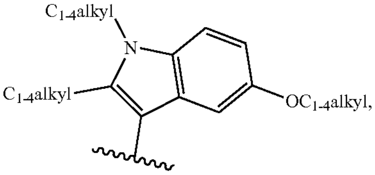

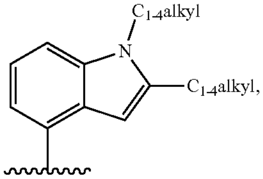

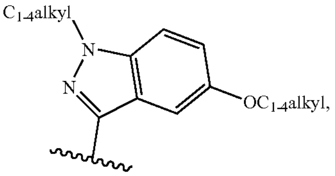

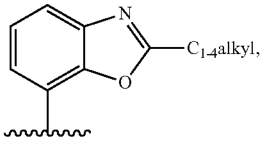

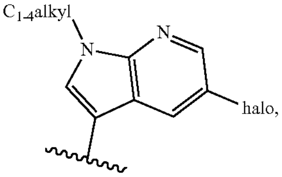

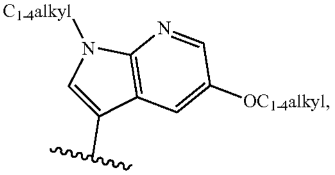

or

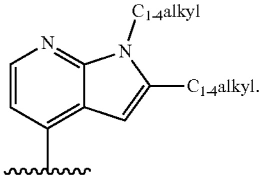

Clause 18. The compound of any of clauses 1-1-7, or a pharmaceutically acceptable salt thereof, wherein $G^{1a}$ is the 4- to 10-membered heterocyclyl.

Clause 19. The compound of clause 18, or a pharmaceutically acceptable salt thereof, wherein the 4- to 10-membered heterocyclyl at $G^{1a}$ is a 4- to 8-membered monocyclic heterocyclyl.

Clause 20. The compound of clause 18 or 19, or a pharmaceutically acceptable salt thereof, wherein the heterocyclyl of $G^{1a}$ has a first nitrogen ring atom and optionally has a second ring heteroatom selected from nitrogen and oxygen, the heterocyclyl of $G^1$ being attached at the first nitrogen ring atom and being optionally substituted with 1-4 substituents independently selected from the group consisting of halogen, $C_{1-4}$alkyl, $C_{1-4}$haloalkyl, oxo, —C(O)$C_{1-4}$alkyl, —C(O)O$C_{1-4}$alkyl, $C_{3-6}$cycloalkyl, and —$C_{1-3}$alkylene-$C_{3-6}$cycloalkyl.

Clause 21. The compound of clause 20, or a pharmaceutically acceptable salt thereof, wherein the heterocyclyl of $G^{1a}$ is a pyrrolidin-1-yl, morpholin-4-yl, or piperazin-1-yl, and optionally substituted with $C_{1-4}$alkyl, oxo, or —C(O)$C_{1-4}$alkyl.

Clause 22 The compound of clause 17, or a pharmaceutically acceptable salt thereof, wherein $G^1$ is

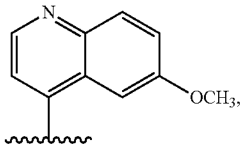
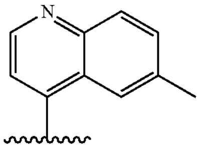
,
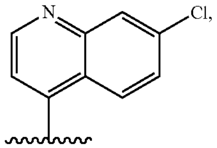
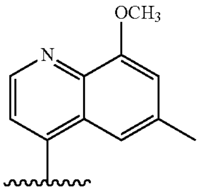
,
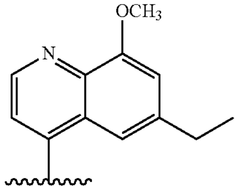
,
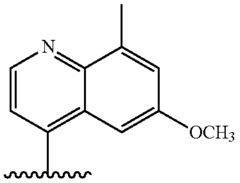
,
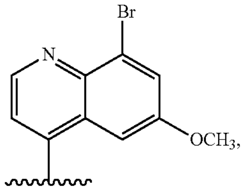
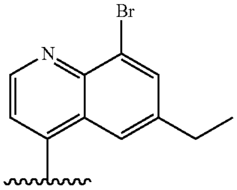
,
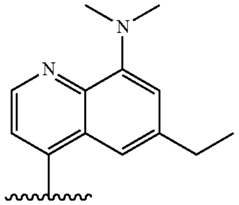
,
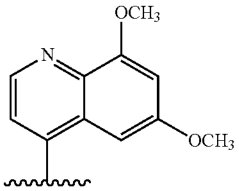
,
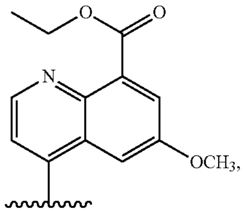
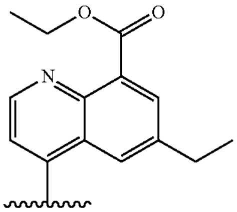
,
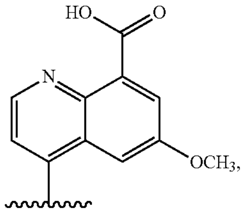
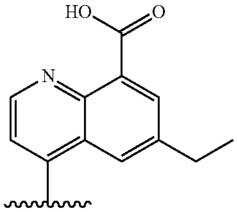
, -continued

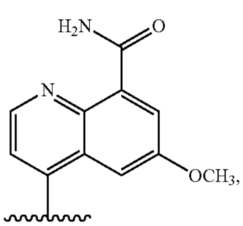
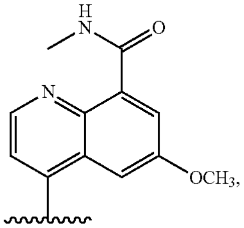
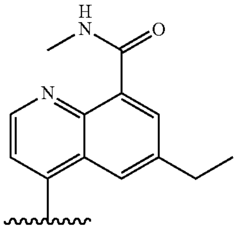
,
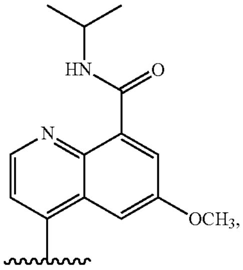
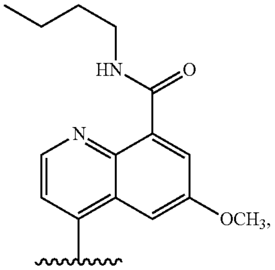
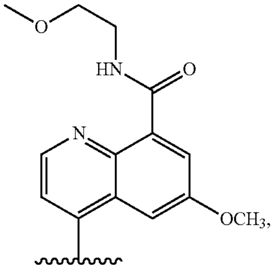
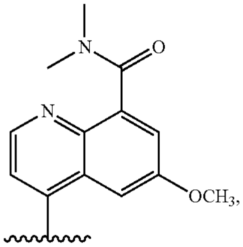
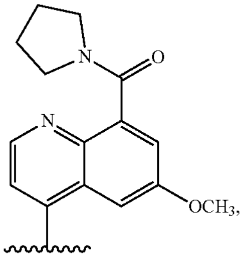
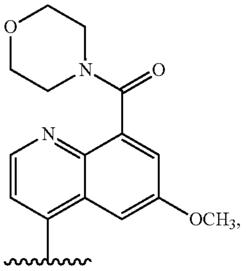

-continued
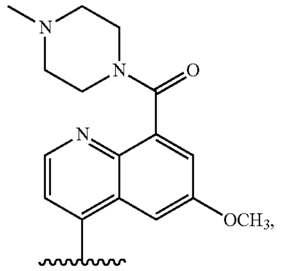
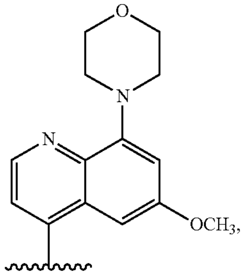
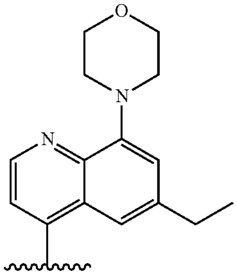
,
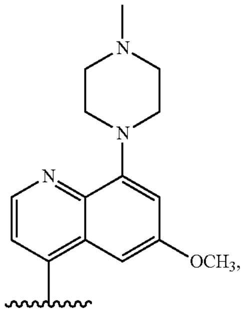
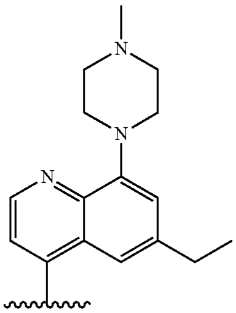
,
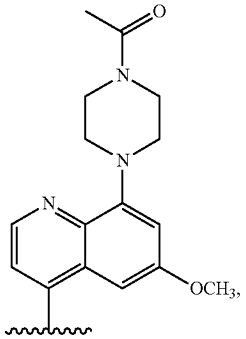
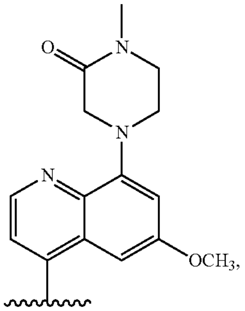
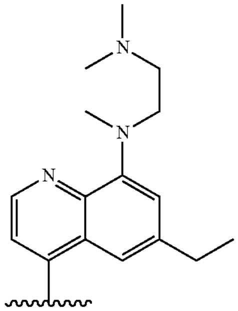
,
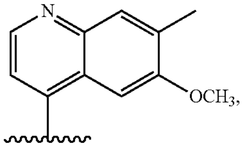
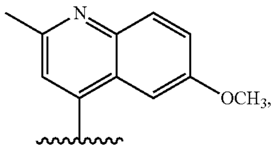
-continued
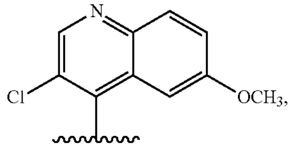
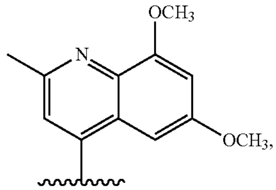
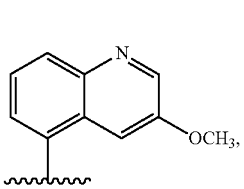
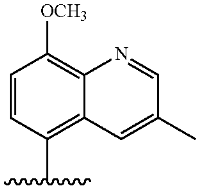
,
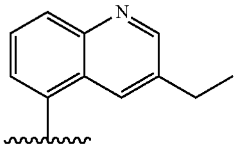
,
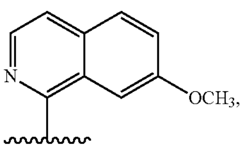
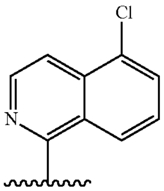
,
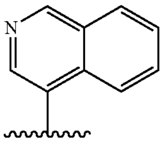
,
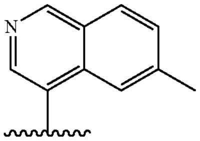
,
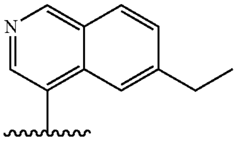
,
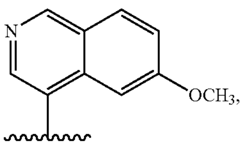
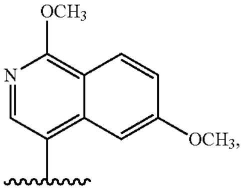
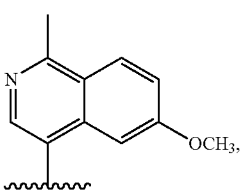
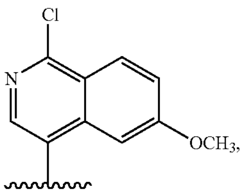
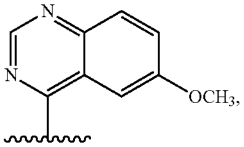
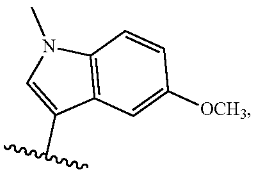

-continued

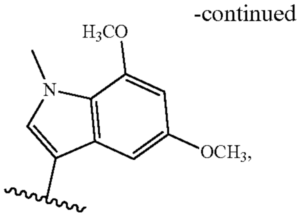

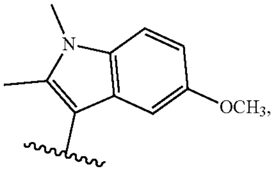

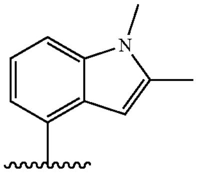
,
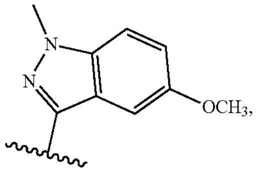

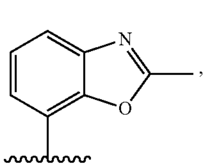
,
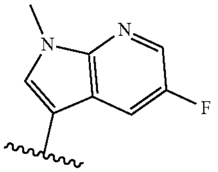
,

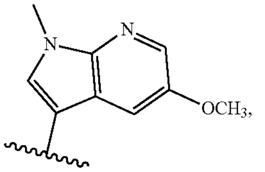

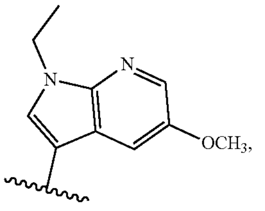
or
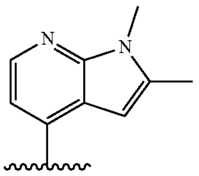
.

Clause 23. The compound of clause 8, or a pharmaceutically acceptable salt thereof, wherein $G^1$ is the 5- to 7-membered monocyclic heterocyclyl fused to a 6-membered arene or fused to a 5- to 6-membered heteroarene.

Clause 24. The compound of clause 23, or a pharmaceutically acceptable salt thereof, wherein the 5- to 7-membered monocyclic heterocyclyl has one oxygen ring atom or one nitrogen atom.

Clause 25. The compound of clause 23 or 24, or a pharmaceutically acceptable salt thereof, wherein the 5- to 6-membered heteroarene is a pyridine.

Clause 26. The compound of clause 25, or a pharmaceutically acceptable salt thereof, wherein the fused 6-membered arene or pyridine is optionally substituted with 1-2 substituents independently selected from the group consisting of halo, $C_{1-4}$alkyl, —$OC_1$alkyl, and $C_{3-6}$cycloalkyl.

Clause 27 The compound of clause 26, or a pharmaceutically acceptable salt thereof, wherein $G^1$ is

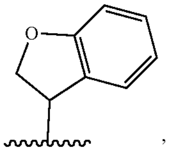
,
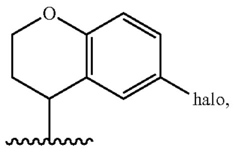

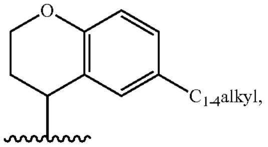

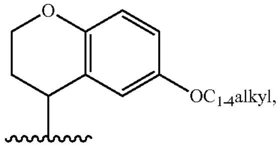

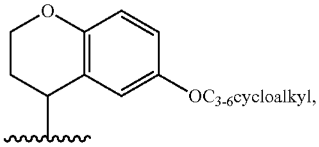

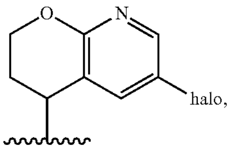
or
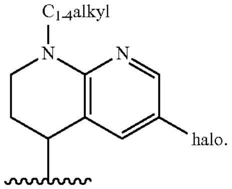

Clause 28. The compound of clause 27, or a pharmaceutically acceptable salt thereof, wherein $G^1$ is

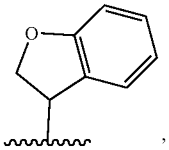
,
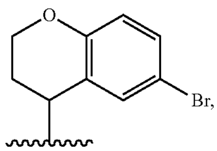

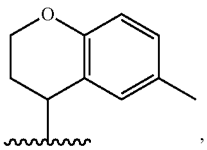
,
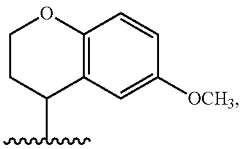

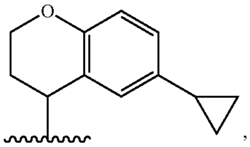
,

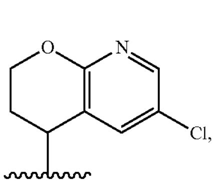
or
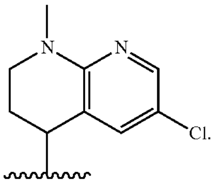

Clause 29. The compound of clause 8, or a pharmaceutically acceptable salt thereof, wherein $G^1$ is the $C_{5-7}$carbocyclyl fused to a 6-membered arene or fused to a 5- to 6-membered heteroarene.

Clause 30. The compound of clause 29, or a pharmaceutically acceptable salt thereof, wherein the $C_{5-7}$carbocyclyl is a monocyclic $C_{5-7}$cycloalkyl.

Clause 31. The compound of clause 29 or 30, or a pharmaceutically acceptable salt thereof, wherein the 5- to 6-membered heteroarene is a pyridine.

Clause 32. The compound of clause 31, or a pharmaceutically acceptable salt thereof, wherein the fused 6-membered arene or pyridine is optionally substituted with halo, $C_{1-4}$alkyl, —$OC_{1-4}$alkyl or $C_{3-6}$cycloalkyl.

Clause 33. The compound of clause 32, or a pharmaceutically acceptable salt thereof, wherein $G^1$, is

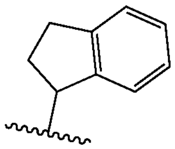

,

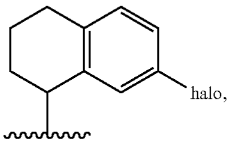

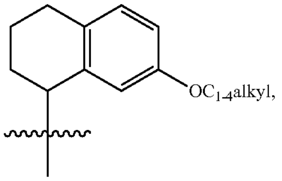

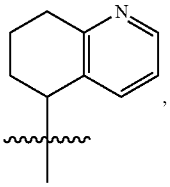

, or

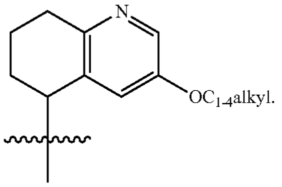

Clause 33.1. The compound of clause 33, or a pharmaceutically acceptable salt thereof, wherein $G^1$ is

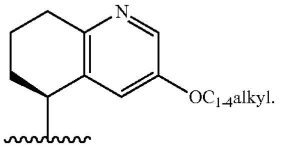

Clause 34. The compound of clause 33, or a pharmaceutically acceptable salt thereof, wherein $G^1$ is

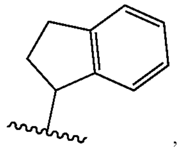

,

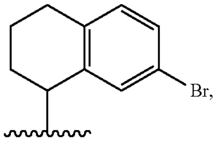

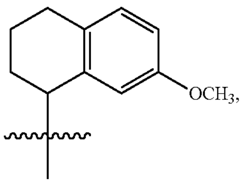

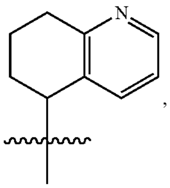

, or

-continued

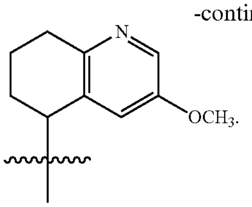

Clause 34.1. The compound of clause 34, or a pharmaceutically acceptable salt thereof, wherein $G^1$ is

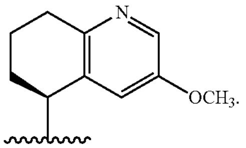 [SMILES: *[C@H]1CCCc2ncc(OC)cc21]

Clause 35 The compound of any of clauses 1-8, or a pharmaceutically acceptable salt thereof, wherein $G^1$ is attached at a ring atom in $G^1$ adjacent to a ring fusion in $G^1$.

Clause 36 The compound of clause 35, or a pharmaceutically acceptable salt thereof, wherein:

$G^1$ is

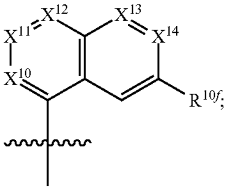

$X^{10}$ is $CR^{10a}$ or N;

$X^{11}$ is $CR^{10b}$ or N;

$X^{12}$ is $CR^{10c}$ or N;

$X^{13}$ is $CR^{10d}$ or N;

$X^{14}$ is $CR^{10e}$ or N;

provided that no more than two of $X^{10}$-$X^{14}$ are N;

$R^{10a}$ is hydrogen, halogen, $C_{1-4}$alkyl, or $C_{1-4}$fluoroalkyl;

$R^{10b}$ is hydrogen, halogen, $C_{1-4}$alkyl, or $C_{1-4}$fluoroalkyl;

$R^{10c}$ is hydrogen, halogen, $C_{1-4}$alkyl, $C_{1-4}$fluoroalkyl, or $OC_{1-4}$alkyl;

$R^{10d}$ is hydrogen, halogen, $C_{1-4}$alkyl, $C_{1-4}$fluoroalkyl, $-L^1-X^1$, or $-L^1-G^{1a}$;

$R^{10e}$ is hydrogen, halogen, $C_{1-4}$alkyl, or $C_{1-4}$fluoroalkyl; and $R^{10f}$ is hydrogen, halogen, $C_{1-4}$alkyl, $C_{1-4}$fluoroalkyl, OH, $OC_{1-4}$alkyl, $OC_{1-4}$fluoroalkyl, $NH_2$, $NHC_{1-4}$alkyl, $N(C_{1-4}alkyl)_2$, or a 4- to 8-membered monocyclic heterocyclyl containing 1-2 heteroatoms selected from N, O, and S, wherein the heterocyclyl is optionally substituted with 1-4 substituents independently selected from the group consisting of halogen, cyano, oxo, $C_{1-4}$alkyl, $C_{1-4}$fluoroalkyl, OH, $OC_{1-4}$alkyl, $OC_{1-4}$fluoroalkyl, $NH_2$, $NHC_{1-4}$alkyl, and $N(C_{1-4}alkyl)_2$.

Clause 36.1. The compound of clause 35, or a pharmaceutically acceptable salt thereof, wherein $G^1$ is an optionally substituted 10-membered fused bicyclic ring system of formula

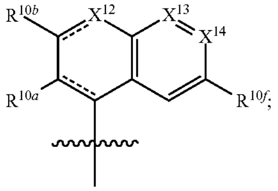

each "⎓" represents a double bond or a single bond;
$X^{12}$ is N, $CR^{10c}$ or $CHR^{10c}$;
$X^{13}$ is $CR^{10d}$ or N;
$X^{14}$ is $CR^{10e}$ or N;
$R^{10a}$ is hydrogen, halogen, $C_{1-4}$alkyl, or $C_{1-4}$fluoroalkyl;
$R^{10b}$ is hydrogen, halogen, $C_{1-4}$alkyl, or $C_{1-4}$fluoroalkyl;
$R^{10c}$ is hydrogen, halogen, $C_{1-4}$alkyl, $C_{1-4}$fluoroalkyl, or —$OC_{1-4}$alkyl;
$R^{10d}$ is $-L^1-X^1$, hydrogen, halogen, $C_{1-4}$alkyl, $C_{1-4}$fluoroalkyl, or $-L^1-G^{1a}$;
$R^{10e}$ is hydrogen, halogen, $C_{1-4}$alkyl, or $C_{1-4}$fluoroalkyl; and
$R^{10f}$ is $C_{1-4}$alkyl, —$OC_{1-4}$alkyl, hydrogen, halogen, $C_{1-4}$fluoroalkyl, OH, —$OC_{1-4}$fluoroalkyl, $NH_2$, $NHC_{1-4}$alkyl, $N(C_{1-4}alkyl)_2$, or a 4- to 8-membered monocyclic heterocyclyl containing 1-2 heteroatoms selected from N, O, and S, wherein the heterocyclyl is optionally substituted with 1-4 substituents independently selected from the group consisting of halogen, cyano, oxo, $C_{1-4}$alkyl, $C_{1-4}$fluoroalkyl, OH, —$OC_{1-4}$alkyl, —$OC_{1-4}$fluoroalkyl, $NH_2$, —$NHC_{1-4}$alkyl, and —$N(C_{1-4}alkyl)_2$.

Clause 36.2. The compound of clause 36.1, or a pharmaceutically acceptable salt thereof, wherein each "⎓" represents a double bond; $X^{12}$ is N; and $X^{13}$ is $CR^{10d}$.

Clause 36.3. The compound of clause 36.2, or a pharmaceutically acceptable salt thereof, wherein $R^{10a}$ is hydrogen; $R^{10b}$ is hydrogen or $C_{1-4}$alkyl; $R^{10d}$ is —$C(O)N(R^{1a})_2$ or —$OR^{1a}$; $R^{10e}$ is hydrogen; and $R^{10f}$ is $C_{1-4}$alkyl or $OC_{1-4}$alkyl.

Clause 37. The compound of any of clauses 36-36.2, or a pharmaceutically acceptable salt thereof, wherein $R^{10d}$ is hydrogen, halogen. $C_{1-4}$alkyl, cyano, $OC_{1-4}$alkyl, $OC_{1-4}$fluoroalkyl, $NH_2$, $NHC_{1-4}$alkyl, $N(C_{1-4}alkyl)_2$, $NHC(O)C_{1-4}$alkyl, $N(C_{1-4}alkyl)C(O)C_{1-4}$alkyl,

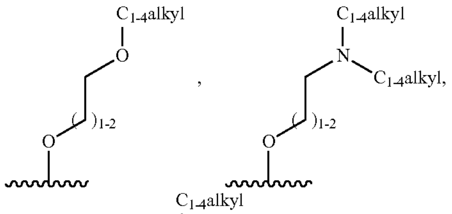

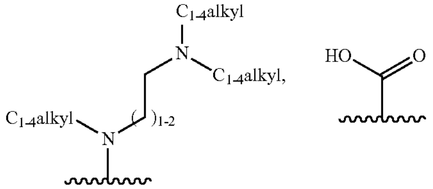

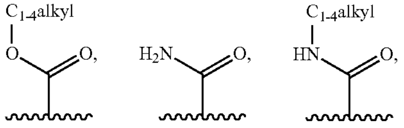

-continued

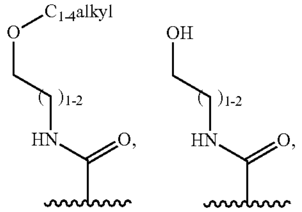

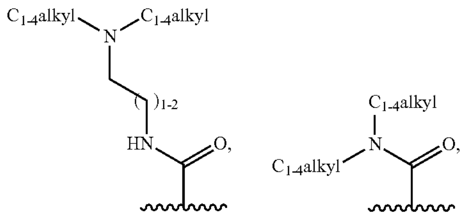

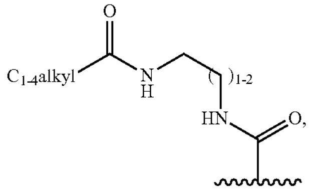

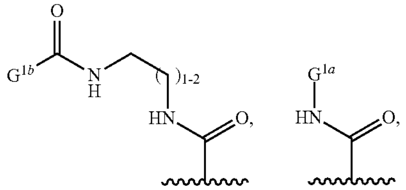

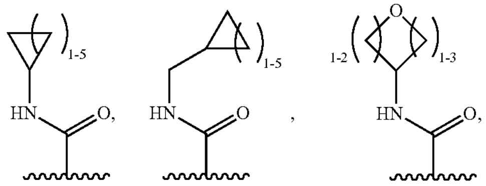

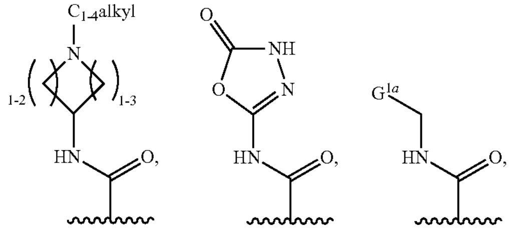

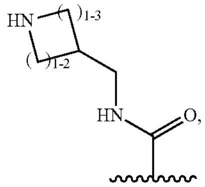

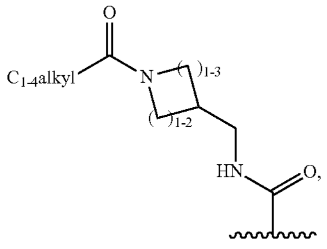

-continued
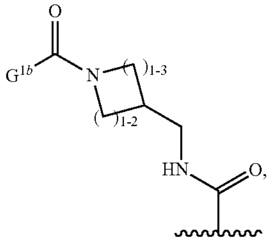
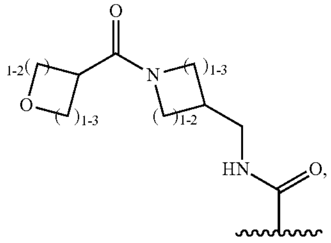
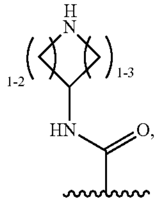
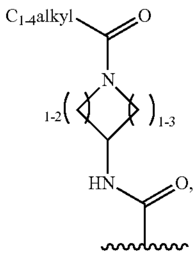
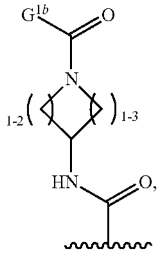
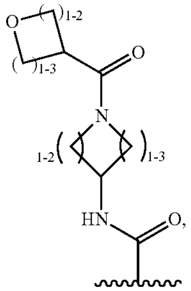
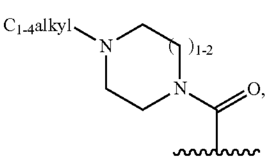
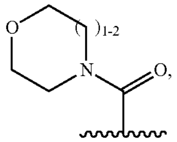
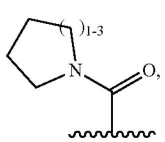
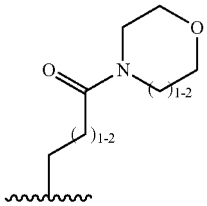
,
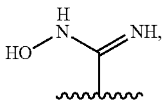
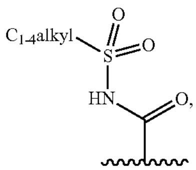
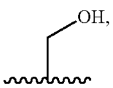
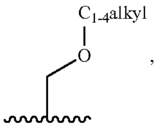
,
-continued
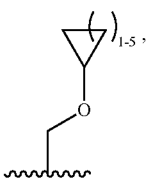
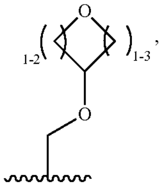
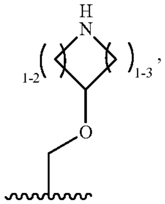
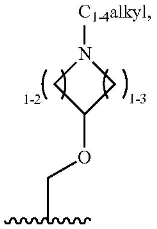
,
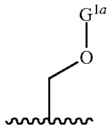
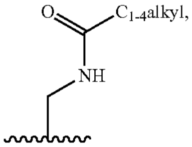
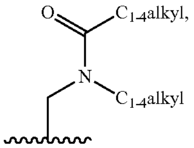
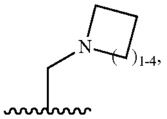
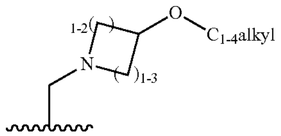
,
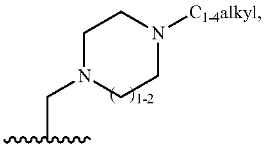
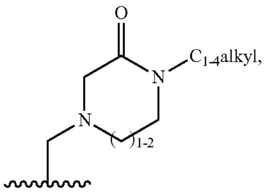
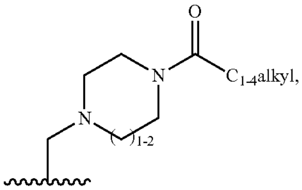
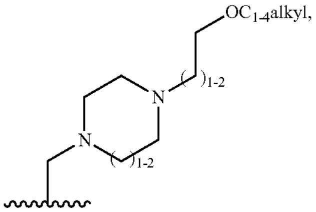
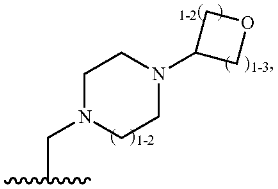
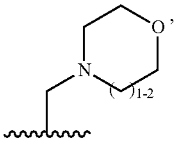

-continued

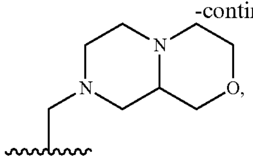
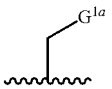
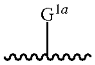

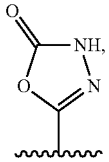
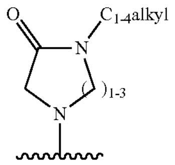
,
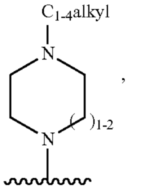
,

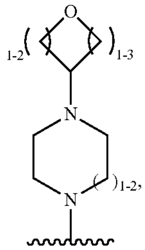
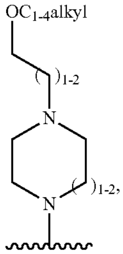
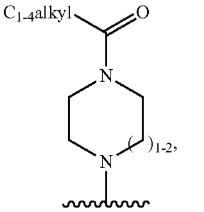

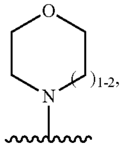
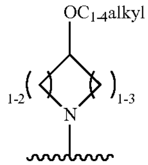
,
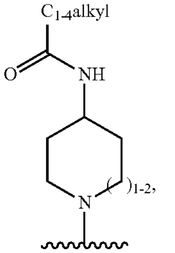

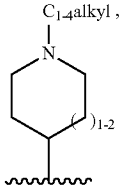
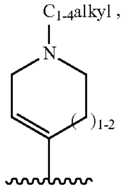
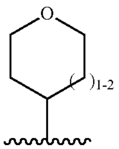
,

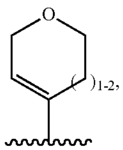
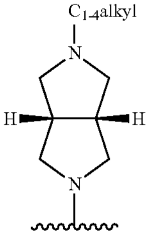
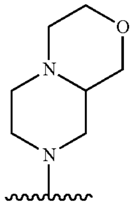
, or

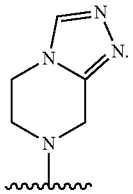

Clause 38. The compound of clause 37, or a pharmaceutically acceptable salt thereof, wherein $G^{1a}$ is a 5- to 6-membered heteroaryl containing 1-4 heteroatoms independently selected from O, N, and S, and optionally substituted with 1-3 substituents independently selected from the group consisting of halogen, cyano, $C_{1-4}$alkyl, $C_{1-4}$fluoroalkyl, $OC_{1-4}$alkyl, $OC_{1-4}$fluoroalkyl, $C_{3-4}$cycloalkyl, and $CH_2C_{3-4}$cycloalkyl.

Clause 39. The compound of clause 37 or 38, or a pharmaceutically acceptable salt thereof, wherein $G^{1b}$ is a 5- to 6-membered heteroaryl containing 1-4 heteroatoms independently selected from O, N, and S, and optionally substituted with 1-3 substituents independently selected from the group consisting of halogen, cyano, $C_{1-4}$alkyl, $C_{1-4}$fluoroalkyl, $OC_{1-4}$alkyl, $OC_{1-4}$fluoroalkyl, $C_{3-4}$cycloalkyl, and $CH_2C_{3-4}$cycloalkyl.

Clause 40. The compound of any of clauses 36-36.2 or a pharmaceutically acceptable salt thereof, wherein $R^{10d}$ is hydrogen, fluoro, chloro, bromo, methyl, ethyl, cyano, $OCH_3$, $OCF_3$, $NH_2$, $N(CH_3)_2$, $NHC(O)CH_3$,

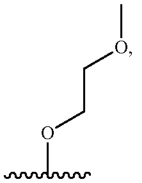
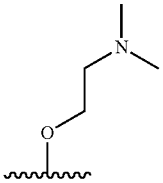

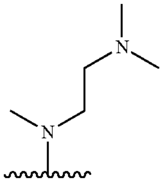
,
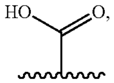
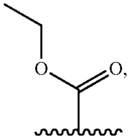

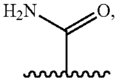
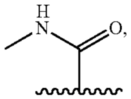
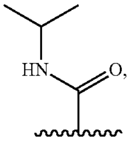

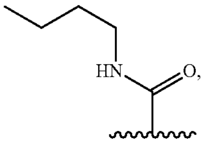
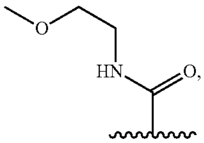

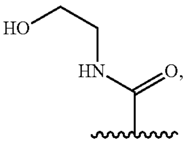
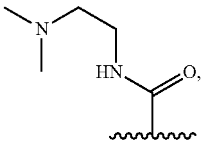

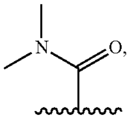
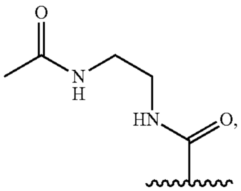

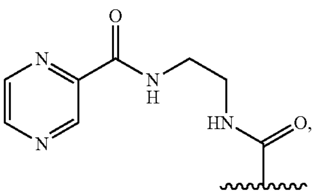

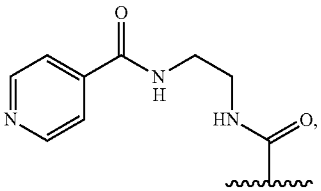

-continued
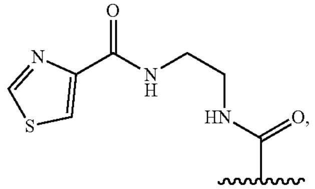
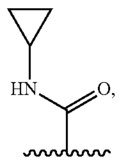
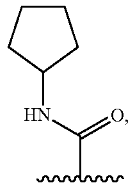
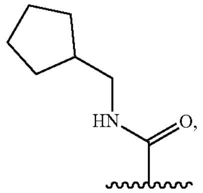
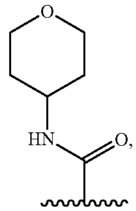
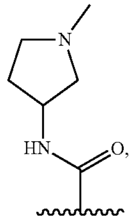
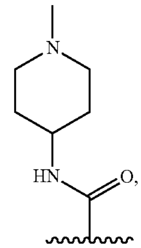
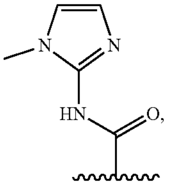
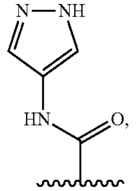
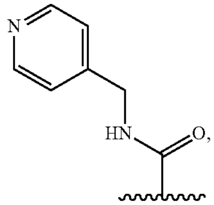
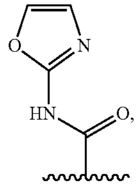
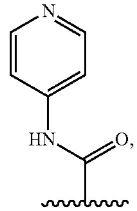
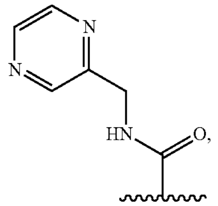
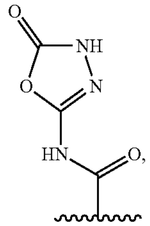
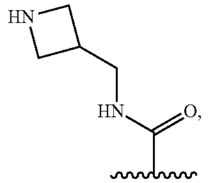
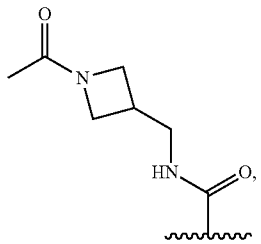
-continued
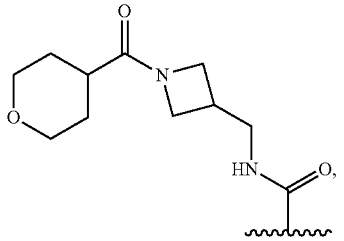
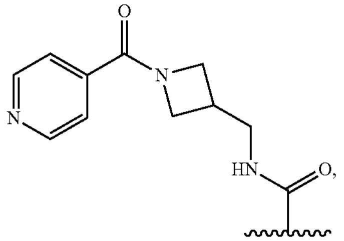
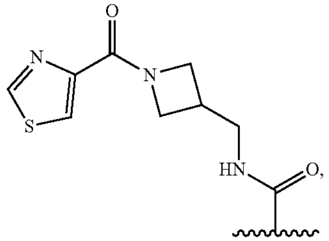
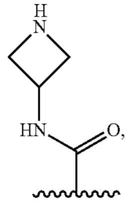
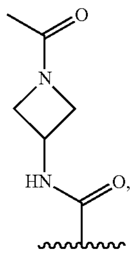
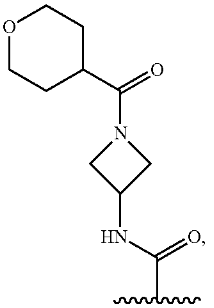
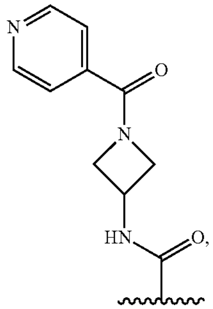
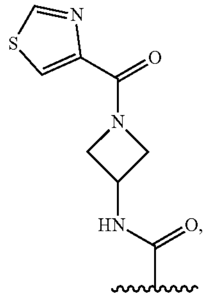
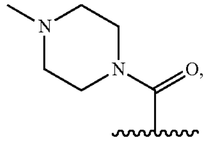
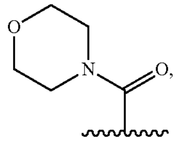
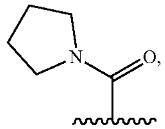
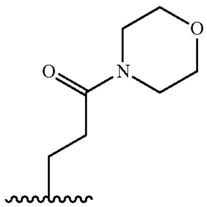
, -continued
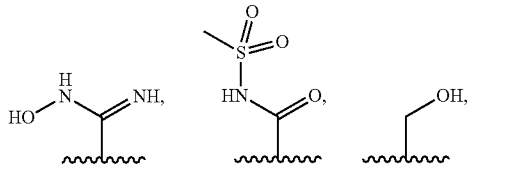
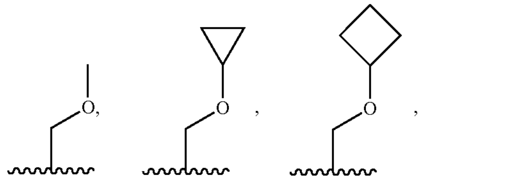
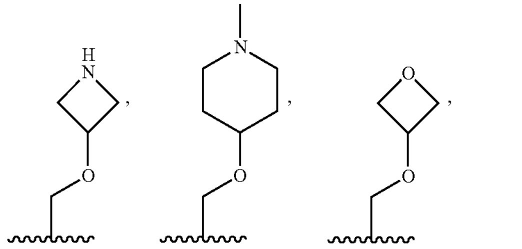
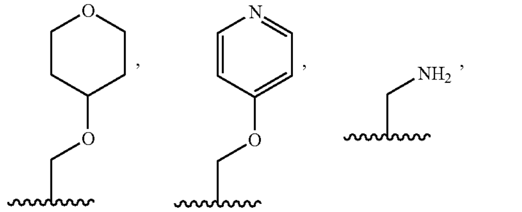
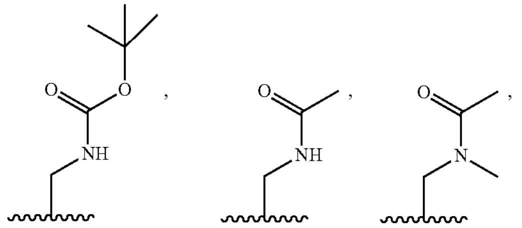
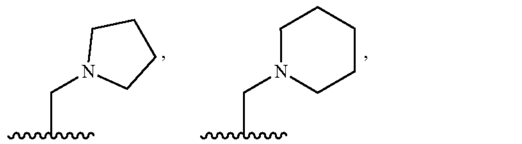
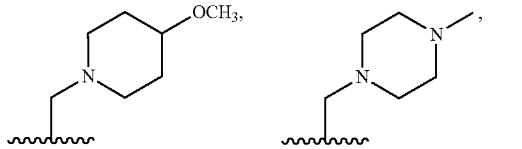
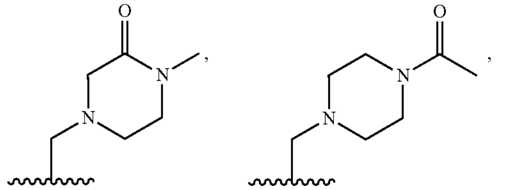
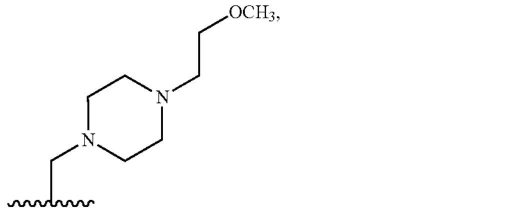
-continued
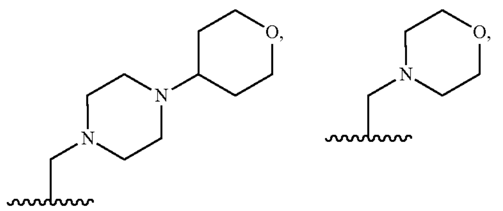
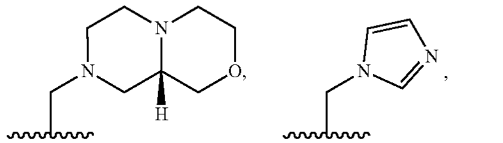
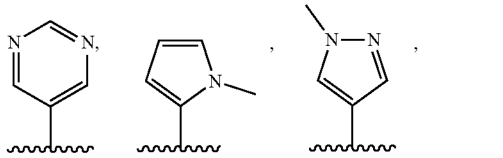
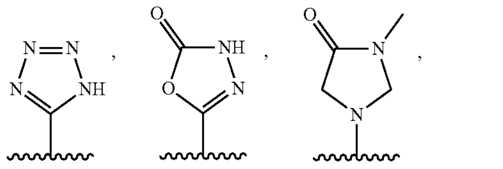
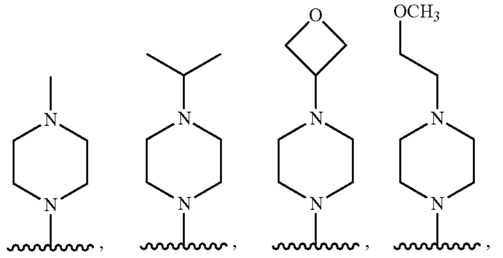
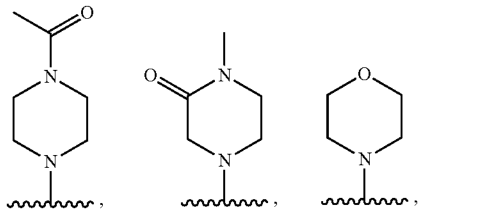
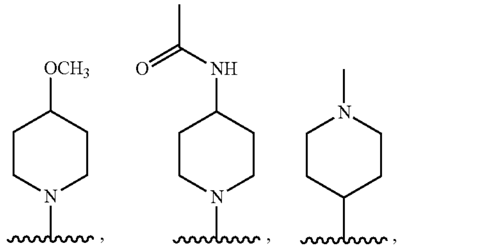
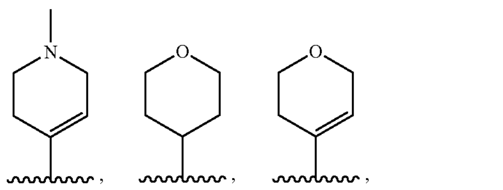

-continued

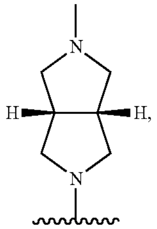
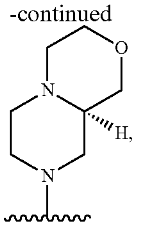
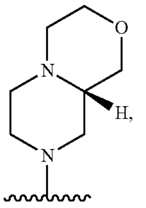
or
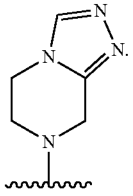

Clause 42. The compound of any of clauses 36-40, or a pharmaceutically acceptable salt thereof, wherein $X^{10}$ is N;

$X^{11}$ is $CR^{10a}$;

$X^{12}$ is $CR^{10c}$;

$X^{13}$ is $CR^{10d}$; and $X^{14}$ is $CR^{10e}$.

Clause 43. The compound of any of clauses 36-40, or a pharmaceutically acceptable salt thereof, wherein $X^{10}$ is $CR^{10a}$;

$X^{11}$ is $CR^{10b}$;

$X^{12}$ is N;

$X^{13}$ is $CR^{10d}$; and $X^{14}$ is $CR^{10e}$.

Clause 44. The compound of clause 36, or a pharmaceutically acceptable salt thereof, wherein $X^{10}$ is $CR^{10a}$;

$X^{11}$ is $CR^{10b}$;

$X^{12}$ is $CR^{10c}$;

$X^{13}$ is N; and $X^{14}$ is $CR^{10e}$.

Clause 44.1. The compound of clause 36.1, or a pharmaceutically acceptable salt thereof, wherein each "⎓" represents a double bond; $X^{12}$ is $CR^{10c}$; $X^{13}$ is N; and $X^{14}$ is $CR^{10e}$.

Clause 44.2. The compound of clause 44.1, or a pharmaceutically acceptable salt thereof, wherein $R^{10a}$ is hydrogen; $R^{10b}$ is hydrogen or $C_{1-4}$alkyl; $R^{10c}$ is hydrogen, $C_{1-4}$alkyl, or —$OC_{1-4}$alkyl; $R^{10e}$ is hydrogen or $C_{1-4}$alkyl; and $R^{10f}$ is $C_{1-4}$alkyl or —$OC_{1-4}$alkyl.

Clause 44.3. The compound of any of clauses 44-44.2, or a pharmaceutically acceptable salt thereof, wherein $G^1$ is

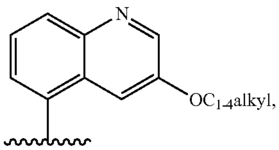
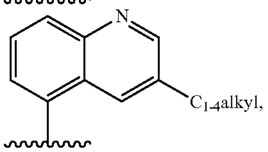

-continued

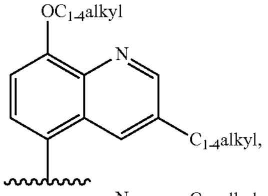
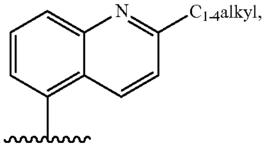
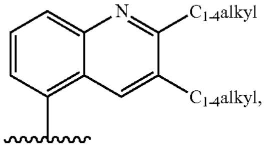
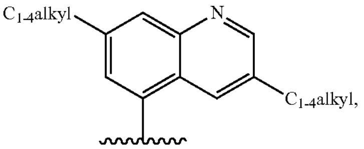
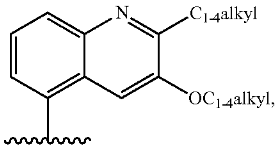
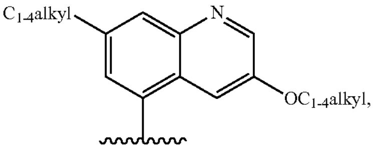
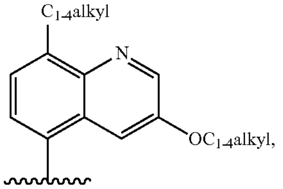
or
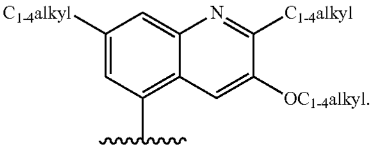

Clause 44.4. The compound of clause 44.3, or a pharmaceutically acceptable salt thereof, wherein $G^1$ is

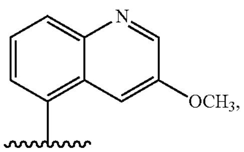
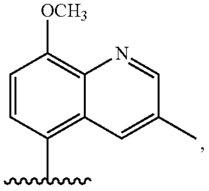
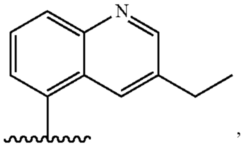
,
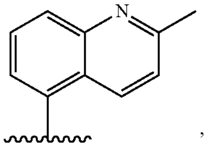
,

-continued

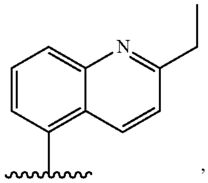, 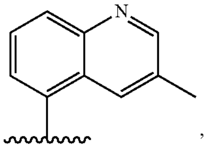,

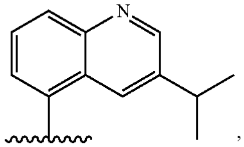, 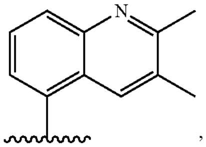,

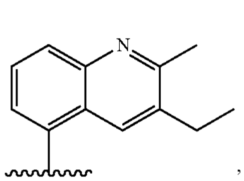, 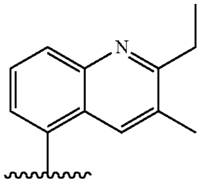,

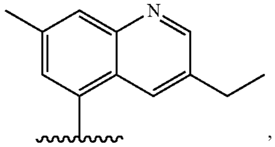, 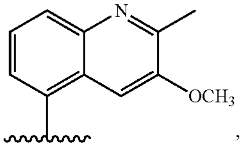,

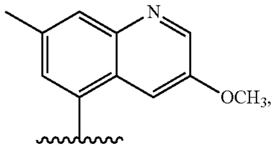

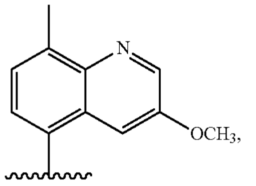 or

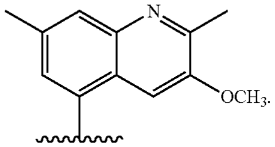

Clause 44.5 The compound of clause 36.1, or a pharmaceutically acceptable salt thereof, wherein each "$\overline{\overline{\phantom{x}}}$" represents a single bond; $X^{12}$ is $CHR^{10c}$; $X^{13}$ is N; and $X^{14}$ is $CR^{10e}$.

Clause 44.6. The compound of clause 44.5, or a pharmaceutically acceptable salt thereof, wherein $R^{10a}$ is hydrogen; $R^{10b}$ is hydrogen or $C_{1-4}$alkyl; $R^{10c}$ is hydrogen or $C_{1-4}$alkyl; $R^{10e}$ is hydrogen or $C_{1-4}$alkyl; and $R^{10f}$ is $C_{1-4}$alkyl or $-OC_{1-4}$alkyl.

Clause 44.7. The compound of clause 44.6, or a pharmaceutically acceptable salt thereof, wherein $G^1$ is

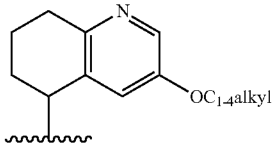

-continued (e.g., 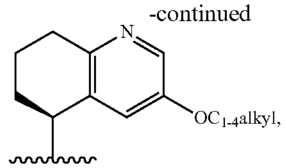

such as

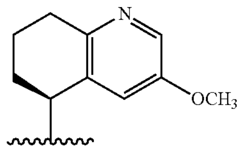).

Clause 45. The compound of any of clauses 36-40, or a pharmaceutically acceptable salt thereof, wherein $X^{10}$ is N;

$X^{11}$ is $CR^{10b}$;

$X^{12}$ is N;

$X^{13}$ is $CR^{10d}$; and $X^{14}$ is $CR^{10e}$.

Clause 46. The compound of any of clauses 36-40, or a pharmaceutically acceptable salt thereof, wherein $X^{10}$ is $CR^{10a}$;

$X^{11}$ is $CR^{10b}$;

$X^{12}$ is N;

$X^{13}$ is $CR^{10d}$; and $X^{14}$ is N.

Clause 47. The compound of clause 36, or a pharmaceutically acceptable salt thereof, wherein $X^{10}$ is $CR^{10a}$;

$X^{11}$ is N;

$X^{12}$ is $CR^{10c}$;

$X^{13}$ is N; and $X^{14}$ is $CR^{10e}$.

Clause 47.1. The compound of clause 36, or a pharmaceutically acceptable salt thereof, wherein $X^{10}$ is $CR^{10a}$;

$X^{11}$ is N;

$X^{12}$ is N;

$X^{13}$ is $CR^{10d}$; and $X^{14}$ is $CR^{10e}$.

Clause 48. The compound of any of clauses 1, 2.1-7, or 36-40, or a pharmaceutically acceptable salt thereof, wherein:

$G^1$ is

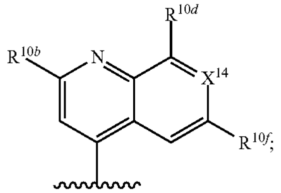

$X^{14}$ is $CR^{10e}$ or N;

$R^{10b}$ is hydrogen, halogen, $C_{1-4}$alkyl, or $C_{1-4}$fluoroalkyl;

$R^{10d}$ is hydrogen, halogen, $C_{1-4}$alkyl, $C_{1-4}$fluoroalkyl, or $-L^1-X^1$, or $-L^1-G^{1a}$;

$R^{10e}$ is hydrogen, halogen, $C_{1-4}$alkyl, or $C_{1-4}$fluoroalkyl; and $R^{10f}$ is hydrogen, halogen, $C_{1-4}$alkyl, $C_{1-4}$fluoroalkyl, OH, —$OC_{1-4}$fluoroalkyl, $NH_2$, $NHC_{1-4}$alkyl, $N(C_{1-4}alkyl)_2$.

Clause 49. The compound of clause 48, or a pharmaceutically acceptable salt thereof, wherein $X^{14}$ is $CR^{10e}$.

Clause 50. The compound of clause 48, or a pharmaceutically acceptable salt thereof, wherein $X^{14}$ is N.

Clause 51. The compound of any of clauses 36-50, or a pharmaceutically acceptable salt thereof, wherein $R^{10d}$ is $-L^1-X^1$.

Clause 52. The compound of any of clauses 1, 2.1-7 or 35-51, or a pharmaceutically acceptable salt thereof, wherein $X^1$ is —$OR^{1a}$, —$N(R^{1a})_2$, cyano, —$C(O)OR^{1a}$, —$C(O)N(R^{1a})_2$, —$C(O)N(R^{1a})SO_2R^{1b}$, —C(NH)NHOH, —$C(O)R^{1b}$, —$NR^{1a}C(O)H$, or —$NR^{1a}C(O)R^{1b}$.

Clause 53. The compound of any of clauses 1, 2.1-7 or 35-52, or a pharmaceutically acceptable salt thereof, wherein $G^{1a}$ is $C_{3-8}$cycloalkyl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, $-L^2-X^2$, and $-L^2-G^{1b}$; and $X^2$, at each occurrence, is independently —$OR^{1c}$, —$N(R^{1c})_2$, —$C(O)N(R^{1c})_2$, —$C(O)R^{1c}$, —$NR^{1c}C(O)R^{1c}$.

Clause 54. The compound of any of clauses 1-7 or 35-53, or a pharmaceutically acceptable salt thereof, wherein $R^{1b}$, at each occurrence, is independently $C_{1-6}$alkyl or $G^{1a}$.

Clause 55. The compound of any of clauses 1, 2.1-7, or 35-54, or a pharmaceutically acceptable salt thereof, wherein $R^{1e}$, at each occurrence, is independently hydrogen, $C_{1-4}$alkyl, or $G^{1b}$.

Clause 56. The compound of any of clauses 1, 2.1-7, or 35-55, or a pharmaceutically acceptable salt thereof, wherein $X^2$, at each occurrence, is independently —$C(O)R^{1c}$.

Clause 57. The compound of any of clauses 1, 2.1-7, or 35-56, or a pharmaceutically acceptable salt thereof, wherein:

$G^{1a}$ is a $C_{3-8}$cycloalkyl, a 5- to 6-membered heteroaryl containing 1-2 heteroatoms independently selected from O, N, and S, or a 4- to 8-membered monocyclic heterocyclyl containing 1-3 heteroatoms independently selected from O, N, and S, the heterocyclyl being attached at a ring carbon atom, wherein $G^{1a}$ is optionally substituted with 1-4 substituents independently selected from the group consisting of halogen, $C_{1-4}$alkyl, $C_{1-4}$haloalkyl, oxo, $-L^2-X^2$, and $-L^2-G^{1b}$.

Clause 58. The compound ofany of clauses 1, 2.1-7, or 35-57, or a pharmaceutically acceptable salt thereof, wherein $G^{1b}$ is a 4- to 6-membered monocyclic heterocyclyl containing 1-2 heteroatoms independently selected from O, N, and S, or a 5- to 6-membered heteroaryl containing 1-2 heteroatoms independently selected from O, N, and S.

Clause 59. The compound of any of clauses 1, 2.1-7, or 35-58, or a pharmaceutically acceptable salt thereof, wherein $R^{1c}$, at each occurrence, is independently hydrogen, $C_{1-6}$alkyl, or $G^{1b}$.

Clause 60. The compound of any of clauses 1, 2.1-7, 35-59, or a pharmaceutically acceptable salt thereof, wherein $G^1$ is

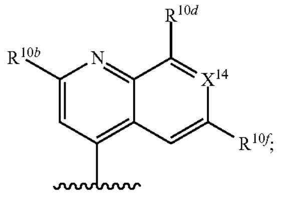

$R^{10b}$ is hydrogen or $C_{1-4}$alkyl;

$R^{10b}$ a is —$C(O)OR^{1a}$, —$C(O)N(R^{1a})_2$, —C(NH)NHOH, or —$C(O)N(H)SO_2R^{1b}$; and $R^{10f}$ is $C_{1-4}$alkyl or $OC_{1-4}$alkyl.

Clause 61. The compound of any of clauses 35-60, or a pharmaceutically acceptable salt thereof, wherein $R^{10d}$ is —$C(O)NHR^{1a}$.

Clause 62. The compound of any of clauses 1-7 or 35-61, or a pharmaceutically acceptable salt thereof, wherein at least one occurrence of $R^{1a}$ is $G^{1a}$ or —$C_{1-6}$alkylene-$G^{1a}$.

Clause 63. The compound of any of clauses 1-7 or 35-62, or a pharmaceutically acceptable salt thereof, wherein $G^{1a}$ is $C_{3-6}$cycloalkyl, 4- to 6-membered heterocyclyl containing 1-3 heteroatoms independently selected from O, N, and S and attached at a ring carbon atom, or a 5- to 6-membered heteroaryl containing 1-2 heteroatoms independently selected from O, N, and S, wherein $G^{1a}$ is optionally substituted with $C_{1-4}$alkyl, oxo, or —$C(O)R^{1c}$.

Clause 64. The compound of clause 63, or a pharmaceutically acceptable salt thereof, wherein the 4- to 6-membered heterocyclyl at $G^{1a}$ is tetrahydropyranyl, azetidinyl, pyrrolidinyl, piperidinyl, or 2,3-dihydro-1,3,4-oxadiazolyl; and the 5- to 6-membered heteroaryl at $G^{1a}$ is imidazolyl, pyrazolyl, oxazolyl, pyridinyl, or pyrazinyl.

Clause 65. The compound of clause 64, or a pharmaceutically acceptable salt thereof, wherein $R^{10d}$ is

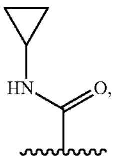,
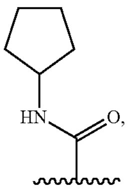,
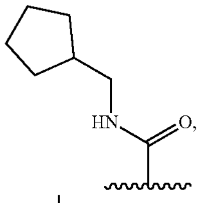,
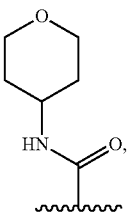,
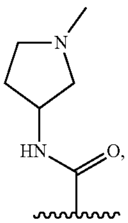,
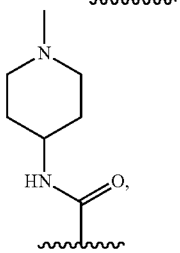,
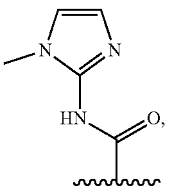,
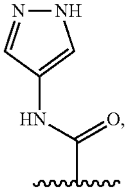,
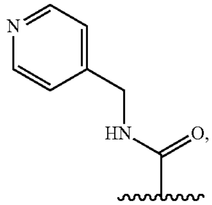, -continued

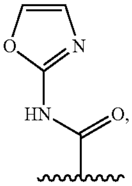
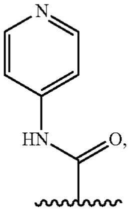
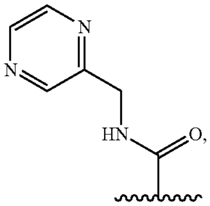
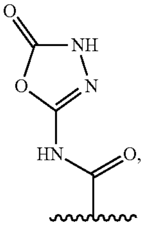
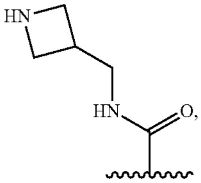
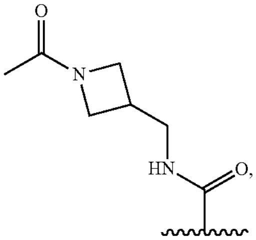
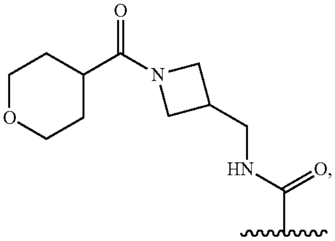
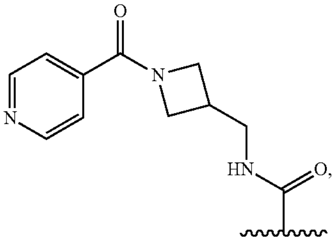
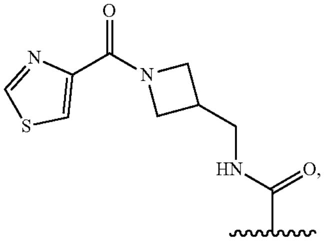
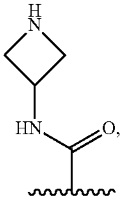
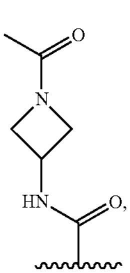
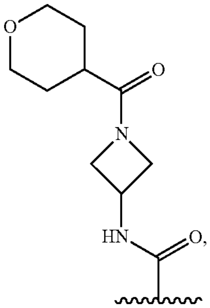

-continued

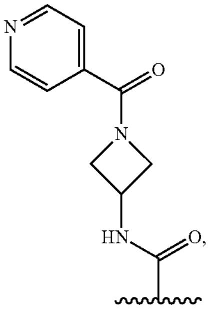

or

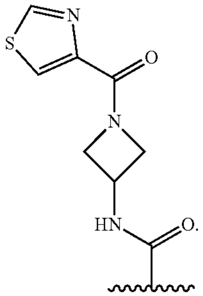

Clause 66. The compound of any of clauses 1-7 or 35-61, or a pharmaceutically acceptable salt thereof, wherein:

$R^{1a}$, at each occurrence, is independently hydrogen, $C_{1-6}$alkyl, $C_{1-6}$haloalkyl, —$C_{2-4}$alkylene-OH—, —$C_{2-4}$alkylene-O$C_{1-4}$alkyl, —$C_{2-4}$alkylene-N($C_{1-4}$alkyl)$_2$, —$C_{2-4}$alkylene-N(H)C(O)$C_{1-4}$alkyl, or —$C_{2-4}$alkylene-N(H)C(O)$G^{1b}$.

Clause 67. The compound of clause 66, or a pharmaceutically acceptable salt thereof, wherein $R^{10d}$ is

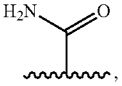
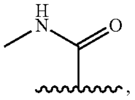
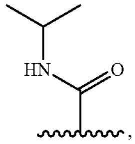
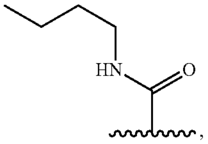
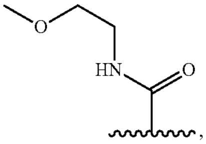
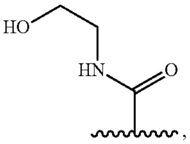
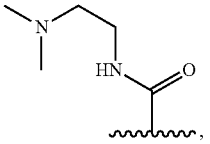
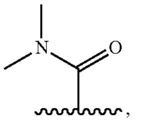
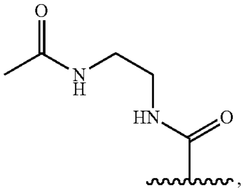
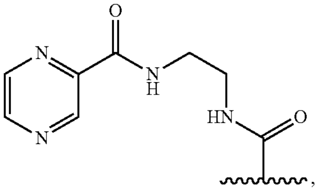
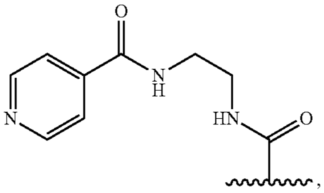

or

-continued

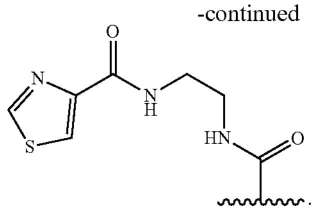

Clause 68 The compound of any of clauses 1, 2.1-7, or 36-40, 43, 48-49, and 51-59, or a pharmaceutically acceptable salt thereof, wherein $G^1$ is

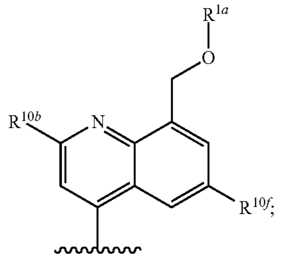

$R^{1a}$ is $C_{1-4}$alkyl or $G^{1a}$;

$G^{1a}$ is $C_{3-8}$cycloalkyl, a 5- to 6-membered heteroaryl containing 1-2 heteroatoms independently selected from O, N, and S, or a 4- to 8-membered monocyclic heterocyclyl containing one heteroatom selected from O, N, and S, the heterocyclyl being attached at a ring carbon atom, wherein $G^{1a}$ is optionally substituted with $C_{1-4}$alkyl;

$R^{10b}$ is hydrogen or $C_{1-4}$alkyl; and $R^{10f}$ is $C_{1-4}$alkyl or $OC_{1-4}$alkyl.

Clause 69. The compound of clause 68, or a pharmaceutically acceptable salt thereof, wherein $G^{1a}$ is cyclopropyl, cyclobutyl, azetidinyl, piperidinyl, oxetanyl, tetrahydropyranyl, or pyridinyl, wherein the azetidinyl, piperidinyl, oxetanyl, and tetrahydropyranyl are attached at a ring carbon atom and $G^{1a}$ is optionally substituted with $C_{1-2}$alkyl.

Clause 70. The compound of clause 68 or 69, or a pharmaceutically acceptable salt thereof, wherein $G^{1a}$ is cyclopropyl, cyclobutyl, azetidin-3-yl, piperidin-4-yl, oxetan-3-yl, tetrahydropyran-4-yl, or pyridin-4-yl, wherein $G^{1a}$ is optionally substituted with $C_{1-2}$alkyl.

Clause 71. The compound of any of clauses 36-50, or a pharmaceutically acceptable salt thereof, wherein $R^{10d}$ is $-L^1-G^{1a}$.

Clause 72. The compound of any of clauses 1, 2.1-7, or 71, or a pharmaceutically acceptable salt thereof, wherein:

$G^{1a}$ is independently a 5- to 10-membered heteroaryl or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, $-L-X^2$, and $-L^2-G^{1b}$.

$G^{1b}$ is a $C_{3-6}$cycloalkyl or a 4- to 6-membered monocyclic heterocyclyl containing 1-2 heteroatoms independently selected from O, N, and S, wherein $G^{1b}$ is optionally substituted with 1-4 substituents independently selected from the group consisting of halogen, cyano, $C_{1-4}$alkyl, $C_{1-4}$haloalkyl, oxo, —OH, and —$OC_{1-4}$alkyl;

$X^2$, at each occurrence, is independently —OR, —$N(R^{1c})_2$, —$C(O)N(R^{1c})_2$, —$C(O)R^{1c}$, or —$NR^{1c}C(O)R^{1c}$; and $R^{1c}$, at each occurrence, is independently hydrogen, $C_{1-6}$alkyl, $C_{1-6}$haloalkyl, $G^{1b}$, or —$C_{1-3}$alkylene-$G^{1b}$, wherein alternatively two $R^{1c}$, together with a common nitrogen atom to which the $R^{1c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl.

Clause 73. The compound of any of clauses 1, 2.1-7, or 71-72, or a pharmaceutically acceptable salt thereof, wherein $G^{1b}$ is a 4- to 6-membered monocyclic heterocyclyl containing 1-2 heteroatoms independently selected from O, N, and S.

Clause 74. The compound of any of clauses 1, 2.1-7, 71-73, or a pharmaceutically acceptable salt thereof, wherein $X^2$, at each occurrence, is independently —$OR^{1c}$, —$C(O)R^{1c}$, or —$NR^{1c}C(O)R^{1c}$.

Clause 75. The compound of any of clauses 1-7 or 71-74, or a pharmaceutically acceptable salt thereof, wherein $R^{1c}$, at each occurrence, is independently $C_{1-6}$alkyl.

Clause 76. The compound of any of clauses 1-7, 35-40, 43, 48-49, or 71-75, or a pharmaceutically acceptable salt thereof, wherein $G^1$ is

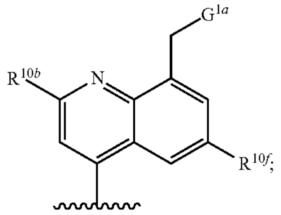

$G^{1a}$ is a 5-membered heteroaryl containing 1-3 heteroatoms independently selected from O, N, and S, a 4- to 8-membered monocyclic heterocyclyl containing 1-2 heteroatoms independently selected from O, N, and S, or an 8- to 10-membered fused bicyclic heterocyclyl containing 1-3 heteroatoms independently selected from O, N, and S, the heterocyclyl and heteroaryl being attached at a ring nitrogen atom, wherein the 4- to 8-membered monocyclic heterocyclyl is optionally substituted with 1-2 substituents independently selected from oxo, $C_{1-4}$alkyl, $OC_{1-4}$alkyl, $C(O)C_{1-4}$alkyl, —$C_{2-3}$alkylene-$OC_{1-4}$alkyl, $G^{1b}$, and —$C_{1-3}$alkylene-$G^{1b}$;

$G^{1b}$ is $C_{3-6}$cycloalkyl or a 4- to 6-membered monocyclic heterocyclyl containing 1-2 heteroatoms independently selected from O, N, and S;

$R^{10b}$ is hydrogen or $C_{1-4}$alkyl; and $R^{10f}$ is $C_{1-4}$alkyl or $OC_{1-4}$alkyl.

Clause 77. The compound of clause 76, or a pharmaceutically acceptable salt thereof, wherein $G^{1a}$ is a piperazin-1-yl, piperidin-1-yl, pyrrolidin-1-yl, morpholin-4-yl, imidazol-1-yl, or hexahydropyrazino [2,1-c][1,4]oxazin-8(1H)-yl, wherein the piperazin-1-yl and piperidin-1-yl are optionally substituted with 1-2 substituents independently selected from oxo, $C_{1-4}$alkyl, $OC_{1-4}$alkyl, $C(O)C_{1-4}$alkyl, —$C_{2-3}$alkylene-$OC_{1-4}$alkyl, and $G^{1b}$.

Clause 78. The compound of clause 76 or 77, or a pharmaceutically acceptable salt thereof, wherein $G^{1a}$ is

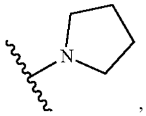 , 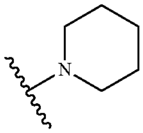 ,

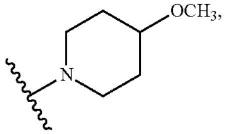 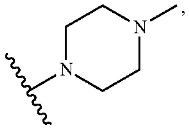

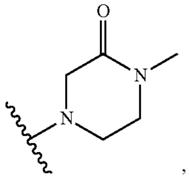 , 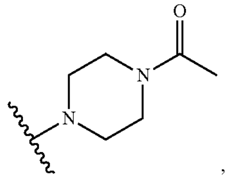 ,

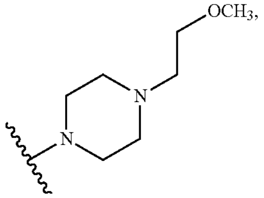 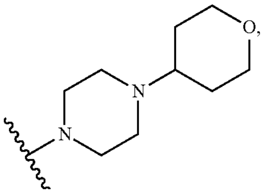

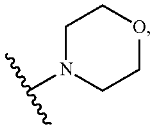 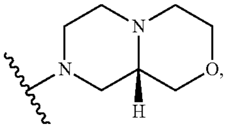 or

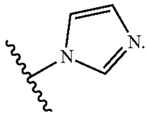

Clause 79. The compound of any of clauses 1-7, 35-40, 43, 48-49, or 71-75, or a pharmaceutically acceptable salt thereof, wherein $G^1$ is

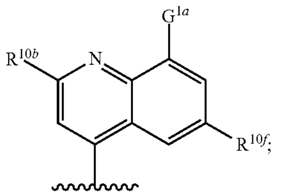

$G^{1a}$ is a 5- to 6-membered heteroaryl containing 1-4 heteroatoms independently selected from O, N, and S, a 4- to 8-membered monocyclic heterocyclyl containing 1-2 heteroatoms independently selected from O, N, and S, or an 8- to 10-membered fused bicyclic heterocyclyl containing 1-3 heteroatoms independently selected from O, N, and S, wherein $G^{1a}$ is optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, $G^{1b}$, and —$C_{1-3}$alkylene-$G^{1b}$;

$G^{1b}$ is $C_{3-6}$cycloalkyl or a 4- to 6-membered monocyclic heterocyclyl containing 1-2 heteroatoms independently selected from O, N, and S;

$R^{10b}$ is hydrogen or $C_{1-4}$alkyl; and $R^{10f}$ is $C_{1-4}$alkyl or $OC_{1-4}$alkyl.

Clause 80. The compound of clause 79, or a pharmaceutically acceptable salt thereof, wherein $G^{1a}$ is a piperazinyl, piperidinyl, tetrahydropyridinyl, morpholinyl, imidazolidinyl, tetrahydropyranyl, dihydropyranyl, 1,3,4-oxadiazol-2(3H)-yl, pyrimidinyl, pyrrolyl, pyrazolyl, tetrazolyl, hexahydropyrazino[2,1-c][1,4]oxazin-8(1H)-yl, hexahydropyrrolo[3,4-c]pyrrol-2(1H)-yl, or 5,6-dihydro-[1,2,4]triazolo[4,3-a]pyrazin-7(8H)-yl, wherein $G^{1a}$ is optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, $G^{1b}$, andqj —$C_{1-3}$-alkylene-$G^{1b}$.

Clause 81. The compound of clause 79 or 80, or a pharmaceutically acceptable salt thereof, wherein $G^{1a}$ is a piperazin-1-yl, piperidin-1-yl, piperidin-4-yl, tetrahydropyridin-4-yl, morpholin-4-yl, imidazolidin-1-yl, tetrahydropyran-4-yl, dihydropyran-4-yl, 1,3,4-oxadiazol-2(3H)-yl, pyrimidin-5-yl, pyrrol-2-yl, pyrazol-4-yl, tetrazol-5-yl, hexahydropyrazino[2,1-c][1,4]oxazin-8(1H)-yl, hexahydropyrrolo[3,4-c]pyrrol-2(1H)-yl, or 5,6-dihydro-[1,2,4]triazolo[4,3-a]pyrazin-7(8H)-yl, wherein the piperazin-1-yl, piperidin-1-yl, piperidin-4-yl, tetrahydropyridin-4-yl, morpholin-4-yl, imidazolidin-1-yl, tetrahydropyran-4-yl, dihydropyran-4-yl, 1,3,4-oxadiazol-2(3H)-yl, pyrimidin-5-yl, pyrrol-2-yl, pyrazol-4-yl, and hexahydropyrrolo[3,4-c]pyrrol-2(1H)-yl are optionally substituted with 1-2 substituents independently selected from oxo, $C_{1-4}$alkyl, $OC_{1-4}$alkyl, $C(O)C_{1-4}$alkyl, —$NHC(O)C_{1-4}$alkyl, —$C_{2-3}$alkylene-$OC_{1-4}$alkyl, ($G^{1b}$, and —$C_{1-3}$alkylene-$G^{1b}$.

Clause 82. The compound of any of clauses 79-81, or a pharmaceutically acceptable salt thereof, wherein $G^{1a}$ is

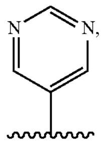 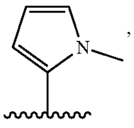 , 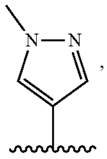 , 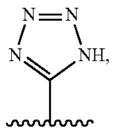

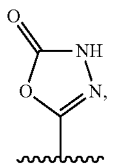 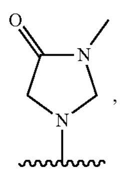 , 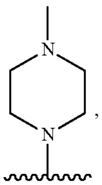 , 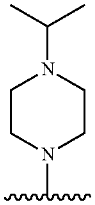 ,

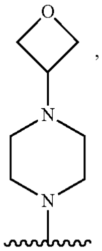 , 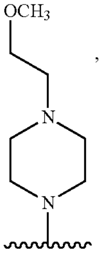 , 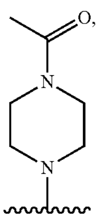 , 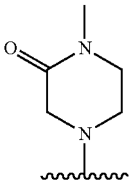

-continued

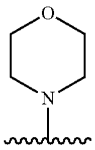, 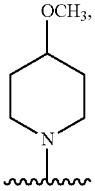 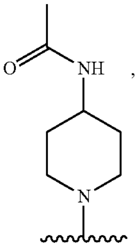, 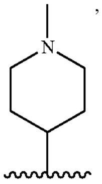,

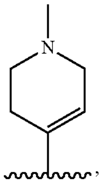 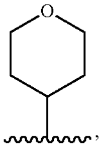 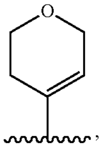 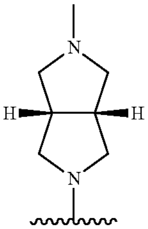

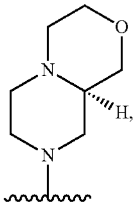 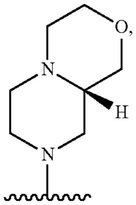 or 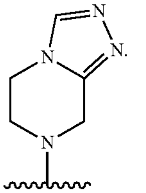 [SMILES: *N1CCn2cnnc2C1]

Clause 83. The compound of any of clauses 36-40-42-44.1, or 46-47.1, or a pharmaceutically acceptable salt thereof, wherein $R^{10a}$ is hydrogen or chloro.

Clause 84. The compound of any of clauses 36-41, 43-46, or 48-83, or a pharmaceutically acceptable salt thereof, wherein $R^{10c}$ is hydrogen or methyl.

Clause 85, The compound of any of clauses 36-42, 44-44.1, 47, or 83-84, or a pharmaceutically acceptable salt thereof, wherein $R^{10c}$ is hydrogen, methyl, chloro, or $OCH_3$.

Clause 86. The compound of any of clauses 36-45, 47-59, or 83-85, or a pharmaceutically acceptable salt thereof, wherein Rice is hydrogen, methyl, ethyl, or chloro.

Clause 87. The compound of any of clauses 36-82, or a pharmaceutically acceptable salt thereof, wherein $R^{10f}$ is hydrogen, methyl, ethyl, isopropyl, $OCH_3$, $NH_2$, $NHCH_3$, or 4-fluoroazeidin-1-yl.

Clause 88. The compound of clause 87, or a pharmaceutically acceptable salt thereof, wherein $R^{10f}$ is ethyl or $OCH_3$.

Clause 89. The compound of any of clauses 1-7 or 35, or a pharmaceutically acceptable salt thereof, wherein $G^1$ is

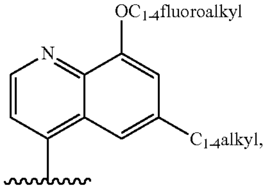 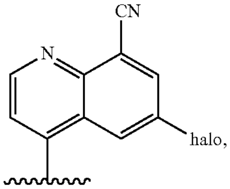

-continued

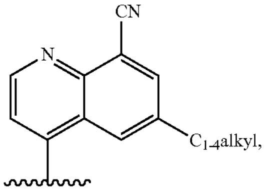

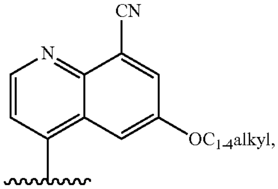 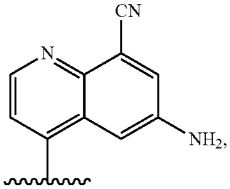

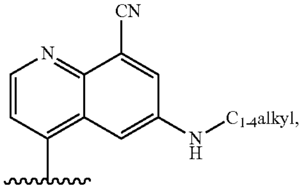

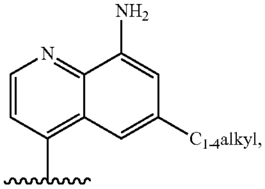

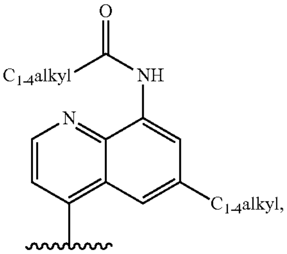

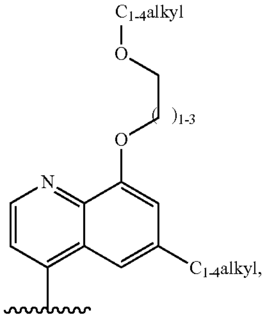

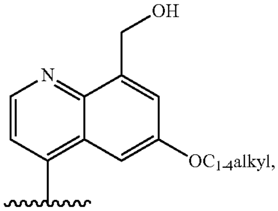

-continued
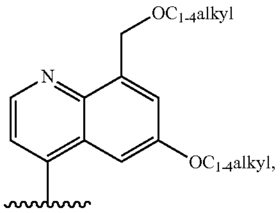
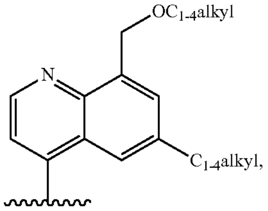
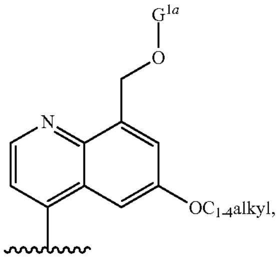
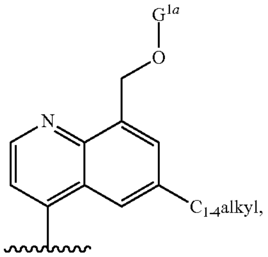
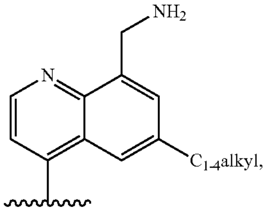
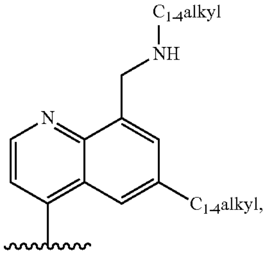
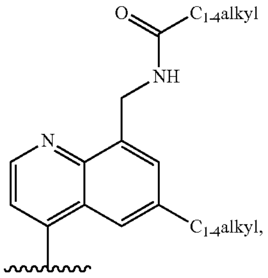
-continued
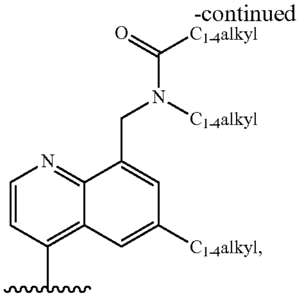
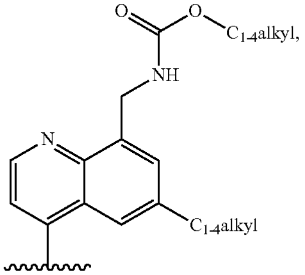
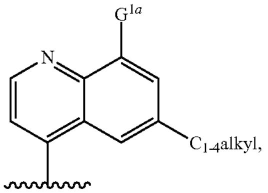
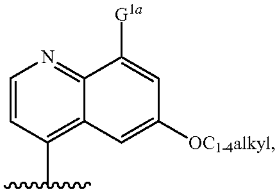
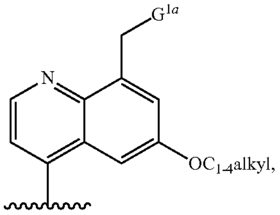
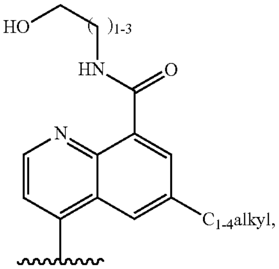
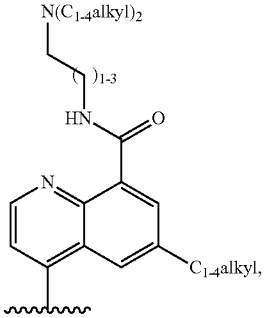

-continued
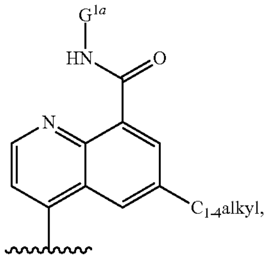
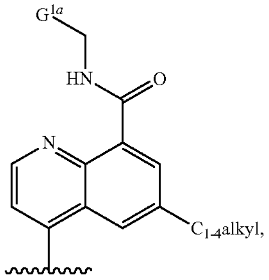
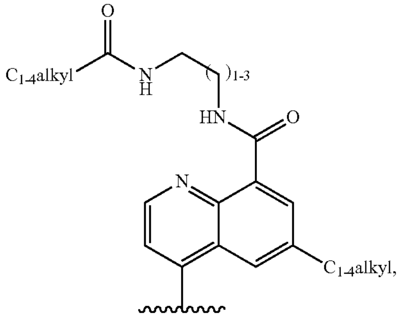
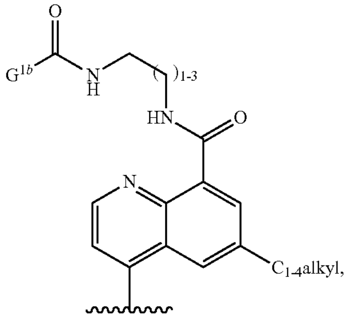
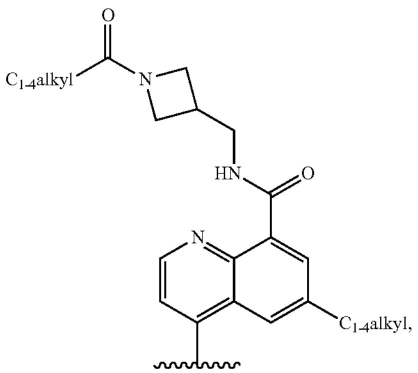
-continued
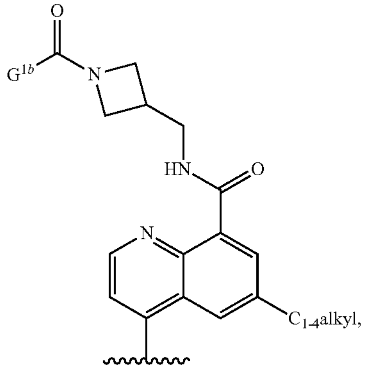
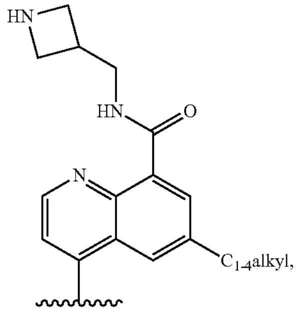
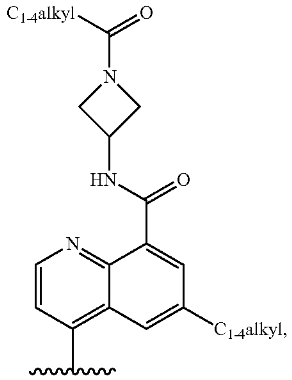
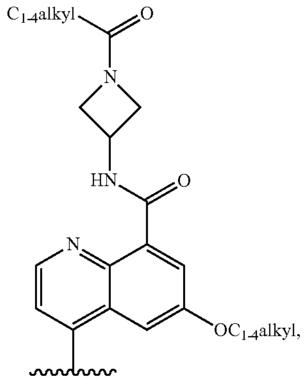

-continued
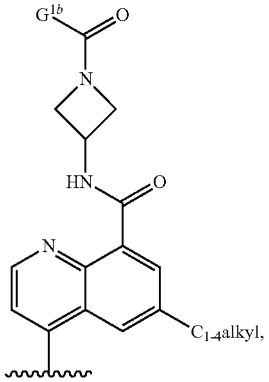
,
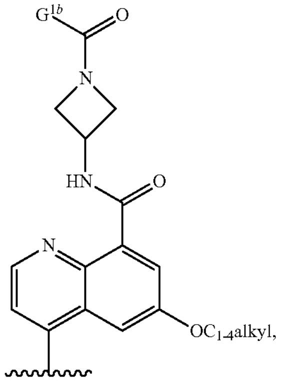
,
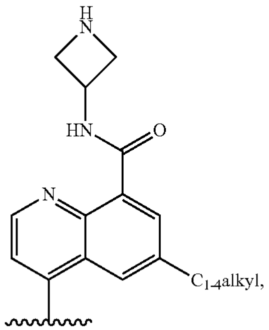
,
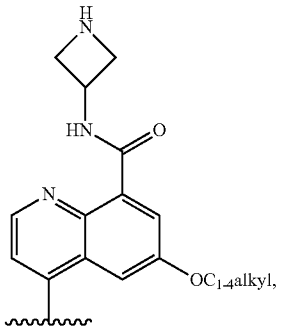
,
-continued
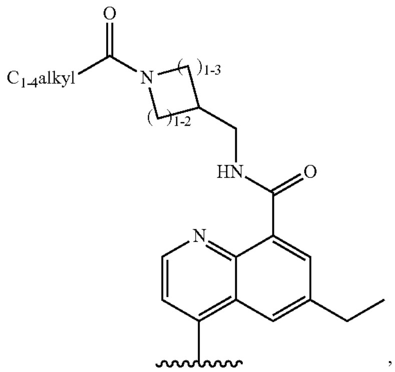
,
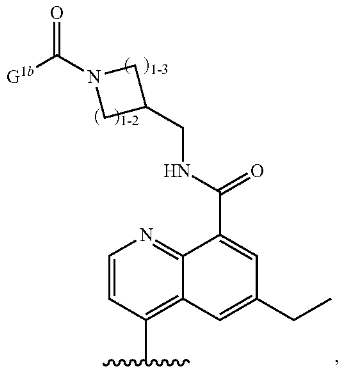
,
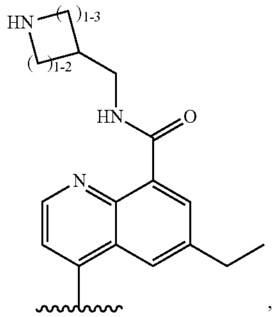
,
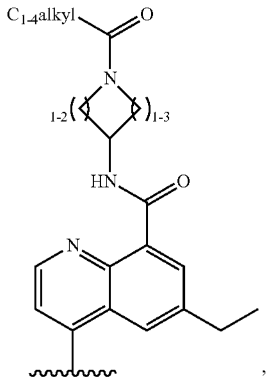
, -continued
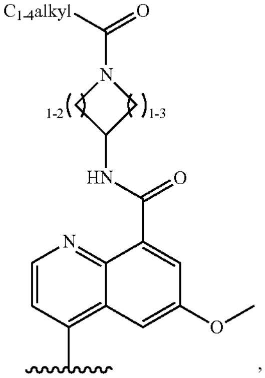
,
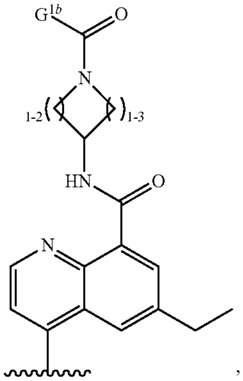
,
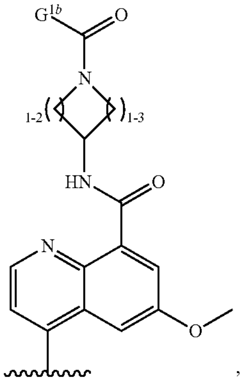
,
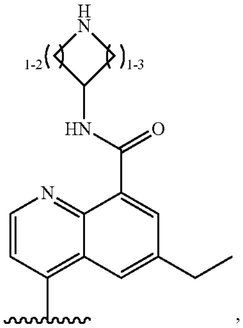
,
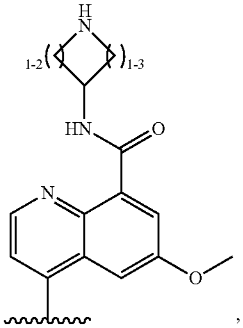
,
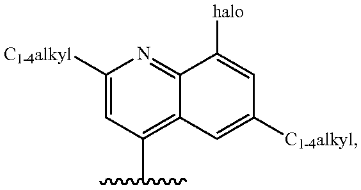
-continued
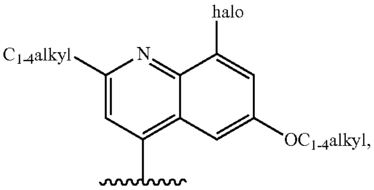
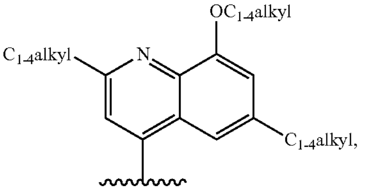
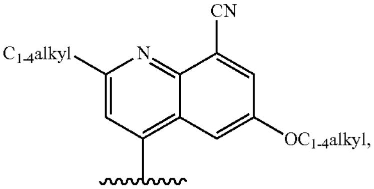
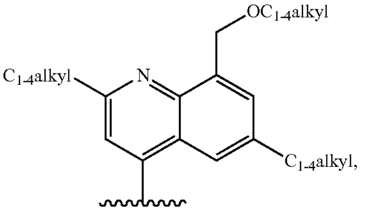
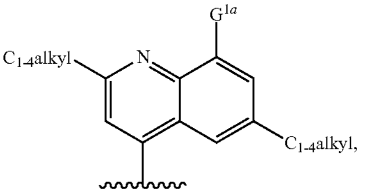
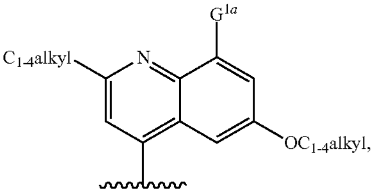
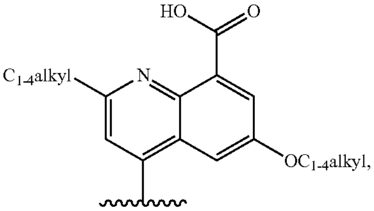
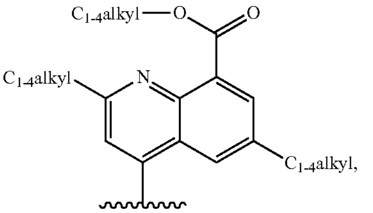

-continued
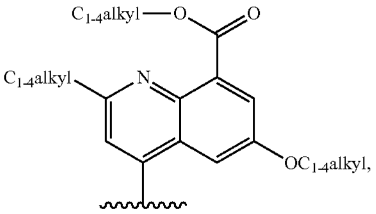
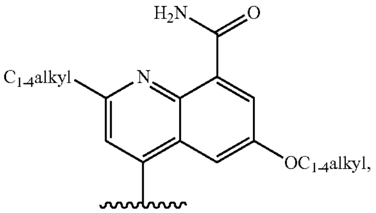
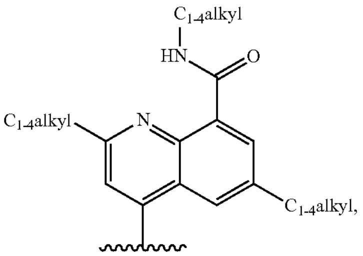
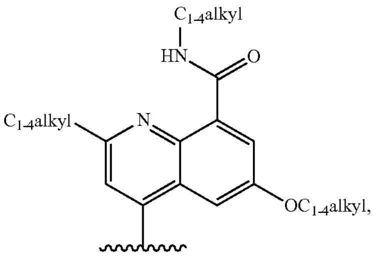
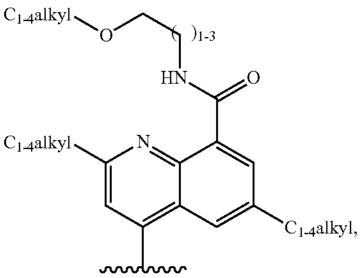
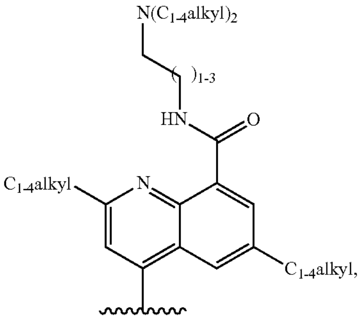
-continued
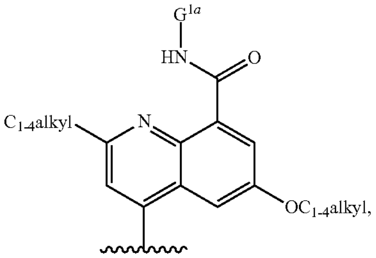
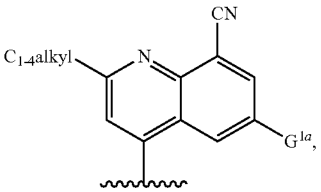
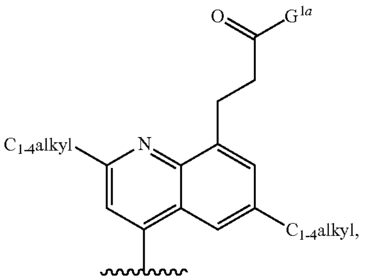
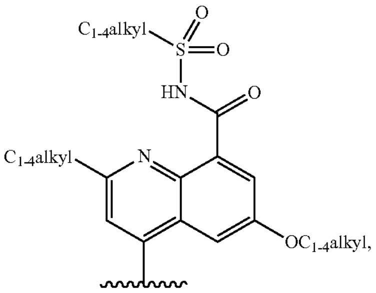
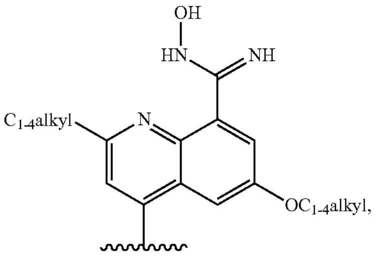
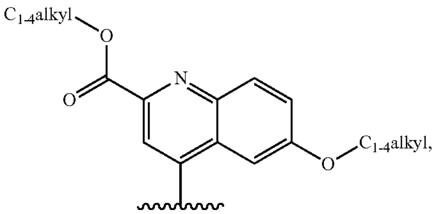
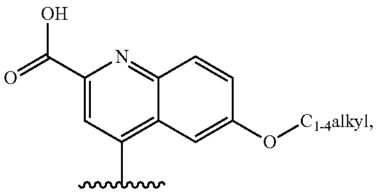

-continued
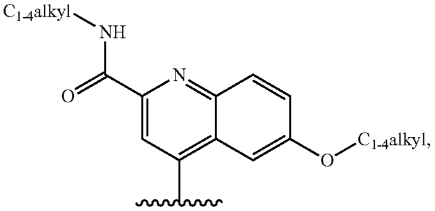
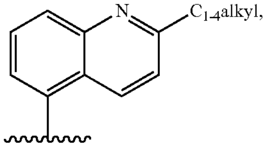
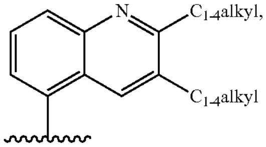
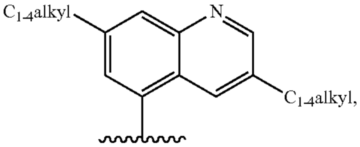
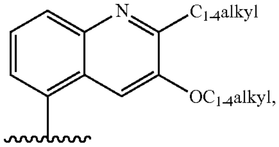
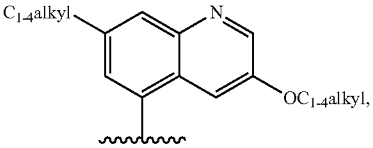
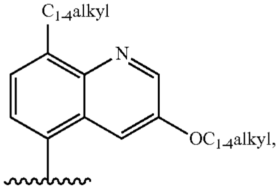
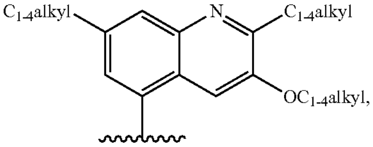
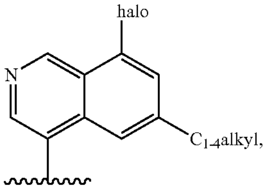
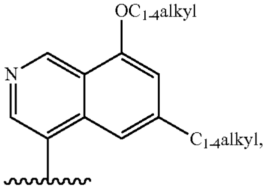
-continued
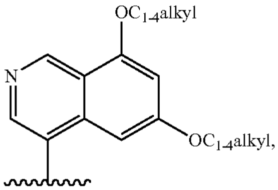
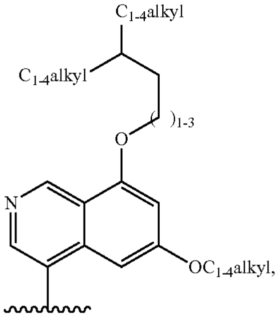
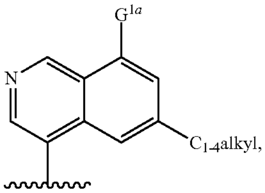
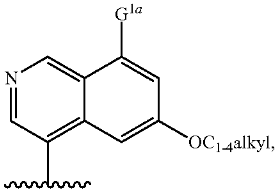
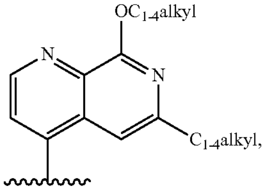
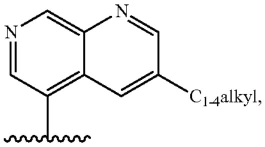
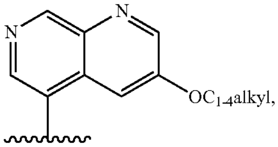
or
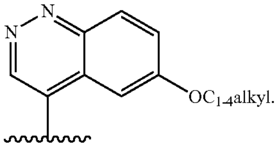
Clause 89.1. The compound of any of clauses 1-7 or 35-36.3, or a pharmaceutically acceptable salt thereof, wherein $G^1$ is -continued
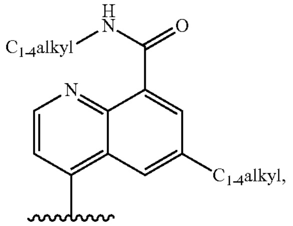
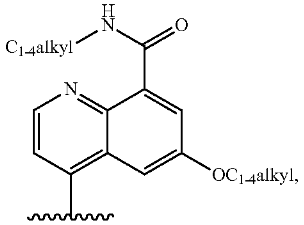
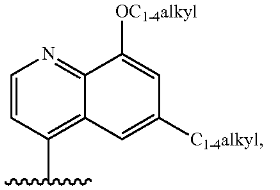
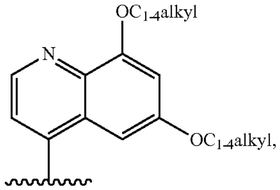
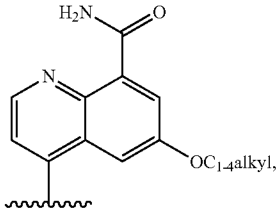
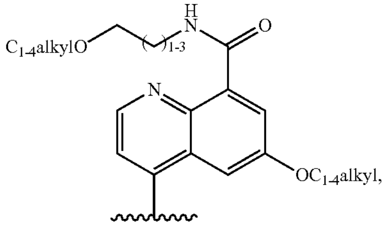
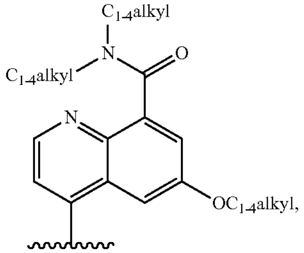
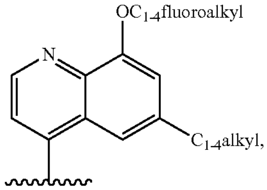
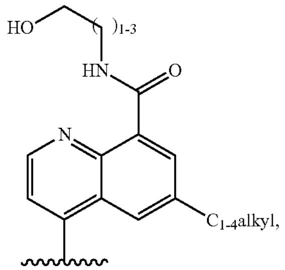
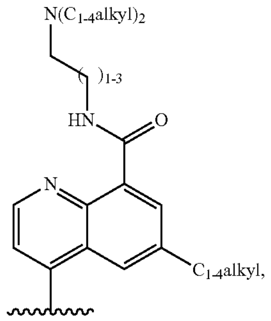
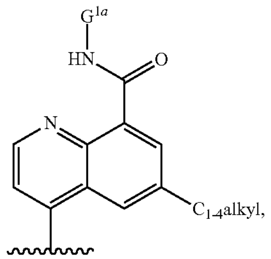
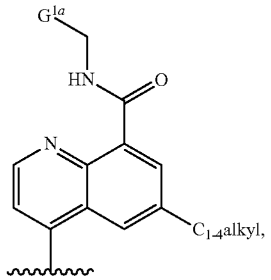
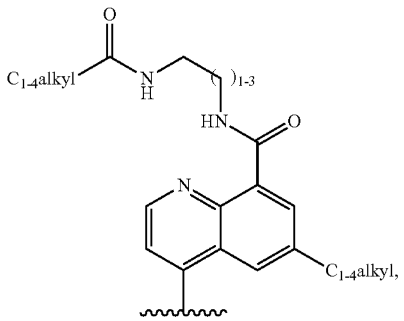

-continued
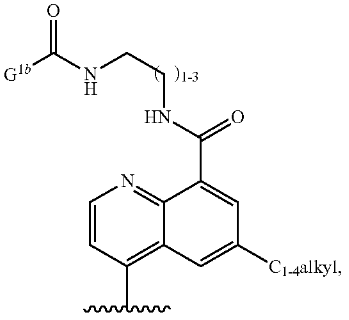
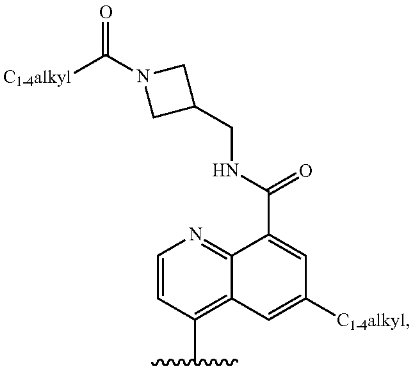
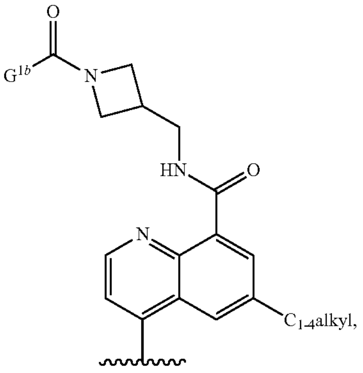
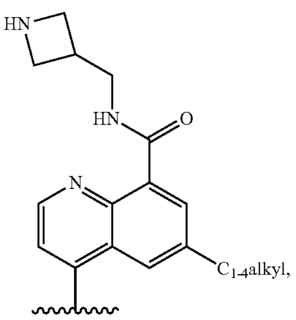
-continued
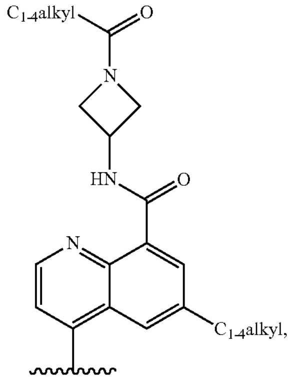
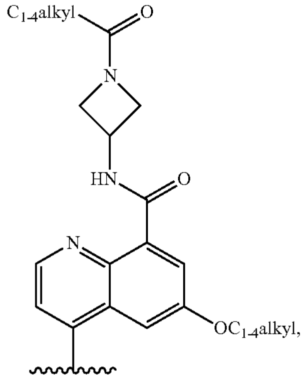
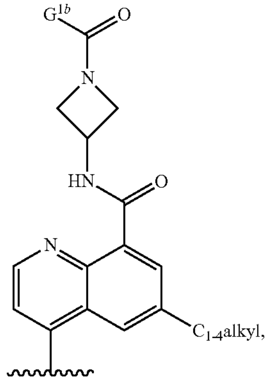
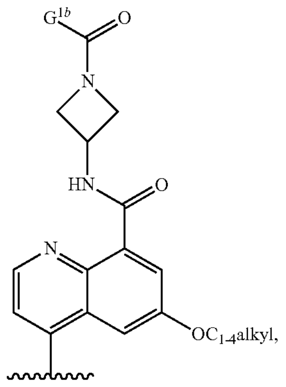

-continued
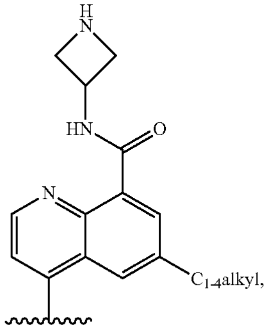
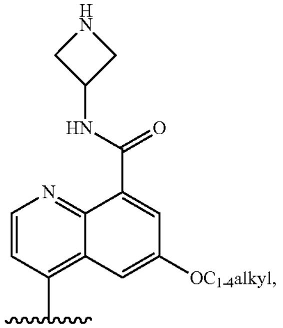
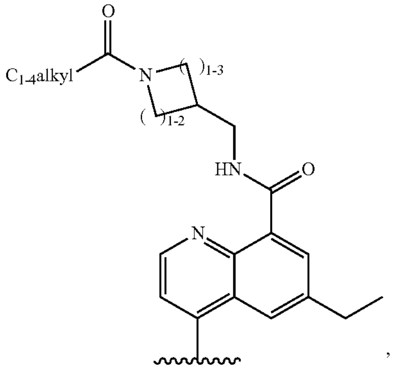
,
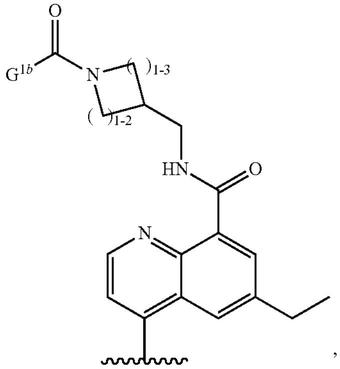
,
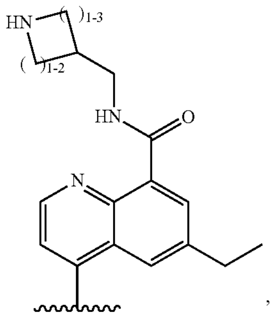
,
-continued
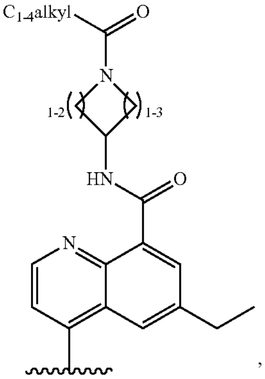
,
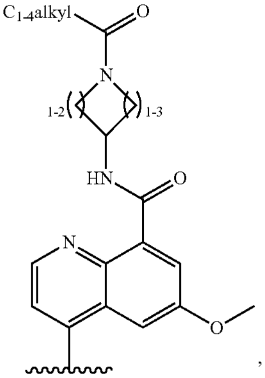
,
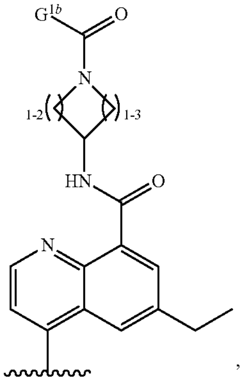
,
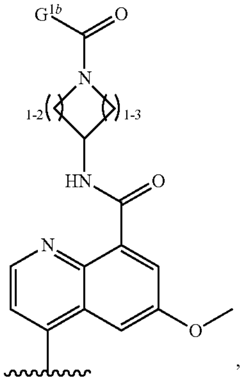
,
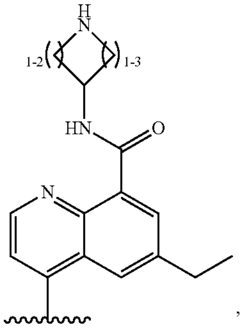
,
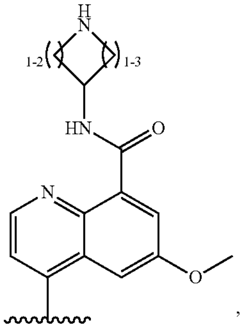
,
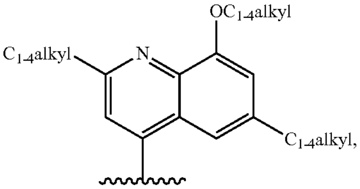

-continued
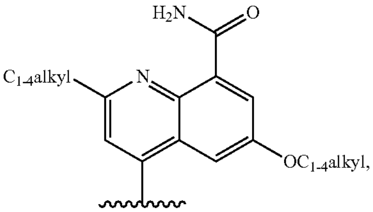
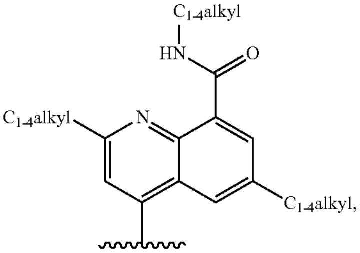
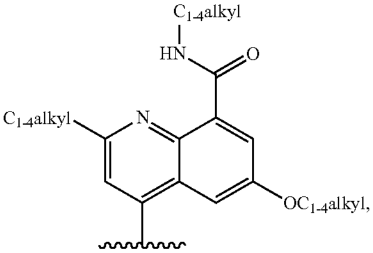
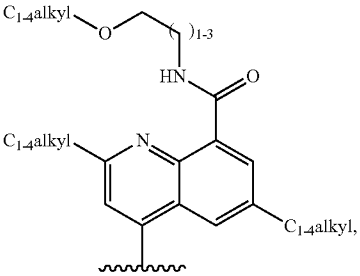
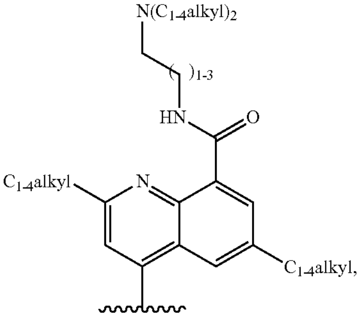
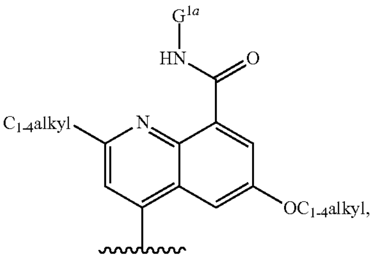
or
-continued
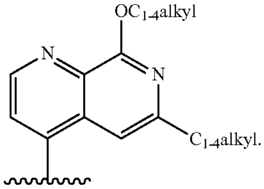
Clause 90. The compound of clause 89 or 891, or a pharmaceutically acceptable salt thereof, wherein $G^1$ is
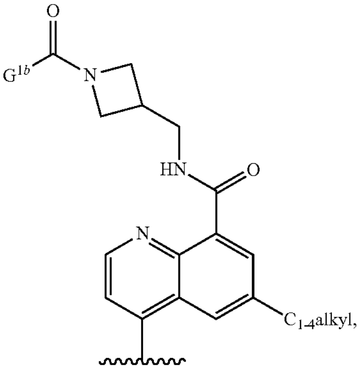
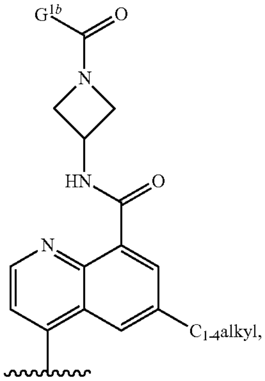
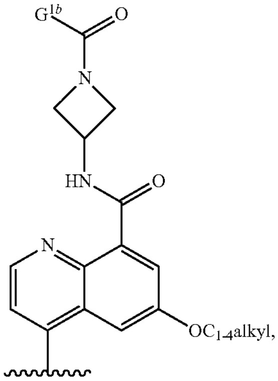

-continued

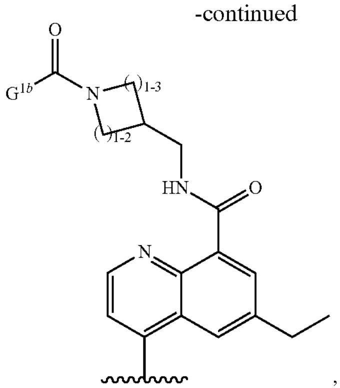

,

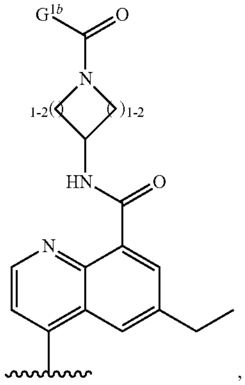

, or

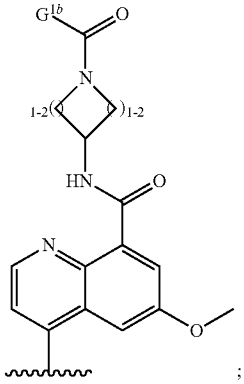

;

$G^{1b}$ is a 4- to 6-membered monocyclic heterocyclyl containing 1-2 heteroatoms independently selected from O, N, and S, or a 5- to 6-membered heteroaryl containing 1-2 heteroatoms independently selected from O, N, and S.

Clause 91 The compound of clause 89, or a pharmaceutically acceptable salt thereof, wherein $G^1$ is

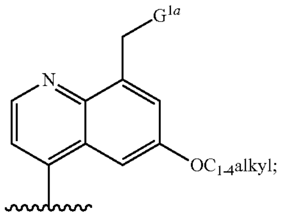

and $G^{1a}$ is as defined in any of clauses 76-78.

Clause 92. The compound of clause 89, or a pharmaceutically acceptable salt thereof, wherein $G^1$ is

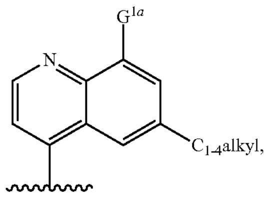

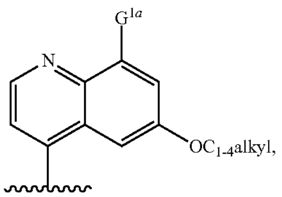

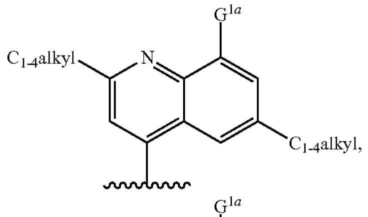

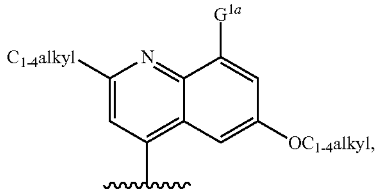

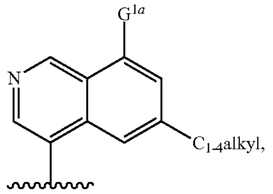

or

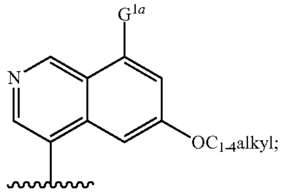

and $G^{1a}$ is as defined in any of clauses 79-82.

Clause 93. The compound of clause 89, or a pharmaceutically acceptable salt thereof, wherein $G^1$ is

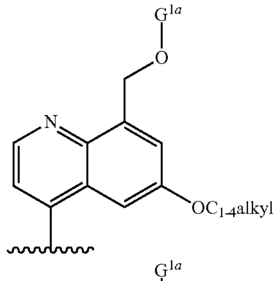

or

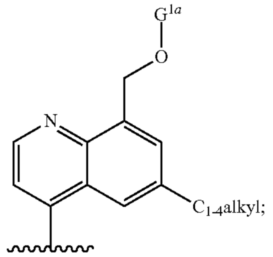

and $G^{1a}$ is as defined in any of clauses 68-70.

Clause 94. The compound of clause 89 or 89.1, or a pharmaceutically acceptable salt thereof, wherein $G^1$ is

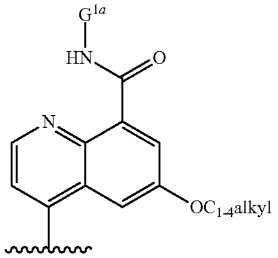
or
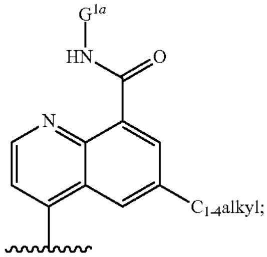
;
and $G^{1a}$ is as defined in any of clauses 62-64.
Clause 95. The compound of clause 89, or a pharmaceutically acceptable salt thereof, wherein $G^1$ is
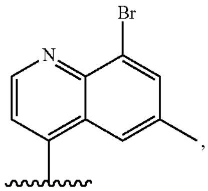
,
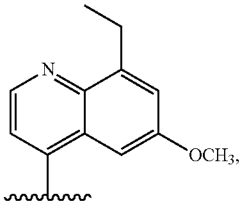
,
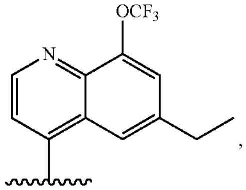
,
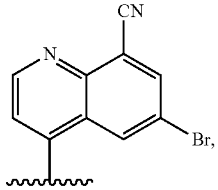
,
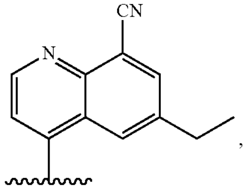
,
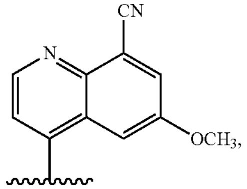
,
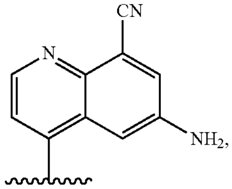
,
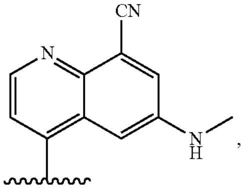
,
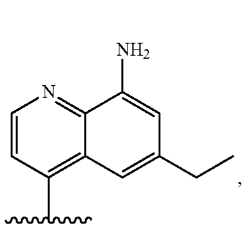
,
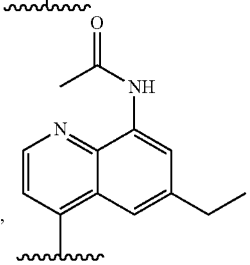
,
-continued
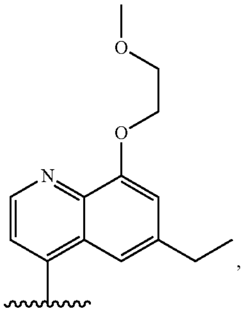
,
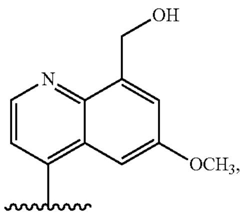
,
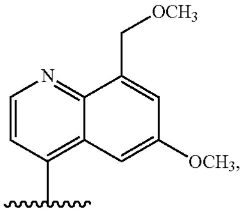
,
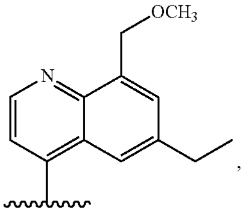
,
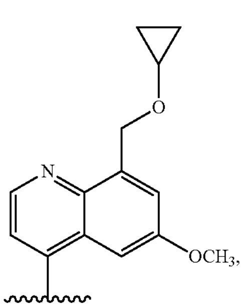
,
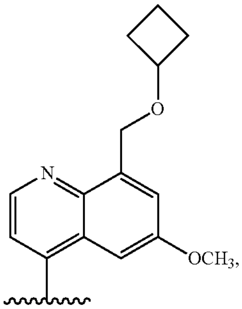
,
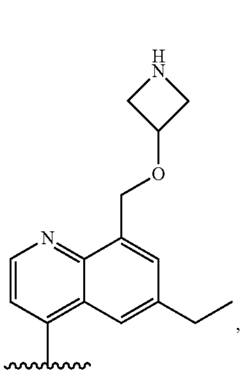
,
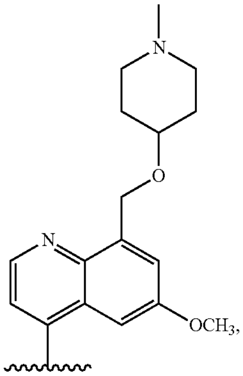
,
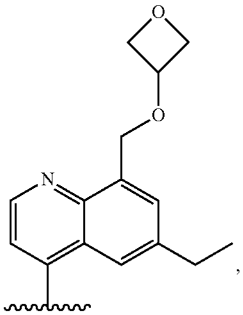
,
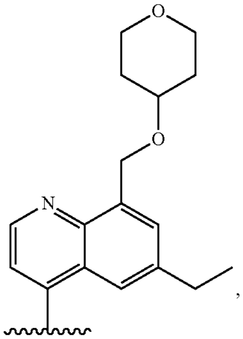
, -continued
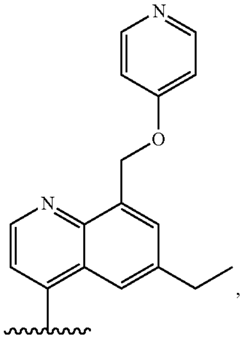,
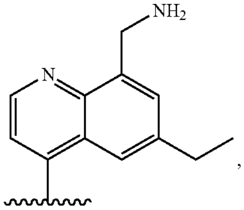,
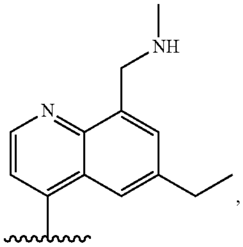,
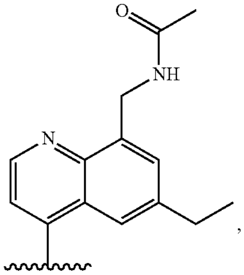,
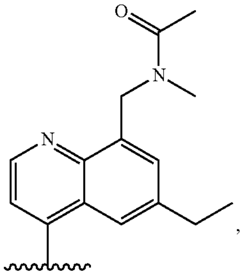,
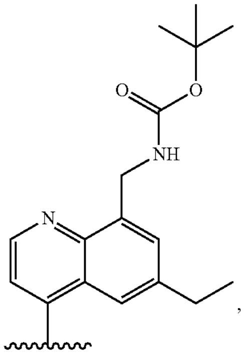,
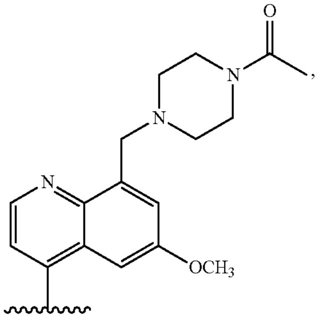,
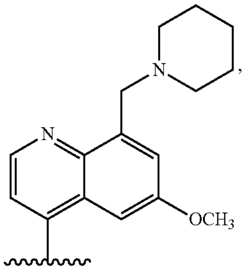,
-continued
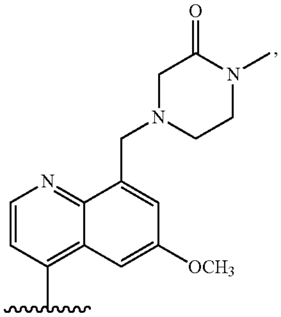,
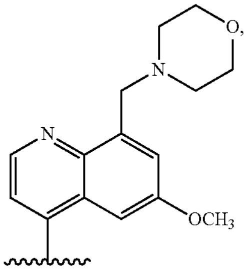,
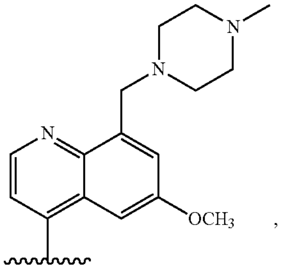,
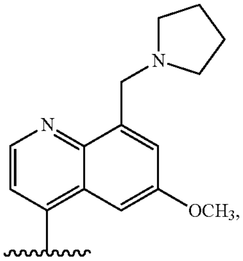,
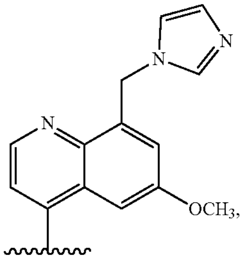,
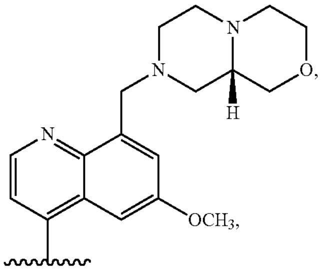,
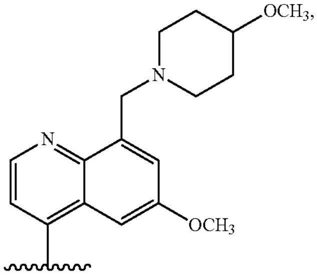

-continued
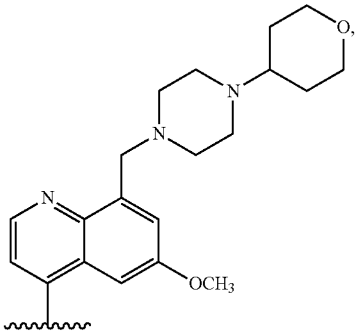
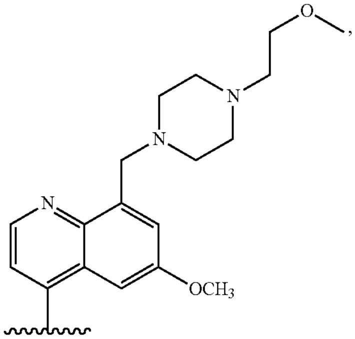
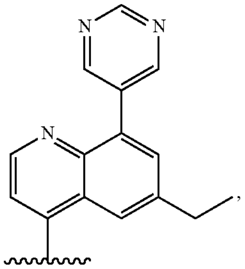,
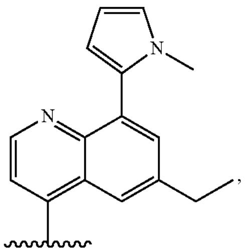,
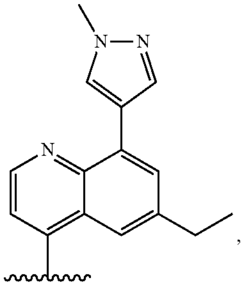,
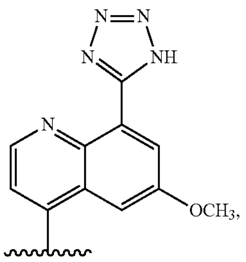,
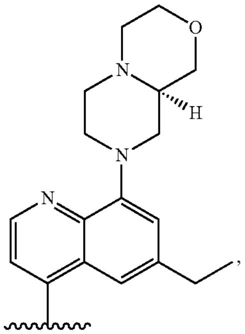,
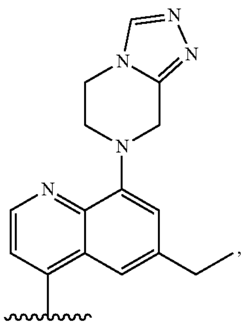,
-continued
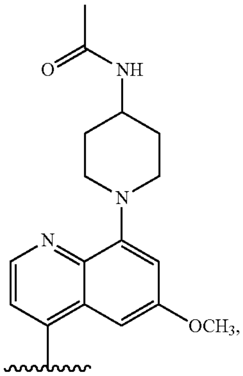,
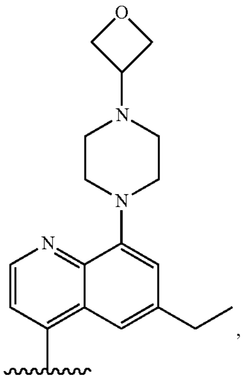,
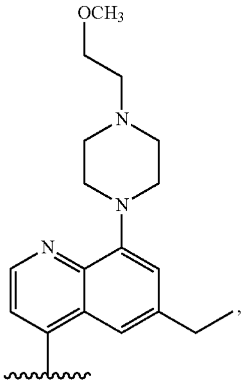,
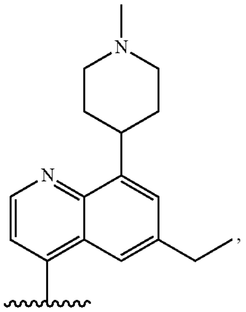,
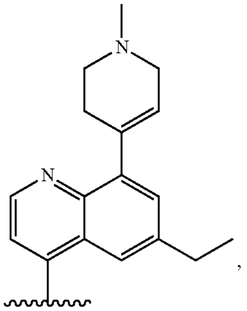,
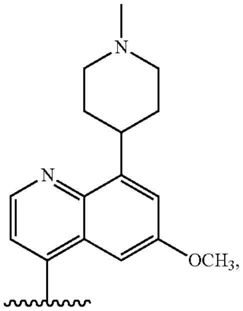,
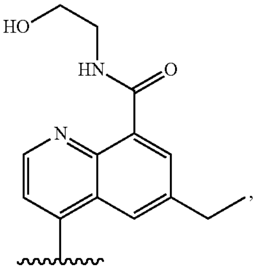,
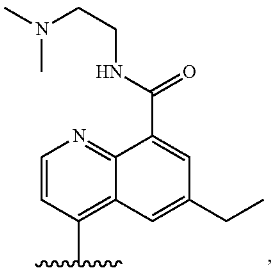,
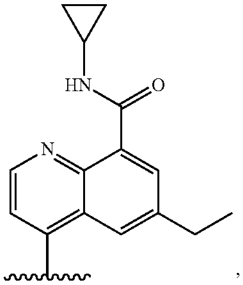, -continued
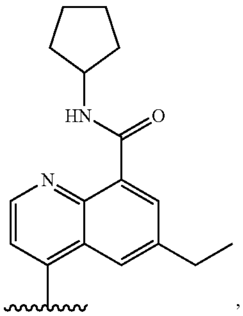
,
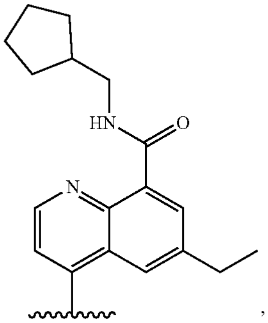
,
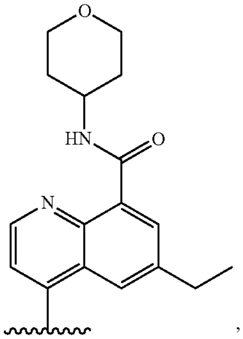
,
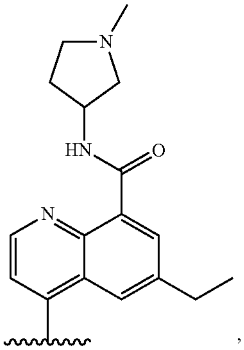
,
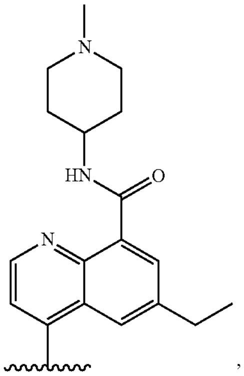
,
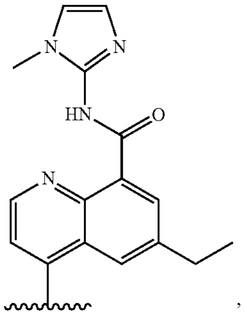
,
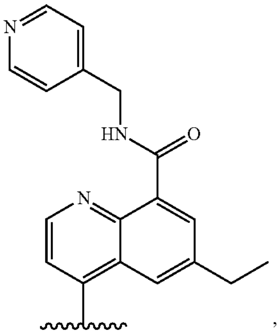
,
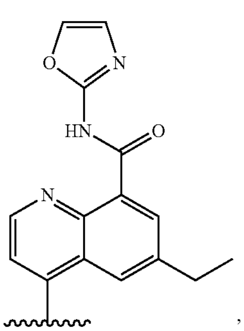
,
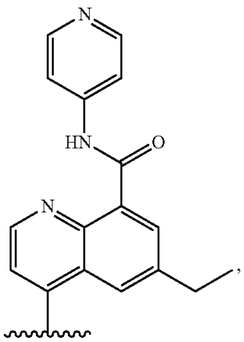
,
-continued
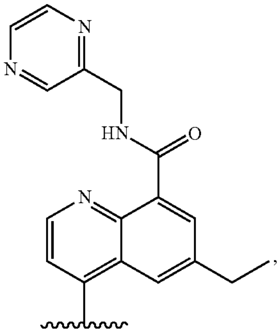
,
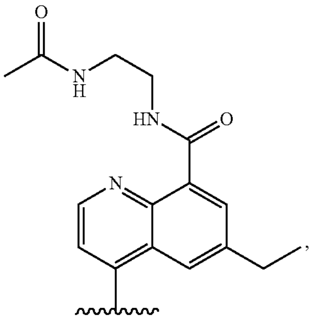
,
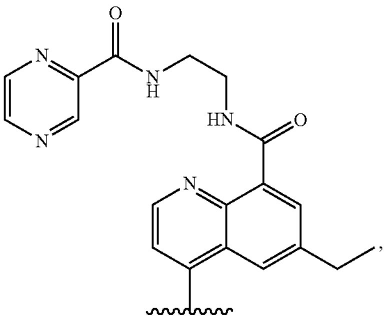
,
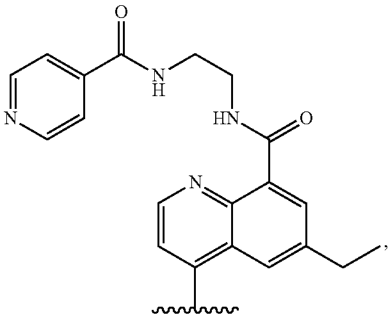
,
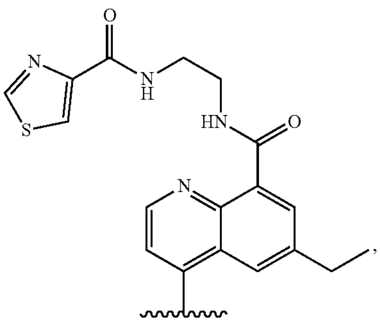
, -continued
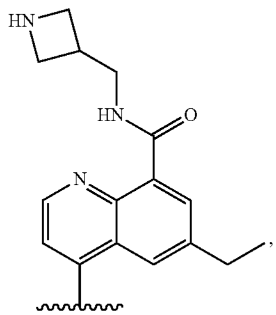
,
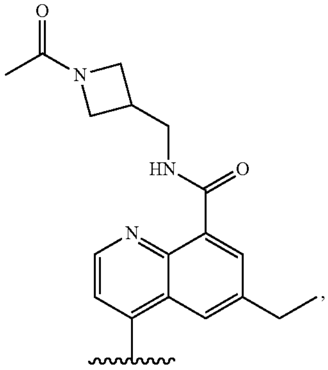
,
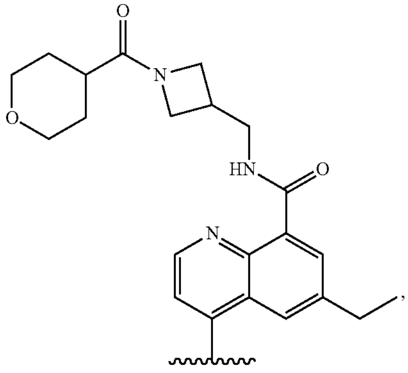
,
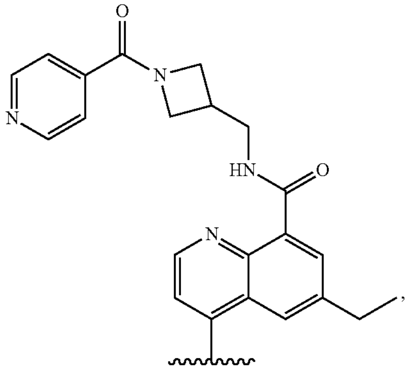
,
-continued
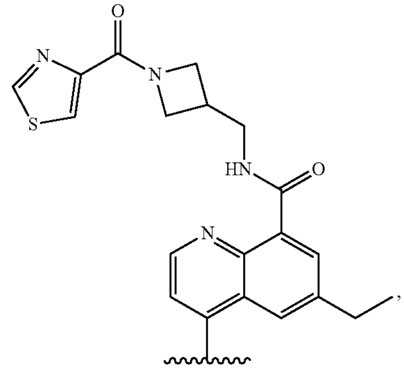
,
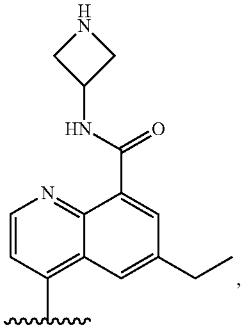
,
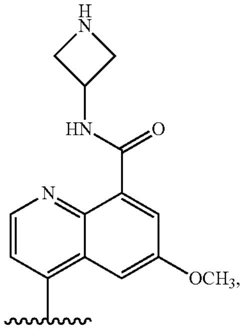
,
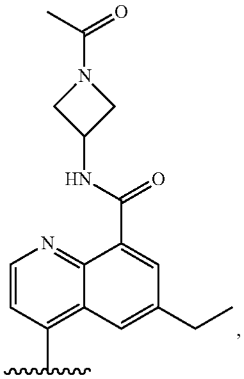
,
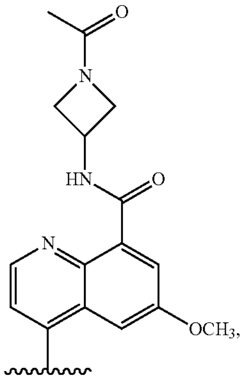
,
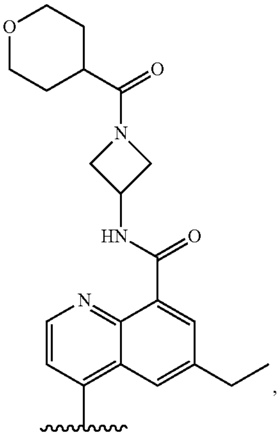
, -continued
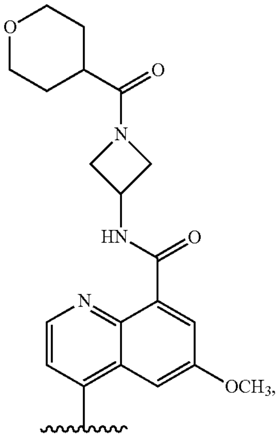
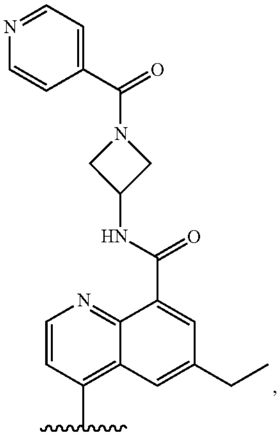
,
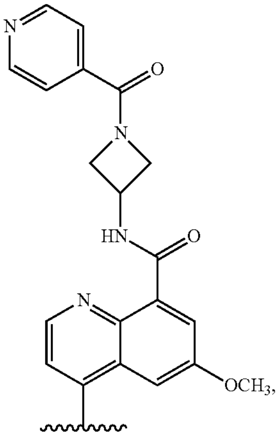
-continued
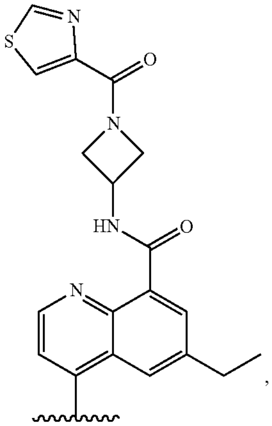
,
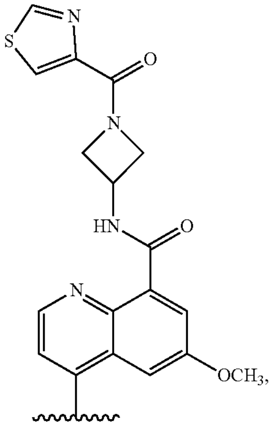
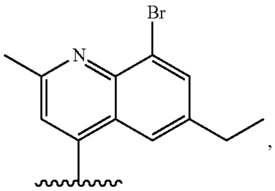
,
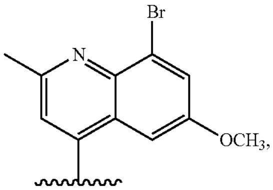
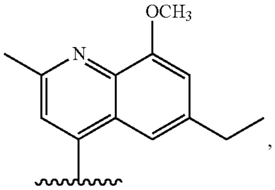
,
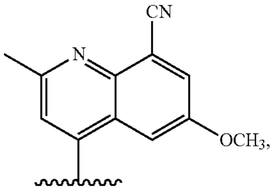

-continued
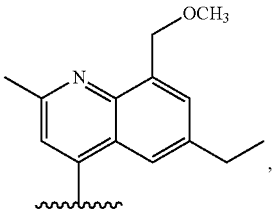,
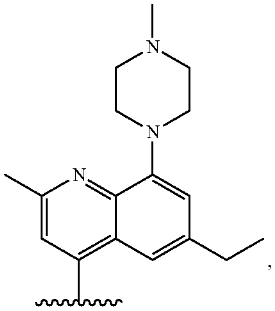,
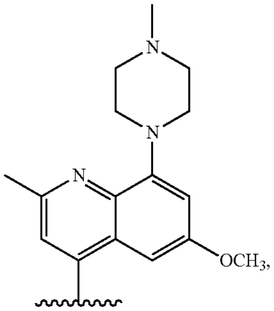,
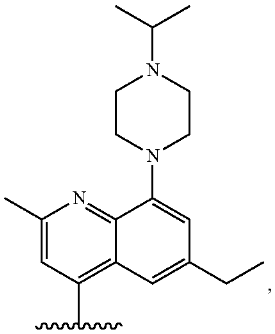,
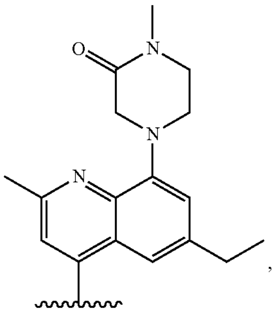,
-continued
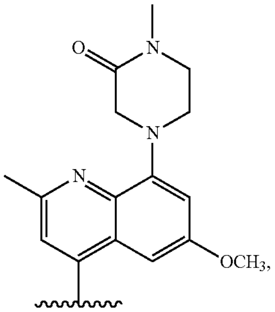,
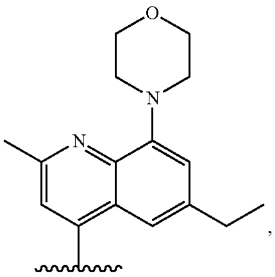,
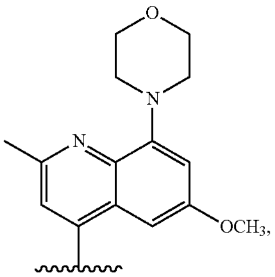,
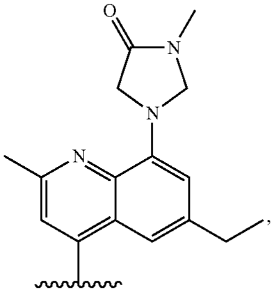,
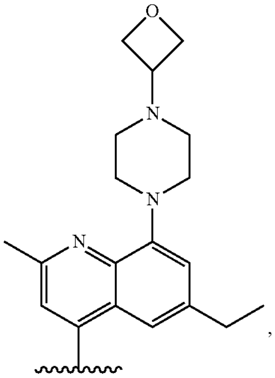, -continued
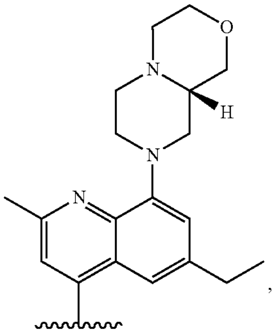
,
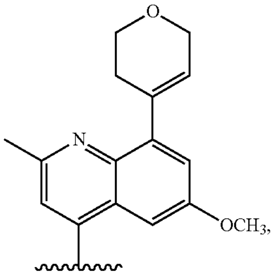
,
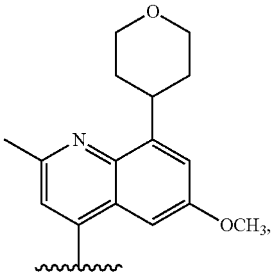
,
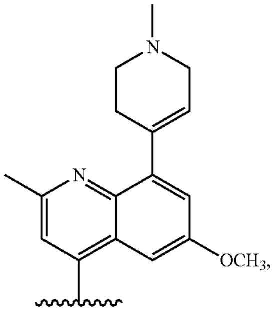
,
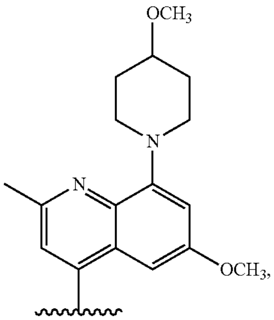
,
-continued
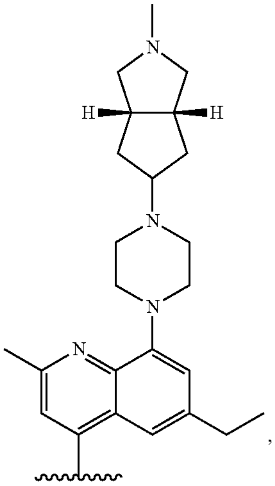
,
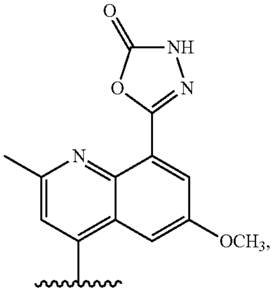
,
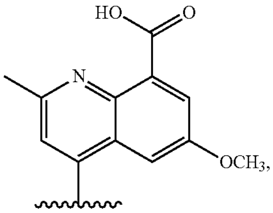
,
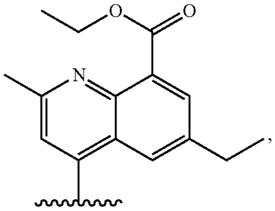
,
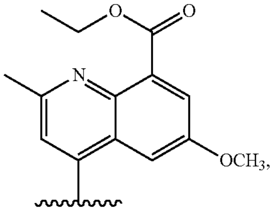
,
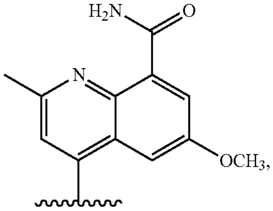
, -continued
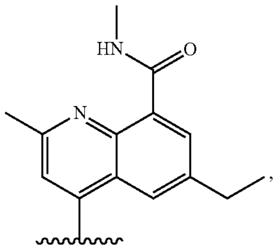
,
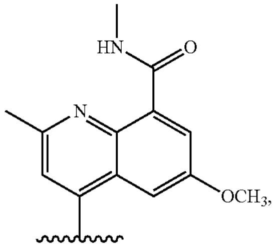
,
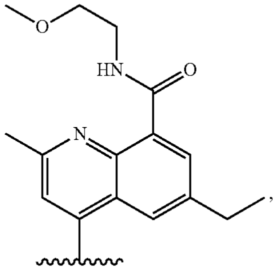
,
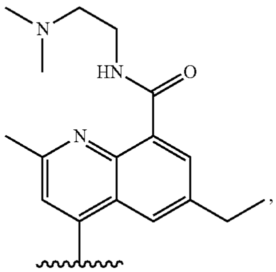
,
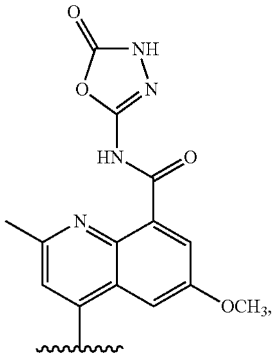
,
-continued
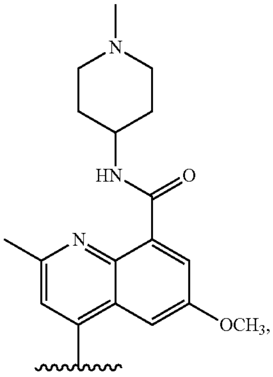
,
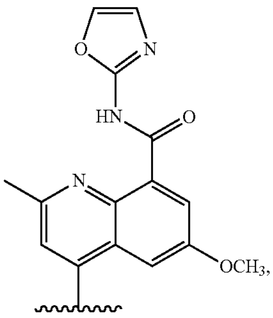
,
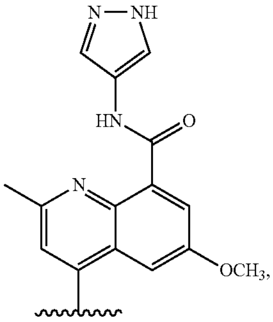
,
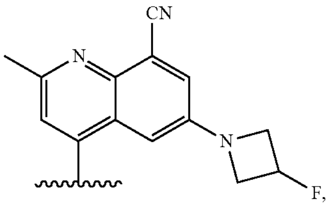
,
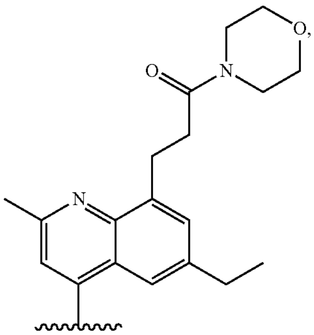

-continued
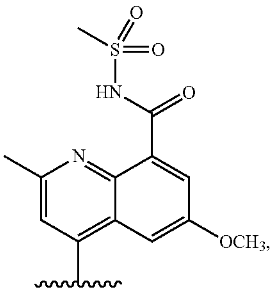
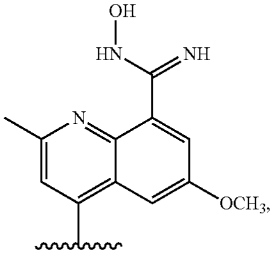
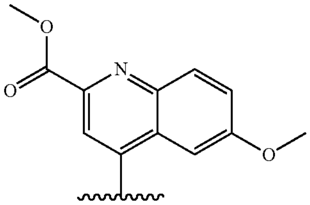,
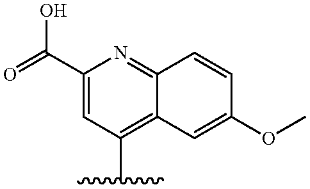,
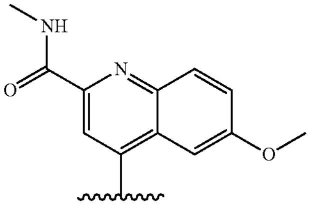, 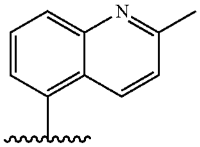,
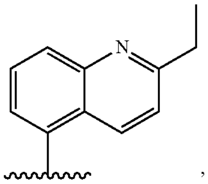, 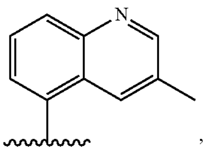,
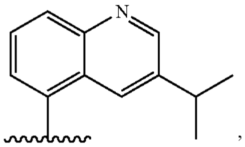, 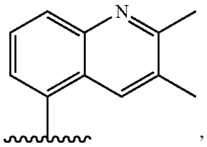,
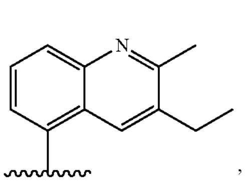, 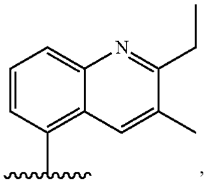,
-continued
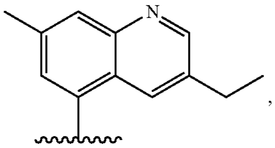, 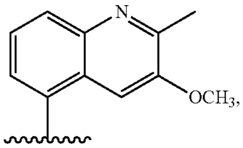
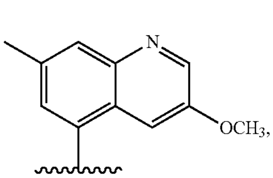 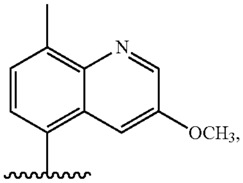
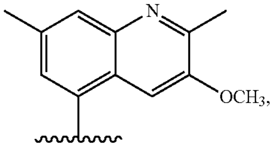 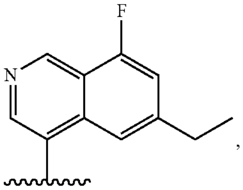,
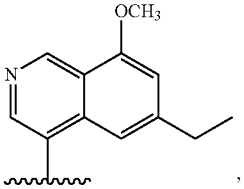, 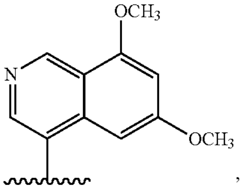,
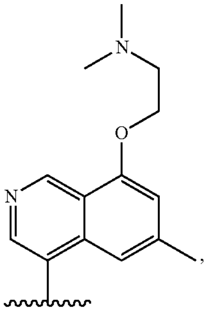, 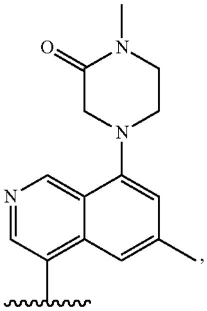,
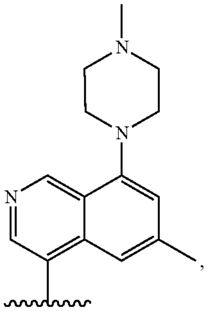, 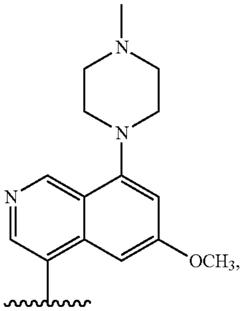
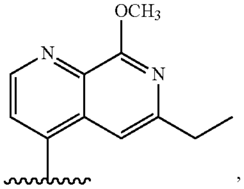, 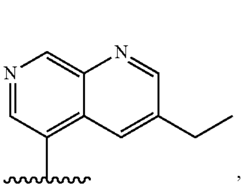,
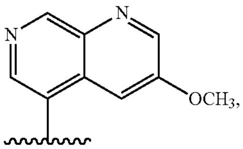 or -continued

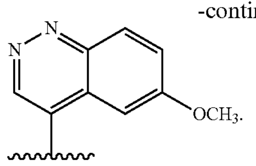

Clause 96, The compound of any of clauses 1-7 or 223, or a pharmaceutically acceptable salt thereof, wherein $G^1$ is

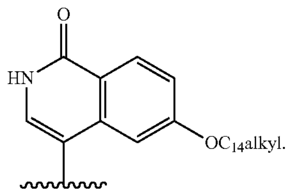

Clause 97 The compound of clause 96, or a pharmaceutically acceptable salt thereof, wherein $G^1$ is

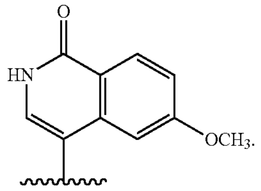 [SMILES: *c1c[nH]c(=O)c2ccc(OC)cc12]

Clause 98. The compound of any of clauses 1-97, or a pharmaceutically acceptable salt thereof, wherein $R^4$ is $G^2$ and $G^2$ is a $C_{3-10}$carbocyclyl, a 6- to 12-membered aryl, or a 5- to 12-membered heteroaryl, and optionally substituted as defined in clause 1 or 2.

Clause 98.1. The compound of any of clauses 1-98, or a pharmaceutically acceptable salt thereof, of formula (I-b)

(I-b)

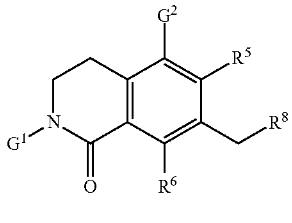

Clause 99. The compound of clause 98 or 98.1, or a pharmaceutically acceptable salt thereof, wherein $G^2$ is a 5- to 6-membered heteroaryl, and optionally substituted as defined in clause 1 or 2.

Clause 100. The compound of any of clauses 1-99, or a pharmaceutically acceptable salt thereof, wherein $G^2$ is optionally substituted with 1-4 substituents independently selected from the group consisting of halogen, $C_{1-6}$alkyl, and $C_{1-6}$haloalkyl.

Clause 101 The compound of clause 100, or a pharmaceutically acceptable salt thereof, wherein, $R^4$ is

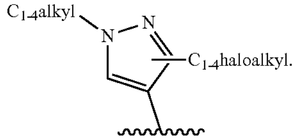

Clause 102. The compound of clause 100, or a pharmaceutically acceptable salt thereof, wherein, $R^4$ is

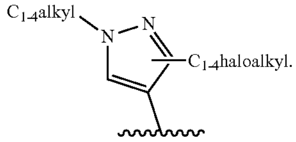

Clause 103. The compound of clause 100, or a pharmaceutically acceptable salt thereof, wherein, $R^4$ is

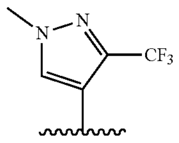 or 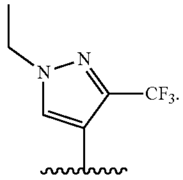

Clause 104. The compound of any of clauses 1-103, or a pharmaceutically acceptable salt thereof, wherein $R^{2a}$, $R^{2b}$, $R^{3a}$, and $R^{3b}$ are each hydrogen.

Clause 105. The compound of any of clauses 1-104, or a pharmaceutically acceptable salt thereof, wherein n is 1.

Clause 106. The compound of any of clauses 1-105, or a pharmaceutically acceptable salt thereof, wherein $R^5$ is hydrogen.

Clause 107. The compound of any of clauses 1-106, or a pharmaceutically acceptable salt thereof, wherein $R^6$ is hydrogen.

Clause 108. The compound of any of clauses 1-107, or a pharmaceutically acceptable salt thereof, wherein $R^{7a}$ and $R^{7b}$ are each hydrogen.

Clause 109. The compound of any of clauses 1-107, or a pharmaceutically acceptable salt thereof, wherein $R^{7a}$ is hydroxy and $R^{7b}$ is hydrogen.

Clause 110. The compound of any of clauses 1-109, or a pharmaceutically acceptable salt thereof, wherein $L^1$ is a bond.

Clause 111. The compound of any of clauses 1-109, or a pharmaceutically acceptable salt thereof, wherein $L^1$ is $C_{1-3}$alkylene.

Clause 112. The compound of any of clauses 1-111, or a pharmaceutically acceptable salt thereof, wherein $L^2$ is a bond.

Clause 113. The compound of any of clauses 1-111, or a pharmaceutically acceptable salt thereof, wherein $L^2$ is $C_{1-3}$alkylene.

Clause 114. The compound of clause 1, selected from the group consisting of 7-((2-Methyl-1H-imidazol-1-yl)methyl)-5-(1-methyl-3-(trifluoromethyl)-1H-pyrazol-4-yl)-2-(naphthalen-1-yl)-3,4-dihydroisoquinolin-1(2H)-one;

2-(7-Chloroquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(3-Methoxyquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(6-Methoxyquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-Methoxy-7'-((2-methyl-1H-imidazol-1-yl)methyl)-5'-(1-methyl-3-(trifluoromethyl)-1H-pyrazol-4-yl)-3',4'-dihydro-1'H-[1,2'-biisoquinolin]-1'-one;

2-(6-Methoxy-7-methylquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(6-Methoxy-8-methylquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(6-Methoxy-2-methylquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(3-Chloro-6-methoxyquinolin-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

6'-Methyl-7-((2-methyl-1H-imidazol-1-yl)methyl)-5-(1-methyl-3-(trifluoromethyl)-1H-pyrazol-4-yl)-3,4-dihydro-1H-[2,4'-biisoquinolin]-1-one;

2-(8-Methoxy-3-methylquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((1H-Imidazol-1-yl)methyl)-2-(3-methoxyquinolin-5-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-methoxyquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-methoxy-2-methylquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-5-(1-methyl-3-(trifluoromethyl)-1H-pyrazol-4-yl)-2-(6-methylquinolin-4-yl)-3,4-dihydroisoquinolin-1(2H)-one;

7-((1H-Imidazol-1-yl)methyl)-6'-methyl-5-(1-methyl-3-(trifluoromethyl)-1H-pyrazol-4-yl)-3,4-dihydro-1H-[2,4'-biisoquinolin]-1-one;

7-((1H-Imidazol-1-yl)methyl)-2-(6,8-dimethoxyquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6,8-dimethoxy-2-methylquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(8-methoxy-6-methylquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-ethyl-8-methoxyquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-1'-chloro-6'-methoxy-5-(1-methyl-3-(trifluoromethyl)-1H-pyrazol-4-yl)-3,4-dihydro-1H-[2,4'-biisoquinolin]-1-one;

7-((1H-Imidazol-1-yl)methyl)-1',6'-dimethoxy-5-(1-methyl-3-(trifluoromethyl)-1H-pyrazol-4-yl)-3,4-dihydro-1H-[2,4'-biisoquinolin]-1-one;

7-((1H-Imidazol-1-yl)methyl)-2-(8-methoxy-3-methylquinolin-5-yl)-5-(1-methyl-3-(trifluoromethyl)-1H-pyrazol-4-yl)-3,4-dihydroisoquinolin-1(2H)-one;

7-((1H-Imidazol-1-yl)methyl)-8'-chloro-6'-methyl-5-(1-methyl-3-(trifluoromethyl)-1H-pyrazol-4-yl)-3,4-dihydro-1H-[2,4'-biisoquinolin]-1-one;

7-((1H-Imidazol-1-yl)methyl)-2-(6-methoxyquinazolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(1,2-dimethyl-1H-indol-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-5-(1-methyl-3-(trifluoromethyl)-1H-pyrazol-4-yl)-2-(2-methylbenzo[d]oxazol-7-yl)-3,4-dihydroisoquinolin-1(2H)-one;

7-((1H-Imidazol-1-yl)methyl)-2-(1,2-dimethyl-1H-pyrrolo[2,3-b]pyridin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(8-bromo-6-methoxyquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-methoxy-8-morpholinoquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-methoxy-8-(4-methylpiperazin-1-yl)quinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(8-(4-acetylpiperazin-1-yl)-6-methoxyquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-methoxy-8-(4-methyl-3-oxopiperazin-1-yl)quinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(8-bromo-6-ethylquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(8-(dimethylamino)-6-ethylquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-ethyl-8-morpholinoquinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-ethyl-8-(4-methylpiperazin-1-yl)quinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(8-((2-(dimethylamino)ethyl)(methyl)amino)-6-ethylquinolin-4-yl)-5-(1-methyl-3-(trifluoromethyl)-1H-pyrazol-4-yl)-3,4-dihydroisoquinolin-1(2H)-one;

ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylate;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxylic acid;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carboxamide;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-methylquinoline-8-carboxamide;

7-((1H-Imidazol-1-yl)methyl)-2-(6-methoxy-8-(4-methylpiperazine-1-carbonyl)quinolin-4-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-methoxy-8-(pyrrolidine-1-carbonyl)quinolin-4-yl)-5-(1-methyl-3-(trifluoromethyl)-1H-pyrazol-4-yl)-3,4-dihydroisoquinolin-1(2H)-one;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N,N-dimethylquinoline-8-carboxamide;

7-((1H-Imidazol-1-yl)methyl)-2-(6-methoxy-8-(morpholine-4-carbonyl)quinolin-4-yl)-5-(1-methyl-3-(trifluoromethyl)-1H-pyrazol-4-yl)-3,4-dihydroisoquinolin-1(2H)-one;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-isopropyl-6-methoxyquinoline-8-carboxamide;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-N-butyl-6-methoxyquinoline-8-carboxamide;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-(2-methoxyethyl)quinoline-8-carboxamide;

5-(1-Ethyl-3-(trifluoromethyl)-1H-pyrazol-4-yl)-2-(3-methoxyquinolin-5-yl)-7-((2-methyl-1H-imidazol-1-yl)methyl)-3,4-dihydroisoquinolin-1(2H)-one;

5-(1-Ethyl-3-(trifluoromethyl)-1H-pyrazol-4-yl)-2-(6-methoxy-2-methylquinolin-4-yl)-7-((2-methyl-1H-imidazol-1-yl)methyl)-3,4-dihydroisoquinolin-1(2H)-one;

7-((1H-Imidazol-1-yl)methyl)-5-(1-ethyl-3-(trifluoromethyl)-1H-pyrazol-4-yl)-2-(3-methoxyquinolin-5-yl)-3,4-dihydroisoquinolin-1(2H)-one;

7-((1H-Imidazol-1-yl)methyl)-5-(1-ethyl-3-(trifluoromethyl)-1H-pyrazol-4-yl)-2-(6-methoxy-2-methylquinolin-4-yl)-3,4-dihydroisoquinolin-1(2H)-one;

7-((1H-Imidazol-1-yl)methyl)-5-(1-ethyl-3-(trifluoromethyl)-1H-pyrazol-4-yl)-6'-methyl-3,4-dihydro-1H-[2,4'-biisoquinolin]-1-one;

7-((1H-imidazol-5-yl)methyl)-6'-methyl-5-(1-methyl-3-(trifluoromethyl)-1H-pyrazol-4-yl)-3,4-dihydro-1H-[2,4'-biisoquinolin]-1-one;

7-((1H-imidazol-2-yl)methyl)-6'-methyl-5-(1-methyl-3-(trifluoromethyl)-1H-pyrazol-4-yl)-3,4-dihydro-1H-[2,4'-biisoquinolin]-1-one;

7-(hydroxy(1-methyl-1H-imidazol-4-yl)methyl)-6'-methyl-5-(1-methyl-3-(trifluoromethyl)-1H-pyrazol-4-yl)-3,4-dihydro-1H-[2,4'-biisoquinolin]-1-one;

6'-methyl-7-((1-methyl-1H-imidazol-4-yl)methyl)-5-(1-methyl-3-(trifluoromethyl)-1H-pyrazol-4-yl)-3,4-dihydro-1H-[2,4'-biisoquinolin]-1-one;

6'-methyl-5-(1-methyl-3-(trifluoromethyl)-1H-pyrazol-4-yl)-7-(pyridin-4-ylmethyl)-3,4-dihydro-1H-[2,4'-biisoquinolin]-1-one;

2-(7-Bromo-1,2,3,4-tetrahydronaphthalen-1-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(6-Bromochroman-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((2-Methyl-1H-imidazol-1-yl)methyl)-5-(1-methyl-3-(trifluoromethyl)-1H-pyrazol-4-yl)-2-(6-methylchroman-4-yl)-3,4-dihydroisoquinolin-1(2H)-one;

2-(6-Cyclopropylchroman-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((2-Methyl-1H-imidazol-1-yl)methyl)-5-(1-methyl-3-(trifluoromethyl)-1H-pyrazol-4-yl)-2-(5,6,7,8-tetrahydroquinolin-5-yl)-3,4-dihydroisoquinolin-1(2H)-one;

2-(3-Methoxy-5,6,7,8-tetrahydroquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((1H-Imidazol-1-yl)methyl)-2-(7-methoxy-1,2,3,4-tetrahydronaphthalen-1-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(6-methoxychroman-4-yl)-5-(1-methyl-3-(trifluoromethyl)-1H-pyrazol-4-yl)-3,4-dihydroisoquinolin-1(2H)-one;

(S)-2-(3-Methoxy-5,6,7,8-tetrahydroquinolin-5-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-2-(6-Methoxychroman-4-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-7-((1H-Imidazol-1-yl)methyl)-2-(6-methoxychroman-4-yl)-5-(1-methyl-3-(trifluoromethyl)-1H-pyrazol-4-yl)-3,4-dihydroisoquinolin-1(2H)-one;

(S)-7-((1H-Imidazol-1-yl)methyl)-2-(3-methoxy-5,6,7,8-tetrahydroquinolin-5-yl)-5-(1-methyl-3-(trifluoromethyl)-1H-pyrazol-4-yl)-3,4-dihydroisoquinolin-1(2H)-one;

((S)-7-((1H-Imidazol-1-yl)methyl)-2-(6-chloro-3,4-dihydro-2H-pyrano[2,3-b]pyridin-4-yl)-5-(1-methyl-3-(trifluoromethyl)-1H-pyrazol-4-yl)-3,4-dihydroisoquinolin-1(2H)-one;

(S)-7-((1H-Imidazol-1-yl)methyl)-2-(6-chloro-1-methyl-1,2,3,4-tetrahydro-1,8-naphthyridin-4-yl)-5-(1-methyl-3-(trifluoromethyl)-1H-pyrazol-4-yl)-3,4-dihydroisoquinolin-1(2H)-one;

(S)-5-(1-Ethyl-3-(trifluoromethyl)-1H-pyrazol-4-yl)-2-(6-methoxychroman-4-yl)-7-((2-methyl-1H-imidazol-1-yl)methyl)-3,4-dihydroisoquinolin-1(2H)-one;

(S)-7-((1H-Imidazol-1-yl)methyl)-5-(1-ethyl-3-(trifluoromethyl)-1H-pyrazol-4-yl)-2-(6-methoxychroman-4-yl)-3,4-dihydroisoquinolin-1(2H)-one;

(S)-2-(2,3-Dihydro-1H-inden-1-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(2,3-Dihydrobenzofuran-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-Methoxy-1-methyl-1H-indol-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-Methoxy-1-methyl-1H-pyrrolo[2,3-b]pyridin-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-Methoxy-1,2-dimethyl-1H-indol-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-Methoxy-1-methyl-1H-indazol-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-Fluoro-1-methyl-1H-pyrrolo[2,3-b]pyridin-3-yl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((1H-Imidazol-1-yl)methyl)-2-(5-methoxy-1-methyl-1H-pyrrolo[2,3-b]pyridin-3-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(1-ethyl-5-methoxy-1H-pyrrolo[2,3-b]pyridin-3-yl)-5-(1-methyl-3-(trifluoromethyl)-1H-pyrazol-4-yl)-3,4-dihydroisoquinolin-1(2H)-one;

7-((1H-Imidazol-1-yl)methyl)-2-(5,7-dimethoxy-1-methyl-1H-indol-3-yl)-5-(1-methyl-3-(trifluoromethyl)-1H-pyrazol-4-yl)-3,4-dihydroisoquinolin-1(2H)-one;

5-(1-Ethyl-3-(trifluoromethyl)-1H-pyrazol-4-yl)-2-(5-methoxy-1-methyl-1H-indol-3-yl)-7-((2-methyl-1H-imidazol-1-yl)methyl)-3,4-dihydroisoquinolin-1(2H)-one;

7-((1H-imidazol-1-yl)methyl)-6'-methoxy-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-6'-methoxy-1'-methyl-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-6'-ethyl-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-2-(3-ethylquinolin-5-yl)-5-(1-methyl-3-(trifluoromethyl)-1H-pyrazol-4-yl)-3,4-dihydroisoquinolin-1(2H)-one;

ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylate;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxylic acid;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-methylquinoline-8-carboxamide;

7-((1H-imidazol-1-yl)methyl)-2-(8-(hydroxymethyl)-6-methoxyquinolin-4-yl)-5-(1-methyl-3-(trifluoromethyl)-1H-pyrazol-4-yl)-3,4-dihydroisoquinolin-1(2H)-one;

ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylate;

7-((1H-imidazol-1-yl)methyl)-2-(6-ethyl-8-(pyrimidin-5-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-(1-methyl-1H-pyrrol-2-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-6'-methoxy-5-(1-methyl-3-(trifluoromethyl)-1H-pyrazol-4-yl)-3,4-dihydro-1H-[2,4'-biisoquinoline]-1,1'(2'H)-dione;

7-((1H-imidazol-1-yl)methyl)-8'-bromo-6'-methyl-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-6'-methyl-5-(1-methyl-3-(trifluoromethyl)-1H-pyrazol-4-yl)-8'-(4-methylpiperazin-1-yl)-3,4-dihydro-1H-[2,4'-biisoquinolin]-1-one;

7-((1H-imidazol-1-yl)methyl)-2-(8-bromo-6-methoxy-2-methylquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-2-methyl-8-(4-methylpiperazin-1-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-5-(1-methyl-3-(trifluoromethyl)-1H-pyrazol-4-yl)-2-(2-methylquinolin-5-yl)-3,4-dihydroisoquinolin-1(2H)-one;

7-((1H-imidazol-1-yl)methyl)-5-(1-methyl-3-(trifluoromethyl)-1H-pyrazol-4-yl)-2-(3-methylquinolin-5-yl)-3,4-dihydroisoquinolin-1(2H)-one;

7-((1H-imidazol-1-yl)methyl)-2-(6-methoxy-2-methyl-8-(4-methyl-3-oxopiperazin-1-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-8'-(2-(dimethylamino)ethoxy)-6'-methyl-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-2-(2-ethylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(2,3-dimethylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(8-bromo-6-ethyl-2-methylquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-2-methyl-8-(4-methylpiperazin-1-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-2-methyl-8-(4-methyl-3-oxopiperazin-1-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-6'-methyl-5-(1-methyl-3-(trifluoromethyl)-1H-pyrazol-4-yl)-8'-(4-methyl-3-oxopiperazin-1-yl)-3,4-dihydro-1H-[2,4'-biisoquinolin]-1-one;

7-((1H-imidazol-1-yl)methyl)-2-(6-ethyl-2-methyl-8-(3-methyl-4-oxoimidazolidin-1-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(3-methoxy-2-methylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-6'-ethyl-8'-fluoro-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-6'-ethyl-8'-methoxy-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-2-(3-ethyl-2-methylquinolin-5-yl)-5-(1-methyl-3-(trifluoromethyl)-1H-pyrazol-4-yl)-3,4-dihydroisoquinolin-1(2H)-one;

2-(6-methoxy-2-methylquinolin-4-yl)-5-(1-methyl-3-(trifluoromethyl)-1H-pyrazol-4-yl)-7-((2-nitro-1H-imidazol-1-yl)methyl)-3,4-dihydroisoquinolin-1(2H)-one;

7-((1H-imidazol-1-yl)methyl)-2-(2-ethyl-3-methylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-methoxy-2-methylquinolin-4-yl)-5-(1-methyl-3-(trifluoromethyl)-1H-pyrazol-4-yl)-3,4-dihydroisoquinolin-1(2H)-one;

7-((2-amino-1H-imidazol-1-yl)methyl)-2-(6-methoxy-2-methylquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-6',8'-dimethoxy-5-(1-methyl-3-(trifluoromethyl)-1H-pyrazol-4-yl)-3,4-dihydro-1H-[2,4'-biisoquinolin]-1-one;

7-((1H-imidazol-1-yl)methyl)-6'-methoxy-5-(1-methyl-3-(trifluoromethyl)-1H-pyrazol-4-yl)-8'-(4-methylpiperazin-1-yl)-3,4-dihydro-1H-[2,4'-biisoquinolin]-1-one;

(R)-7-((1H-imidazol-1-yl)methyl)-2-(6-ethyl-8-(hexahydropyrazino[2,1-c][1,4]oxazin-8(1H)-yl)-2-methylquinolin-4-yl)-5-(1-methyl-3-(trifluoromethyl)-1H-pyrazol-4-yl)-3,4-dihydroisoquinolin-1(2H)-one;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxylic acid;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-bromo-2-methylquinoline-8-carbonitrile;

7-((1H-imidazol-1-yl)methyl)-2-(8-((4-acetylpiperazin-1-yl)methyl)-6-methoxyquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-(piperidin-1-ylmethyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(3-ethyl-7-methylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(3-cyclopropylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-((4-methyl-3-oxopiperazin-1-yl)methyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-2-methyl-8-(4-(oxetan-3-yl)piperazin-1-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-(morpholinomethyl)quinolin-4-yl)-5-(1-methyl-3-(trifluoromethyl)-1H-pyrazol-4-yl)-3,4-dihydroisoquinolin-1(2H)-one;

(S)-7-((1H-imidazol-1-yl)methyl)-2-(6-ethyl-8-(hexahydropyrazino[2,1-c][1,4]oxazin-8(1H)-yl)-2-methylquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-((4-methylpiperazin-1-yl)methyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-(methoxymethyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-(4-isopropylpiperazin-1-yl)-2-methylquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-(pyrrolidin-1-ylmethyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(8-((1H-imidazol-1-yl)methyl)-6-methoxyquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-(2-methoxyethoxy)quinolin-4-yl)-5-(1-methyl-3-(trifluoromethyl)-1H-pyrazol-4-yl)-3,4-dihydroisoquinolin-1(2H)-one;

(S)-7-((1H-imidazol-1-yl)methyl)-2-(8-((hexahydropyrazino[2,1-c][1,4]oxazin-8(1H)-yl)methyl)-6-methoxyquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-((4-methoxypiperidin-1-yl)methyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-((4-(tetrahydro-2H-pyran-4-yl)piperazin-1-yl)methyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-((4-(2-methoxyethyl)piperazin-1-yl)methyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-2-methyl-8-morpholinoquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-2-methyl-8-morpholinoquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-2-methyl-8-(1-methyl-1,2,3,6-tetrahydropyridin-4-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-2-methyl-8-(1-methylpiperidin-4-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(8-ethyl-6-methoxyquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-8-(methoxymethyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(8-(3,6-dihydro-2H-pyran-4-yl)-6-methoxy-2-methylquinolin-4-yl)-5-(1-methyl-3-(trifluoromethyl)-1H-pyrazol-4-yl)-3,4-dihydroisoquinolin-1(2H)-one;

tert-butyl ((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)(methyl)carbamate;

7-((1H-imidazol-1-yl)methyl)-2-(6-ethyl-2-methyl-8-(3-morpholino-3-oxopropyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-2-methyl-8-(1-methyl-1,2,3,6-tetrahydropyridin-4-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(3-methoxy-2,7-dimethylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-(methoxymethyl)-2-methylquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-2-methyl-8-(1-methylpiperidin-4-yl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(pyridin-4-yl)quinoline-8-carboxamide;

7-((1H-imidazol-1-yl)methyl)-2-(8-(cyclobutoxymethyl)-6-methoxyquinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(oxazol-2-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-methyl-1H-imidazol-2-yl)quinoline-8-carboxamide;

ethyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-2-methylquinoline-8-carboxylate;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(pyridin-4-ylmethyl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-cyclopentyl-6-ethylquinoline-8-carboxamide;

7-((1H-imidazol-1-yl)methyl)-2-(6-methoxy-2-methyl-8-(tetrahydro-2H-pyran-4-yl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(2-(dimethylamino)ethyl)-6-ethylquinoline-8-carboxamide;

7-((1H-imidazol-1-yl)methyl)-2-(8-(cyclopropoxymethyl)-6-methoxyquinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-hydroxyethyl)quinoline-8-carboxamide;

7-((1H-imidazol-1-yl)methyl)-2-(6-methoxy-8-(((1-methylpiperidin-4-yl)oxy)methyl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(cyclopentylmethyl)-6-ethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(tetrahydro-2H-pyran-4-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-cyclopropyl-6-ethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(pyrazin-2-ylmethyl)quinoline-8-carboxamide;

7-((1H-Imidazol-1-yl)methyl)-2-(6-methoxycinnolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carbonitrile;

7-((1H-imidazol-1-yl)methyl)-2-(6-ethyl-8-(trifluoromethoxy)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-((methylamino)methyl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N,2-dimethylquinoline-8-carboxamide;

7-((1H-imidazol-1-yl)methyl)-2-(8-((azetidin-3-yloxy)methyl)-6-ethylquinolin-4-yl)-5-(1-methyl-3-(trifluoromethyl)-1H-pyrazol-4-yl)-3,4-dihydroisoquinolin-1(2H)-one;

5-(4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinolin-8-yl)-1,3,4-oxadiazol-2(3H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methyl-N-(methylsulfonyl)quinoline-8-carboxamide;

7-((1H-imidazol-1-yl)methyl)-2-(6-ethyl-8-(((tetrahydro-2H-pyran-4-yl)oxy)methyl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N,2-dimethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-hydroxy-6-methoxy-2-methylquinoline-8-carboximidamide;

7-((1H-imidazol-1-yl)methyl)-2-(6-ethyl-8-methoxyquinolin-4-yl)-5-(2-(trifluoromethyl)pyridin-3-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-methylpiperidin-4-yl)quinoline-8-carboxamide;

7-((1H-imidazol-1-yl)methyl)-2-(6-ethyl-8-((pyridin-4-yloxy)methyl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-(methoxymethyl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methyl-N-(1-methylpiperidin-4-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-methoxyethyl)-2-methylquinoline-8-carboxamide;

7-((1H-imidazol-1-yl)methyl)-2-(6-ethyl-8-((oxetan-3-yloxy)methyl)quinolin-4-yl)-5-(1-methyl-3-(trifluoromethyl)-1H-pyrazol-4-yl)-3,4-dihydroisoquinolin-1(2H)-one;

N-(1-(4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinolin-8-yl)piperidin-4-yl)acetamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-methylpyrrolidin-3-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(2-(dimethylamino)ethyl)-6-ethyl-2-methylquinoline-8-carboxamide;

7-((1H-imidazol-1-yl)methyl)-2-(6-methoxy-8-(4-methoxypiperidin-1-yl)-2-methylquinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-methoxy-2-methyl-8-(1H-tetrazol-5-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-2-methyl-8-((3aR,6aS)-5-methylhexahydropyrrolo[3,4-c]pyrrol-2(1H)-yl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methylquinoline-8-carboxamide;

4-(7-((1H-imidazol-1-yl)methyl)-1-oxo-5-(2-(trifluoromethyl)pyridin-3-yl)-3,4-dihydroisoquinolin-2(1H)-yl)-6-ethyl-N-methylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methyl-N-(oxazol-2-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-2-methyl-N-(1H-pyrazol-4-yl)quinoline-8-carboxamide;

7-((1H-imidazol-1-yl)methyl)-2-(3-methoxy-7-methylquinolin-5-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-(3-fluoroazetidin-1-yl)-2-methylquinoline-8-carbonitrile;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carbonitrile;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-8-carbonitrile;

7-((1H-imidazol-1-yl)methyl)-2-(3-methoxy-8-methylquinolin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-methoxy-1,7-naphthyridin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(8-(5,6-dihydro-[1,2,4]triazolo[4,3-a]pyrazin-7(8H)-yl)-6-ethylquinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-(pyrazine-2-carboxamido)ethyl)quinoline-8-carboxamide;

7-((1H-imidazol-1-yl)methyl)-2-(6-ethyl-8-(4-(2-methoxyethyl)piperazin-1-yl)quinolin-4-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(3-ethyl-1,7-naphthyridin-5-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(2-acetamidoethyl)-6-ethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(2-(isonicotinamido)ethyl)quinoline-8-carboxamide;

7-((1H-imidazol-1-yl)methyl)-2-(3-methoxy-1,7-naphthyridin-5-yl)-5-(1-methyl-3-(trifluoromethyl)-1H-pyrazol-4-yl)-3,4-dihydroisoquinolin-1(2H)-one;

7-((1H-imidazol-1-yl)methyl)-2-(6-ethyl-8-(4-(oxetan-3-yl)piperazin-1-yl)quinolin-4-yl)-5-(1-methyl-3-(trifluoromethyl)-1H-pyrazol-4-yl)-3,4-dihydroisoquinolin-1(2H)-one;

N-(2-(4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinoline-8-carboxamido)ethyl)thiazole-4-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-ylmethyl)-6-ethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-((1-acetylazetidin-3-yl)methyl)-6-ethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-((1-isonicotinoylazetidin-3-yl)methyl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-((1-(thiazole-4-carbonyl)azetidin-3-yl)methyl)quinoline-8-carboxamide;

7-((2-amino-1H-imidazol-1-yl)methyl)-2-(3-methoxy-7-methylquinolin-5-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-ethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-(tetrahydro-2H-pyran-4-carbonyl)azetidin-3-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(azetidin-3-yl)-6-methoxyquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-isonicotinoylazetidin-3-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(1-acetylazetidin-3-yl)-6-methoxyquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-(1-(thiazole-4-carbonyl)azetidin-3-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-(1-(thiazole-4-carbonyl)azetidin-3-yl)quinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-(1-(tetrahydro-2H-pyran-4-carbonyl)azetidin-3-yl)quinoline-8-carboxamide;

7-((1H-imidazol-1-yl)methyl)-2-(8-amino-6-ethylquinolin-4-yl)-5-(1-methyl-3-(trifluoromethyl)-1H-pyrazol-4-yl)-3,4-dihydroisoquinolin-1(2H)-one;

N-(4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)acetamide;

7-((1H-imidazol-1-yl)methyl)-2-(6-ethyl-8-(1-methyl-1H-pyrazol-4-yl)quinolin-4-yl)-5-(1-methyl-3-(trifluoromethyl)-1H-pyrazol-4-yl)-3,4-dihydroisoquinolin-1(2H)-one;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethyl-N-((1-(tetrahydro-2H-pyran-4-carbonyl)azetidin-3-yl)methyl)quinoline-8-carboxamide;

tert-butyl ((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl) carbamate;

Methyl 4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-2-carboxylate;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxyquinoline-2-carboxylic acid;

4-(7-((1H-Imidazol-1-yl)methyl)-5-(1-methyl-3-(trifluoromethyl)-1H-pyrazol-4-yl)-1-oxo-3,4-dihydroisoquinolin-2(1H)-yl)-6-methoxy-N-methylquinoline-2-carboxamide;

N-((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)-N-methylacetamide;

7-((1H-imidazol-1-yl)methyl)-2-(8-(aminomethyl)-6-ethylquinolin-4-yl)-5-(1-methyl-3-(trifluoromethyl)-1H-pyrazol-4-yl)-3,4-dihydroisoquinolin-1(2H)-one;

N-((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)acetamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(1-acetylazetidin-3-yl)-6-ethylquinoline-8-carboxamide;

4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-N-(1-isonicotinoylazetidin-3-yl)-6-methoxyquinoline-8-carboxamide; and N-((4-(7-((1H-imidazol-1-yl)methyl)-5-(1-methyl-3-(trifluoromethyl)-1H-pyrazol-4-yl)-1-oxo-3,4-dihydroisoquinolin-2(1H)-yl)-6-ethylquinolin-8-yl)methyl)isonicotinamide;

or a pharmaceutically acceptable salt thereof.

Clause 115. The compound of any of clauses 1-114, or a pharmaceutically acceptable salt thereof, wherein the compound is isotopically labeled.

Clause 116. A pharmaceutical composition comprising the compound of any of clauses 1-115, or a pharmaceutically acceptable salt thereof, and a pharmaceutically acceptable carrier.

Clause 117. A method of treating cancer comprising administering to a subject in need thereof, a therapeutically effective amount of the compound of any of clauses 1-115, or a pharmaceutically acceptable salt thereof, or the pharmaceutical composition of clause 116.

Clause 118. A method of inhibiting cancer cell proliferation, comprising administering to a subject in need thereof, the compound of any of clauses 1-115, or a pharmaceutically acceptable salt thereof or the pharmaceutical composition of clause 116, in an amount effective to inhibit the cancer cell proliferation.

Clause 119. Use of the compound of any of clauses 1-115, or a pharmaceutically acceptable salt thereof, or the pharmaceutical composition of clause 116, in the manufacture of a medicament for the treatment of cancer.

Clause 120, Use of the compound of any of clauses 1-115, or a pharmaceutically acceptable salt thereof, or the pharmaceutical composition of clause 116, in the manufacture of a medicament for the inhibition of cancer cell proliferation.

Clause 121. The compound of any of clauses 1-115, or a pharmaceutically acceptable salt thereof, or the pharmaceutical composition of clause 116, for use in the treatment of cancer.

Clause 122. The compound of any of clauses 1-115, or a pharmaceutically acceptable salt thereof, or the pharmaceutical composition of clause 116, for use in the inhibition of cancer cell proliferation.

What is claimed is:

1. A compound of formula (I-b)

(I-b)

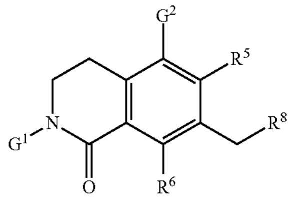

or a pharmaceutically acceptable salt thereof, wherein:

$G^1$ is an optionally substituted 10-membered fused bicyclic ring system of formula

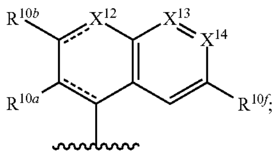

each ------ represents a double bond;

$X^{12}$ is N;

$X^{13}$ is $CR^{10d}$;

$X^{14}$ is $CR^{10e}$ or N;

$R^{10a}$ is hydrogen;

$R^{10b}$ is hydrogen or $C_{1-4}$alkyl;

$R^{10d}$ is —C(O)N($R^{1a}$)$_2$ or -O$R^{1a}$;

$R^{10e}$ is hydrogen;

$R^{10f}$ is $C_{1-4}$ alkyl or O$C_{1-4}$alkyl;

$R^{1a}$, at each occurrence, is independently hydrogen, $C_{1-6}$alkyl, $C_{1-6}$haloalkyl, -$C_{2-4}$alkylene-O$R^{1e}$, —$C_{2-4}$alkylene-N($R^{1e}$)$_2$, -$C_{2-4}$alkylene-N($R^{1e}$)C(O)$R^{1e}$, $G^{1a}$, or -$C_{1-6}$alkylene-$G^{1a}$;

$G^{1a}$ is $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, -$L^2$-$X^2$, and -$L^2$-$G^{1b}$;

$L^2$, at each occurrence, is independently a bond or $C_{1-3}$alkylene;

$X^2$, at each occurrence, is independently $-OR^{1c}$, $-N(R^{1c})_2$, $-SR^{1c}$, cyano, $—C(O)OR^{1c}$, $—C(O)N(R^{1c})_2$, $—C(O)R^{1c}$, $-SOR^{1d}$, $—SO_2R^{1d}$, $-SO_2N(R^{1c})_2$, $—NR^{1c}C(O)R^{1c}$, $—NR^{1c}C(O)OR^{1c}$, $—NR^{1c}C(O)N(R^{1c})_2—NR^{1c}S(O)_2R^{1d}$, or $—NR^{1c}S(O)_2N(R^{1c})_2$;

$R^{1c}$, at each occurrence, is independently hydrogen, $C_{1-6}$alkyl, $C_{1-6}$haloalkyl, $G^{1b}$, or $-C_{1-3}$alkylene-$G^{1b}$, wherein alternatively two $R^{1c}$, together with a common nitrogen atom to which the $R^{1c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and $-OC_{1-4}$alkyl;

$R^{1d}$, at each occurrence, is independently $C_{1-6}$alkyl, $C_{1-6}$haloalkyl, $G^{1b}$, or $—C_{1-3}$alkylene-$G^{1b}$;

$R^{1e}$, at each occurrence, is independently hydrogen, $C_{1-4}$alkyl, $C_{1-4}$haloalkyl, $G^{1b}$, or $-C_{1-3}$alkylene-$G^{1b}$, wherein alternatively two $R^{1e}$, together with a common nitrogen atom to which the $R^{1e}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and $-OC_{1-4}$alkyl;

$G^{1b}$ is a $C_{3-6}$cycloalkyl, a 4- to 6-membered monocyclic heterocyclyl containing 1-2 heteroatoms independently selected from O, N, and S, a 5- to 6-membered heteroaryl containing 1-4 heteroatoms independently selected from O, N, and S, or a phenyl, wherein $G^{1b}$ is optionally substituted with 1-4 substituents independently selected from the group consisting of halogen, cyano, $C_{1-4}$alkyl, $C_{1-4}$haloalkyl, oxo, —OH, and $-OC_{1-4}$alkyl;

$G^2$ is a 5- to 12-membered heteroaryl, a $C_{3-10}$carbocyclyl, a 6- to 12-membered aryl, or a 4- to 12-membered heterocyclyl, wherein $G^2$ is optionally substituted with 1-5 substituents independently selected from the group consisting of $C_{1-6}$alkyl, $C_{1-6}$haloalkyl, halogen, oxo, $—OR^{4c}$, $—N(R^{4c})_2$, $—SR^{4c}$, cyano, $—C(O)OR^{4c}$, $—C(O)N(R^{4c})_2$, $—C(O)R^{4c}$, $—SOR^{4d}$, $—SO_2R^{4d}$, $—SO_2N(R^{4c})_2$, $—NR^{4c}C(O)R^{4c}$, $—NR^{4c}C(O)OR^{4c}$, $—NR^{4c}C(O)N(R^{4c})_2$, $—NR^{4c}S(O)_2R^{4d}$, $—NR^{4c}S(O)_2N(R^{4c})_2$, $C_{3-8}$cycloalkyl, and $-C_{1-3}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^{4c}$, at each occurrence, is independently hydrogen, $C_{1-6}$alkyl, $C_{1-6}$haloalkyl, $C_{3-8}$cycloalkyl, or $-C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein alternatively two $R^{4c}$, together with a common nitrogen atom to which the $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and $-OC_{1-4}$alkyl;

$R^{4d}$, at each occurrence, are independently $C_{1-6}$alkyl, $C_{1-6}$haloalkyl, $C_{3-8}$cycloalkyl, or $-C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^5$ and $R^6$ are each independently hydrogen, halogen, $C_{1-4}$alkyl, $C_{1-4}$haloalkyl, or $-OC_{1-4}$alkyl; and $R^8$ is an imidazolyl unsubstituted or substituted with 1-3 substituents independently selected from the group consisting of halogen, $C_{1-4}$alkyl, $C_{1-4}$haloalkyl, $NO_2$, $NH_2$, $—NH(C_{1-4}alkyl)$, $—N(C_{1-4}alkyl)_2$, $C_{3-8}$cycloalkyl, and $-C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and $-OC_{1-4}$alkyl.

2. The compound of claim 1, or a pharmaceutically acceptable salt thereof, wherein $R^8$ is

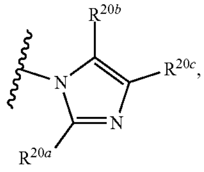
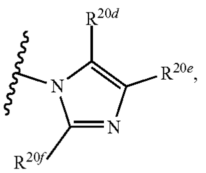
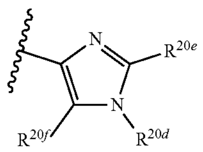
or
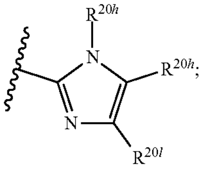

$R^{20a}$ is hydrogen, $C_{1-4}$alkyl, $NH_2$, $—NH(C_{1-4}alkyl)$, $—N(C_{1-4}alkyl)_2$, or $C_{3-8}$cycloalkyl; and $R^{20b}$, $R^{20c}$, $R^{20d}$, $R^{20e}$, $R^{20f}$, $R^{20g}$, $R^{20h}$, and $R^{20i}$ are each independently hydrogen, $C_{1-4}$alkyl, or $C_{3-8}$cycloalkyl.

3. The compound of claim 2, or a pharmaceutically acceptable salt thereof, wherein $R^8$ is

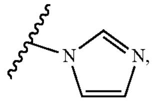
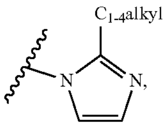
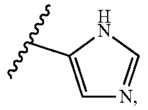
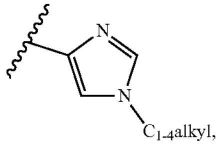
or
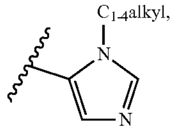
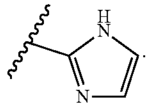

4. The compound of claim 1, or a pharmaceutically acceptable salt thereof, wherein $G^1$ is -continued
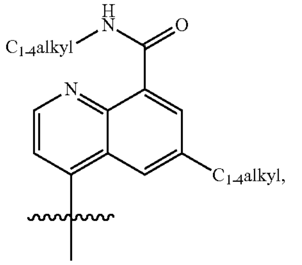
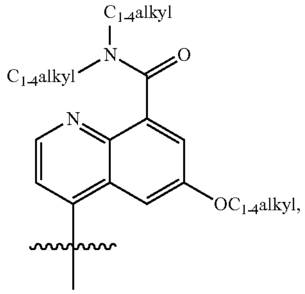
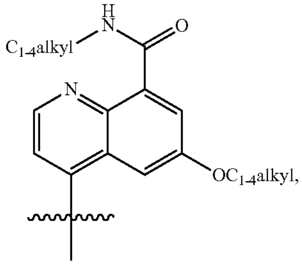
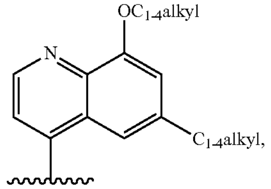
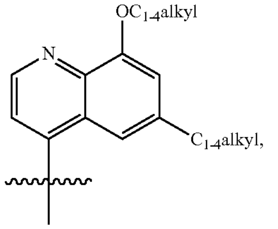
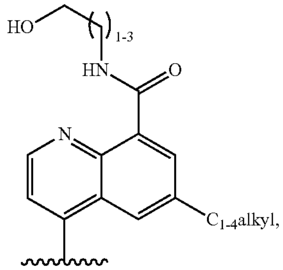
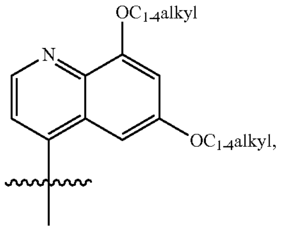
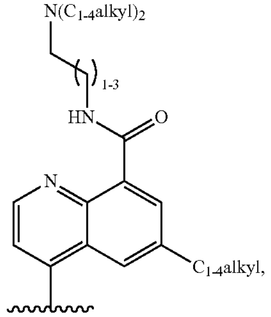
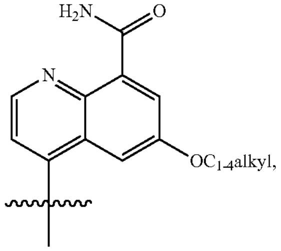
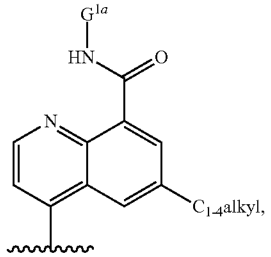
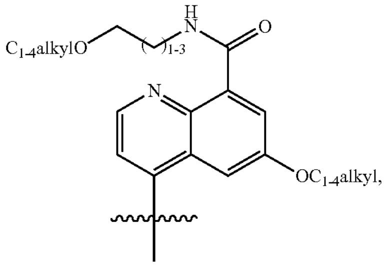
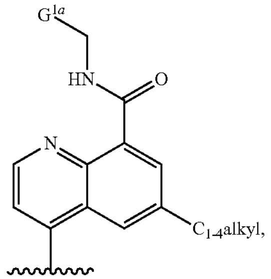

-continued
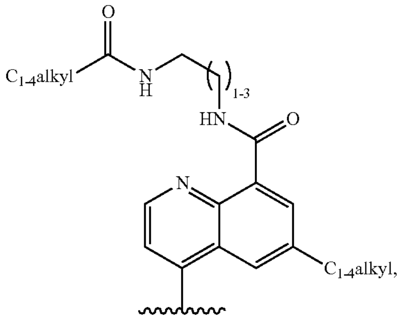
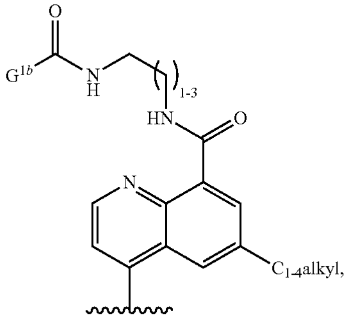
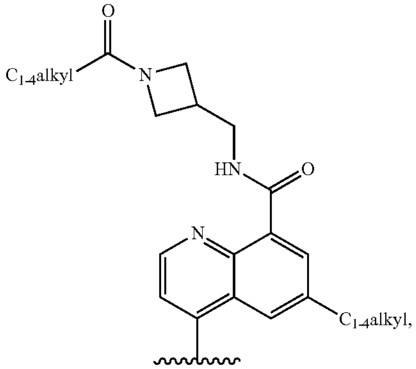
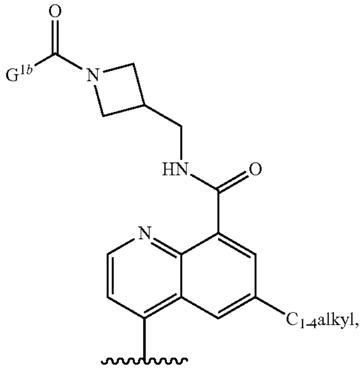
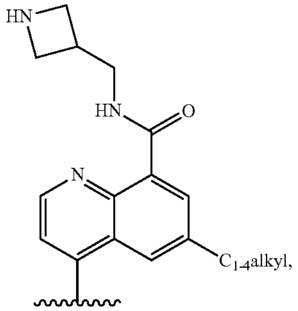
-continued
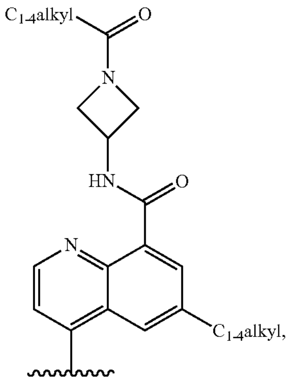
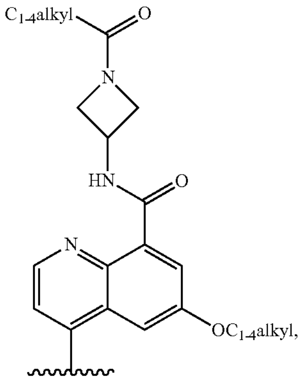
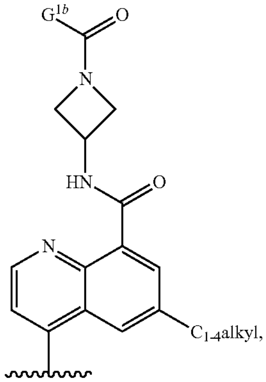
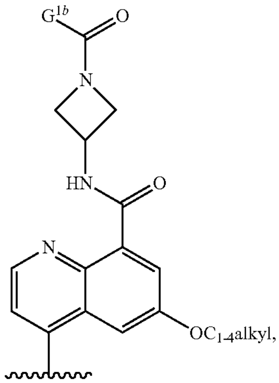

-continued
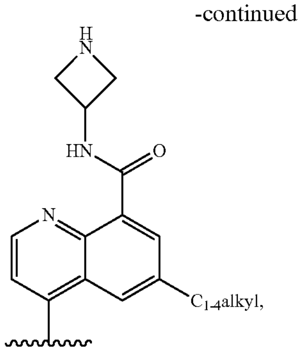
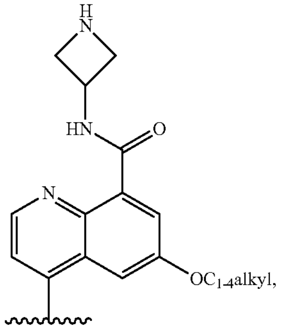
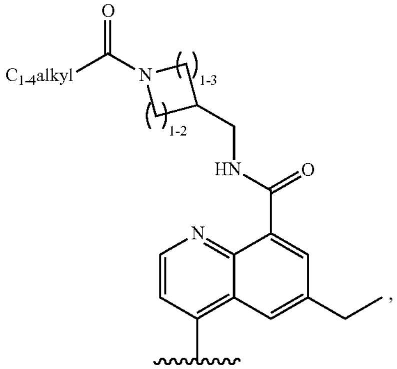
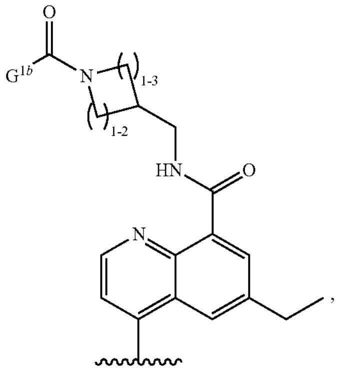
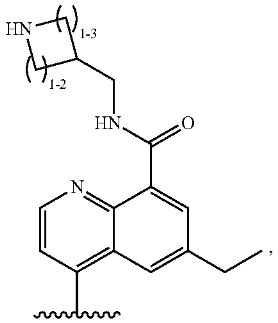
-continued
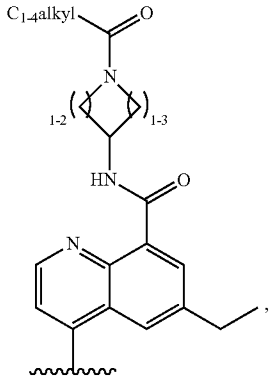
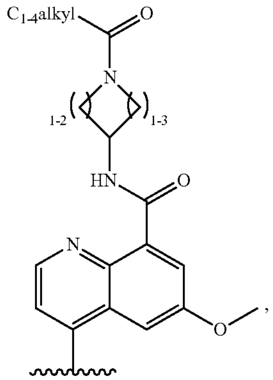
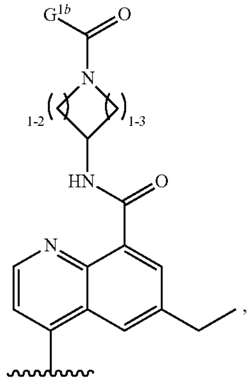
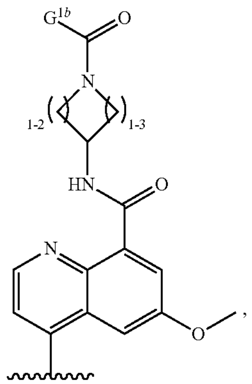
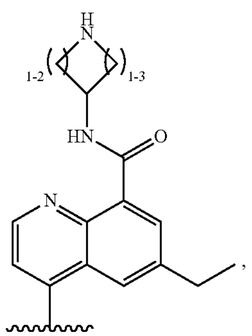

-continued
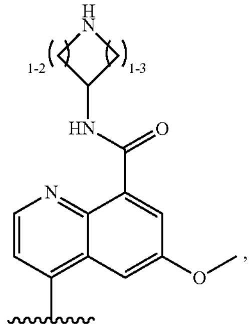
,
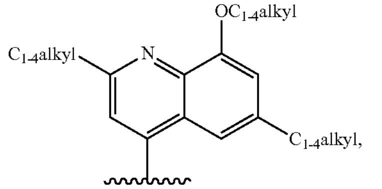
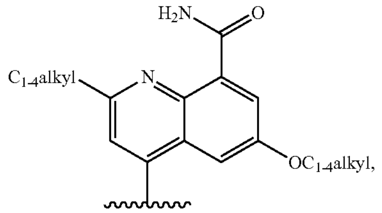
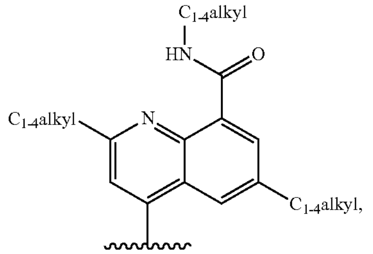
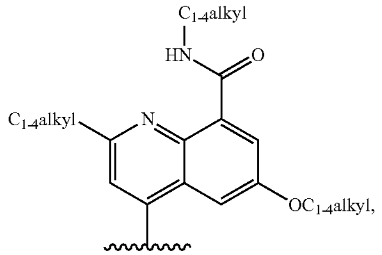
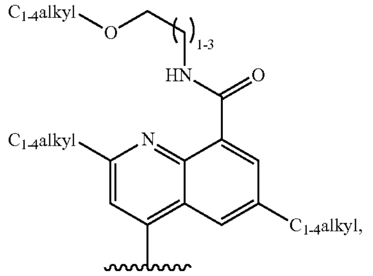
-continued
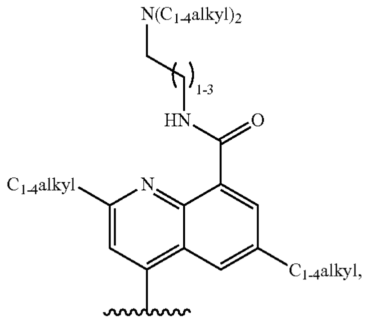
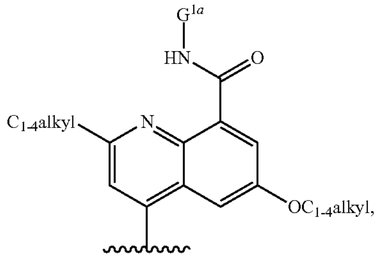
or
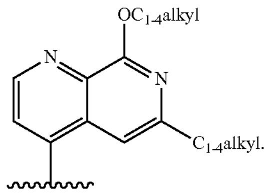
5. The compound of claim 1, or a pharmaceutically acceptable salt thereof, wherein
$R^{10d}$ is
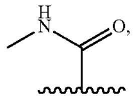
$OCH_3$, $OCF_3$,
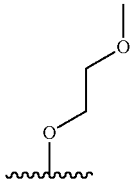
,
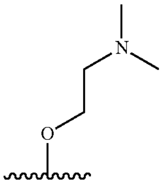
,
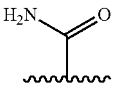
,
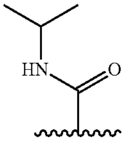
,
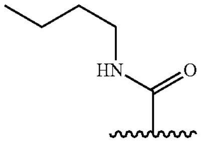
,
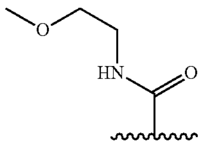
,
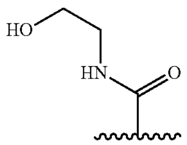
, -continued
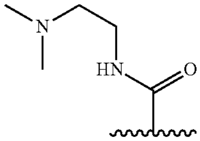 , 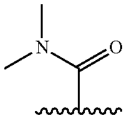 ,
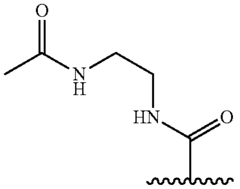 ,
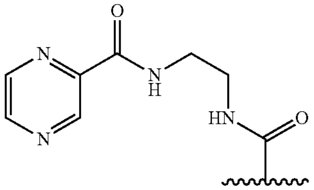 ,
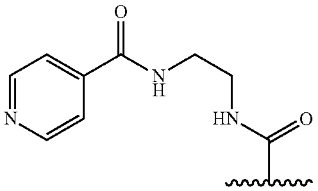 ,
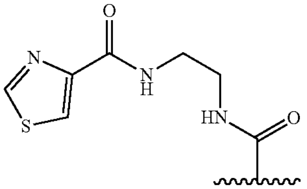 ,
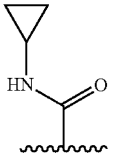 , 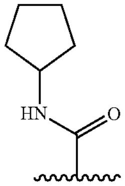 , 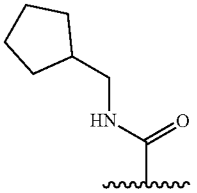 ,
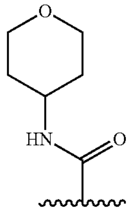 , 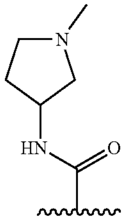 , 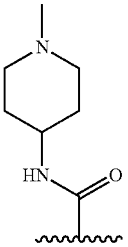 ,
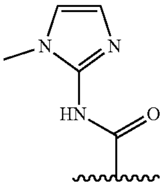 , 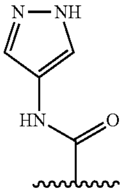 ,
-continued
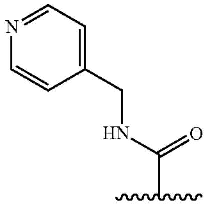 , 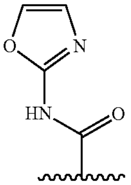 ,
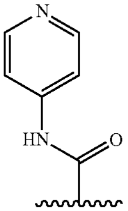 , 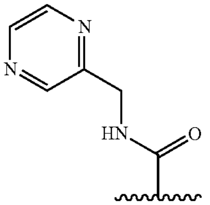 ,
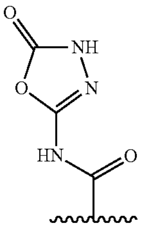 , 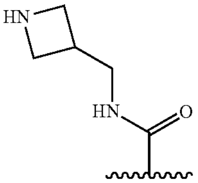 ,
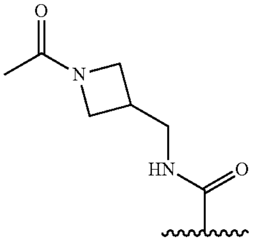 ,
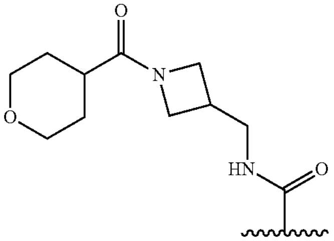 ,
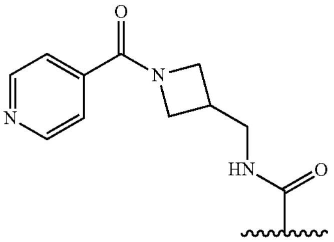 ,
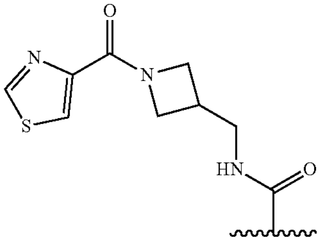 , 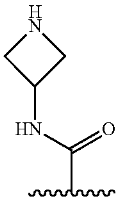 , -continued

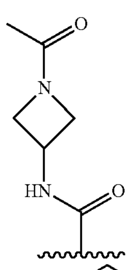
,
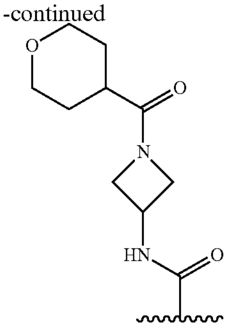
,
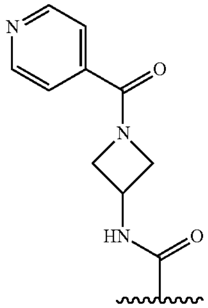
, or
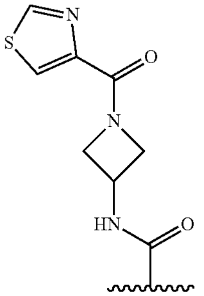
.

6. The compound of claim 1, or a pharmaceutically acceptable salt thereof, wherein $G^2$ is a 5- to 6-membered heteroaryl, and optionally substituted as defined in claim 1.

7. The compound of claim 6, or a pharmaceutically acceptable salt thereof, wherein $G^2$ is optionally substituted with 1-4 substituents independently selected from the group consisting of halogen, $C_{1-6}$alkyl, and $C_{1-6}$haloalkyl.

8. The compound of claim 7, or a pharmaceutically acceptable salt thereof, wherein, $G^2$ is

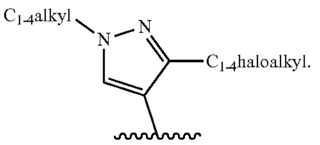

9. The compound of claim 8, or a pharmaceutically acceptable salt thereof, wherein, $G^2$ is

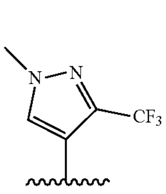
or
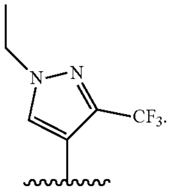

10. The compound of claim 1, or a pharmaceutically acceptable salt thereof, wherein $R^5$ is hydrogen.

11. The compound of claim 10, or a pharmaceutically acceptable salt thereof, wherein $R^6$ is hydrogen.

12. A pharmaceutical composition comprising the compound of claim 1, or a pharmaceutically acceptable salt thereof, and a pharmaceutically acceptable carrier.

13. A method of treating cancer comprising administering to a subject in need thereof, a therapeutically effective amount of the compound of claim 1, or a pharmaceutically acceptable salt thereof, wherein the cancer is leukemia, ovarian cancer, breast cancer, colorectal cancer, pancreatic cancer, gastric cancer, stomach cancer, lung cancer, cervical cancer, uterine cancer, or a cancer of the lymphatic system.

14. A method of inhibiting cancer cell proliferation, comprising administering to a subject in need thereof, the compound of claim 1, or a pharmaceutically acceptable salt thereof, wherein the cancer is leukemia, ovarian cancer, breast cancer, colorectal cancer, pancreatic cancer, gastric cancer, stomach cancer, lung cancer, cervical cancer, uterine B cancer, or a cancer of the lymphatic system.

15. The compound of claim 1, or a pharmaceutically acceptable salt thereof, wherein $X^{14}$ is N.

16. The compound of claim 15, or a pharmaceutically acceptable salt thereof, wherein $R^{10b}$ is hydrogen or methyl.

17. The compound of claim 15, or a pharmaceutically acceptable salt thereof, wherein $R^{10f}$ is ethyl or $OCH_3$.

18. The compound of claim 4, or a pharmaceutically acceptable salt thereof, wherein $G^1$ is

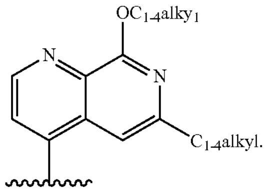

19. The compound of claim 18, or a pharmaceutically acceptable salt thereof, wherein $G^1$ is

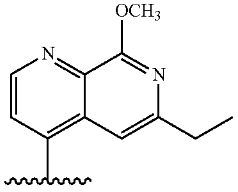
.

20. The compound of claim 1, or a pharmaceutically acceptable salt thereof, wherein the compound is

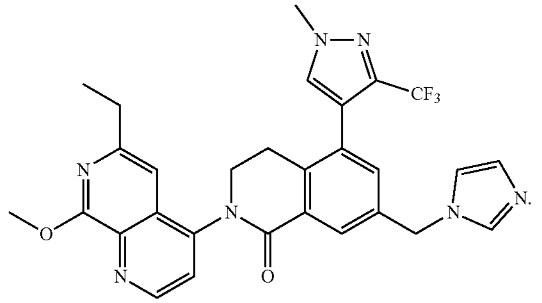 [SMILES: CCc1cc2c(N3CCc4c(cc(Cn5ccnc5)cc4-c4cn(C)nc4C(F)(F)F)C3=O)ccnc2c(OC)n1]

21. A method of treating cancer comprising administering to a subject in need thereof, a therapeutically effective amount of the compound of claim 1, or a pharmaceutically acceptable salt thereof, wherein the cancer is a cancer of the blood.

22. A method of inhibiting cancer cell proliferation, comprising administering to a subject in need thereof, the compound of claim 1, or a pharmaceutically acceptable salt thereof, wherein the cancer is a cancer of the blood.

23. The method of claim 13, wherein the compound is

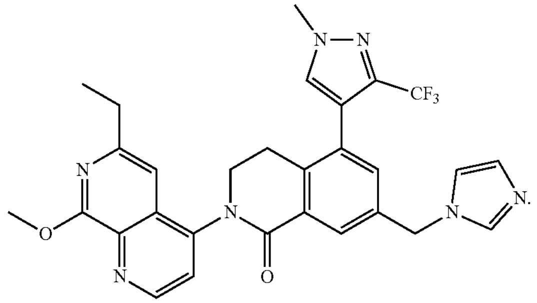 [SMILES: CCc1cc2c(N3CCc4c(cc(Cn5ccnc5)cc4-c4cn(C)nc4C(F)(F)F)C3=O)ccnc2c(OC)n1]

24. The method of claim 23, wherein the cancer is leukemia.

25. The method of claim 23, wherein the cancer is a cancer of the lymphatic system.

26. The method of claim 23, wherein the cancer is breast cancer.

27. The method of claim 23, wherein the cancer is ovarian cancer.

28. The method of claim 23, wherein the cancer is bladder cancer.

29. The method of claim 23, wherein the cancer is pancreatic cancer.

* * * * *